United States Patent
Lee et al.

(10) Patent No.: US 11,387,417 B2
(45) Date of Patent: Jul. 12, 2022

(54) ORGANIC ELECTROLUMINESCENT DEVICE

(71) Applicant: ROHM AND HAAS ELECTRONIC MATERIALS KOREA LTD., Chungcheongnam-do (KR)

(72) Inventors: Tae-Jin Lee, Gyeonggi-do (KR); Jeong-Eun Yang, Gyeonggi-do (KR); Dong-Hyung Lee, Gyeonggi-do (KR); Sang-Hee Cho, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 290 days.

(21) Appl. No.: 16/483,062

(22) PCT Filed: Feb. 27, 2018

(86) PCT No.: PCT/KR2018/002357
§ 371 (c)(1),
(2) Date: Aug. 2, 2019

(87) PCT Pub. No.: WO2018/159970
PCT Pub. Date: Sep. 7, 2018

(65) Prior Publication Data
US 2020/0013964 A1   Jan. 9, 2020

(30) Foreign Application Priority Data

| Feb. 28, 2017 | (KR) | 10-2017-0026014 |
| Sep. 26, 2017 | (KR) | 10-2017-0124258 |
| Sep. 26, 2017 | (KR) | 10-2017-0124285 |
| Dec. 27, 2017 | (KR) | 10-2017-0180988 |
| Feb. 26, 2018 | (KR) | 10-2018-0022906 |

(51) Int. Cl.
| *C07D 487/06* | (2006.01) |
| *H01L 51/00* | (2006.01) |
| *H01L 51/50* | (2006.01) |
| *C07D 403/14* | (2006.01) |
| *C07D 405/14* | (2006.01) |
| *C07D 491/048* | (2006.01) |

(52) U.S. Cl.
CPC ........ *H01L 51/0072* (2013.01); *H01L 51/006* (2013.01); *H01L 51/0061* (2013.01); *H01L 51/0067* (2013.01); *H01L 51/0073* (2013.01); *H01L 51/0074* (2013.01); *C07D 403/14* (2013.01); *C07D 405/14* (2013.01); *C07D 487/06* (2013.01); *C07D 491/048* (2013.01); *H01L 51/5004* (2013.01); *H01L 51/5012* (2013.01); *H01L 51/5056* (2013.01); *H01L 51/5072* (2013.01); *H01L 51/5088* (2013.01)

(58) Field of Classification Search
None
See application file for complete search history.

(56) References Cited

U.S. PATENT DOCUMENTS

| 2017/0229672 A1 | 8/2017 | Denker et al. |
| 2018/0062089 A1 | 3/2018 | Kamtekar |
| 2018/0114916 A1 | 4/2018 | Hayashi et al. |

FOREIGN PATENT DOCUMENTS

| JP | 3065125 B2 | 7/2000 |
| JP | 2009060089 A | 3/2009 |
| KR | 2015-0066202 A | 6/2015 |
| KR | 2015-0121337 A | 10/2015 |
| WO | 2015167300 A1 | 11/2015 |
| WO | 2016204394 A1 | 12/2016 |

OTHER PUBLICATIONS

Danel et al. "Synthesis of novel twisted heterocyclic analogues of s-indacenes" Arkivoc, 2011 (ix) 272-280. (Year: 2011).*
Danel et al. "Unexpected intramolecular cyclization of 4-(2-halophenyl)-1H-pyrazolo[3,4-b]quinolines: formation of 5- and 7-membered rings from one starter" Arkivoc 2009 (x) 71-78. (Year: 2009).*
Szlachcic, P. et al: 'Organic Light Emitting Diodes (OLED) Based on Helical Structures Containing 7-Membered Fused Rings', Dyes and Pigments (2015), 114, 184-195.
Gasiorski, P. et al: 'Synthesis And Spectroscopic Study of Several Novel Annulated Azulene and Azafluoranthene Based Derivatives', Journal of Fluorescence (2011), 21(1), 443-451.
Gasiorski, P. et al: 'From Pirazoloquinolines to Annulated Azulene Dyes: UV-VIS Spectroscopy and Quantum Chemical Study', Journal of Luminescence (2010), 130(12), 2460-2468.
Calus, S. et al: 'Optical Absorption and Fluorescence Spectra of Novel Annulated Analogues of Azafluoranthene and Azulene Dyes', Materials Chemistry and Physics (2010), 121(3), 477-483.
Search Report from the China National IP Administration of the People's Republic of China, Application No. 201880011305.9, Application Date: Feb. 27, 2018.
Cited Reference for Japanese Patent Application No. 2019-544041, Application Date: Feb. 27, 2018.

* cited by examiner

*Primary Examiner* — Robert S Loewe
(74) *Attorney, Agent, or Firm* — G. Creston Campbell

(57) ABSTRACT

The present disclosure relates to an organic electroluminescent device comprising a light-emitting layer and a hole transport zone. By comprising a specific combination of a light-emitting layer and a hole transport zone, it is possible to provide an organic electroluminescent device having low driving voltage, high luminous efficiency and/or long lifespan properties.

10 Claims, No Drawings

ORGANIC ELECTROLUMINESCENT DEVICE

TECHNICAL FIELD

The present disclosure relates to an organic electroluminescent device comprising a light-emitting layer and a hole transport zone.

BACKGROUND ART

In 1987, Tang et al. of Eastman Kodak first developed a small molecule green organic electroluminescent device (OLED) of TPD/Alq3 bilayer consisting of a light-emitting layer and a charge transport layer. Since then, the research on an OLED has been rapidly carried out, and it has been commercialized. At present, an OLED mainly uses phosphorescent materials having excellent luminous efficiency in panel implementation. Low driving voltage and high luminous efficiency are required for long lifespan and high resolution of display.

U.S. Pat. No. 6,902,831 discloses an azulene derivative as an organic electroluminescent compound, but it does not specifically disclose an organic electroluminescent compound of a fused azulene derivative. In addition, the document does not specifically disclose that the performance of an OLED can be improved by combining a host compound containing a fused azulene derivative and a specific material contained in a hole transport zone.

DISCLOSURE OF THE INVENTION

Problems to be Solved

The objective of the present disclosure is to provide an organic electroluminescent device having low driving voltage, high luminous efficiency and/or long lifespan properties by a combination of a light-emitting layer comprising a compound according to the present disclosure, and a hole transport zone comprising a compound having a specific HOMO (Highest Occupied Molecular Orbital) energy level.

Solution to Problems

A light-emitting layer comprising a phosphorescent dopant is preferable to have a light-emitting material having excellent hole and electron current properties for low driving voltage, high efficiency, and long lifespan, and the material having the thermal stability for improvement of lifespan. In addition, for efficient energy transport from the host to the dopant of the light-emitting layer, using a light-emitting material having a narrow energy band gap can contribute to improve driving voltage and luminous efficiency by minimizing the charge trap. While the azulene derivative comprised in the device of the present disclosure has a slow transition constant of the internal conversion of $S_2 \rightarrow S_1$, i.e. $7*10^{-8}$ s, the transition constant of the internal conversion of $S_1 \rightarrow S_0$ is fast, i.e. $7*10^{-12}$ s. Thus, the fluorescence quantum yield of $S_2 \rightarrow S_0$ increases, and so the azulene derivative is one of the representative materials which violates Kasha's rule. According to a non-patent document of [Phys. Chem. Chem. Phys. 2015, 17, 23573, J. Phys. Chem. A, Vol. 103, No. 15, 1999 2529], the levels of $S_2$ and $S_1$ of azulene are 3.565 eV and 1.771 eV, respectively, while the level difference of $T_1$ and $S_0$ is very small, i.e. the $T_1$-$S_0$ transition is 1.711 eV. In addition, the intersystem crossing transition of $S_2 \rightarrow T_n$ transition is improved according to the conditions of the substitution material and the solvent polarity. Accordingly, there was report that due to the increase of the transition to the triplet, there may be an advantage in improvement of the phosphorous luminous properties. These azulene derivatives show a small energy gap of $S_1 \rightarrow T_1$, and have a relatively high HOMO characteristic compared to carbazole- or benzocarbazole-type compounds, thereby providing a narrow energy band gap.

However, the conventional hole transport zone has limitations in increasing the efficiency of the light-emitting layer comprising the fused azulene derivative compound. A hole transport zone requires a compound having a high HOMO energy level in order to have a high hole mobility. If the HOMO energy level is high, the driving voltage decreases, but the efficiency of the light-emitting layer also decreases. On the contrary, if the HOMO energy level is low, the efficiency of the light-emitting layer increases, but the driving voltage also increases, and thus it is difficult to realize high luminous efficiency of the device.

The present inventors found that the above-mentioned problems can be solved by comprising a fused azulene derivative of the present disclosure in a light-emitting layer, and an arylamine derivative having a specific HOMO energy level of the present disclosure in a hole transport zone. Specifically, the present inventors found that the above objective can be achieved by an organic electroluminescent device comprising a first electrode, a second electrode facing the first electrode, a light-emitting layer between the first electrode and the second electrode, and a hole transport zone between the first electrode and the light-emitting layer, wherein the light-emitting layer comprises a compound represented by the following formula 1:

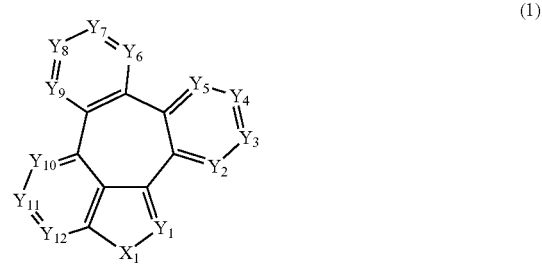

(1)

wherein, $X_1$ represents N-L-(Ar)$_a$, S, or O,

L represents a single bond, a substituted or unsubstituted (C6-C30)arylene, or a substituted or unsubstituted (3- to 30-membered)heteroarylene, Ar represents hydrogen, deuterium, a halogen, a cyano, a substituted or unsubstituted (C1-C30)alkyl, a substituted or unsubstituted (C6-C30)aryl, a substituted or unsubstituted (3-to 30-membered)heteroaryl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, $Y_1$ to $Y_{12}$, each independently, represent N or $CR_1$, $R_1$, each independently, represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or are linked to an adjacent substituent(s) to form a substituted or unsubstituted ring, and a represents an integer of 1 to 4, where if a is an integer of 2 or more, each of Ar may be the same or different; and the hole transport zone comprises an arylamine derivative, and the HOMO energy level of the arylamine derivative satisfies the following equation 11:

$$-5.0 \text{ eV} \leq \text{HOMO} \leq -4.65 \text{ eV} \tag{11}$$

Effects of the Invention

According to the present disclosure, an organic electroluminescent device having low driving voltage, high luminous efficiency and/or long lifespan properties can be provided. Also, it is possible to produce a display device or a lighting device by using the organic electroluminescent device of the present disclosure.

Embodiments of the Invention

Hereinafter, the present disclosure will be described in detail. However, the following description is intended to explain the disclosure, and is not meant in any way to restrict the scope of the present disclosure.

The organic electroluminescent device of the present disclosure comprises a first electrode, a second electrode facing the first electrode, a light-emitting layer between the first electrode and the second electrode, a hole transport zone between the first electrode and the light-emitting layer, and an electron transport zone between the light-emitting layer and the second electrode. One of the first and second electrodes may be an anode, and the other may be a cathode.

The hole transport zone means a zone wherein holes are transported between the first electrode and the light-emitting layer. For example, the hole transport zone may comprise at least one of a hole injection layer, a hole transport layer, a hole auxiliary layer, a light-emitting auxiliary layer and an electron blocking layer. The hole injection layer, the hole transport layer, the hole auxiliary layer, the light-emitting auxiliary layer and the electron blocking layer, respectively, may be a single layer, or a plurality of layers in which two or more layers are stacked. According to one embodiment of the present disclosure, the hole transport zone may comprise a first hole transport layer and a second hole transport layer, wherein the second hole transport layer may be at least one layer of a plurality of hole transport layers, and it may comprise at least one of a hole auxiliary layer, a light-emitting auxiliary layer and a electron blocking layer. According to another embodiment of the present disclosure, the hole transport zone may comprise a first hole transport layer and a second hole transport layer, wherein the first hole transport layer may be placed between the first electrode and the light-emitting layer, the second hole transport layer may be placed between the first hole transport layer and the light-emitting layer, and the second hole transport layer may serve as a hole transport layer, a light-emitting auxiliary layer, a hole auxiliary layer and/or an electron blocking layer.

According to another embodiment of the present disclosure, the hole transport zone may comprise a p-doped hole injection layer, a hole transport layer, and a light-emitting auxiliary layer. Herein, the p-doped hole injection layer means a hole injection layer doped with a p-dopant. The p-dopant is a material capable of imparting p-type semiconductor properties. The p-type semiconductor properties mean the properties of injecting or transporting holes at the HOMO energy level, i.e., the properties of materials having a high hole conductivity.

The hole transport layer may be placed between the anode (or the hole injection layer) and the light-emitting layer. The hole transport layer may function to smoothly move the holes transferred from the anode to the light-emitting layer, and to block the electrons transferred from the cathode to remain in the light-emitting layer. The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. Also, the hole auxiliary layer may be placed between the hole transport layer (or hole injection layer) and the light-emitting layer, and may be effective to promote or block the hole transport rate (or the hole injection rate), thereby enabling the charge balance to be controlled. Further, the electron blocking layer may be placed between the hole transport layer (or hole injection layer) and the light-emitting layer, and can confine the excitions within the light-emitting layer by blocking the overflow of electrons from the light-emitting layer to prevent a light-emitting leakage. When an organic electroluminescent device includes two or more hole transport layers, the further included hole transport layer may be used as a hole auxiliary layer or an electron blocking layer. The light-emitting auxiliary layer, the hole auxiliary layer and/or the electron blocking layer may have an effect of improving the efficiency and/or the lifespan of the organic electroluminescent device.

The electron transport zone may comprise at least one of an electron buffer layer, a hole blocking layer, an electron transport layer and an electron injection layer, and preferably, at least one of an electron transport layer and an electron injection layer. The electron buffer layer is a layer capable of improving the problem that light-emitting luminance deteriorates due to the change of current properties in the device when the device is exposed to a high temperature during a process of producing panels, and it can control the charge flow properties.

The light-emitting layer, in which light is emitted, may be a single layer, or a plurality of layers in which two or more layers are stacked. The doping concentration of the dopant compound with respect to the host compound of the light-emitting layer is preferably less than 20% by weight.

Herein, "(C1-C30)alkyl" is meant to be a linear or branched alkyl having 1 to 30 carbon atoms constituting the chain, in which the number of carbon atoms is preferably 1 to 10, more preferably 1 to 6, and includes methyl, ethyl, n-propyl, isopropyl, n-butyl, isobutyl, tert-butyl, etc. "(C3-C30)cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "(3- to 7-membered)heterocycloalkyl" is a cycloalkyl having at least one heteroatom selected from the group consisting of B, N, O, S, Si, and P, preferably O, S, and N, and 3 to 7 ring backbone atoms, and includes tetrahydrofuran, pyrrolidine, thiolan, tetrahydropyran, etc. "(C6-C30)aryl(ene)" is a monocyclic or fused ring-type radical derived from an aromatic hydrocarbon having 6 to 30 ring backbone carbon atoms, in which the number of ring backbone carbon atoms is preferably 6 to 20, more preferably 6 to 15, may be partially saturated, and includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, etc. "(3- to 30-membered)heteroaryl(ene)" is an aryl group having at least one, preferably 1 to 4 heteroatoms selected from the group consisting of B, N, O, S, Si, and P, and 3 to 30 ring backbone atoms, in which the number of ring backbone atoms is preferably 3 to 20, more preferably 5 to 15; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzonaphthothiophenyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc. "Halogen" includes F, Cl, Br, and I.

Herein, "substituted" in the expression "substituted or unsubstituted" means that a hydrogen atom in a certain functional group is replaced with another atom or functional group, i.e., a substituent. The substituents of the substituted alkyl, the substituted aryl(ene), the substituted heteroaryl (ene), the substituted cycloalkyl, the substituted heterocycloalkyl, the substituted alkoxy, the substituted arylalkyl, the substituted trialkylsilyl, the substituted dialkylarylsilyl, the substituted alkyldiarylsilyl, the substituted triarylsilyl, the substituted mono- or di-alkylamino, the substituted mono- or di-arylamino, the substituted alkylarylamino, and the substituted ring in L, Ar, $R_1$, $L_a$ to $L_d$, $Ar_1$ to $Ar_3$, and $R_8$ to $R_{43}$ in the formulas of the present disclosure, each independently, are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30) aryloxy, a (C6-C30)arylthio, a (5- to 50-membered) heteroaryl unsubstituted or substituted with a (C1-C30) alkyl(s) and/or a (C6-C30)aryl(s), a (C6-C30)aryl unsubstituted or substituted with a (3- to 50-membered)heteroaryl, a tri(C1-C30)alkylsilyl, a tri(C6-C30)arylsilyl, a di(C1-C30) alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl (C6-C30)aryl; preferably, at least one selected from the group consisting of a (C1-C20)alkyl, a (C6-C25)aryl unsubstituted or substituted with a (C1-C20)alkyl(s) and/or a (3- to 30-membered)heteroaryl(s); a (5- to 40-membered)heteroaryl unsubstituted or substituted with a (C1-C20)alkyl(s) and/or a (C6-C25)aryl(s); and a di(C6-C20)arylamino. For example, the above substituents may be at least one selected from the group consisting of a methyl, a tert-butyl, a phenyl unsubstituted or substituted with a pyridinyl(s), a naphthyl, a biphenyl, a dimethylfluorenyl, a phenylfluorenyl, a diphenylfluorenyl, a phenanthrenyl, a triphenylenyl, a pyridinyl, a triazinyl substituted with a phenyl(s) and/or a naphthyl(s), an indolyl substituted with a diphenyl(s), a benzoimidazolyl substituted with a phenyl(s), a quinolyl, a quinazolinyl substituted with a phenyl(s), a carbazolyl, a dibenzofuranyl, a dibenzothiophenyl, a benzocarbazolyl unsubstituted or substituted with a phenyl(s), a dibenzocarbazolyl, a benzophenanthrothiophenyl, a diphenylamino, a dimethylfluorenylphenylamino, or a substituted or unsubstituted (16- to 33-membered)heteroaryl containing at least one of nitrogen, oxygen and sulfur.

In formula 1, $X_1$ represents N-L-(Ar)$_a$, S, or O.

In formula 1, L represents a single bond, a substituted or unsubstituted (C6-C30)arylene, or a substituted or unsubstituted (3- to 30-membered)heteroarylene; preferably, a single bond, a substituted or unsubstituted (C6-C25)arylene, or a substituted or unsubstituted (5- to 25-membered)heteroarylene; and more preferably, a single bond, an unsubstituted (C6-C18)arylene, or an unsubstituted (5- to 18-membered)heteroarylene, wherein the heteroarylene may comprise at least one of nitrogen, oxygen, and/or sulfur.

According to one embodiment of the present disclosure, L may represent a single bond, a substituted or unsubstituted phenylene, a substituted or unsubstituted naphthylene, a substituted or unsubstituted biphenylene, a substituted or unsubstituted pyridylene, a substituted or unsubstituted pyrimidinylene, a substituted or unsubstituted triazinylene, a substituted or unsubstituted quinazolinylene, a substituted or unsubstituted quinoxalinylene, a substituted or unsubstituted naphthyridinylene, a substituted or unsubstituted benzoquinazolinylene, a substituted or unsubstituted benzothienopyrimidinylene, a substituted or unsubstituted acenaphthopyrimidinylene, a substituted or unsubstituted (13- to 16-membered)heteroarylene containing at least one of nitrogen, oxygen, and sulfur.

In formula 1, Ar represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; preferably, hydrogen, a substituted or unsubstituted (C6-C25)aryl, a substituted or unsubstituted (5- to 30-membered)heteroaryl, or a substituted or unsubstituted di(C6-C25)arylamino; and more preferably, hydrogen, a substituted or unsubstituted (C6-C18)aryl, a substituted or unsubstituted (5- to 25-membered)heteroaryl, or a substituted or unsubstituted di(C6-C18)arylamino.

According to one embodiment of the present disclosure, Ar may represent a substituted or unsubstituted phenyl, a substituted or unsubstituted naphthyl, a substituted or unsubstituted biphenyl, a substituted or unsubstituted terphenyl, a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted carbazolyl, a substituted or unsubstituted dibenzothiophenyl, a substituted or unsubstituted benzothiophenyl, a substituted or unsubstituted dibenzofuranyl, a substituted or unsubstituted benzofuranyl, a substituted or unsubstituted naphthyridinyl, a substituted or unsubstituted benzothienopyrimidinyl, a substituted or unsubstituted benzothienoquinolinyl, a substituted or unsubstituted benzofuroquinolinyl, a substituted or unsubstituted triaindenyl, a substituted or unsubstituted phenanthroimidazolyl, a substituted or unsubstituted (9- to 25-membered)heteroaryl containing at least one of nitrogen, oxygen, and sulfur, a substituted or unsubstituted diphenylamino, a substituted or unsubstituted phenylbiphenylamino, or a substituted or unsubstituted fluorenylphenylamino.

In formula 1, a represents an integer of 1 to 4, preferably, 1 or 2, where if a is an integer of 2 or more, each of Ar may be the same or different.

In formula 1, $Y_1$ to $Y_{12}$, each independently, represent N or $CR_1$. According to one embodiment of the present disclosure, all of $Y_1$ to $Y_{12}$ may represent $CR_1$, and according to another embodiment of the present disclosure, at least one of $Y_1$ to $Y_{12}$ may represent N. Where there are a plurality of $R_1$'s, each of $R_1$ may be the same or different.

$R_1$, each independently, represents hydrogen, deuterium, a halogen, a cyano, a substituted or unsubstituted (C1-C30) alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or are linked to an adjacent substituent(s) to form a substituted or unsubstituted ring; preferably, hydrogen, a substituted or unsubstituted (C1-C20)alkyl, a substituted or unsubstituted (C6-C25)aryl, a substituted or unsubstituted (5- to 25-membered)heteroaryl, or a substituted or unsubstituted di(C6-C25)arylamino; or are linked to an adjacent substituent(s) to form a substituted or unsubstituted, mono- or polycyclic, (C3-C25) aromatic ring, whose carbon atom (s) may be replaced with at least one heteroatom selected from nitrogen, oxygen, and sulfur; and more preferably, hydrogen, a substituted or unsubstituted (C1-C10)alkyl, a substituted or unsubstituted (C6-C18)aryl, a substituted or unsubstituted (5- to 18-membered)heteroaryl, or a substituted or unsubstituted di(C6-C18)arylamino; or are linked to an adjacent substituent(s) to form a substituted or unsubstituted, mono- or polycyclic, (C5-C18) aromatic ring, whose carbon atom(s) may be replaced with at least one heteroatom selected from nitrogen, oxygen, and sulfur.

According to one embodiment of the present disclosure, $R_1$ may each independently represent hydrogen, a substituted or unsubstituted methyl, a substituted or unsubstituted phenyl, a substituted or unsubstituted naphthyl, a substituted or unsubstituted biphenyl, a substituted or unsubstituted pyridyl, a substituted or unsubstituted pyrimidinyl, a substituted or unsubstituted triazinyl, a substituted or unsubstituted quinazolinyl, a substituted or unsubstituted quinoxalinyl, a substituted or unsubstituted phenylbiphenylamino, etc.

According to one embodiment of the present disclosure, at least one adjacent pair of $Y_1$ to $Y_{12}$ in formula 1 are $CR_1$, and the adjacent two $R_1$'s of $CR_1$ are fused together to each independently form a ring represented by any one of the following formulas 2 to 6, but is not limited thereto. For example, the formed ring may be a substituted or unsubstituted benzene ring, a naphthalene ring, a furan ring, a thiophene ring, a substituted or unsubstituted pyrrole ring, a pyridine ring, a benzofuran ring, a benzothiophene ring, a substituted or unsubstituted indole ring, a dibenzofuran ring, a dibenzothiophene ring, a substituted or unsubstituted carbazole ring, a phenanthrene ring, etc., including the ring of formulas 2 to 6.

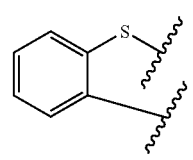

(2)


(3)

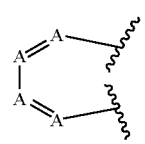

(4)

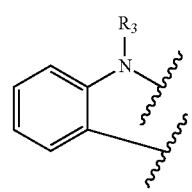

(5)

(6)

In formulas 2 to 6, ✦ represents a bonding site of between C and $R_1$ in the adjacent $CR_1$ of formula 1.

In formulas 4 and 6, A represents N or $CR_2$. According to one embodiment of the present disclosure, A may all represent $CR_2$, and according to another embodiment of the present disclosure, at least one of A may represent N. Where there are a plurality of $R_2$'s, each of $R_2$ may be the same or different.

$R_2$, each independently, represents hydrogen, deuterium, a halogen, a cyano, a substituted or unsubstituted (C1-C30) alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; preferably, a substituted or unsubstituted (C6-C25)aryl, or a substituted or unsubstituted (5- to 25-membered)heteroaryl; and more preferably a substituted or unsubstituted (C6-C18)aryl, or a substituted or unsubstituted (5- to 18-membered)heteroaryl.

In formula 5, $R_3$ represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; preferably, a substituted or unsubstituted (C6-C25)aryl, or a substituted or unsubstituted (5- to 25-membered)heteroaryl; and more preferably an unsubstituted (C6-C18)aryl, or an unsubstituted (5- to 18-membered)heteroaryl. For example, $R_3$ may represent a phenyl.

The OLED according to the present disclosure comprises a hole transport zone between the first electrode and the light-emitting layer, wherein the hole transport zone comprises an arylamine derivative, and the HOMO energy level of the arylamine derivative satisfies the following equation 11.

$$-5.0\ eV \leq HOMO \leq -4.65\ eV \quad (11)$$

According to one embodiment of the present disclosure, the HOMO energy level of the arylamine derivative satisfies the following equation 12.

$$-5.0\ eV \leq HOMO \leq -4.70\ eV \quad (12)$$

According to one embodiment of the present disclosure, the OLED according to the present disclosure comprises a first hole transport layer between the first electrode and the light-emitting layer, and a second hole transport layer between the first hole transport layer and the light-emitting layer, wherein the second hole transport layer comprises an arylamine derivative containing a fluorene or a fused flourene, and the HOMO energy level of the arylamine derivative satisfies the equation 11. Herein, the second hole transport layer may be a single layer or a plurality of layers, and the second hole transport layer may serve as a hole transport layer, a light-emitting auxiliary layer, a hole auxiliary layer and/or an electron blocking layer.

When the hole transport zone includes a compound having a HOMO energy level of less than −5.0, e.g., −5.1 or less, it has a value lower than the HOMO energy level of the compound represented by the formula 1 comprised in the light-emitting layer. As a result, the injection of holes is hindered, and the driving voltage is increased. That is, even if the luminous efficiency of the device increases, since the driving voltage increases as the luminous efficiency increases, there is no gain in terms of power efficiency (lm/W), and rather low power efficiency can be exhibited.

Meanwhile, if the hole transport zone comprises a compound having a HOMO energy level exceeding −4.65, the energy barrier between the layer containing it, e.g., the second hole transport layer, and the light-emitting layer becomes too large, and the injection of holes is hindered. As a result, the luminous efficiency can be reduced. Further, according to one embodiment of the present disclosure, the difference between the upper limit value and the lower limit value of the HOMO energy level of the compound comprised in the hole transport zone may be more appropriate about 0.3 eV or less.

According to one embodiment of the present disclosure, the arylamine derivative comprised in the hole transport zone, preferably the second hole transport layer, for example, at least one of the light-emitting auxiliary layer and the hole auxiliary layer may comprise a compound represented by the following formula 11.

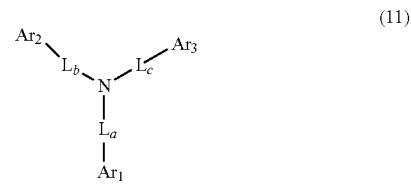

(11)

In formula 11, $L_a$ to $L_c$, each independently, represent a single bond, a substituted or unsubstituted (C6-C30)arylene, a substituted or unsubstituted (3- to 30-membered)heteroarylene, or a substituted or unsubstituted (C3-C30)cycloalkylene; preferably, a single bond, a substituted or unsubstituted (C6-C25)arylene, a substituted or unsubstituted (5- to 25-membered)heteroarylene, or a substituted or unsubstituted (C3-C25)cycloalkylene; more preferably, a single bond, a (C6-C18)arylene unsubstituted or substituted with a di(C6-C18)arylamino(s), an unsubstituted (5- to 18-membered)heteroarylene, or an unsubstituted (C3-C18)cycloalkylene. According to one embodiment of the present disclosure, $L_a$ to $L_c$, each independently, may represent a single bond, a phenylene unsubstituted or substituted with a diphenylamino(s), or an unsubstituted biphenylene.

In formula 11, $Ar_1$ to $Ar_3$, each independently, represent a substituted or unsubstituted (C6-C30)aryl, or a substituted or unsubstituted (5- to 30-membered)heteroaryl, with the proviso that at least one of $Ar_1$ to $Ar_3$ is selected from the following formulas.

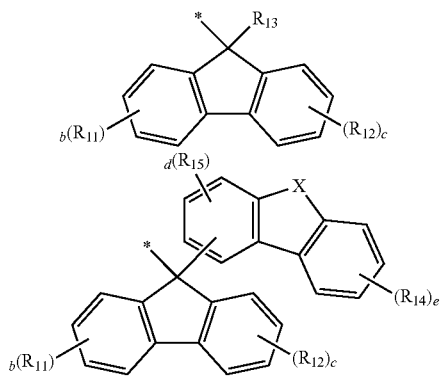

-continued
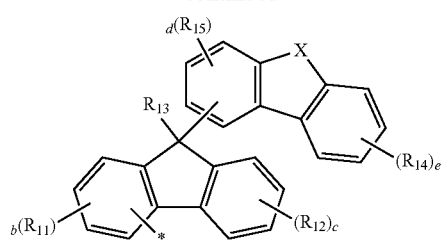
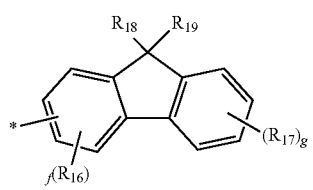
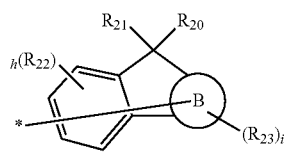
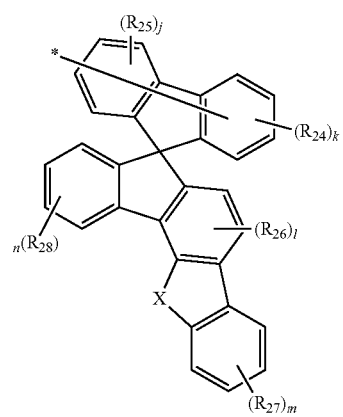
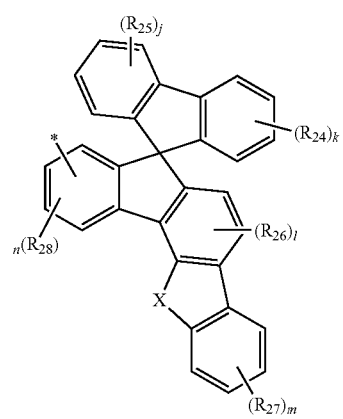
-continued
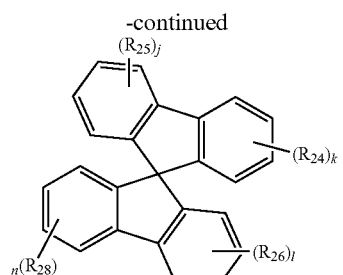
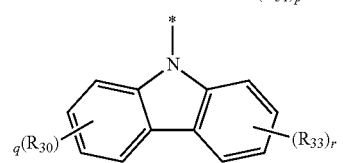
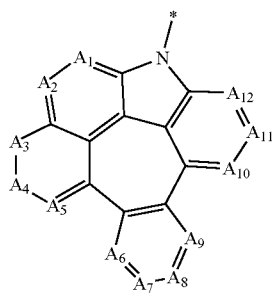
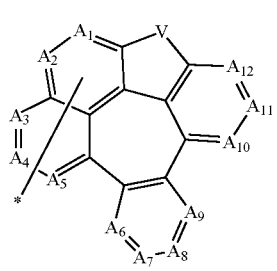

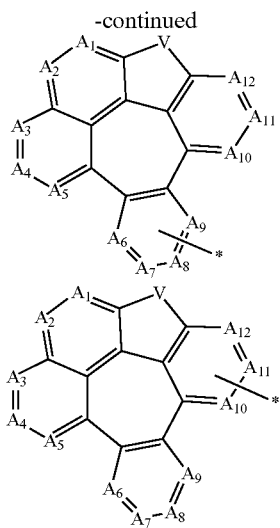

In the above formulas, * represents a bonding site with $L_a$, $L_b$, or $L_c$.

In the above formulas, X, each independently, represents O, S, $NR_8$, or $CR_9R_{10}$, and Z and V, each independently, represent O or S.

In the above formulas, B ring represents a substituted or unsubstituted C10 aryl; preferably, an unsubstituted C10 aryl. According to one embodiment of the present disclosure, B ring may represent a naphthalene ring.

In the above formulas, $L_d$ represents a single bond, or a substituted or unsubstituted (C6-C30)arylene.

In the above formulas, $R_{11}$ to $R_{35}$, each independently, represent hydrogen, deuterium, a halogen, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (3- to 7-membered)heterocycloalkyl, a substituted or unsubstituted (C6-C30)aryl(C1-C30)alkyl, —$NR_{36}R_{37}$, —$SiR_{38}R_{39}R_{40}$, —$SR_{41}$, —$OR_{42}$, a cyano, a nitro, or a hydroxyl, or may be linked to an adjacent substituent(s) to form a substituted or unsubstituted ring, wherein the ring comprises a spiro structure; preferably, hydrogen, a substituted or unsubstituted (C1-C20)alkyl, a substituted or unsubstituted (C6-C25)aryl, a substituted or unsubstituted (5- to 25-membered)heteroaryl, or —$NR_{36}R_{37}$, or may be linked to an adjacent substituent to form a substituted or unsubstituted ring, wherein the ring may comprise a spiro structure; and more preferably, hydrogen, an unsubstituted (C1-C10)alkyl, a (C6-C18)aryl unsubstituted or substituted with a di(C6-C18)arylamino(s), or —$NR_{36}R_{37}$, or may be linked to an adjacent substituent to form an unsubstituted ring, wherein the ring may comprise a Spiro structure. According to one embodiment of the present disclosure, $R_{11}$ to $R_{35}$ may represent hydrogen; $R_{11}$, $R_{12}$, $R_{14}$ to $R_{17}$, $R_{22}$ to $R_{28}$, and $R_{30}$ to $R_{35}$, each independently, may be fused with the other adjacent $R_{11}$, $R_{12}$, $R_{14}$ to $R_{17}$, $R_{22}$ to $R_{28}$, and $R_{30}$ to $R_{35}$ to form a substituted or unsubstituted benzene ring. For example, $R_{13}$ and $R_{17}$, each independently, may represent a biphenyl; $R_{17}$ may represent a phenyl substituted with a diphenylamino; two adjacent $R_{16}$'s may be fused with each other to form an unsubstituted benzene ring; $R_{18}$ and $R_{19}$, each independently, may represent a methyl, a phenyl, or a triphenylenyl, and may be the same or different from each other; $R_{21}$ and $R_{22}$, each independently, may represent a methyl; $R_{28}$ and $R_{29}$, each independently, may represent a methyl or a phenyl, and may be the same or different from each other; and $R_{18}$ and $R_{19}$, or $R_{20}$ and $R_{21}$ may be linked to each other to form a spiro structure, e.g., spiro[fluorene-fluorene] or spiro[fluorene-benzofluorene].

Herein, $R_8$ to $R_{10}$ and $R_{36}$ to $R_{42}$, each independently, represent hydrogen, deuterium, a cyano, a halogen, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (3- to 7-membered)heterocycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or may be linked to an adjacent substituent to form a substituted or unsubstituted ring; preferably, hydrogen, a substituted or unsubstituted (C6-C25)aryl, or a substituted or unsubstituted (5- to 25-membered)heteroaryl; more preferably, a (C6-C18)aryl unsubstituted or substituted with a (C1-C10)alkyl. According to one embodiment of the present disclosure, $R_{36}$ and $R_{37}$, each independently, may represent a phenyl, a naphthylphenyl, a biphenyl, or a dimethylfluorenyl.

In the above formulas, $A_1$ to $A_{12}$, each independently, represent N or $CR_{43}$. When $R_{43}$ is plural, each $R_{43}$ may be the same or different from each other. $R_{43}$, each independently, represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or may be linked to an adjacent substituent to form a substituted or unsubstituted ring; preferably, hydrogen, deuterium, a substituted or unsubstituted (C6-C18)aryl, or a substituted or unsubstituted (5- to 25-membered)heteroaryl, or two or more adjacent $R_{43}$'s may be linked to each other to form a substituted or unsubstituted ring; more preferably, hydrogen, deuterium, an unsubstituted (C6-C18)aryl, or unsubstituted (5- to 18-membered)heteroaryl, or two or more adjacent $R_{43}$'s may be linked to each other to form an unsubstituted ring. According to one embodiment of the present disclosure, $R_{43}$, each independently, may represent hydrogen, or an unsubstituted pyridine, or two adjacent $R_{43}$'s may be linked to each other to form a benzene ring.

In the above formulas, b, c, e, g, h, j, k, m, n, o, q, r, and s, each independently, represent an integer of 1 to 4; d, f, p, and t, each independently, represent an integer of 1 to 3; i represents an integer of 1 to 6; l represents 1 or 2; where each of b to t is an integer of 2 or more, each of $R_{11}$, $R_{12}$, $R_{14}$ to $R_{17}$, $R_{22}$ to $R_{28}$, and $R_{30}$ to $R_{35}$ may be the same or different.

The heteroaryl(ene) or the heterocycloalkyl contains at least one heteroatom selected from B, N, O, S, Si, and P, and preferably, at least one heteroatom selected from N, O, and S.
The compound represented by formula 1 may be specifically exemplified by the following compounds, but is not limited thereto.
C-1
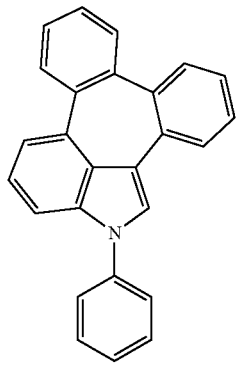
C-2
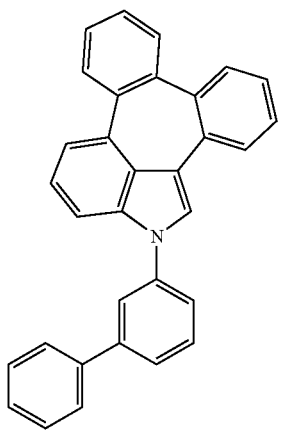
C-3
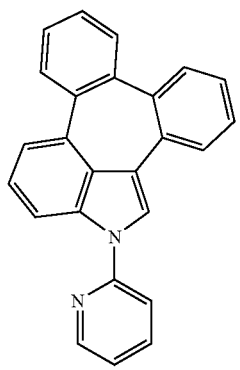
C-4
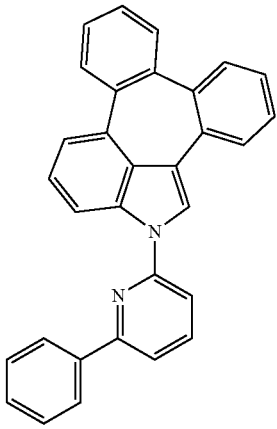
C-5
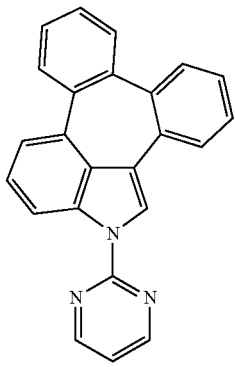
C-6
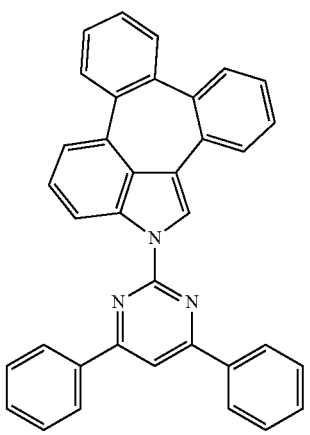

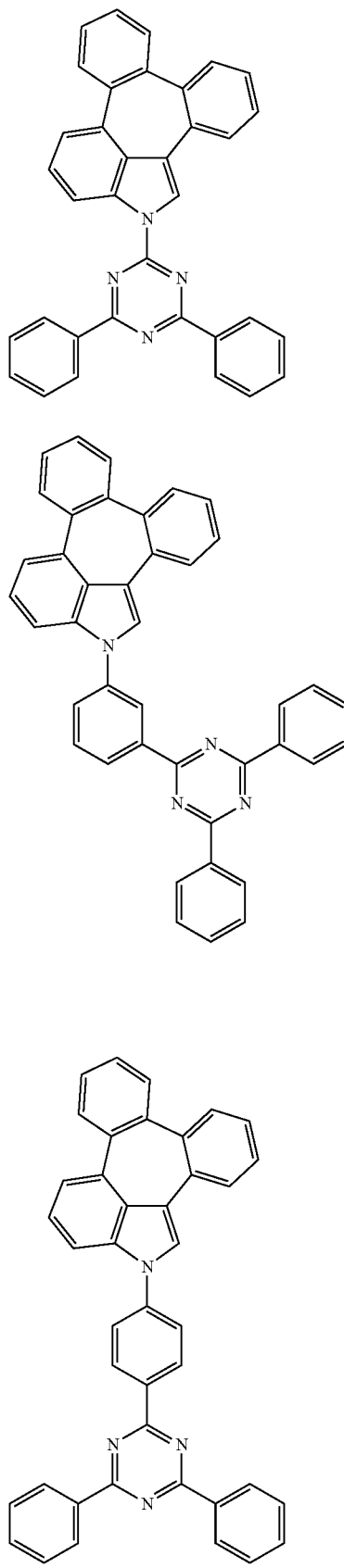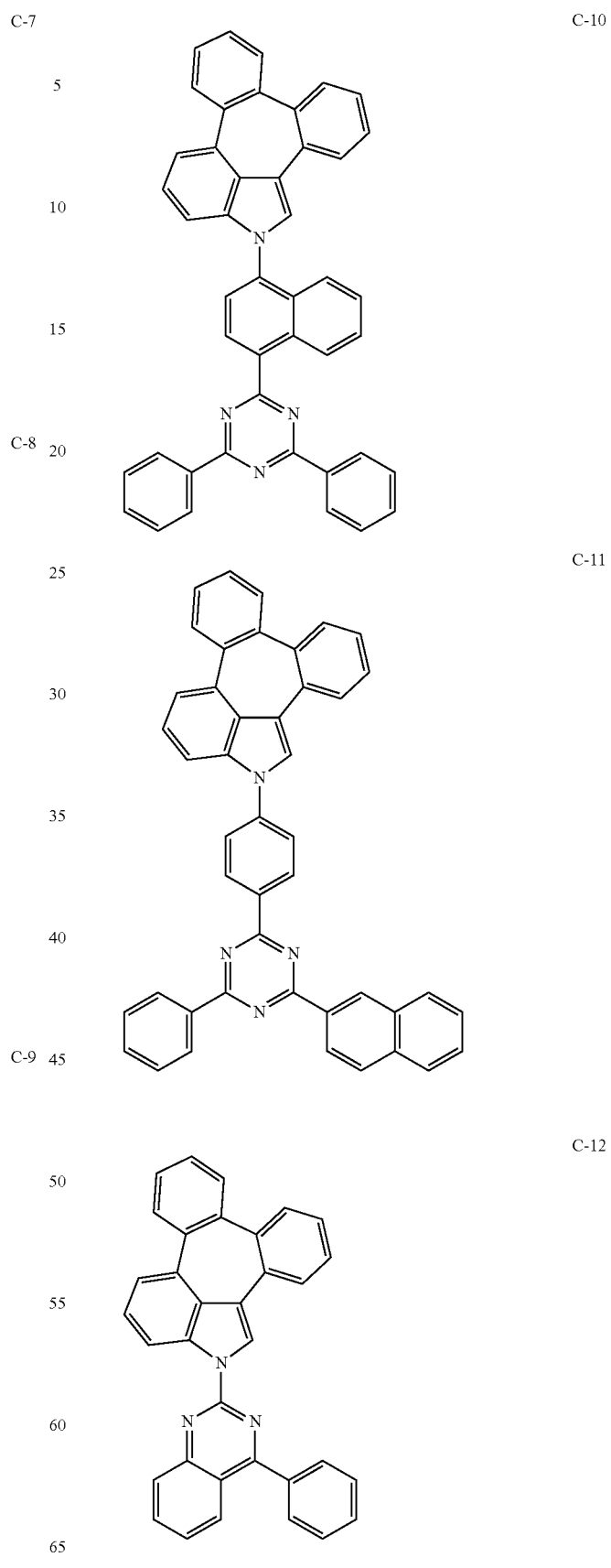

-continued
C-13
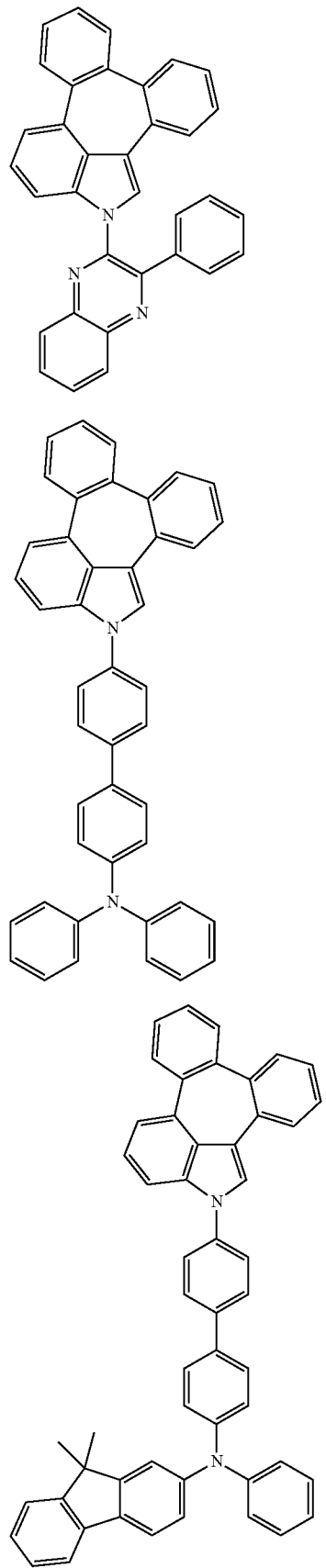
C-14
C-15
C-16
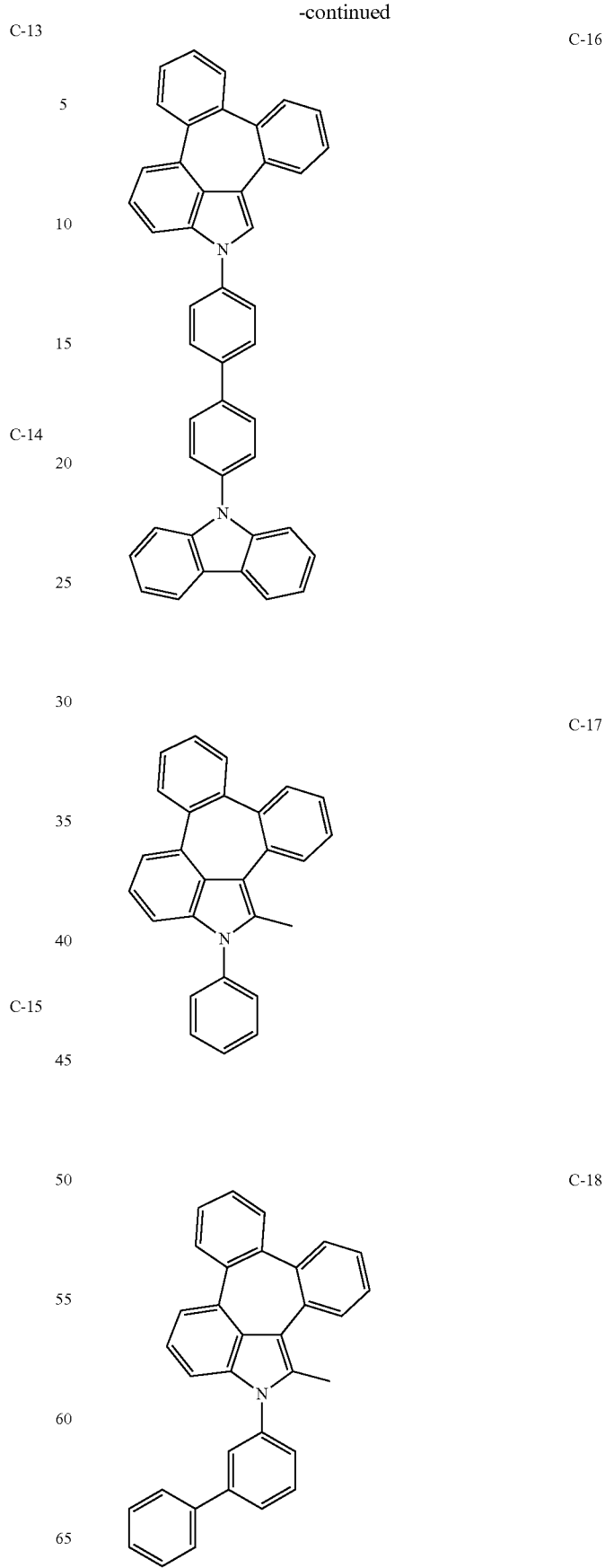
C-17
C-18

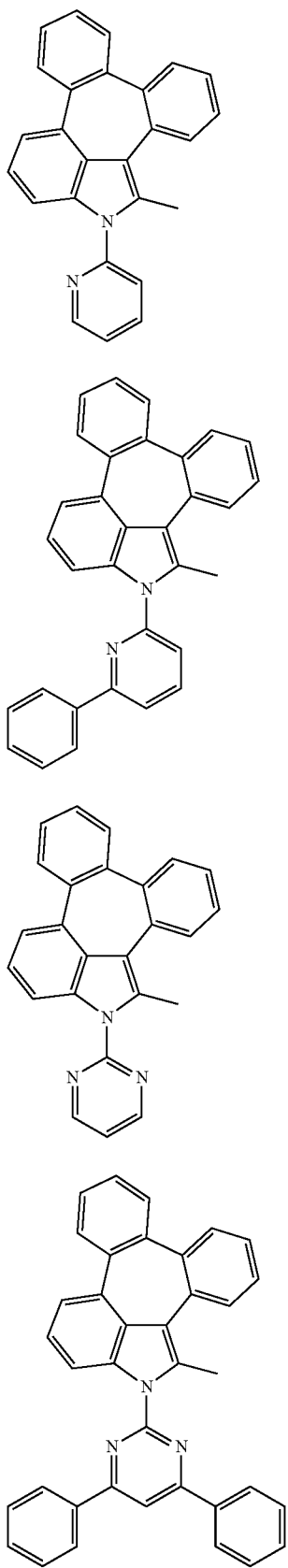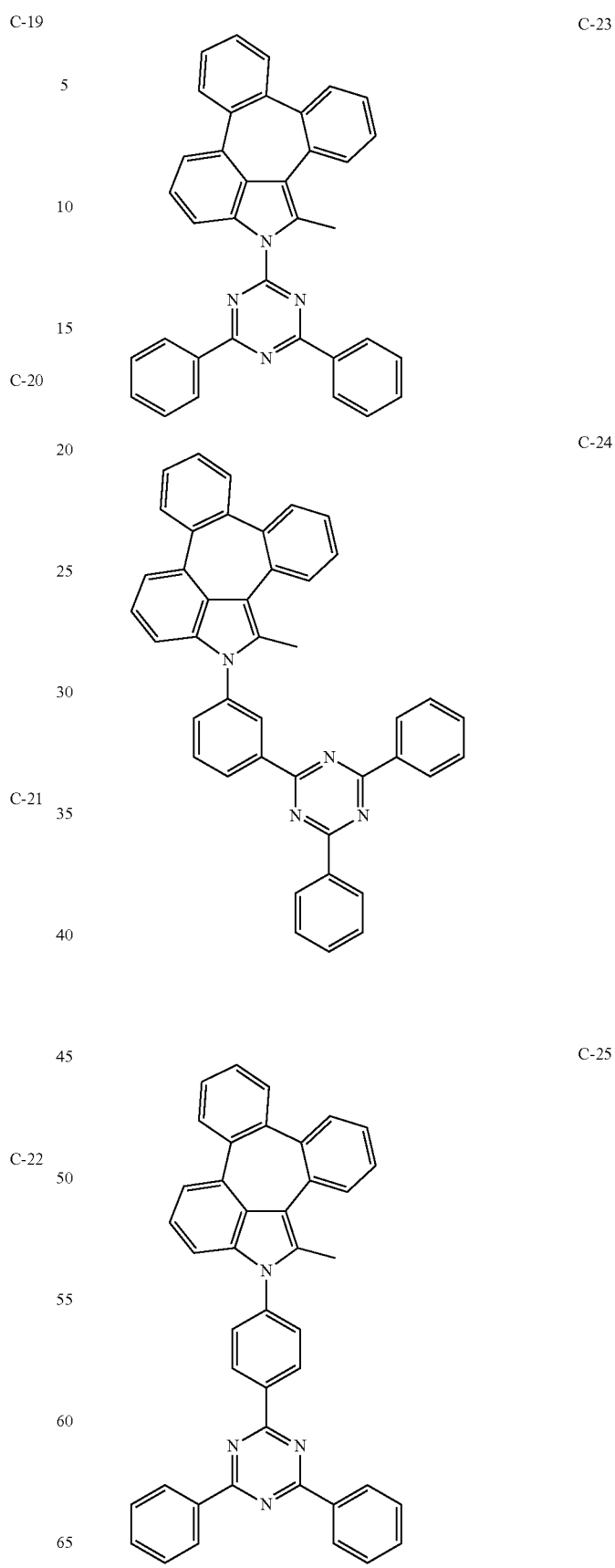

C-26
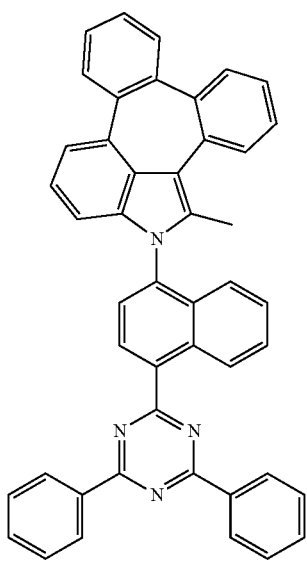
C-27
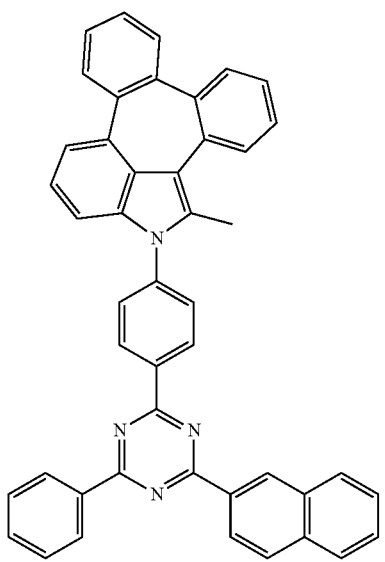
C-28
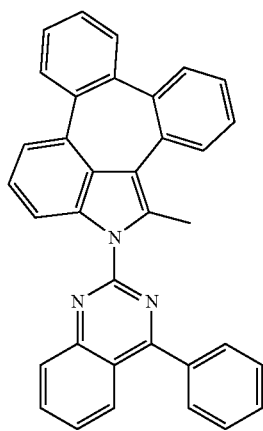
C-29
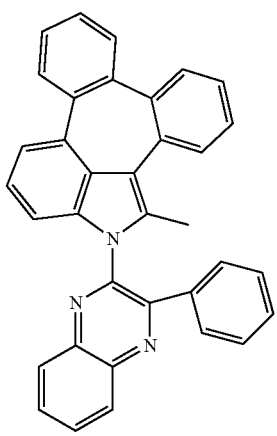
C-30
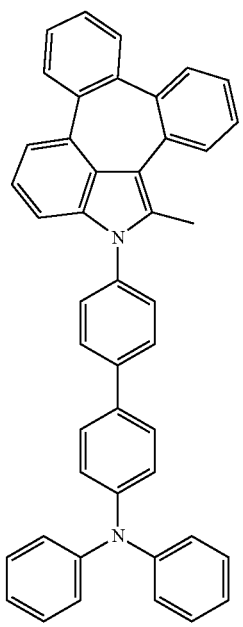

-continued
C-31
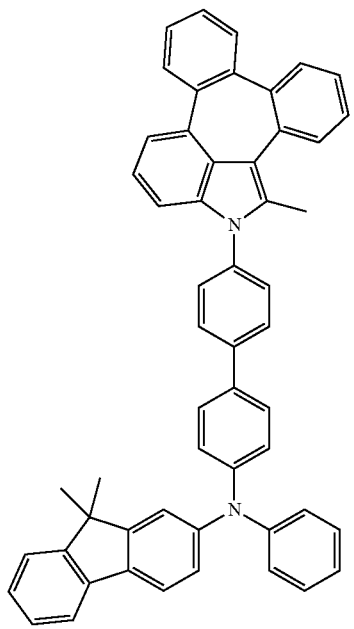
C-32
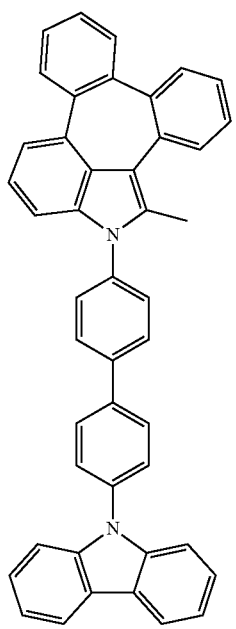
C-33
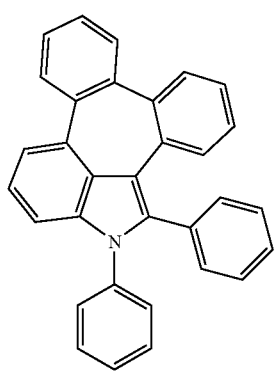
C-34
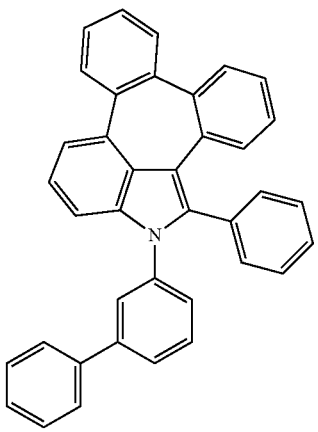
C-35
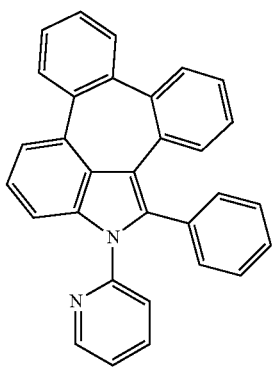
C-36
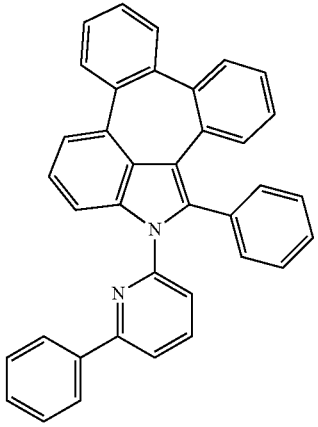
C-37
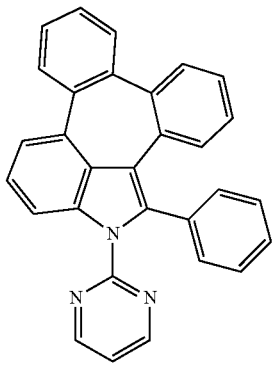

C-38
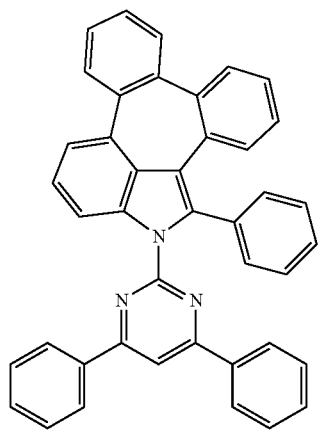
C-39
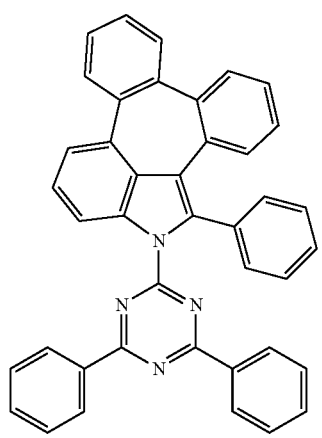
C-40
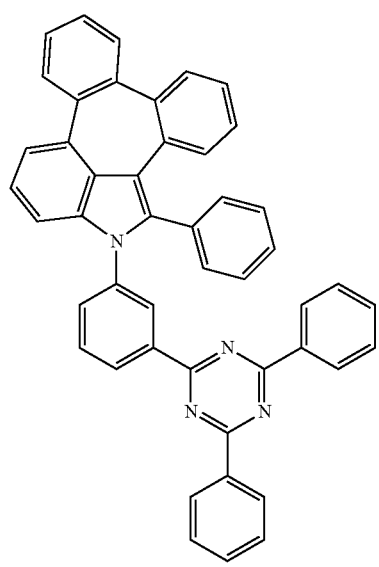
C-41
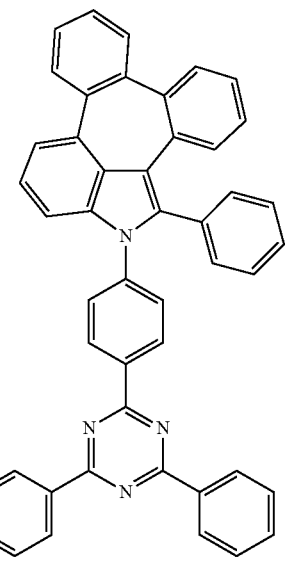
C-42
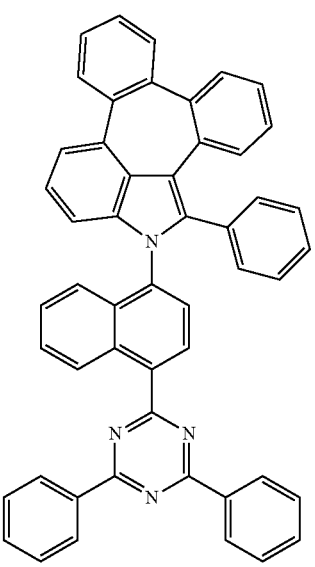
C-43
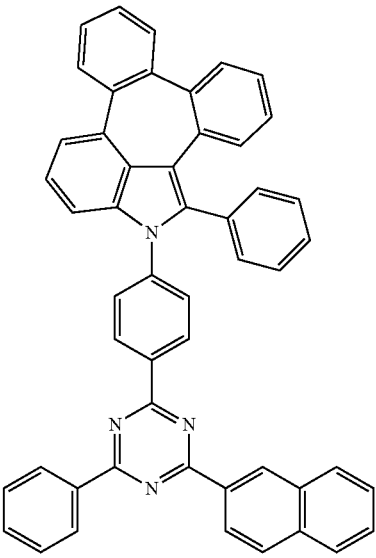

C-44
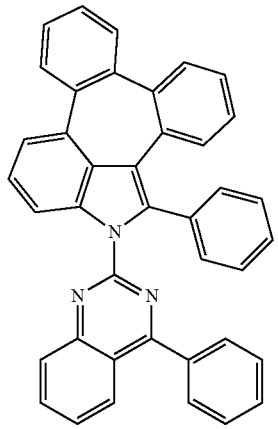
C-45
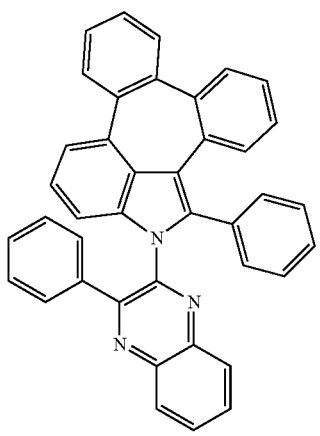
C-46
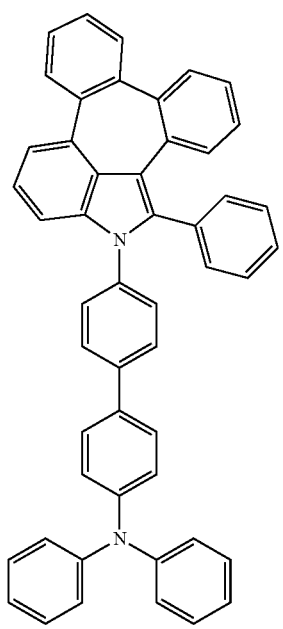
C-47
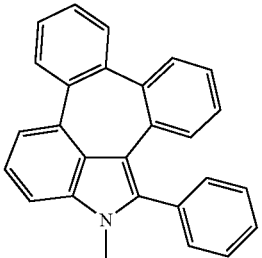
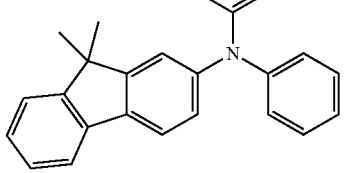
C-48
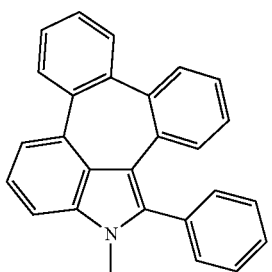
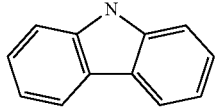
C-49
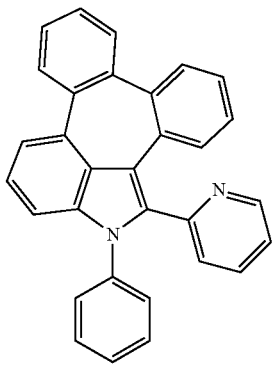

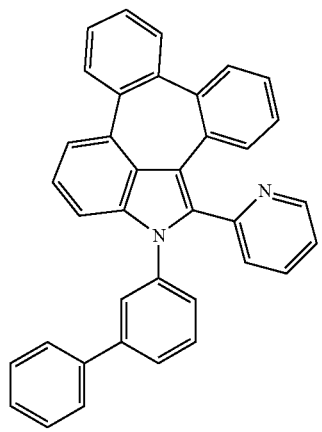
C-50
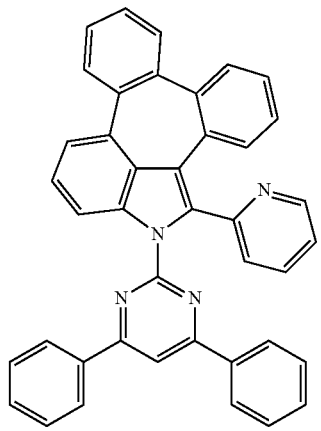
C-54
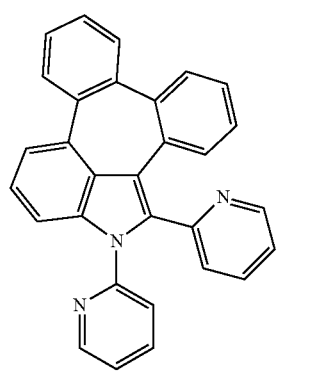
C-51
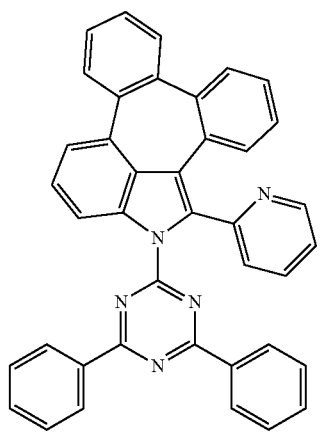
C-55
C-52
C-56
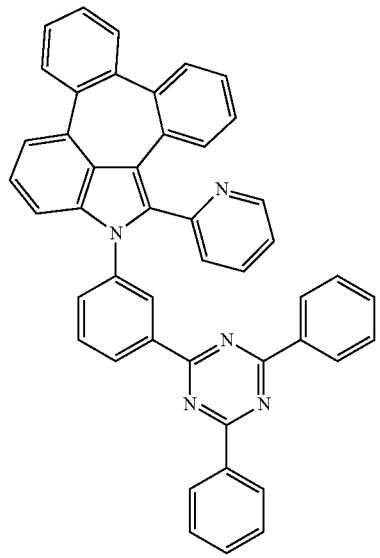
C-53

-continued
C-57
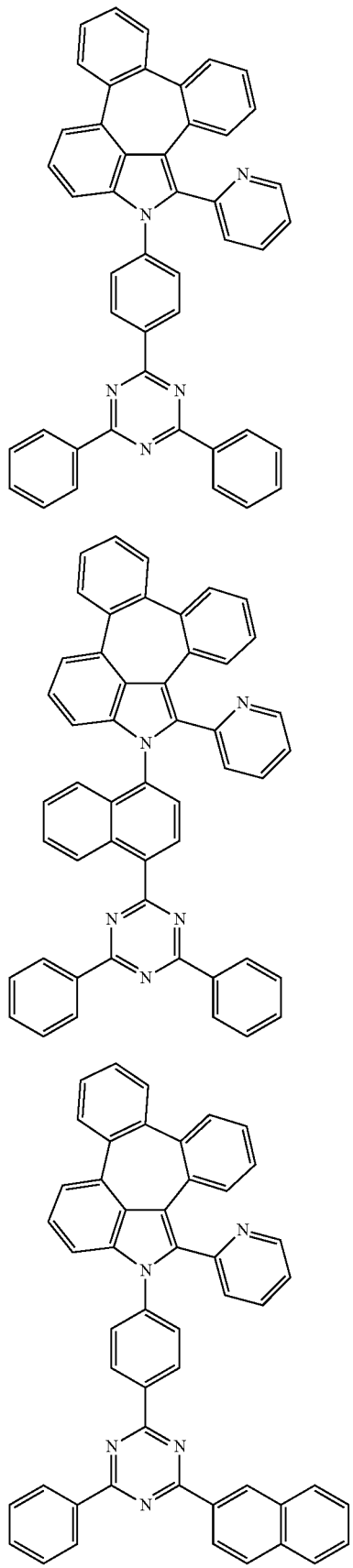
C-58
C-59
C-60
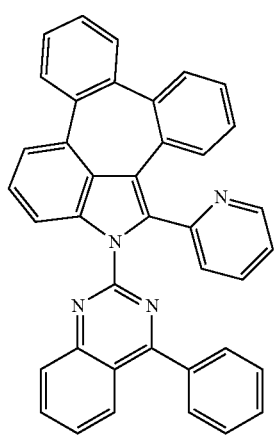
C-61
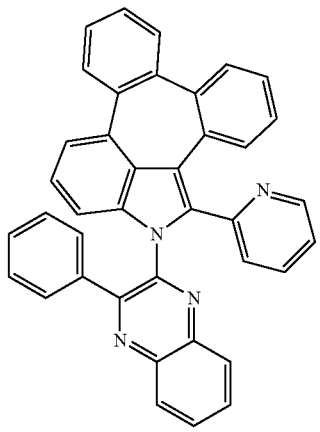
C-62
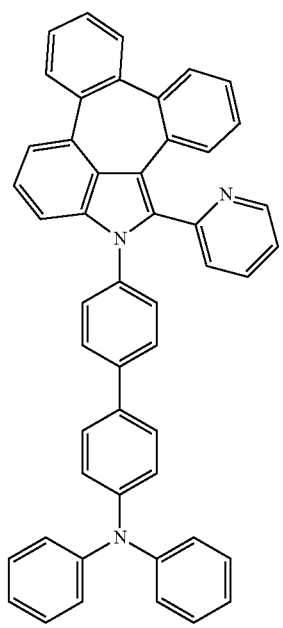

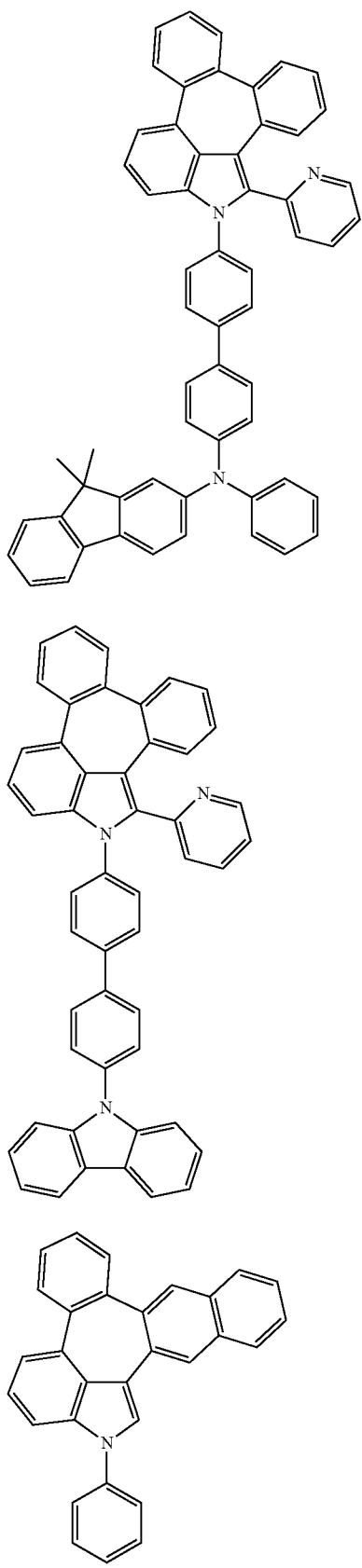
C-63
C-64
C-65
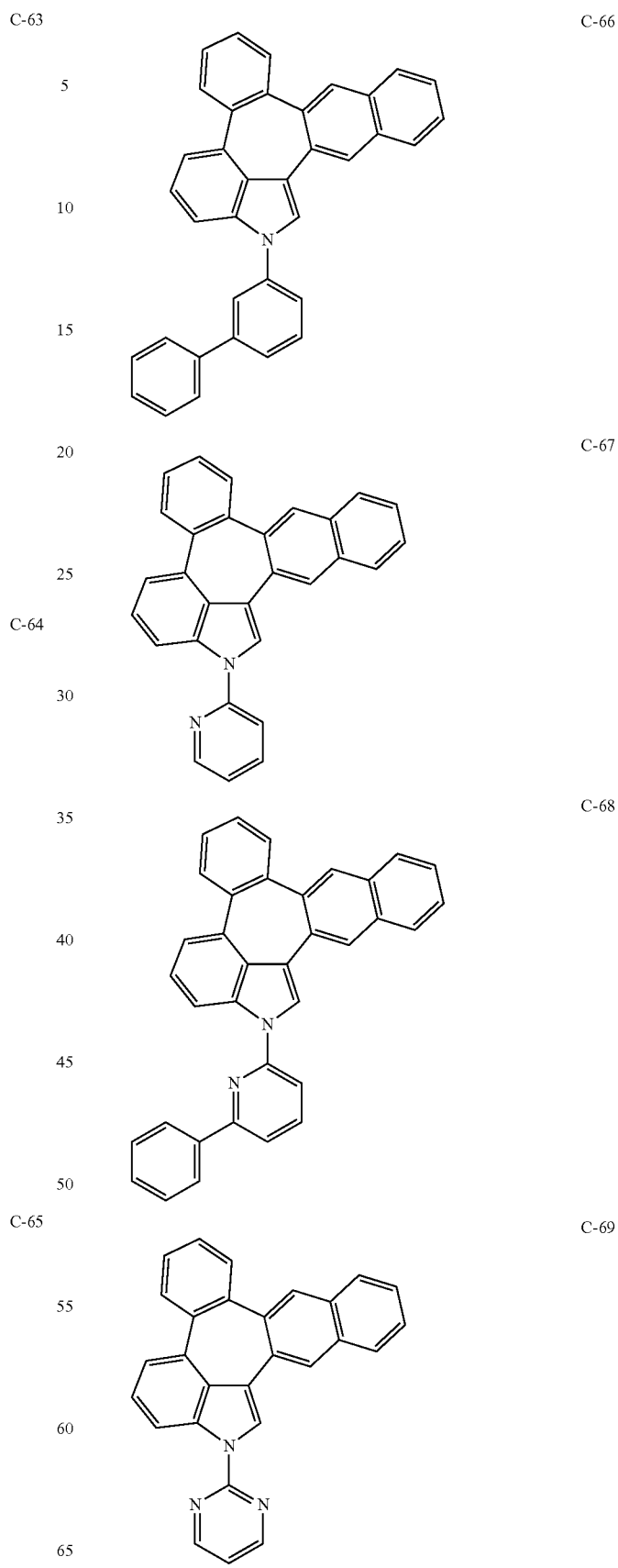
C-66
C-67
C-68
C-69

C-70
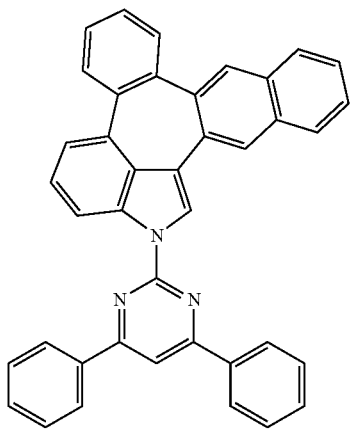
C-71
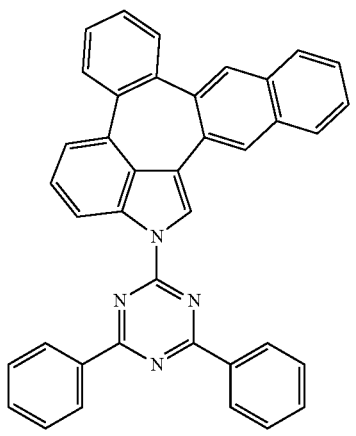
C-72
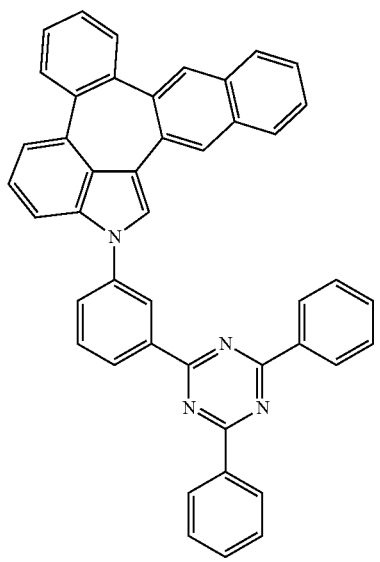
C-73
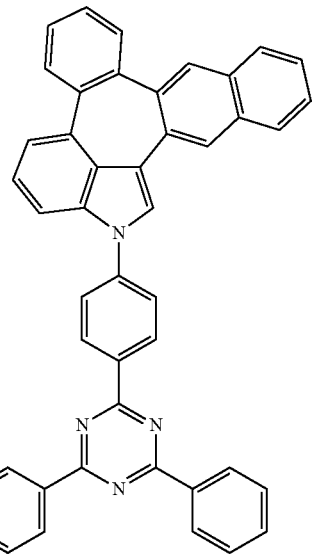
C-74
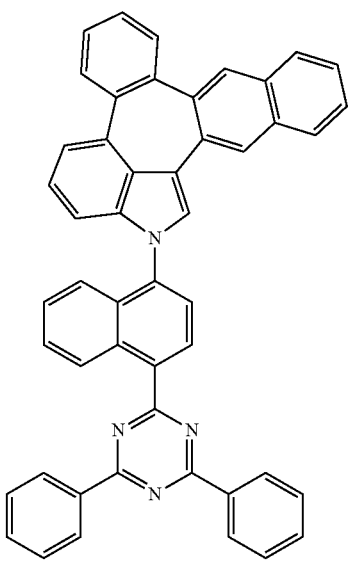
C-75
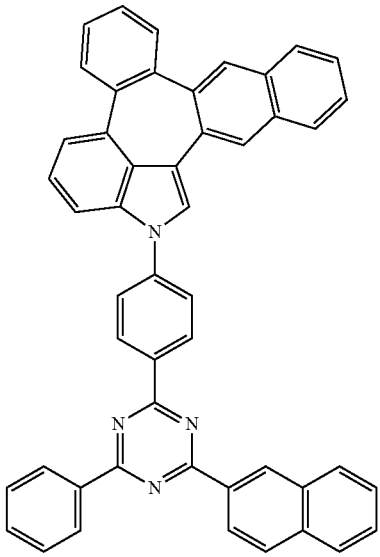

C-76
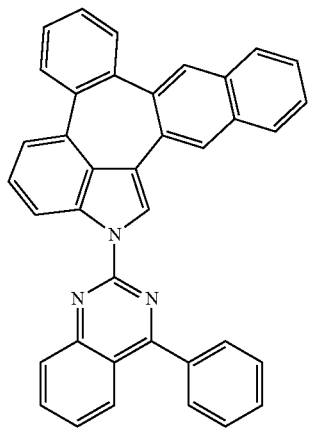
C-77
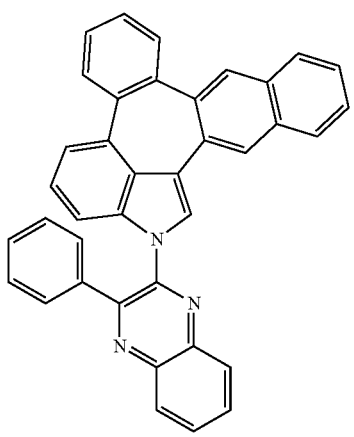
C-78
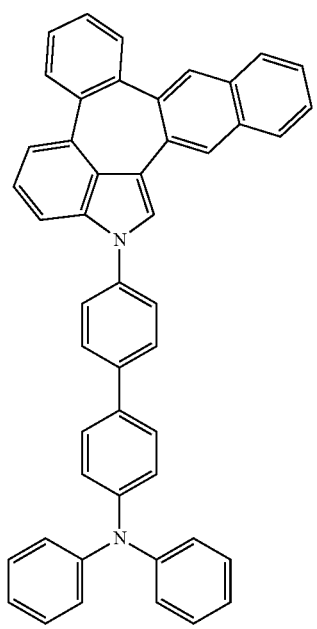
C-79
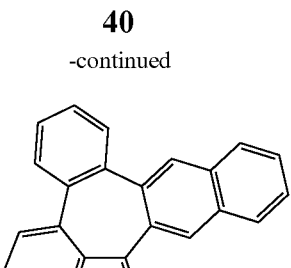
C-80
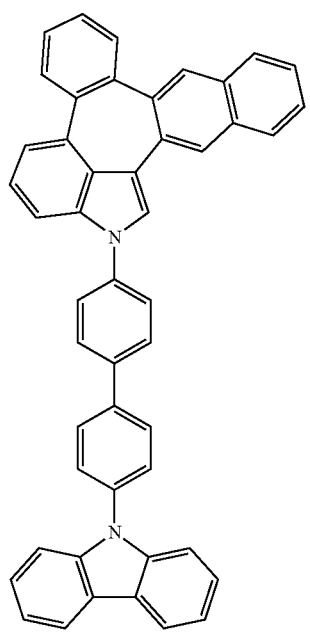
C-81
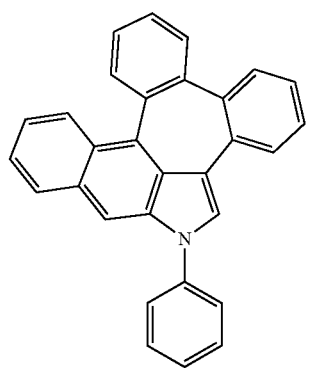

C-82
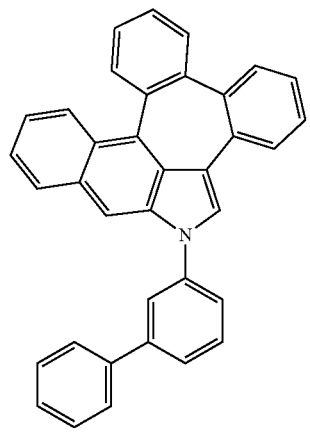
C-83
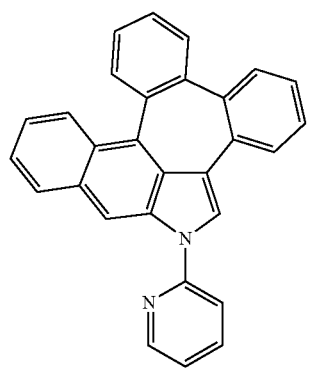
C-84
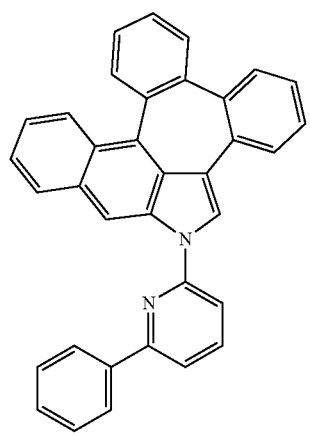
C-85
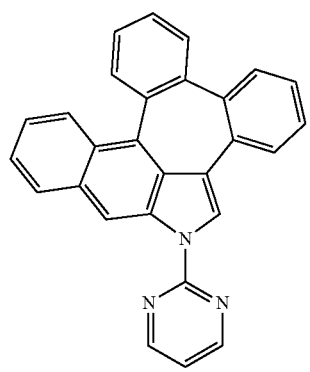
C-86
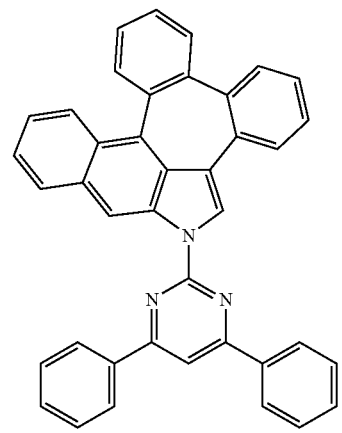
C-87
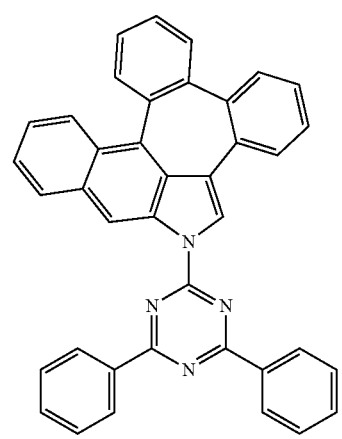
C-88
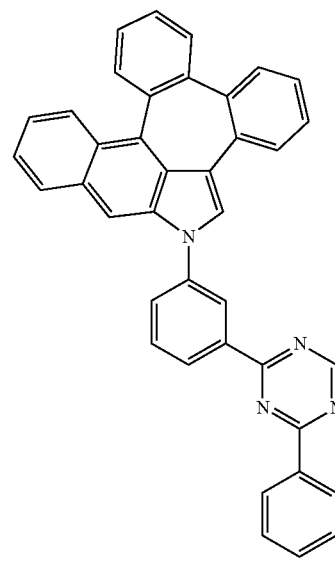

C-89
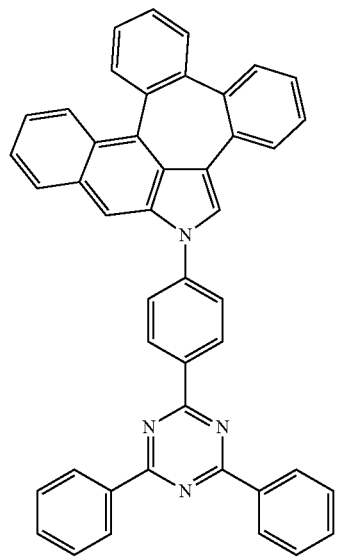
C-90
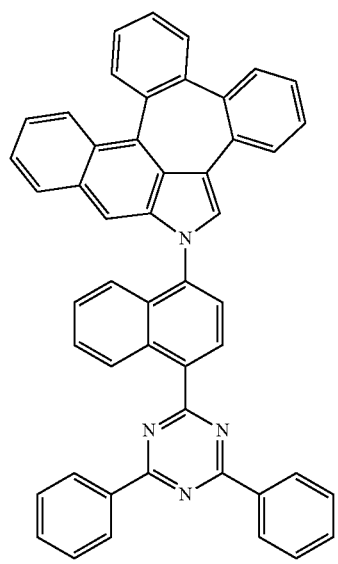
C-91
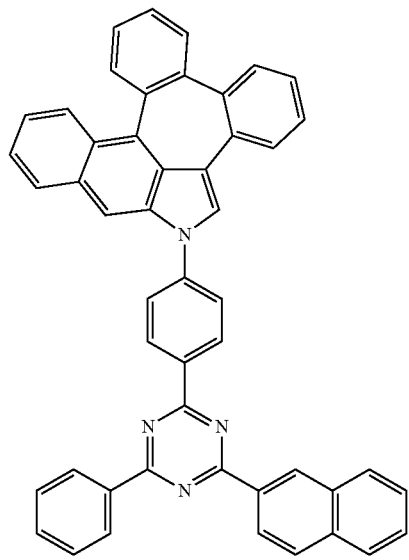
C-92
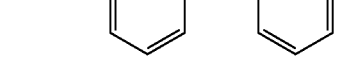
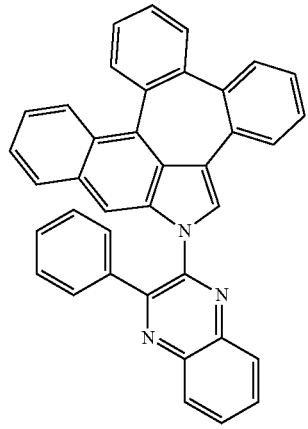
C-93

C-94
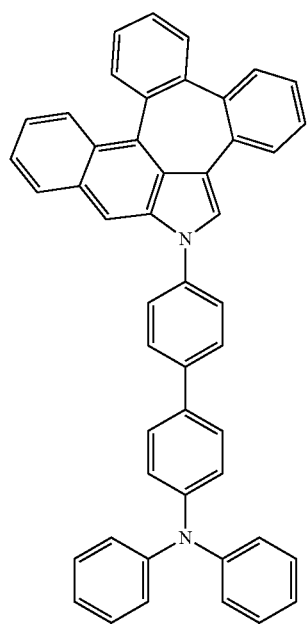
C-95
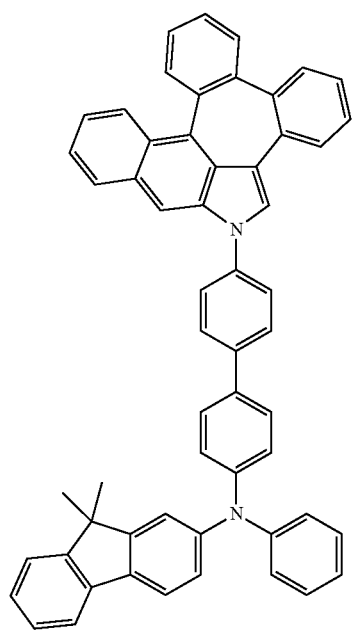
C-96
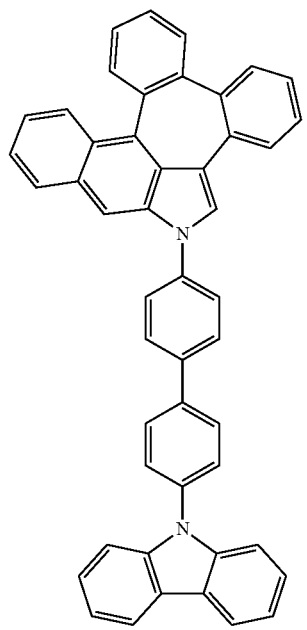
C-97
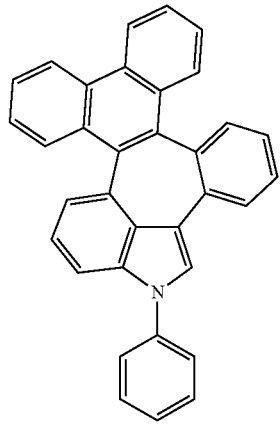
C-98

C-99
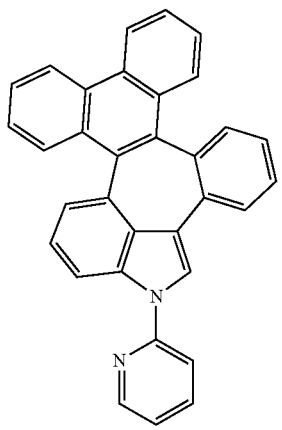
C-100
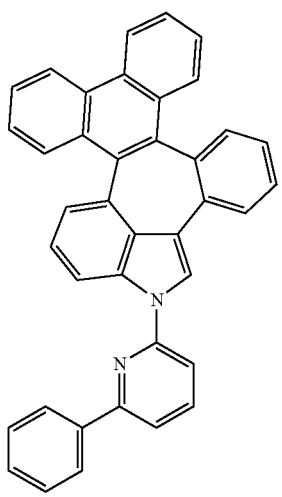
C-101
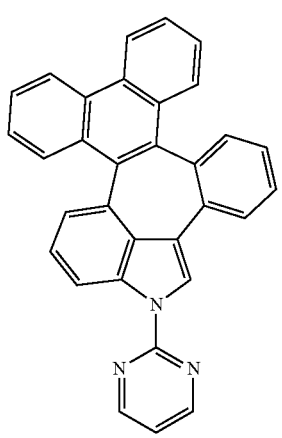
C-102
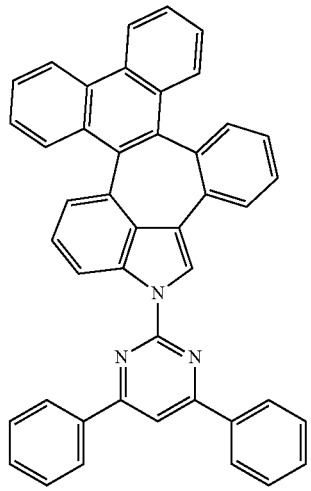
C-103
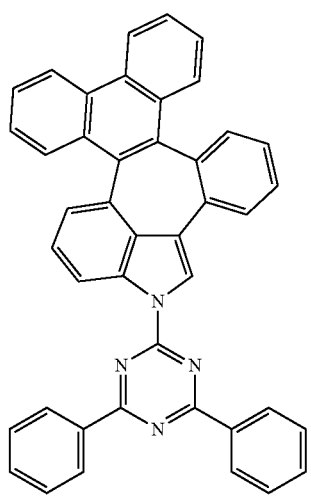
C-104
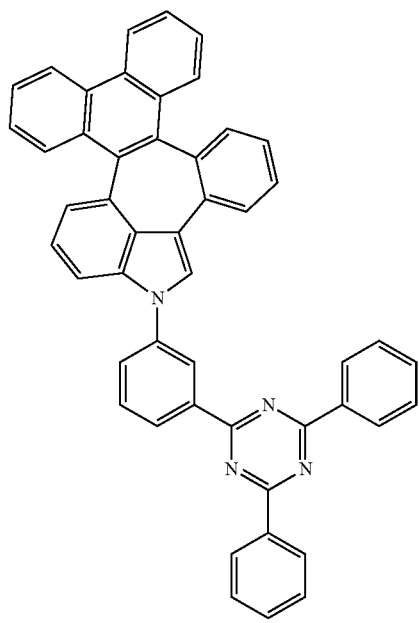

C-105
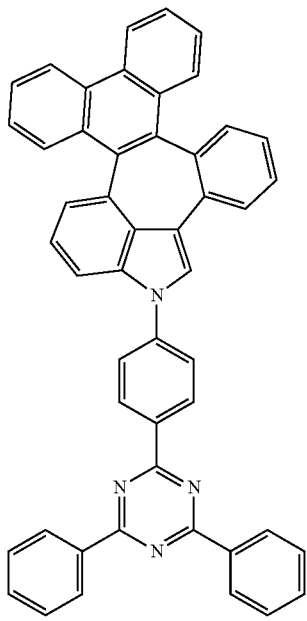
C-106
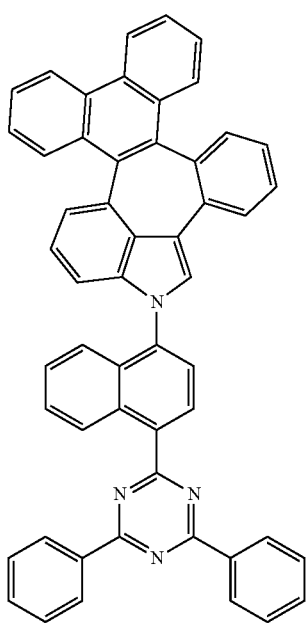
C-107
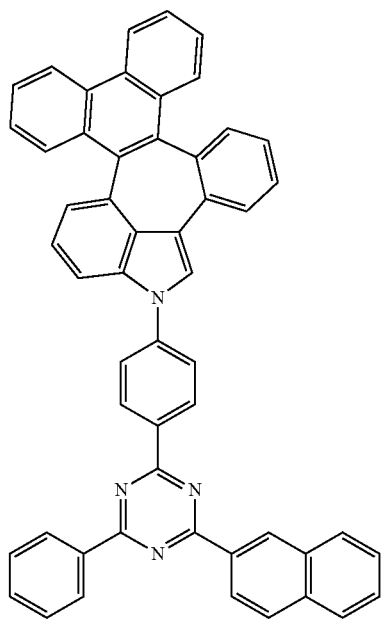
C-108
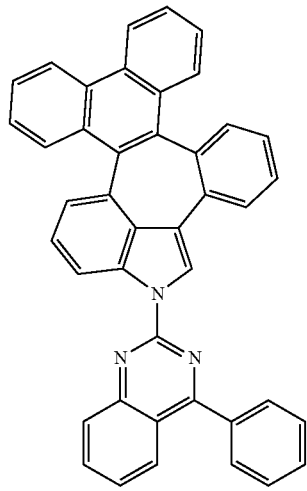
C-109
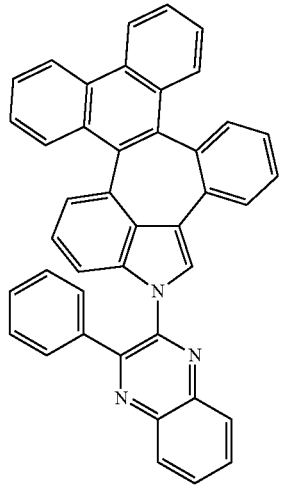

C-110
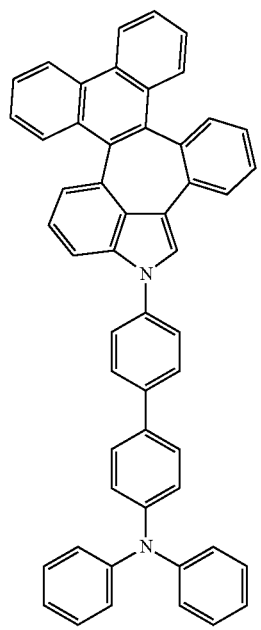
C-111
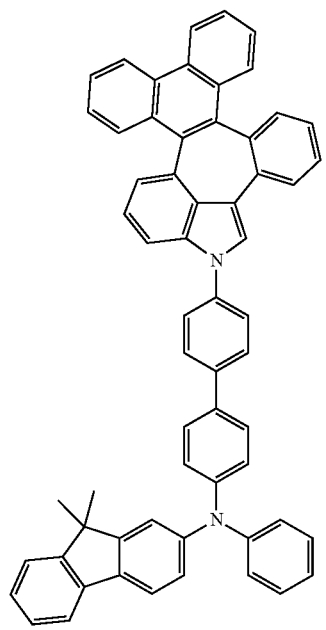
C-112
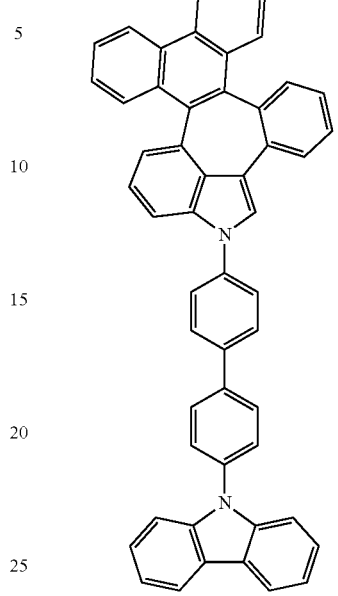
C-113
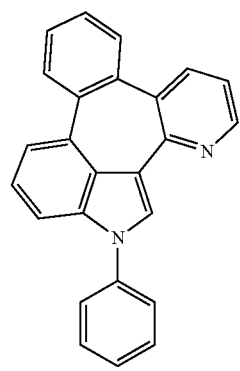
C-114
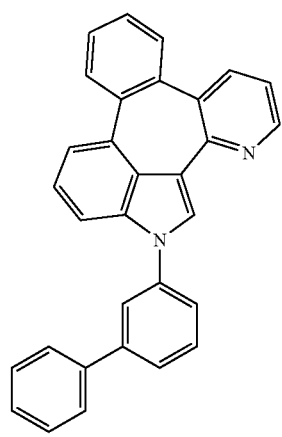

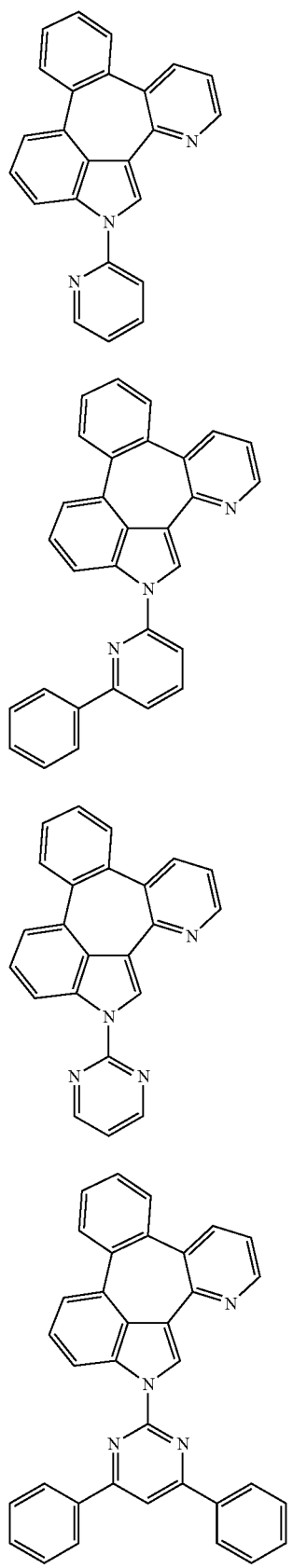
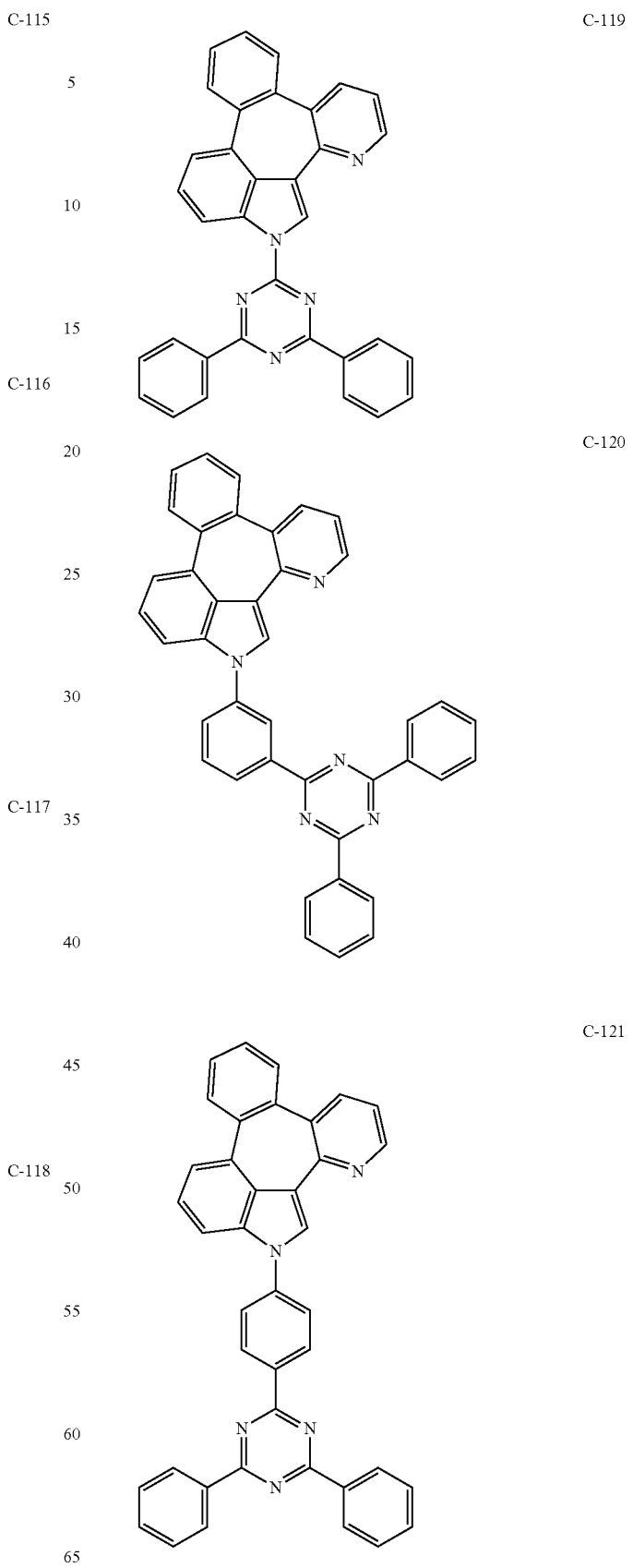

C-122
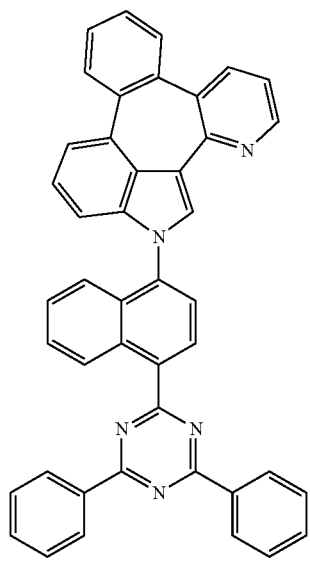
C-123
C-124
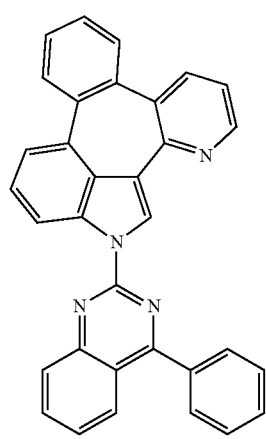
C-125
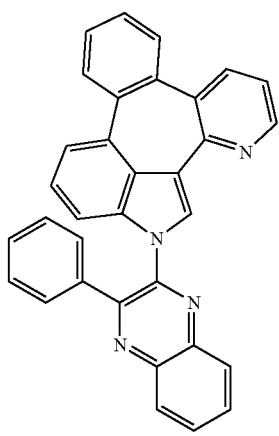
C-126
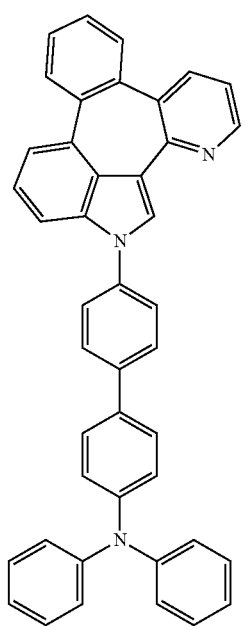

C-127
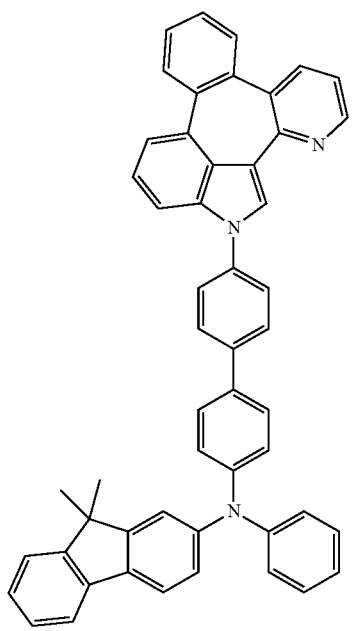
C-129
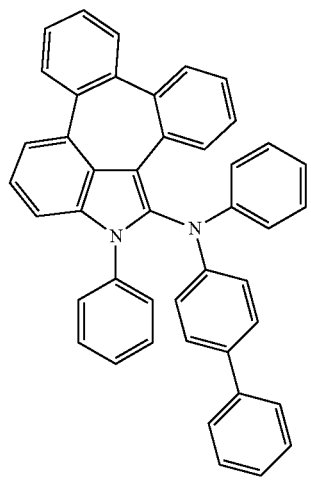
C-130
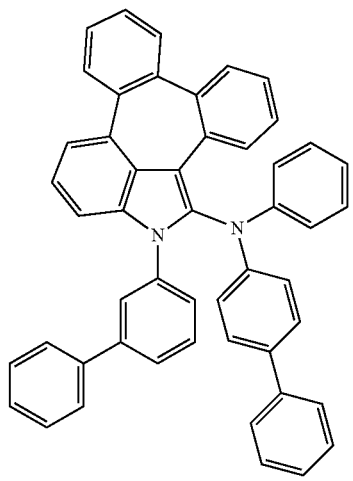
C-128
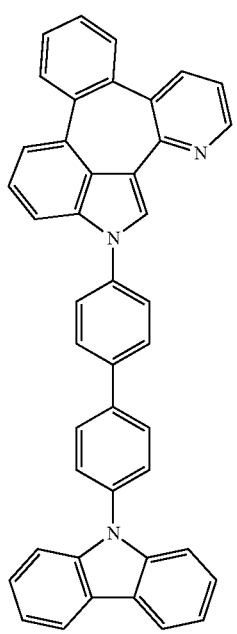
C-131
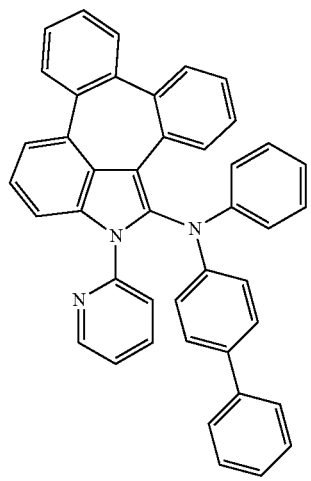

C-132
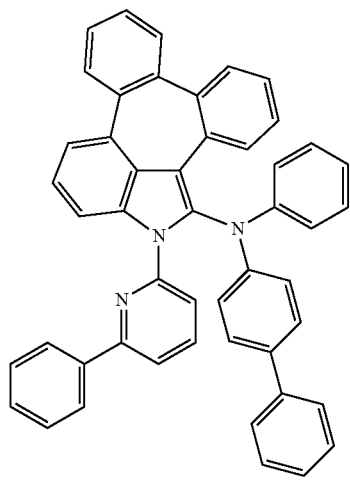
C-135
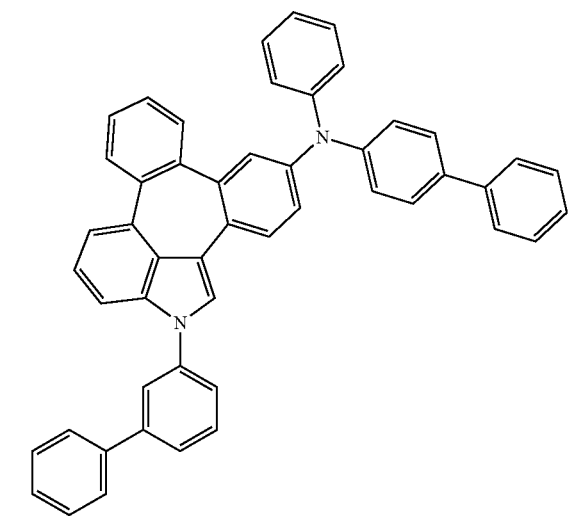
C-133
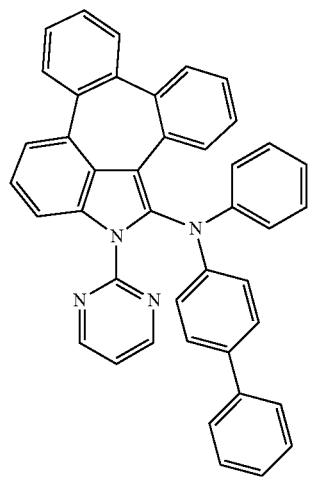
C-136
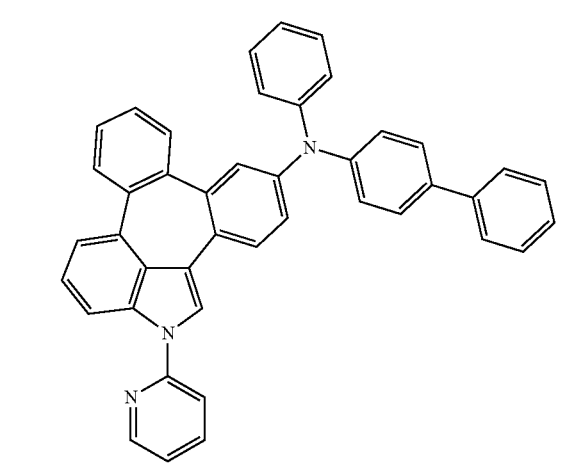
C-134
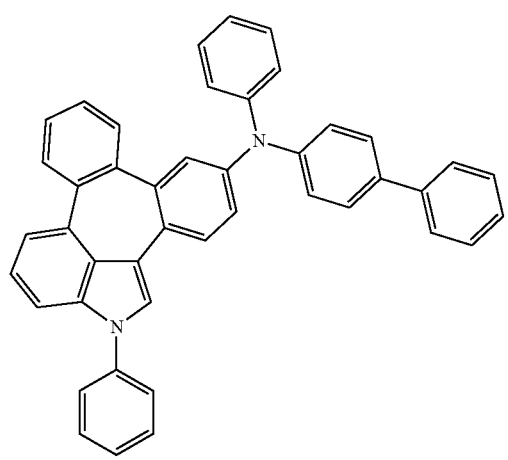
C-137
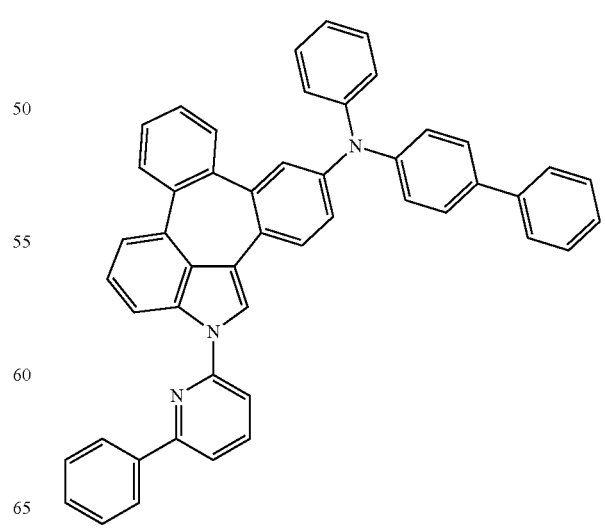

C-138
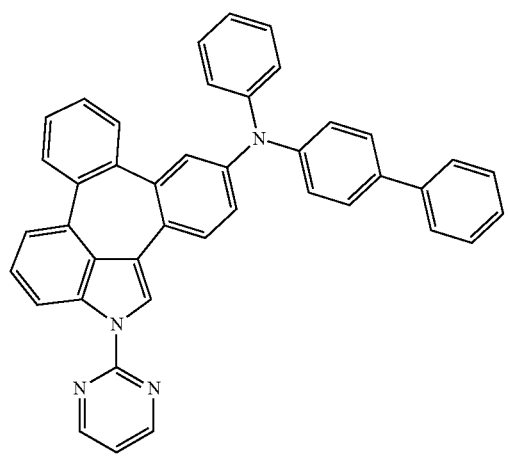
C-139
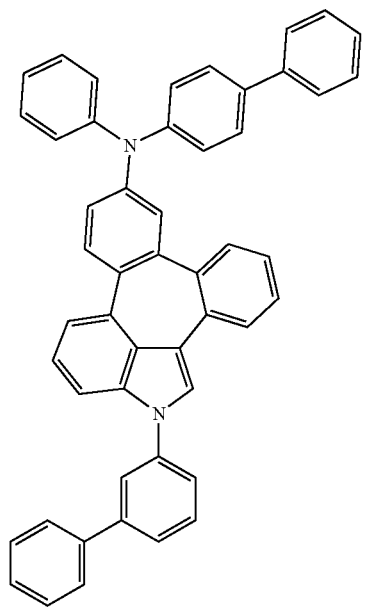
C-140
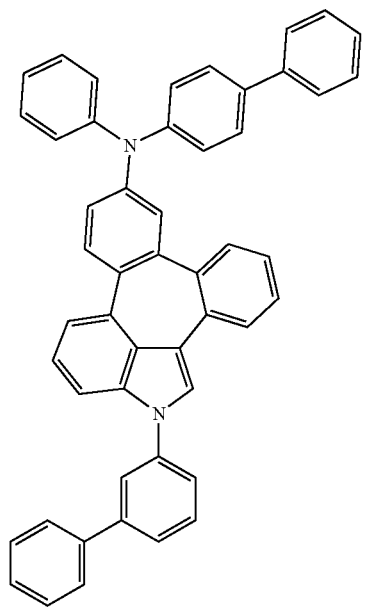
C-141
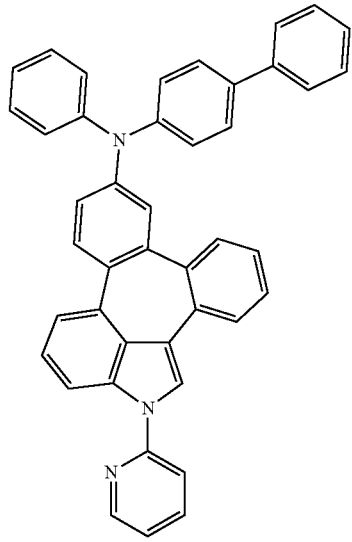
C-142
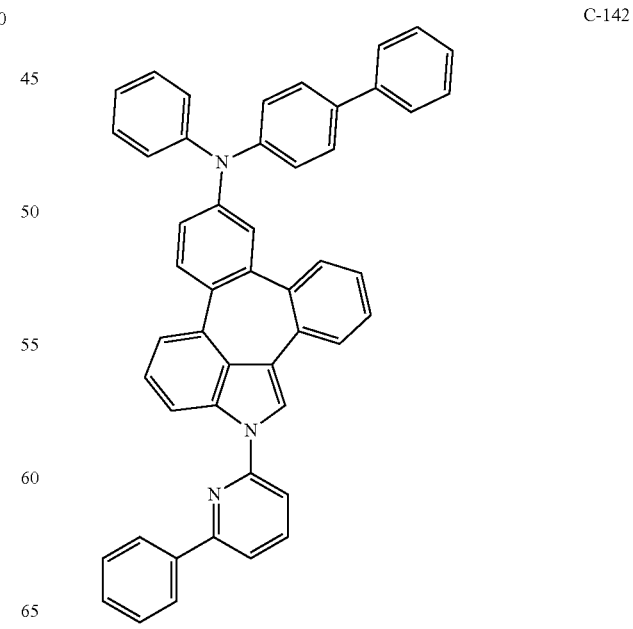

-continued
C-143
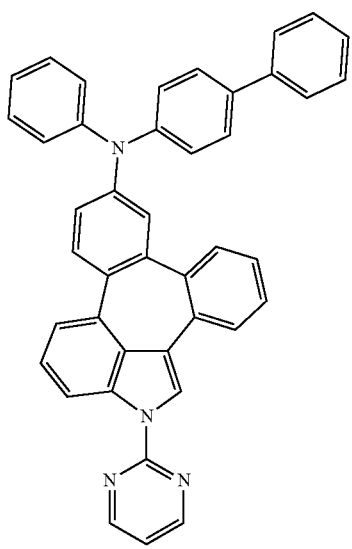
C-144
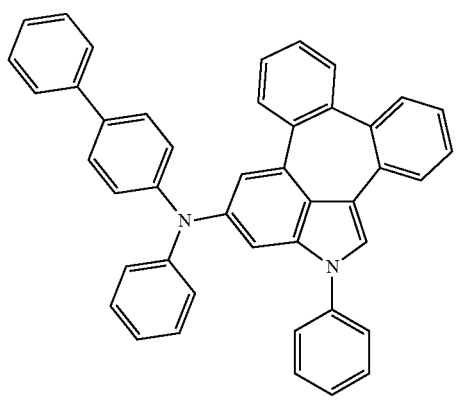
C-145
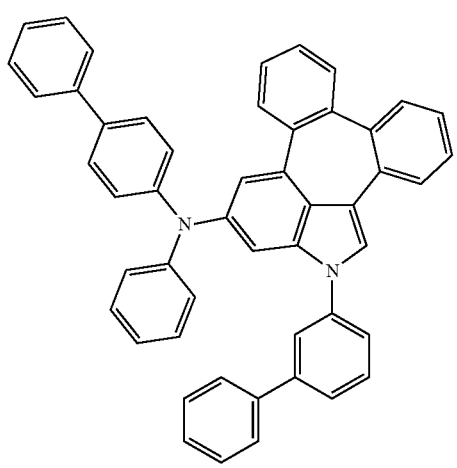
-continued
C-146
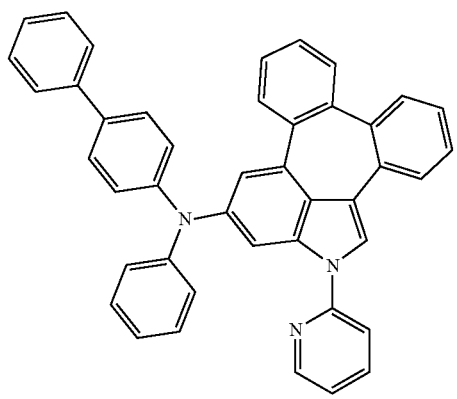
C-147
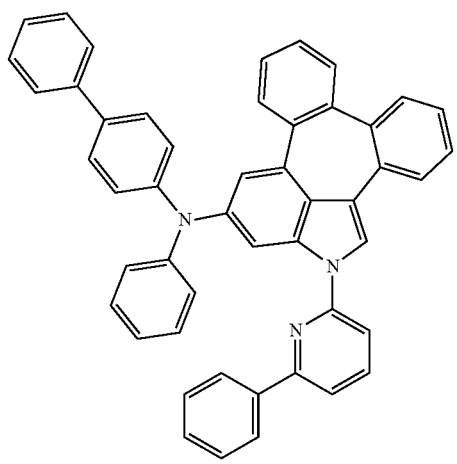
C-148
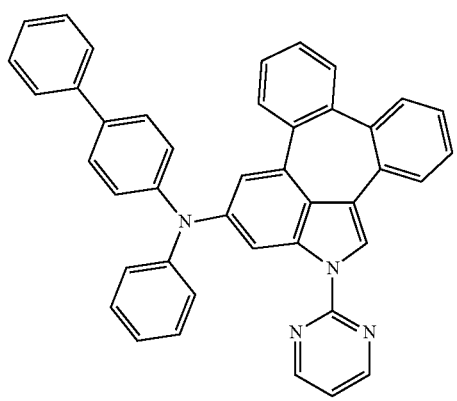
C-149
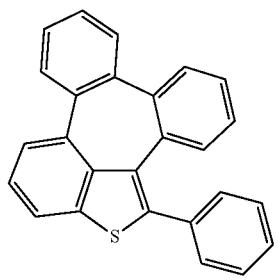

C-150
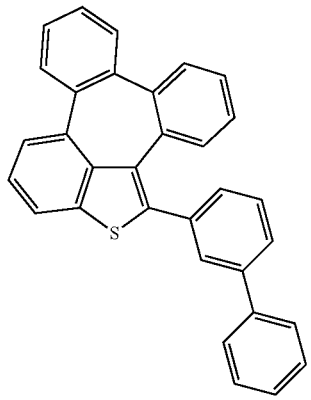
C-151
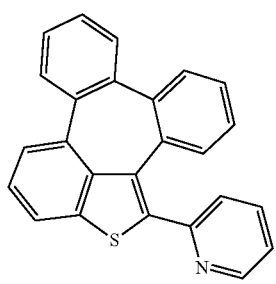
C-152
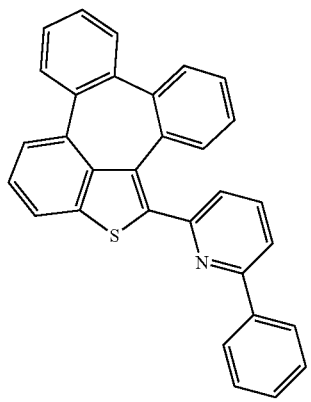
C-153
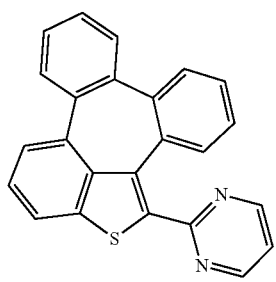
C-154
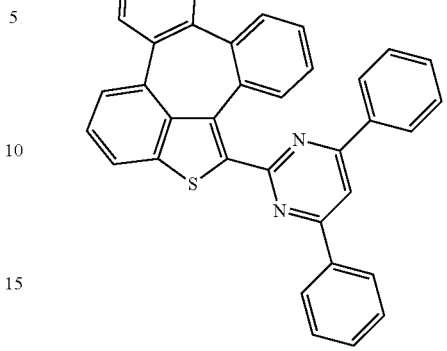
C-155
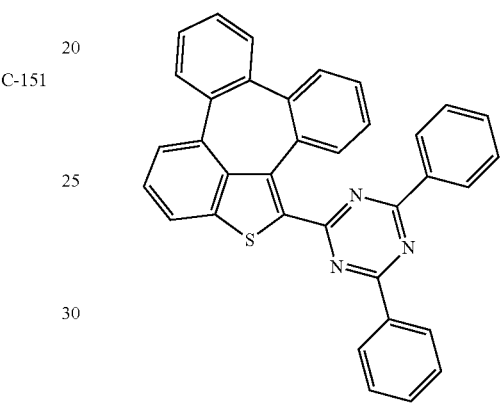
C-156
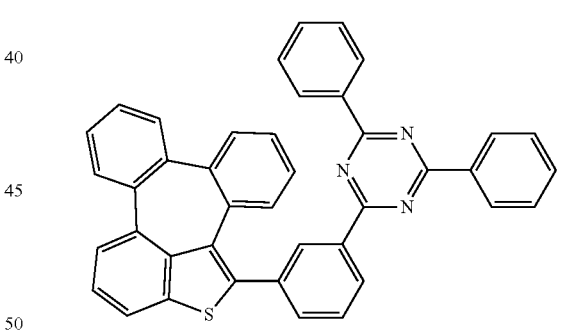
C-157
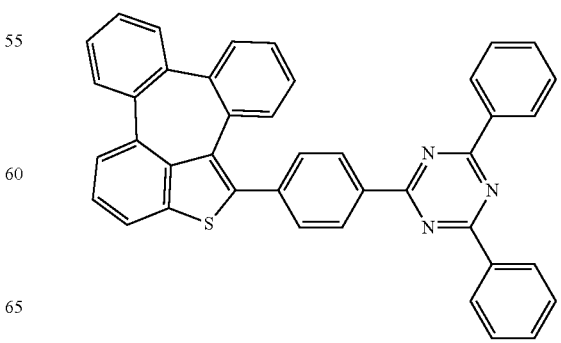

C-158
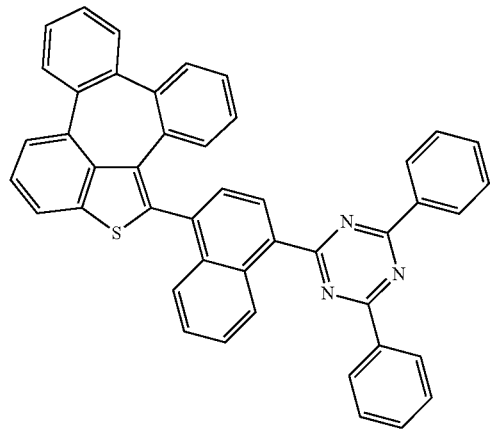
C-159
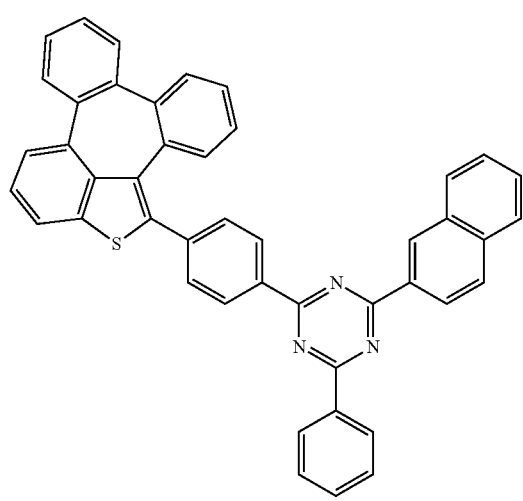
C-160
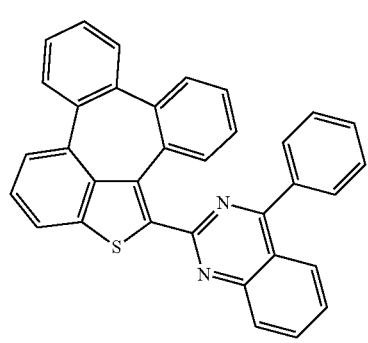
C-161
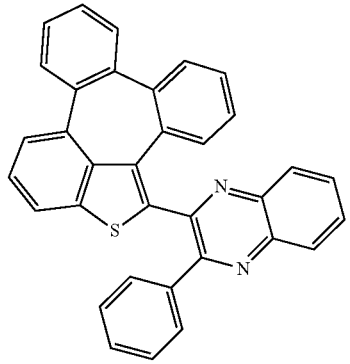
C-162
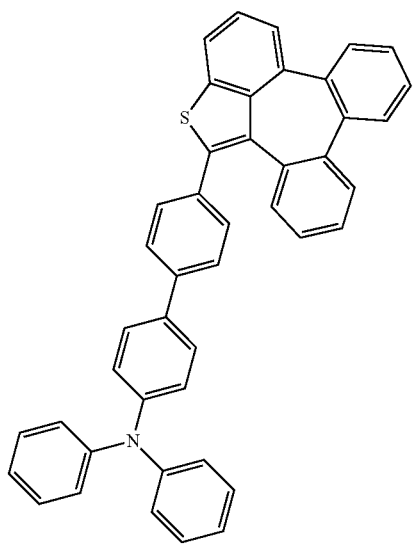
C-163
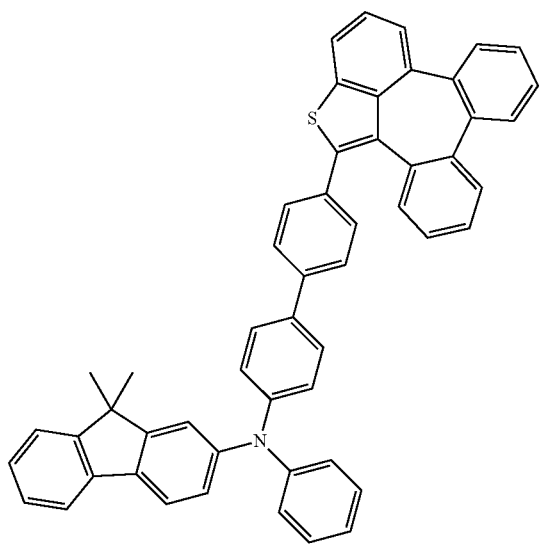

C-164
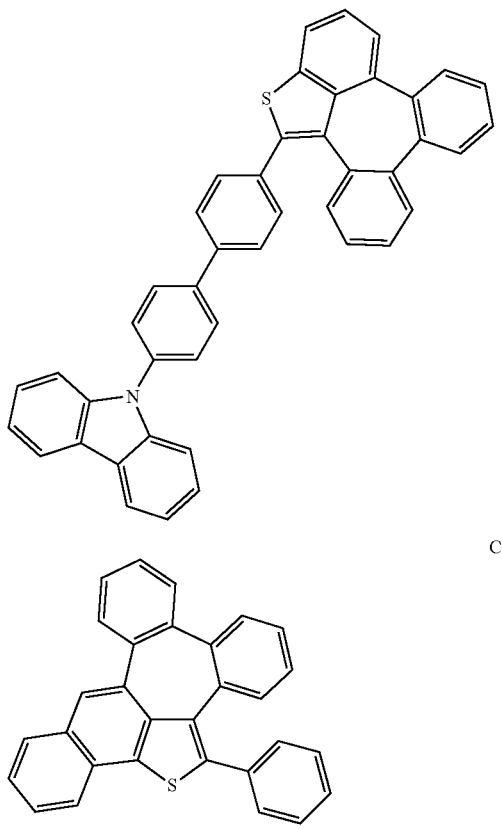
C-165
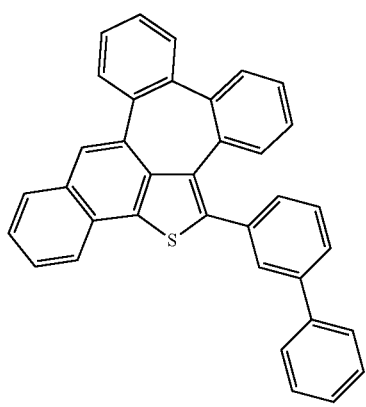
C-166
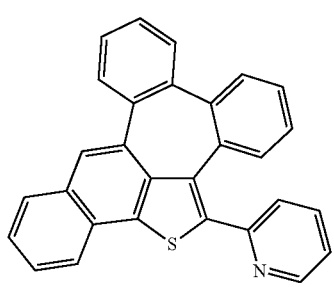
C-167
C-168
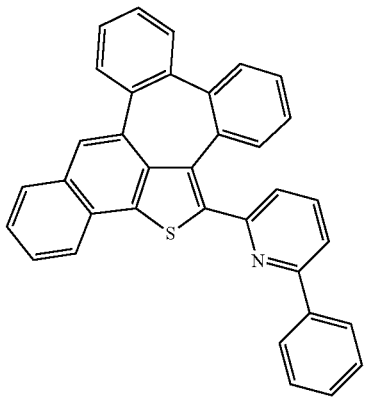
C-169
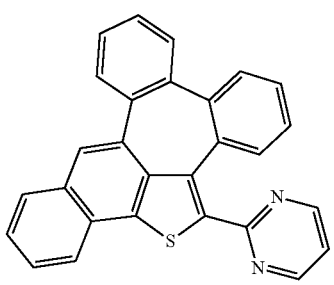
C-170
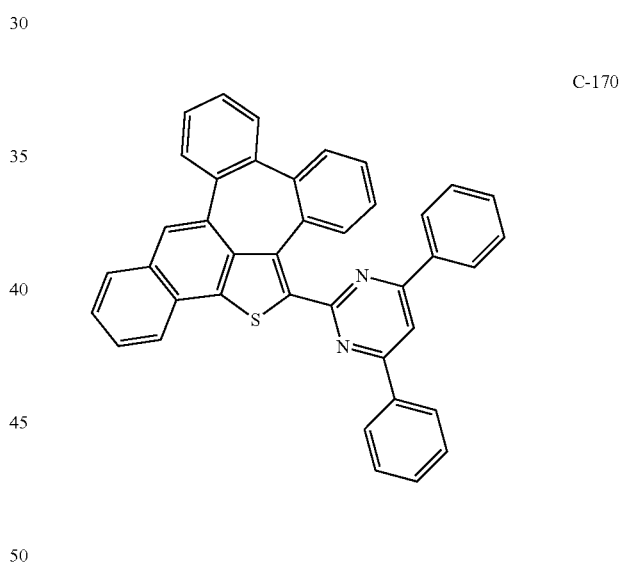
C-171
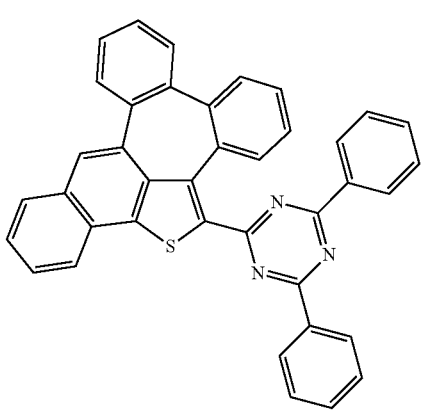

-continued
C-172
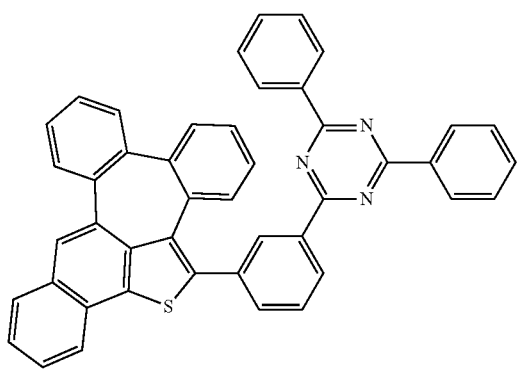
C-173
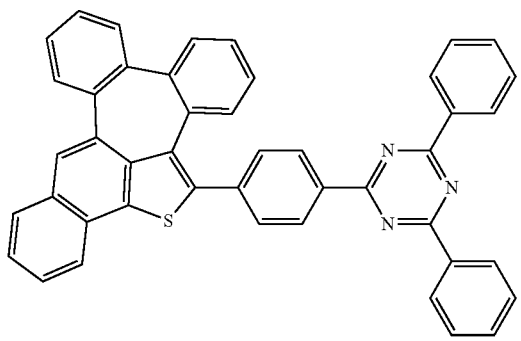
C-174
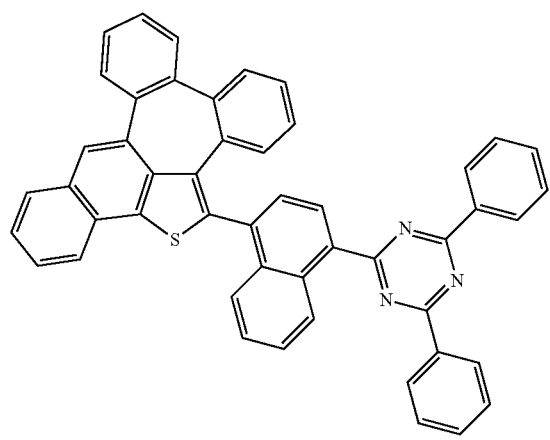
-continued
C-175
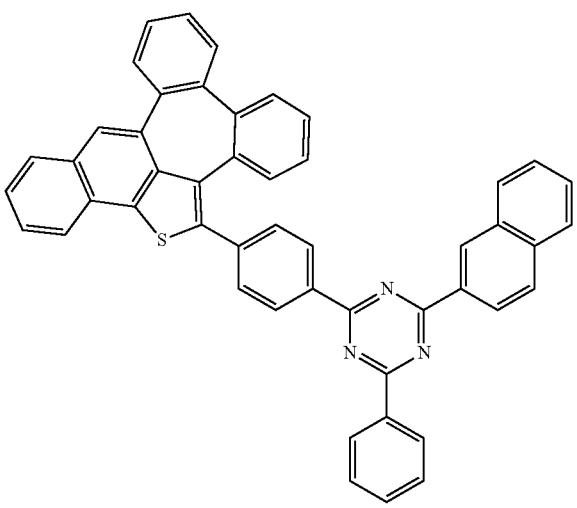
C-176
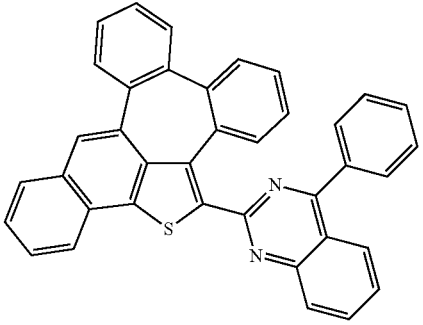
C-177
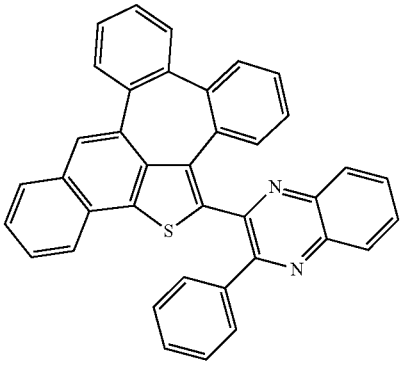

C-178
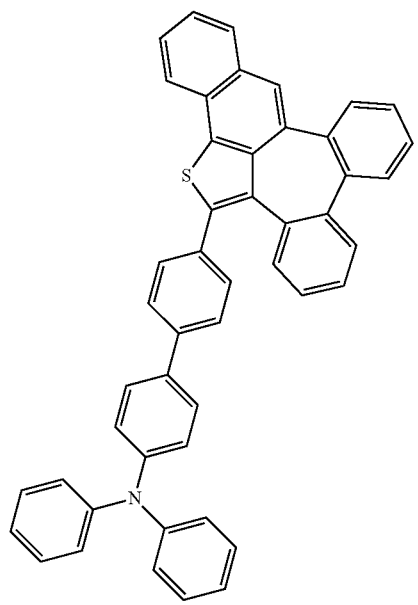
C-179
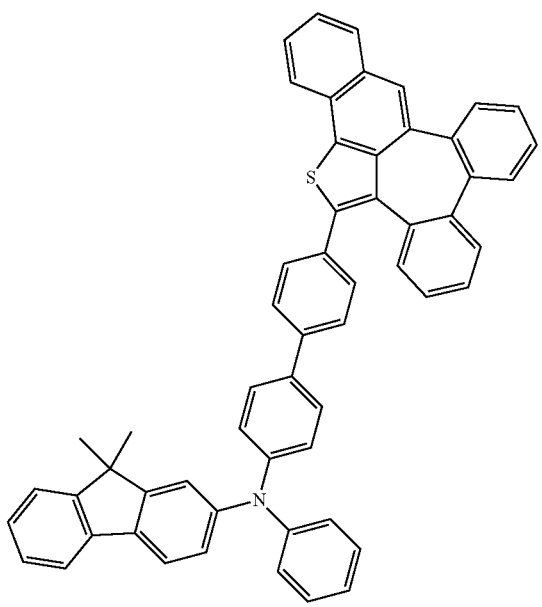
C-180
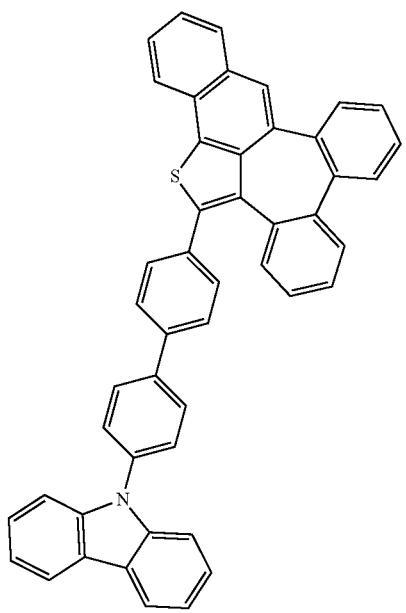
C-181
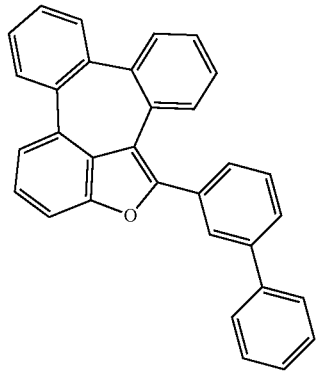
C-182
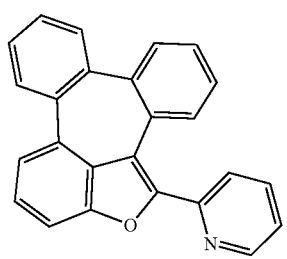
C-183

-continued
C-184
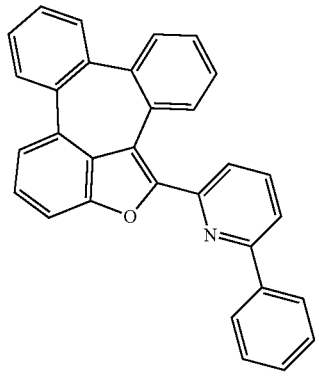
C-185
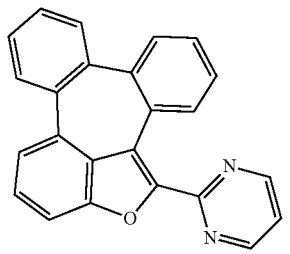
C-186
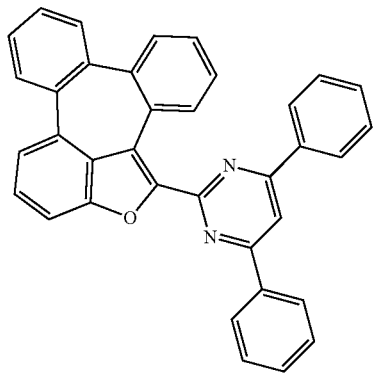
C-187
-continued
C-188
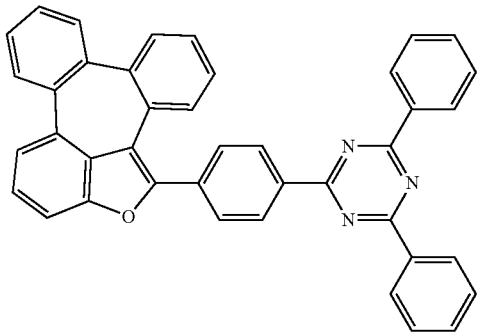
C-189
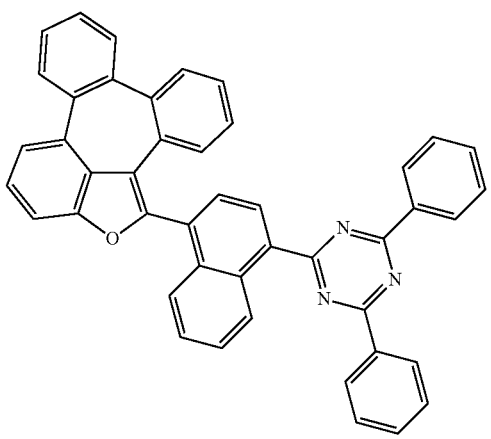
C-190
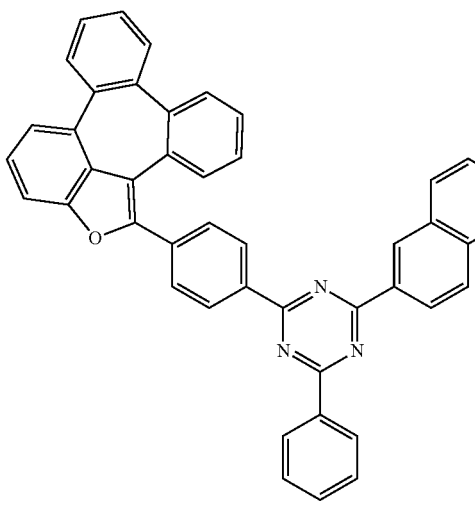

C-191 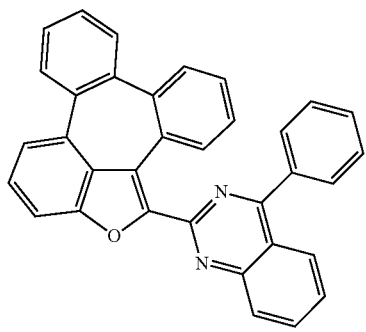
C-192 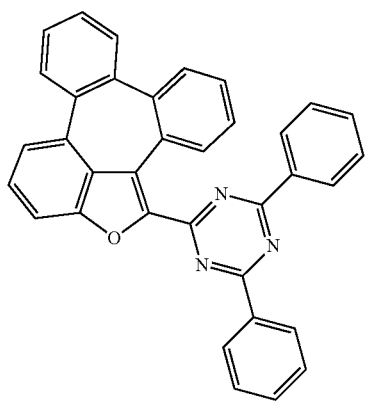
C-193 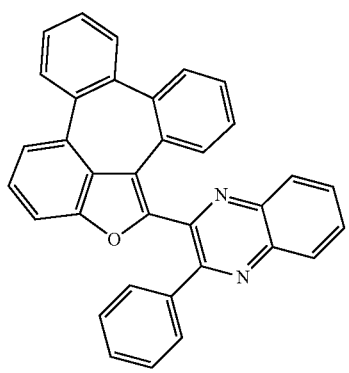
C-194
C-195 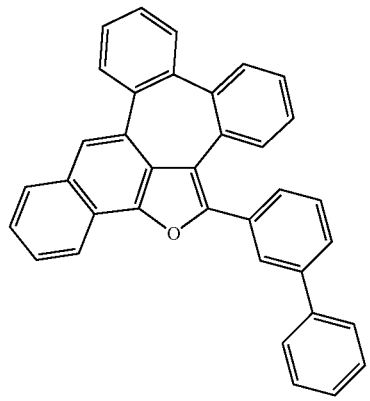
C-196 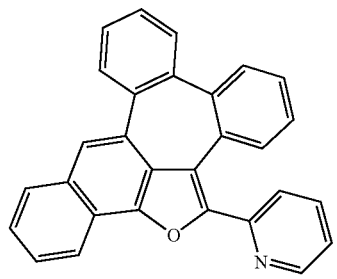
C-197
C-198 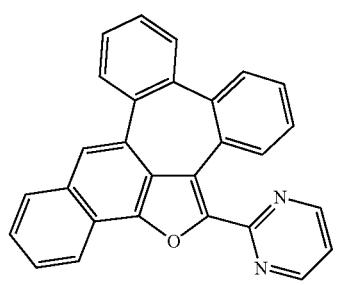

C-199
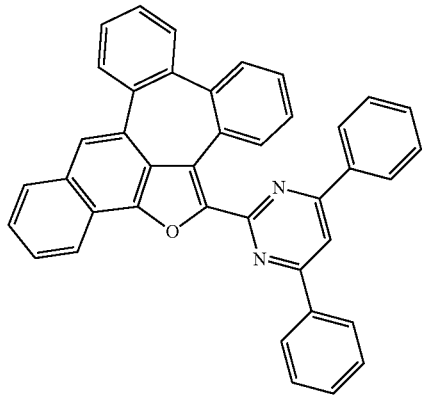
C-200
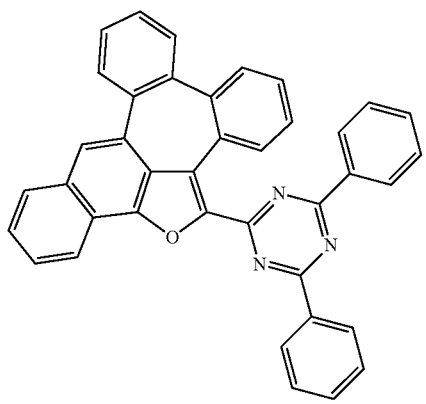
C-201
C-202
C-203
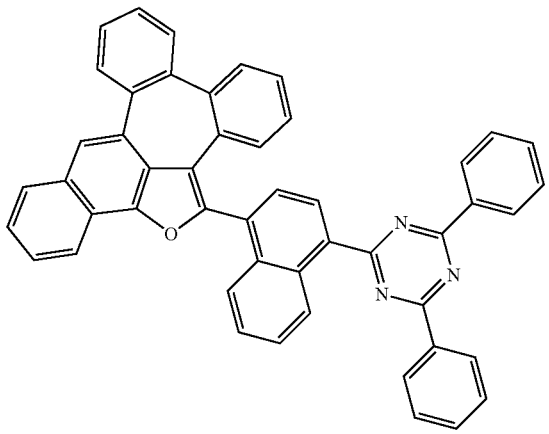
C-204
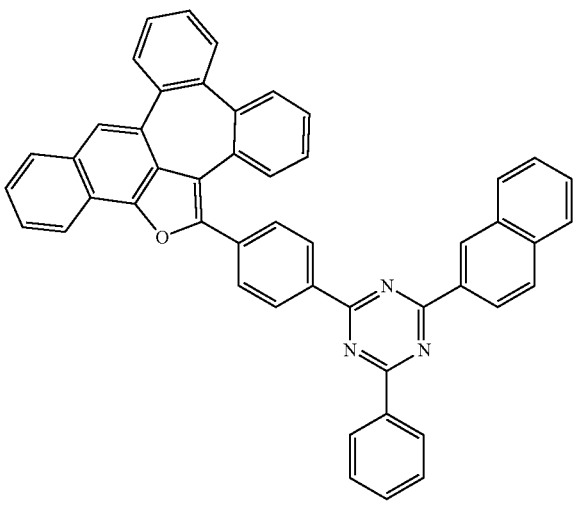
C-205
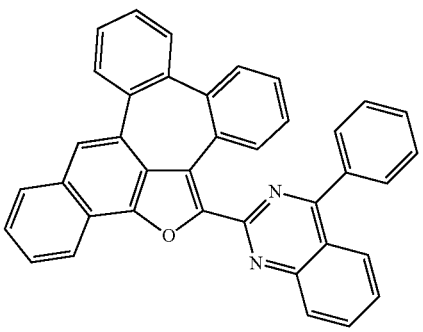

-continued
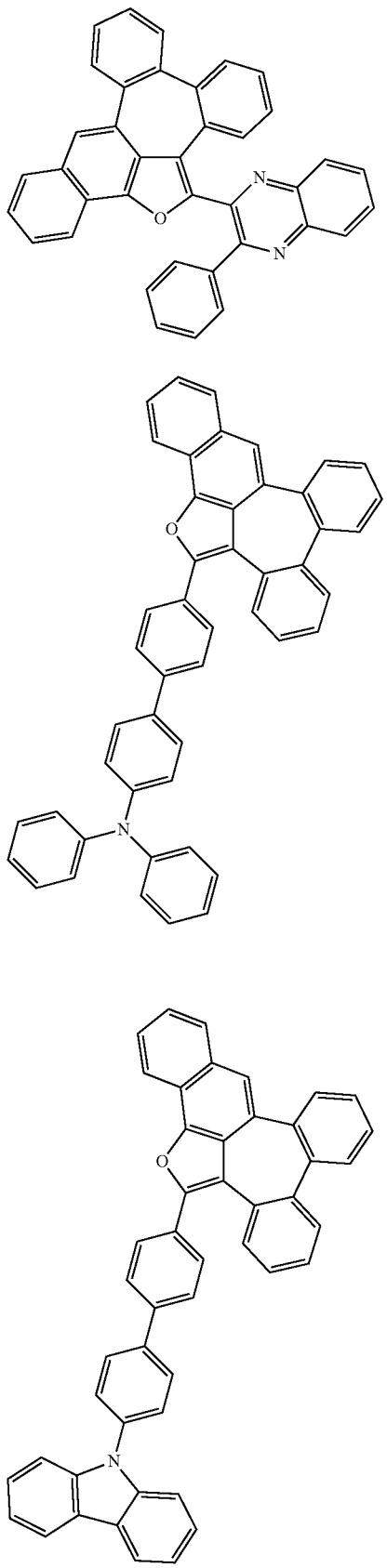
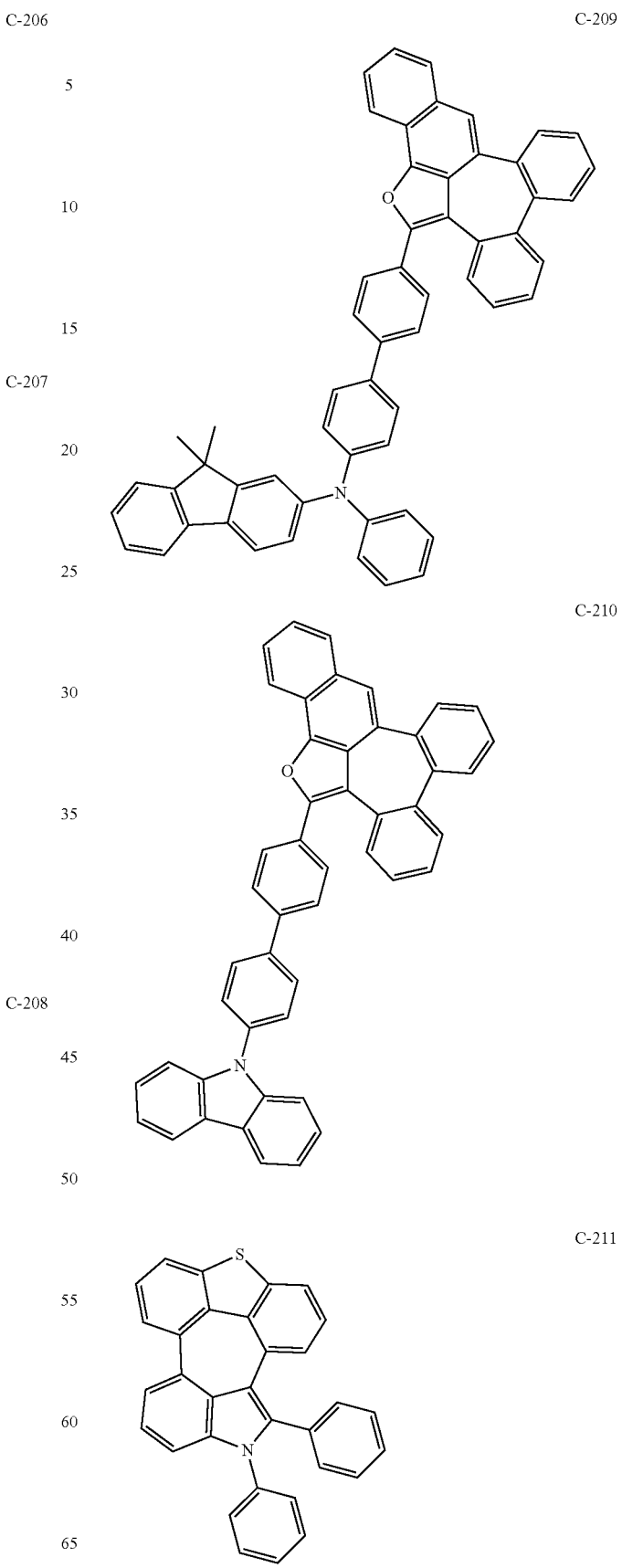

C-212 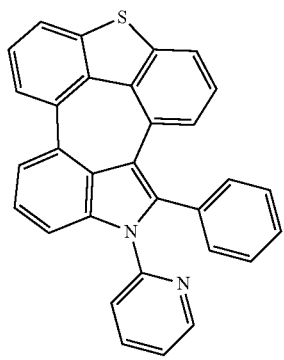
C-215 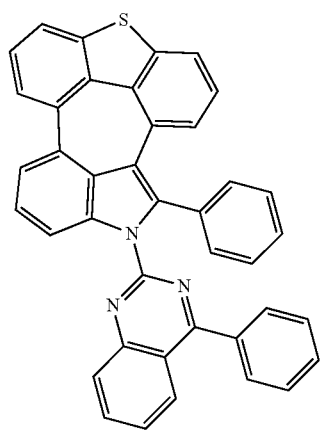
C-213 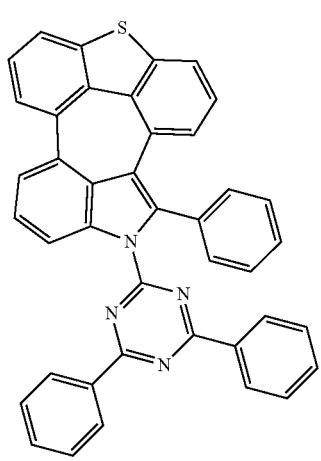
C-216 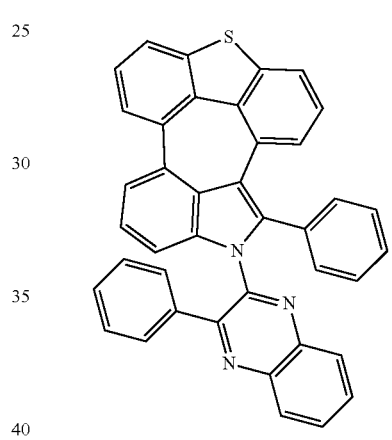
C-214 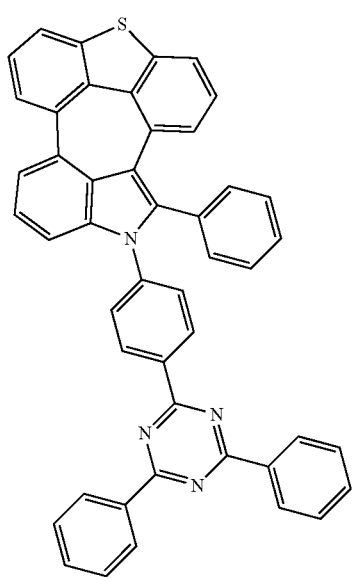
C-217 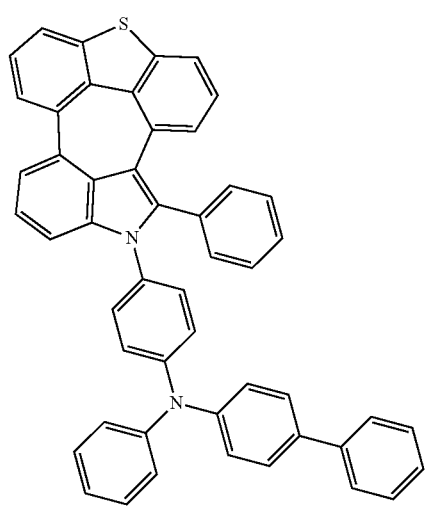

-continued
C-218
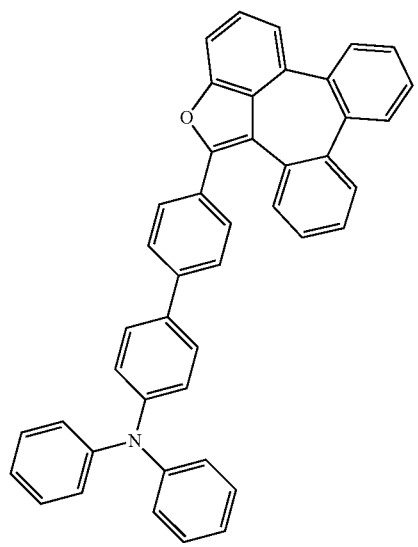
C-221
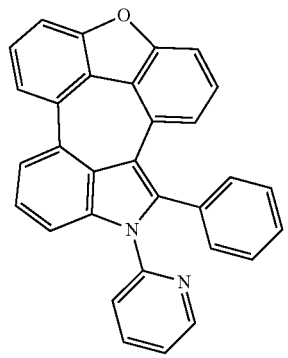
C-219
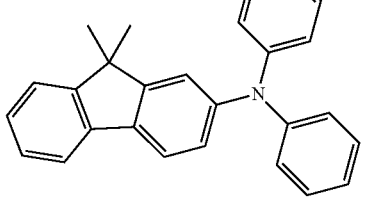
C-222
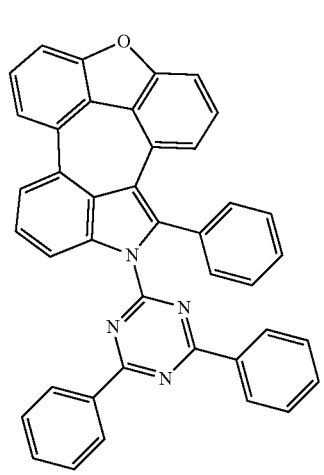
C-220
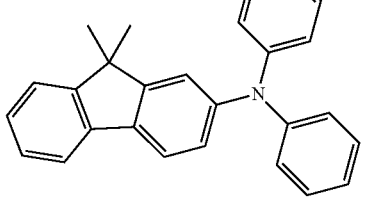
C-223
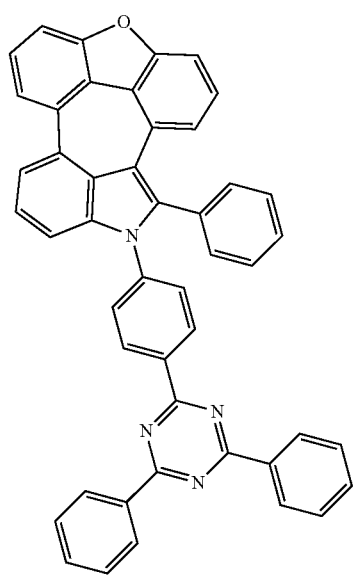

C-224 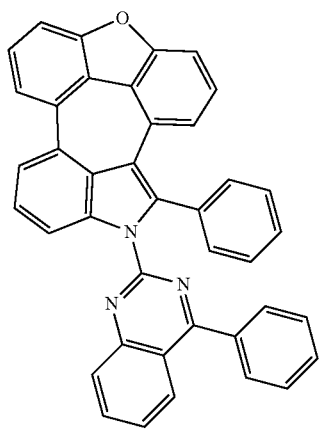
C-227 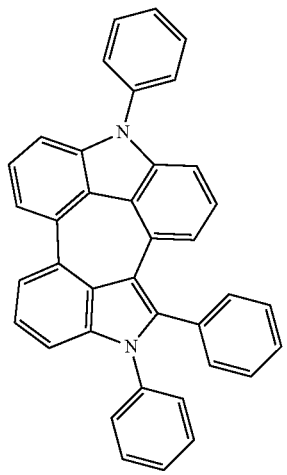
C-225 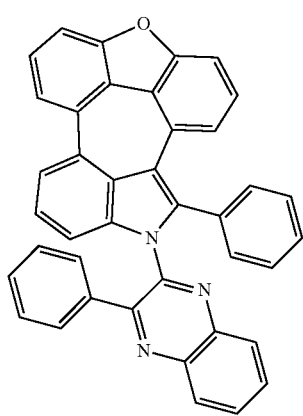
C-228 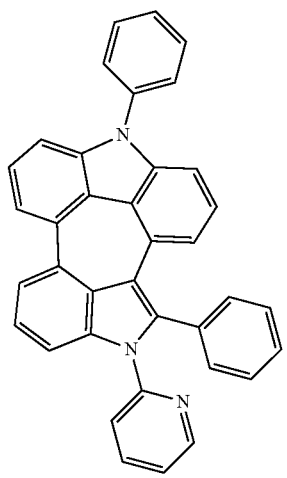
C-226 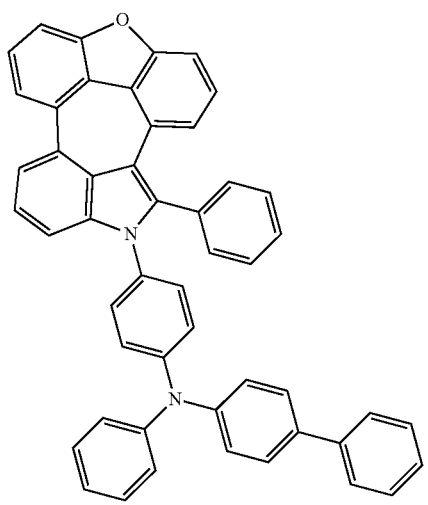
C-229 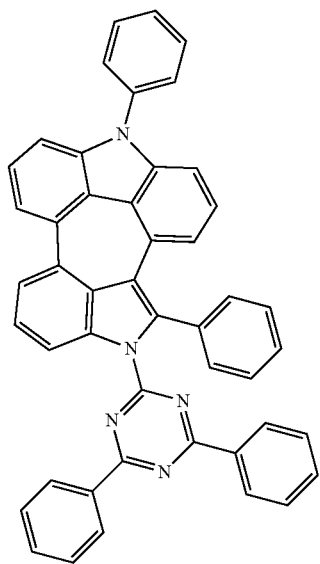

-continued
C-230
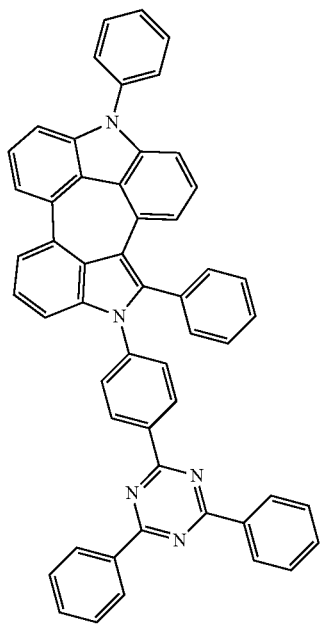
C-231
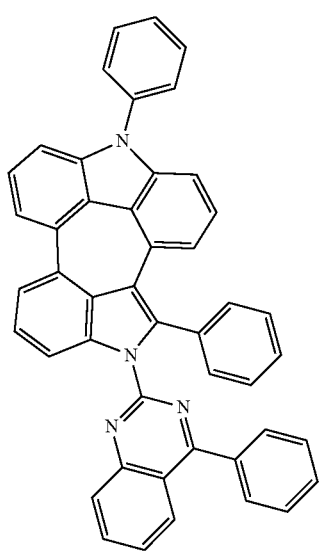
C-232
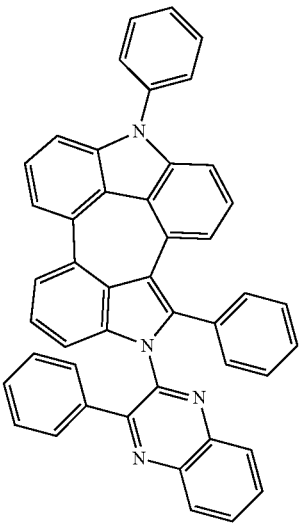
C-233
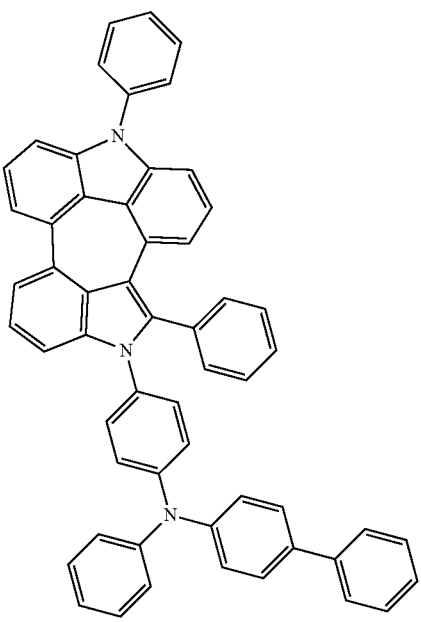
C-234
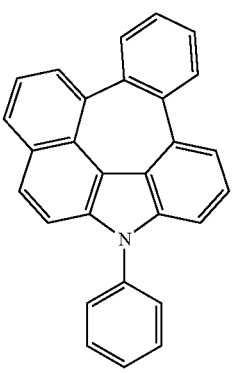

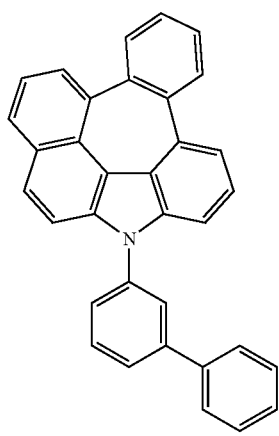
C-235
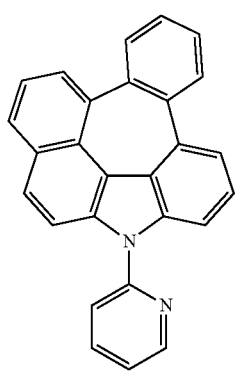
C-236
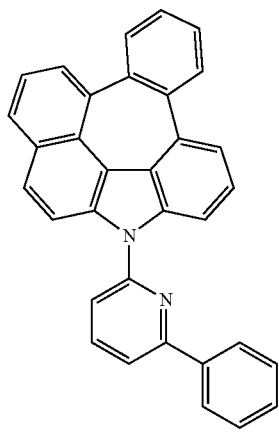
C-237
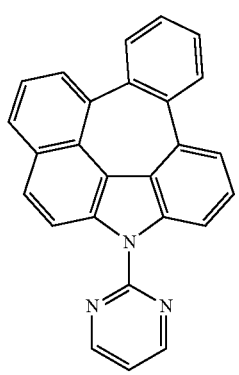
C-238
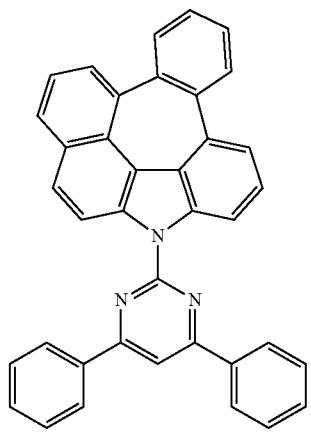
C-239
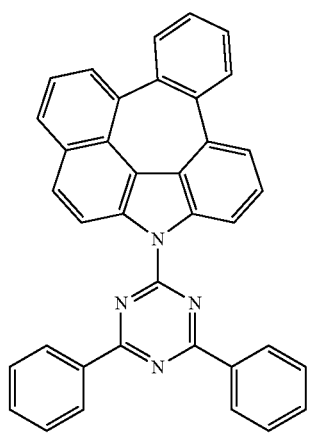
C-240
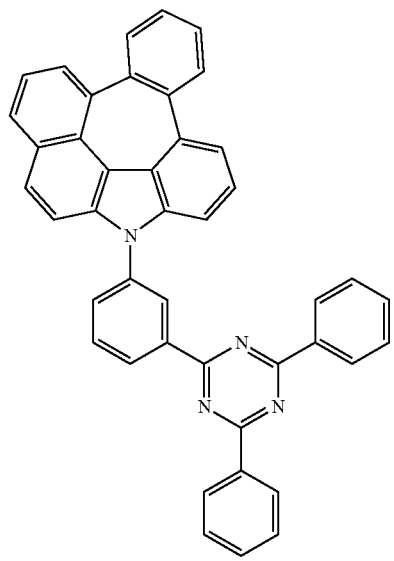
C-241

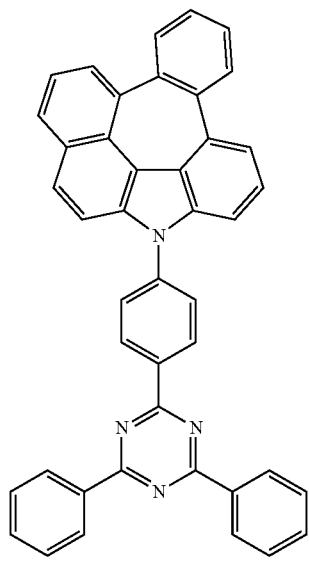
C-242
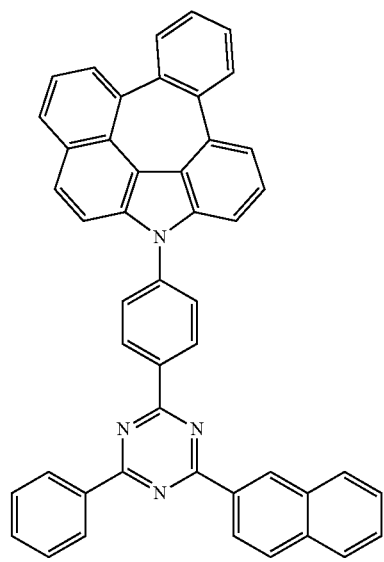
C-244
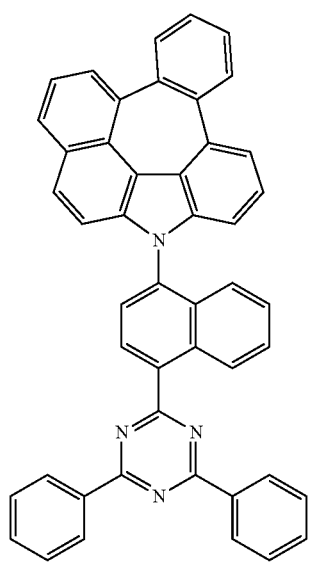
C-243
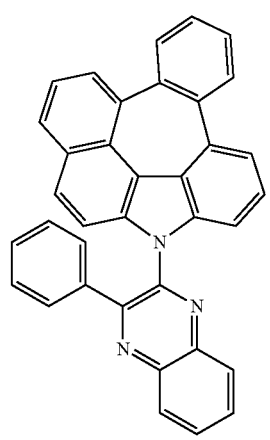
C-245
C-246

C-247
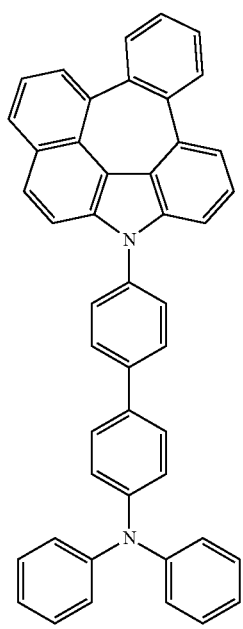
C-249
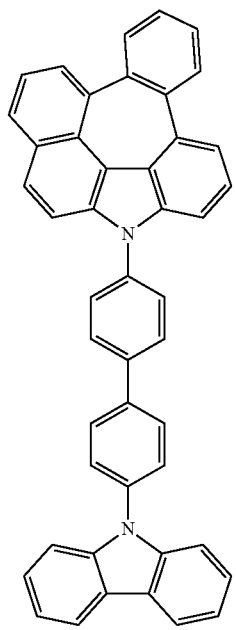
C-248
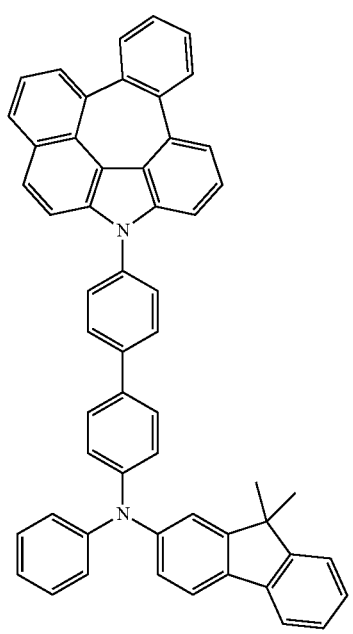
C-250
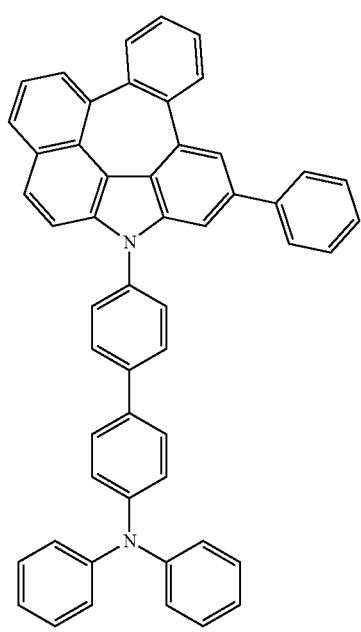

C-251
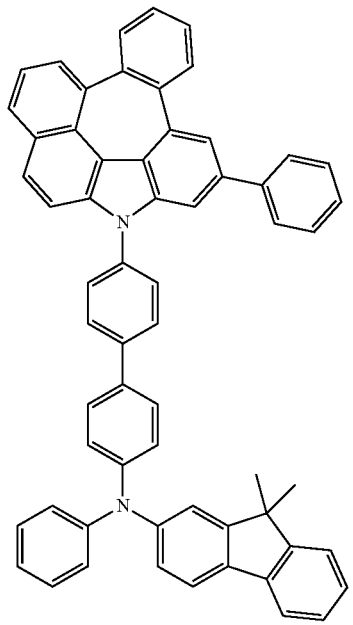
C-252
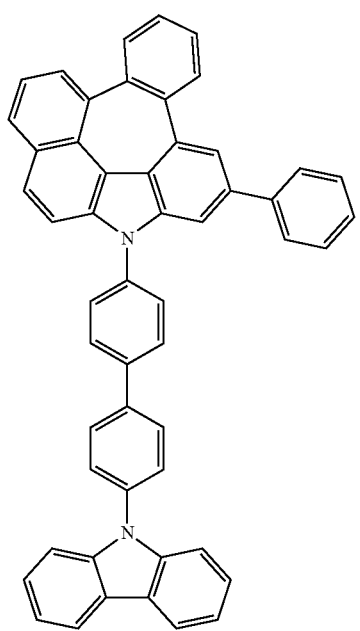
C-253
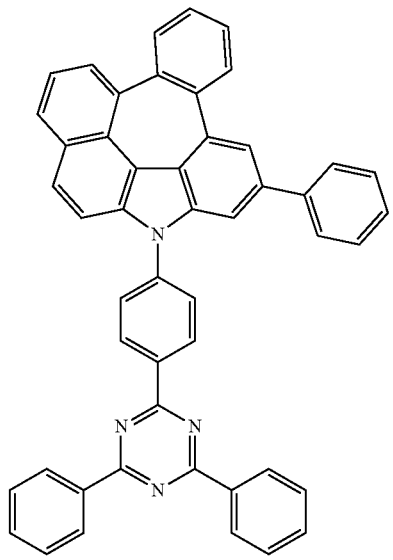
C-254
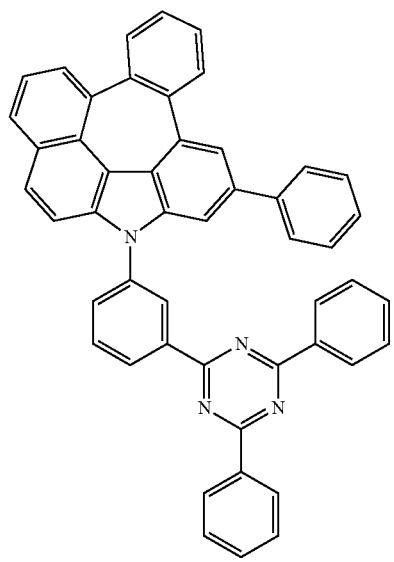

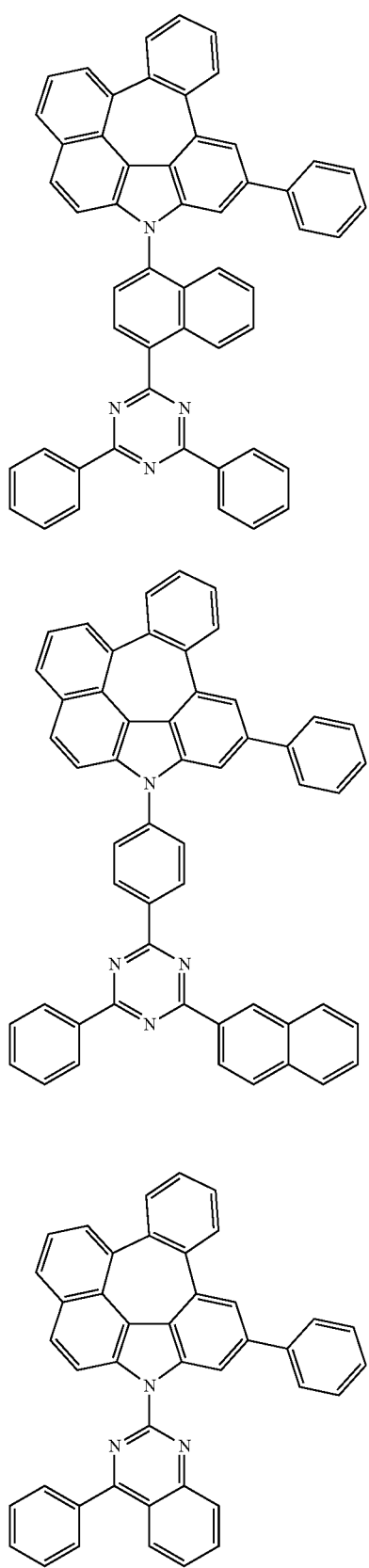
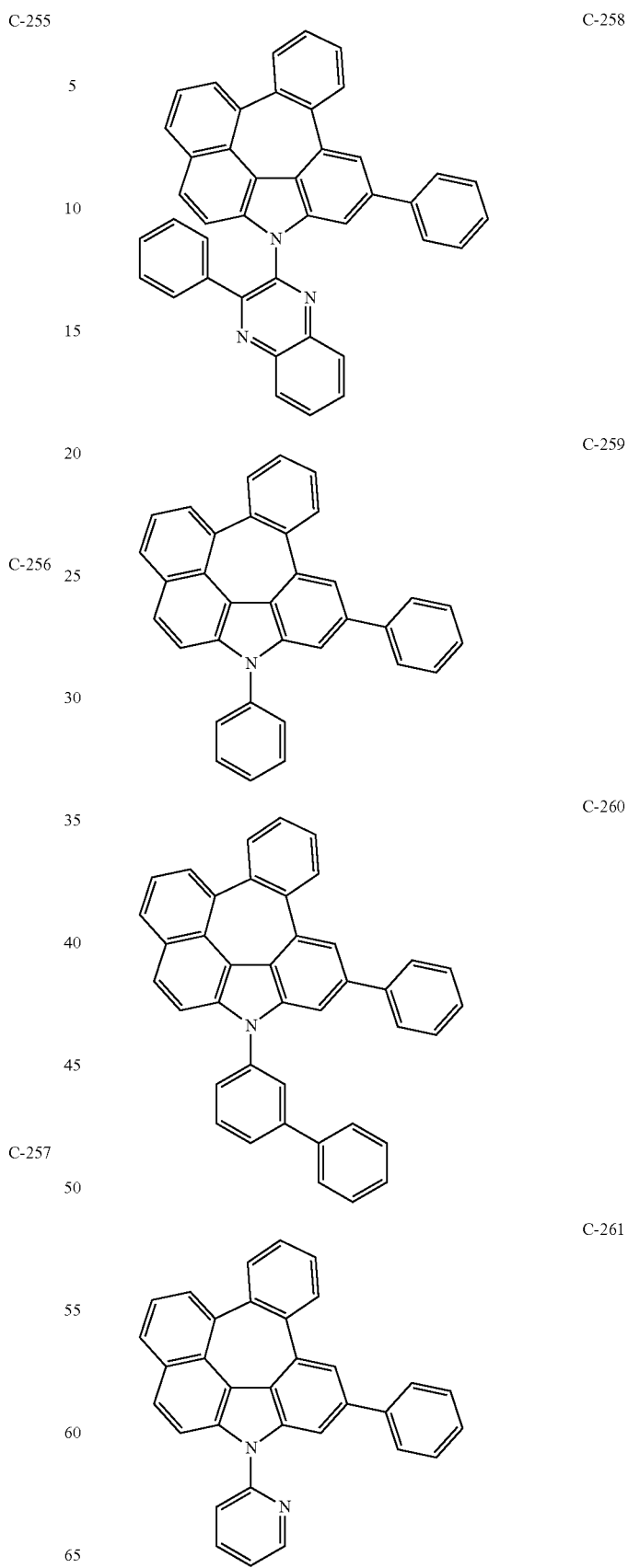

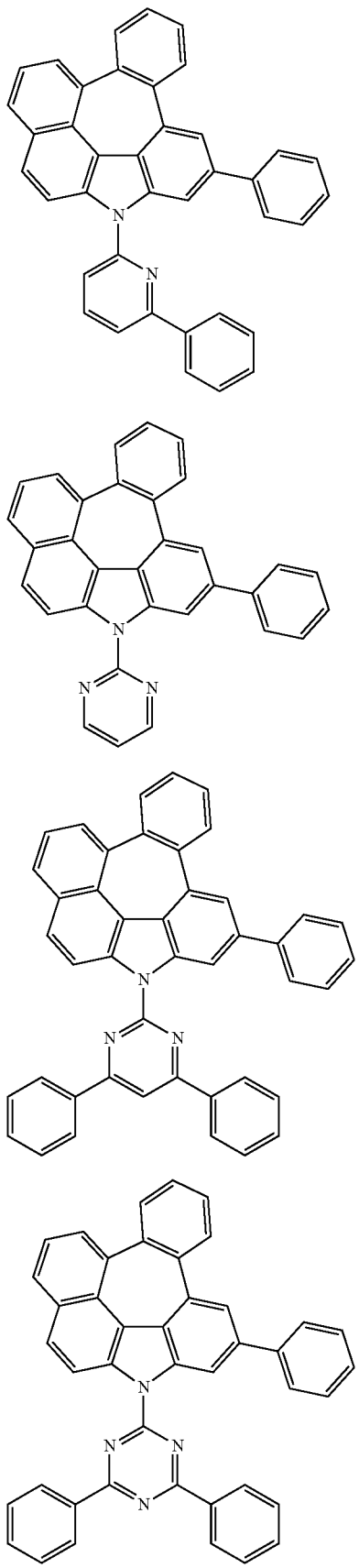
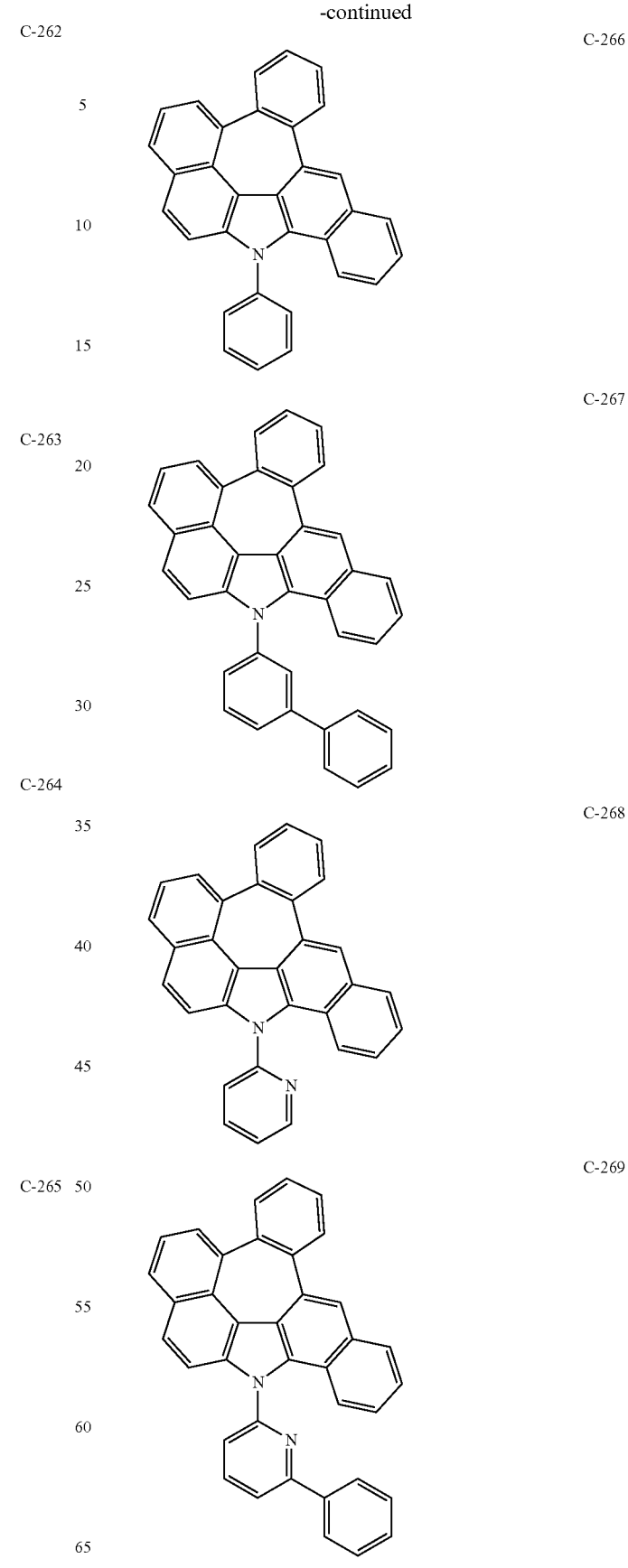

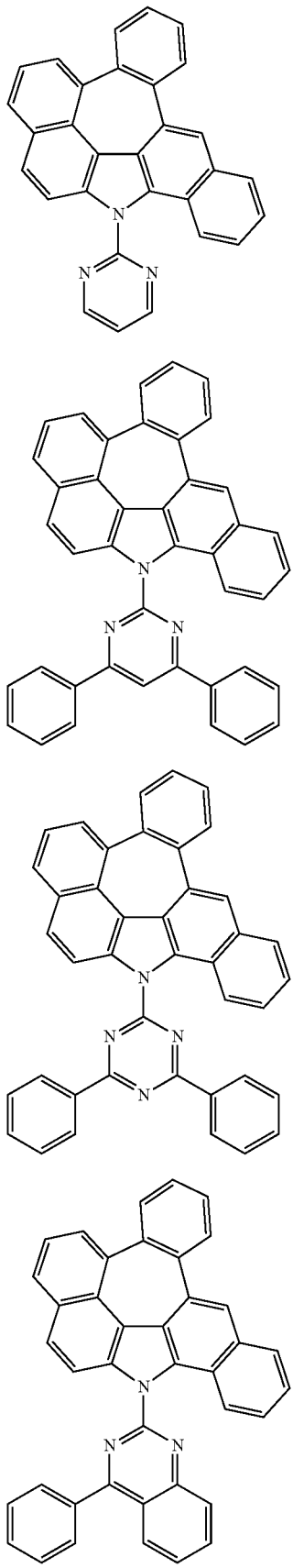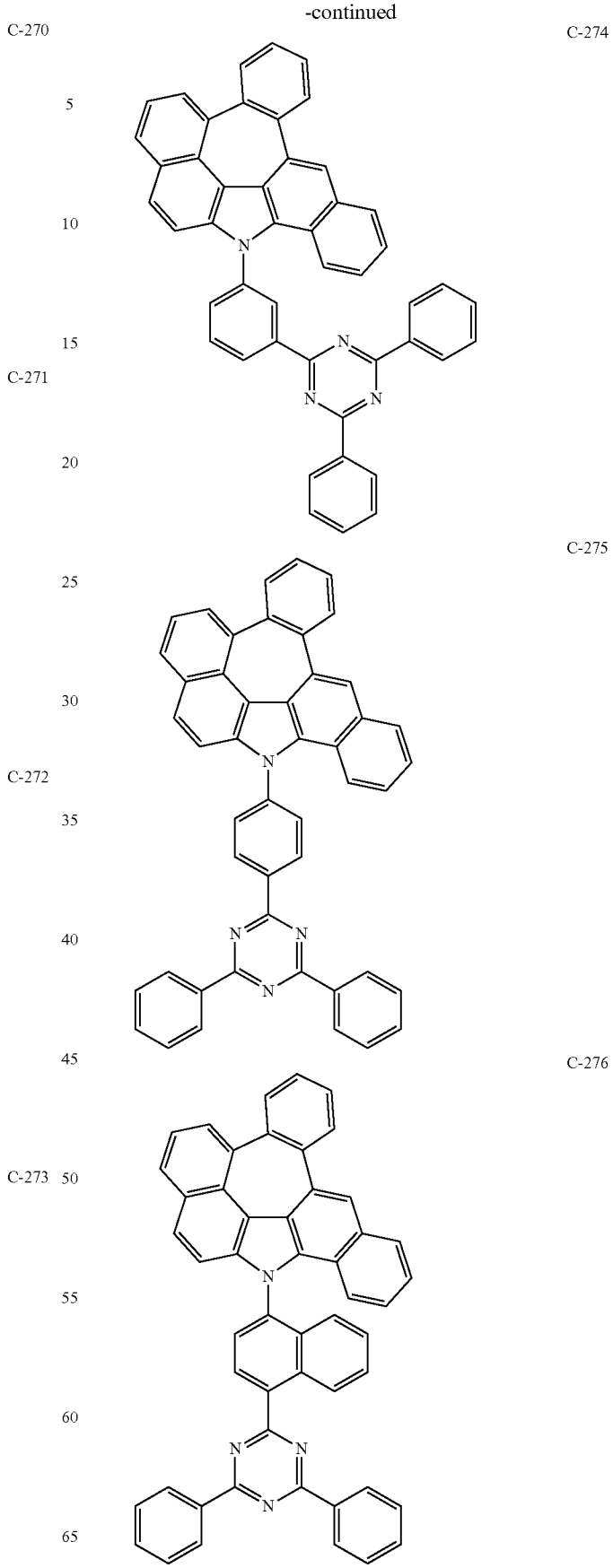

C-277
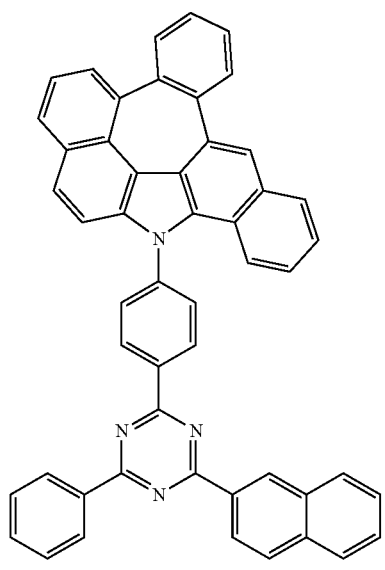
C-280
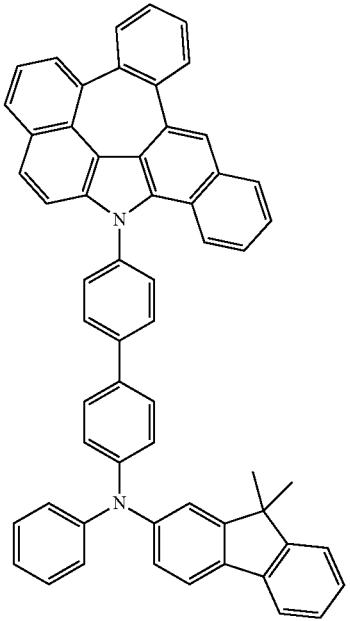
C-278
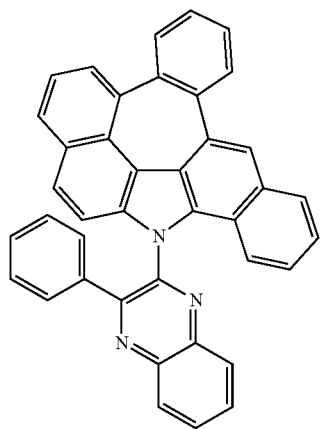
C-279
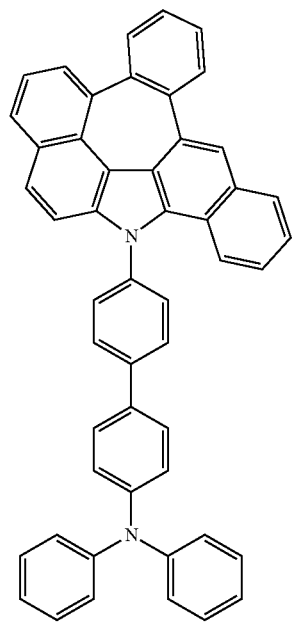
C-281
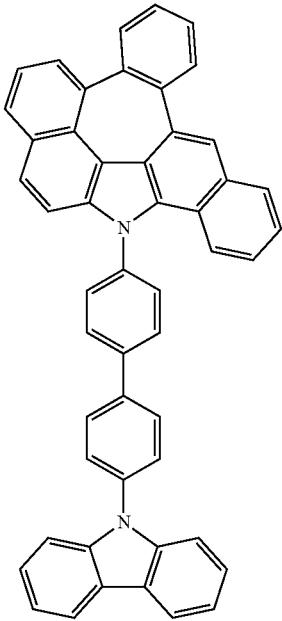

C-282
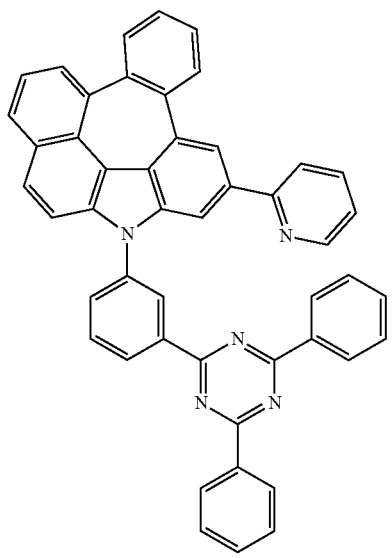
C-283
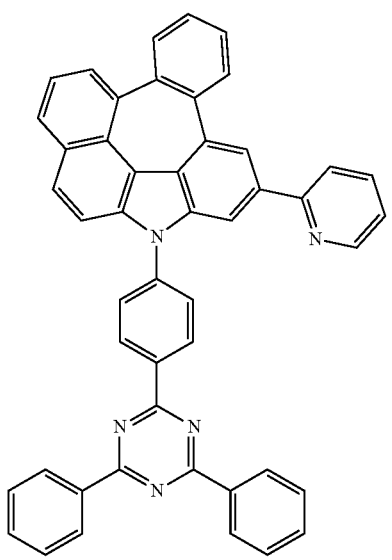
C-284
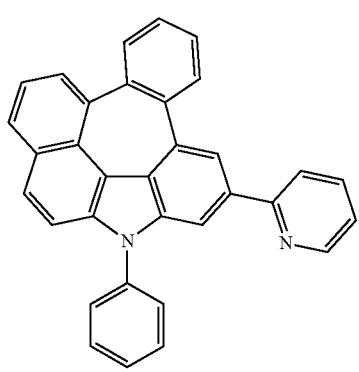
C-285
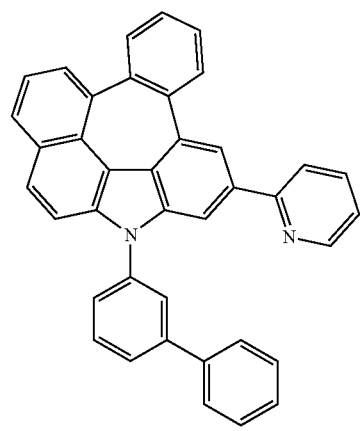
C-286
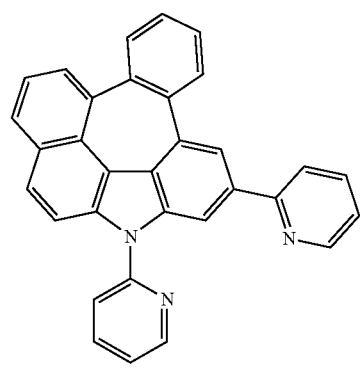
C-287
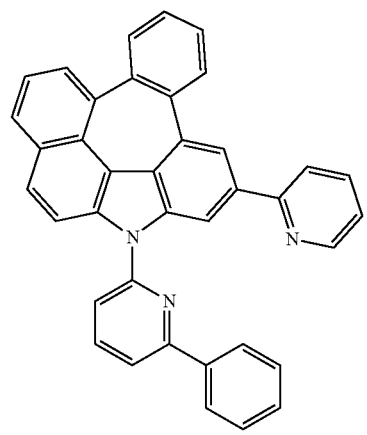

C-288
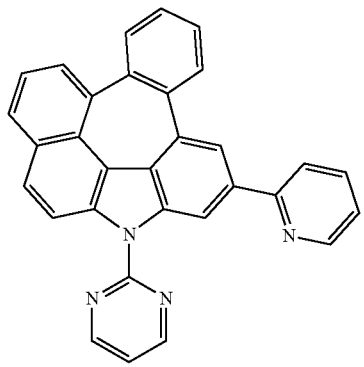
C-289
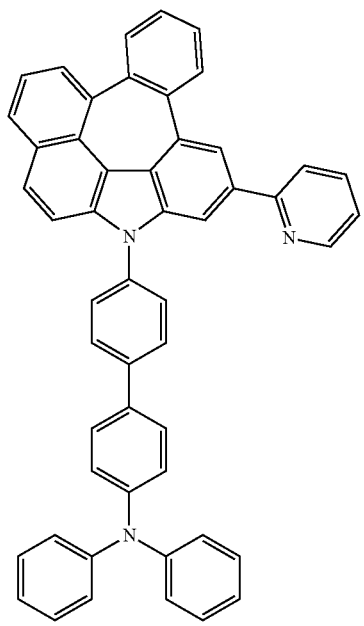
C-290
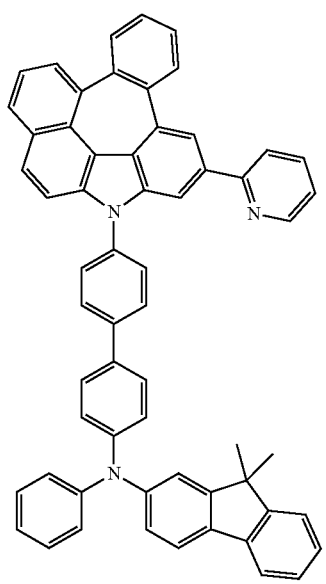
C-291
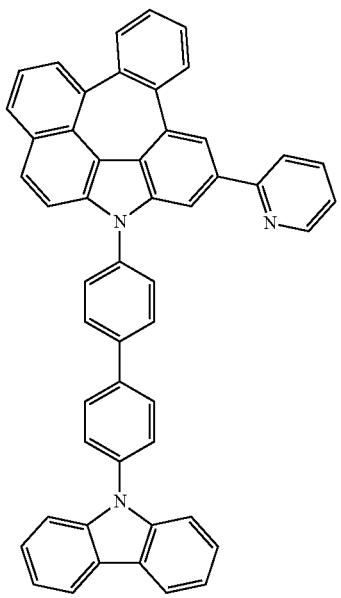
C-292
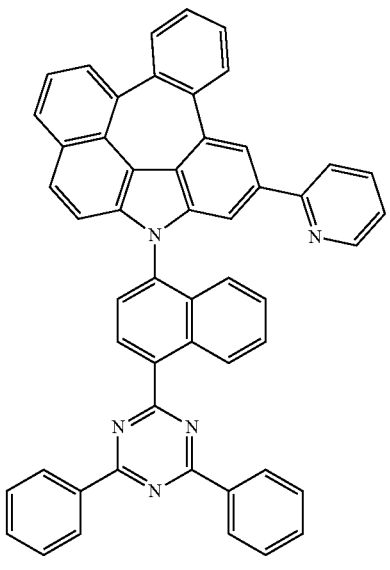

-continued
C-293
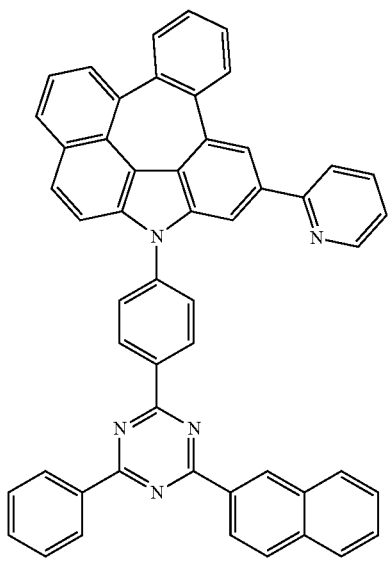
C-294
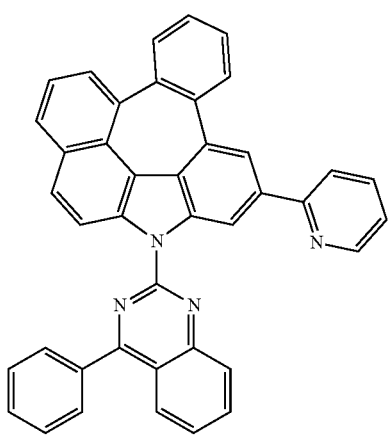
C-295
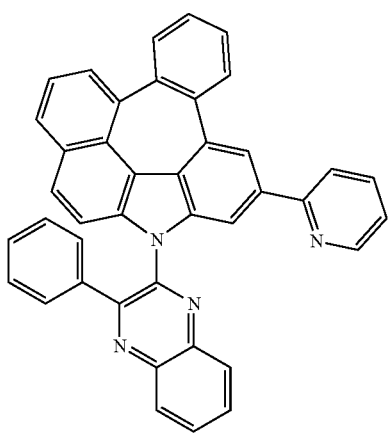
-continued
C-296
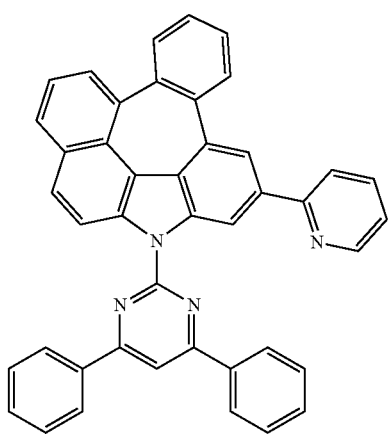
C-297
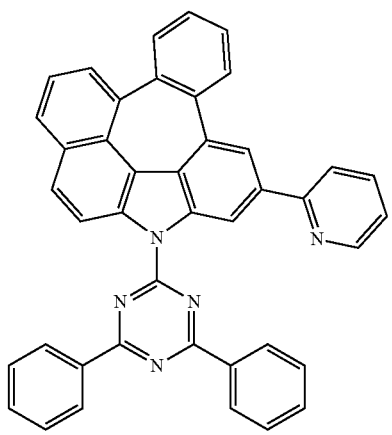
C-298
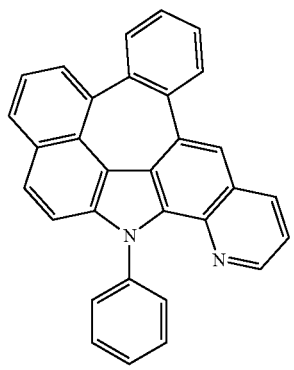

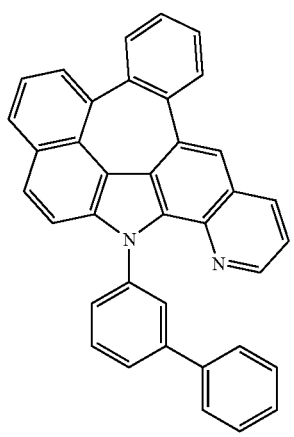
C-299
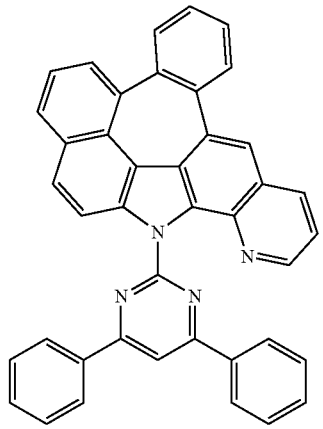
C-303
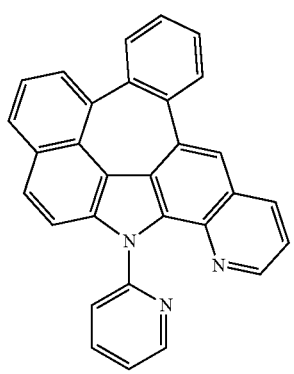
C-300
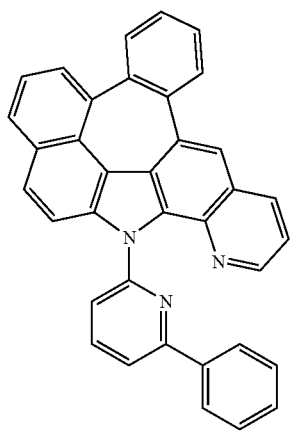
C-301
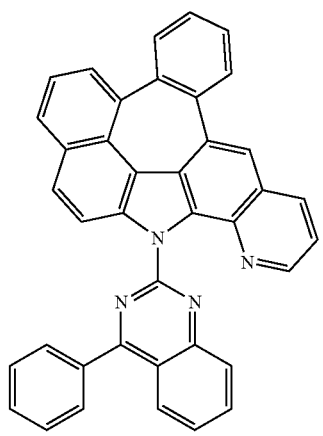
C-304
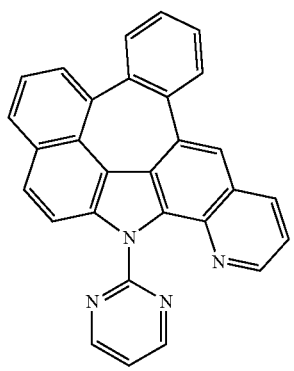
C-302
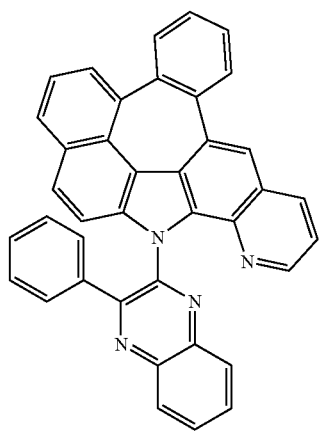
C-305

C-306
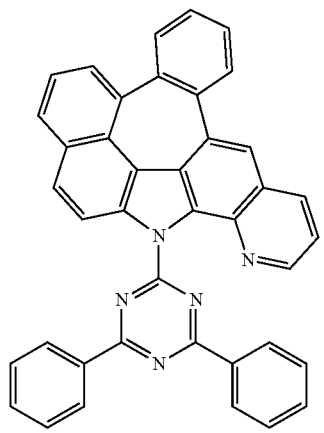
C-307
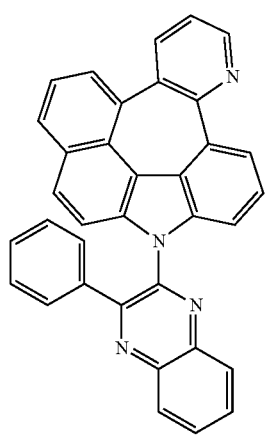
C-308
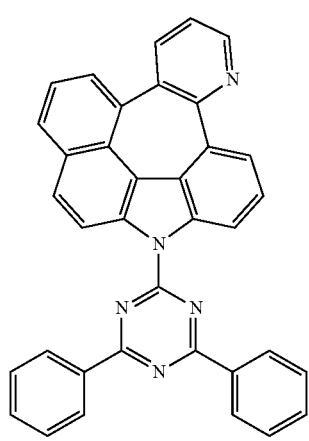
C-309
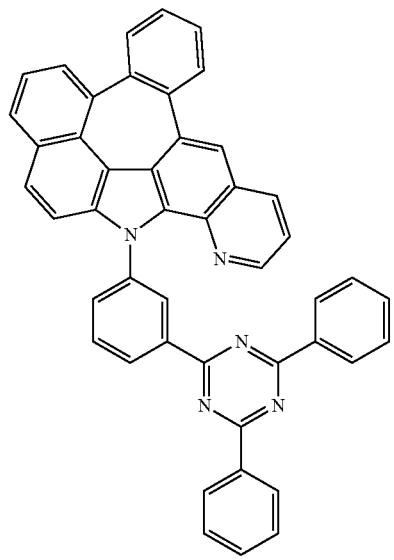
C-310
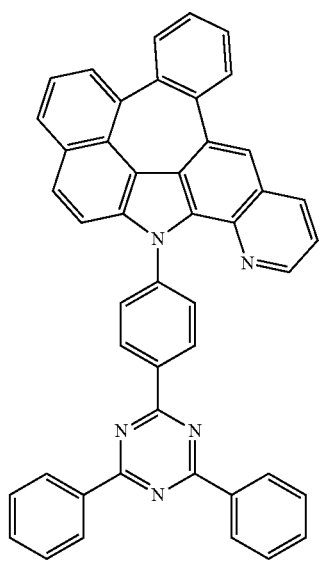
C-311
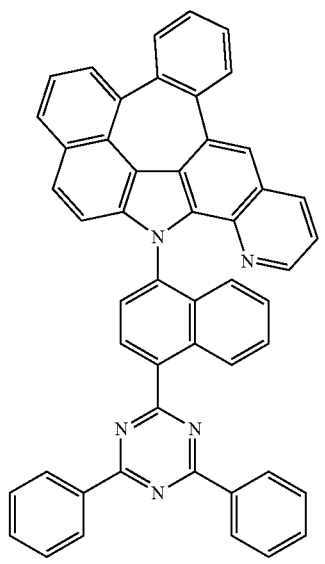

-continued
C-312
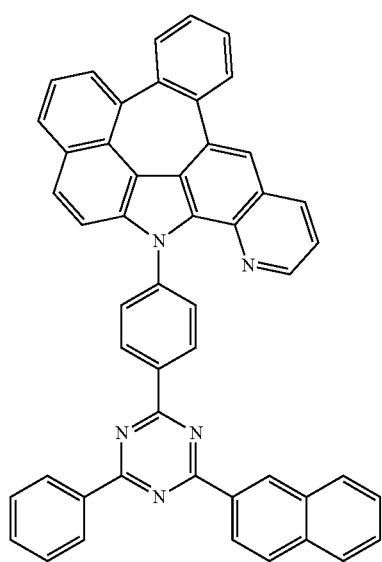
C-313
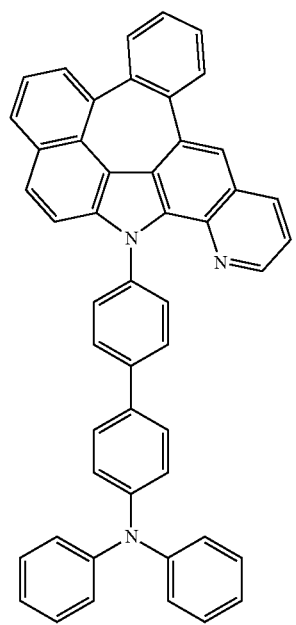
-continued
C-314
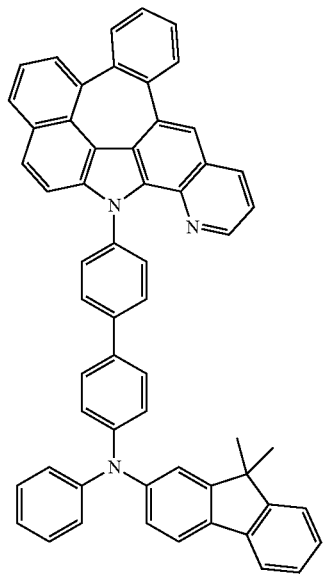
C-315
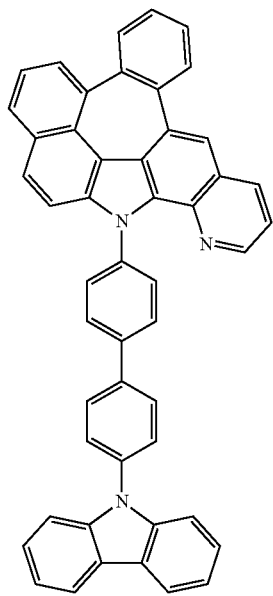

C-316
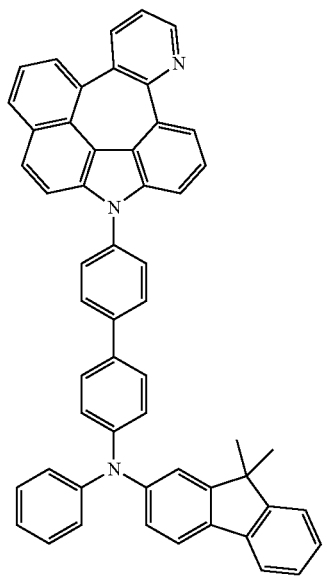
C-317
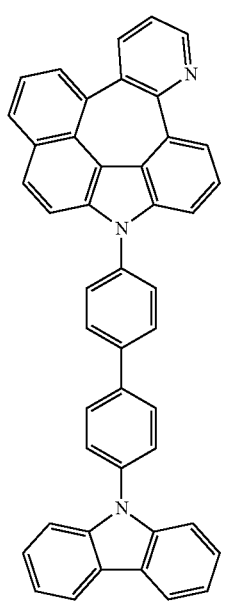
C-318
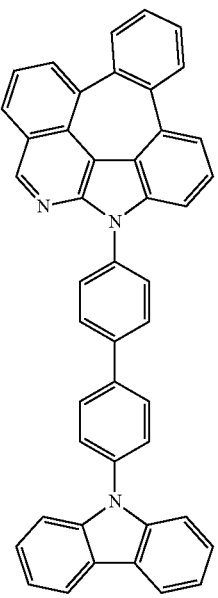
C-319
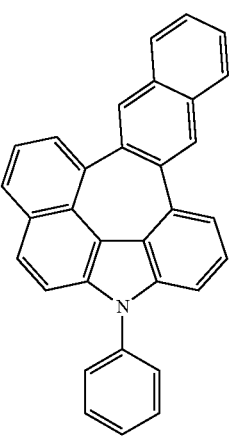
C-320
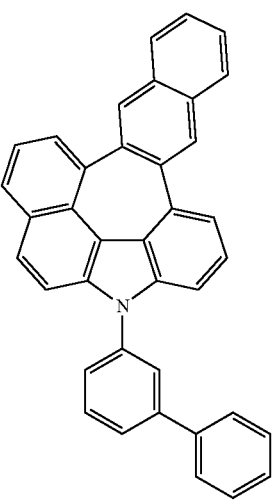

C-321
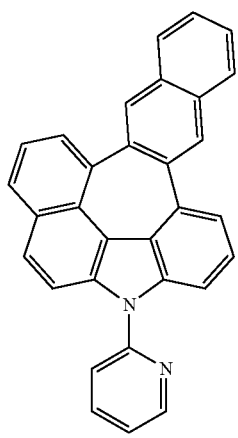
C-322
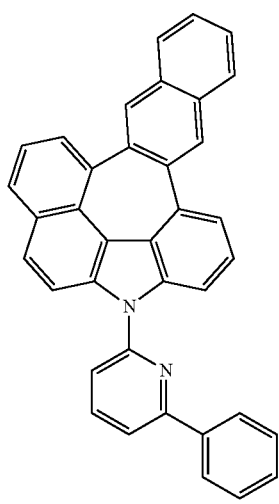
C-323
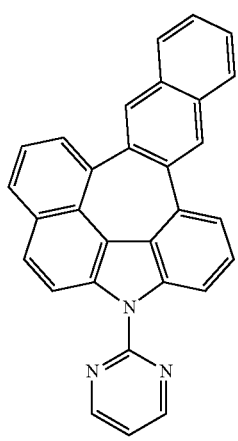
C-324
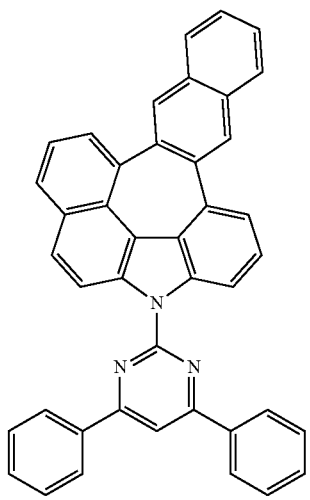
C-325
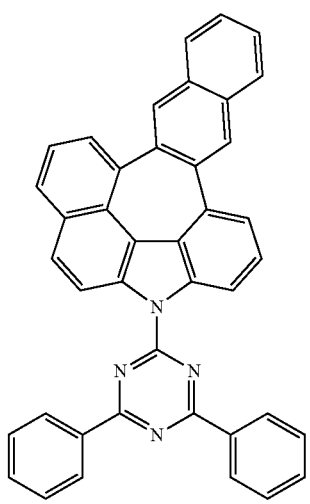
C-326
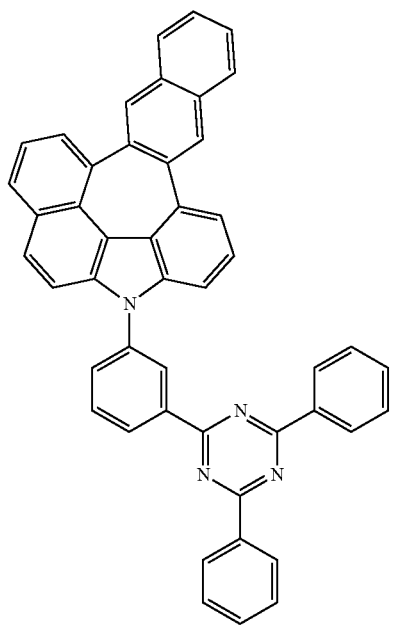

-continued
C-327
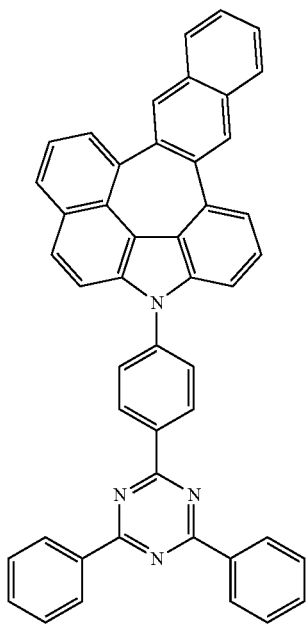
C-329
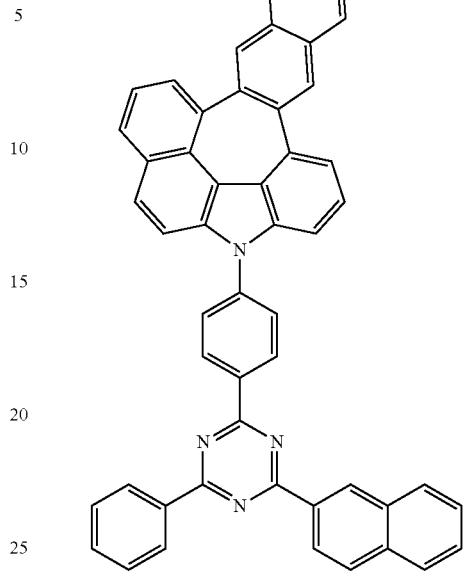
C-328
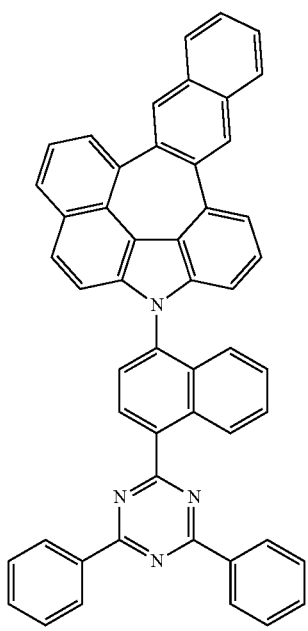
C-330
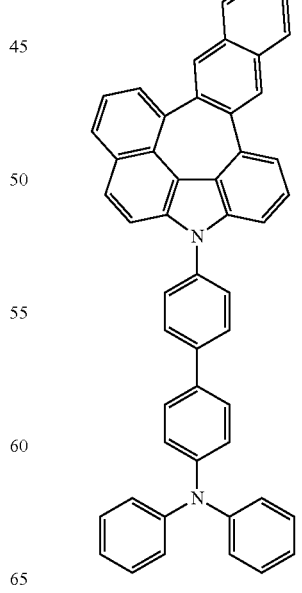

125
-continued
C-331
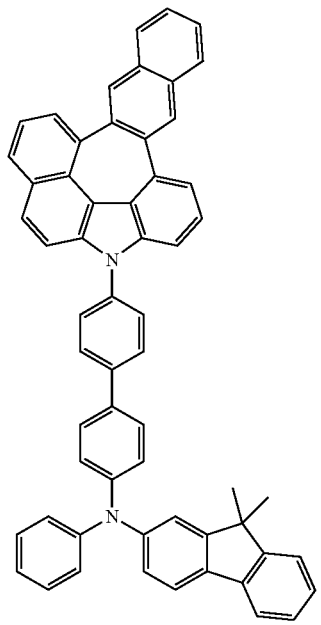
C-332
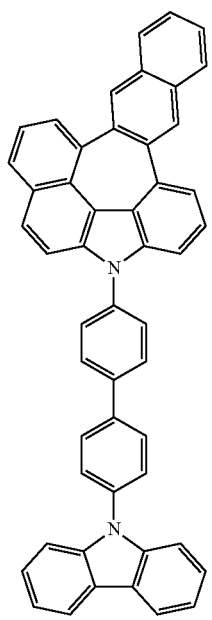
126
-continued
C-333
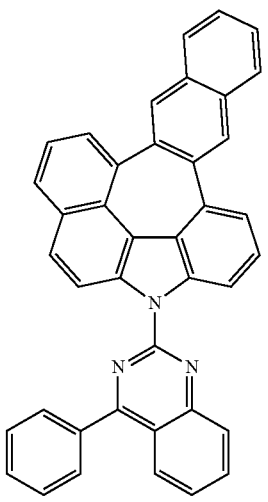
C-334
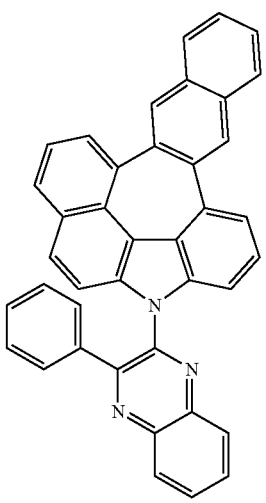
C-335

-continued
C-336
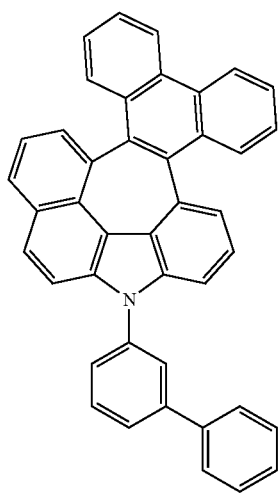
C-337
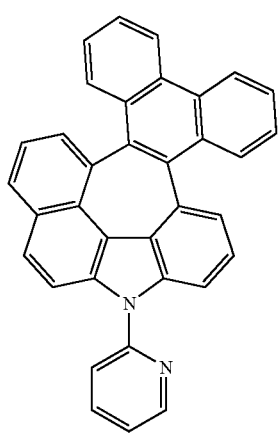
C-338
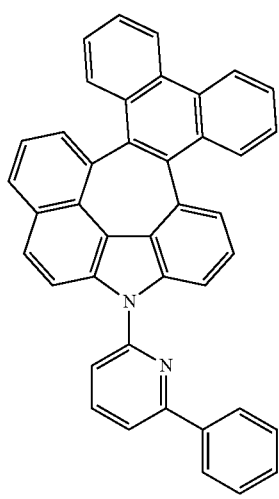
-continued
C-339
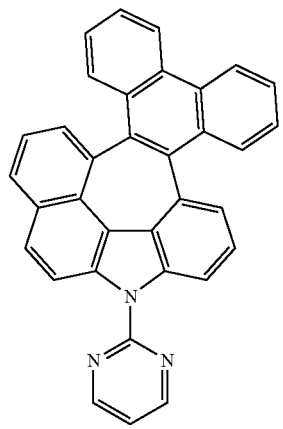
C-340
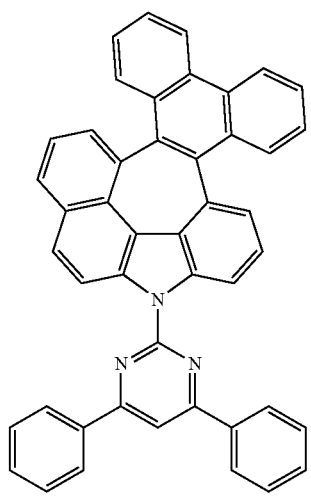
C-341
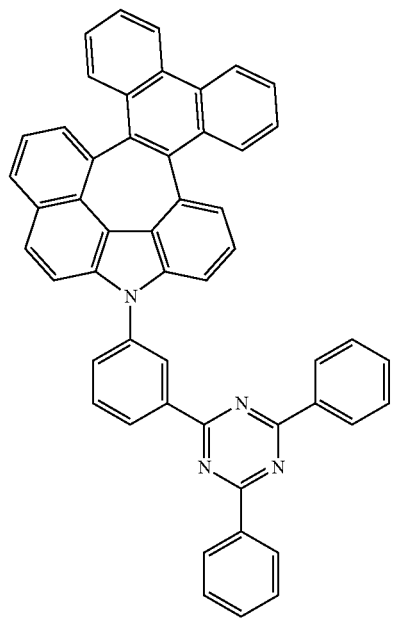

C-342
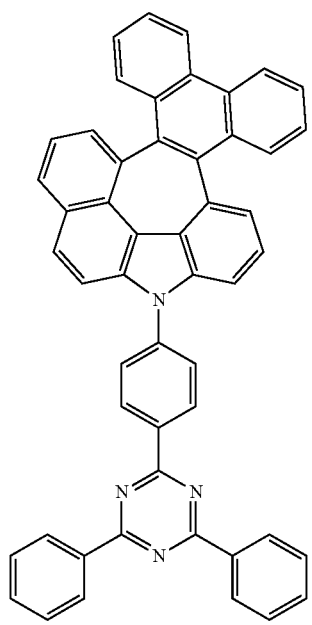
C-343
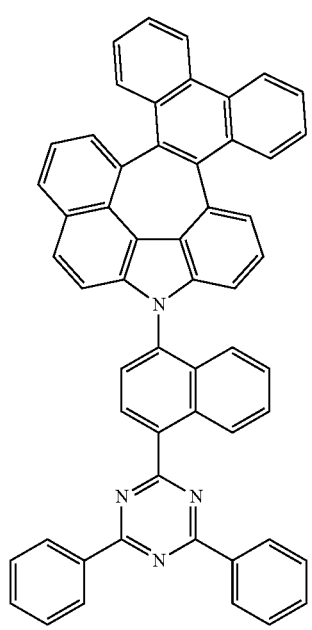
C-344
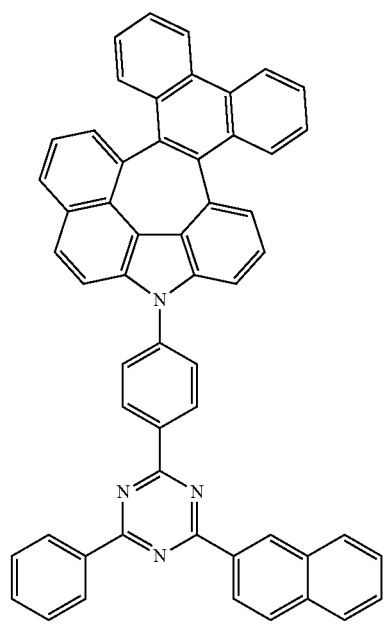
C-345
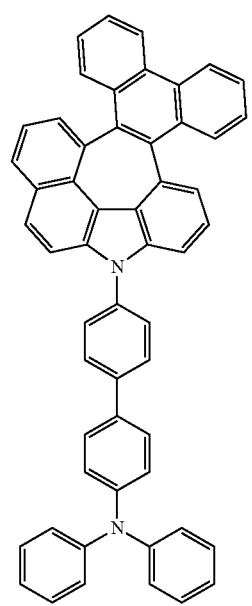

-continued
C-346
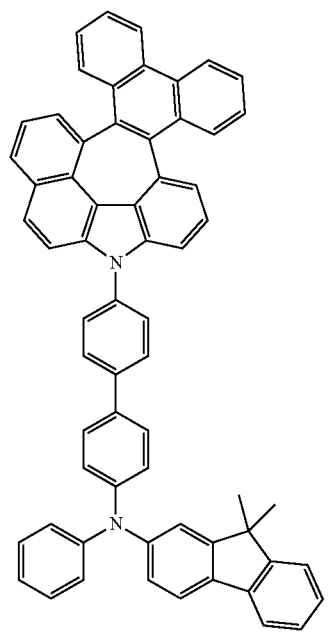
C-347
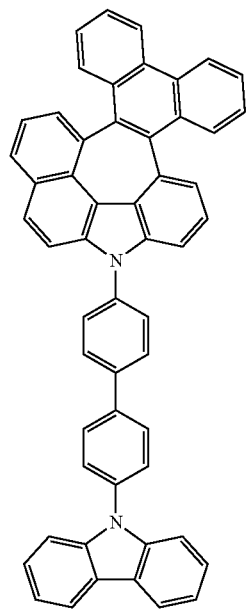
C-348
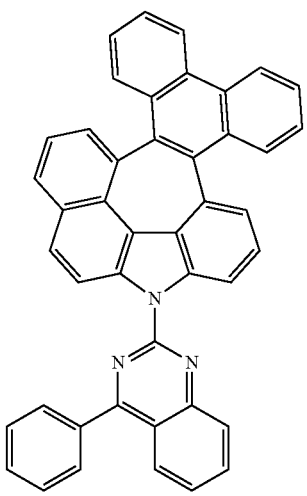
C-349
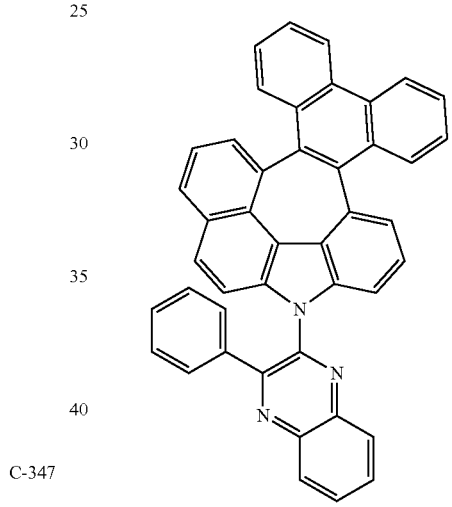
C-350
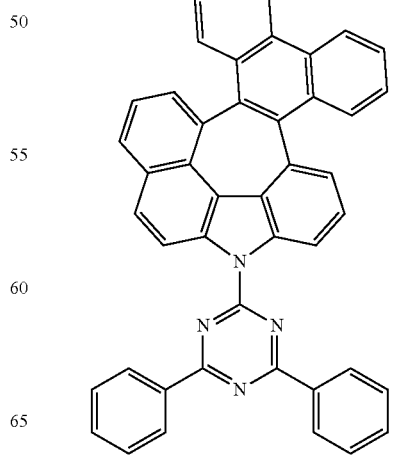

-continued
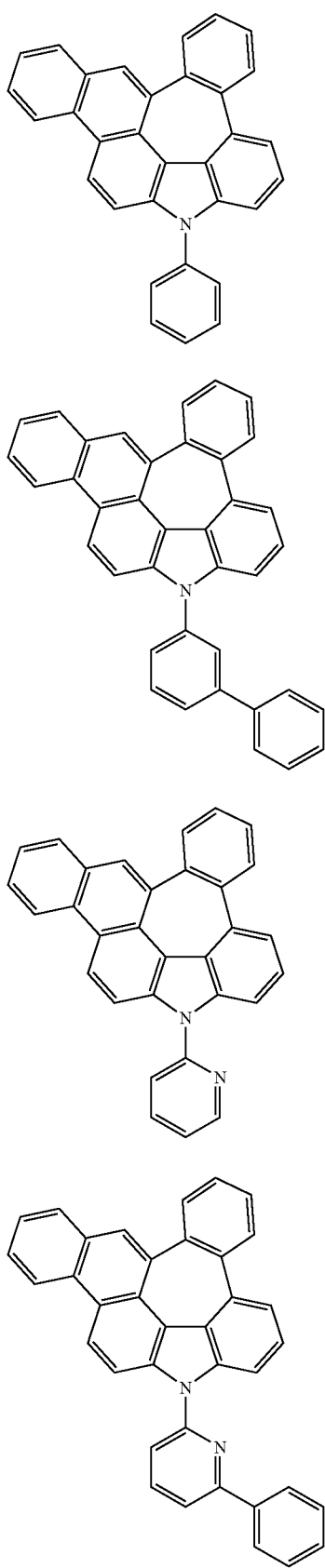
C-351
C-352
C-353
C-354
-continued
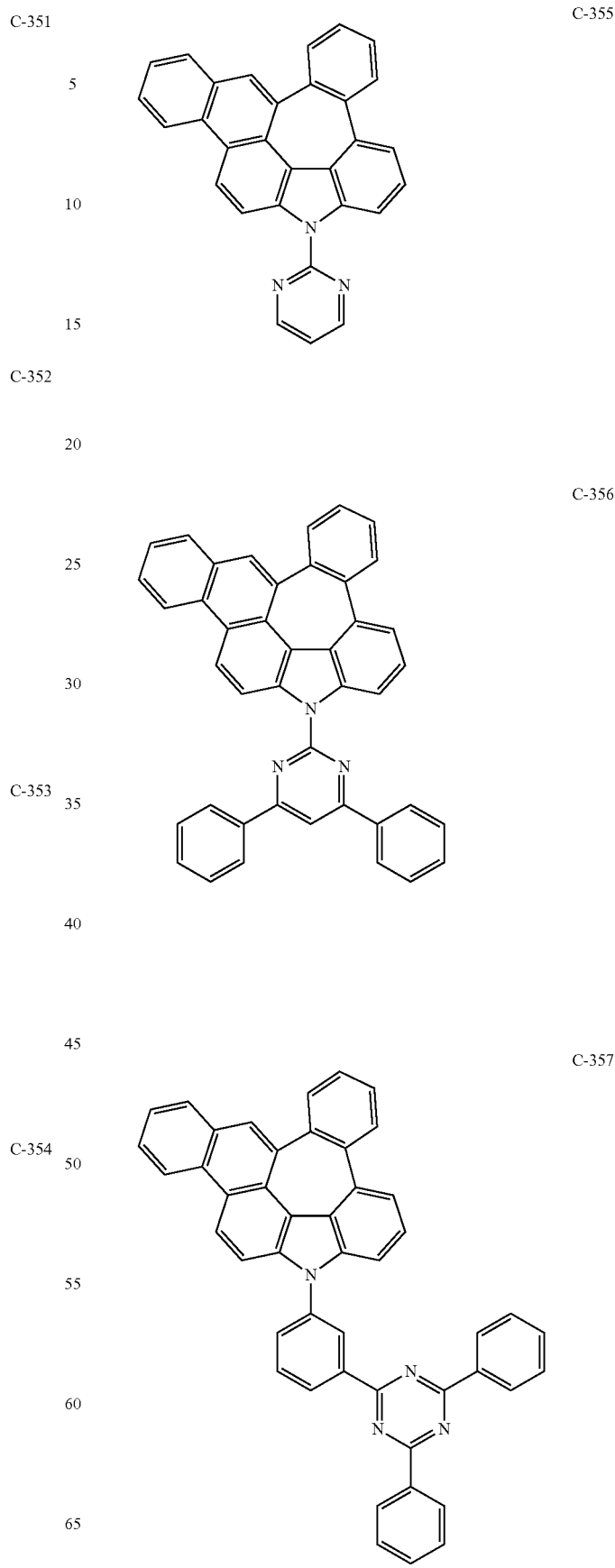
C-355
C-356
C-357

C-358
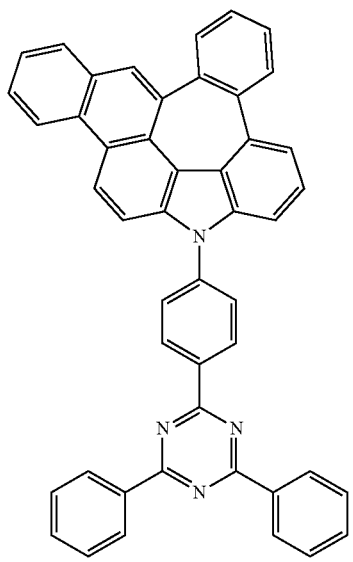
C-359
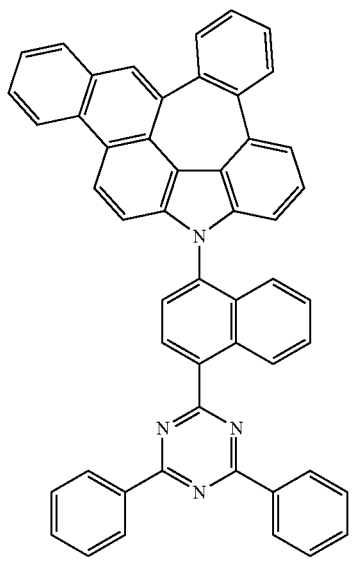
C-360
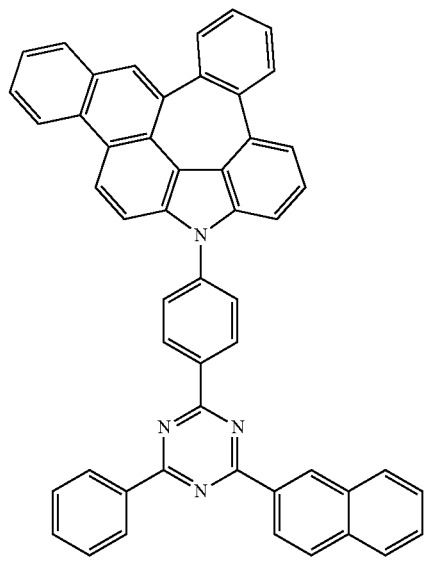
C-361
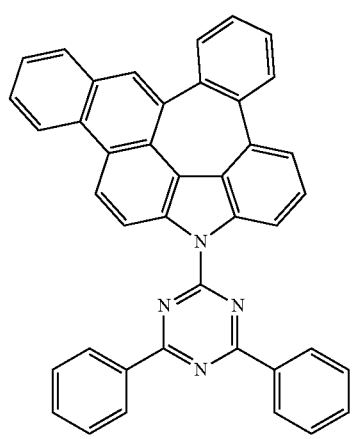
C-362
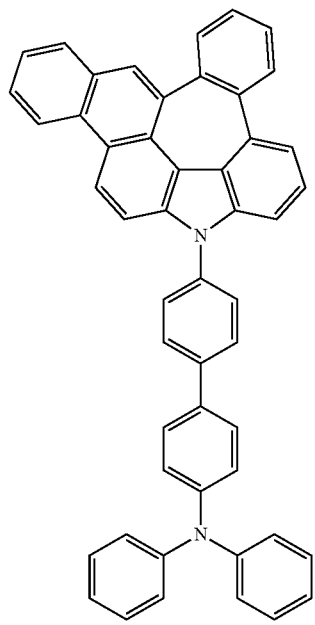

-continued
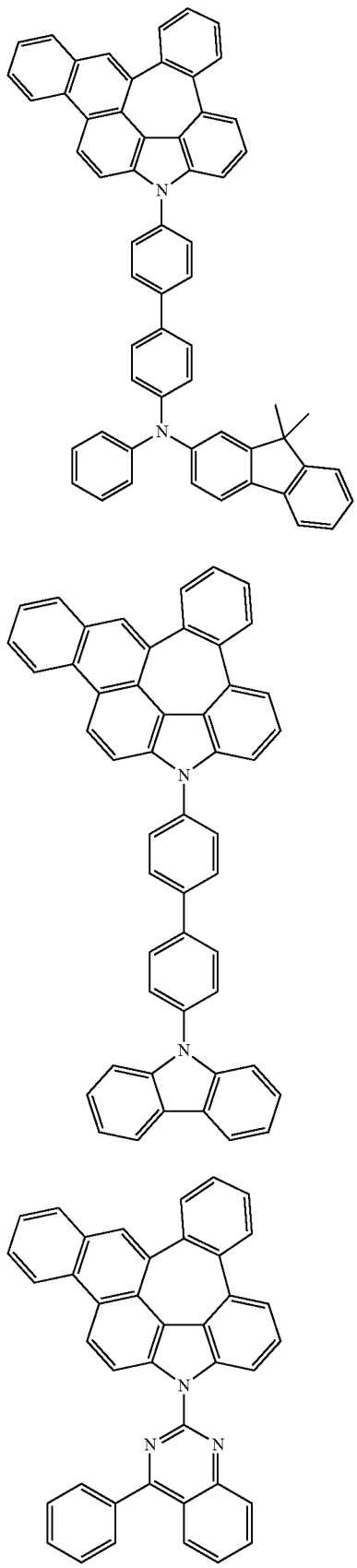
C-363
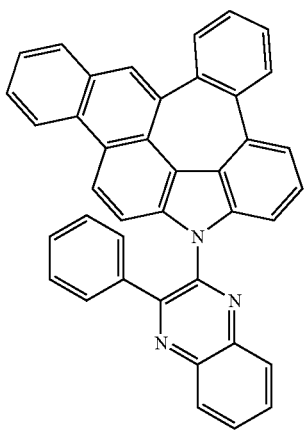
C-366
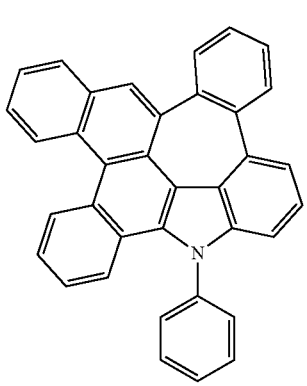
C-367
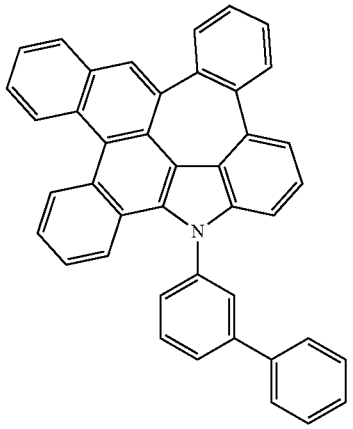
C-368
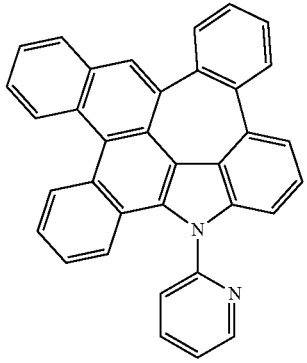
C-369

C-370
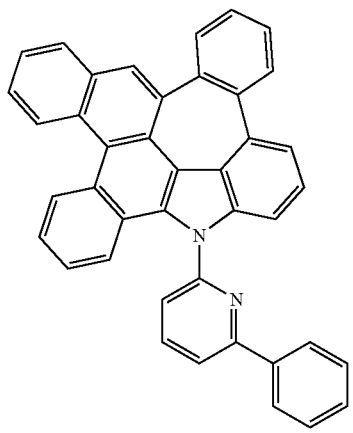
C-371
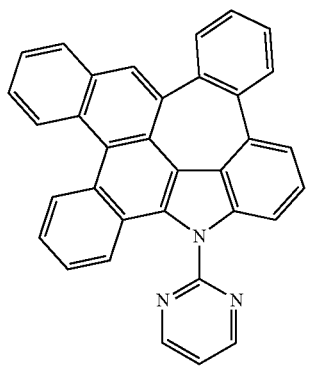
C-372
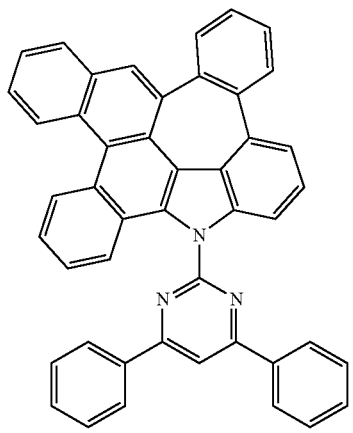
C-373
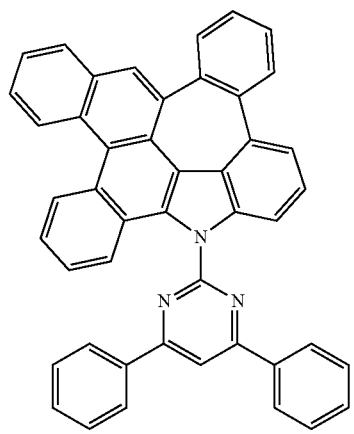
C-374
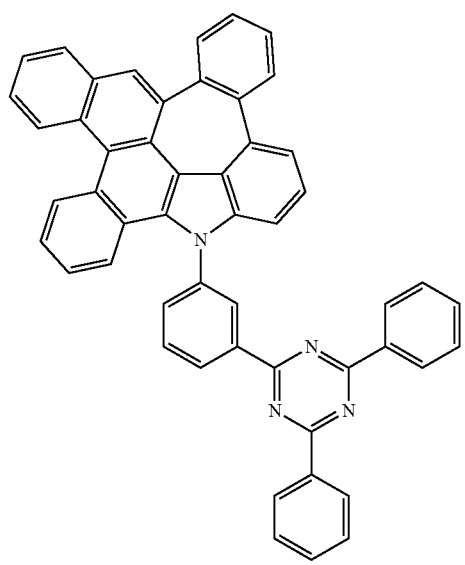
C-375
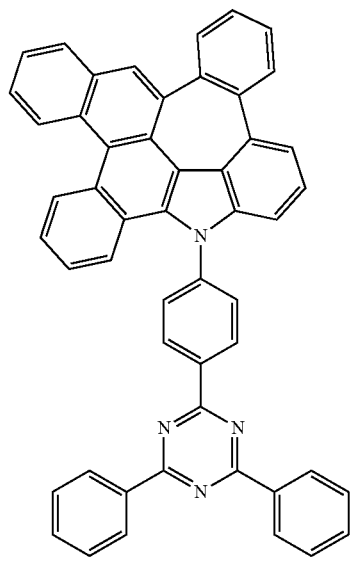

C-376
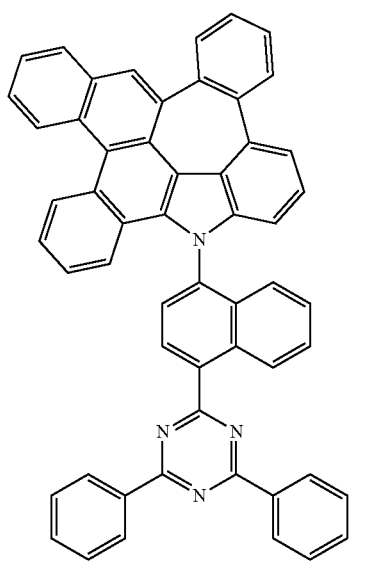
C-377
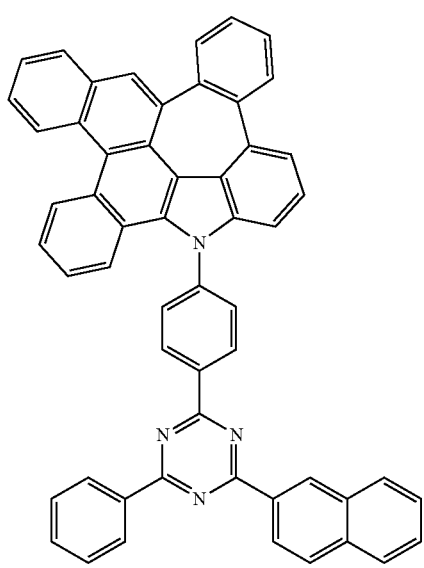
C-378
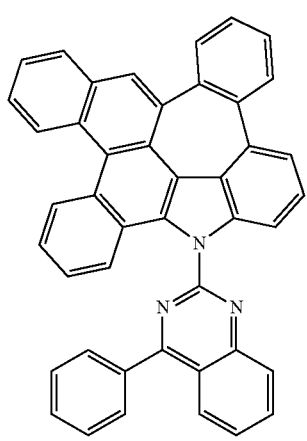
C-379
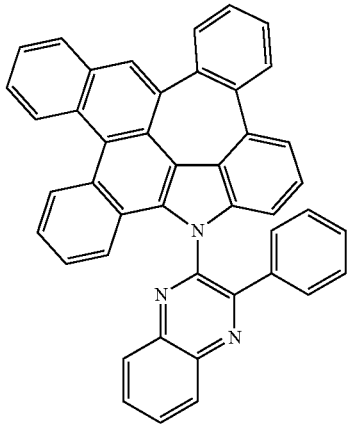
C-380
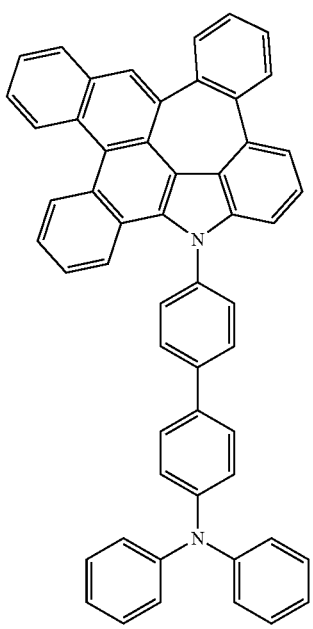
C-381
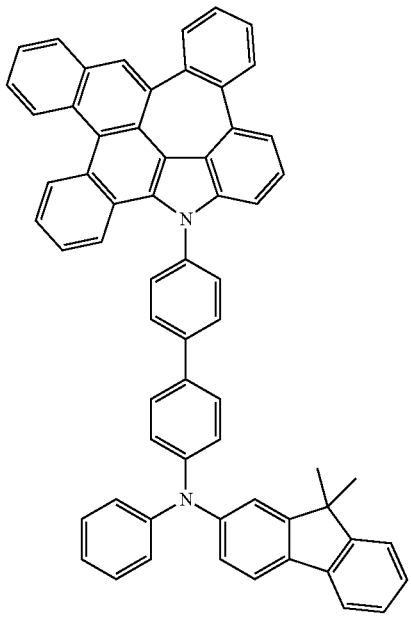

C-382
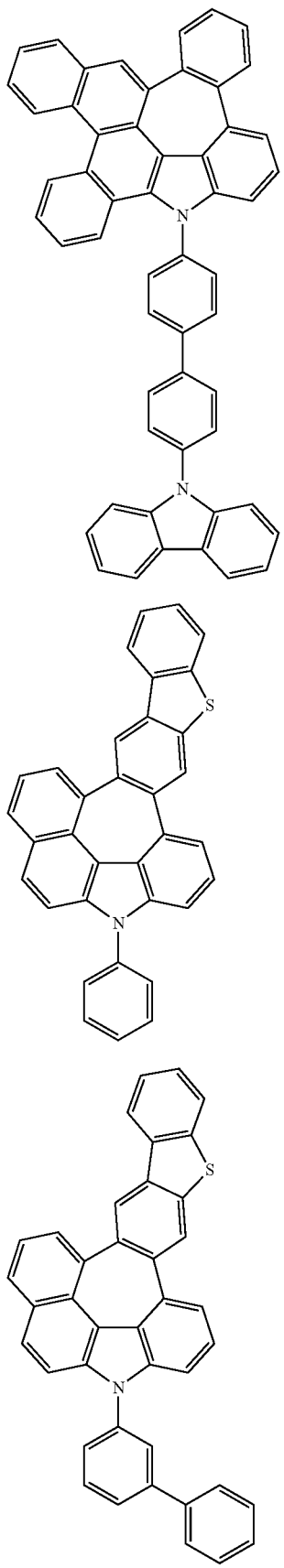
C-383
C-384
C-385
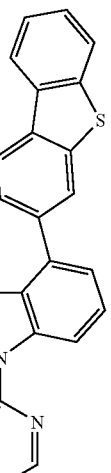
C-386
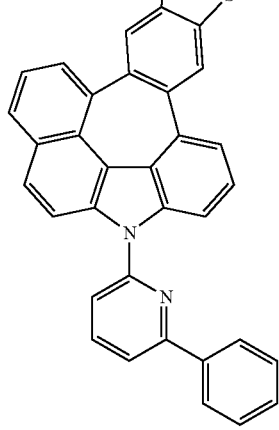
C-387
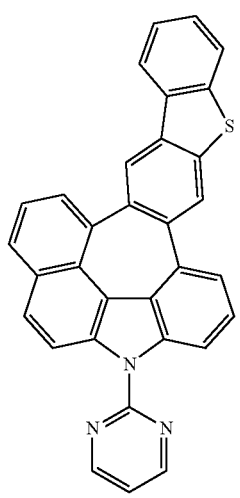

C-388
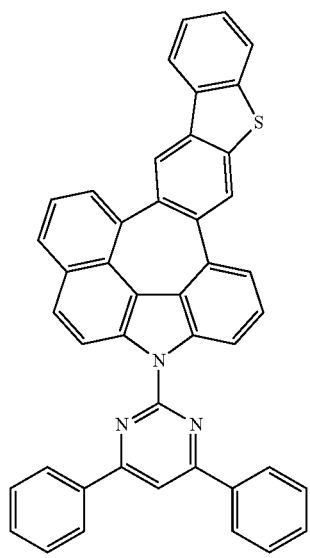
C-390
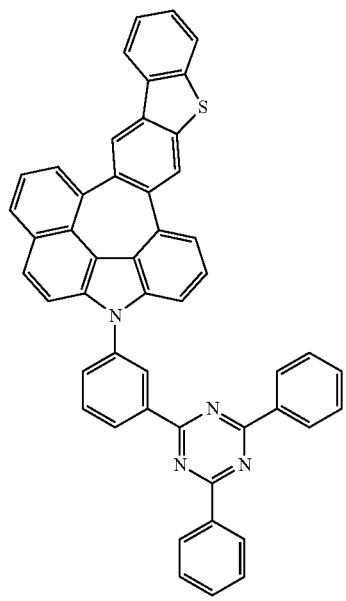
C-389
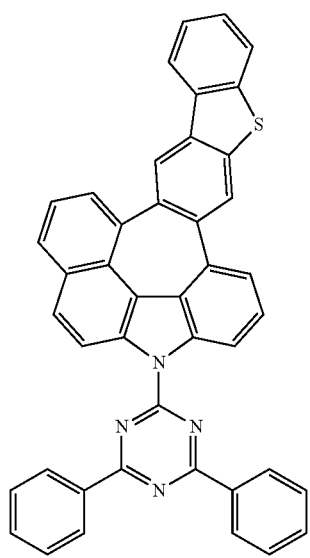
C-391
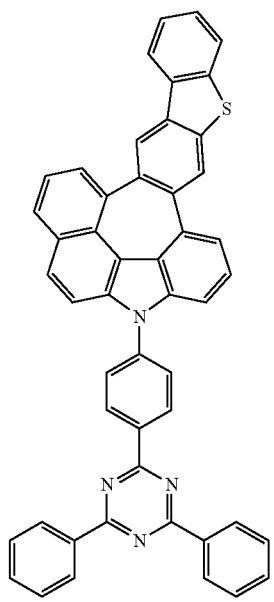

C-392
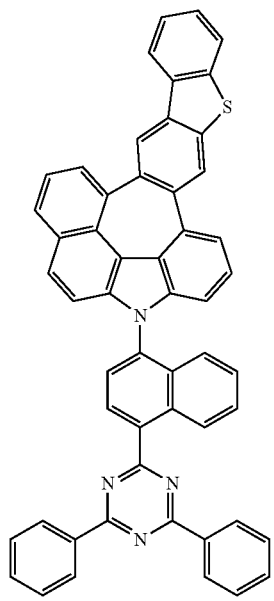
C-394
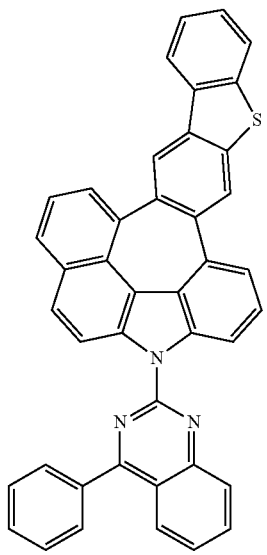
C-393
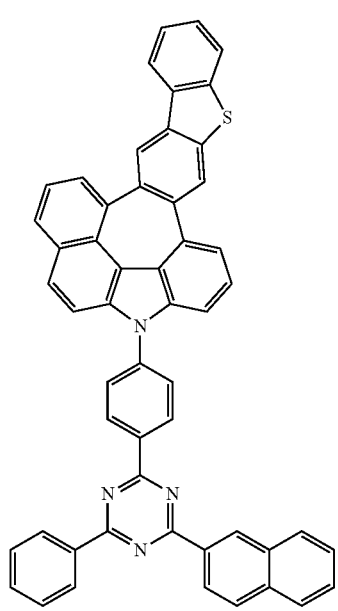
C-395
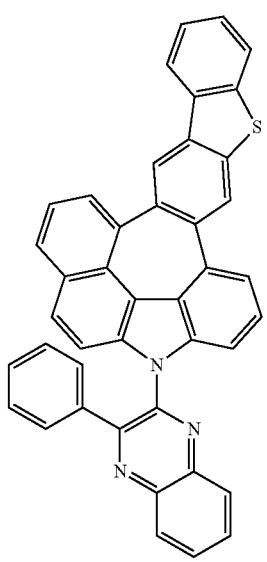

C-396
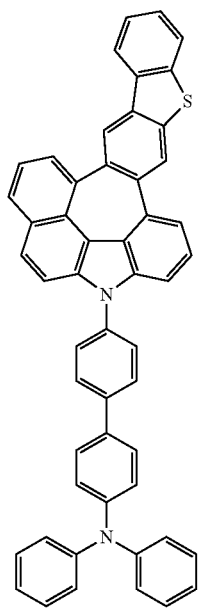
C-397
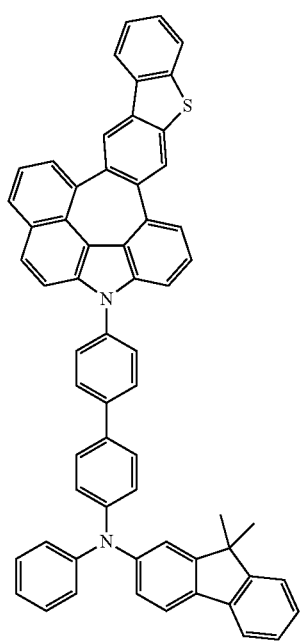
C-398
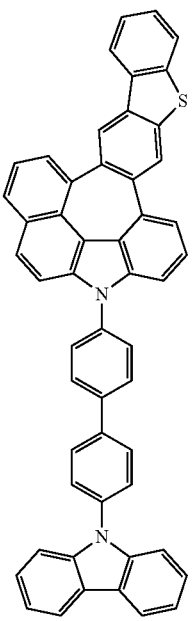
C-399
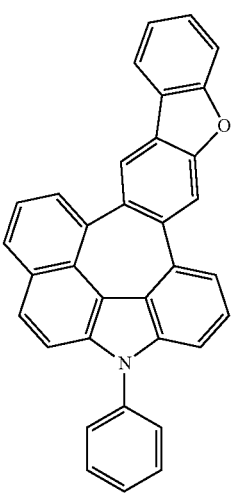
C-400

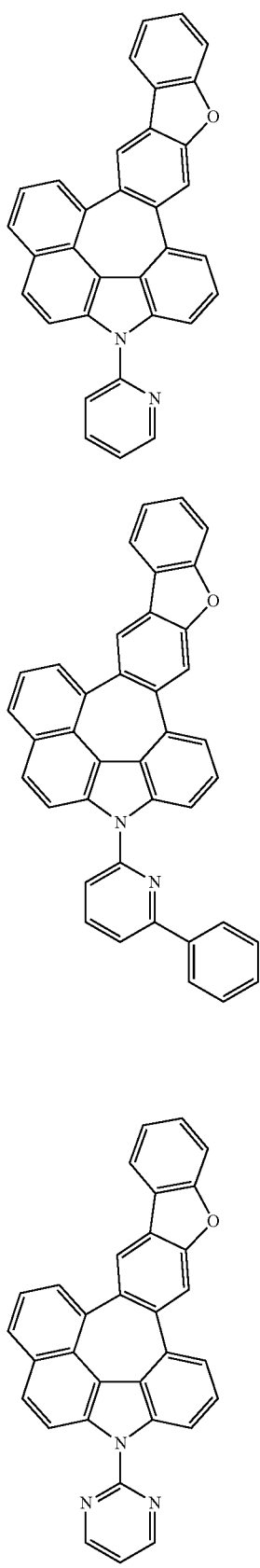

C-406
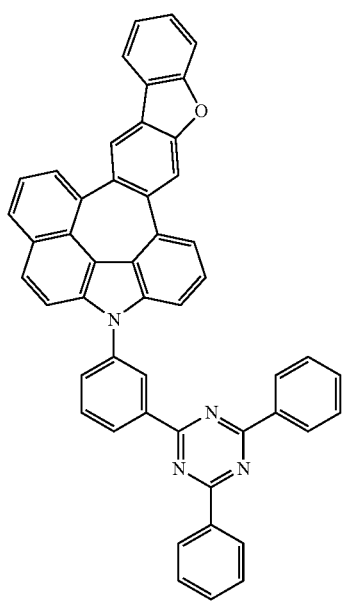
C-407
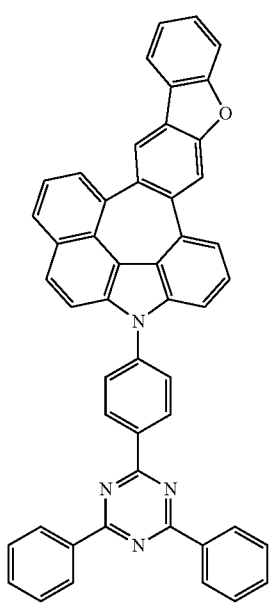
C-408
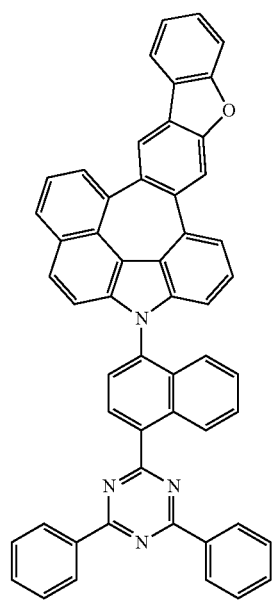
C-409
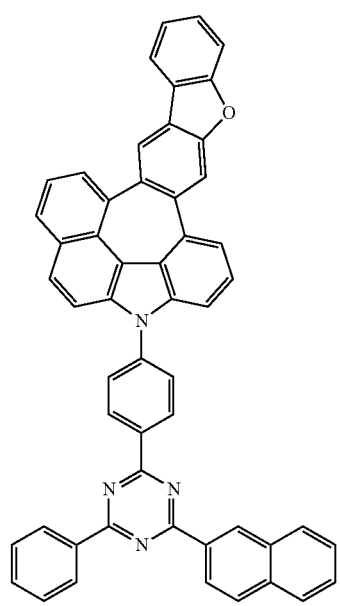

C-410
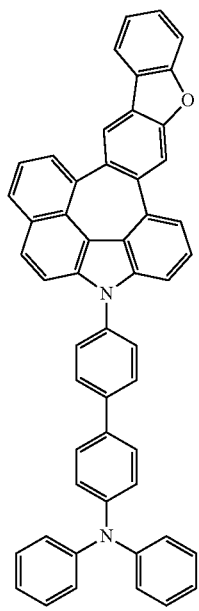
C-411
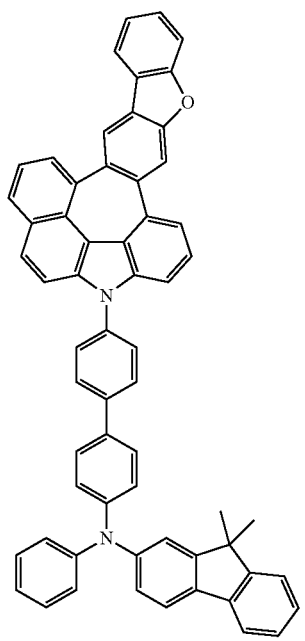
C-412
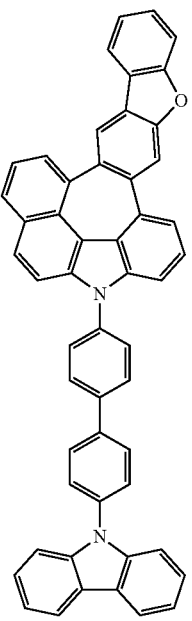
C-413
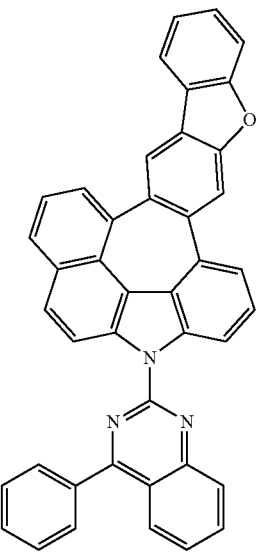

C-414
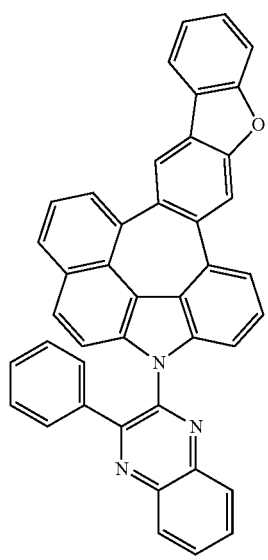
C-415
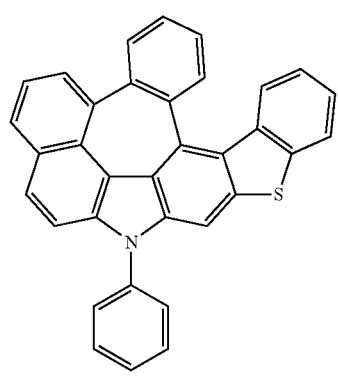
C-416
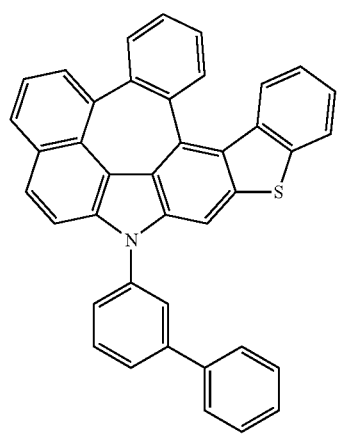
C-417
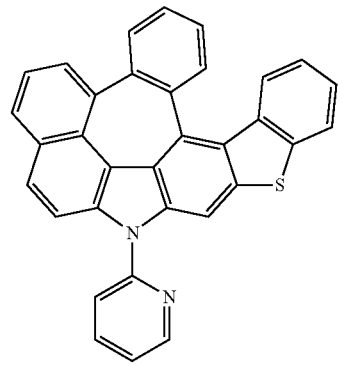
C-418
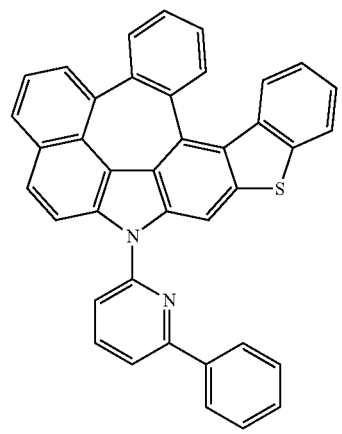
C-419
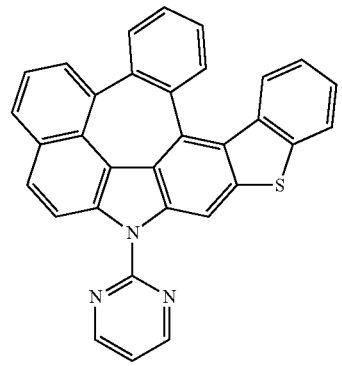
C-420
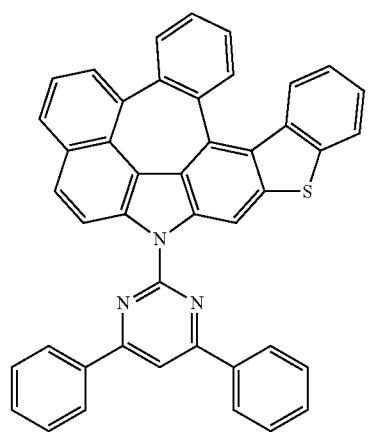

C-421
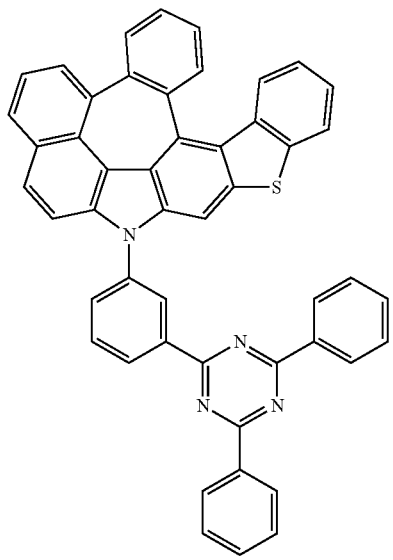
C-422
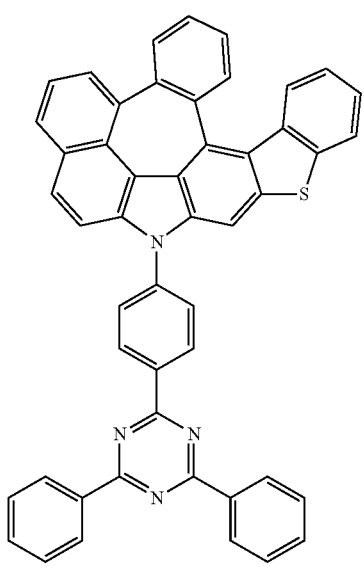
C-423
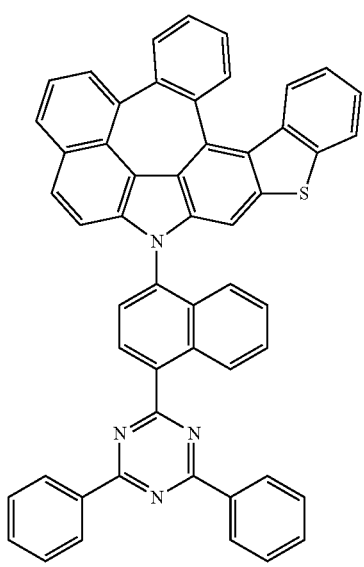
C-424
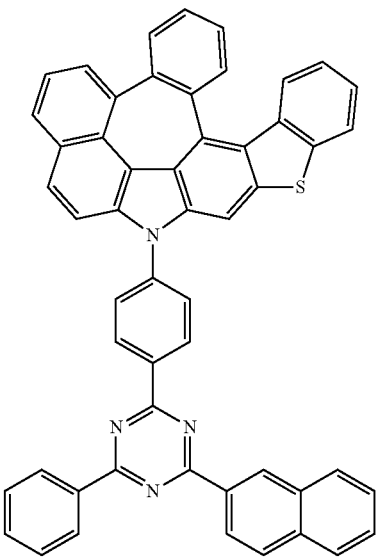
C-425
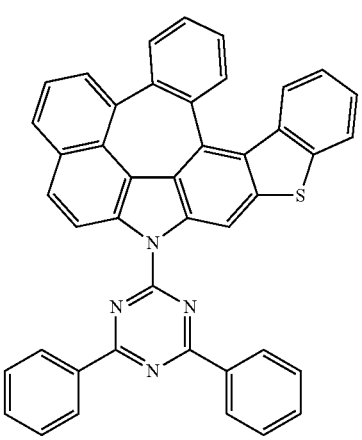
C-426
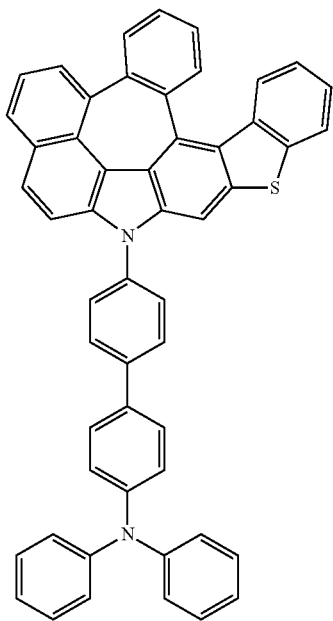

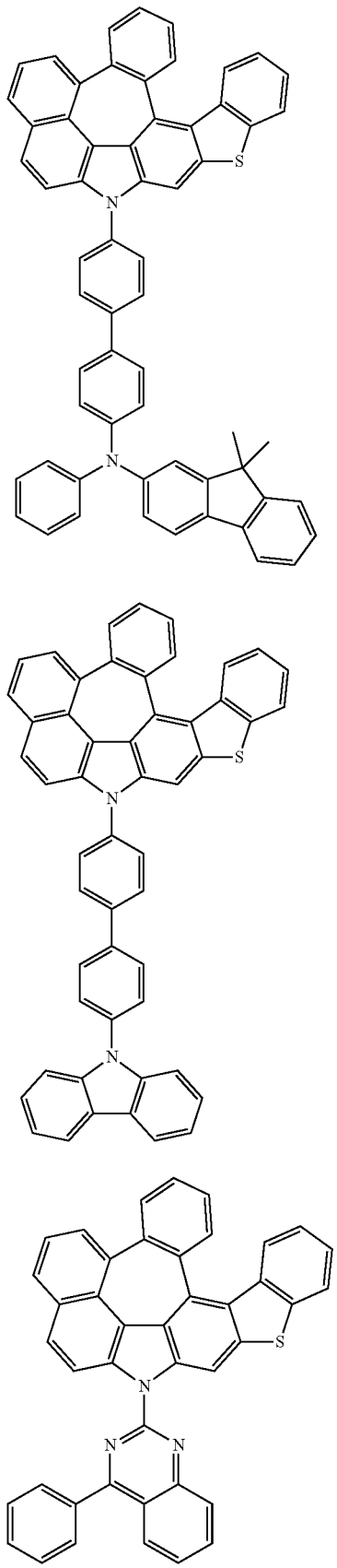
C-427
C-428
C-429
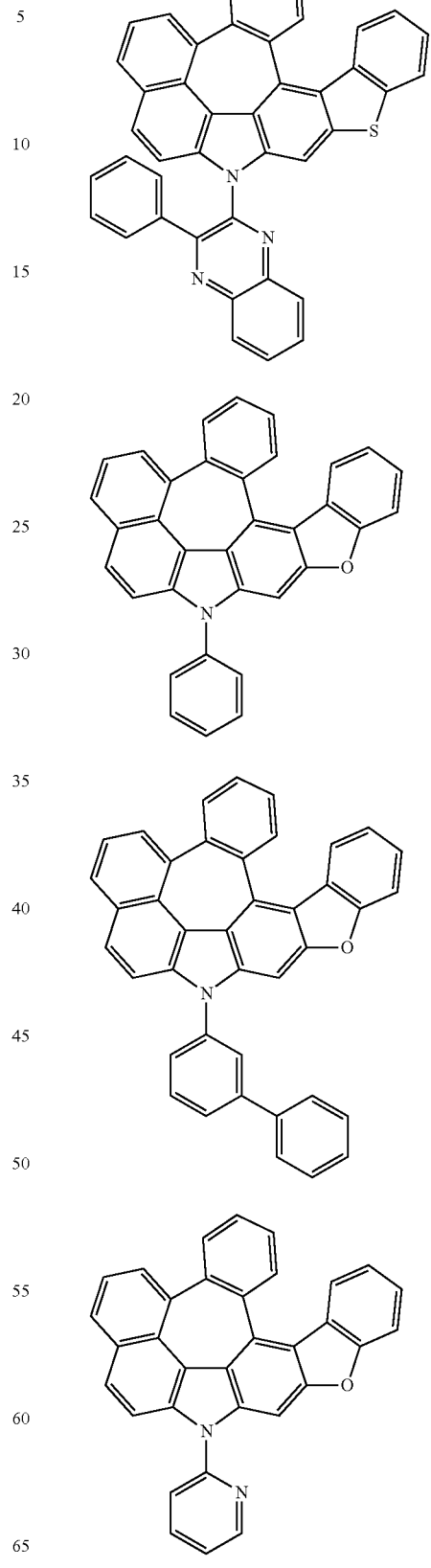
C-430
C-431
C-432
C-433

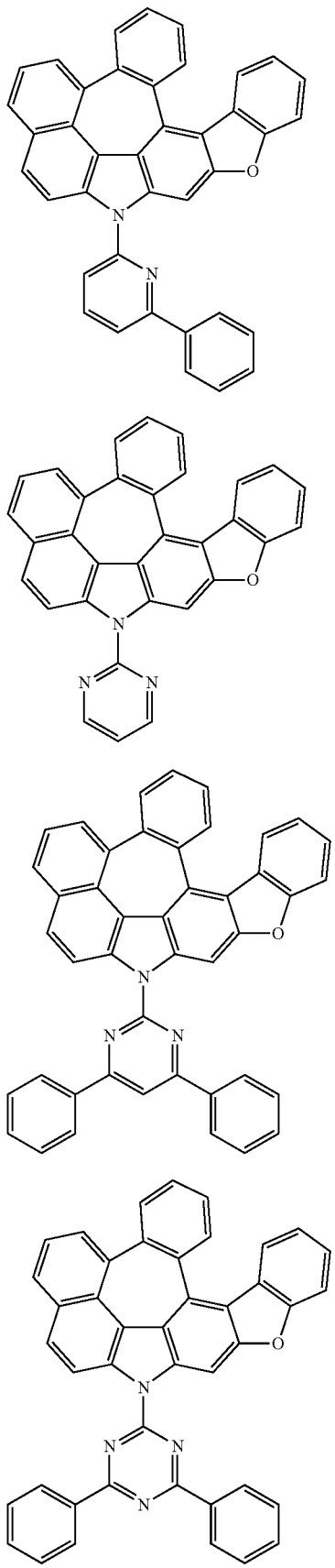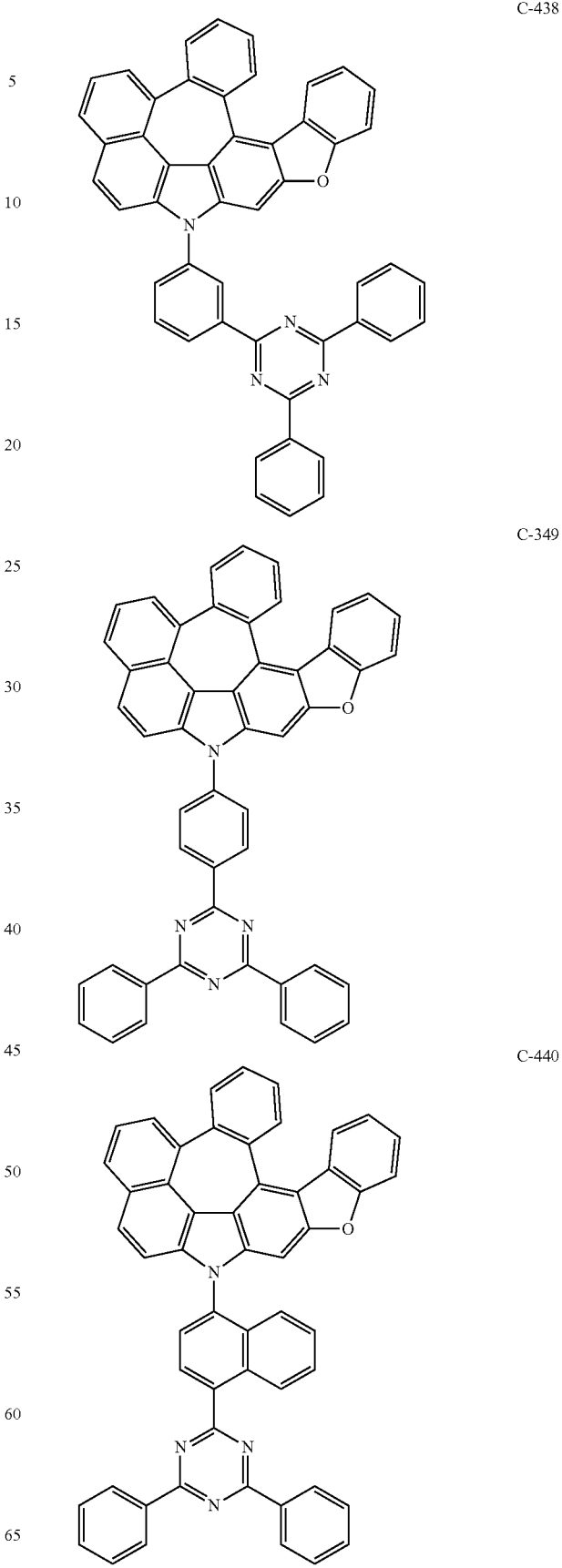

C-441
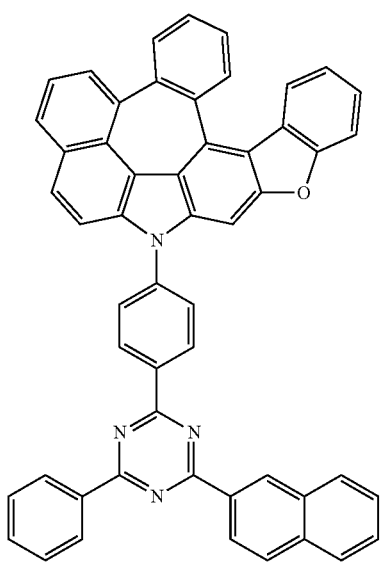
C-442
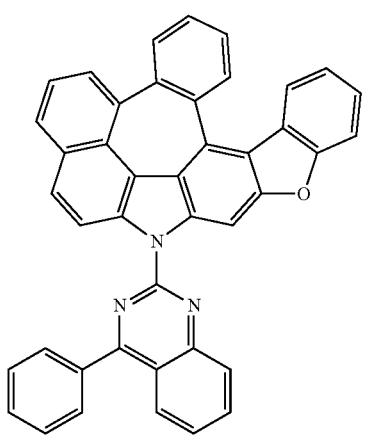
C-443
C-444
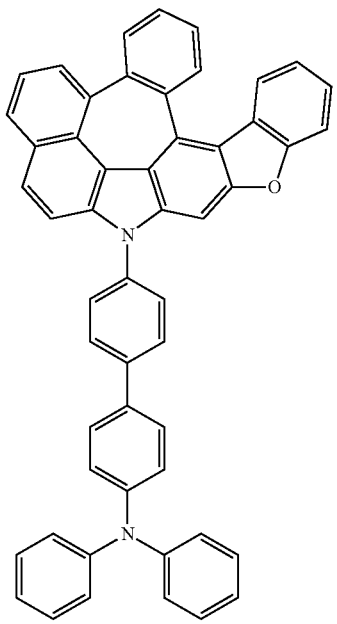
C-445
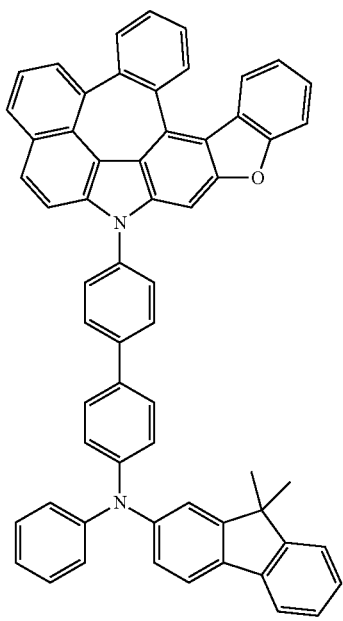

C-446
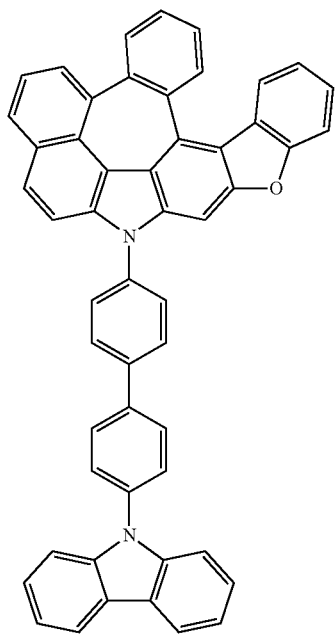
C-447
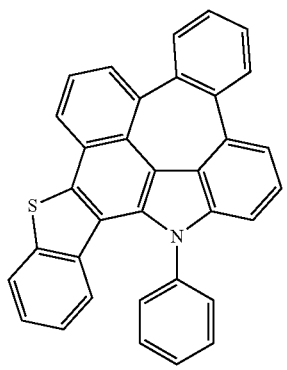
C-448
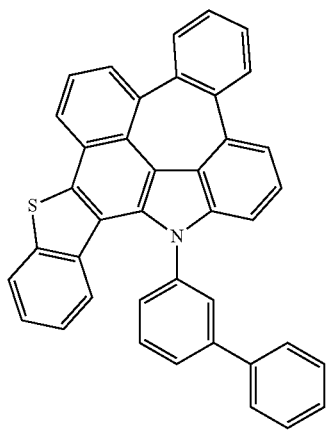
C-449
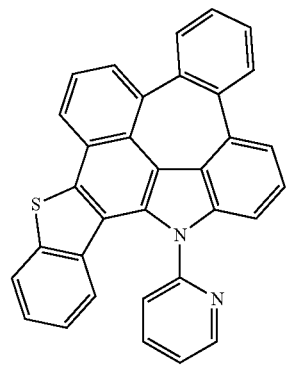
C-450
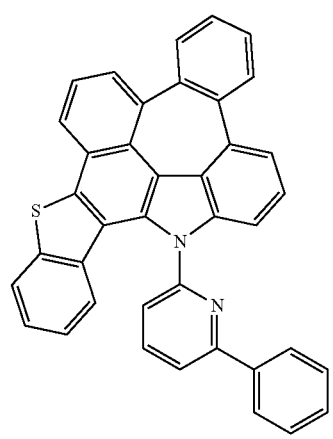
C-451
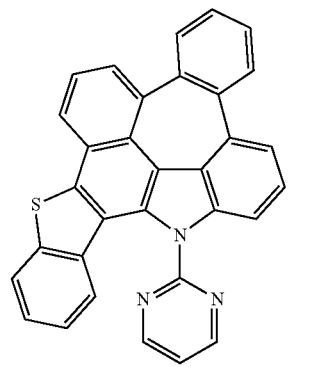
C-452
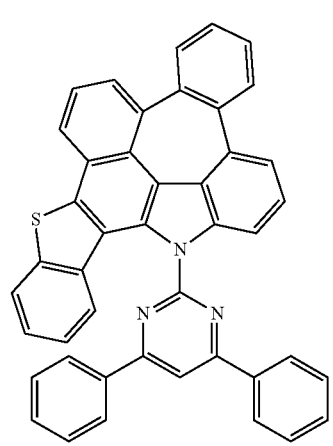

C-453
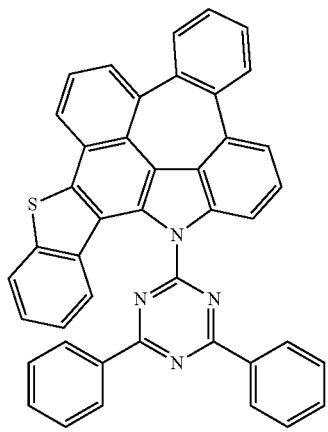
C-454
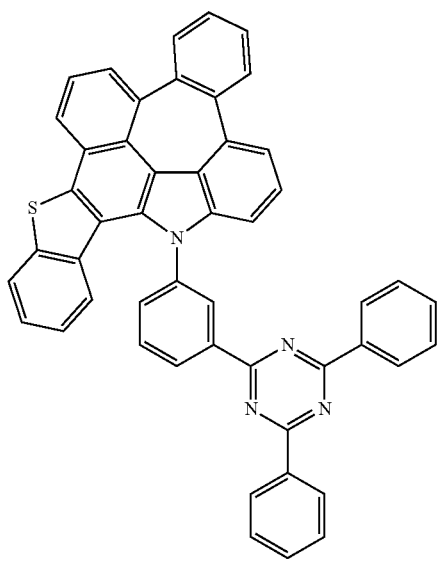
C-455
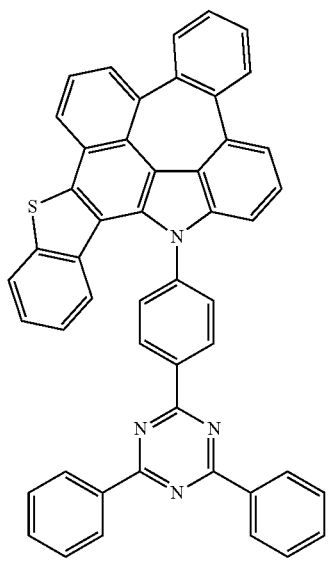
C-456
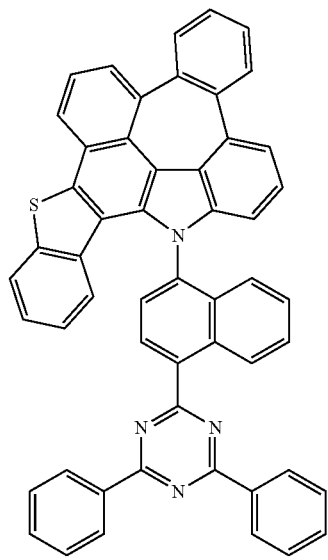
C-457
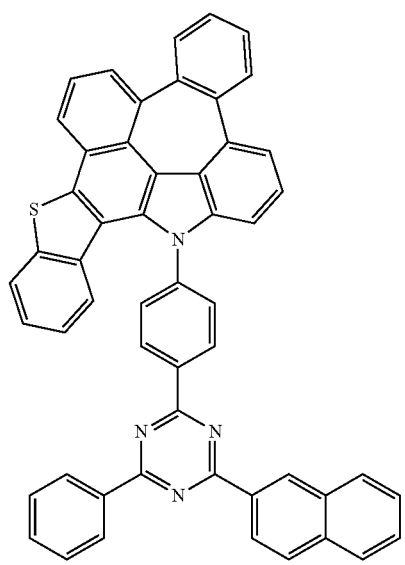
C-458
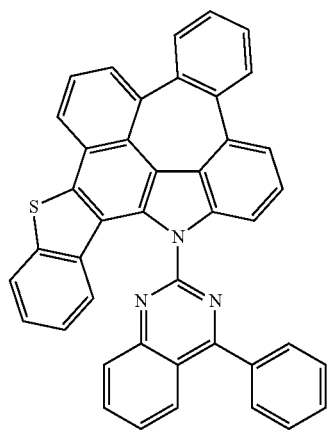

C-459
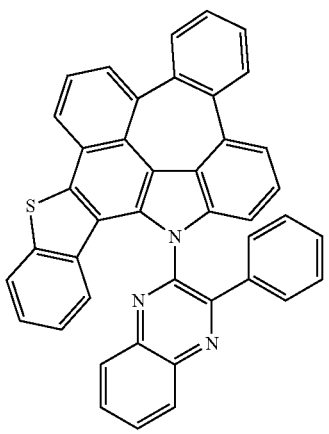
C-460
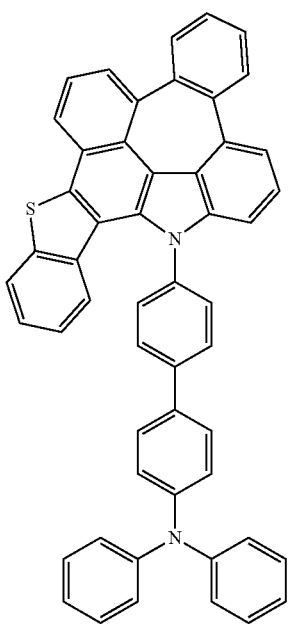
C-461
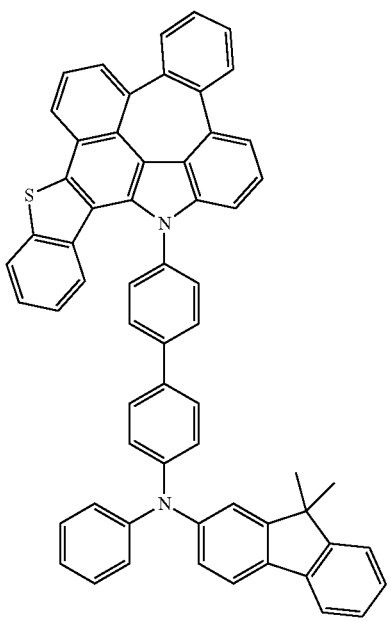
C-462
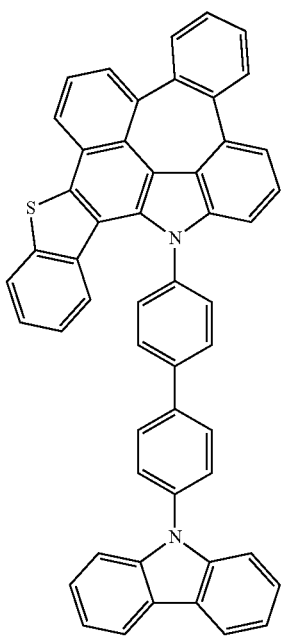
C-463
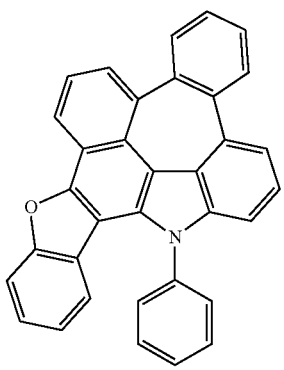
C-464
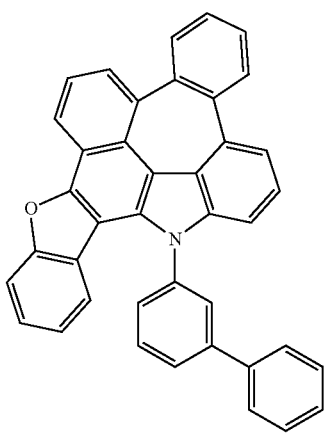

-continued
C-465
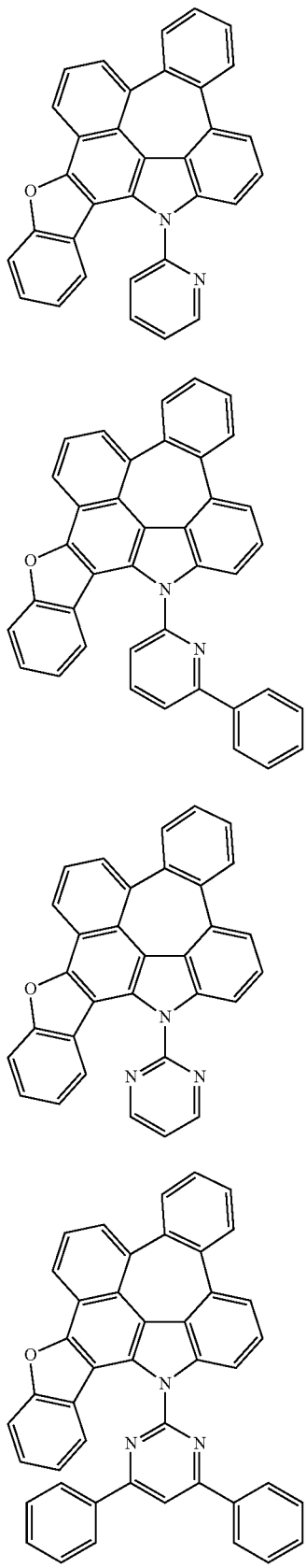
C-466
C-467
C-468
-continued
C-469
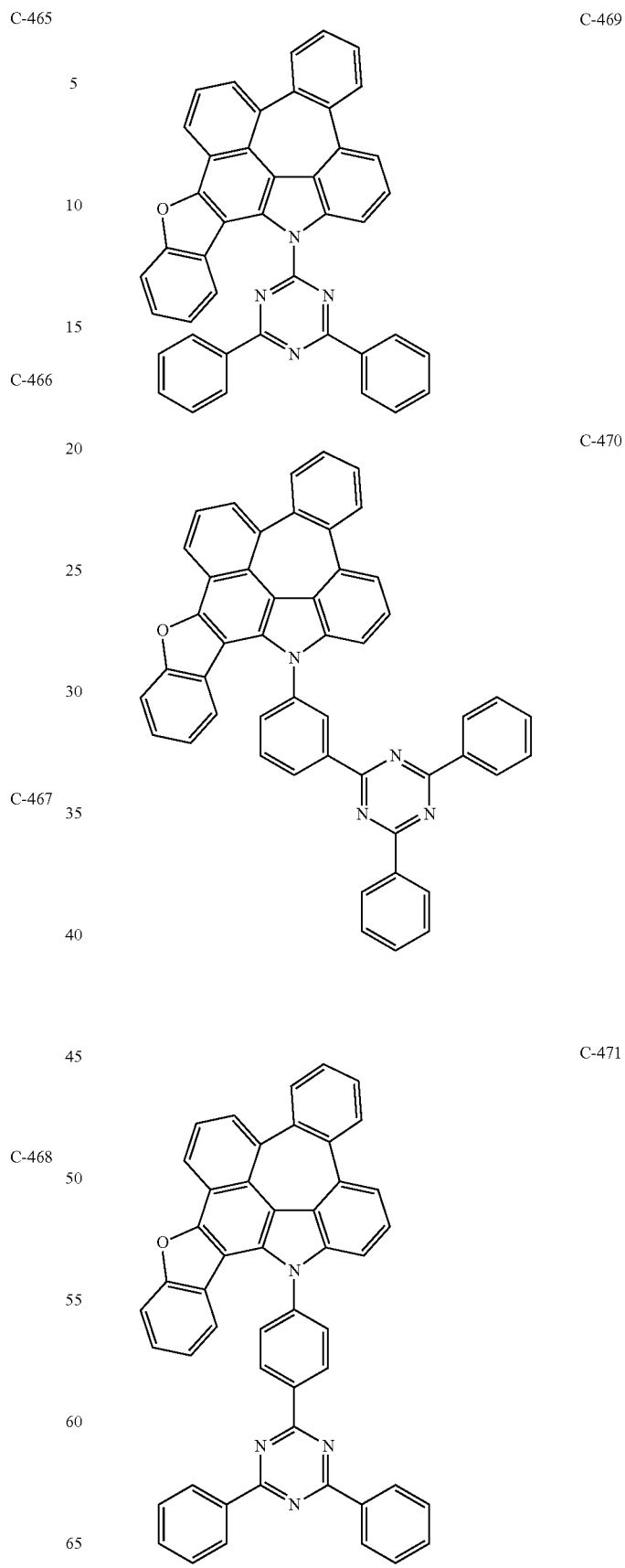
C-470
C-471

C-472
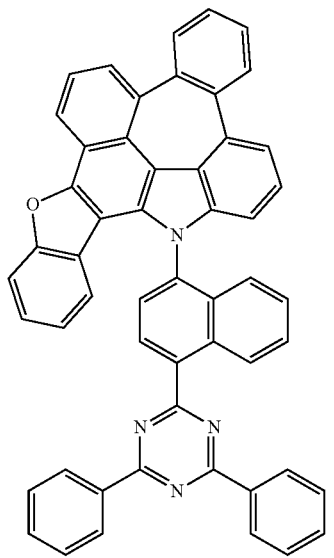
C-473
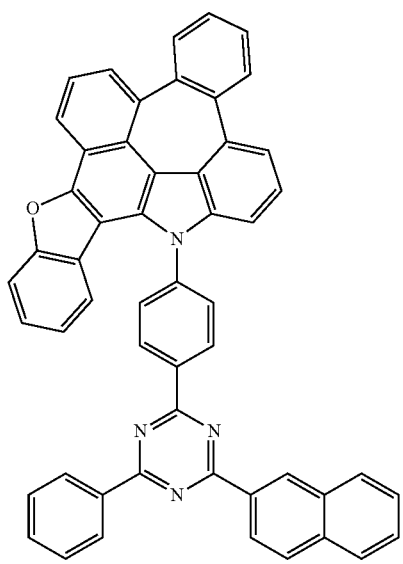
C-474
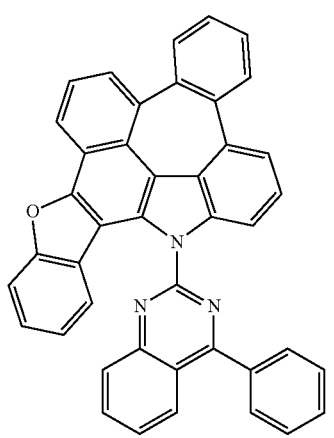
C-475
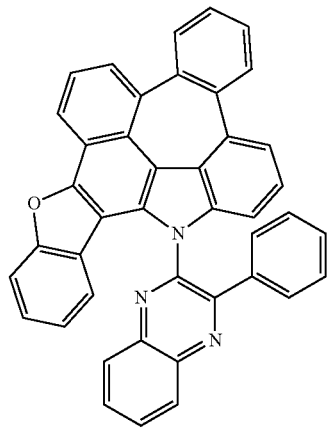
C-476
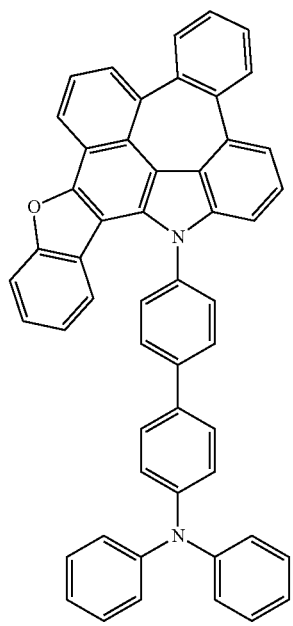
C-477
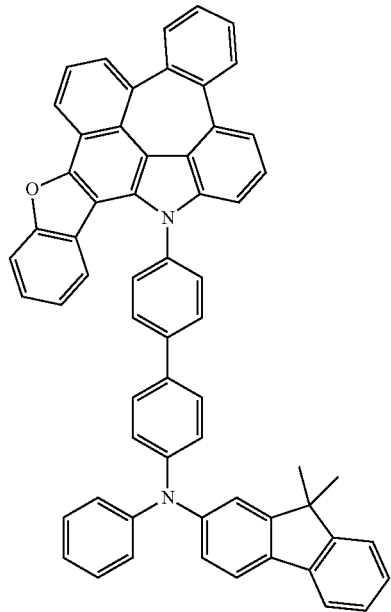

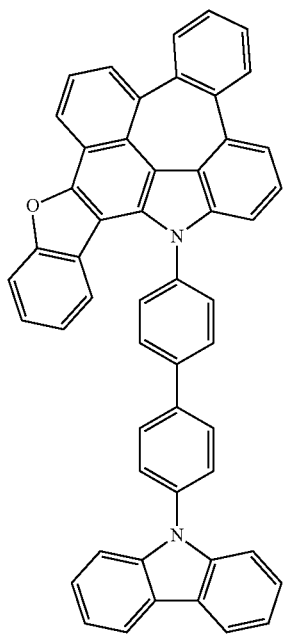
C-478
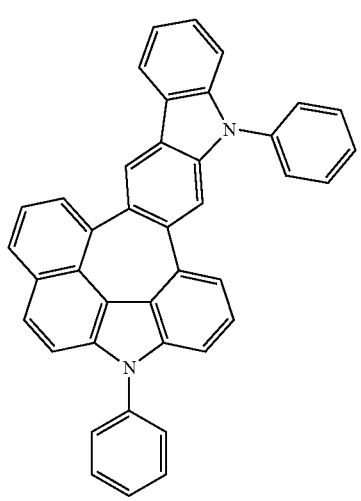
C-479
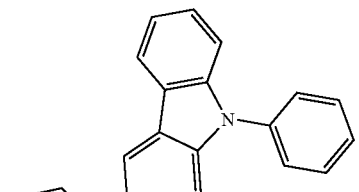
C-480
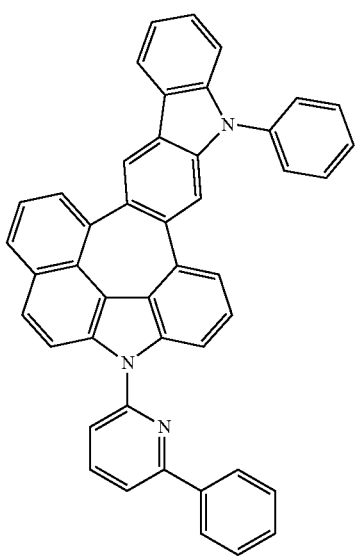
C-481
C-482

C-483
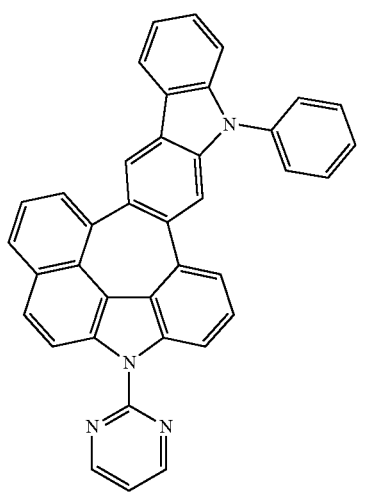
C-484
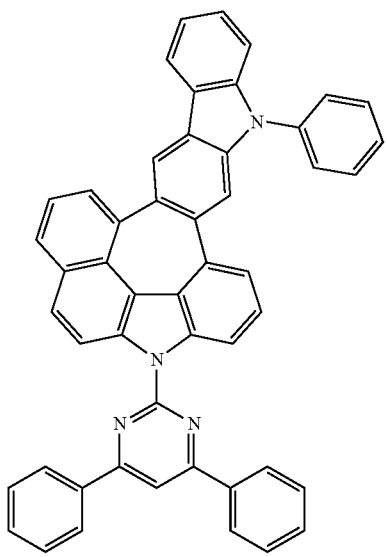
C-485
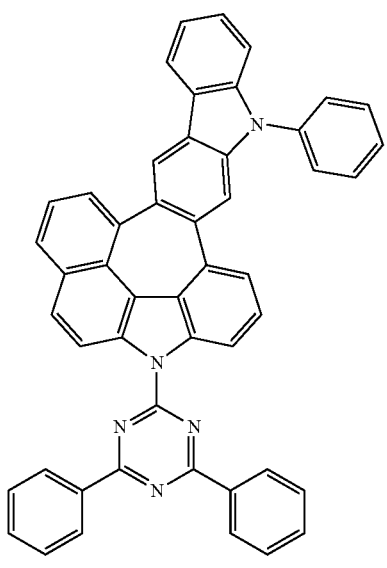
C-486
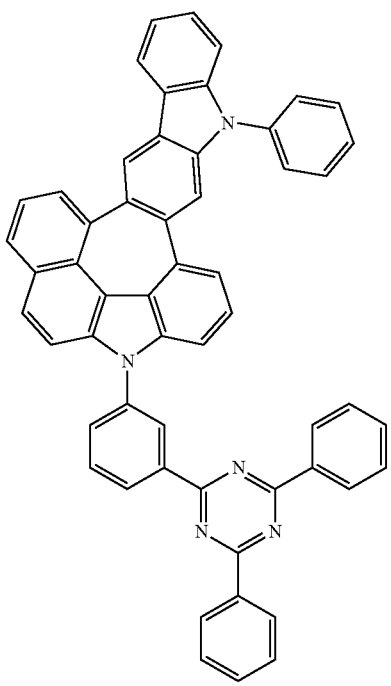
C-487
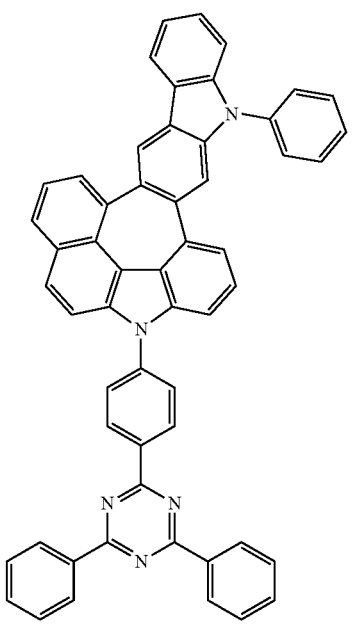

C-488
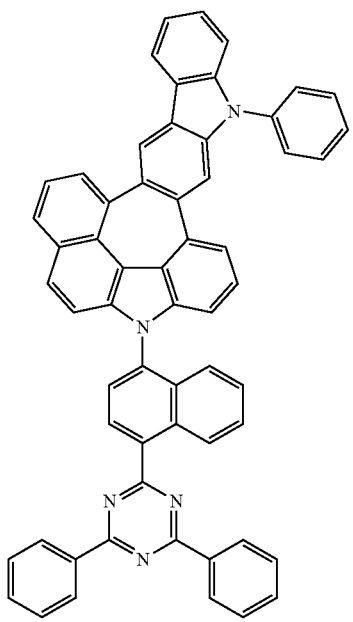
C-489
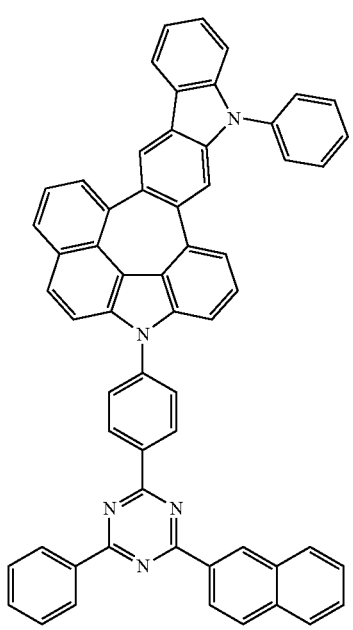
C-490
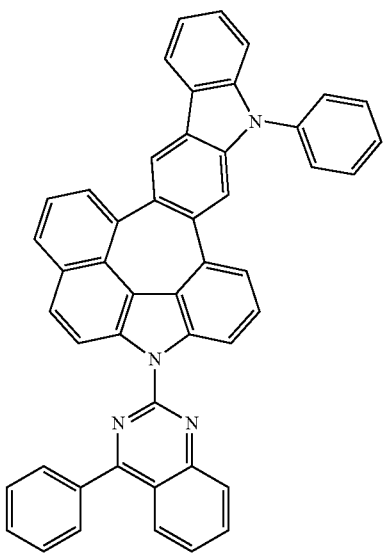
C-491
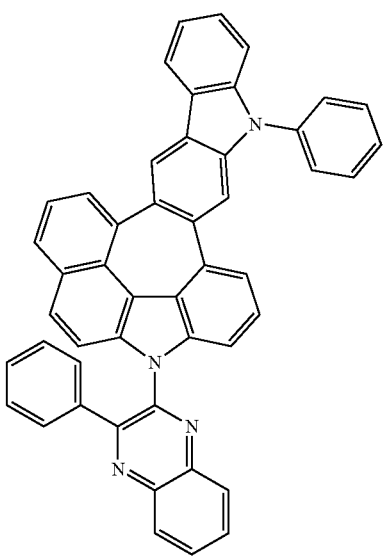

C-492
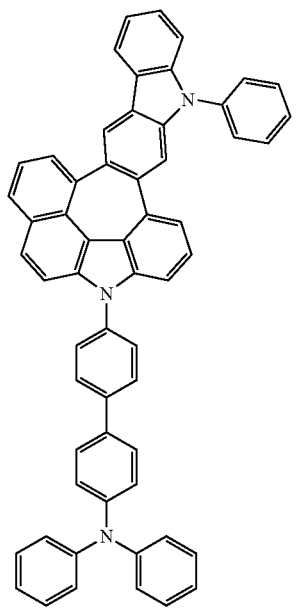
C-493
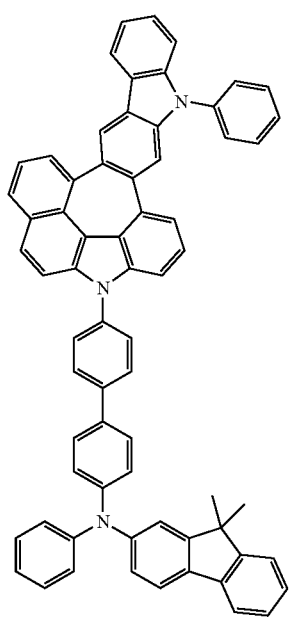
C-494
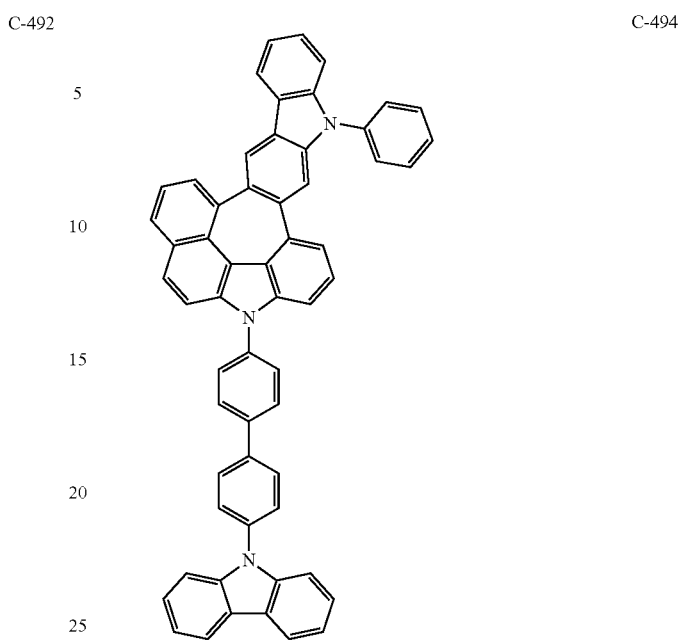
C-495
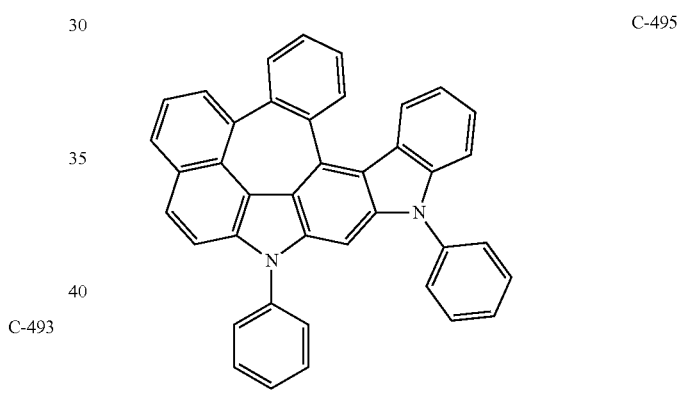
C-496
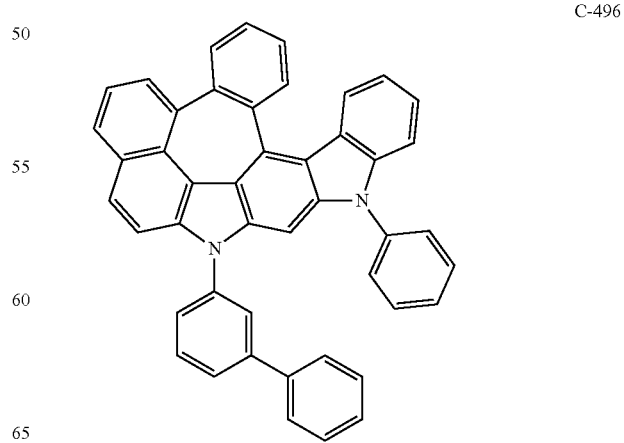

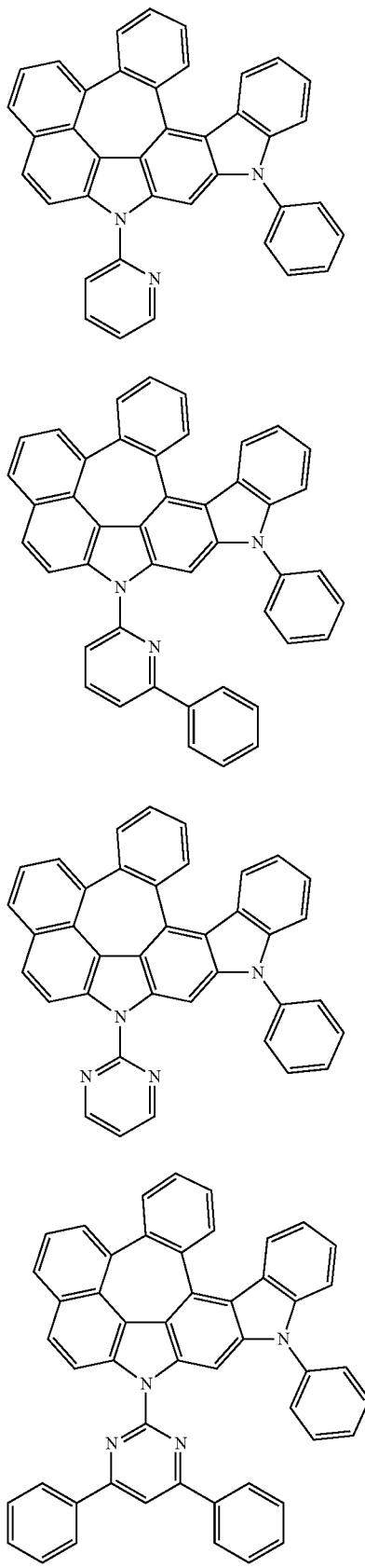
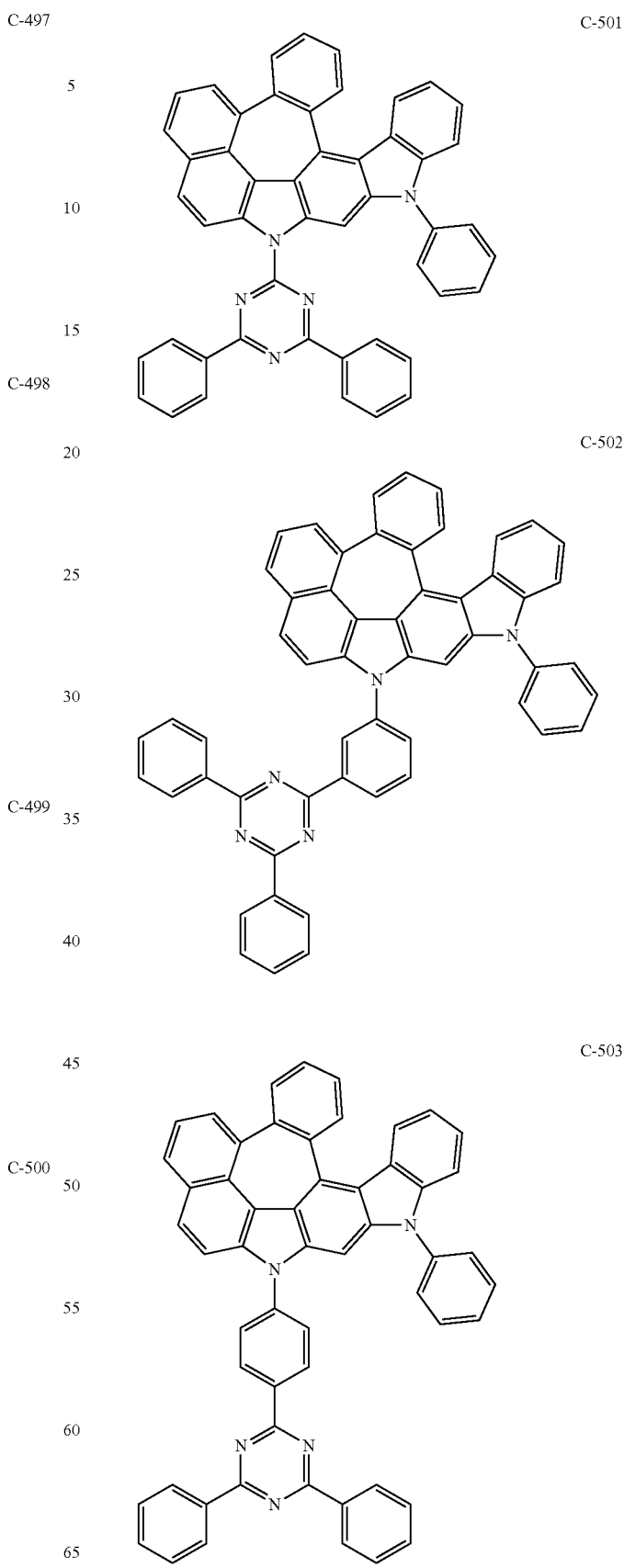

C-504
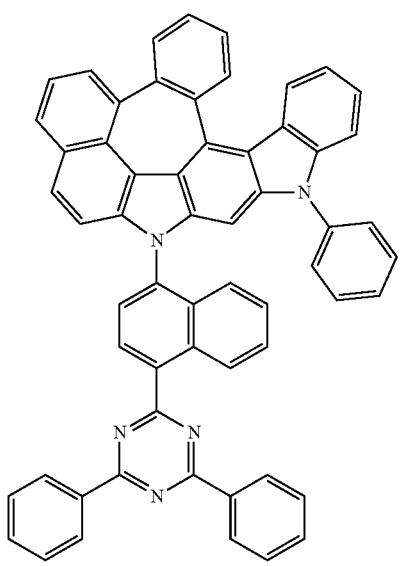
C-505
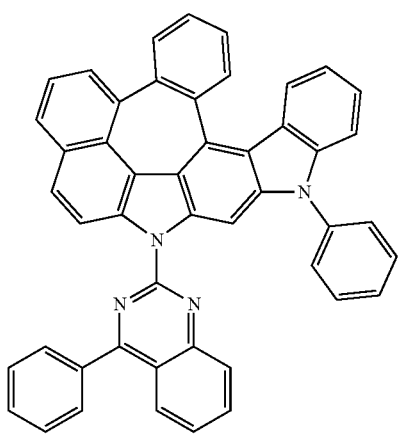
C-506
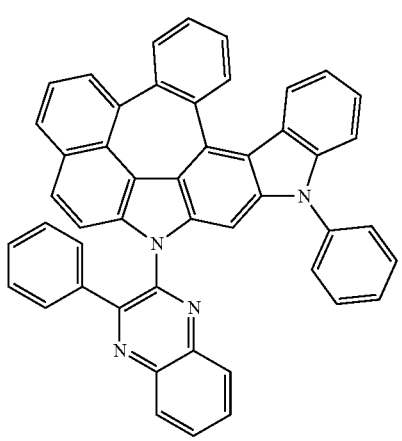
C-507
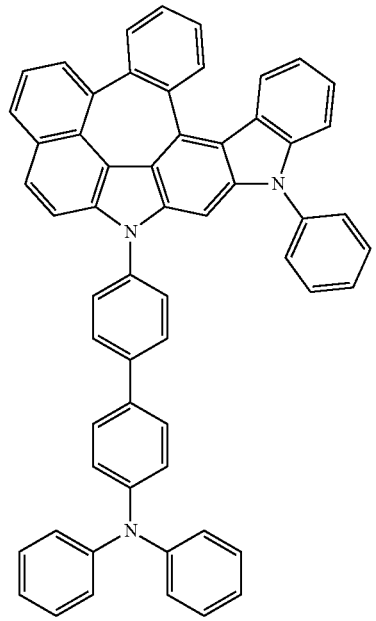
C-508
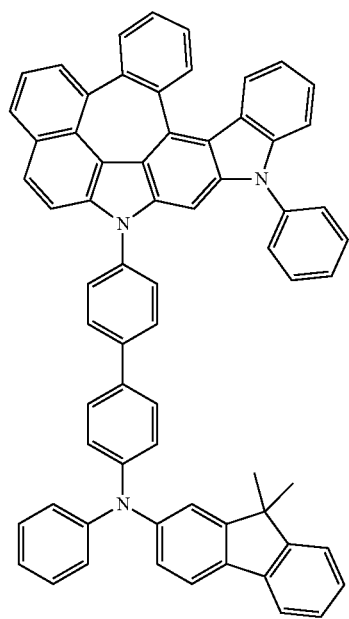

C-509
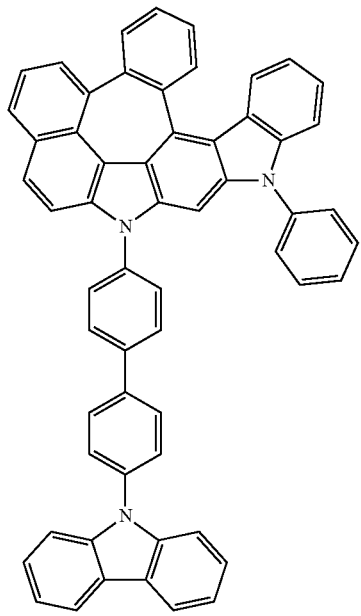
C-510
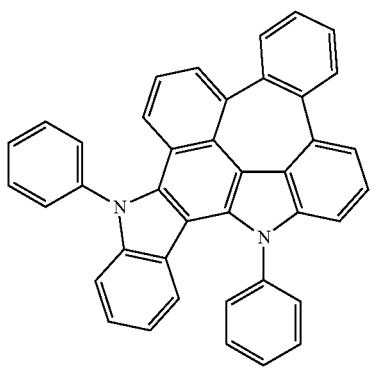
C-511
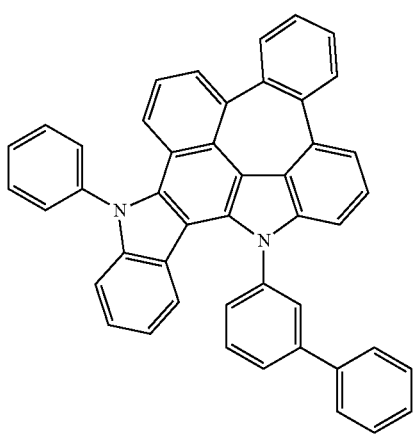
C-512
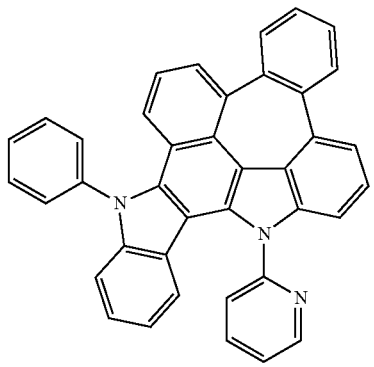
C-513
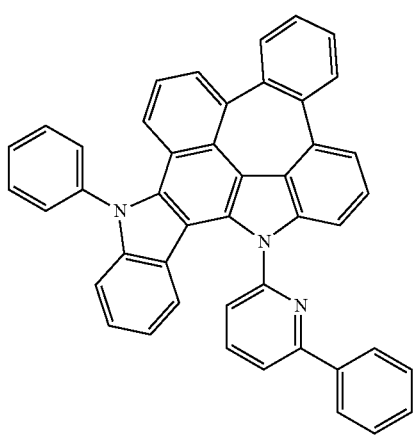
C-514
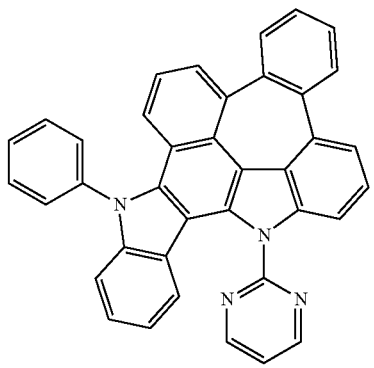
C-515
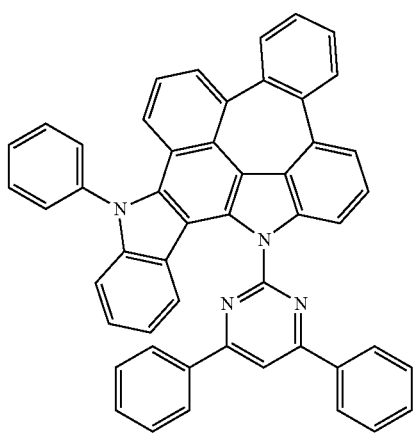

C-516
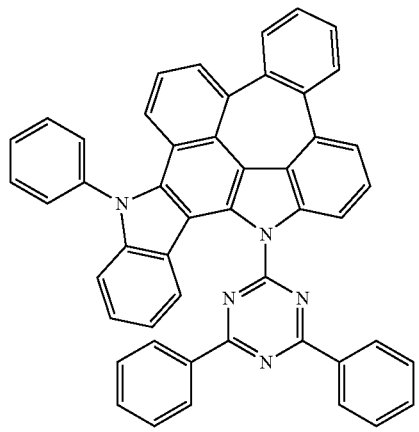
C-517
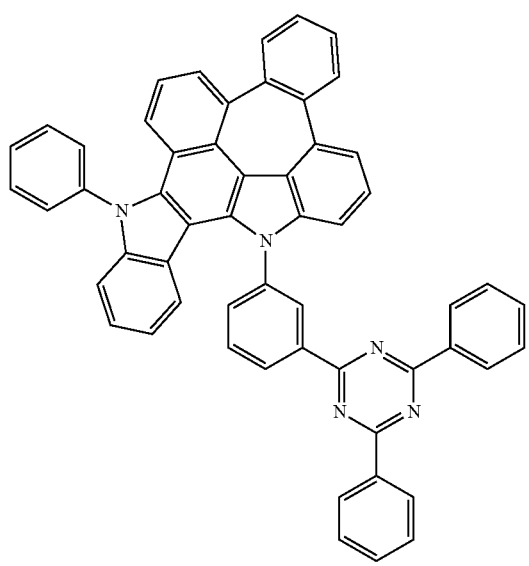
C-518
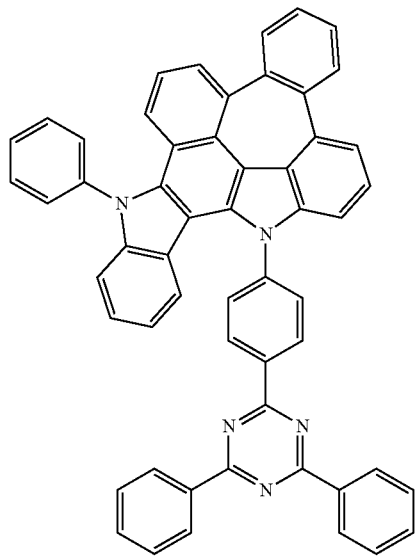
C-519
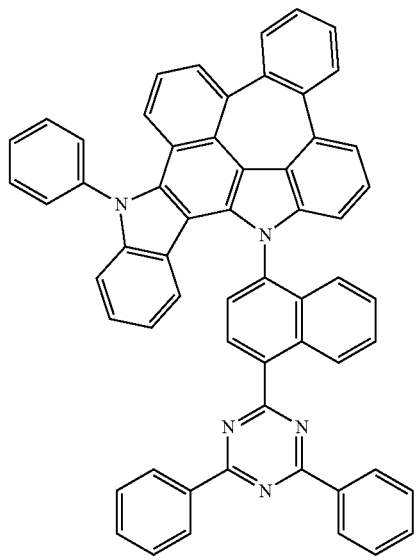
C-520
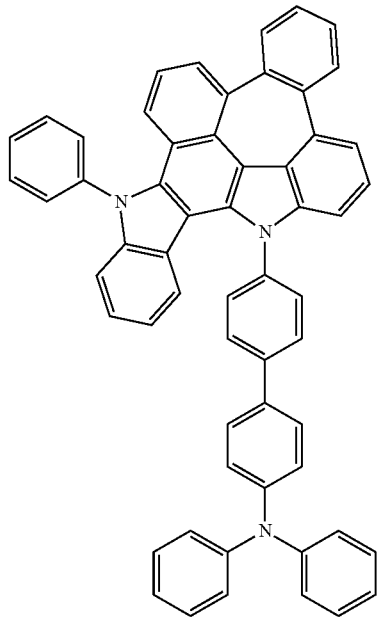

C-521
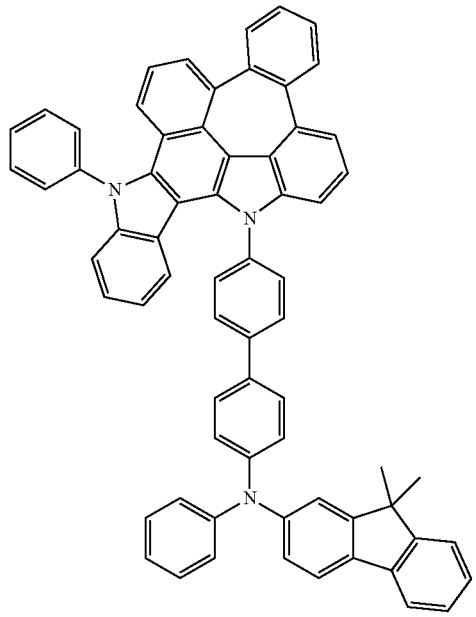
C-522
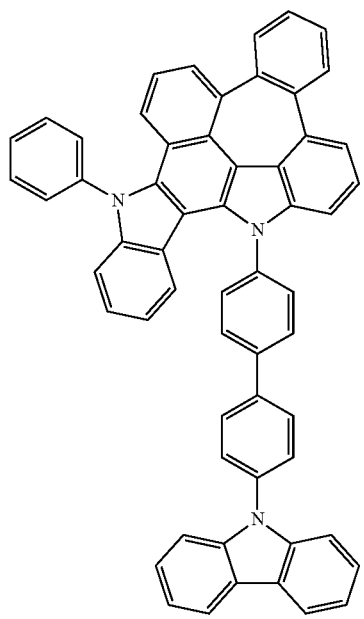
C-523
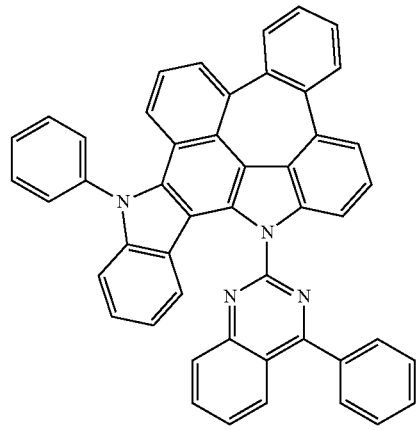
C-524
C-525
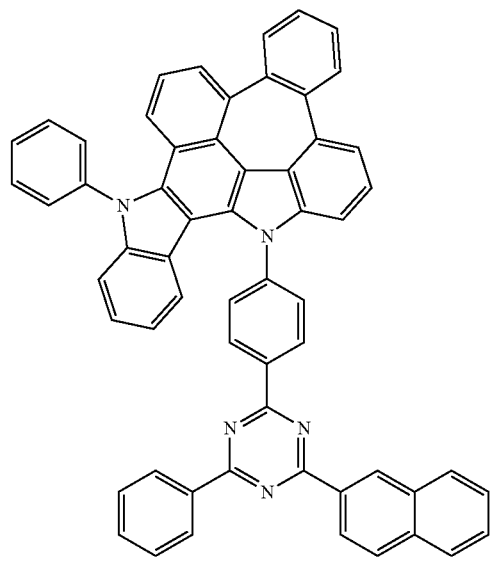

C-526
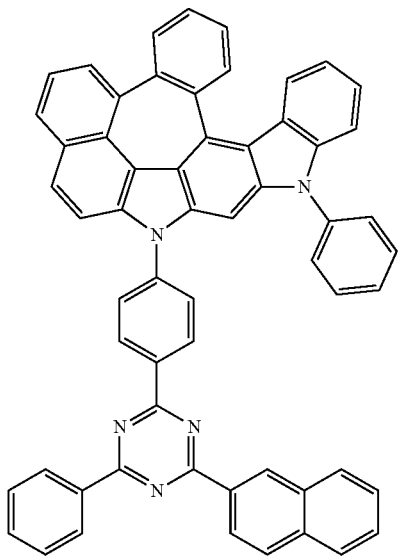
C-529
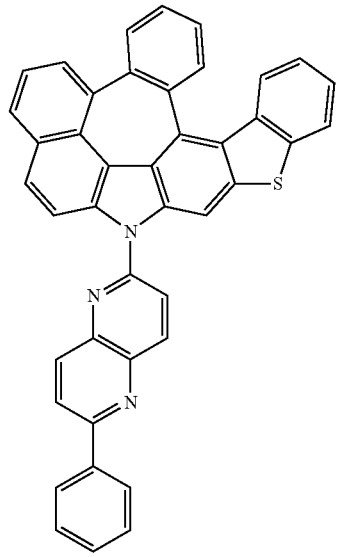
C-527
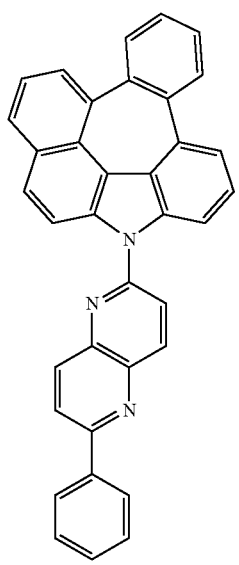
C-530
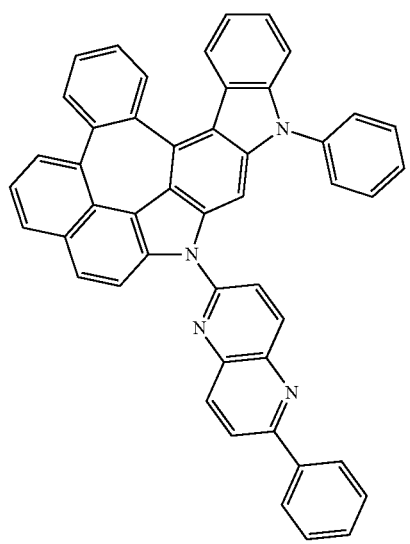
C-528
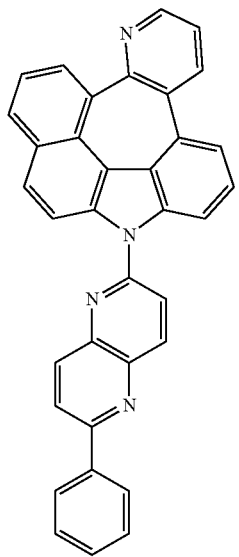
C-531
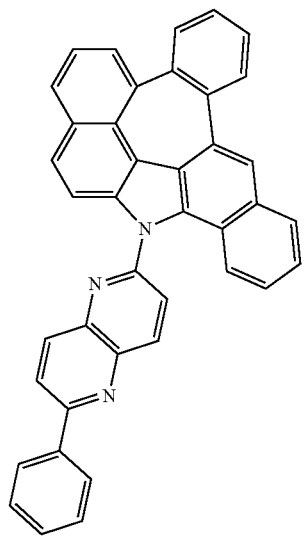

-continued
C-532
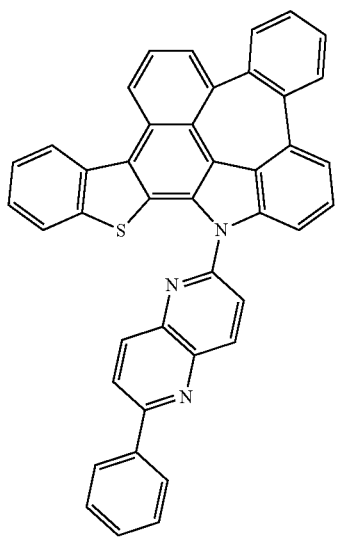
C-533
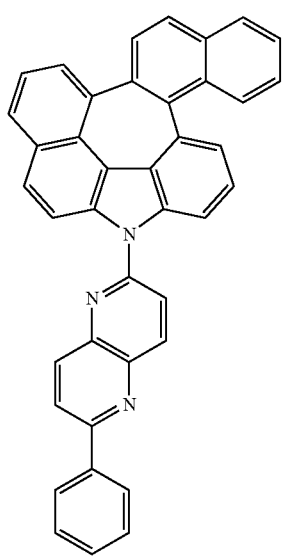
C-534
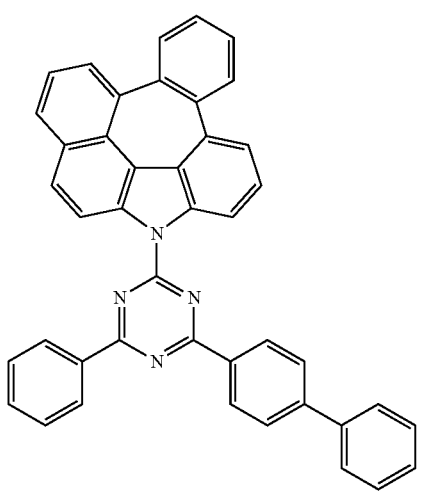
-continued
C-535
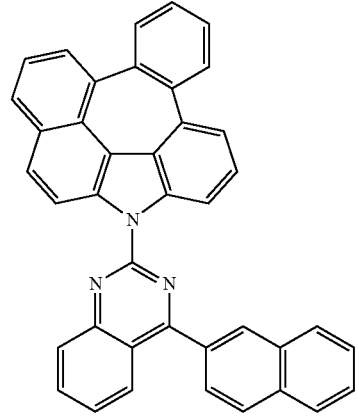
C-536
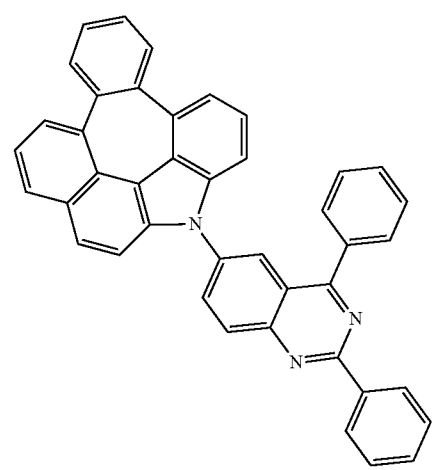
C-537
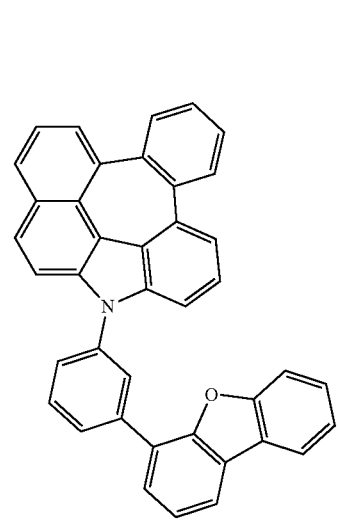

C-538
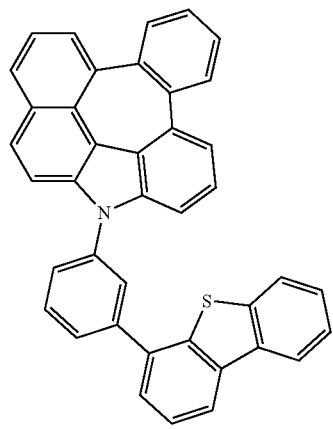
C-539
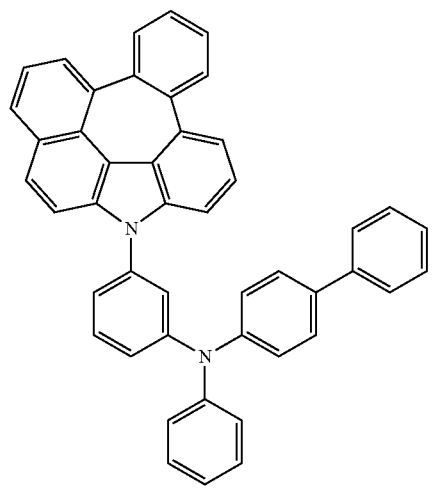
C-540
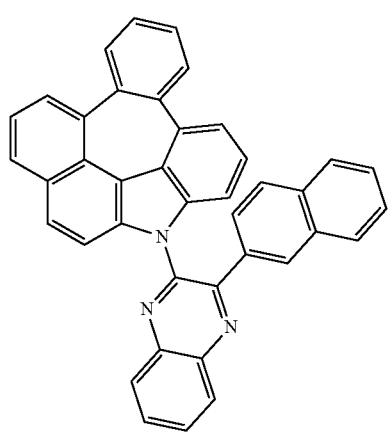
C-541
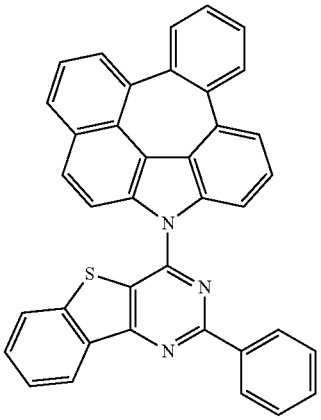
C-542
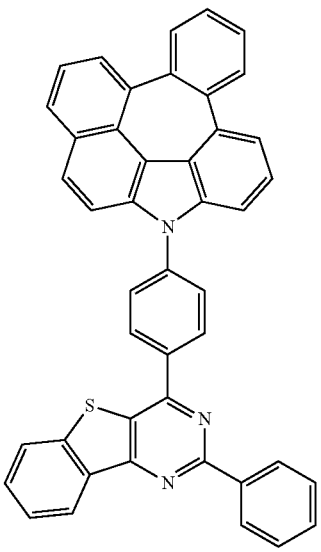
C-543
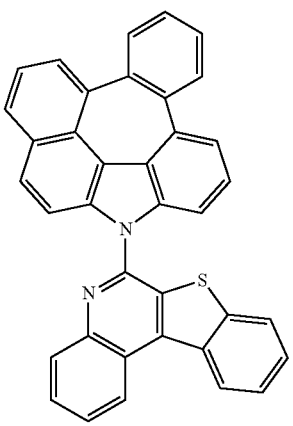

-continued
C-544
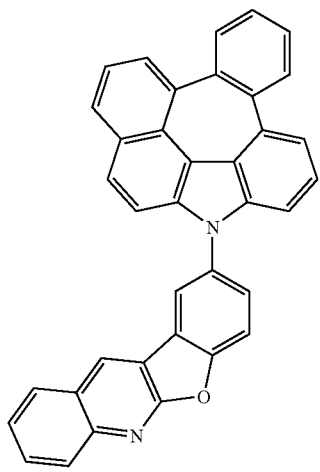
C-545
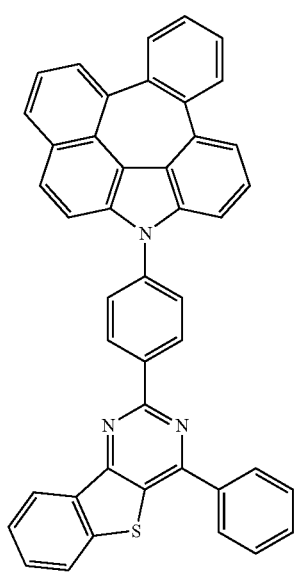
C-546
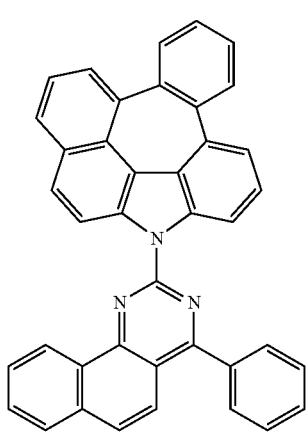
-continued
C-547
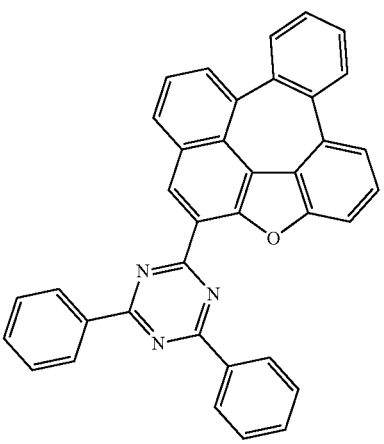
C-548
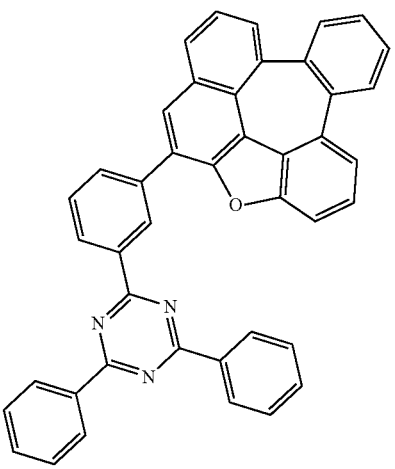
C-549
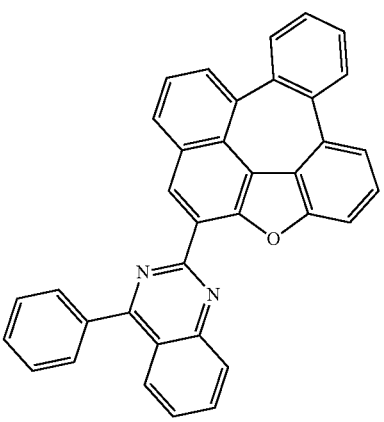

C-550
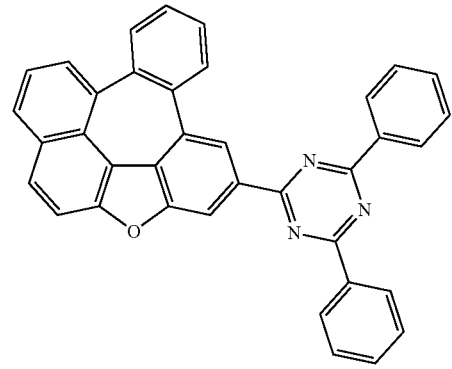
C-551
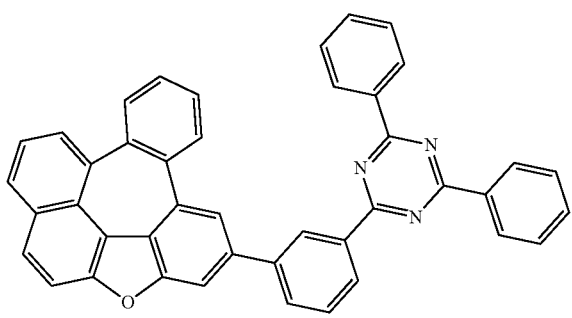
C-552
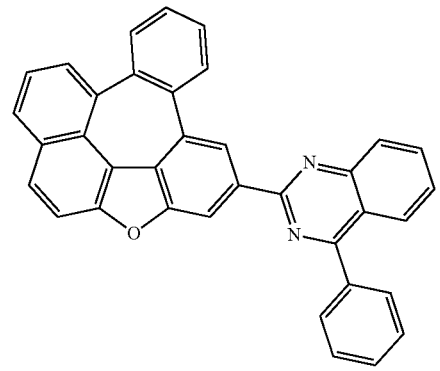
C-553
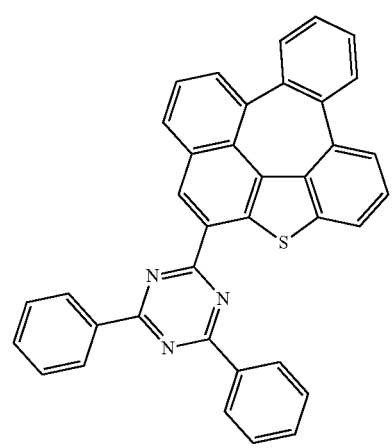
C-554
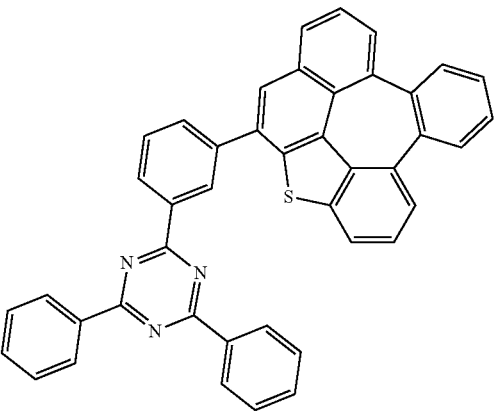
C-555
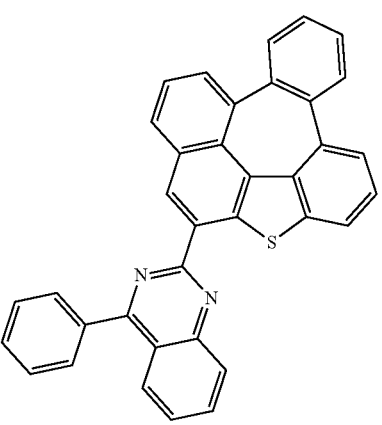
C-556
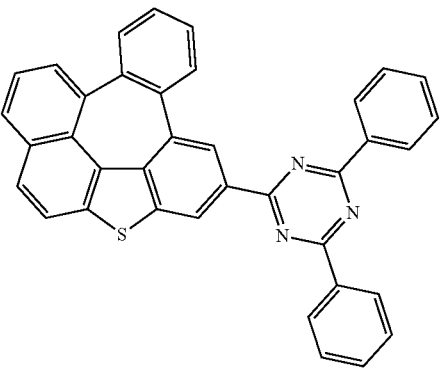
C-557
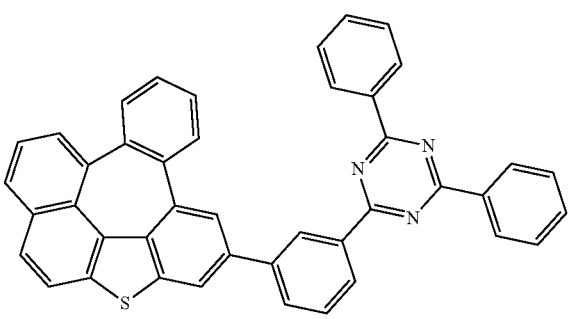

-continued
C-558
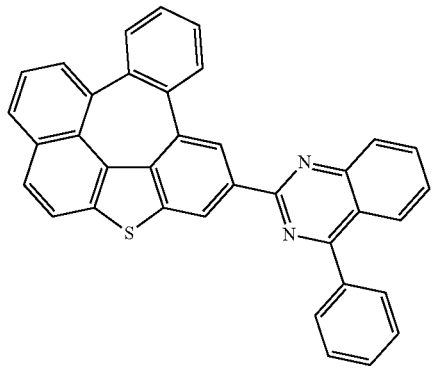
C-559
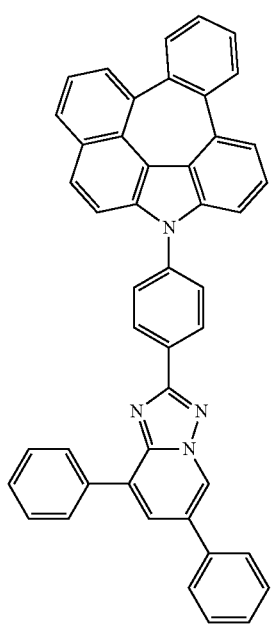
C-560
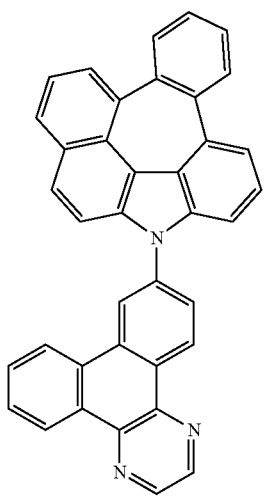
-continued
C-561
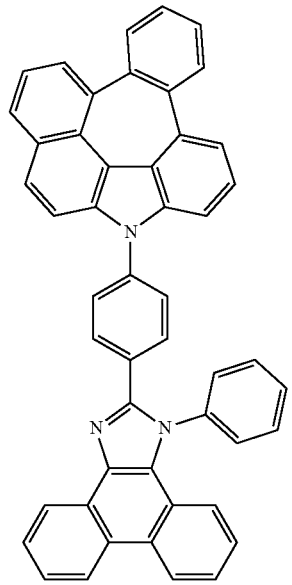
C-562
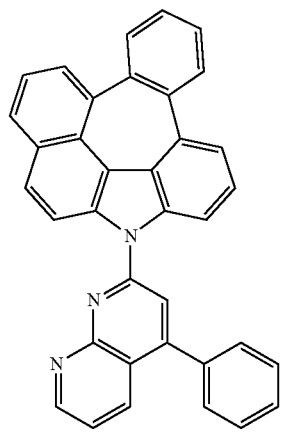
C-563
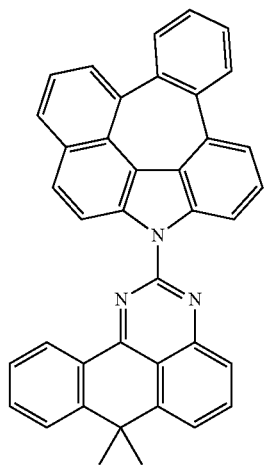

C-564
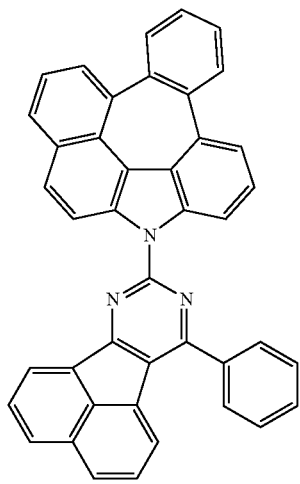
C-565
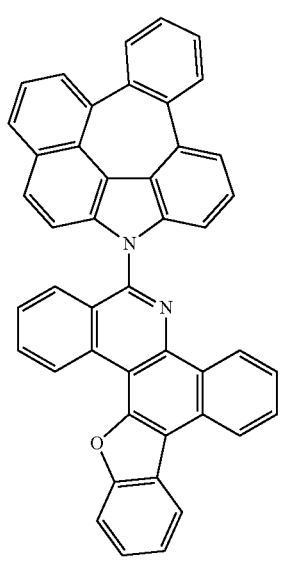
C-566
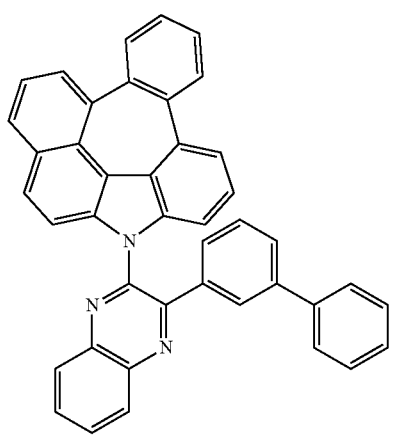
C-567
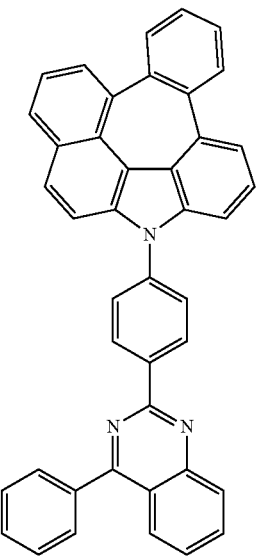
C-568
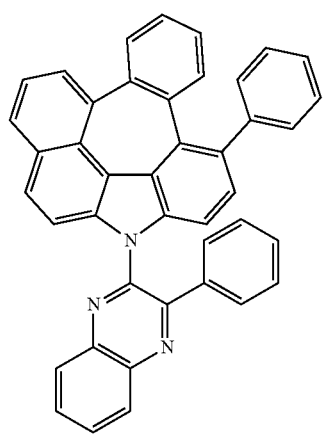
C-569
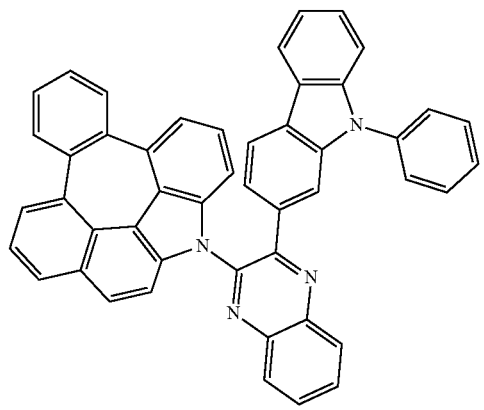

C-570
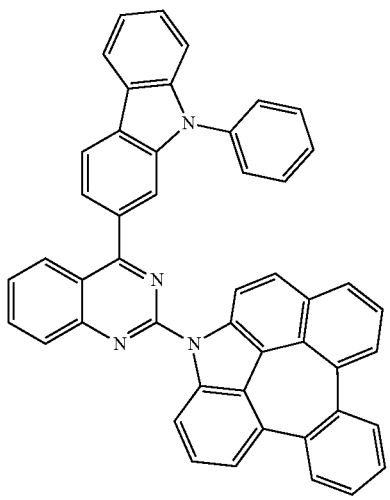
The arylamine derivative satisfying the equation 11 may be specifically exemplified by the following compounds, but is not limited thereto.
HT-2-1
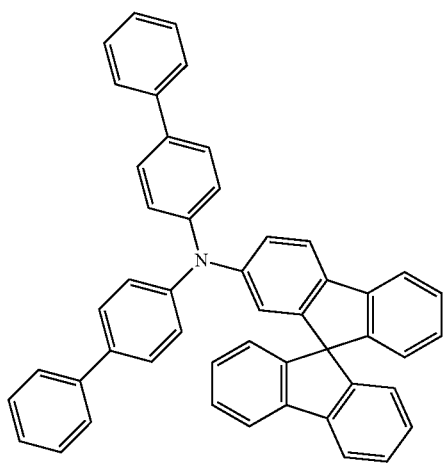
HT-2-2
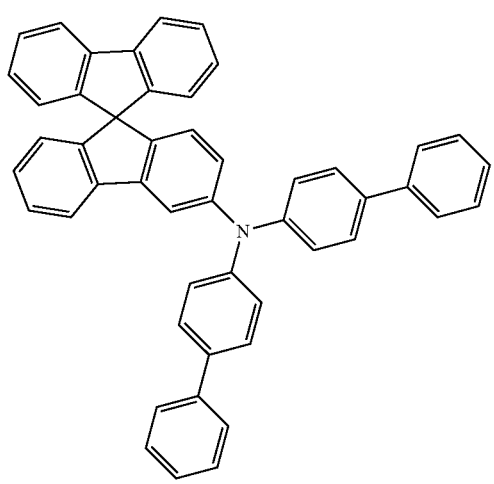
HT-2-3
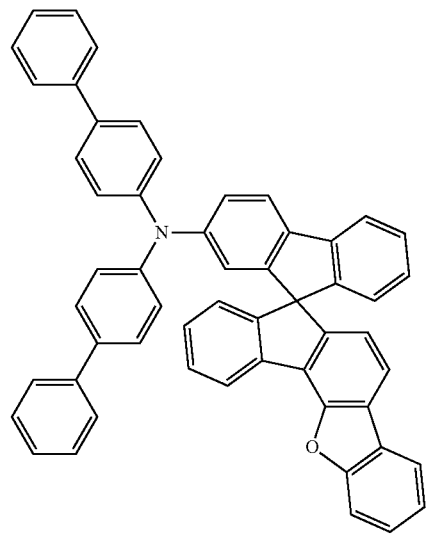
HT-2-4
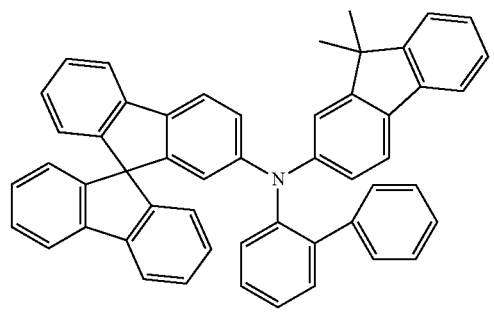
HT-2-5
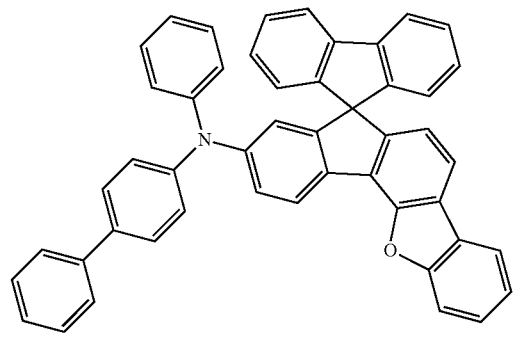

HT-2-6
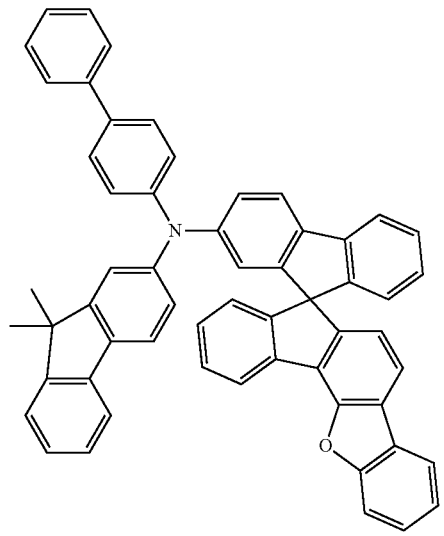
HT-2-7
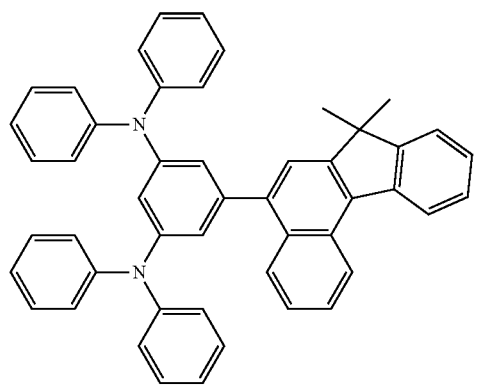
HT-2-8
HT-2-9
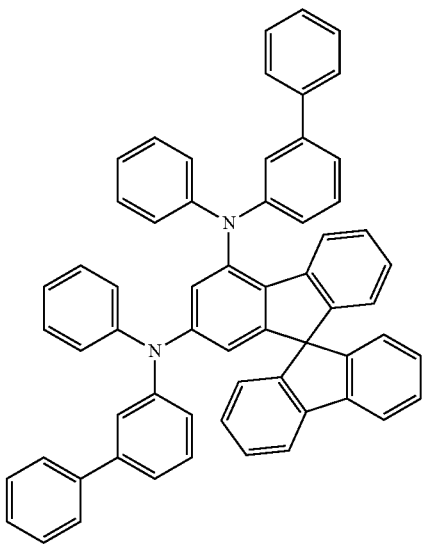
HT-2-10
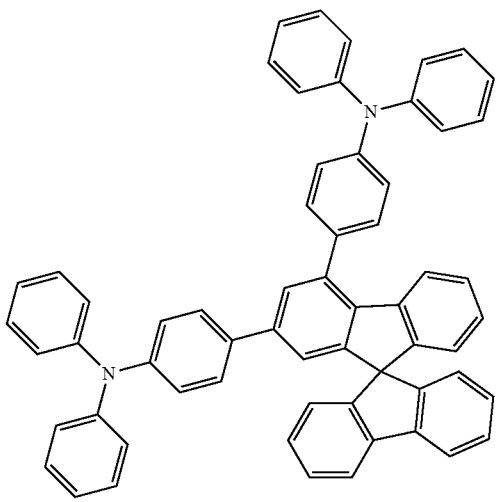
HT-2-11
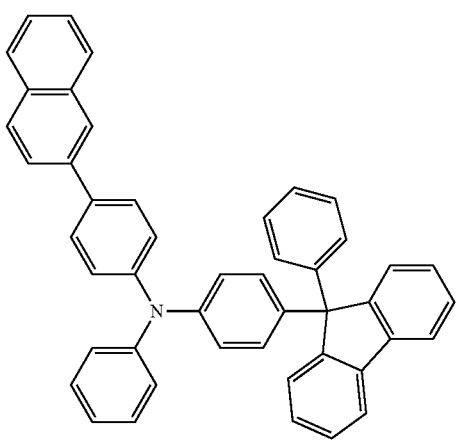

-continued
HT-2-12
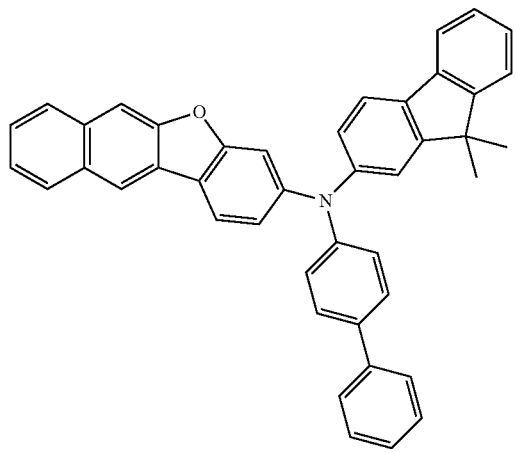
HT-2-15
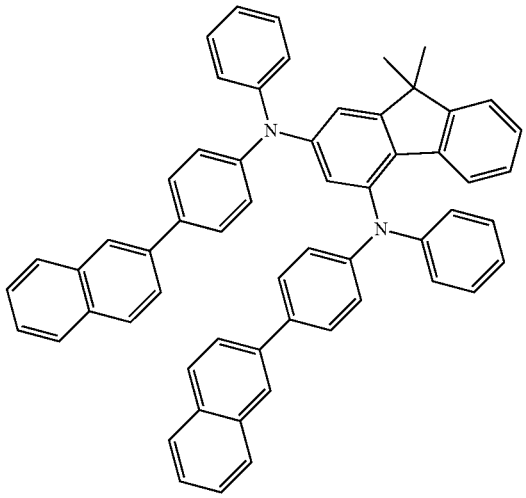
HT-2-13
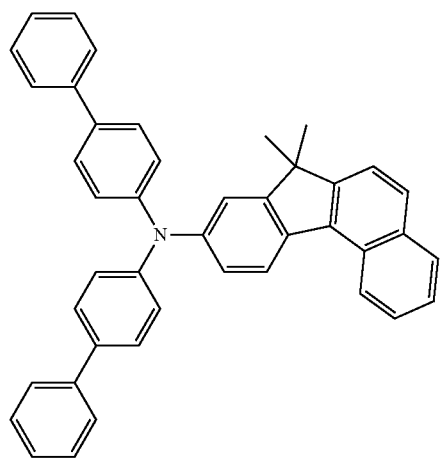
HT-2-16
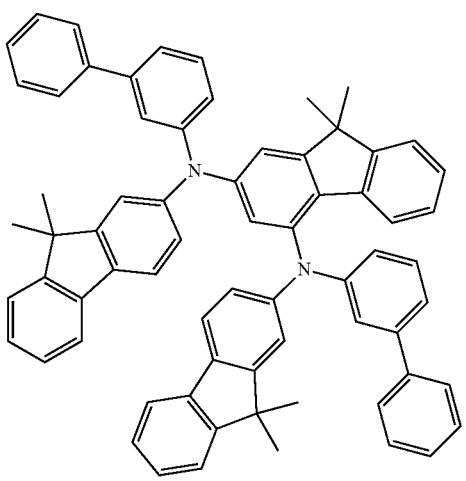
HT-2-14
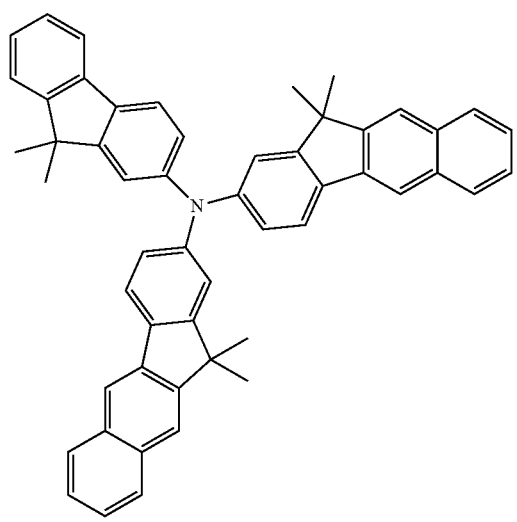
HT-2-17

-continued
HT-2-18
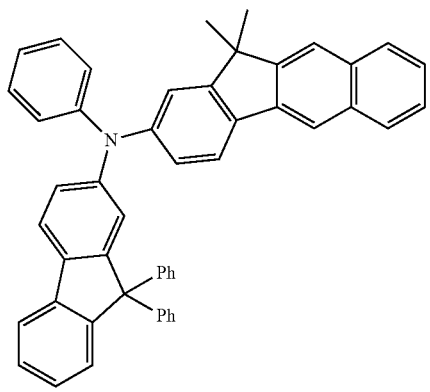
HT-2-19
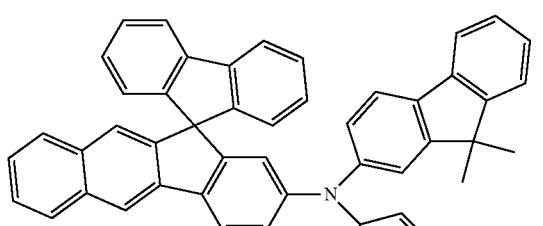
HT-2-20
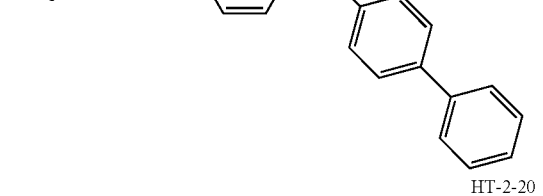
HT-2-21
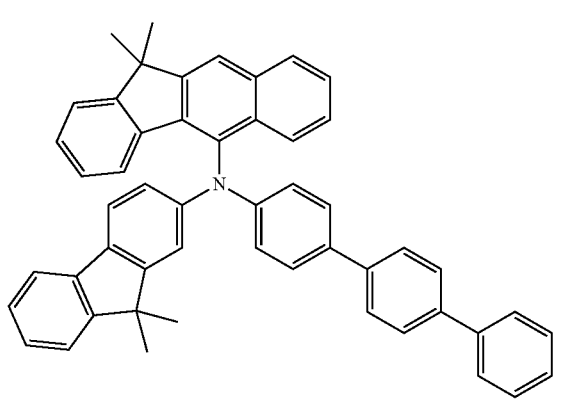
-continued
HT-2-22
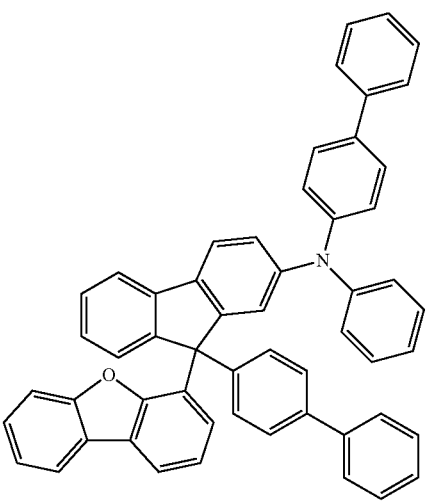
HT-2-23
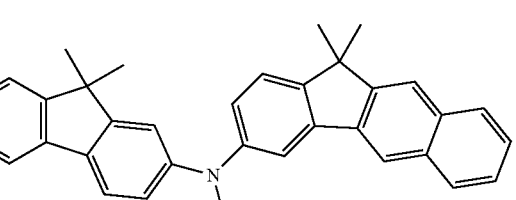
HT-2-24
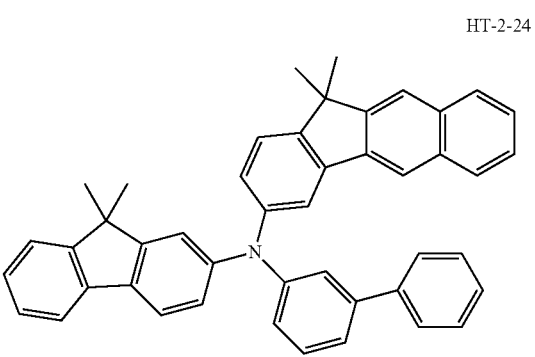

HT-2-25
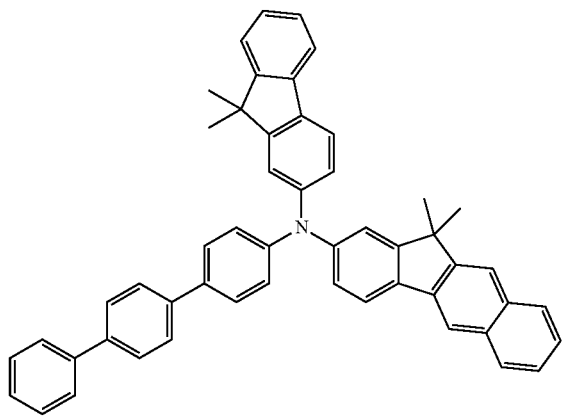
HT-2-26
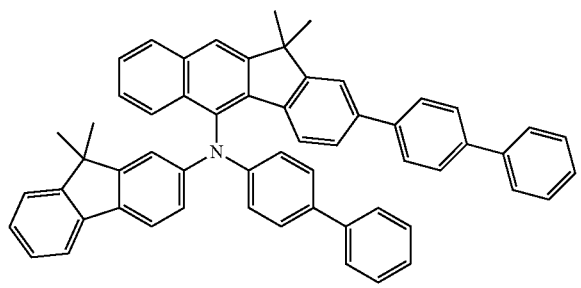
HT-2-27
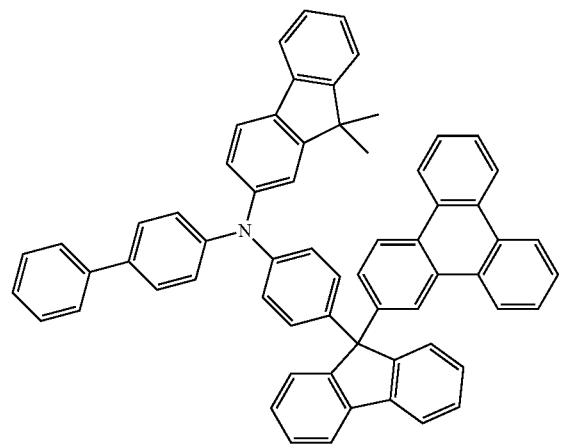
HT-2-28
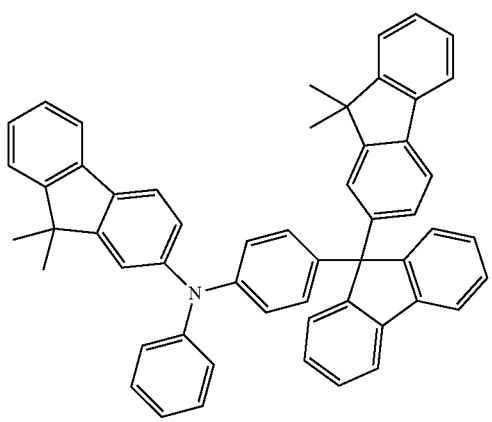
HT-2-29
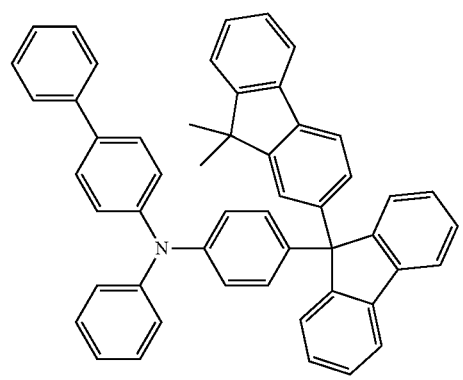
HT-2-30
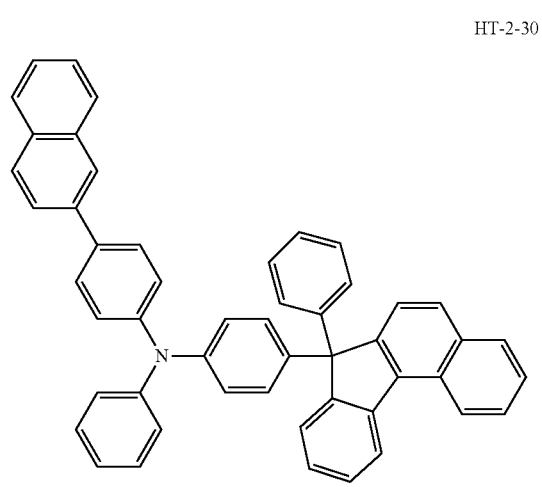
HT-2-31
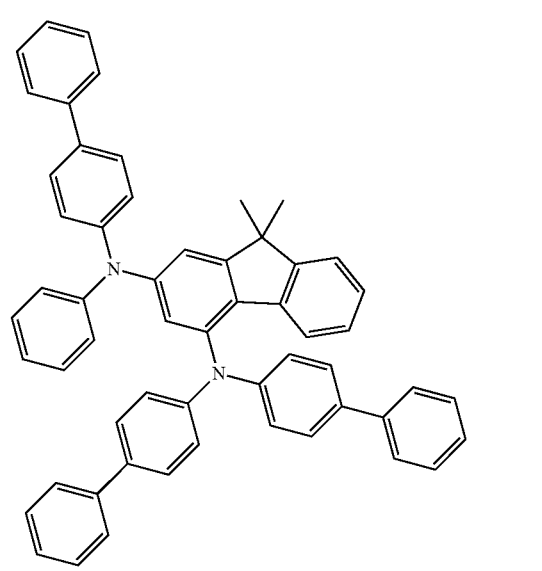

HT-2-32
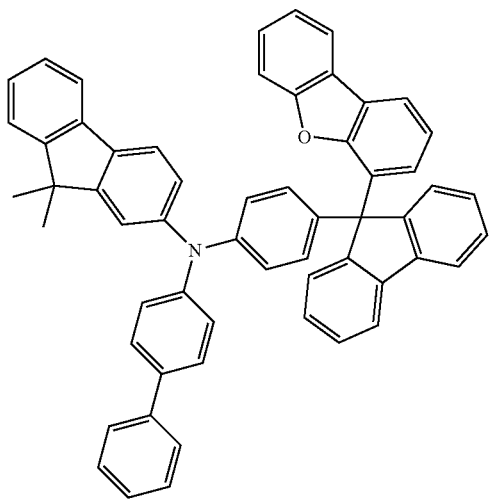
HT-2-33
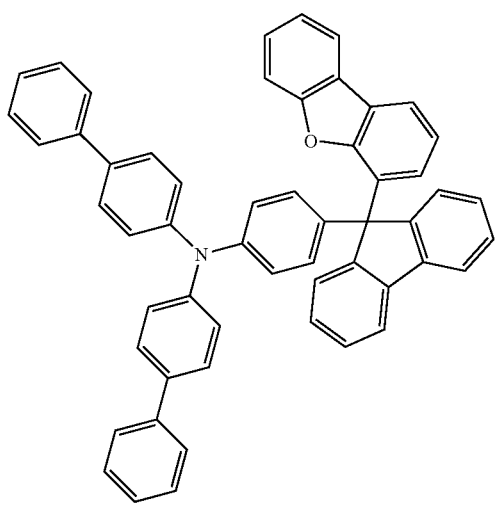
HT-2-34
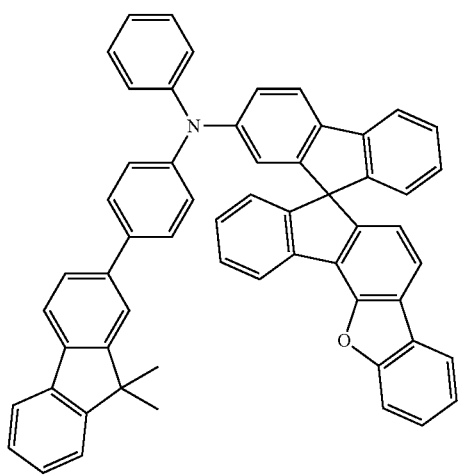
HT-2-35
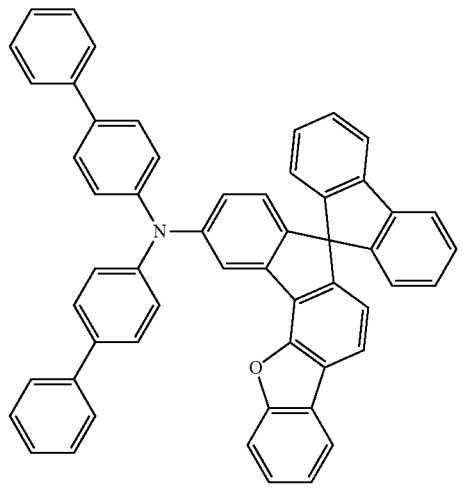
HT-2-36
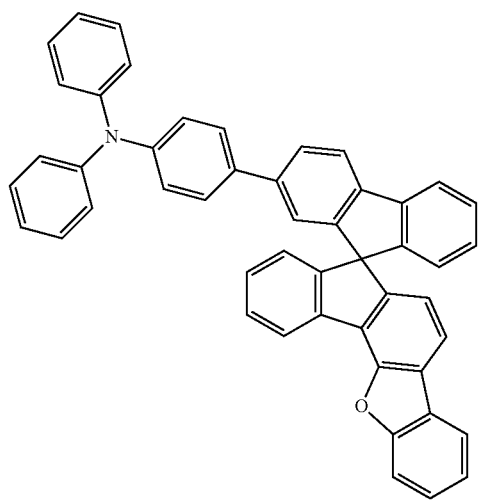
HT-2-37
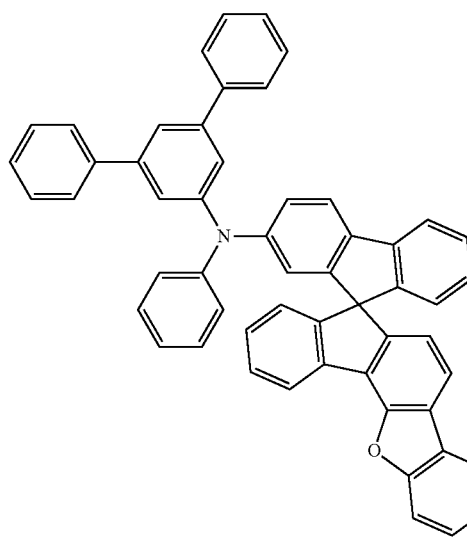

HT-2-38
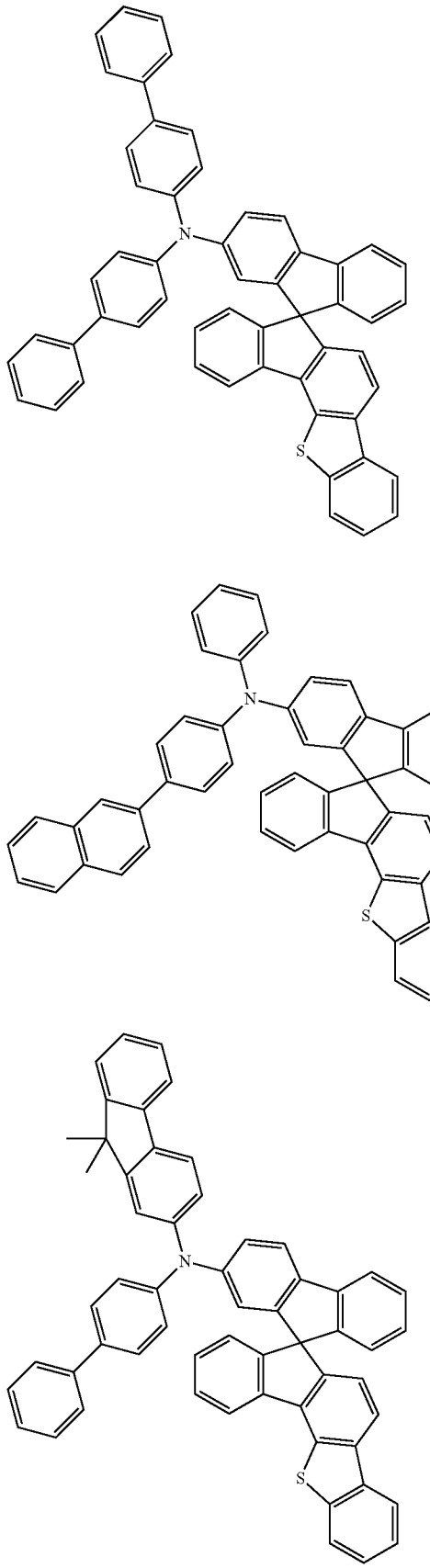
HT-2-39
HT-2-40
HT-2-41
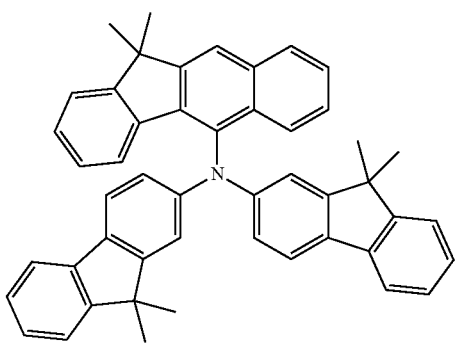
HT-2-42
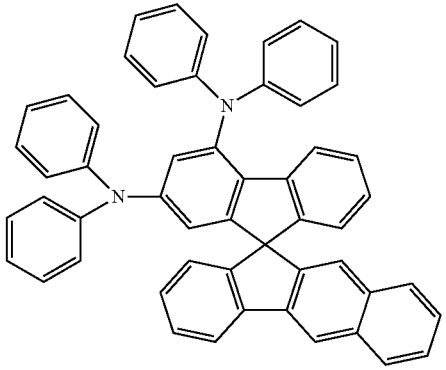
HT-2-43
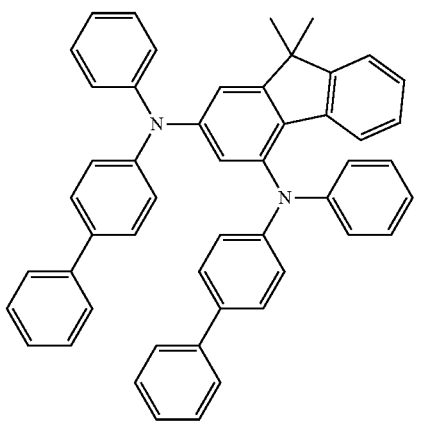
HT-2-44
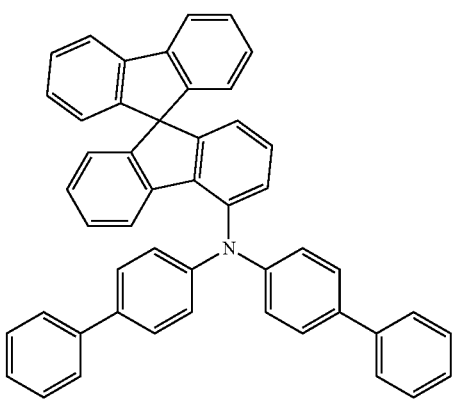

HT-2-45
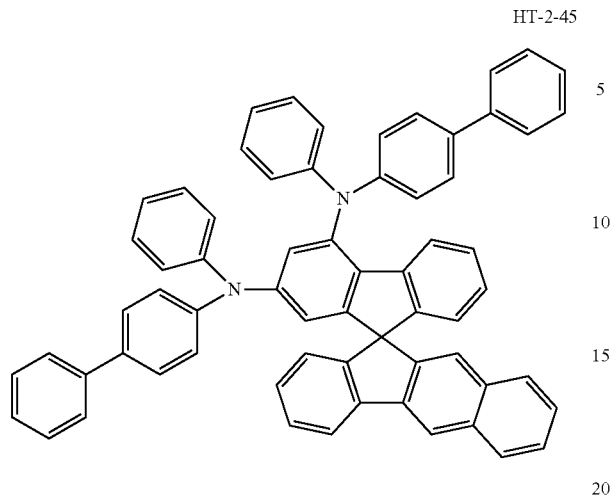
HT-2-46
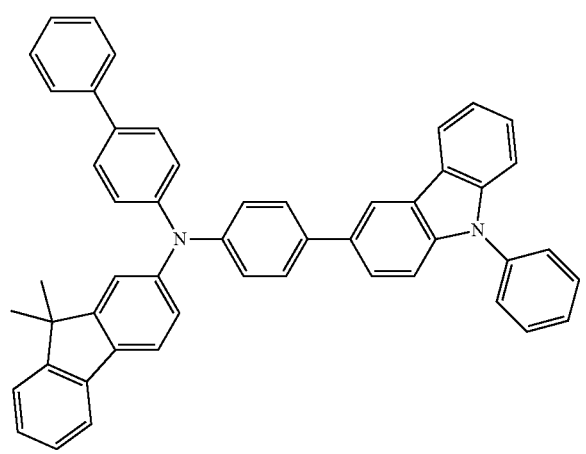
HT-2-47
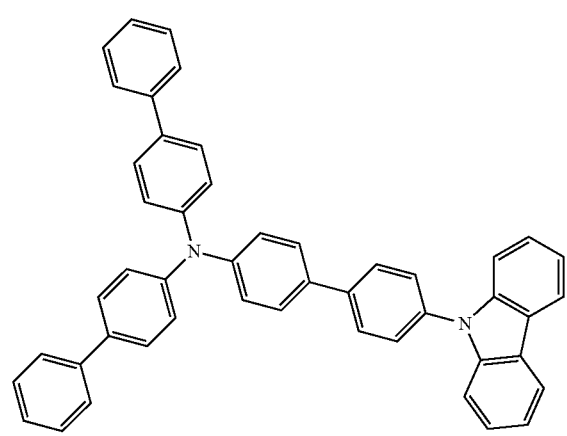
HT-2-48
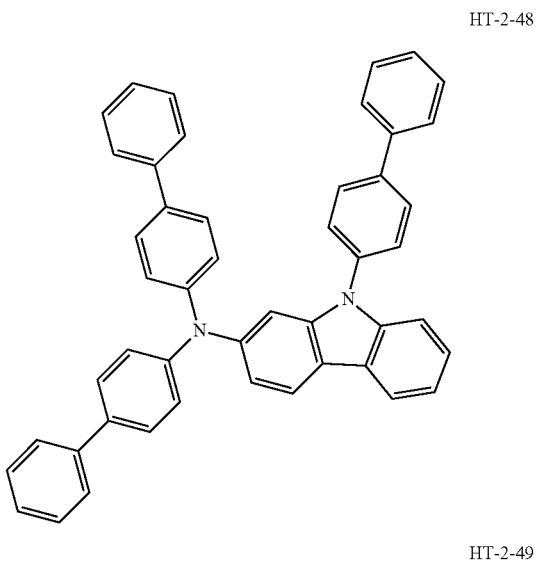
HT-2-49
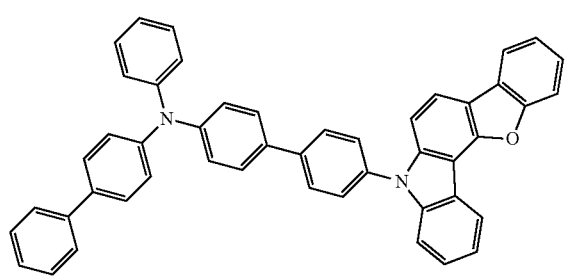
HT-2-50
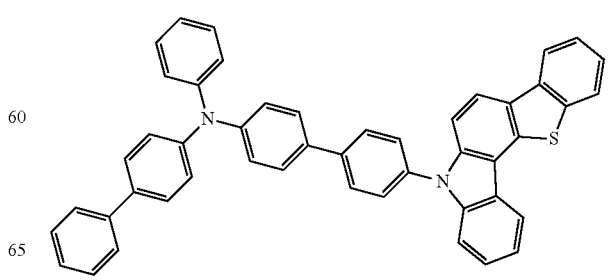
HT-2-51

HT-2-52
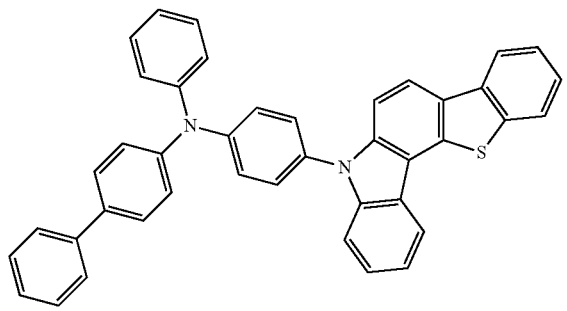
HT-2-53
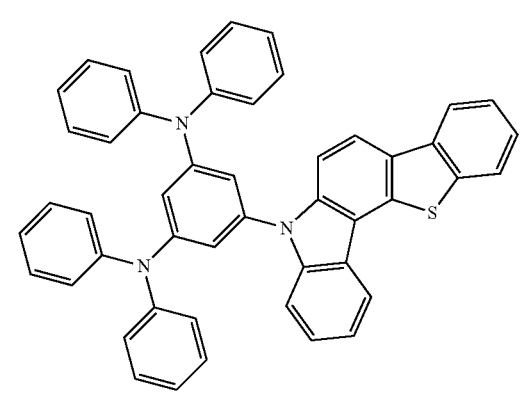
HT-2-54
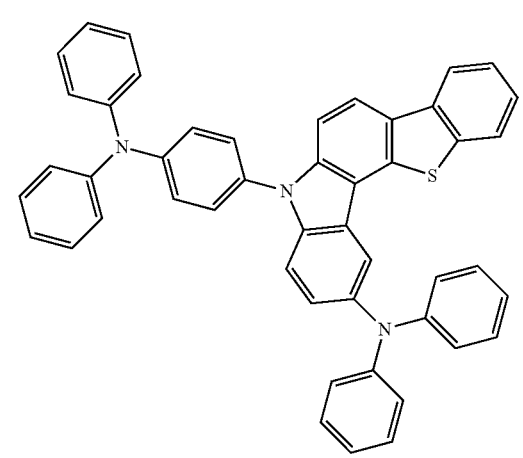
HT-2-55
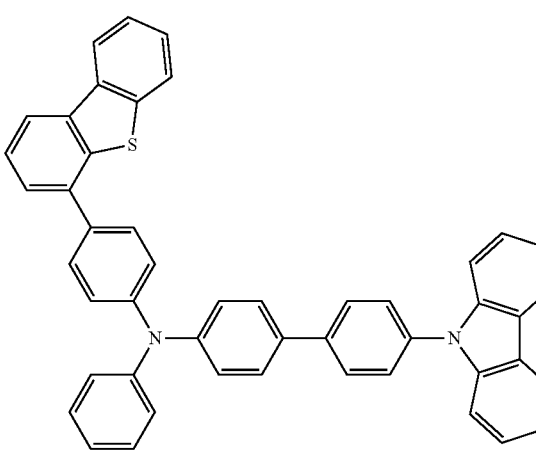
HT-2-56
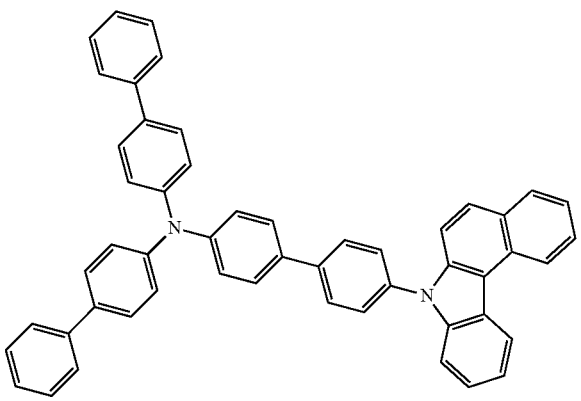
HT-2-57
HT-2-58
HT-2-59
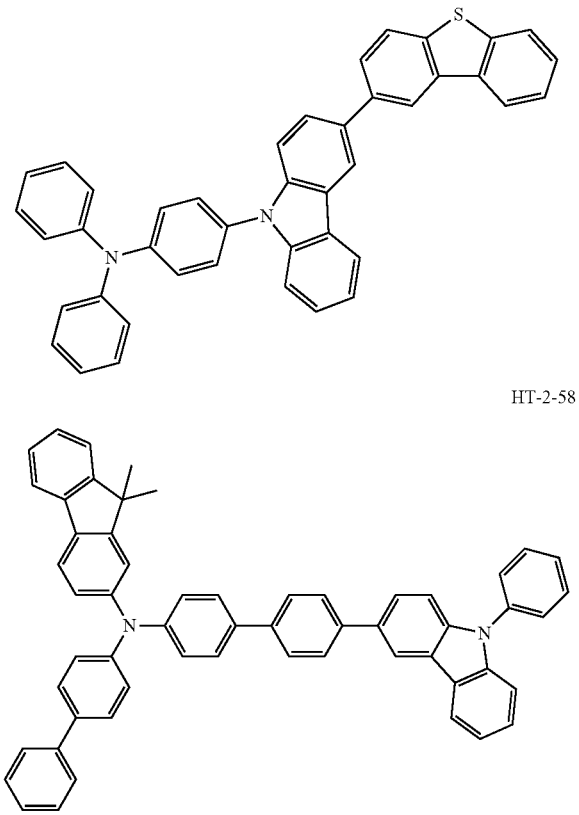

HT-2-60
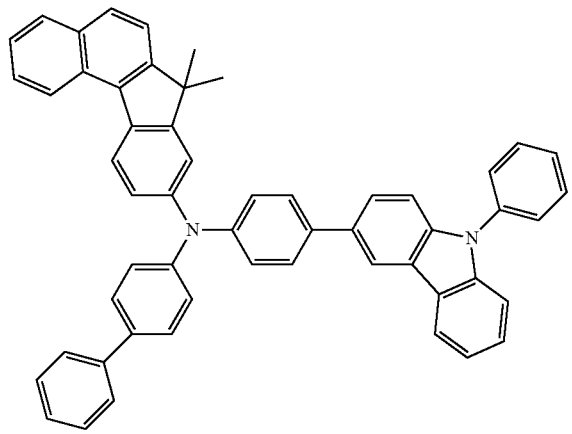
HT-2-63
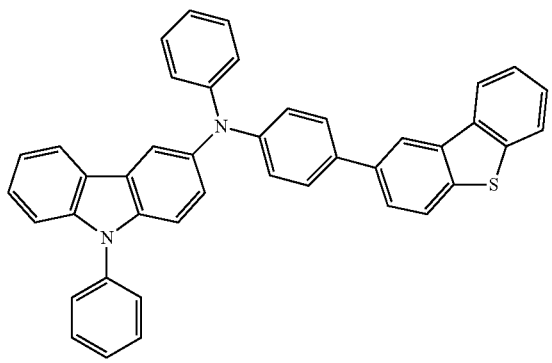
HT-2-61
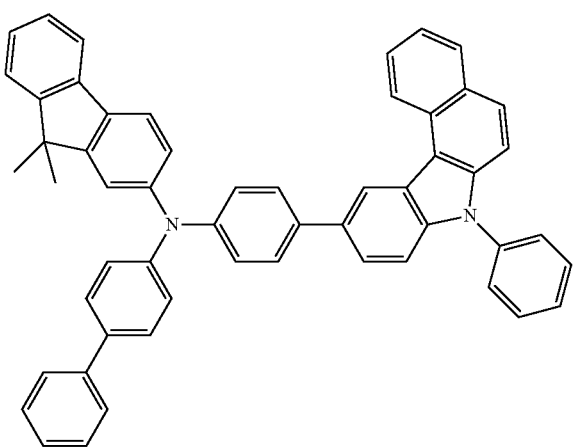
HT-2-64
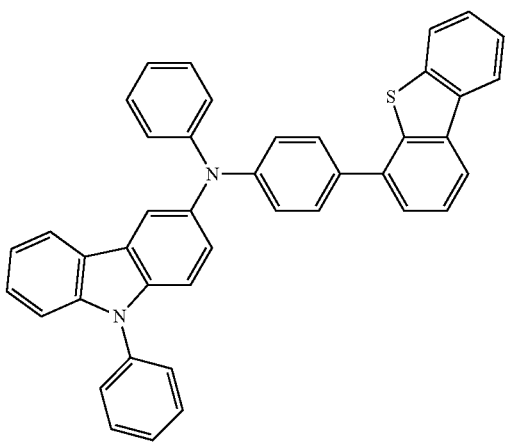
HT-2-62
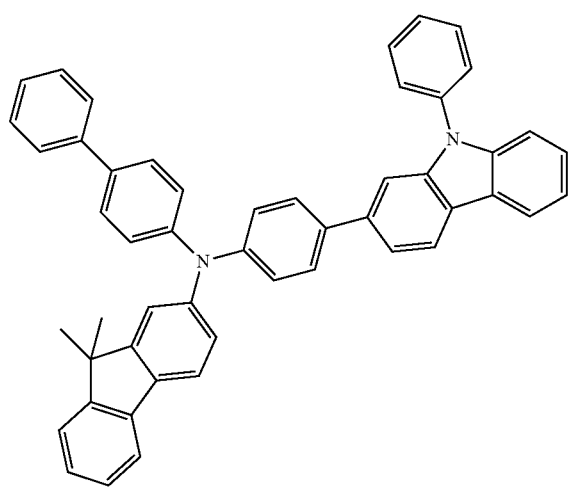
HT-2-65
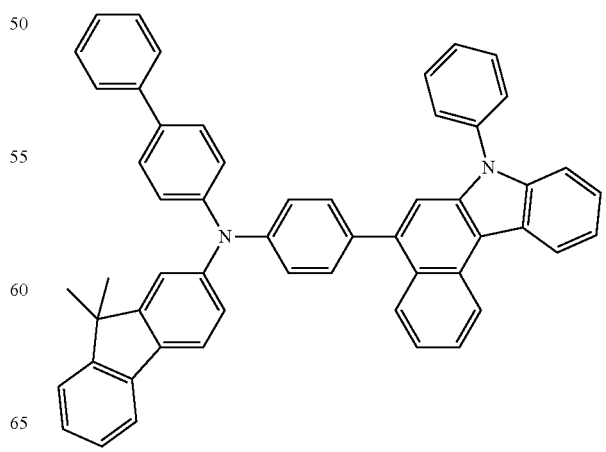

HT-2-66
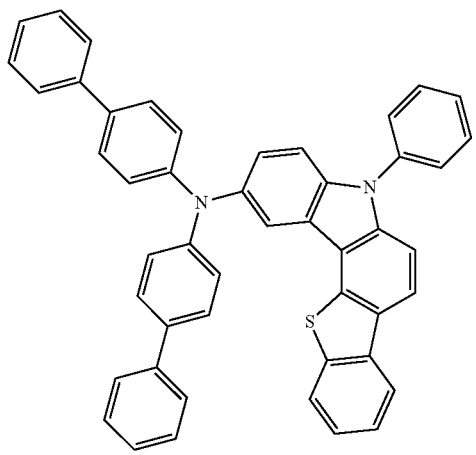
HT-2-67
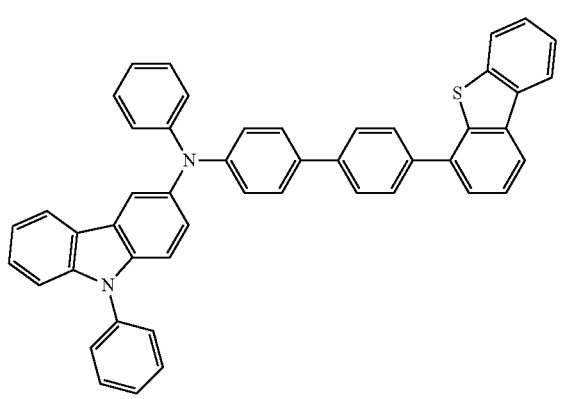
HT-2-68
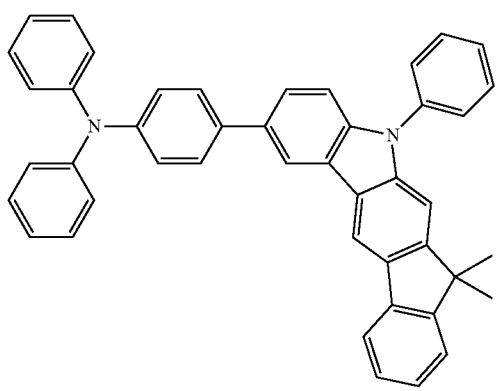
HT-2-69
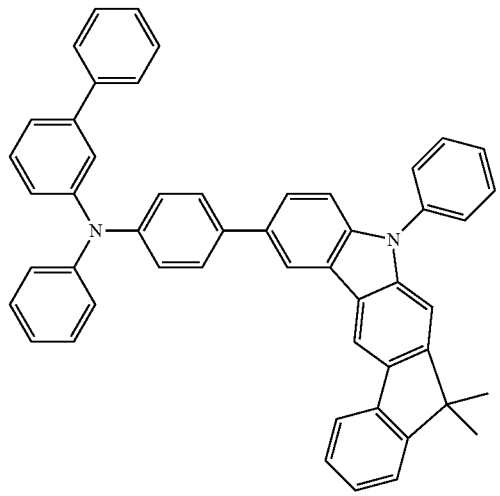
HT-2-70
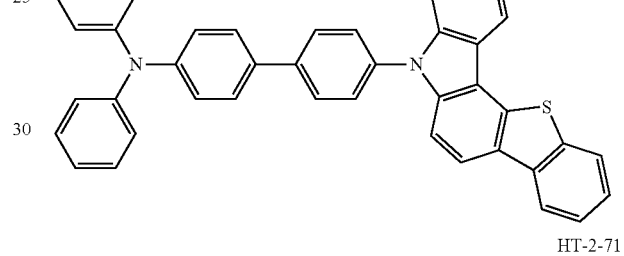
HT-2-71
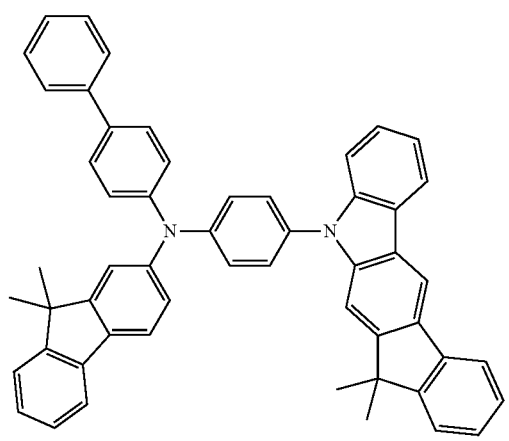
HT-2-72

HT-2-73
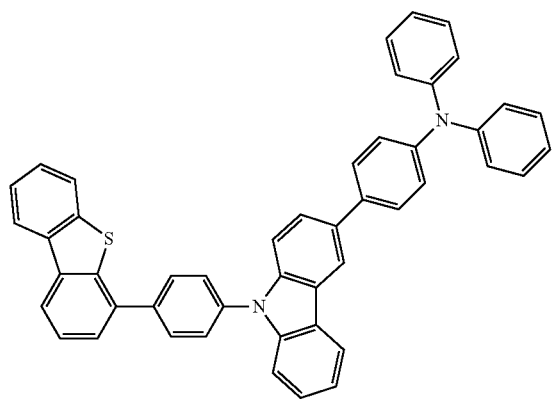
HT-2-76
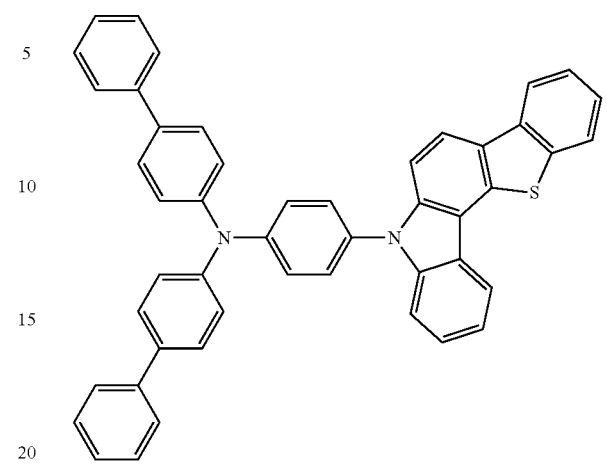
HT-2-74
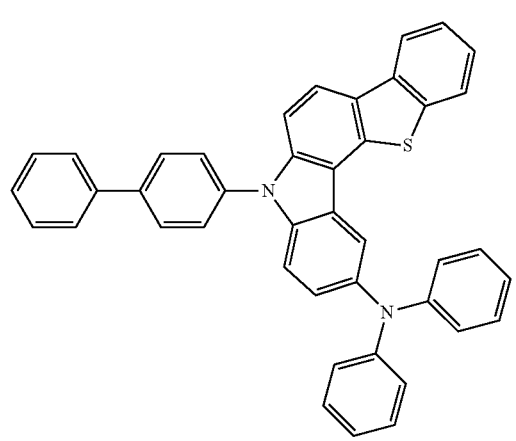
HT-2-77
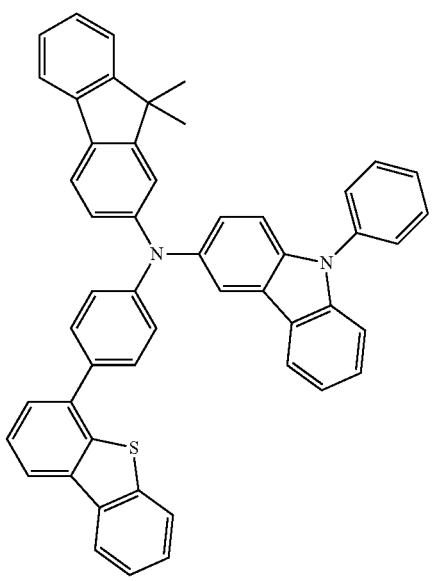
HT-2-75
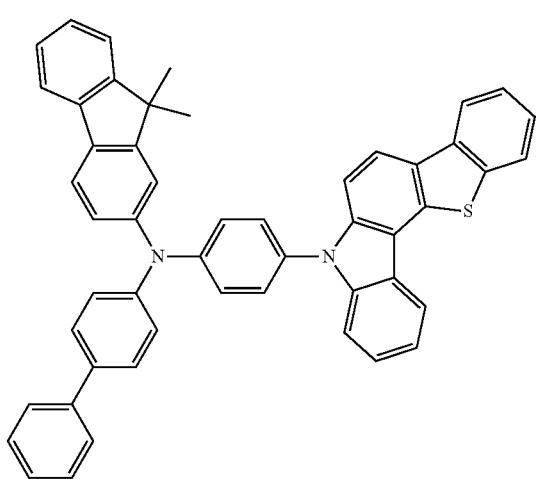
HT-2-78

HT-2-79
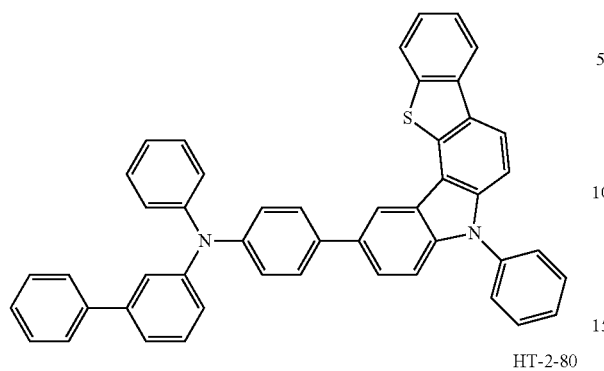
HT-2-80
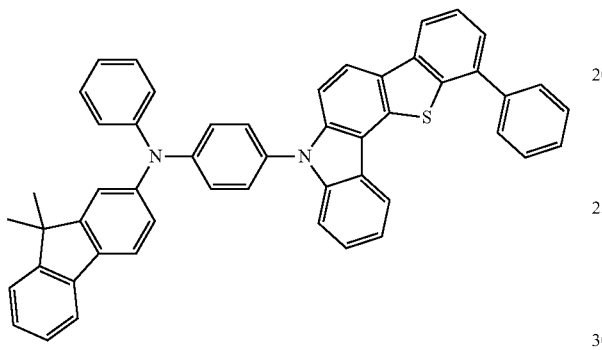
HT-2-81
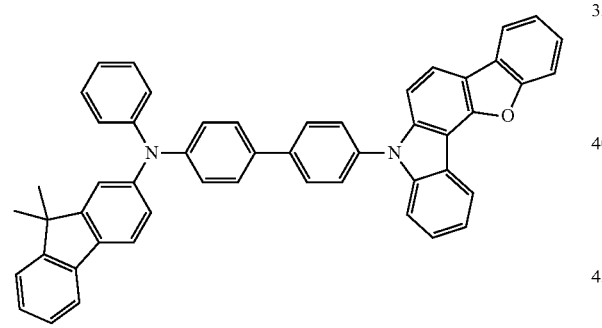
HT-2-82
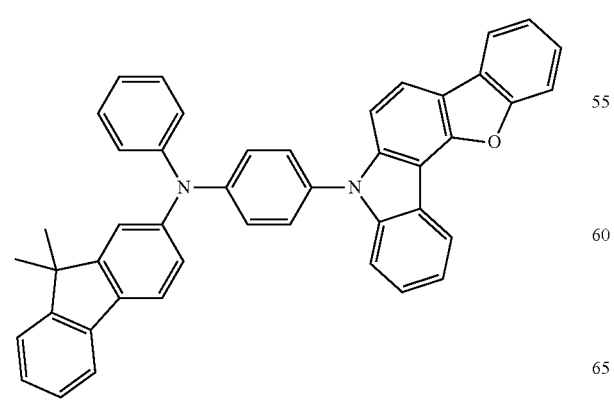
HT-2-83
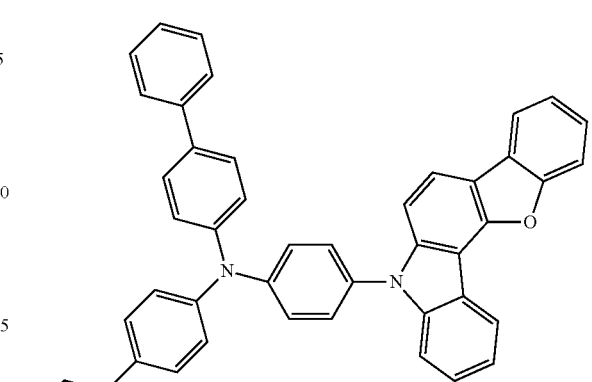
HT-2-84
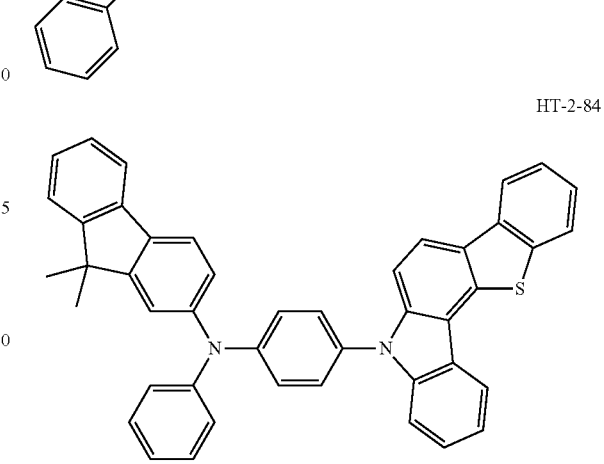
HT-2-85
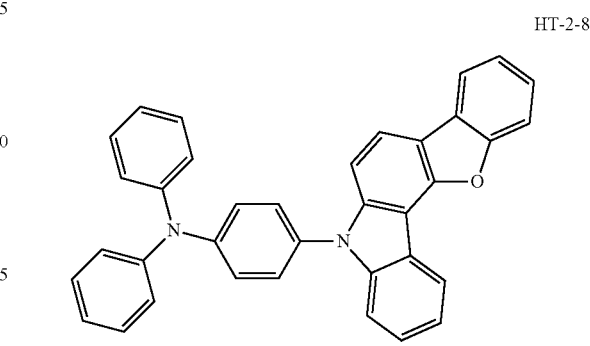
HT-2-86

HT-2-87
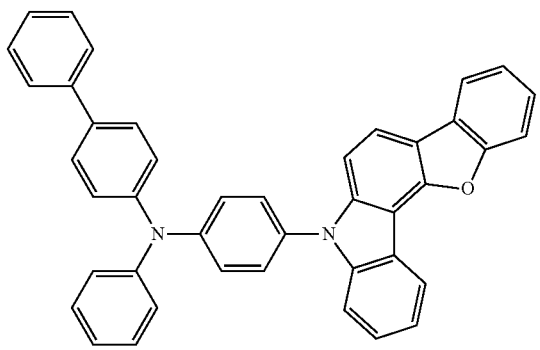
HT-2-91
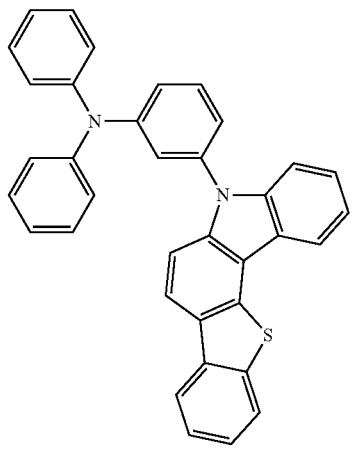
HT-2-88
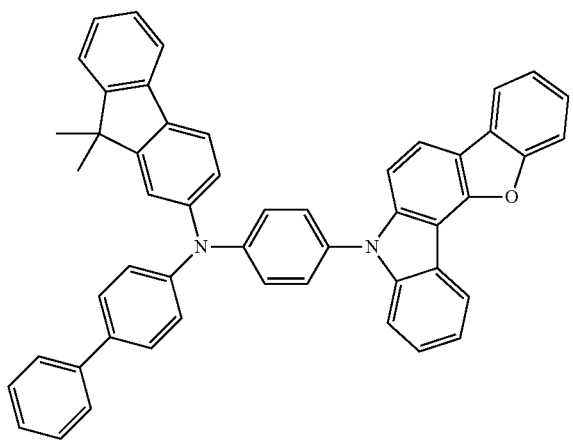
HT-2-92
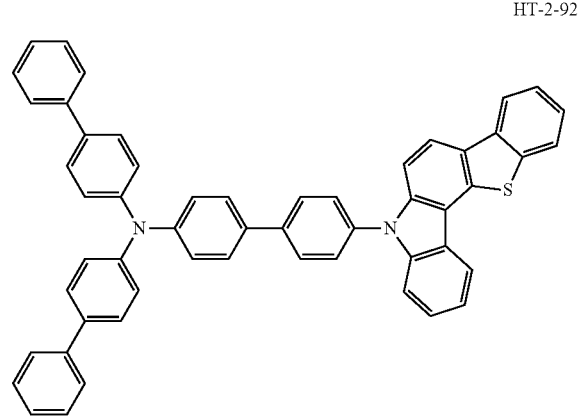
HT-2-89
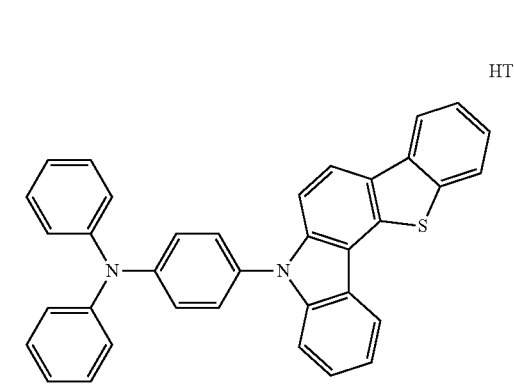
HT-2-93
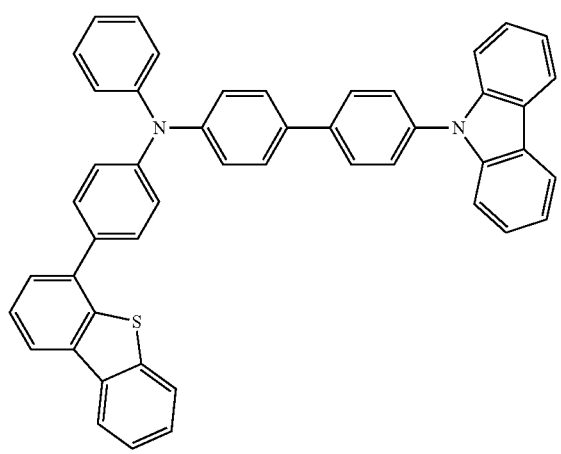
HT-2-90
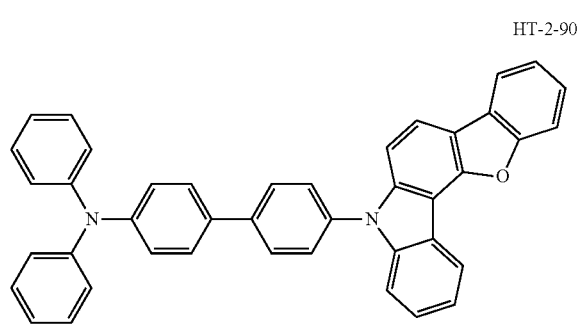
HT-2-94
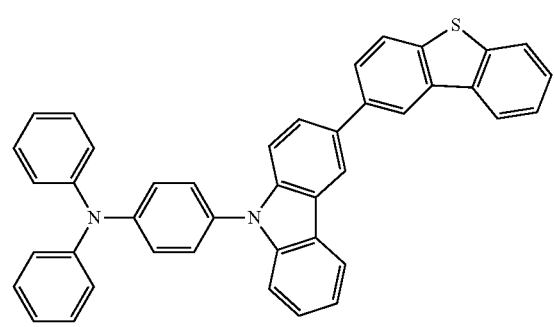

237
-continued
HT-2-95
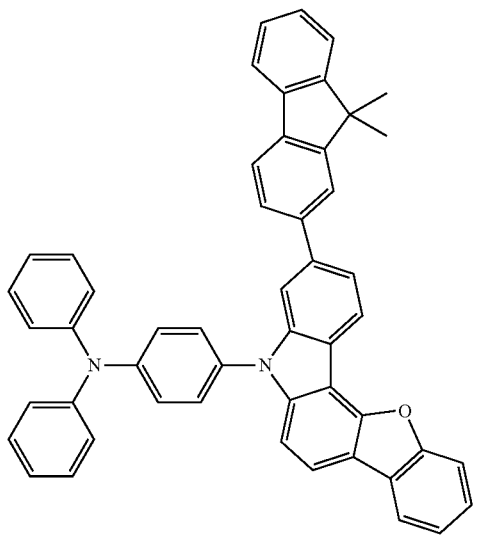
HT-2-96
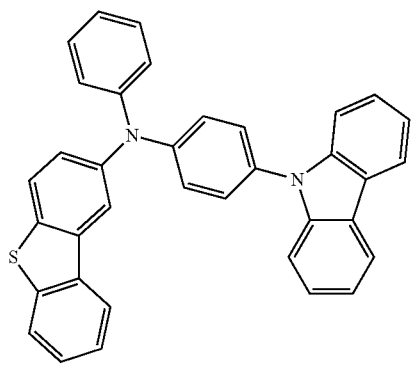
HT-2-97
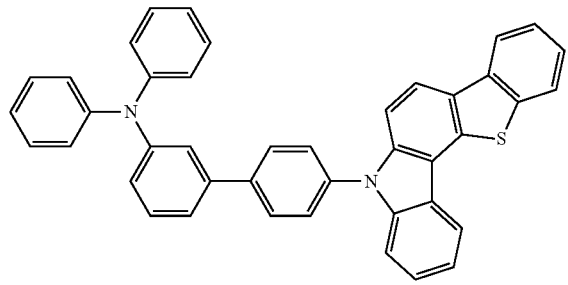
HT-2-98
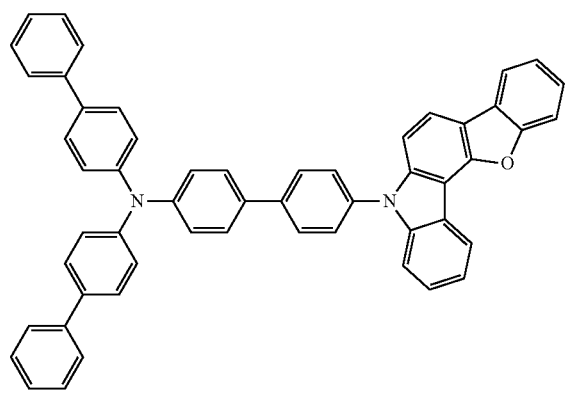
238
-continued
HT-2-99
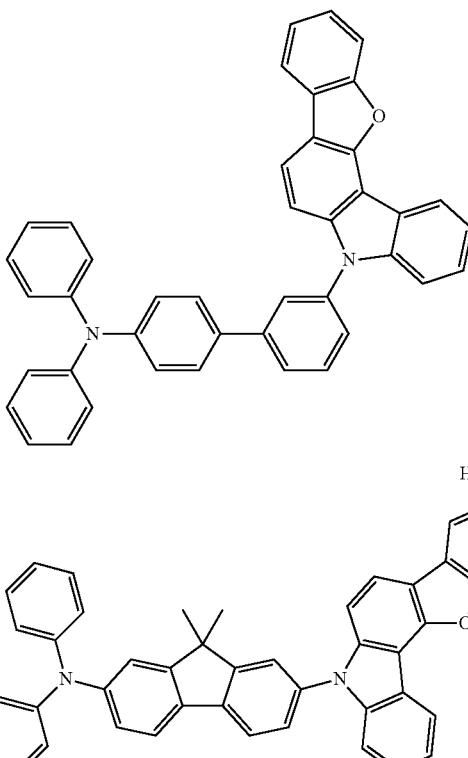
HT-2-100
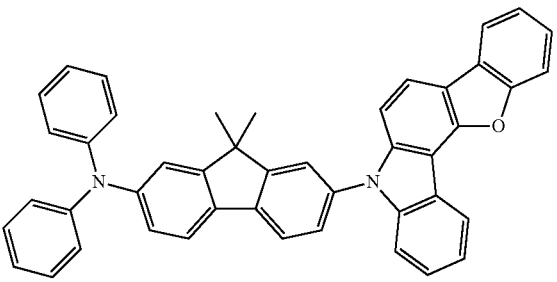
HT-2-101
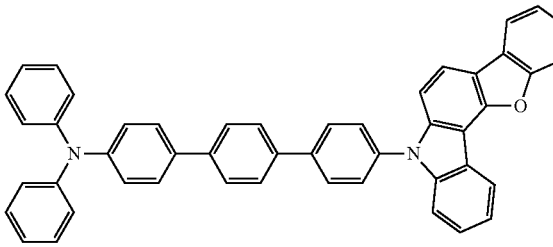
HT-2-102
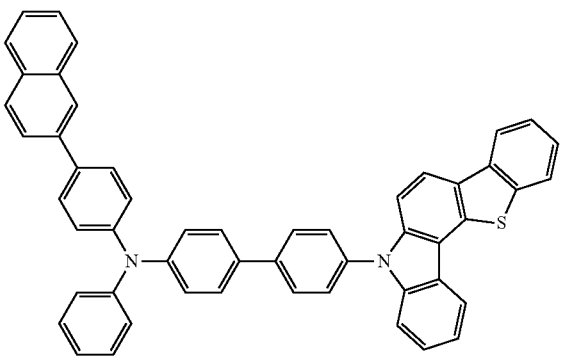

HT-2-103
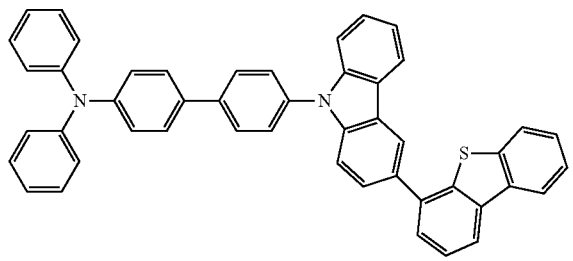
HT-2-104
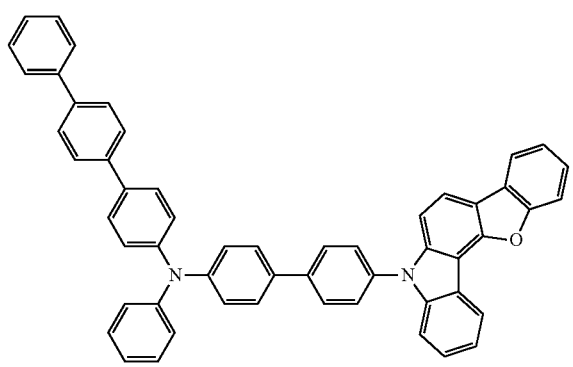
HT-2-105
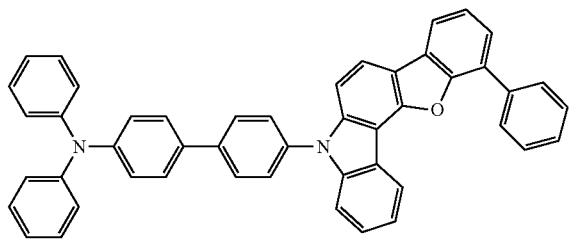
HT-2-106
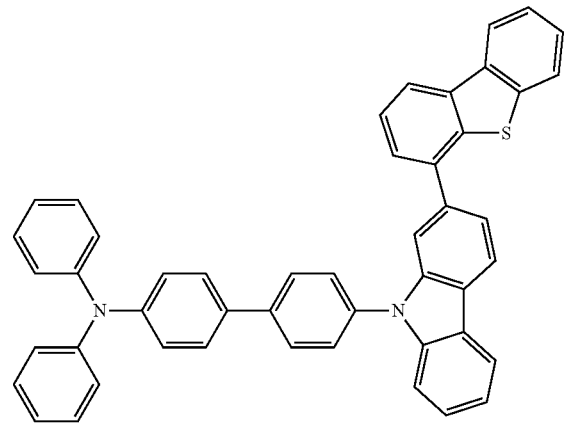
HT-2-107
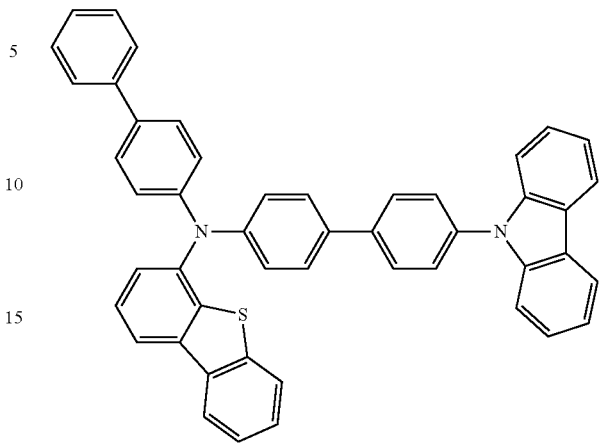
HT-2-108
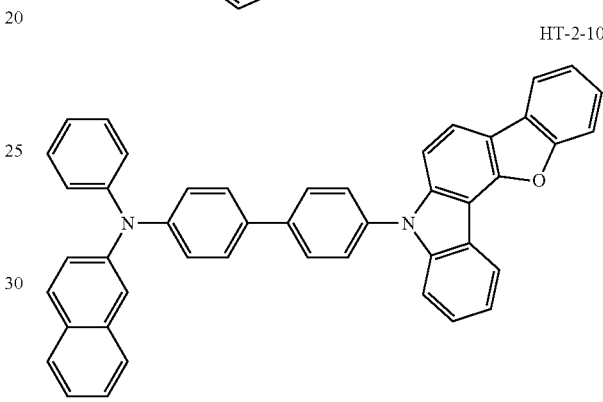
HT-2-109
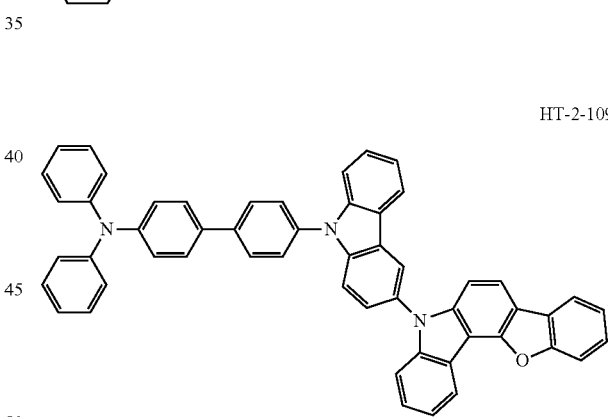
HT-2-110
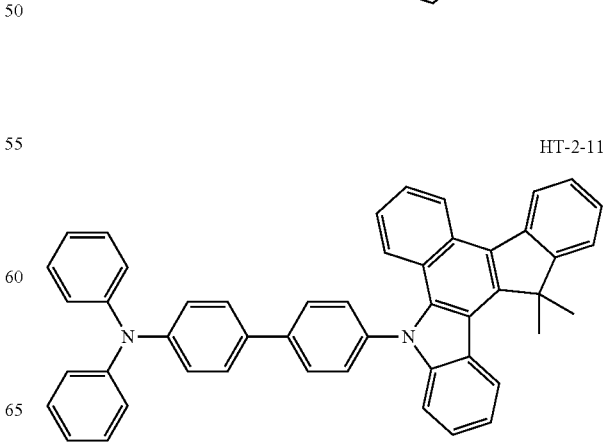

HT-2-111
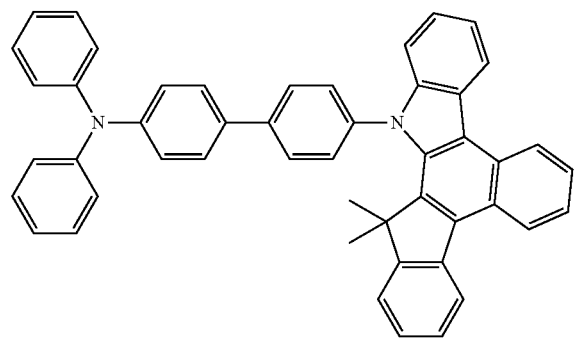
HT-2-114
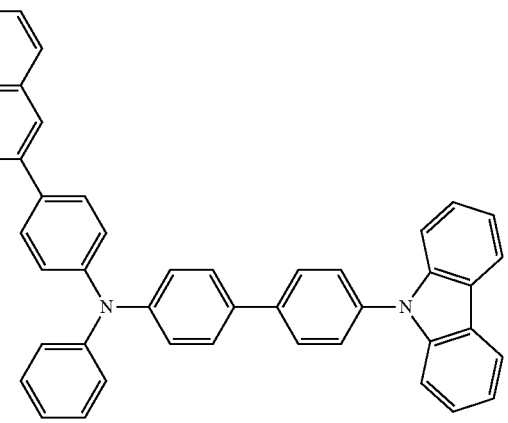
HT-2-112
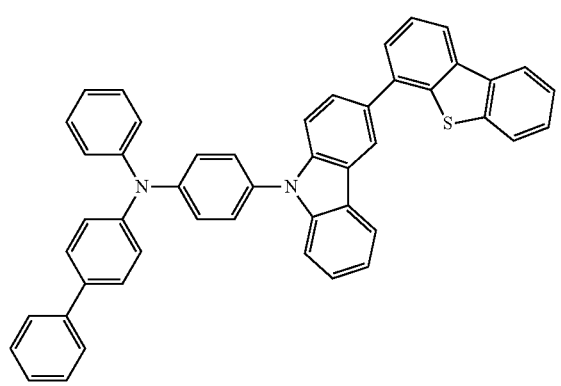
HT-2-115
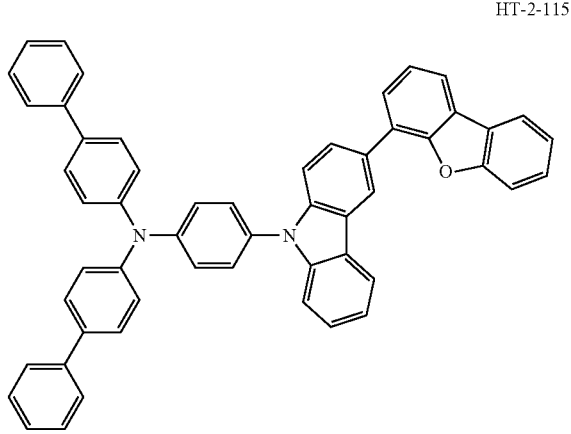
HT-2-113
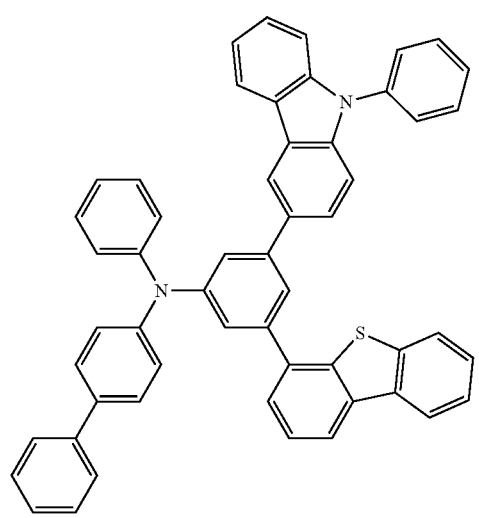
HT-2-116
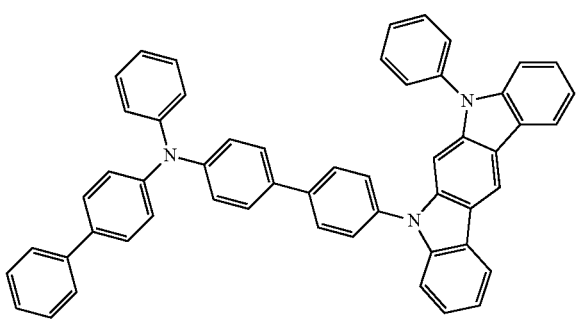

HT-2-117
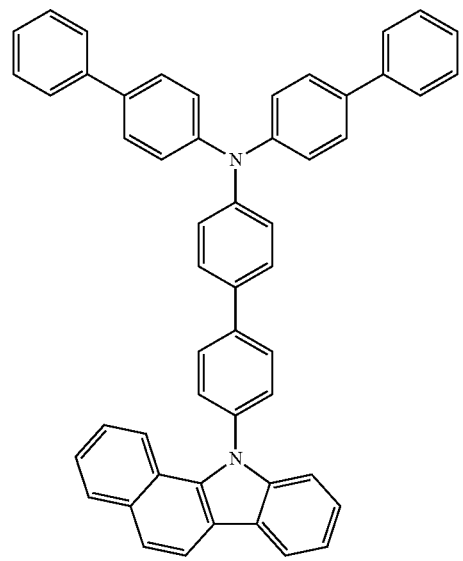
HT-2-118
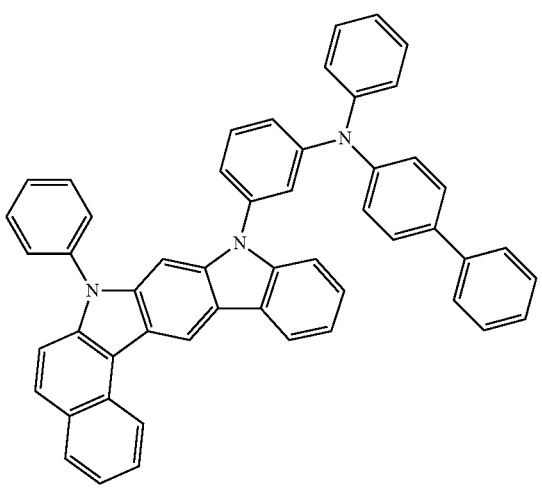
HT-2-119
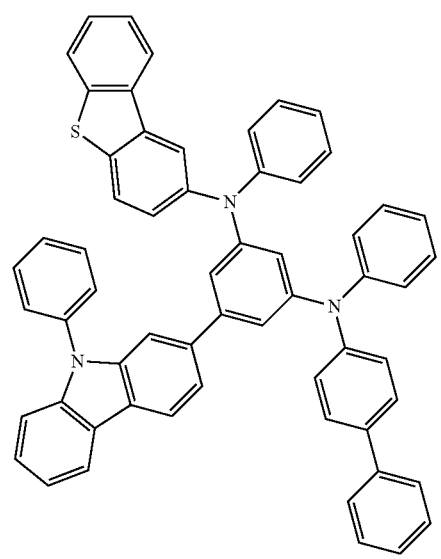
HT-2-120
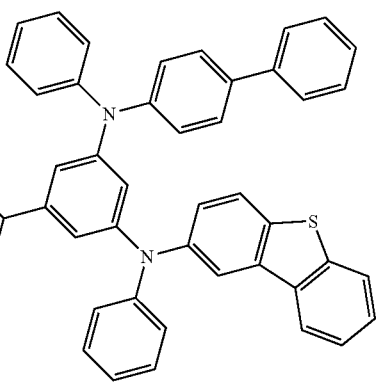
HT-2-121
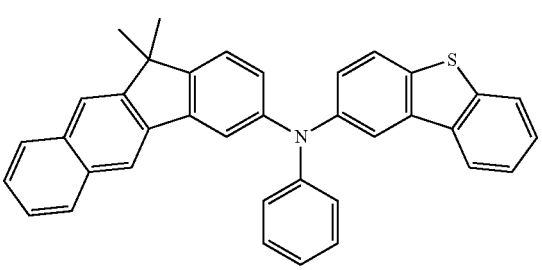
HT-2-122
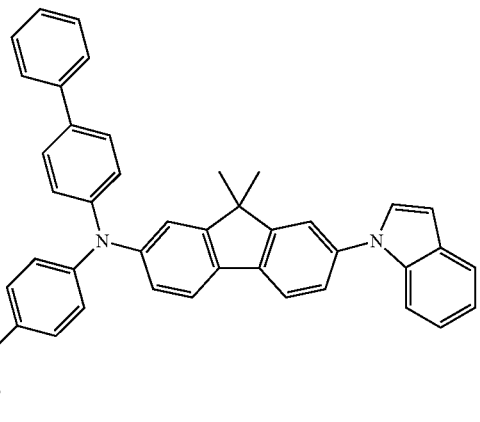
HT-2-123

HT-2-124
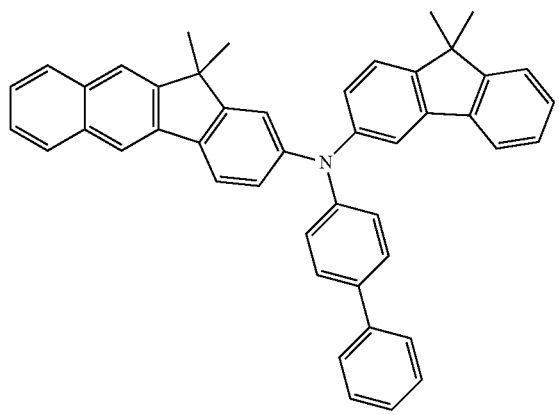
HT-2-125
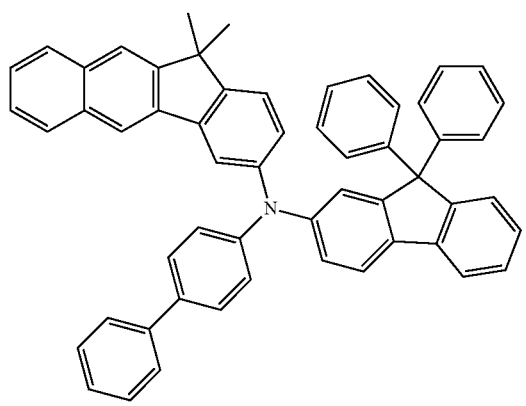
HT-2-126
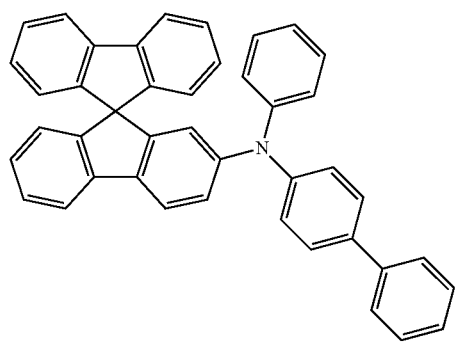
HT-2-127
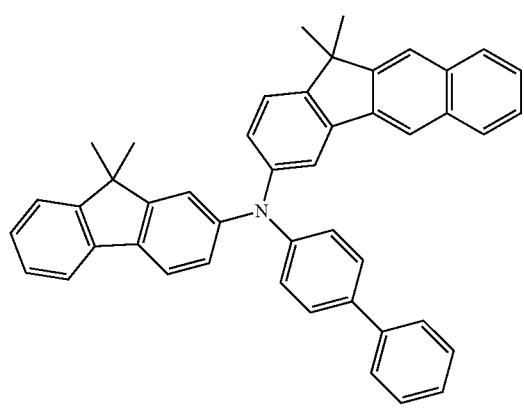
HT-2-128
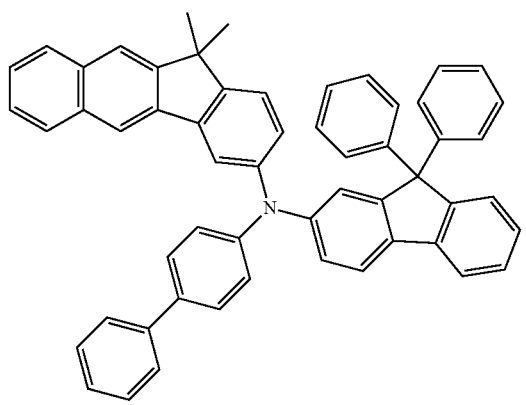
HT-2-129
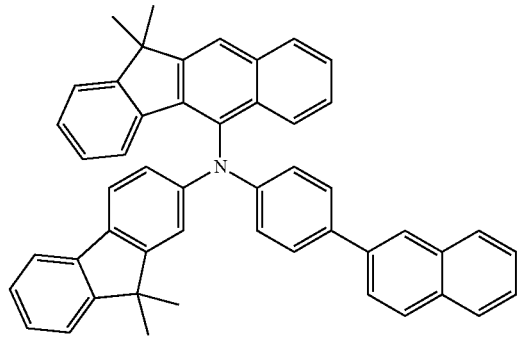
HT-2-130
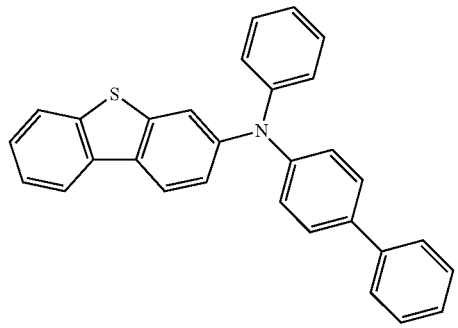
HT-2-131
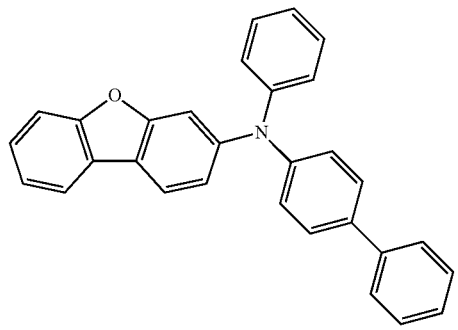

HT-2-132
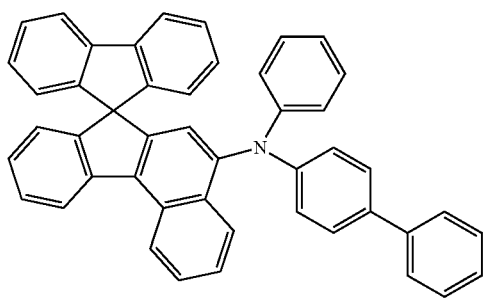
HT-2-135
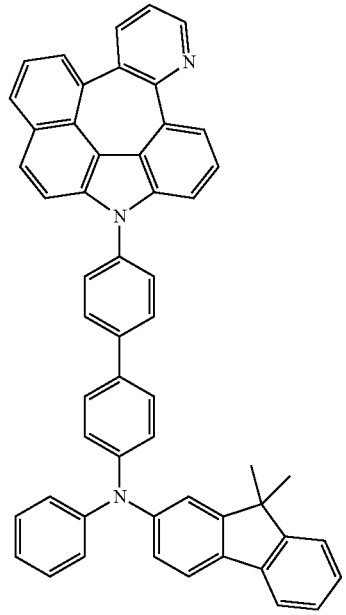
HT-2-133
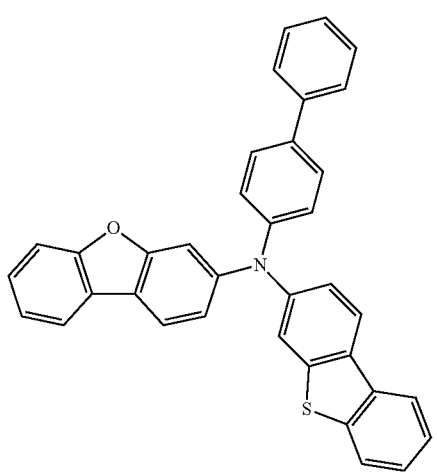
HT-2-134
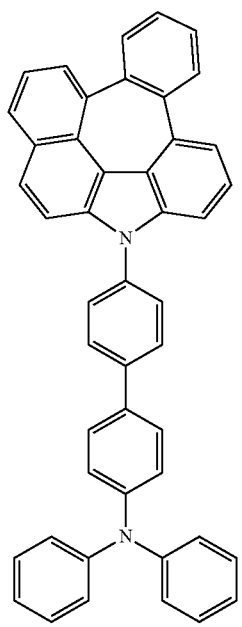
HT-2-136
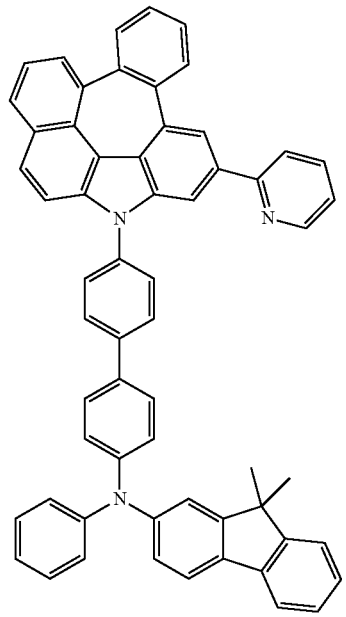

HT-2-137
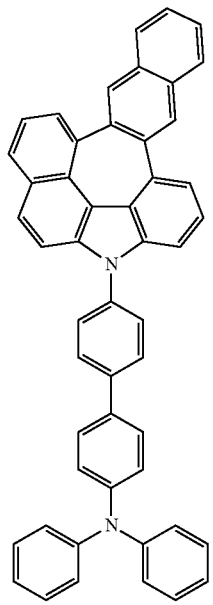
The compound of formula 1 according to the present disclosure may be produced by a synthetic method known to one skilled in the art. For example, the compound of formula 1 may be produced by referring to the following reaction schemes, but are not limited thereto.
[Reaction Scheme 1]
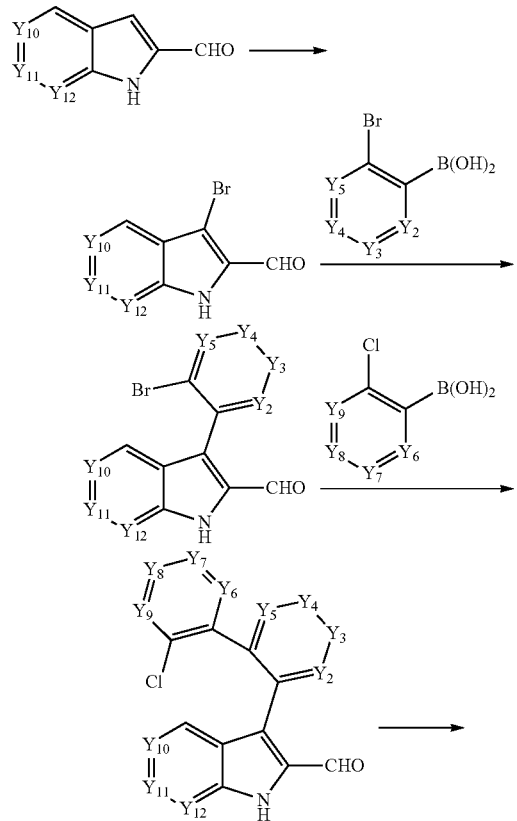
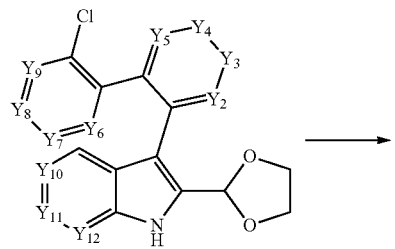
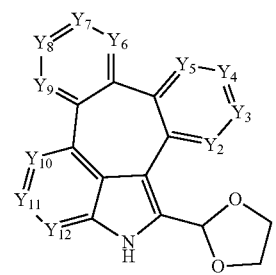
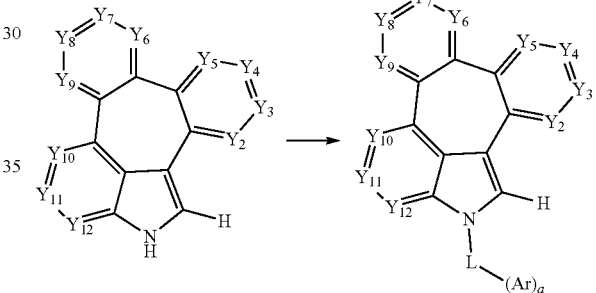
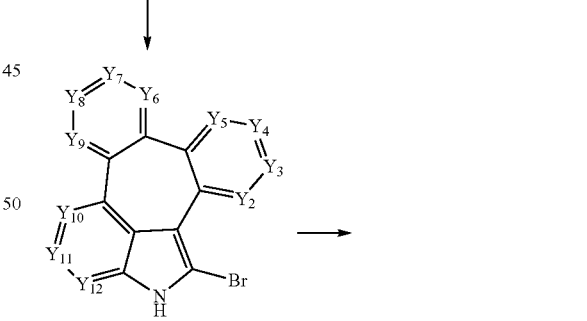
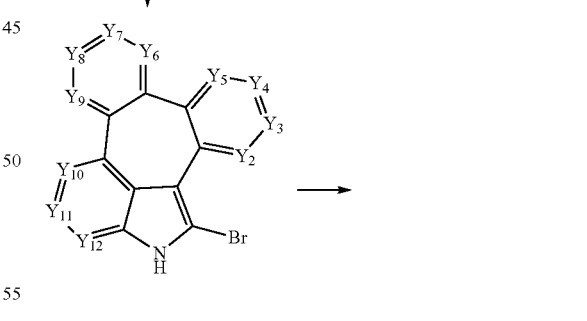
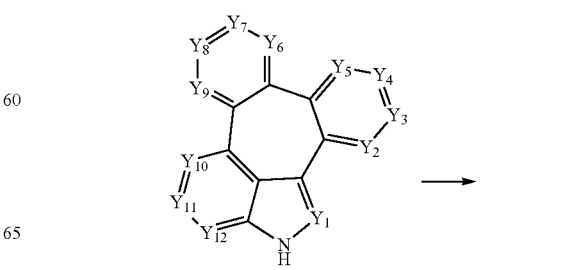

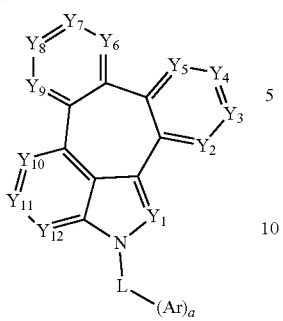
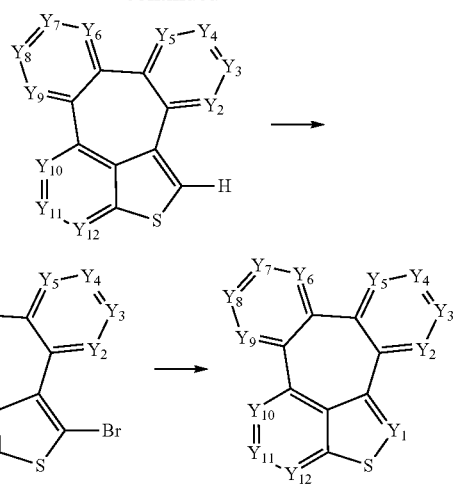
[Reaction Scheme 2]
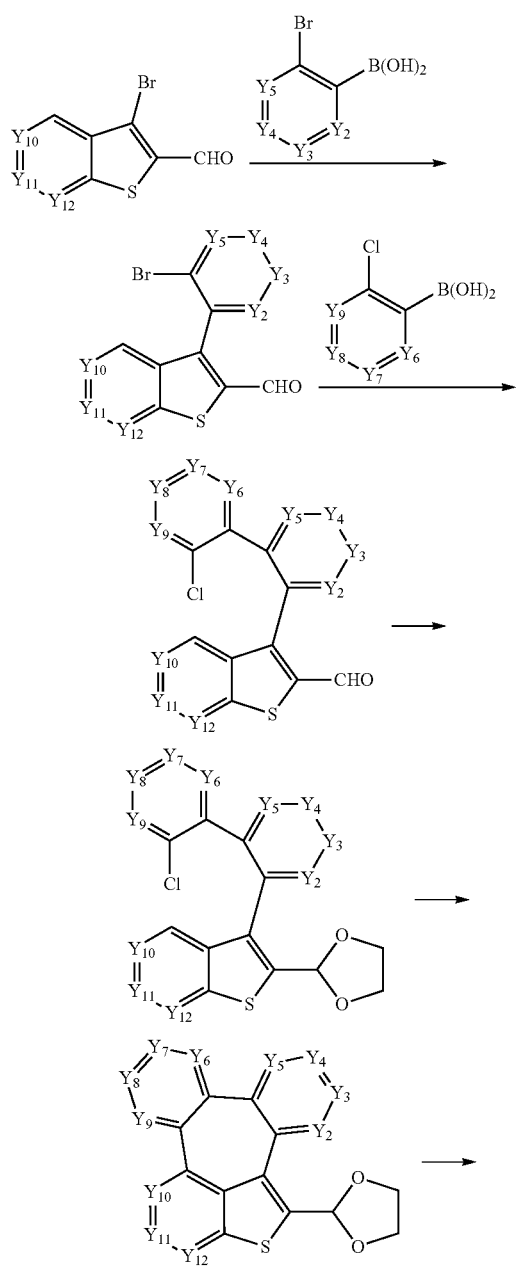
[Reaction Scheme 3]
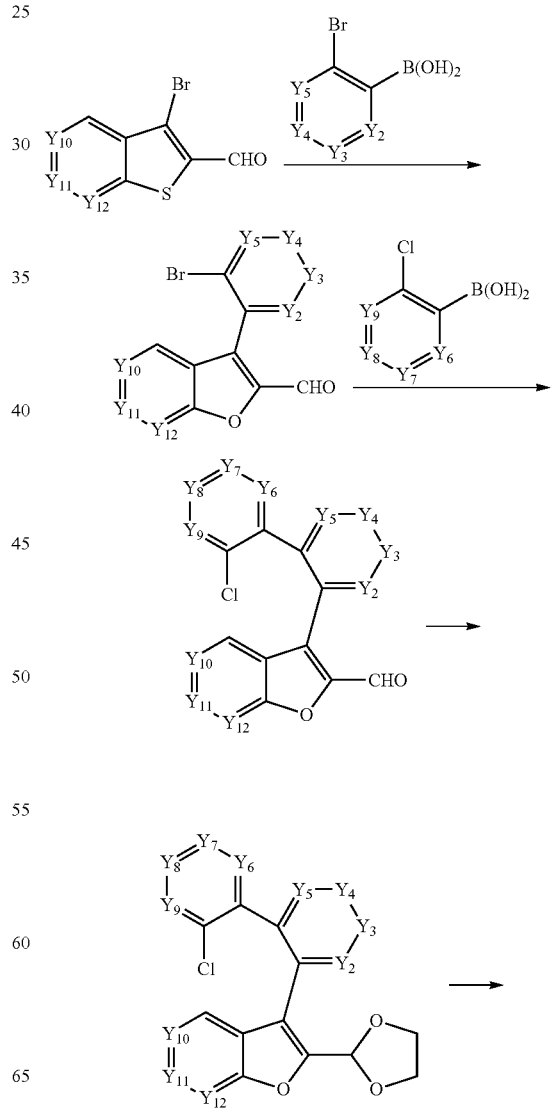

-continued

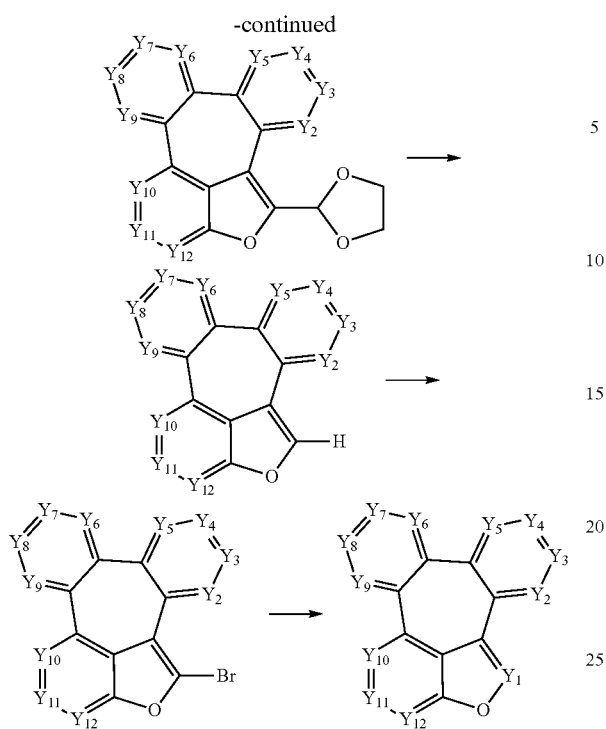

In reaction schemes 1 to 3, L, Ar, $Y_1$ to $Y_{12}$, and a are as defined in formula 1.

The compound represented by formula 11 may be produced by a synthetic method known to one skilled in the art, and for example, by using or modifying the synthetic methods disclosed in Korean Patent Application Laid-Open Nos. 2014-0104895 A, 2015-0012488 A, 2015-0066202 A, and Korean Patent No. 1476231 B.

The organic electroluminescent device of the present disclosure may comprise a p-doped hole injection layer. The p-doped hole injection layer is doped with a p-dopant, and the p-dopant may preferably be distributed substantially uniformly in the p-doped layer, which may be achieved by co-deposition of a p-dopant and a hole injection material. Also, the p-dopant may be contained in an amount of 0.01 to 50 wt %, preferably 0.1 to 20 wt %, more preferably 1 to 10 wt %, based on the hole injection material.

The p-dopant according to one embodiment of the present disclosure may include at least one of the following compounds P-1 to P-7.

P-1

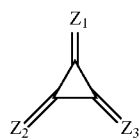

P-2

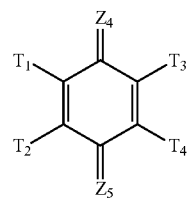

-continued

P-3

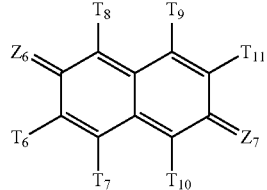

P-4

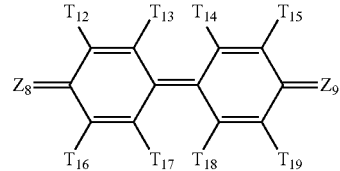

P-5

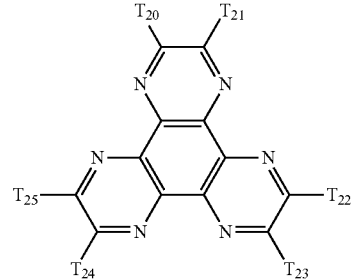

P-6

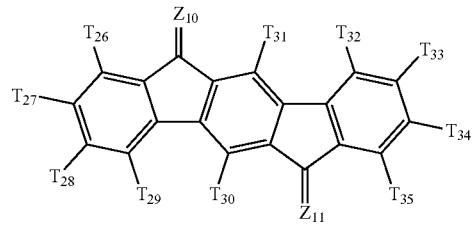

P-7

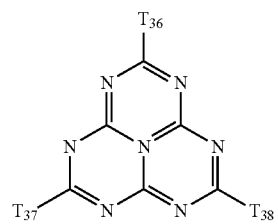

In the above formulas, $T_1$ to $T_{38}$, each independently, represent hydrogen, deuterium, a halogen, a substituted or unsubstituted (C1-050)alkyl fluoride, a cyano, a substituted or unsubstituted (C1-050)alkoxy, a substituted or unsubstituted (C1-050)alkyl, a substituted or unsubstituted (C6-050) aryl, or substituted or unsubstituted (3-30 membered)heteroaryl. In the above formulas, $=Z_1$ to $=Z_{11}$, each independently, may be represented by any one of the following formulas.

K-1

K-2

K-3 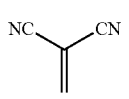

K-4 

K-5 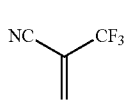

K-6 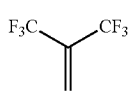

K-7 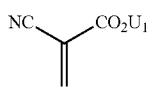

K-8 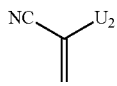

K-9 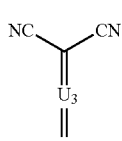

K-10 

K-11 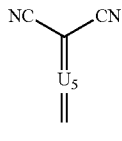

K-12 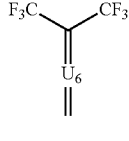

K-13 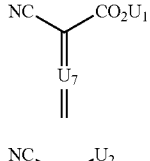

K-14 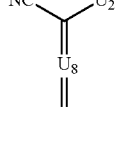

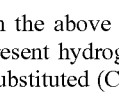

In the above formulas, $U_1$ and $U_2$, each independently, represent hydrogen, deuterium, a halogen, a substituted or unsubstituted (C1-050)alkyl fluoride, a cyano, a substituted or unsubstituted (C1-050)alkoxy, a substituted or unsubstituted (C1-050)alkyl, a substituted or unsubstituted (C6-050)aryl, or substituted or unsubstituted (3-30 membered)heteroaryl. $U_3$ to $U_8$, each independently, represent a substituted or unsubstituted (C1-050)alkylene fluoride, a substituted or unsubstituted (C1-050)alkylene, a substituted or unsubstituted (C6-C50)arylene, or substituted or unsubstituted (3-30 membered)heteroarylene.

The p-dopant may be specifically exemplified by the following compounds, but is not limited thereto.

PD-1 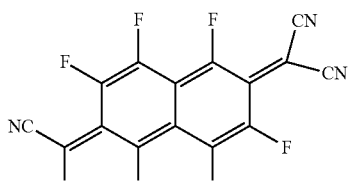

PD-2 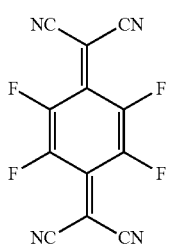

PD-3 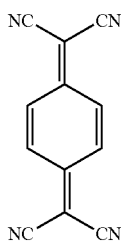

PD-4 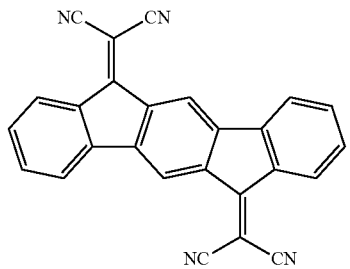

PD-5 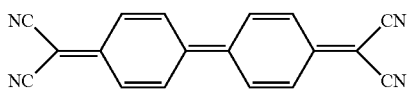

PD-6 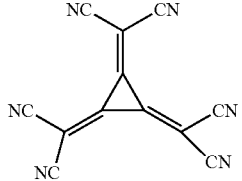

PD-7 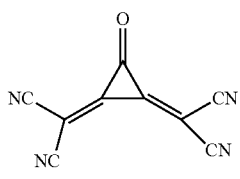

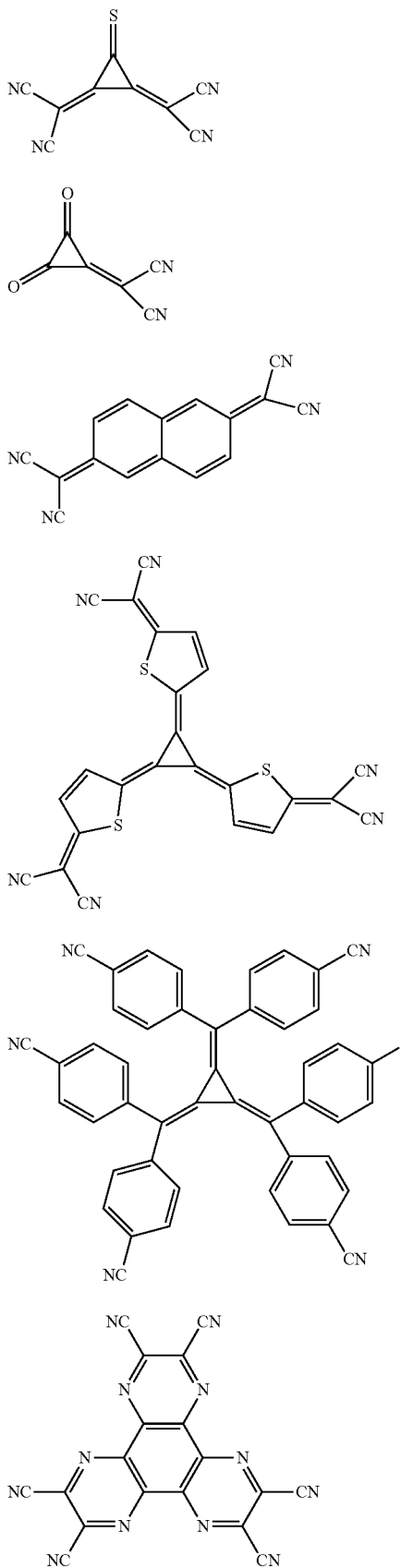

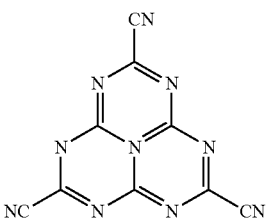

The dopant comprised in the light-emitting layer of the organic electroluminescent device of the present disclosure may be at least one phosphorescent or fluorescent dopont, and is preferably at least one phosphorescent dopant. The phosphorescent dopant material applied to the organic electroluminescent device of the present disclosure is not particulary limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the light-emitting layer of the organic electroluminescent device of the present disclosure may comprise the compound represented by the following formula 101, but is not limited thereto.

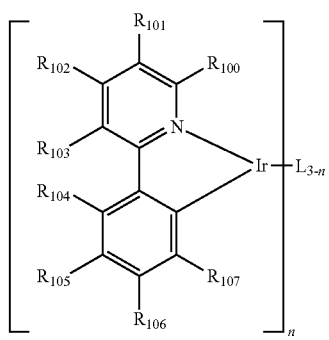

(101)

In formula 101, L is selected from the following structures 1 and 2:

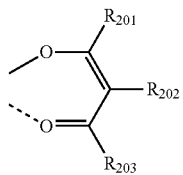

[Structure 1]

[Structure 2]

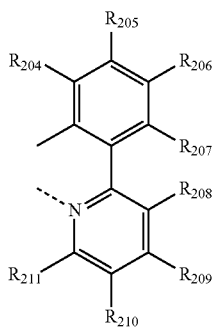

wherein, $R_{100}$ to $R_{103}$, and $R_{104}$ to $R_{107}$, each independently, represent hydrogen, deuterium, a halogen, a (C1-C30)alkyl unsubstituted or substituted with a halogen and/or deuterium, a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or $R_{100}$ to $R_{103}$ may be linked to adjacent $R_{100}$ to $R_{103}$, to form a substituted or unsubstituted fused ring, e.g., a substituted or unsubstituted, quinoline, benzofuropyridine, benzothienopyridine, indenopyridine, benzofuroquinoline, benzothienoquinoline, or indenoquinoline ring; and $R_{104}$ to $R_{107}$ may be linked to adjacent $R_{104}$ to $R_{107}$ to form a substituted or unsubstituted fused ring, e.g., a substituted or unsubstituted, naphthyl, fluorene, dibenzothiophene, dibenzofuran, indenopyridine, benzofuropyridine, or benzothienopyridine ring;

$R_{201}$ to $R_{211}$, each independently, represent hydrogen, deuterium, a halogen, a (C1-C30)alkyl unsubstituted or substituted with a halogen and/or deuterium, a substituted or unsubstituted (C3-C30)cycloalkyl, or a substituted or unsubstituted (C6-C30)aryl; or may be linked to adjacent $R_{201}$ to $R_{211}$ to form a substituted or unsubstituted fused ring; and n represents an integer of 1 to 3.

The specific examples of the dopant compound are as follows, but are not limited thereto.

D-1

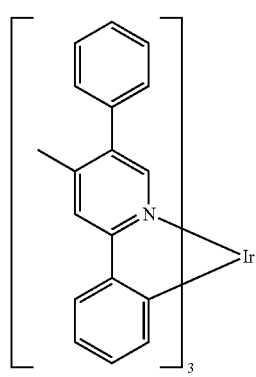

D-2

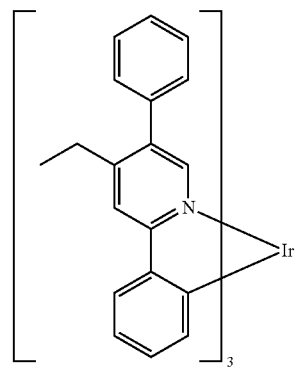

D-3

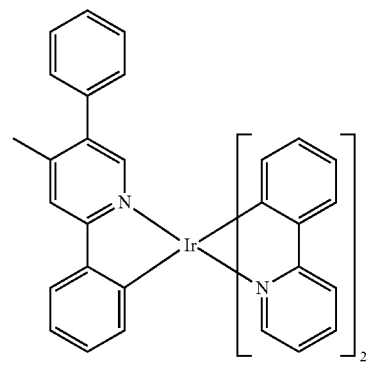

D-4

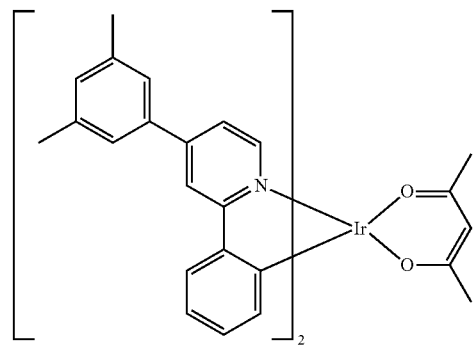

D-5

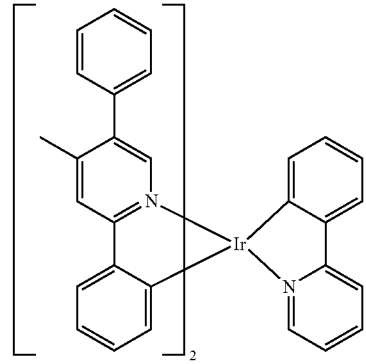

-continued
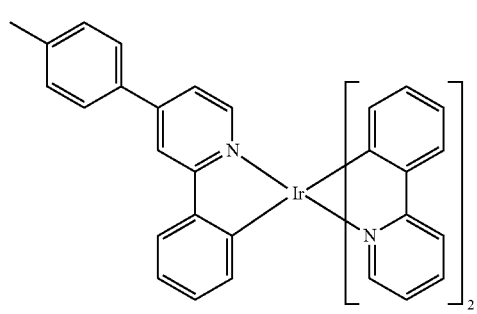
D-6
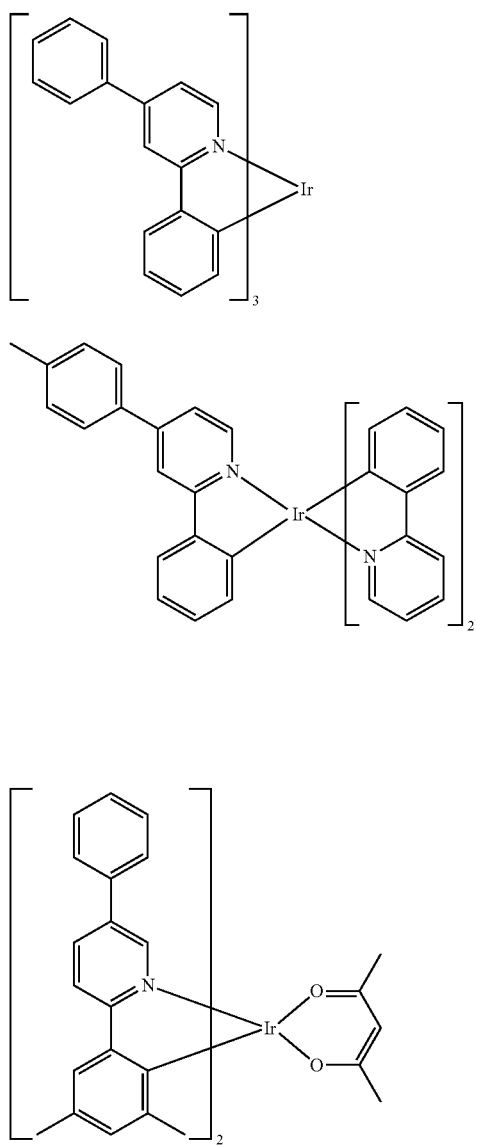
D-7
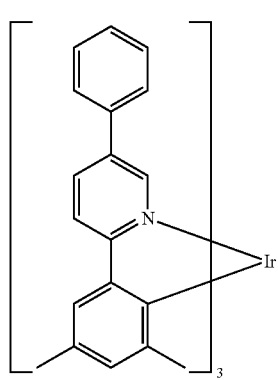
D-9
-continued
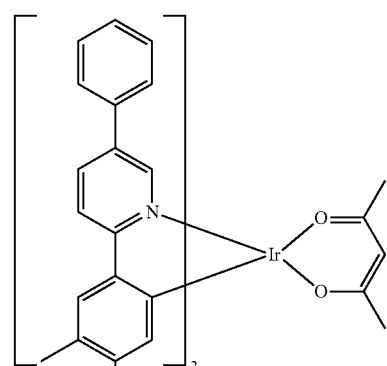
D-10
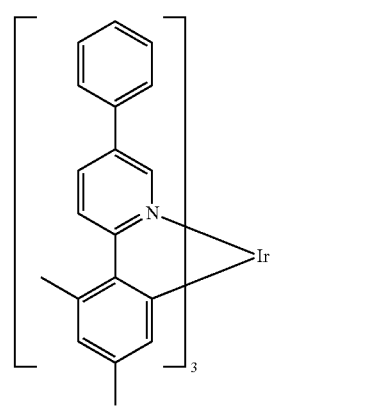
D-11
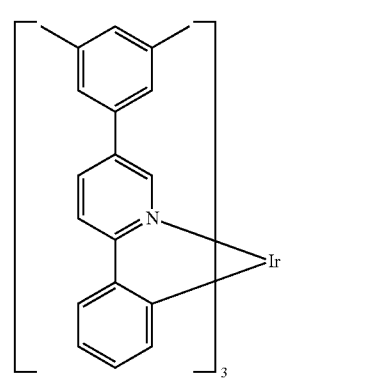
D-12
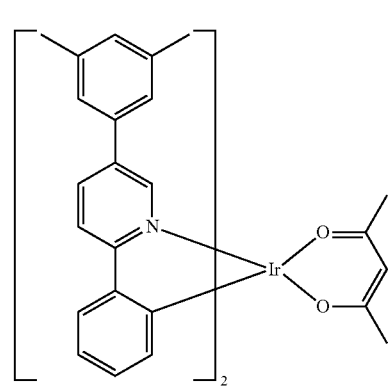
D-13

-continued
D-14
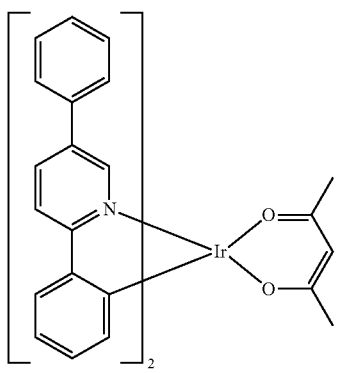
D-15
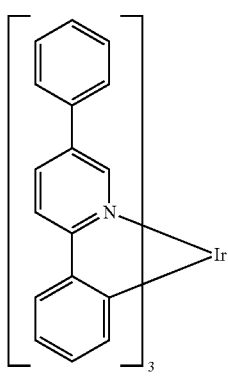
D-16
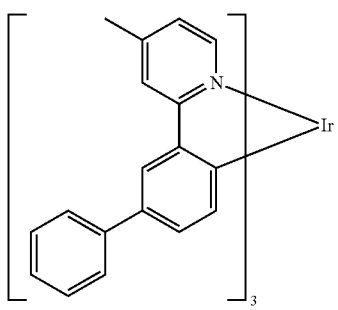
D-17
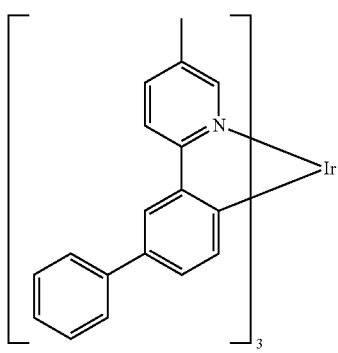
-continued
D-18
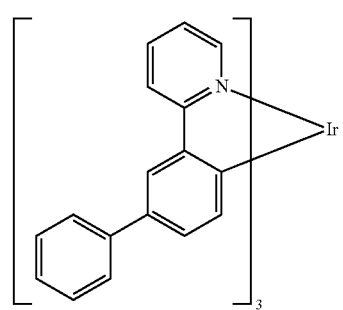
D-19
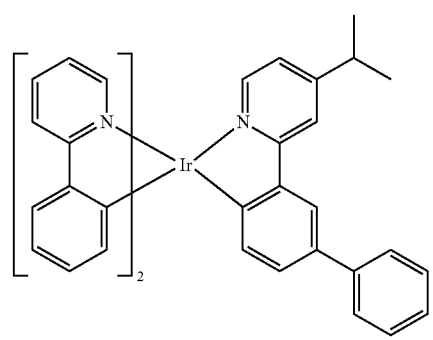
D-20
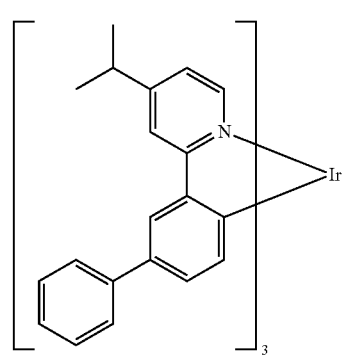
D-21
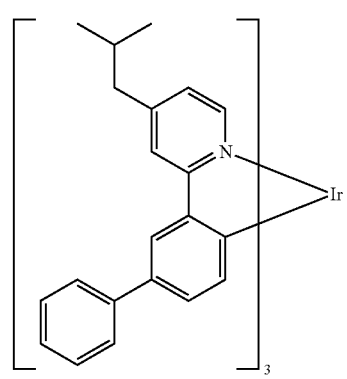

D-22
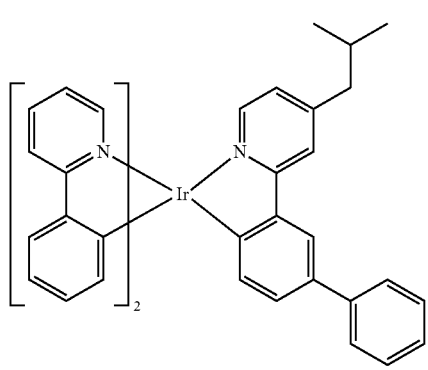
D-23
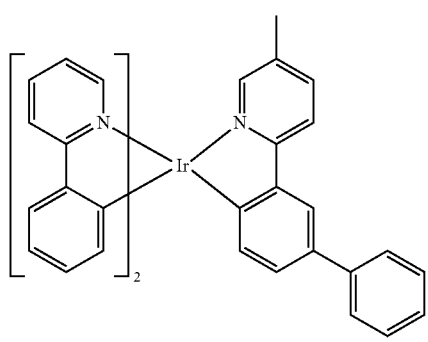
D-24
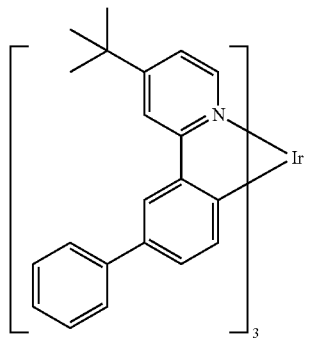
D-25
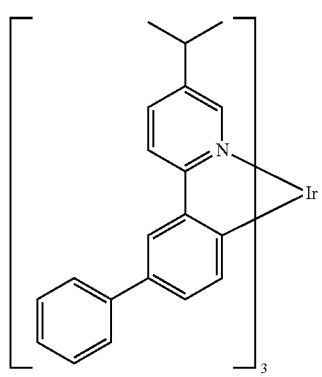
D-26
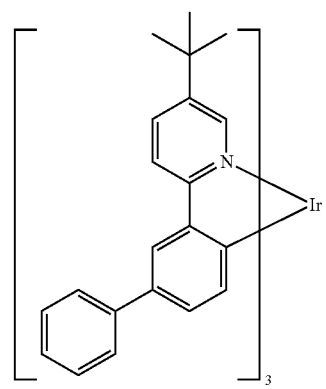
D-27
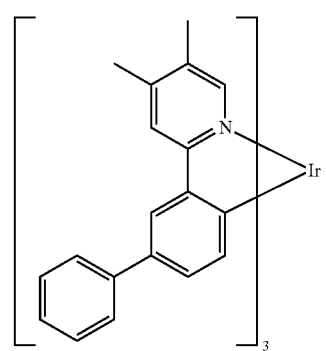
D-28
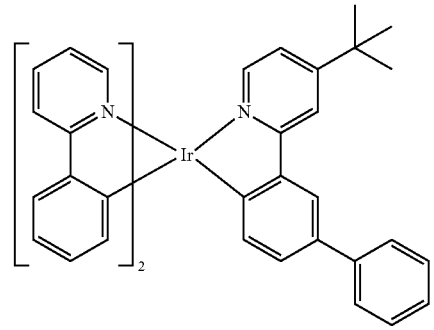
D-29
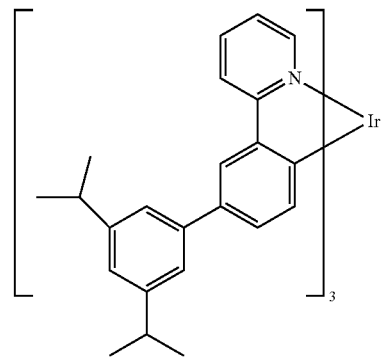

D-30
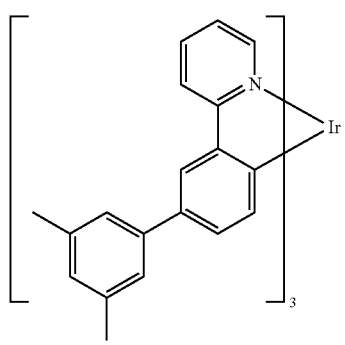
D-31
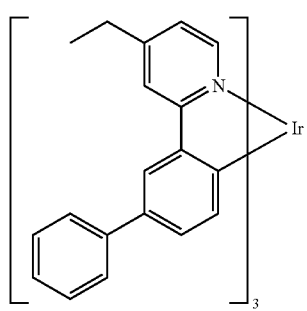
D-32
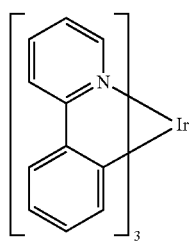
D-33
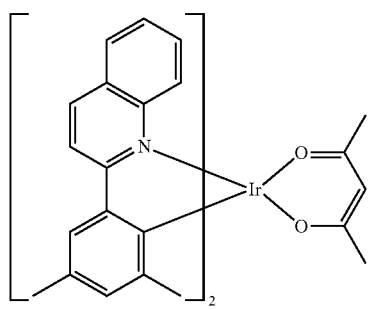
D-34
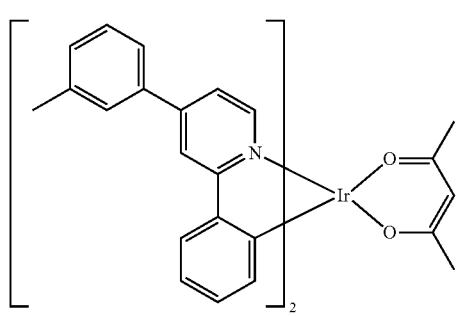
D-35
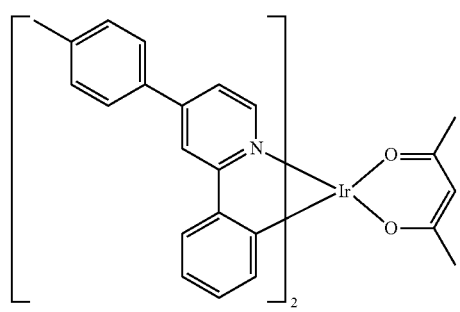
D-36
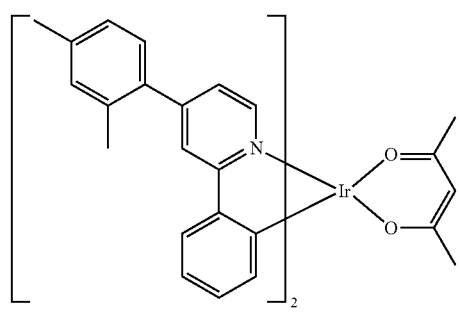
D-37
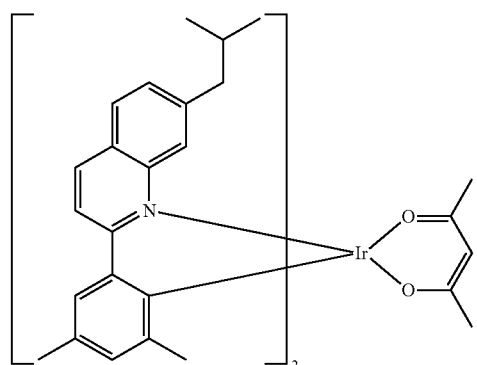
D-38
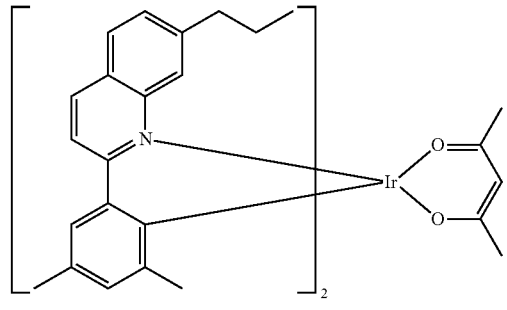

D-39
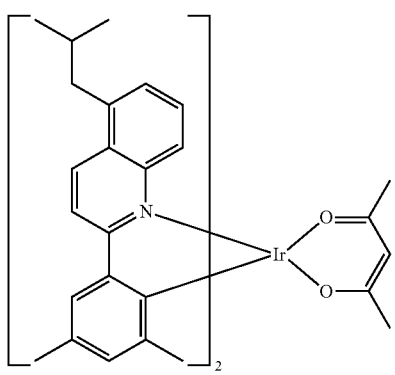
D-43
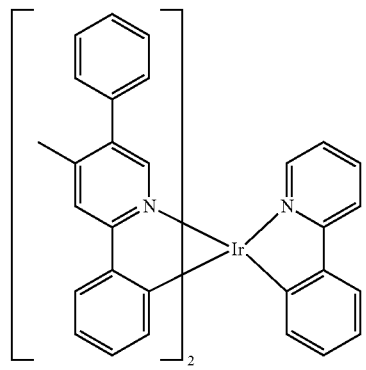
D-40
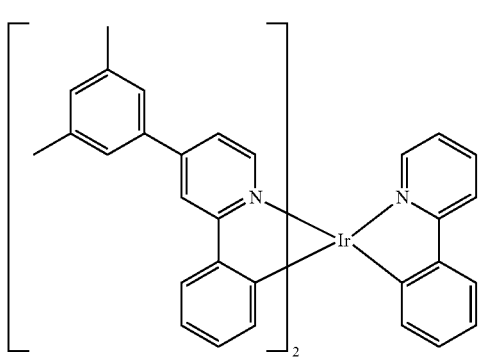
D-44
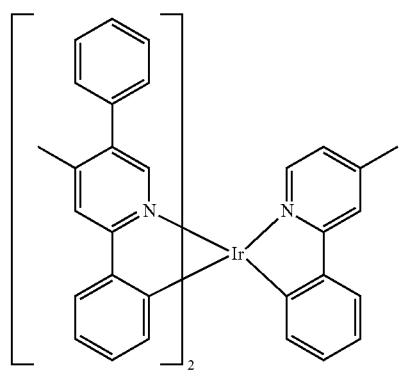
D-41
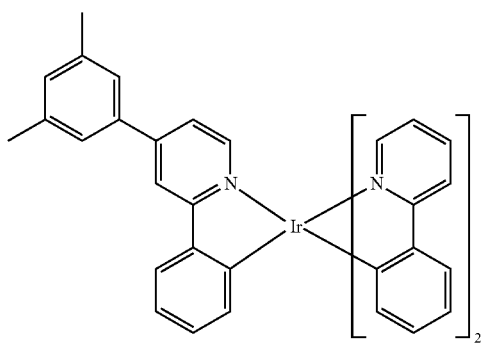
D-45
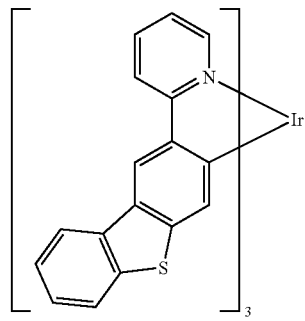
D-42
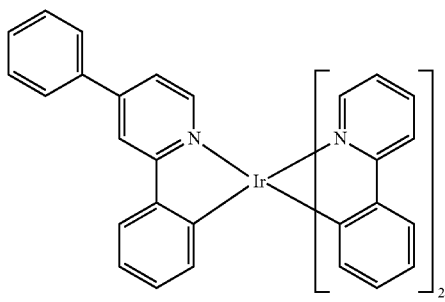
D-46
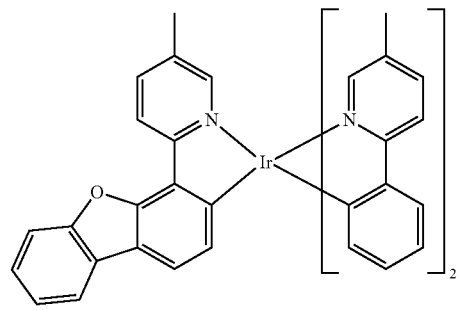

D-47
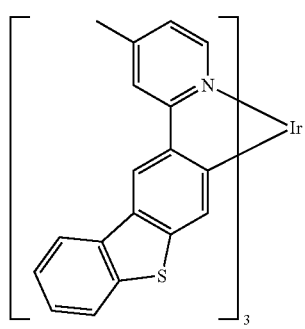
D-48
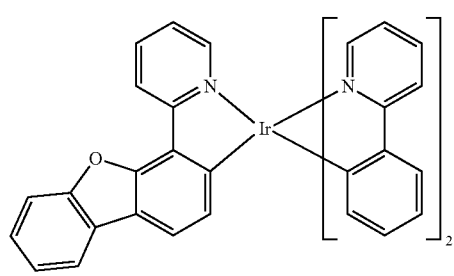
D-49
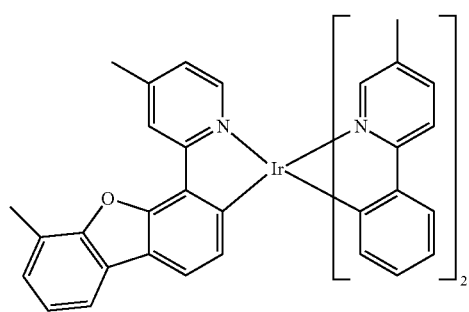
D-50
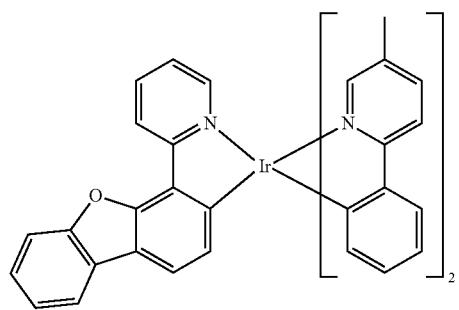
D-51
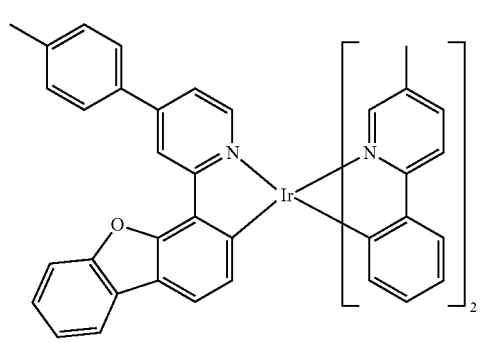
D-52
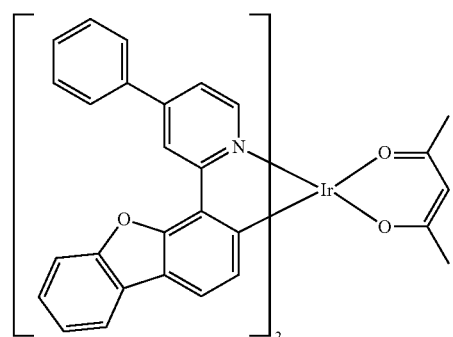
D-53
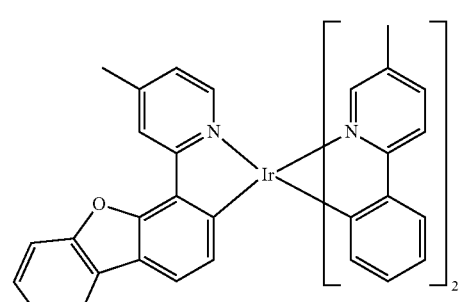
D-54
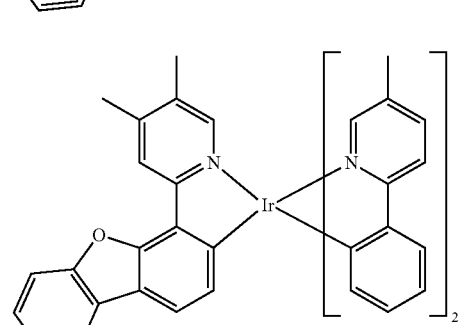
D-55
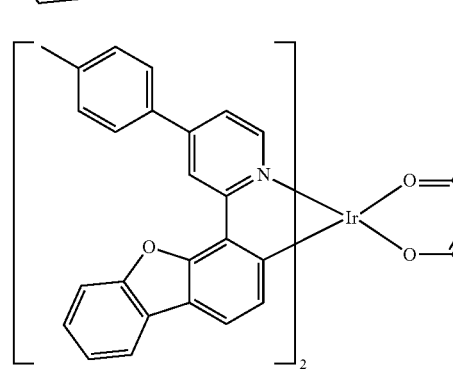
D-56
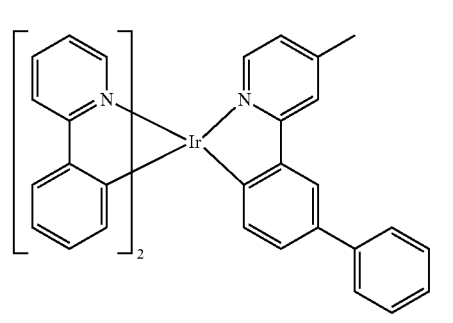

-continued
D-57
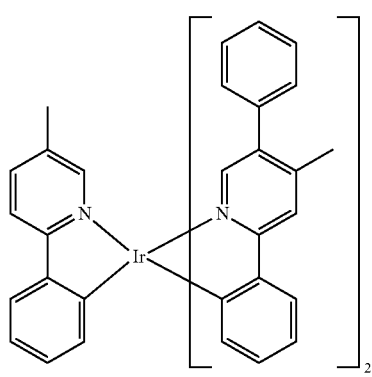
D-58
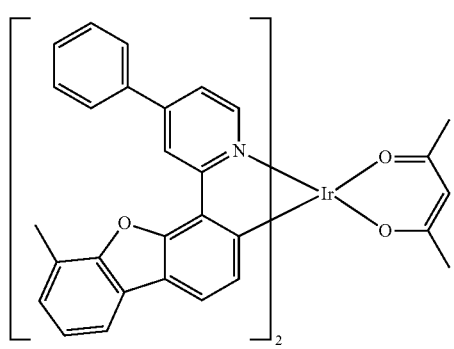
D-59
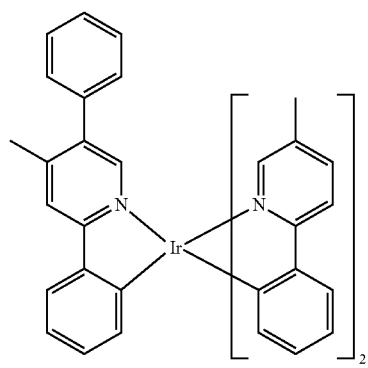
D-60
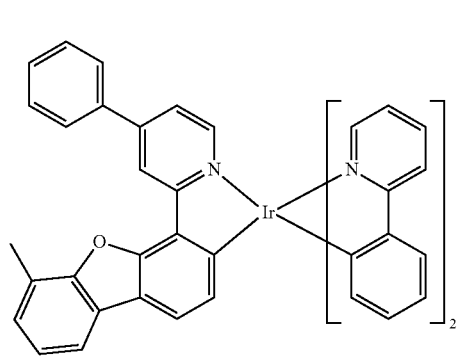
-continued
D-61
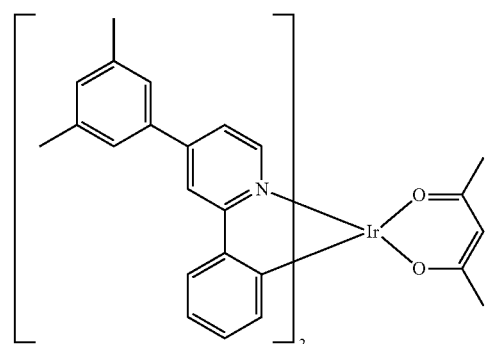
1p;2p
D-62
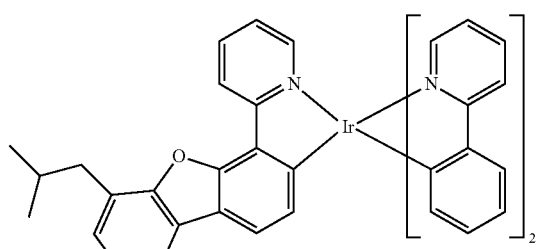
D-63
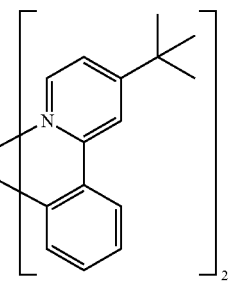
D-64
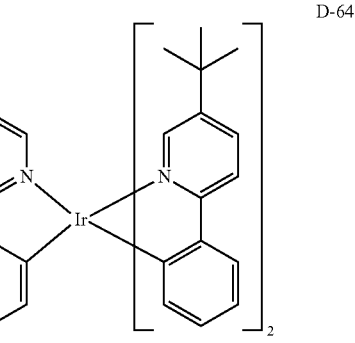

D-65
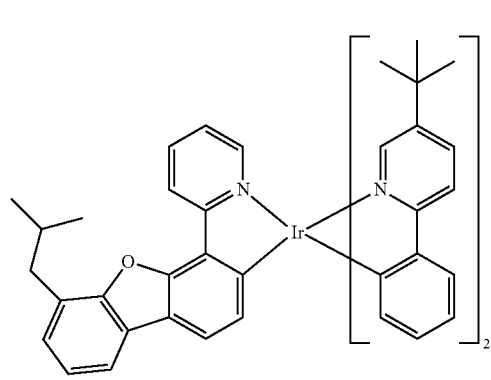
D-66
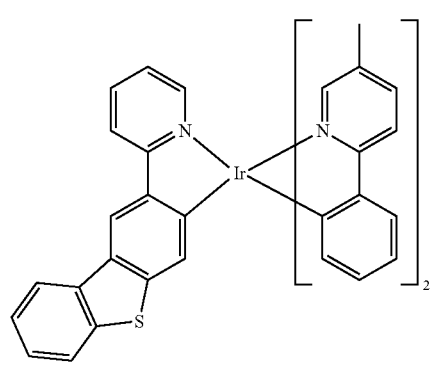
D-67
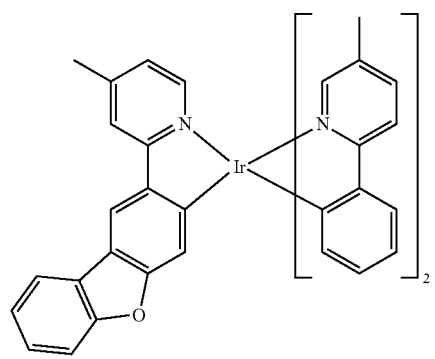
D-68
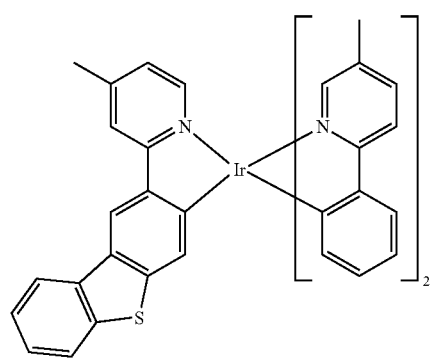
D-69
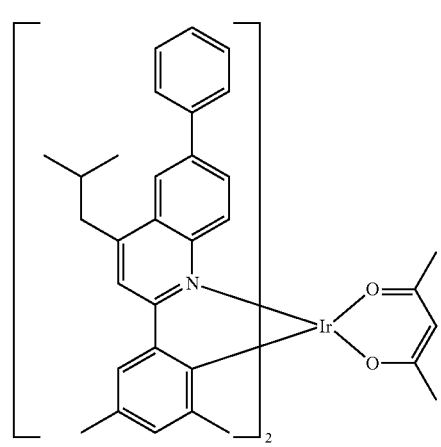
D-70
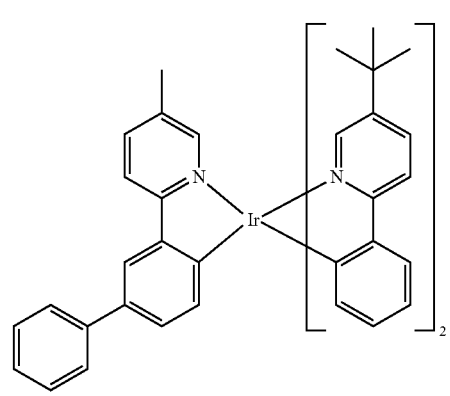
D-71
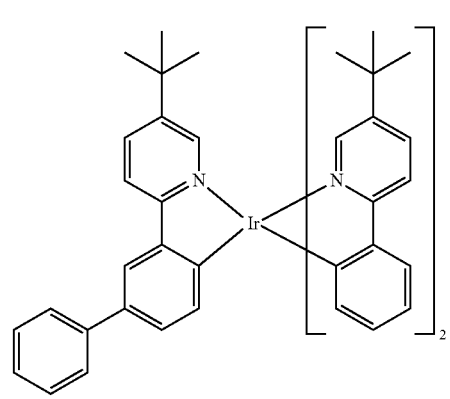
D-72
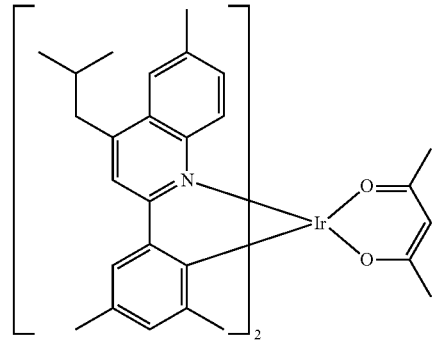

D-73
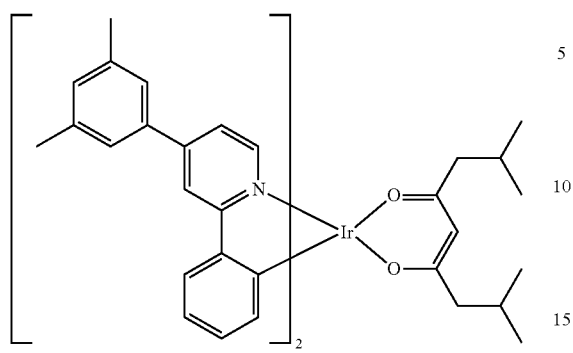
D-74
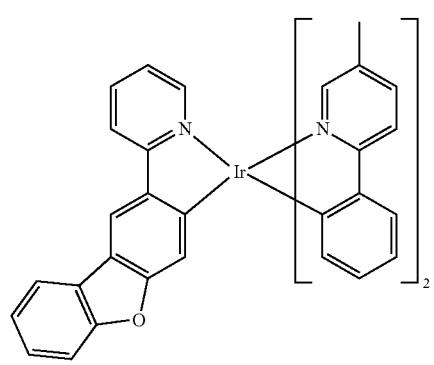
D-75
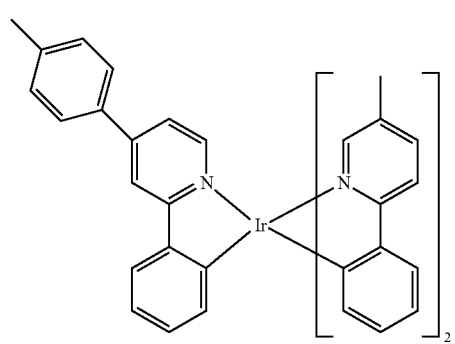
D-76
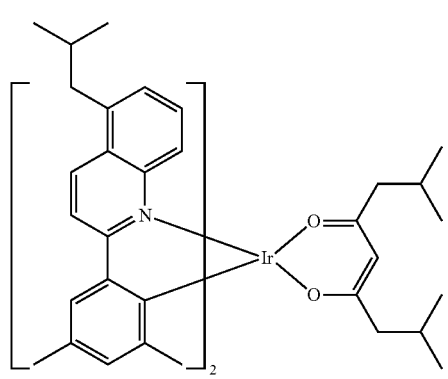
D-77
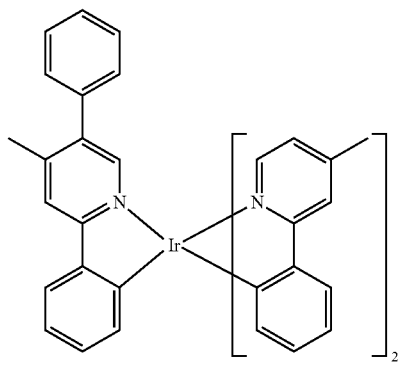
D-78
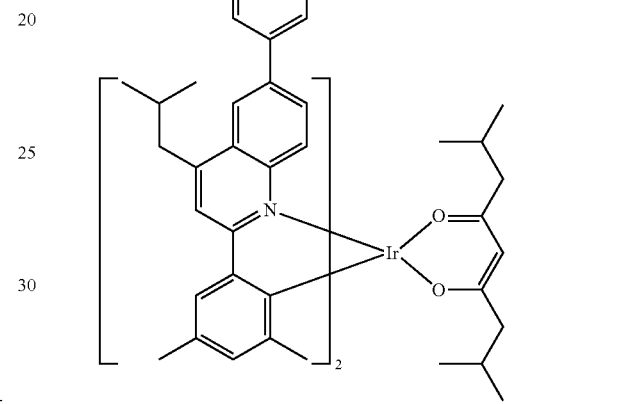
D-79
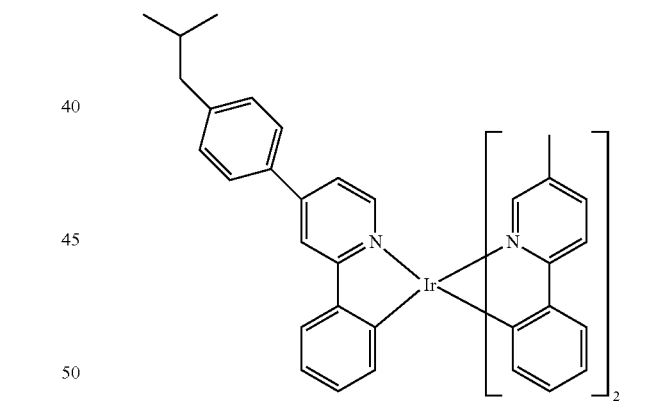
D-80
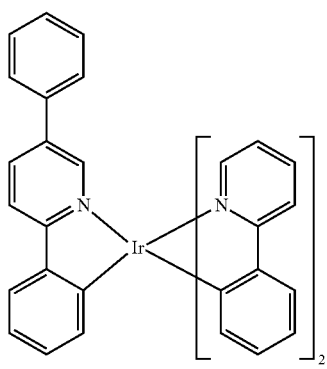

D-81
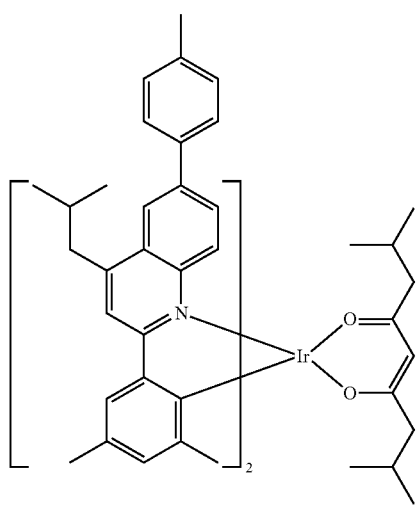
D-82
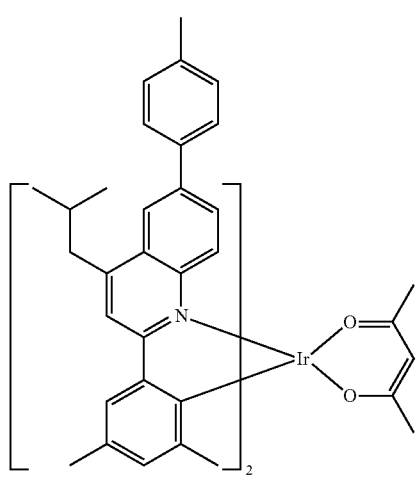
D-83
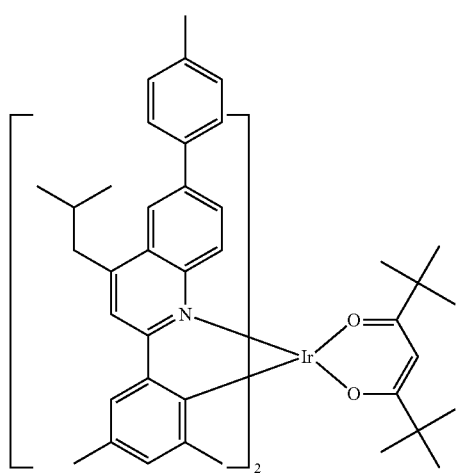
D-84
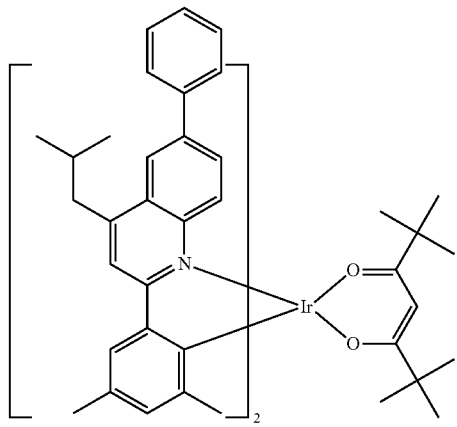
D-85
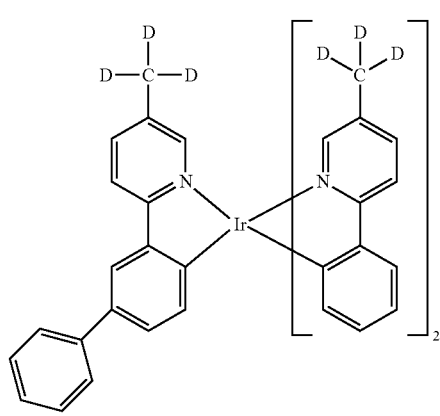
D-86
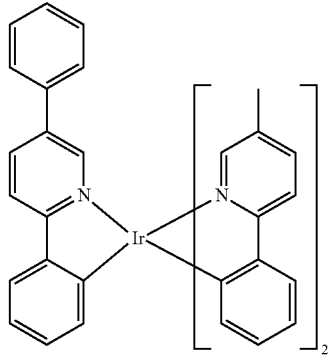
D-87
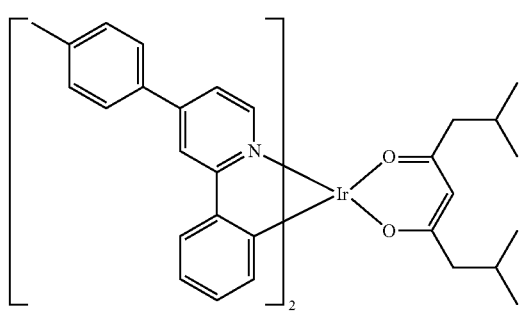

-continued
D-88
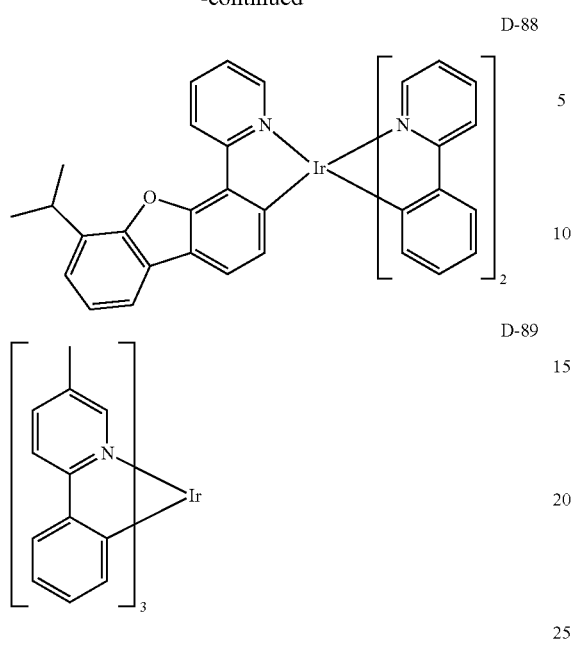
D-89
D-92
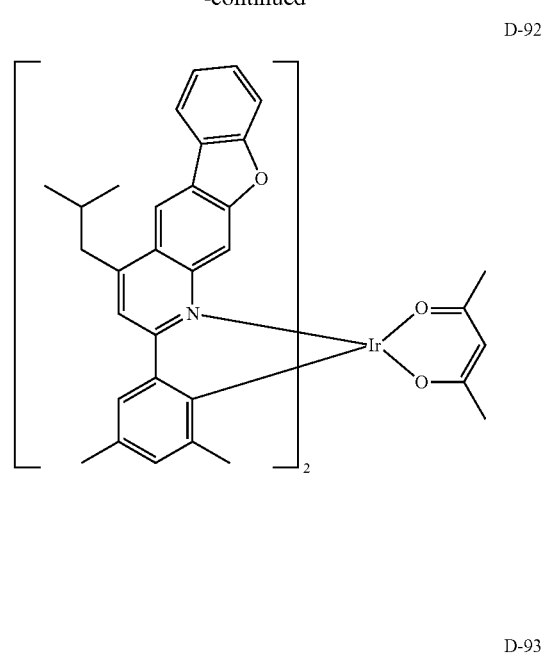
D-93
D-90
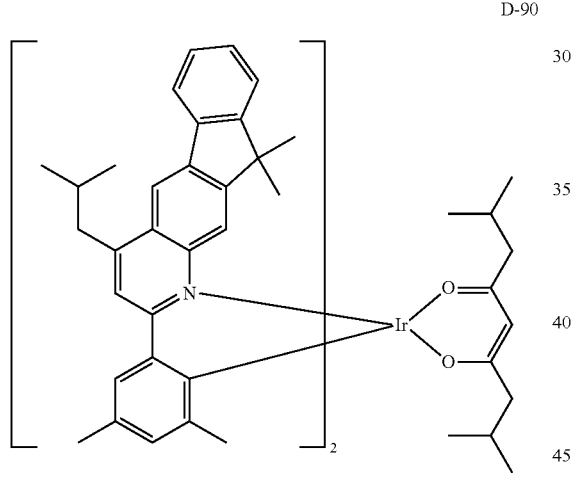
D-91
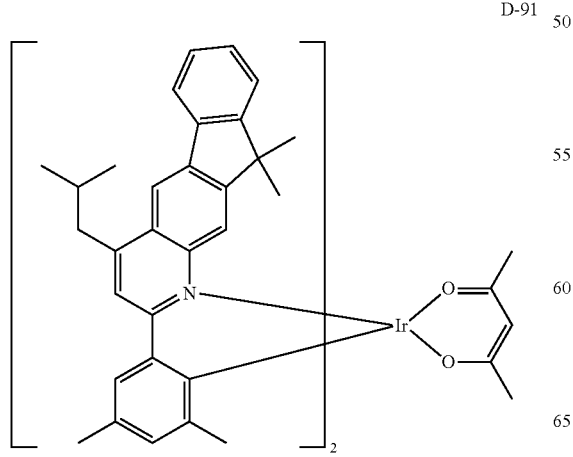
D-94
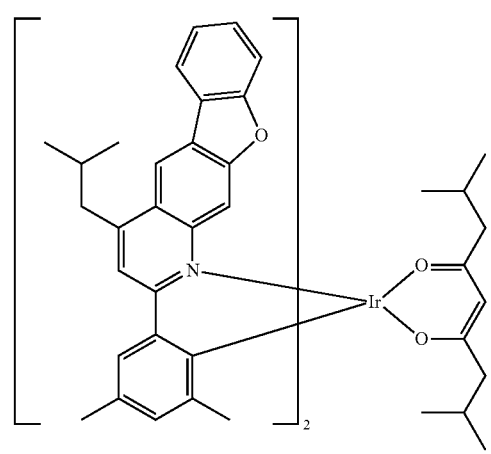
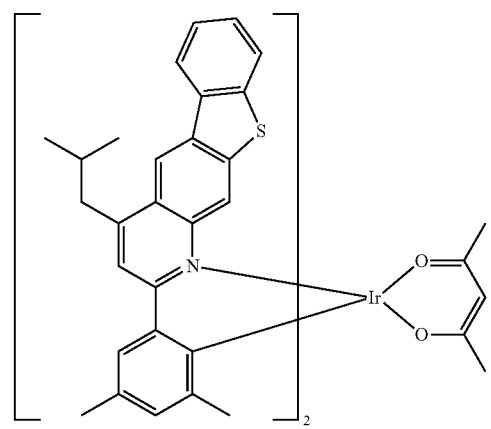

D-95
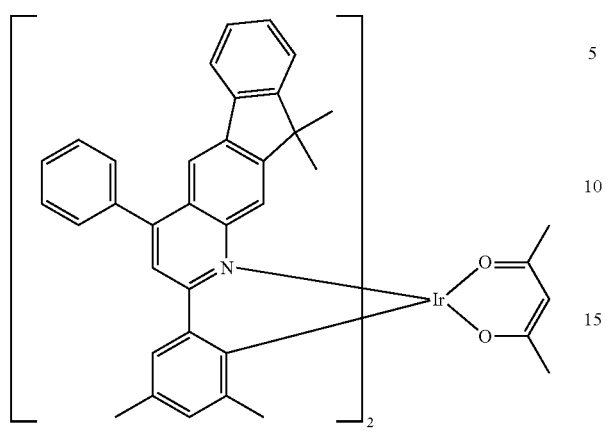
D-96
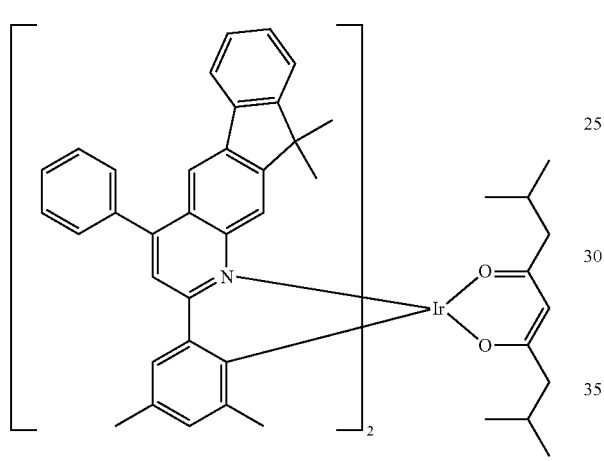
D-97
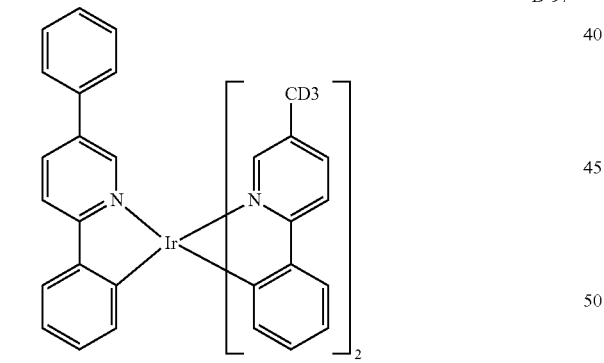
D-98
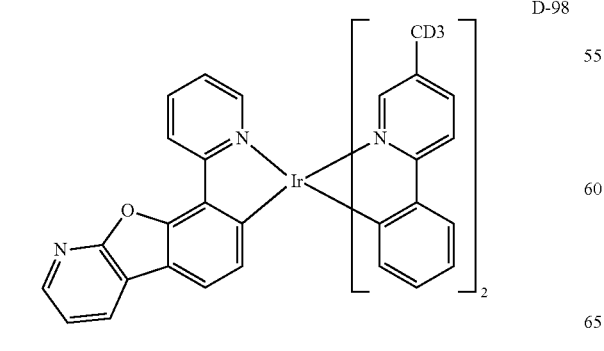
D-99
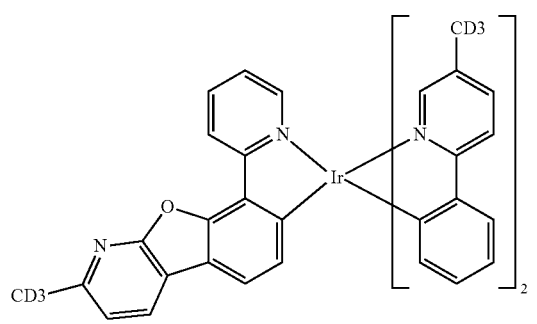
D-100
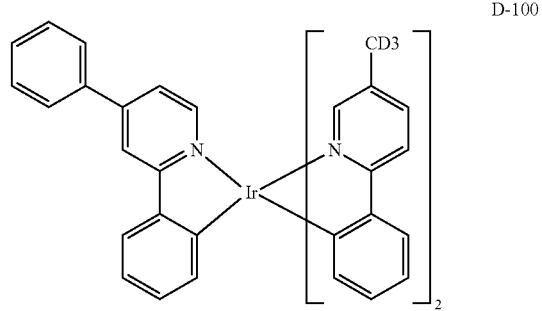
D-101
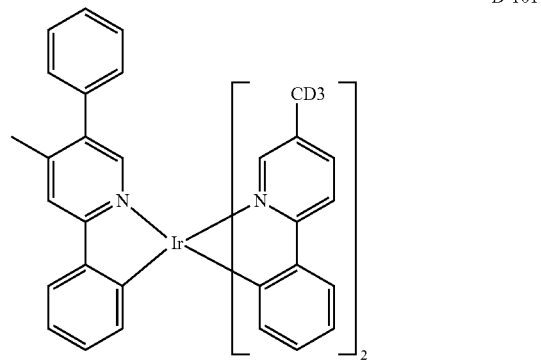
D-102
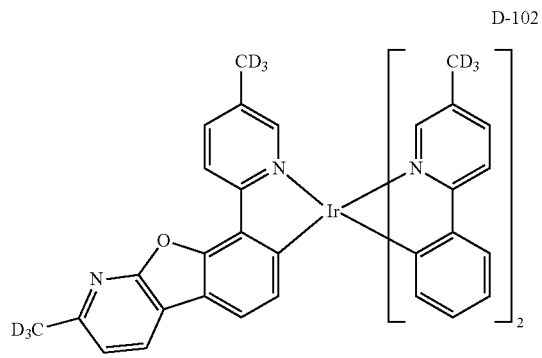

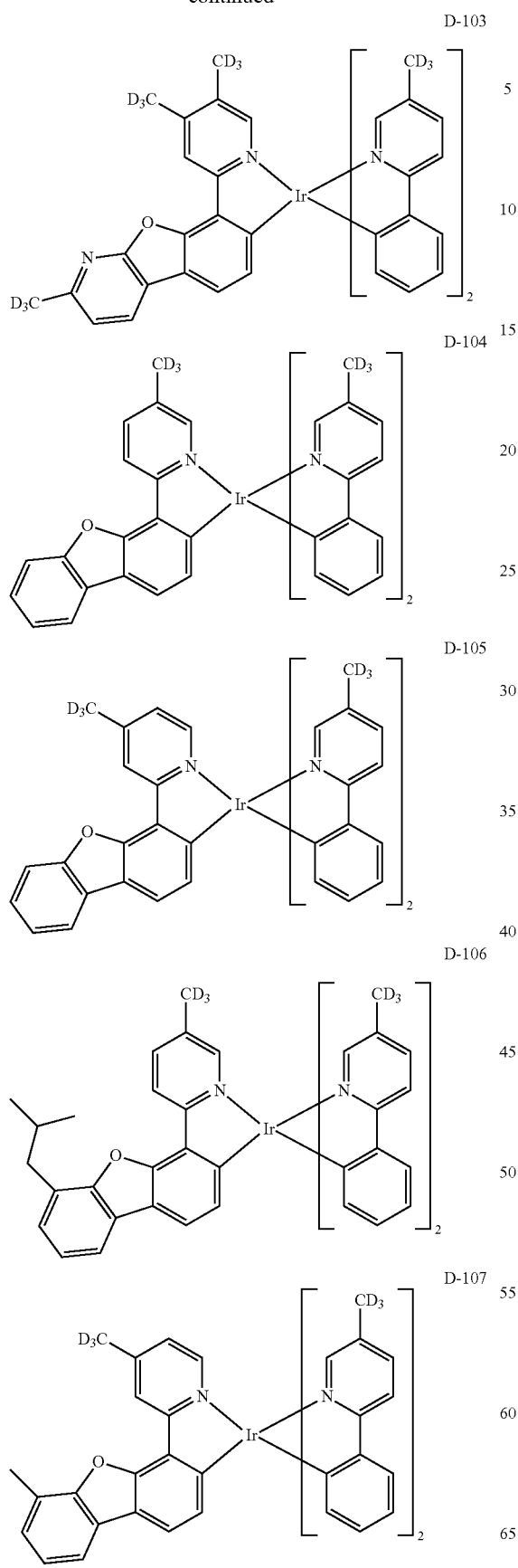
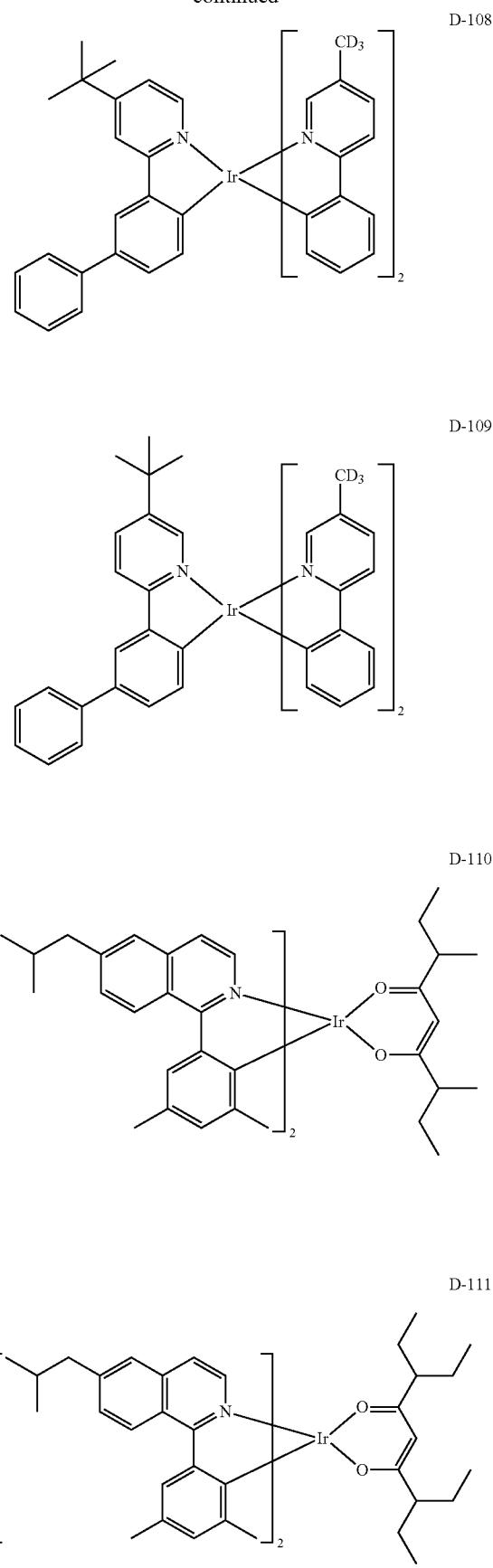

D-112
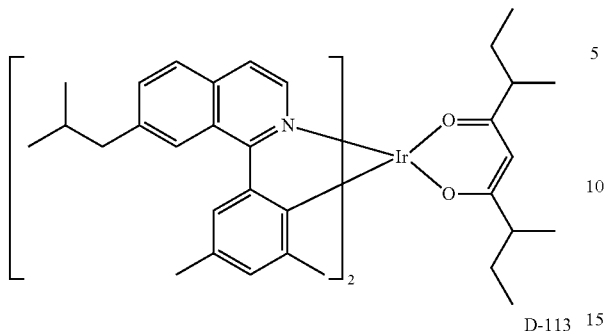

D-113
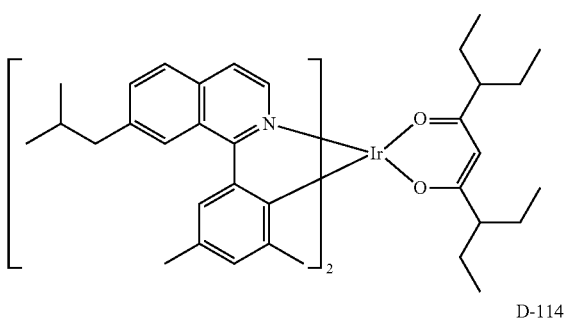

D-114
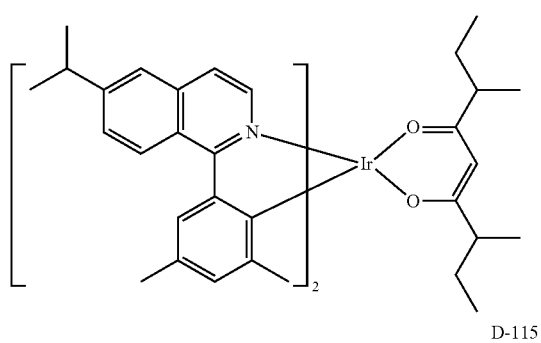

D-115
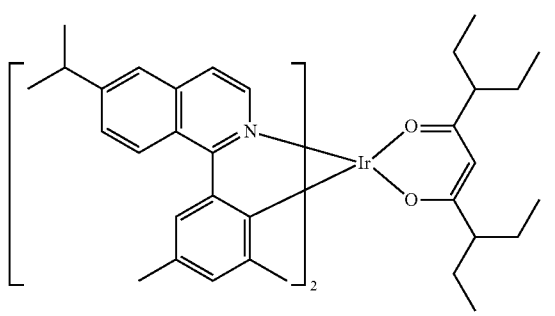

D-116
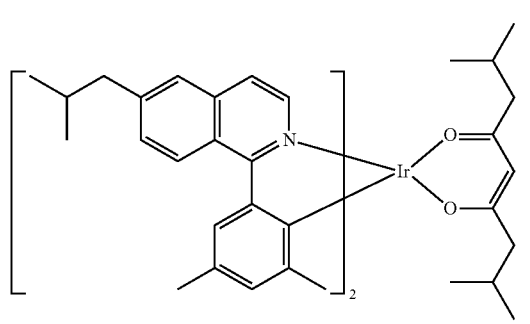

D-117
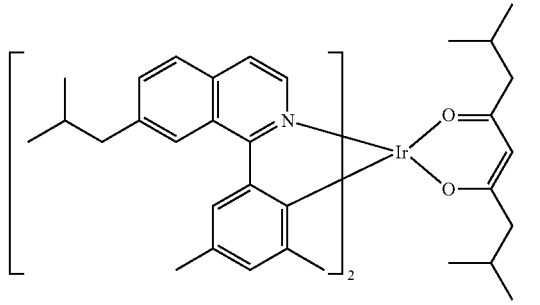

D-118
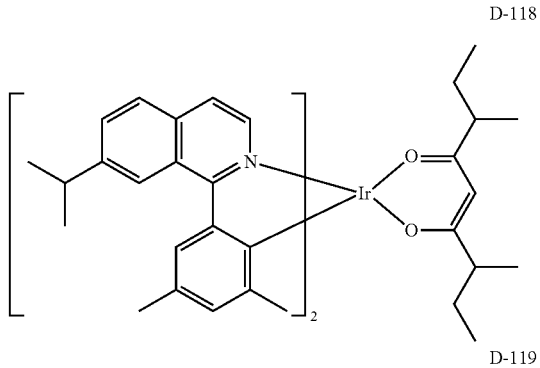

D-119
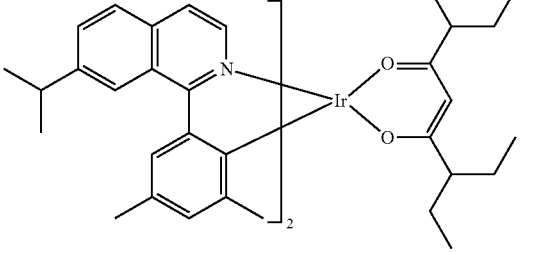

By using the organic electroluminescent device of the present disclosure, a display system, e.g., a display system for smart phones, tablets, notebooks, PCs, TVs, or cars; or a lighting system, e.g., an outdoor or indoor lighting system, can be produced.

The organic electroluminescent device of the present disclosure is intended to explain one embodiment of the present disclosure, and is not meant in any way to restrict the scope of the disclosure. The present disclosure may be embodied in other forms. The present disclosure may be embodied in other forms.

The HOMO energy levels of the present disclosure were measured by using a density functional theory (DFT) in a Gaussian 03 program of Gaussian, Inc. Specifically, the HOMO and LUMO energy levels in the Device Examples and Comparative Examples of the present disclosure were extracted from the structure with the lowest energy by comparing the calculated energies of isomers after structurally optimizing all possible isomer structures at the level of B3LYP/6-31 g*.

Hereinafter, it will be explained whether the efficiency of the OLED device can be improved by comprising the compound of formula 1 in the light-emitting layer and the arylamine derivative having a specific HOMO energy level in the hole transport zone. However, the following examples merely explain the properties of the OLED device according to the present disclosure for a detailed understanding thereof, but the present disclosure is not limited by the following examples.

DEVICE EXAMPLES 1 to 27

Producing an OLED Device According to the Present Disclosure

OLED devices according to the present disclosure were produced. A transparent electrode indium tin oxide (ITO) thin film (10 Ω/sq) on a glass substrate for an OLED device (GEOMATEC CO., LTD., Japan) was subjected to an ultrasonic washing with acetone and isopropyl alcohol, sequentially, and then was stored in isopropyl alcohol. The ITO substrate was then mounted on a substrate holder of a vacuum vapor deposition apparatus. Compound HI-1 was introduced into a cell of the vacuum vapor deposition apparatus, and then the pressure in the chamber of the apparatus was controlled to $10^{-6}$ torr. Thereafter, an electric current was applied to the cell to evaporate the above-introduced material, thereby forming a first hole injection layer having a thickness of 90 nm on the ITO substrate. Next, compound HI-2 was introduced into another cell of the vacuum vapor deposition apparatus and was evaporated by applying an electric current to the cell, thereby forming a second hole injection layer having a thickness of 5 nm on the first hole injection layer. Compound HT-2-46 was then introduced into a cell of the vacuum vapor deposition apparatus and was evaporated by applying an electric current to the cell, thereby forming a first hole transport layer having a thickness of 10 nm on the second hole injection layer. The compound of the second hole transport layer shown in Table 1 was then introduced into another cell of the vacuum vapor deposition apparatus and was evaporated by applying an electric current to the cell, thereby forming a second hole transport layer (auxiliary layer) having a thickness of 60 nm on the first hole transport layer. After forming the hole injection layer and the hole transport layer, a light-emitting layer was formed thereon as follows: The host material shown in Table 1 was introduced into one cell of the vacuum vapor depositing apparatus as a host, and compound D-39 was introduced into another cell as a dopant. The two materials were evaporated and the dopant was deposited in a doping amount of 2 wt % based on the amount of the host and dopant to form a light-emitting layer having a thickness of 40 nm on the hole transport layer. Compound ET-1 and compound EI-1 were then introduced into the other two cells and evaporated at a rate of 1:1 to form an electron transport layer having a thickness of 35 nm on the light-emitting layer. After depositing compound EI-1 as an electron injection layer having a thickness of 2 nm on the electron transport layer, an Al cathode having a thickness of 80 nm was deposited on the electron injection layer by another vacuum vapor deposition apparatus. Thus, an OLED device was produced.

COMPARATIVE EXAMPLES 1 to 19

Producing an OLED Device not According to the Present Disclosure

OLED devices were produced in the same manner as in Device Example 1, except that the compound shown in the following Table 1 was used in the second hole transport layer, and the compound CBP was used in the host.

COMPARATIVE EXAMPLE 20

Producing an OLED Device not According to the Present Disclosure

An OLED device was produced in the same manner as in Device Example 1, except that the compound shown in the following Table 1 was used in the second hole transport layer.

The compounds used in Device Examples 1 to 27 and Comparative Examples 1 to 20 are as follows.

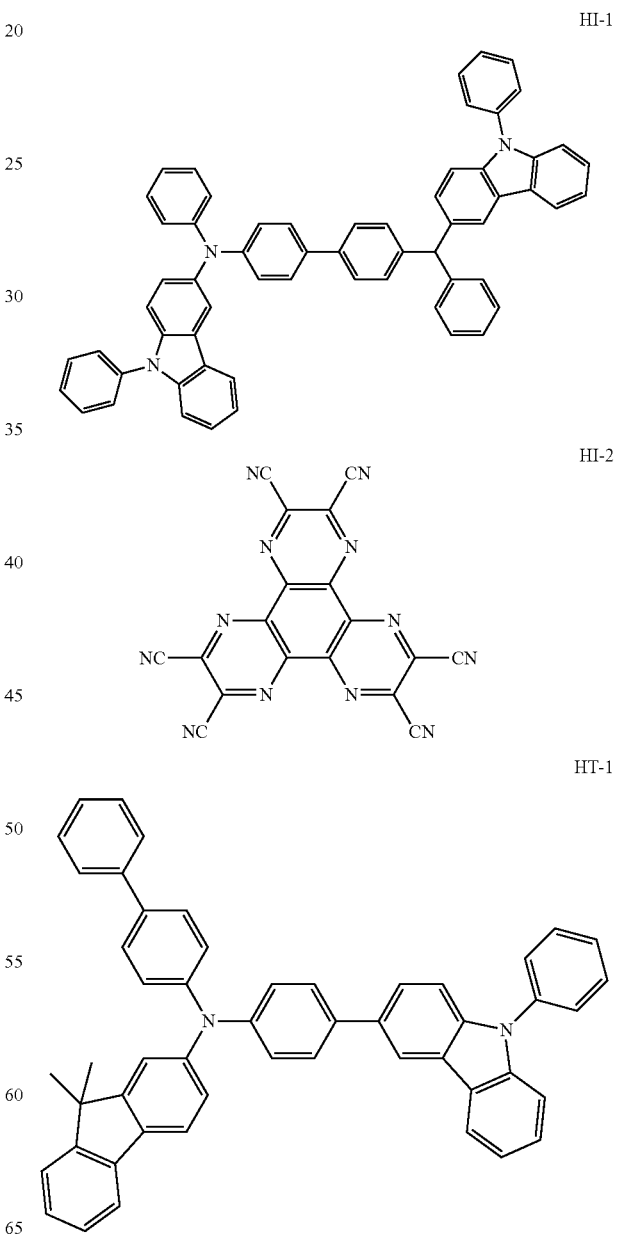

-continued

ET-1

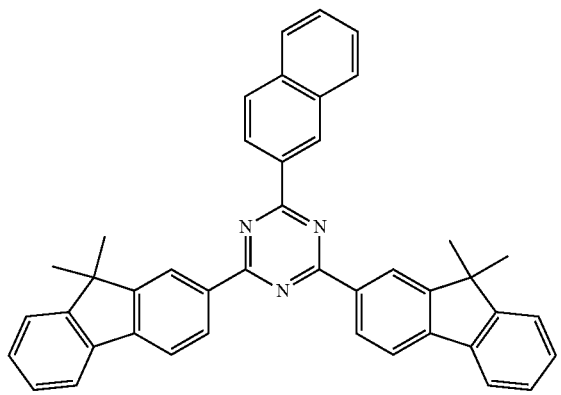

EI-1

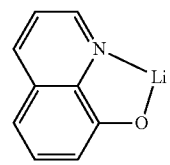

HT-1-1

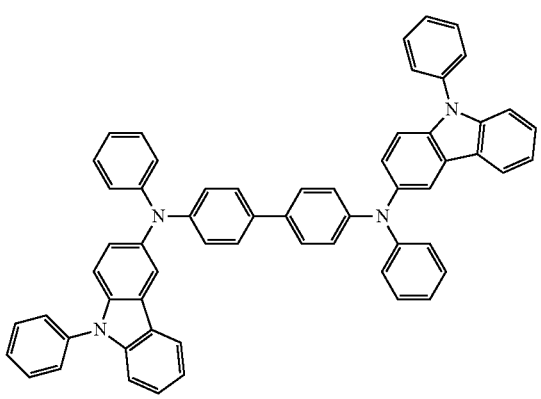

-continued

HT-1-2

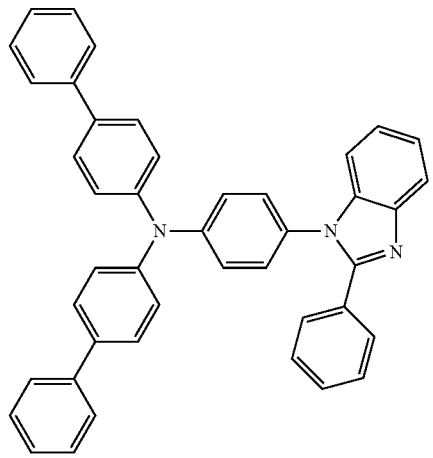

CBP

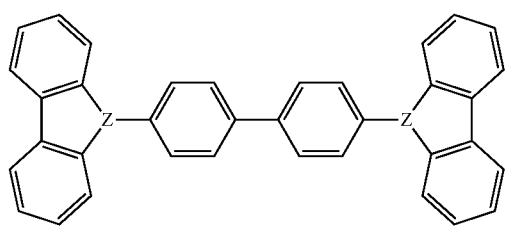

DEVICE EXAMPLES 28 to 33

Producing an OLED Device According to the Present Disclosure

OLED devices were produced in the same manner as in Device Example 1, except that compound HT-1 and compound HI-2 were deposited at a ratio of 1:0.03 instead of the first and second hole injection layers to form a hole injection layer having a thickness of 5 nm, and compound HT-1 was then evaporated to form a first hole transport layer having a thickness of 100 nm, and the compound shown in Table 1 was used in the second hole transport layer.

The driving voltage, the luminous efficiency, and the CIE color coordinates at luminance of 1,000 nits, and the lifespan (measured as the percentage to which the luminance decreased from 100% after 16.6 hours at a constant current and at a luminance of 5,000 nits) of the OLED devices produced in Device Examples 1 to 33 and Comparative Examples 1 to 20 are provided in Table 1 below.

TABLE 1

|  | Second Hole Transport Layer | Host | Driving Voltage (V) | | Luminous Efficiency (cd/A) | | CIE | | Lifespan |
|---|---|---|---|---|---|---|---|---|---|
|  |  |  | At 1000 nits | At 50 mA/cm² | At 1000 nits | At 5000 nits | x | y |  |
| Device Example 1 | HT-2-46 | C-241 | 2.8 | 4.7 | 22.2 | 19.1 | 0.667 | 0.333 | 99.7 |
| Device Example 2 | HT-2-47 |  | 3.4 | 5.5 | 27.2 | 24.9 | 0.668 | 0.332 | 99.6 |
| Device Example 3 | HT-2-51 |  | 3.1 | 5.4 | 26.4 | 24.0 | 0.668 | 0.332 | 99.7 |
| Device Example 4 | HT-2-122 |  | 4.6 | 6.9 | 25.5 | 22.7 | 0.667 | 0.332 | 99.0 |
| Device Example 5 | HT-2-48 |  | 2.8 | 4.6 | 27.1 | 23.1 | 0.667 | 0.332 | 99.3 |
| Device Example 6 | HT-2-49 |  | 3.0 | 5.3 | 26.1 | 23.0 | 0.667 | 0.333 | 99.2 |
| Device Example 7 | HT-2-118 |  | 3.4 | 5.5 | 16.2 | 12.6 | 0.659 | 0.339 | 99.0 |
| Device Example 8 | HT-2-119 |  | 2.7 | 4.5 | 27.8 | 25.0 | 0.667 | 0.332 | 99.6 |

TABLE 1-continued

| | Second Hole Transport Layer | Host | Driving Voltage (V) At 1000 nits | At 50 mA/cm² | Luminous Efficiency (cd/A) At 1000 nits | At 5000 nits | CIE x | y | Life-span |
|---|---|---|---|---|---|---|---|---|---|
| Device Example 9 | HT-2-17 | | 2.7 | 4.4 | 26.0 | 22.5 | 0.668 | 0.332 | 99.5 |
| Device Example 10 | HT-2-19 | | 2.7 | 4.3 | 24.0 | 20.6 | 0.668 | 0.332 | 99.9 |
| Device Example 11 | HT-2-20 | | 2.7 | 4.4 | 28.9 | 25.9 | 0.668 | 0.332 | 99.7 |
| Device Example 12 | HT-2-24 | | 2.8 | 4.6 | 29.5 | 26.6 | 0.667 | 0.332 | 99.8 |
| Device Example 13 | HT-2-23 | | 2.9 | 4.8 | 29.3 | 26.3 | 0.667 | 0.333 | 99.5 |
| Device Example 14 | HT-2-120 | | 3.3 | 5.4 | 26.4 | 24.2 | 0.668 | 0.332 | 99.9 |
| Device Example 15 | HT-2-121 | | 2.9 | 4.6 | 25.3 | 23.6 | 0.664 | 0.335 | 99.6 |
| Device Example 16 | HT-2-1 | | 3.4 | 5.4 | 26.0 | 23.5 | 0.668 | 0.332 | 99.7 |
| Device Example 17 | HT-2-28 | | 3.2 | 5.5 | 30.4 | 28.1 | 0.667 | 0.332 | 99.7 |
| Device Example 18 | HT-2-43 | | 2.8 | 4.7 | 27.6 | 24.8 | 0.667 | 0.332 | 99.7 |
| Device Example 19 | HT-2-43 | C-246 | 3.0 | 5.2 | 26.2 | 24.0 | 0.669 | 0.330 | 99.4 |
| Device Example 20 | HT-2-23 | | 3.0 | 5.2 | 27.9 | 25.8 | 0.669 | 0.331 | 99.3 |
| Device Example 21 | HT-2-24 | | 3.0 | 4.9 | 27.8 | 25.8 | 0.669 | 0.331 | 99.4 |
| Device Example 22 | HT-2-43 | C-540 | 3.1 | 5.2 | 27.1 | 24.8 | 0.669 | 0.331 | 98.3 |
| Device Example 23 | HT-2-23 | | 3.0 | 5.1 | 26.9 | 24.6 | 0.669 | 0.331 | 99.0 |
| Device Example 24 | HT-2-24 | | 3.1 | 5.2 | 27.0 | 24.8 | 0.669 | 0.331 | 99.0 |
| Device Example 25 | HT-2-43 | C-566 | 3.3 | 5.4 | 27.7 | 25.3 | 0.669 | 0.331 | 99.4 |
| Device Example 26 | HT-2-24 | | 3.3 | 5.3 | 27.8 | 26.1 | 0.666 | 0.334 | 99.2 |
| Device Example 27 | HT-2-17 | | 3.1 | 5.0 | 26.7 | 23.5 | 0.667 | 0.333 | 99.3 |
| Device Example 28 | HT-2-47 | C-241 | 3.4 | 5.7 | 29.7 | 27.7 | 0.672 | 0.328 | 99.2 |
| Device Example 29 | HT-2-48 | | 2.8 | 4.7 | 29.1 | 25.8 | 0.671 | 0.329 | 99.5 |
| Device Example 30 | HT-2-120 | C-241 | 3.4 | 5.7 | 29.4 | 28.0 | 0.671 | 0.329 | 100.0 |
| Device Example 31 | HT-2-126 | | 4.0 | 6.4 | 34.1 | 31.9 | 0.671 | 0.329 | 99.1 |
| Device Example 32 | HT-2-127 | | 2.8 | 4.9 | 33.5 | 31.8 | 0.671 | 0.328 | 99.3 |
| Device Example 33 | HT-2-17 | | 2.7 | 4.7 | 29.6 | 26.4 | 0.672 | 0.328 | 99.7 |
| Comparative Example 1 | HT-1-1 | CBP | 10.5 | 11.7 | 4.5 | 0.0 | 0.625 | 0.320 | 65.5 |
| Comparative Example 2 | HT-1-2 | | 10.2 | 13.3 | 15.8 | 13.1 | 0.645 | 0.328 | 80.8 |
| Comparative Example 3 | HT-2-46 | | 9.1 | 11.2 | 10.0 | 7.7 | 0.650 | 0.331 | 84.0 |
| Comparative Example 4 | HT-2-47 | | 9.3 | 11.8 | 17.1 | 13.3 | 0.655 | 0.334 | 86.6 |
| Comparative Example 5 | HT-2-51 | | 9.1 | 11.7 | 14.7 | 11.6 | 0.649 | 0.331 | 88.5 |
| Comparative Example 6 | HT-2-122 | | 10.1 | 12.6 | 14.4 | 11.1 | 0.658 | 0.339 | 87.9 |
| Comparative Example 7 | HT-2-48 | | 8.9 | 10.8 | 11.9 | 9.1 | 0.653 | 0.334 | 84.5 |
| Comparative Example 8 | HT-2-49 | | 9.2 | 11.6 | 12.7 | 9.8 | 0.639 | 0.326 | 59.1 |
| Comparative Example 9 | HT-2-118 | | 9.8 | 12.4 | 11.4 | 8.5 | 0.634 | 0.321 | 73.0 |
| Comparative Example 10 | HT-2-119 | | 9.1 | 11.2 | 13.1 | 9.9 | 0.659 | 0.336 | 60.0 |
| Comparative Example 11 | HT-2-1 | | 9.4 | 11.5 | 11.6 | 9.1 | 0.656 | 0.334 | 79.1 |

TABLE 1-continued

| | Second Hole Transport Layer | Host | Driving Voltage (V) | | Luminous Efficiency (cd/A) | | CIE | | Life-span |
|---|---|---|---|---|---|---|---|---|---|
| | | | At 1000 nits | At 50 mA/cm² | At 1000 nits | At 5000 nits | x | y | |
| Comparative Example 12 | HT-2-28 | | 9.3 | 11.9 | 15.3 | 11.8 | 0.662 | 0.336 | 68.4 |
| Comparative Example 13 | HT-2-43 | | 8.8 | 11.1 | 12.2 | 9.5 | 0.660 | 0.335 | 76.6 |
| Comparative Example 14 | HT-2-47 | | 8.7 | 10.6 | 12.7 | 9.3 | 0.652 | 0.330 | 76.7 |
| Comparative Example 15 | HT-2-19 | | 9.1 | 10.8 | 9.2 | 7.1 | 0.644 | 0.328 | 71.5 |
| Comparative Example 16 | HT-2-20 | | 8.8 | 10.7 | 11.1 | 8.4 | 0.659 | 0.334 | 86.2 |
| Comparative Example 17 | HT-2-24 | | 8.7 | 11.0 | 15.1 | 11.1 | 0.661 | 0.333 | 78.0 |
| Comparative Example 18 | HT-2-23 | | 8.8 | 11.1 | 14.3 | 10.5 | 0.660 | 0.333 | 82.9 |
| Comparative Example 19 | HT-2-120 | | 9.4 | 11.6 | 13.8 | 10.9 | 0.657 | 0.335 | 63.2 |
| Comparative Example 20 | HT-1-2 | C-241 | 5.0 | 7.0 | 10.0 | 8.6 | 0.665 | 0.342 | 84.2 |

The HOMO energy levels of the compounds comprised in the second hole transport layer of Device Examples 1 to 33 and Comparative Examples 1 to 20 are shown in Table 2 below.

TABLE 2

| | Second Hole Transport Layer | HOMO (eV) |
|---|---|---|
| Device Example 1 | HT-2-46 | −4.688 |
| Device Examples 2 and 28 | HT-2-47 | −4.942 |
| Device Example 3 | HT-2-51 | −4.970 |
| Device Example 4 | HT-2-122 | −4.943 |
| Device Examples 5 and 29 | HT-2-48 | −4.767 |
| Device Example 6 | HT-2-49 | −4.930 |
| Device Example 7 | HT-2-118 | −4.817 |
| Device Example 8 | HT-2-119 | −4.854 |
| Device Examples 9 and 33 | HT-2-17 | −4.752 |
| Device Example 10 | HT-2-19 | −4.748 |
| Device Example 11 | HT-2-20 | −4.828 |
| Device Example 12 | HT-2-24 | −4.790 |
| Device Example 13 | HT-2-23 | −4.831 |
| Device Examples 14 and 30 | HT-2-120 | −4.911 |
| Device Example 15 | HT-2-121 | −4.902 |
| Device Example 16 | HT-2-1 | −4.798 |
| Device Example 17 | HT-2-28 | −4.773 |
| Device Example 18 | HT-2-43 | −4.859 |
| Device Example 31 | HT-2-126 | −4.857 |
| Device Example 32 | HT-2-127 | −4.790 |
| Comparative Example 1 | HT-1-1 | −4.469 |
| Comparative Example 2 | HT-1-2 | −5.124 |

From Table 1 above, it can be confirmed that Device Examples 1 to 33 exhibit lower driving voltage, higher luminous efficiency and/or longer lifespan than the Comparative Examples, by comprising the fused azulene derivative compound of the present disclosure in the light-emitting layer and the compound having the specific HOMO energy level of the present disclosure between the first hole transport layer and the light-emitting layer.

The invention claimed is:

1. An organic electroluminescent device comprising a first electrode, a second electrode facing the first electrode, a light-emitting layer between the first electrode and the second electrode, and a hole transport zone between the first electrode and the light-emitting layer, wherein the light-emitting layer comprises a compound represented by the following formula 1:

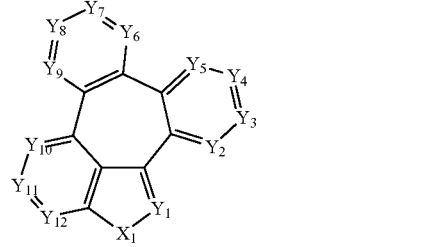

(1)

wherein, $X_1$ represents N-L-(Ar)$_a$, S, or O,

L represents a single bond, a substituted or unsubstituted (C6-C30)arylene, or a substituted or unsubstituted (3- to 30-membered)heteroarylene, Ar represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, $Y_1$ to $Y_{12}$, each independently, represent N or CR$_1$, R$_1$, each independently, represents hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or are linked to an adjacent substituent(s) to form a substituted or unsubstituted ring, and a represents an integer of 1 to 4, where if a is an integer of 2 or more, each of Ar may be the same or different; and the hole transport zone comprises an arylamine derivative, and the HOMO energy level of the arylamine derivative satisfies the following equation 11:

$$-5.0 \text{ eV} \leq \text{HOMO} \leq -4.65 \text{ eV} \quad (11).$$

2. The organic electroluminescent device according to claim 1, wherein the substituents of the substituted alkyl, the substituted aryl(ene), the substituted heteroaryl(ene), the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, the substituted alkylarylamino, and the substituted ring in L, Ar, and $R_1$, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 50-membered)heteroaryl unsubstituted or substituted with a (C1-C30)alkyl(s) or a (C6-C30)aryl(s); a (C6-C30)aryl unsubstituted or substituted with a (3- to 50-membered) heteroaryl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl (C6-C30)arylamino; a (C1-C30)alkylcarbonyl; a (C1-C30) alkoxycarbonyl; a (C6-C30)arylcarbonyl; a di(C6-C30) arylboronyl; a di(C1-C30)alkylboronyl; a (C1-C30)alkyl (C6-C30)arylboronyl; a (C6-C30)aryl(C1-C30)alkyl; and a (C1-C30)alkyl(C6-C30)aryl.

3. The organic electroluminescent device according to claim 1, wherein at least one adjacent pair of $Y_1$ to $Y_{12}$ in formula 1 are $CR_1$ and the adjacent two $R_1$'s of $CR_1$ are fused together to each independently form a ring represented by any one of the following formulas 2 to 6:

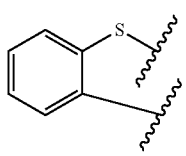
(2)

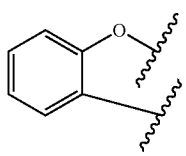
(3)

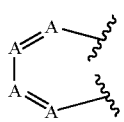
(4)

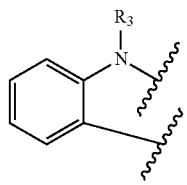
(5)

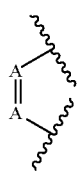
(6)

wherein,

A represents N or $CR_2$;

$R_2$ and $R_3$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; and

 represents a bonding site of between C and $R_1$ in the adjacent $CR_1$.

4. The organic electroluminescent device according to claim 1, wherein the arylamine derivative comprises a compound represented by the following formula 11:

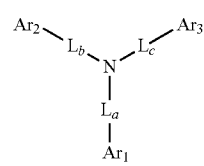
(11)

wherein, $L_a$ to $L_c$, each independently, represent a single bond, a substituted or unsubstituted (C6-C30)arylene, a substituted or unsubstituted (3- to 30-membered)heteroarylene, or a substituted or unsubstituted (C3-C30) cycloalkylene, $Ar_1$ to $Ar_3$, each independently, represent a substituted or unsubstituted (C6-C30)aryl, or a substituted or unsubstituted (5- to 30-membered)heteroaryl, with the proviso that at least one of $Ar_1$ to $Ar_3$ is selected from the following formulas:

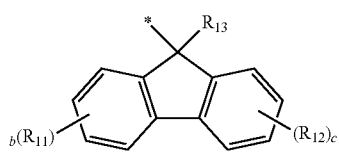

-continued

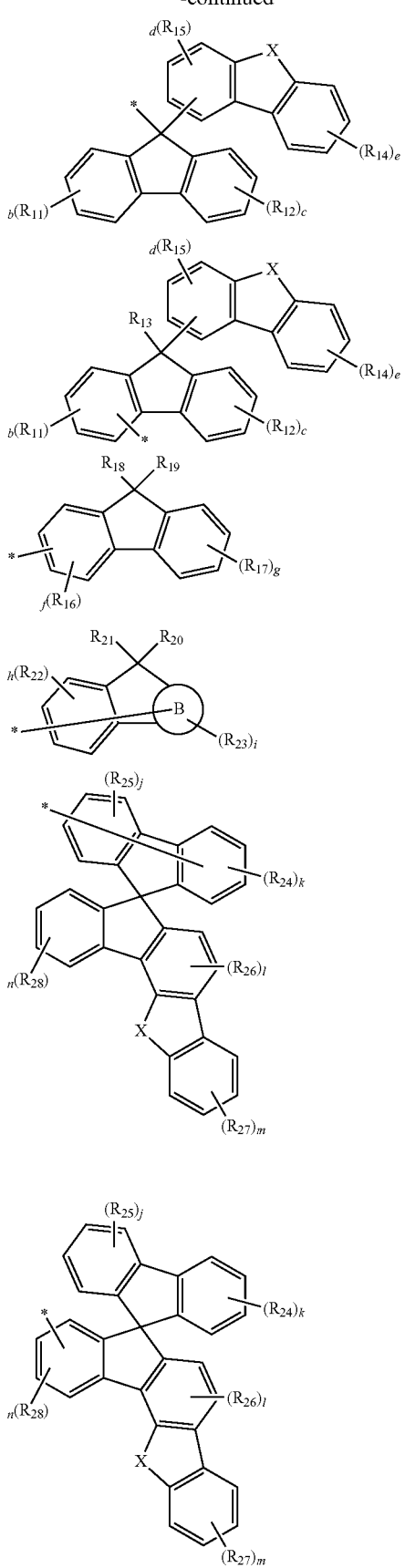

-continued

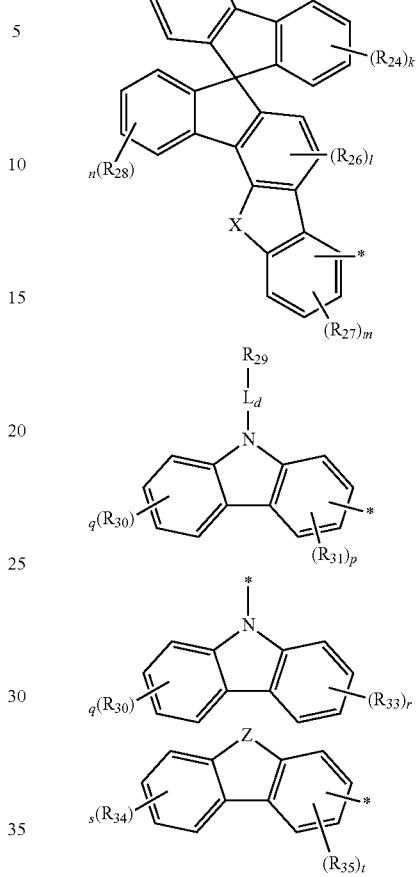

wherein,
X, each independently, represents O, S, $NR_8$, or $CR_9R_{10}$,
B ring represents a substituted or unsubstituted C10 aryl,
Z and V, each independently, represent O or S,
$A_1$ to $A_{12}$, each independently, represent N or $CR_{43}$,
$L_d$ represents a single bond, or a substituted or unsubstituted (C6-C30)arylene,
$R_{11}$ to $R_{35}$, each independently, represent hydrogen, deuterium, a halogen, a substituted or unsubstituted (C1-C30)alkyl, a substituted or unsubstituted (C6-C30)aryl, a substituted or unsubstituted (5- to 30-membered) heteroaryl, a substituted or unsubstituted (C3-C30) cycloalkyl, a substituted or unsubstituted (3- to 7-membered)heterocycloalkyl, a substituted or unsubstituted (C6-C30)aryl(C1-C30)alkyl, —$NR_{36}R_{37}$, —$SiR_{38}R_{39}R_{40}$, —$OR_{42}$, a cyano, a nitro, or a hydroxyl, or may be linked to an adjacent substituent to form a substituted or unsubstituted ring, wherein the ring comprises a spiro structure,
$R_8$ to $R_{10}$ and $R_{36}$ to $R_{43}$, each independently, represent hydrogen, deuterium, a cyano, a halogen, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (3- to 7-membered)heterocycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or may be linked to an adjacent substituent to form a substituted or unsubstituted ring, and b, c, e, g, h, j, k, m, n, o, q, r, and s, each independently, represent an integer of 1 to 4; d, f, p, and t, each independently, represent an integer of 1 to 3; i represents an integer of 1 to 6; l represents 1 or 2; where each of b to t is an integer of 2 or more, each of $R_{11}$, $R_{12}$, $R_{14}$ to $R_{17}$, $R_{22}$ to $R_{28}$, and $R_{30}$ to $R_{35}$ may be the same or different.

5. The organic electroluminescent device according to claim 4, wherein the substituents of the substituted alkyl, the substituted aryl(ene), the substituted heteroaryl(ene), the substituted cycloalkyl, the substituted heterocycloalkyl, the substituted arylalkyl, and the substituted ring in $L_a$ to $L_d$, $Ar_1$ to $Ar_3$, and $R_8$ to $R_{43}$, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 50-membered)heteroaryl unsubstituted or substituted with a (C1-C30)alkyl(s) or a (C6-C30)aryl(s); a (C6-C30)aryl unsubstituted or substituted with a (3- to 50-membered)heteroaryl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

6. The organic electroluminescent device according to claim 1, wherein the HOMO energy level of the arylamine derivative satisfies the following equation 12:

$$-5.0 \text{ eV} \leq HOMO \leq -4.70 \text{ eV} \quad (12).$$

7. The organic electroluminescent device according to claim 1, comprising a first hole transport layer between the first electrode and the light-emitting layer, and a second hole transport layer between the first hole transport layer and the light-emitting layer, wherein the second hole transport layer comprises an arylamine derivative containing a fluorene or a fused flourene, and the HOMO energy level of the arylamine derivative satisfies the equation 11.

8. The organic electroluminescent device according to claim 1, wherein the arylamine derivative is at least one selected from the following compounds:

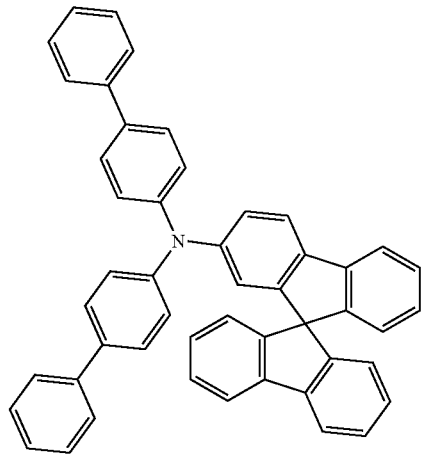

HT-2-1

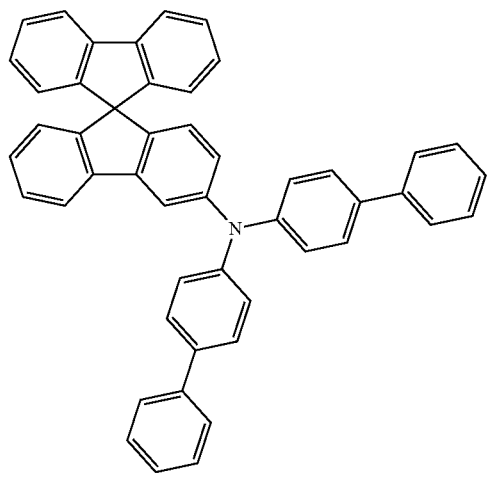

HT-2-2

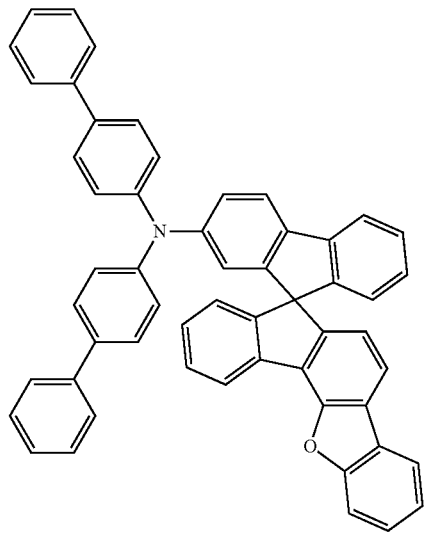

HT-2-3

HT-2-4
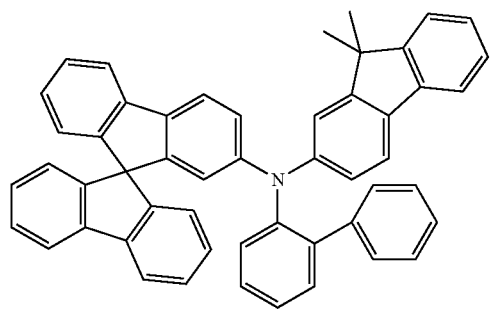
HT-2-5
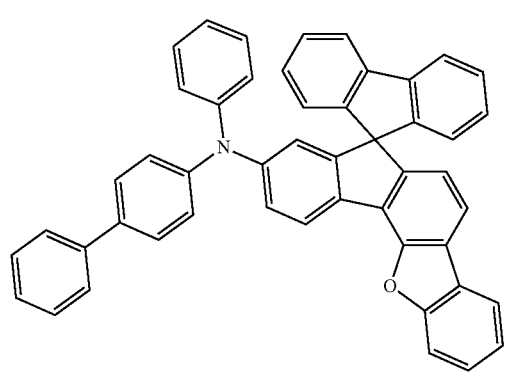
HT-2-6
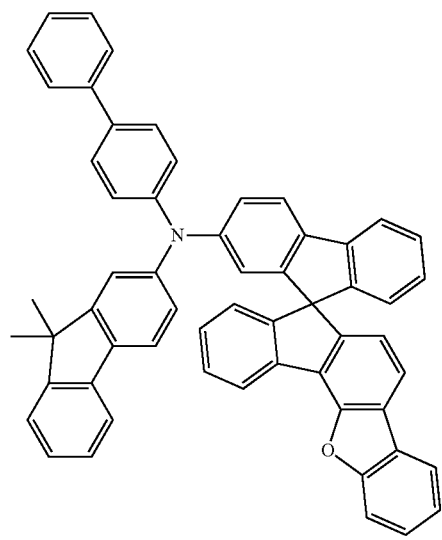
HT-2-7
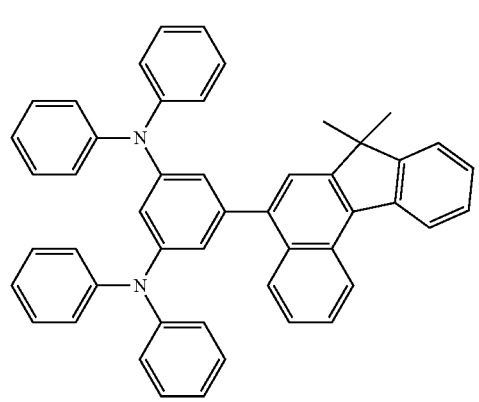
HT-2-8
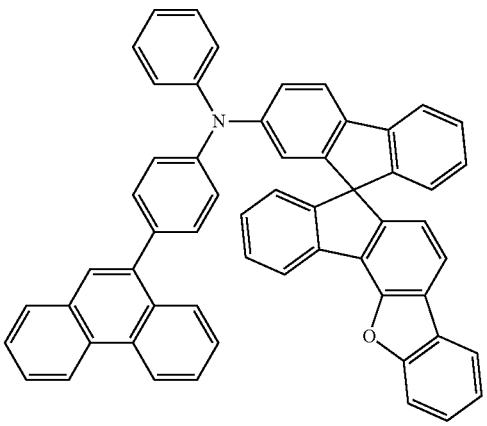
HT-2-9
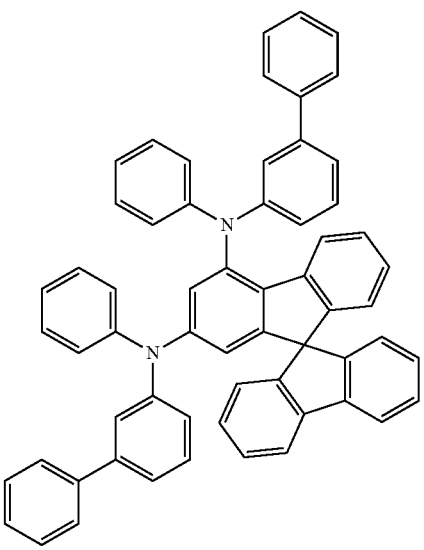
HT-2-10
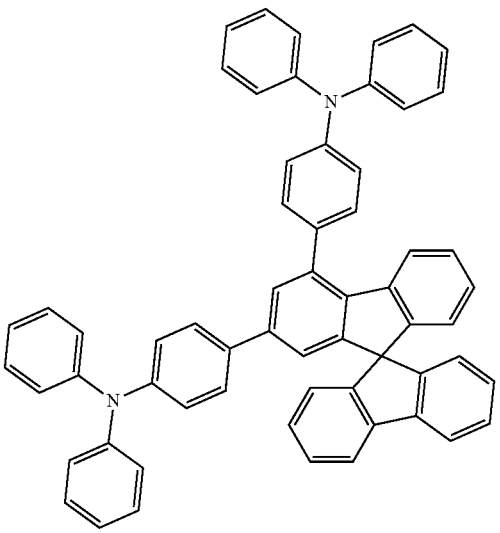

HT-2-11
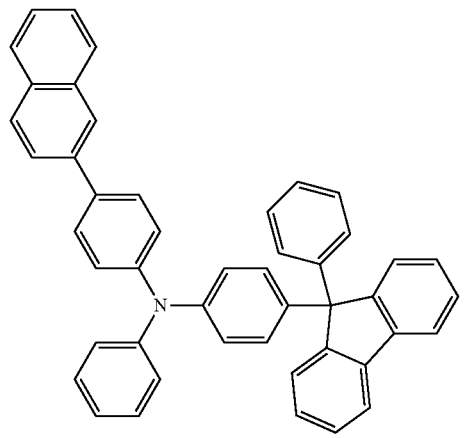
HT-2-14
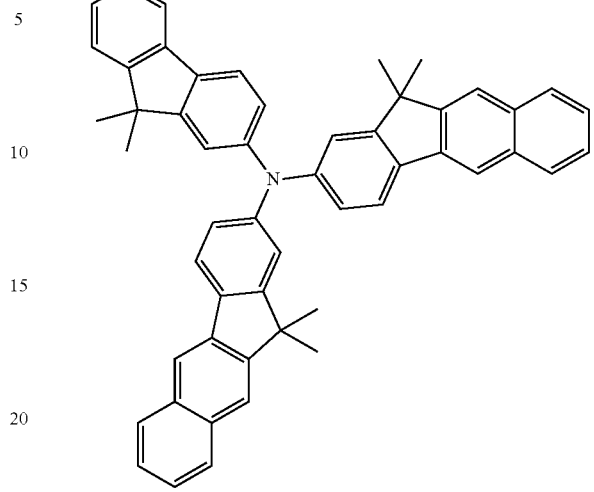
HT-2-12
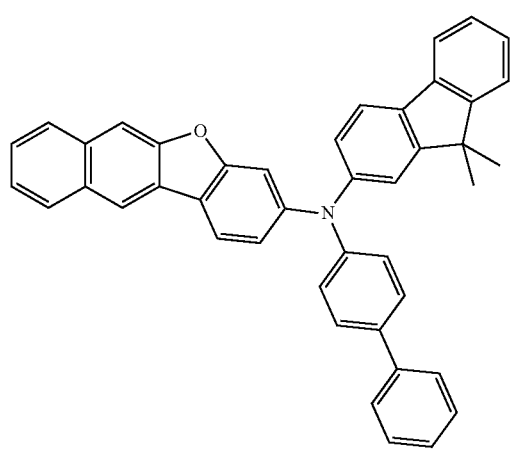
HT-2-15
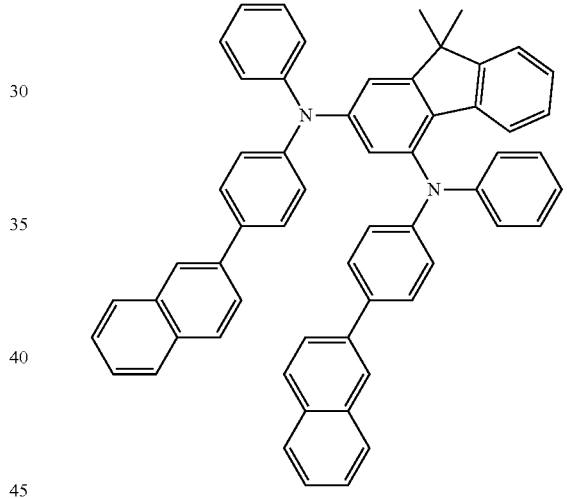
HT-2-13
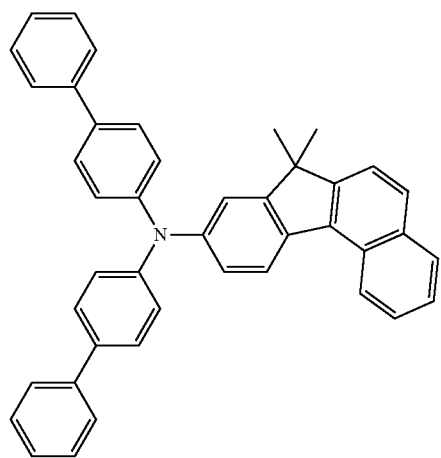
HT-2-16
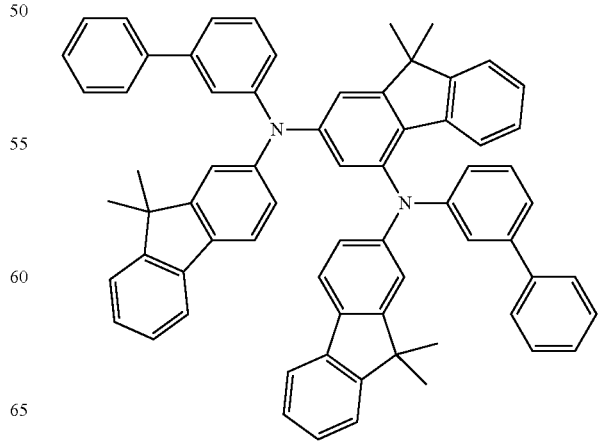

HT-2-17
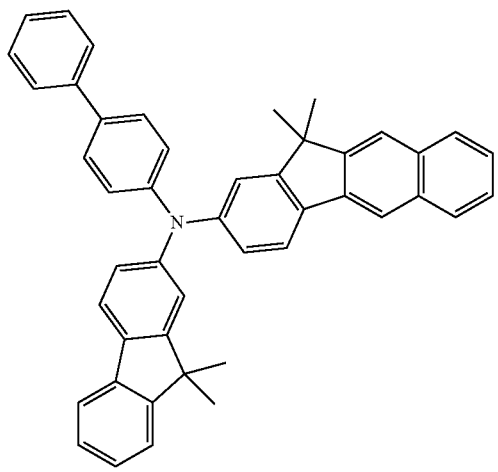
HT-2-18
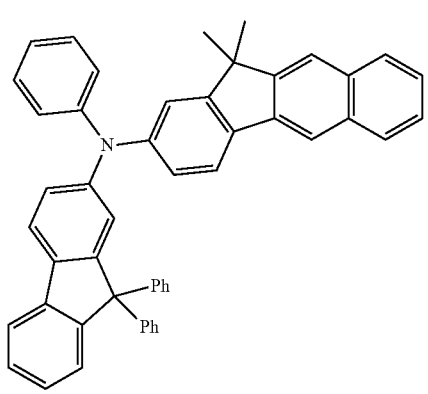
HT-2-19
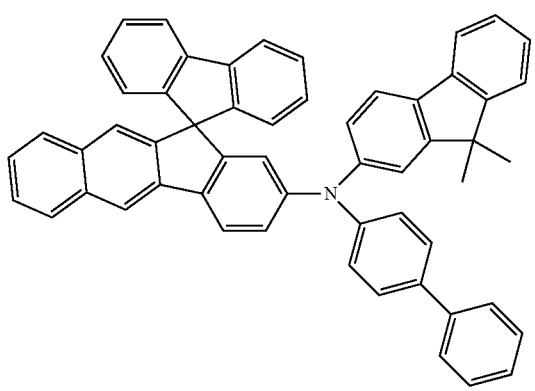
HT-2-20
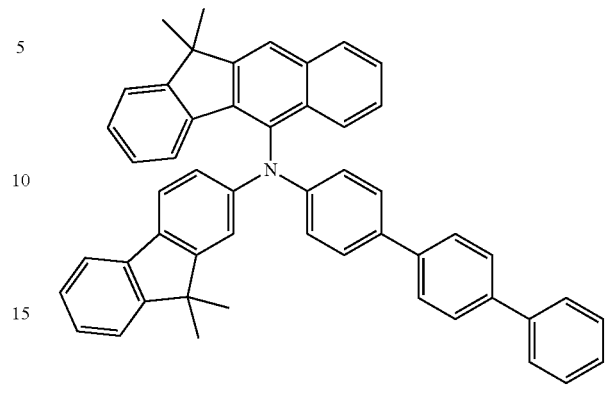
HT-2-21
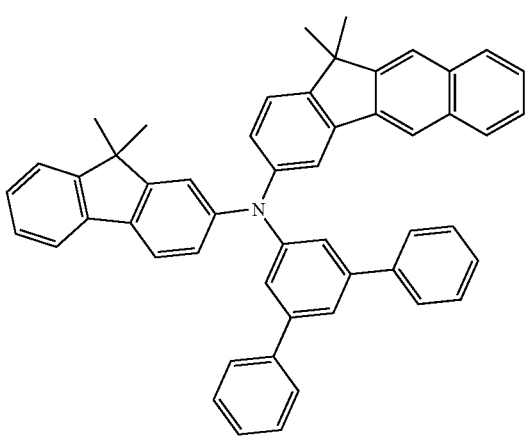
HT-2-22
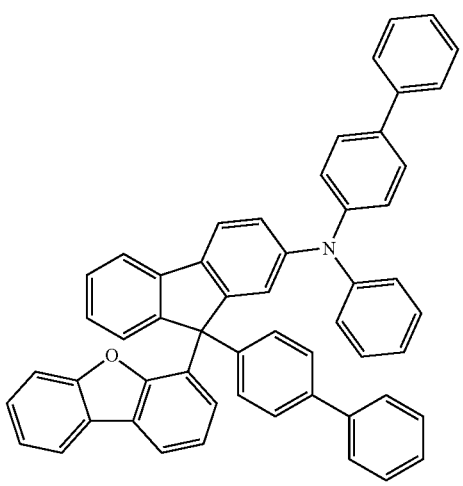

HT-2-23
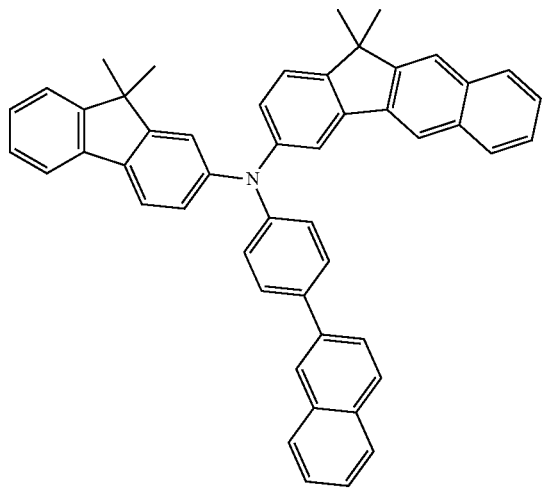
HT-2-24
HT-2-25
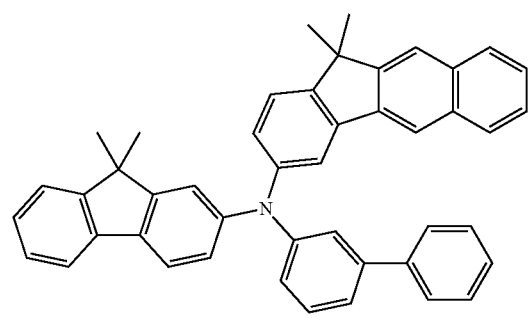
HT-2-26
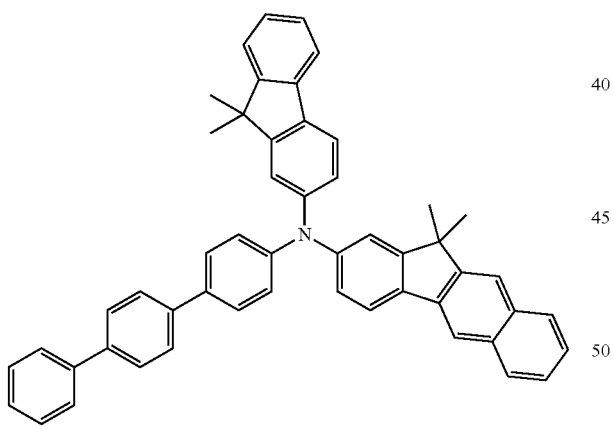
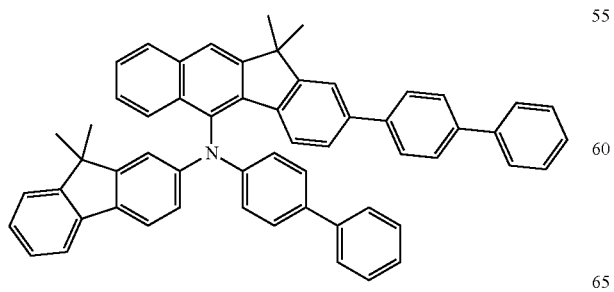
HT-2-27
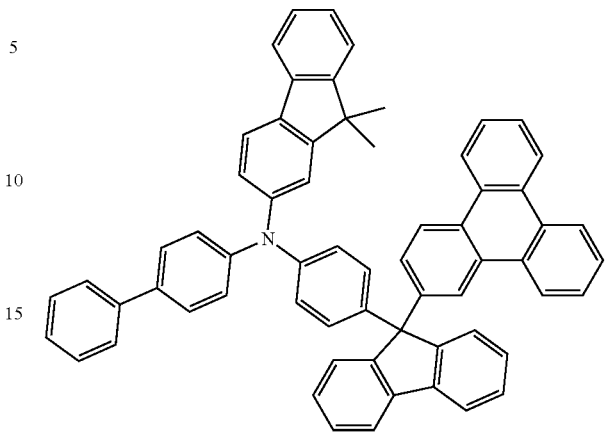
HT-2-28
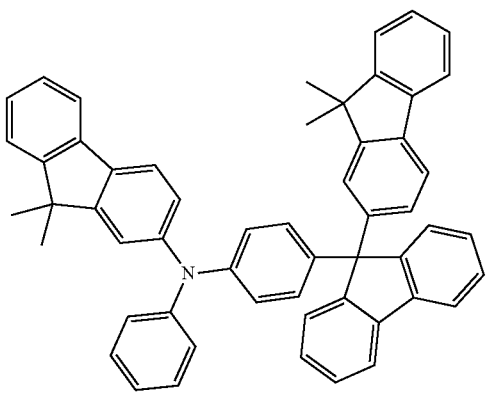
HT-2-29
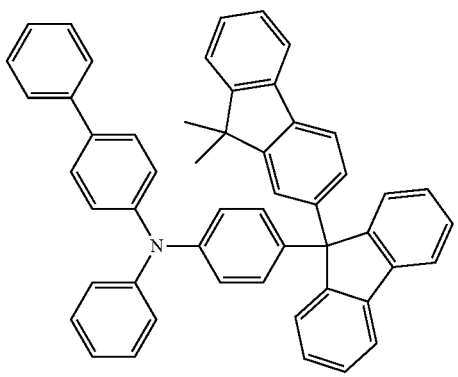

HT-2-30
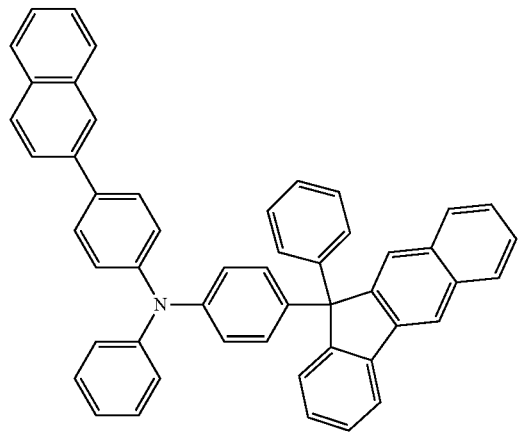
HT-2-31
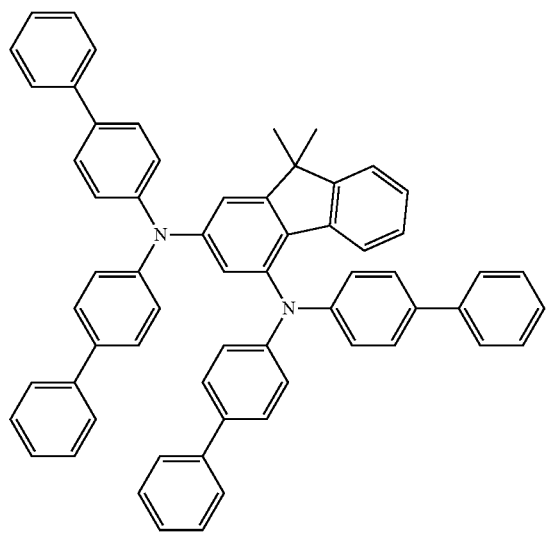
HT-2-32
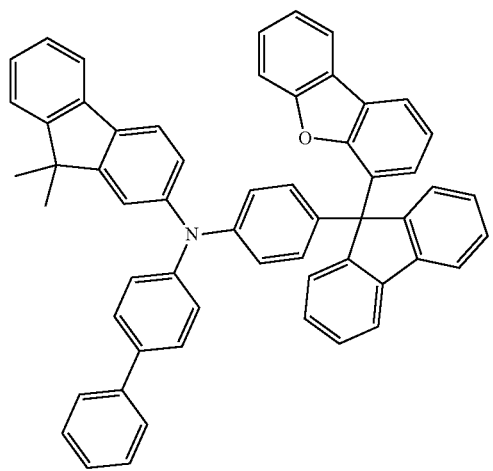
HT-2-33
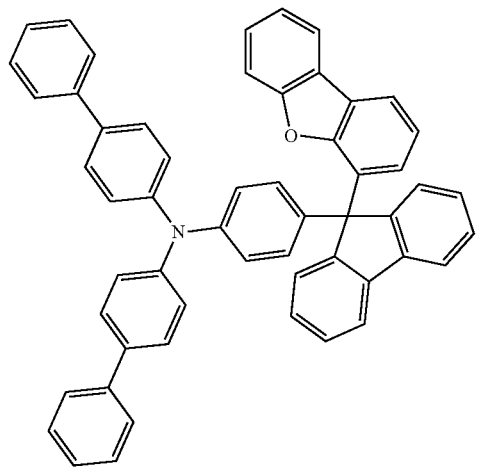
HT-2-34
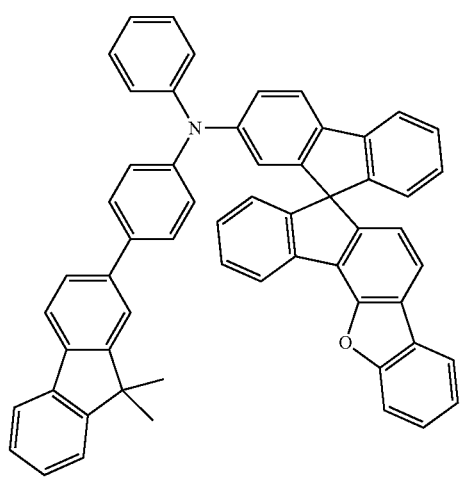
HT-2-35
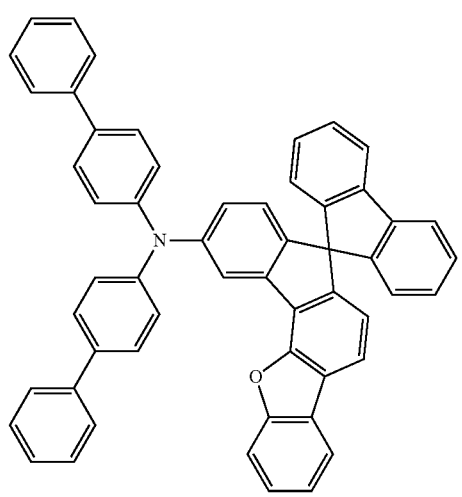

HT-2-36
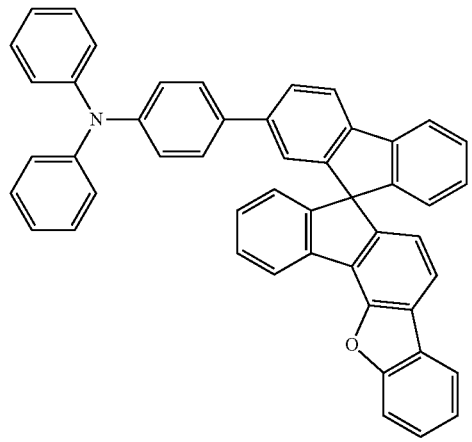
HT-2-37
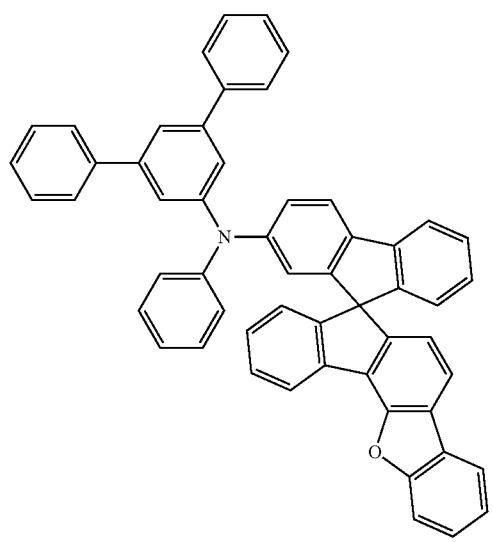
HT-2-38
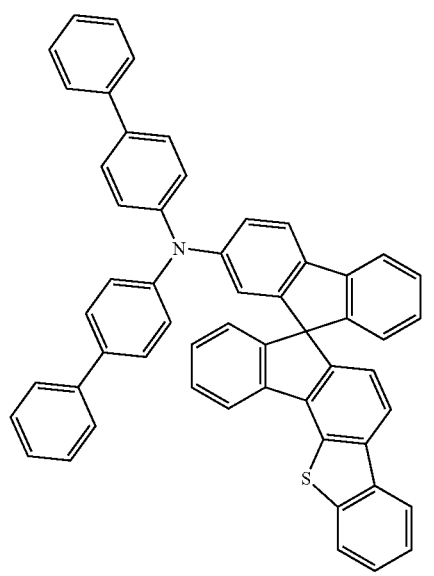
HT-2-39
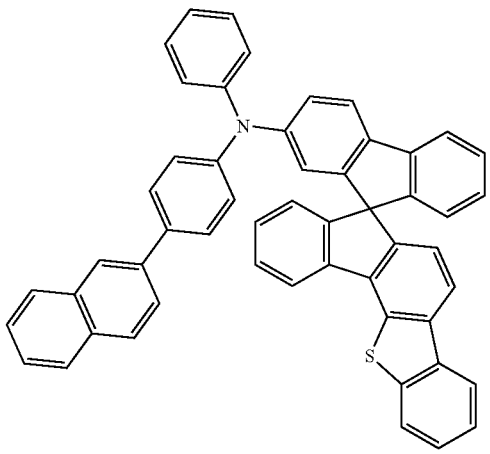
HT-2-40
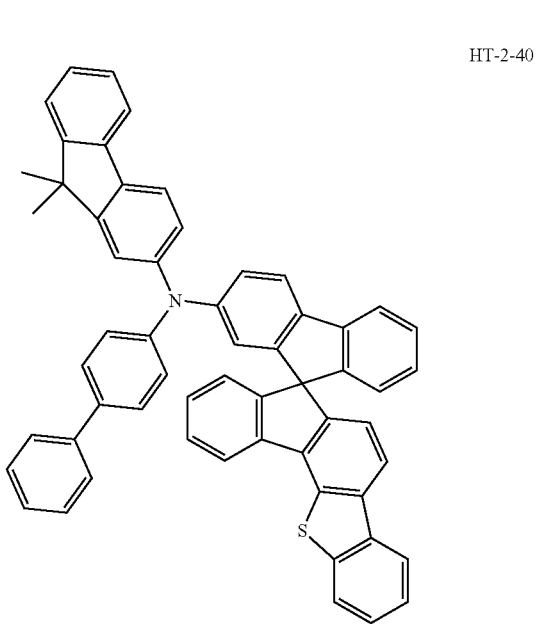
HT-2-41
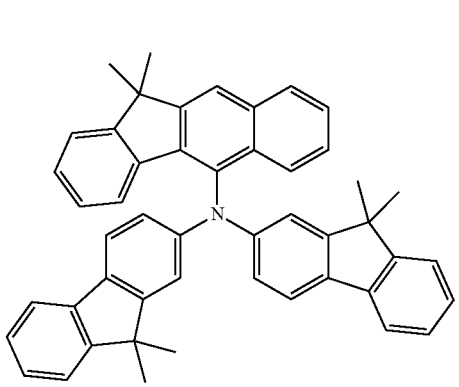

HT-2-42
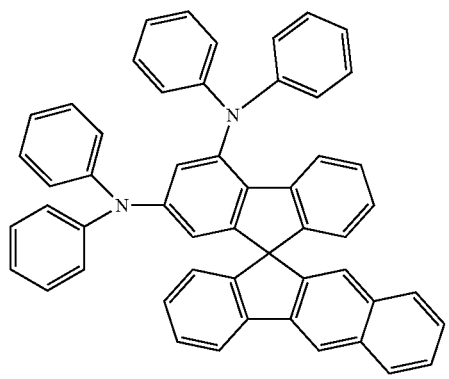
HT-2-45
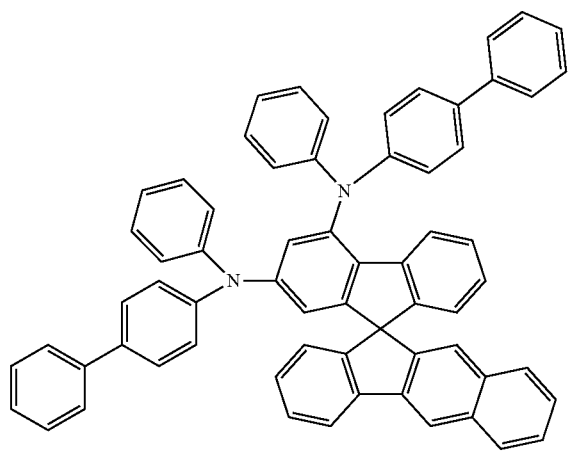
HT-2-43
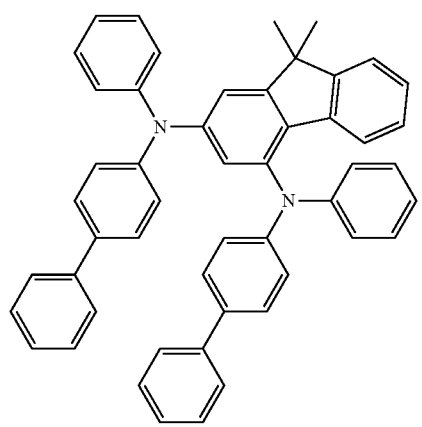
HT-2-46
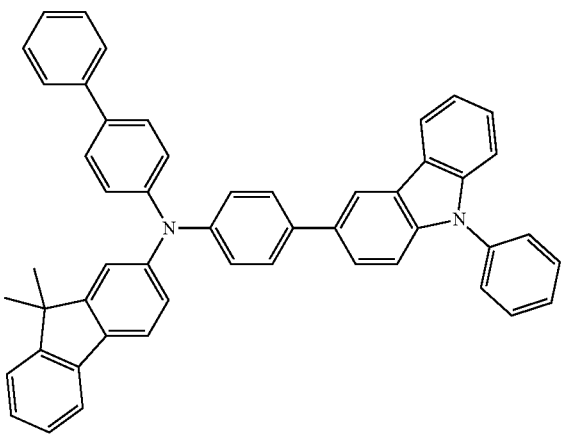
HT-2-44
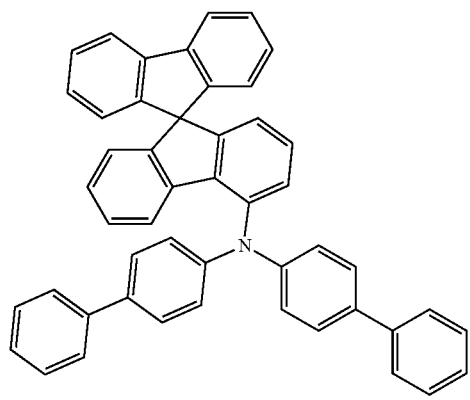
HT-2-47
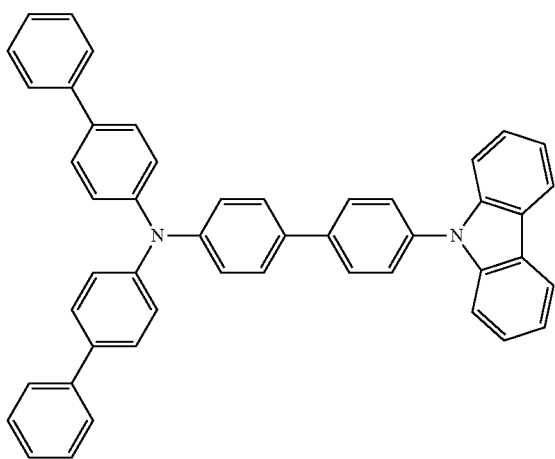

HT-2-48
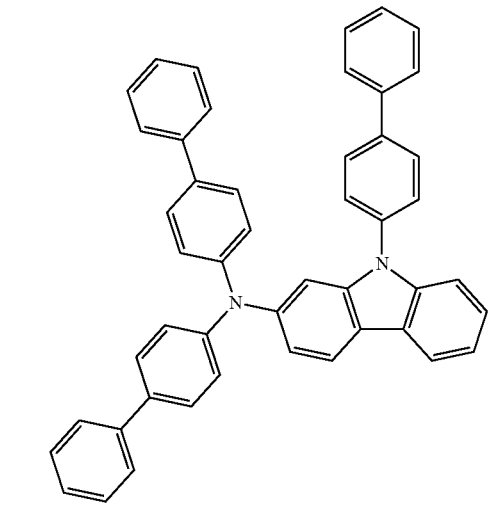
HT-2-49
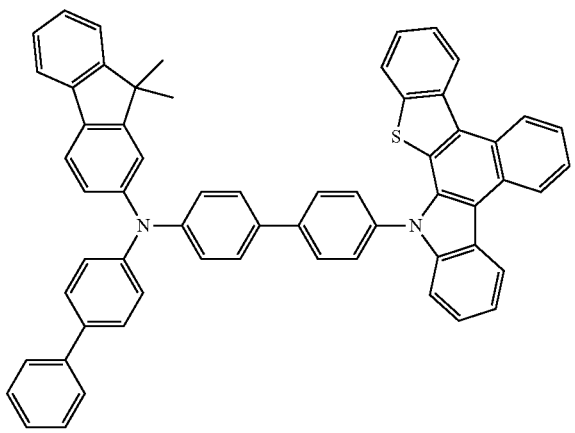
HT-2-50
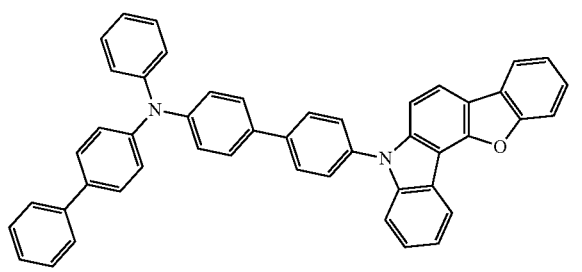
HT-2-51
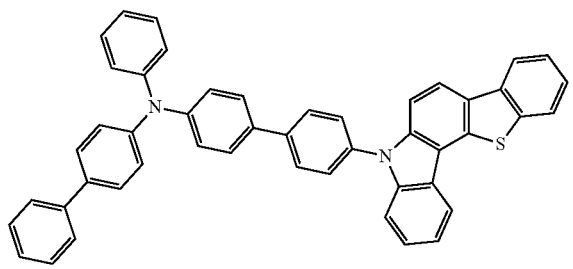
HT-2-52
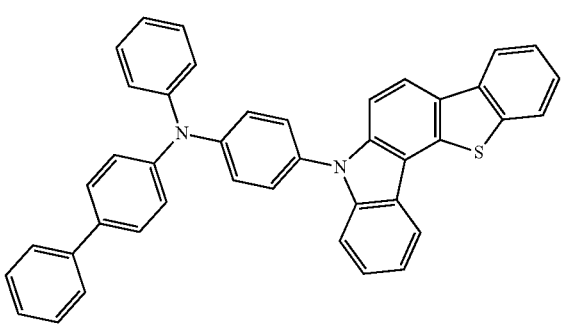
HT-2-53
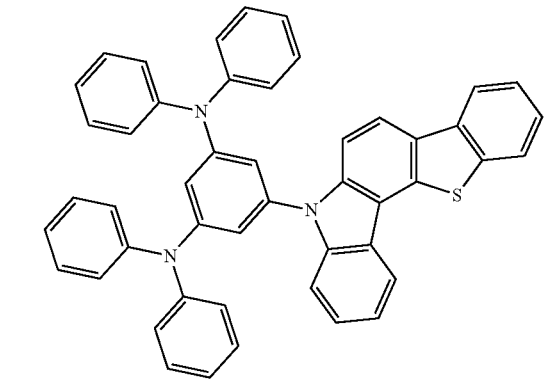
HT-2-54
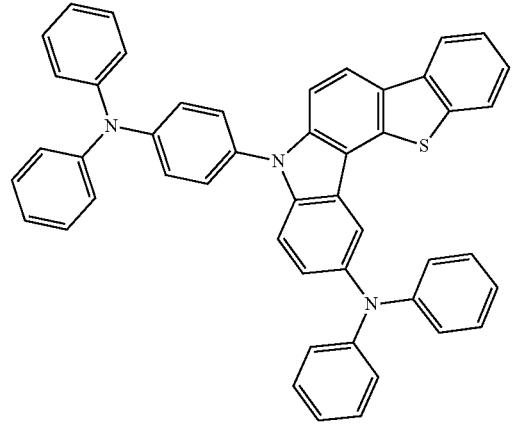
HT-2-55
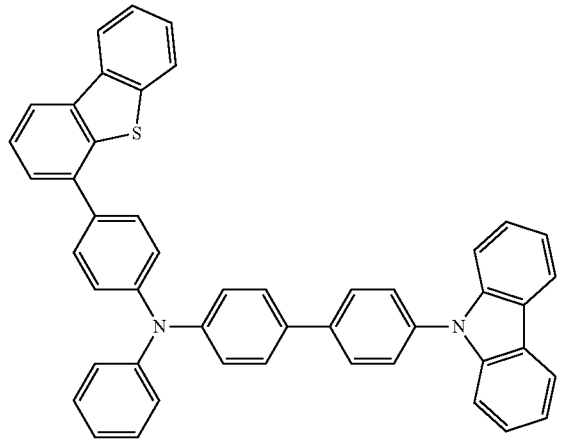

-continued
HT-2-56
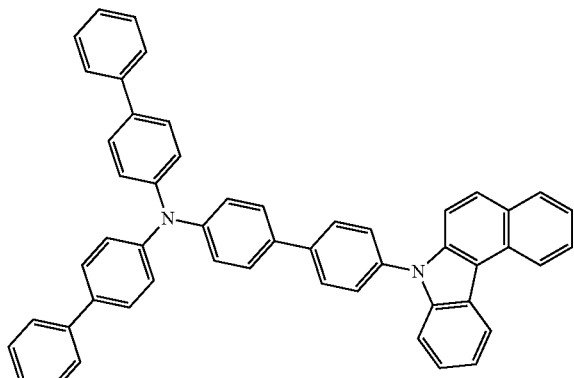
HT-2-57
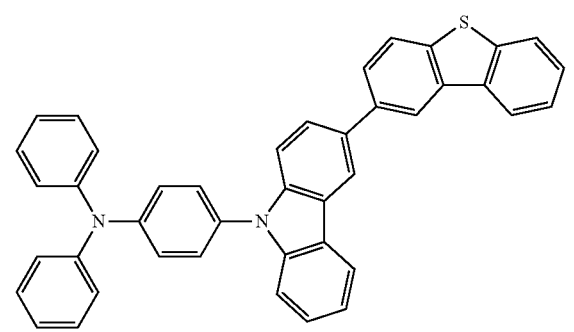
HT-2-58
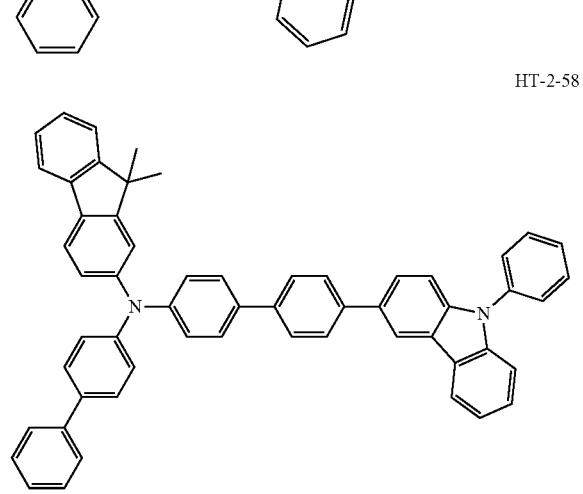
HT-2-59
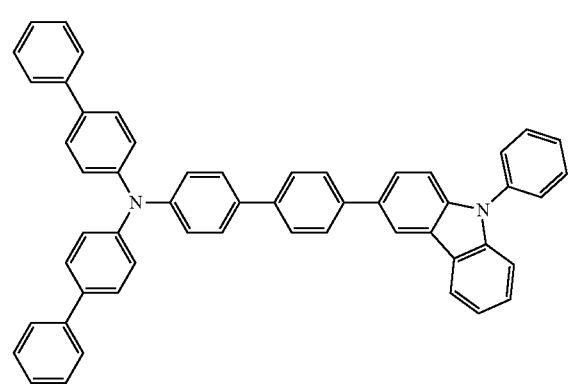
-continued
HT-2-60
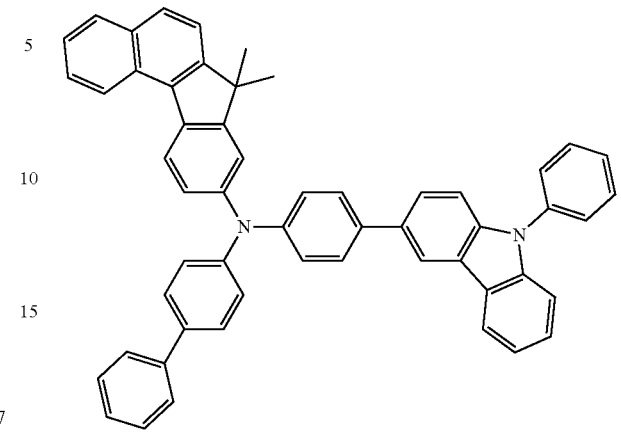
HT-2-61
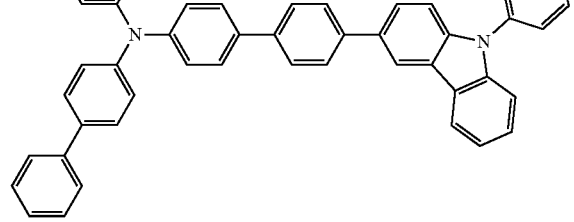
HT-2-62
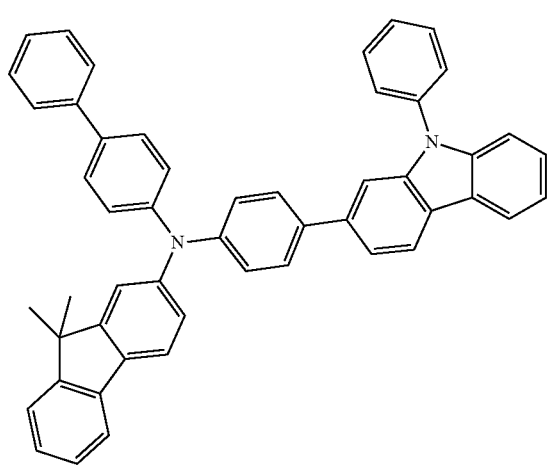

-continued
HT-2-63
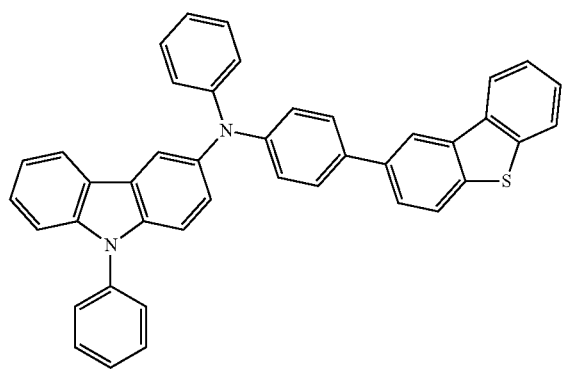
HT-2-64
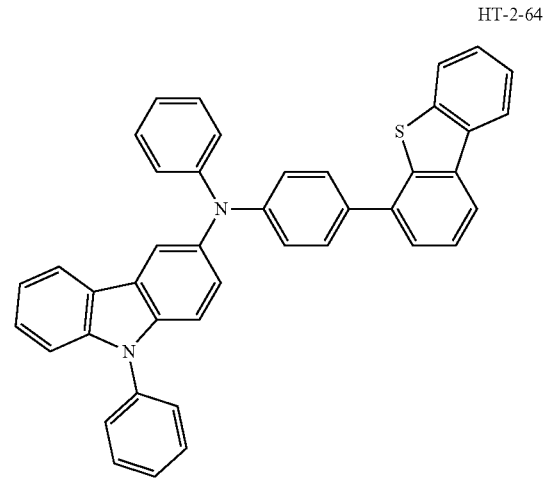
HT-2-65
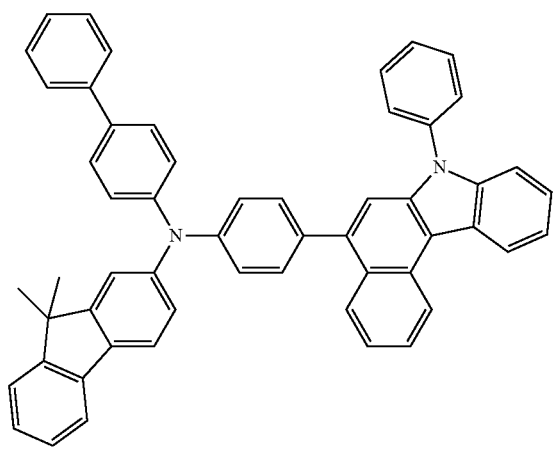
-continued
HT-2-66
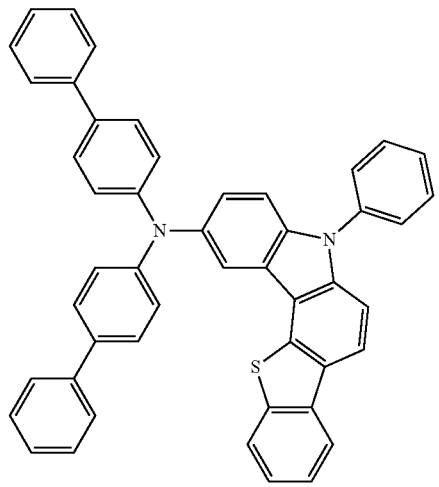
HT-2-67
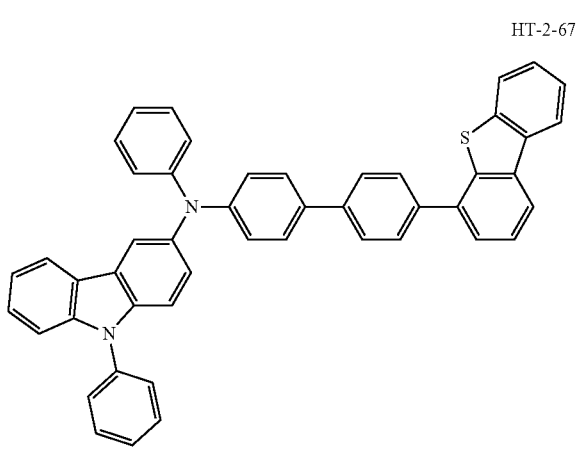
HT-2-68
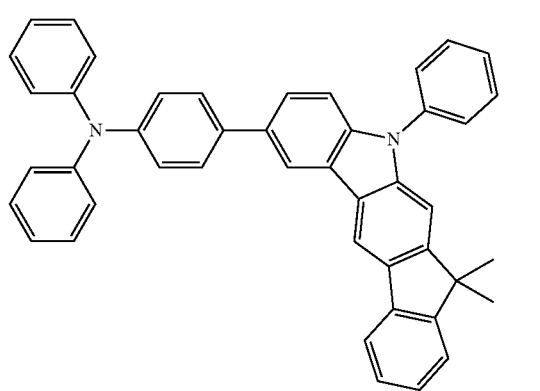

-continued
HT-2-69
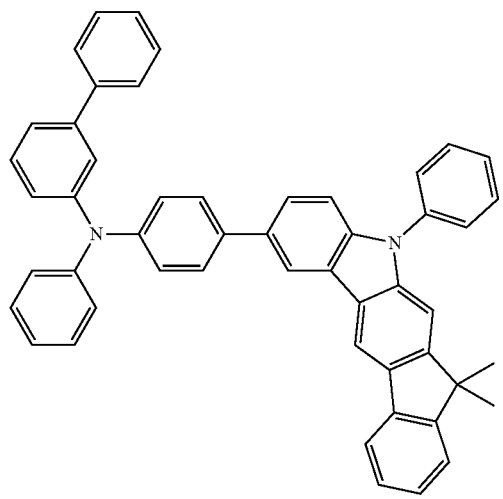
HT-2-70
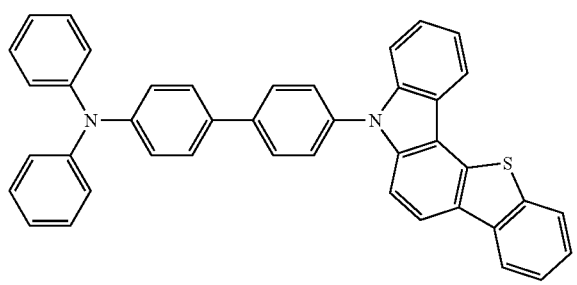
HT-2-71
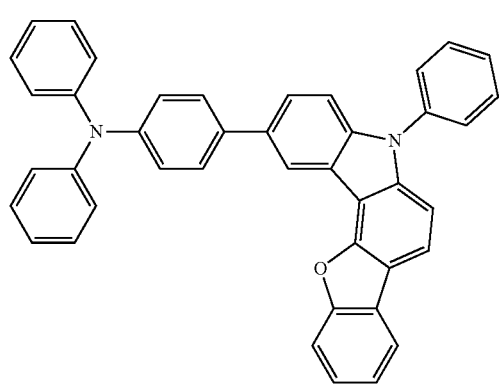
-continued
HT-2-72
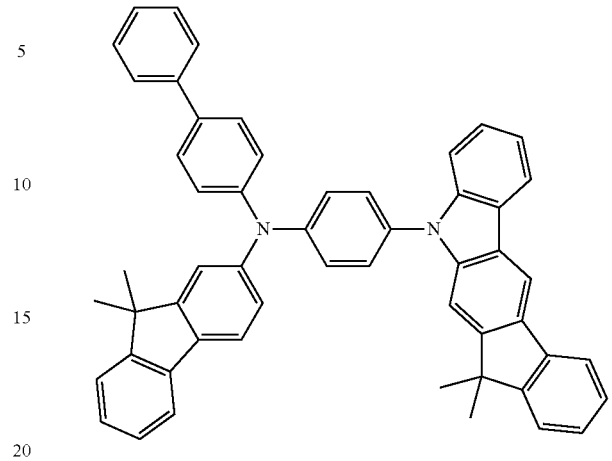
HT-2-73
HT-2-74
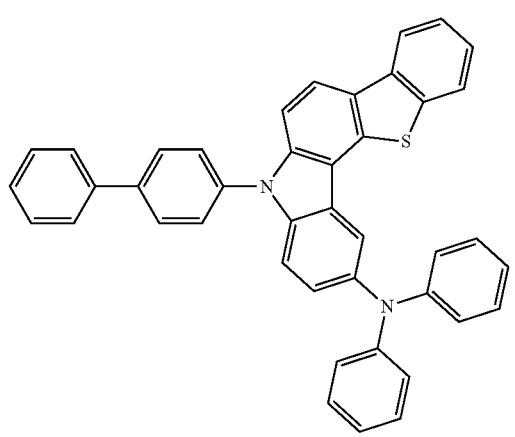

HT-2-75
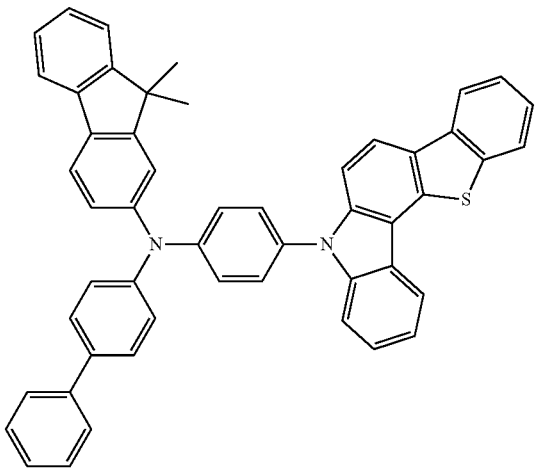
HT-2-76
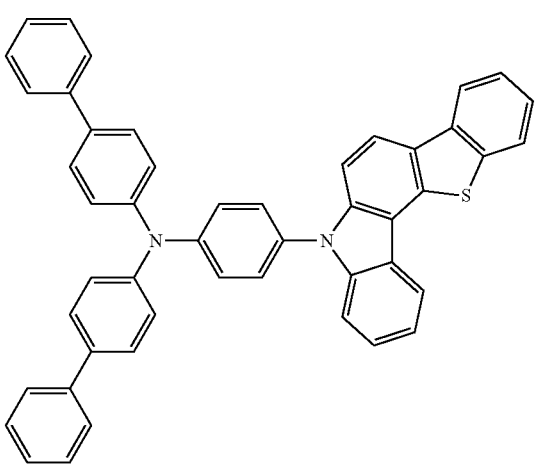
HT-2-77
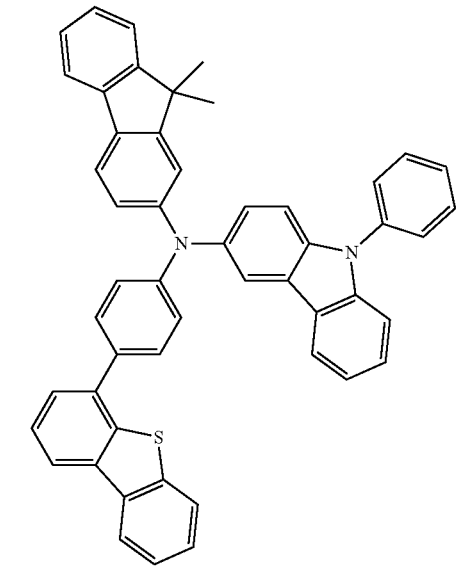
HT-2-78
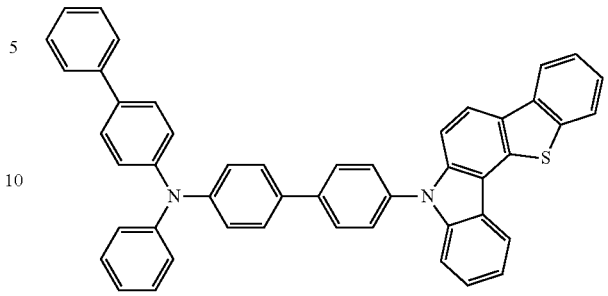
HT-2-79
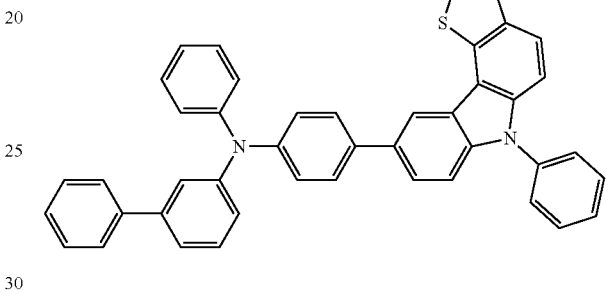
HT-2-80
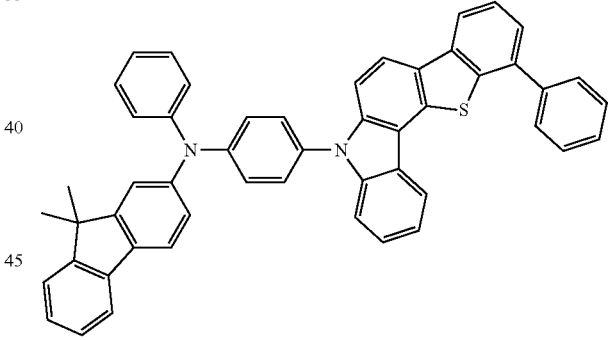
HT-2-81
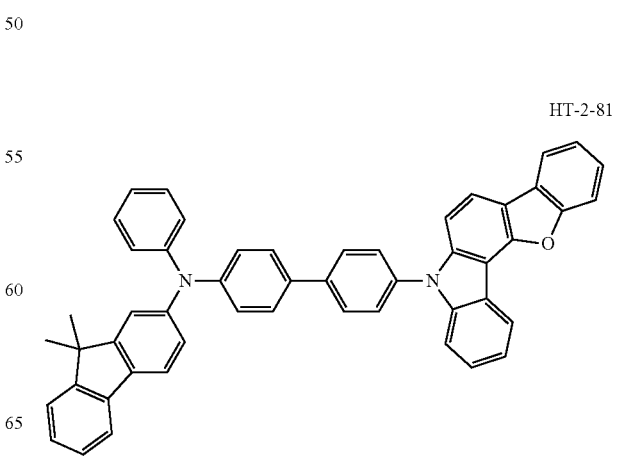

-continued
HT-2-82
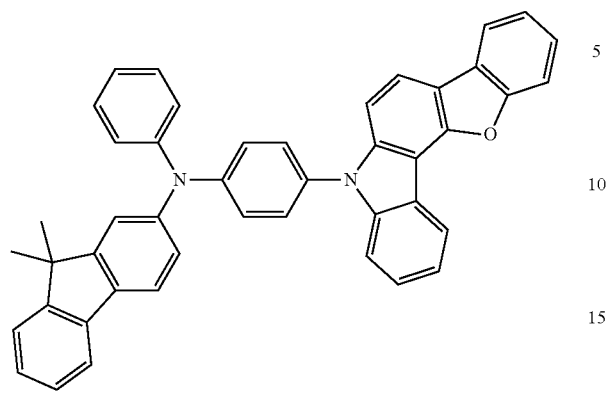
HT-2-83
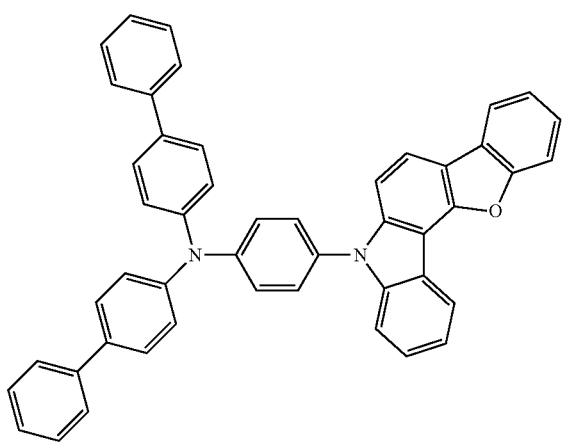
HT-2-84
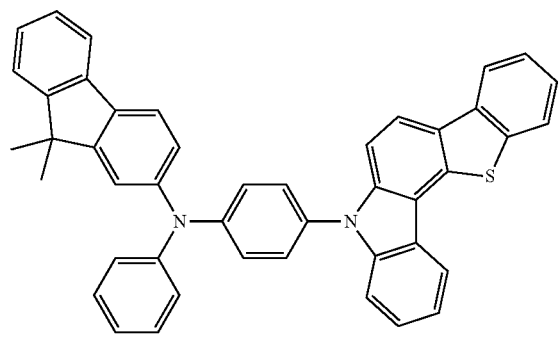
HT-2-85
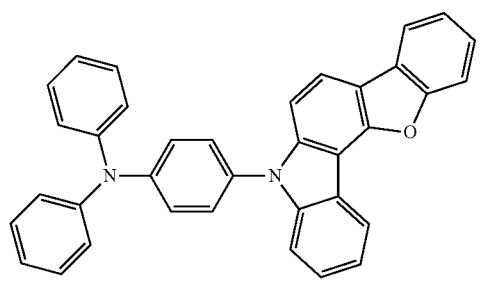
HT-2-86
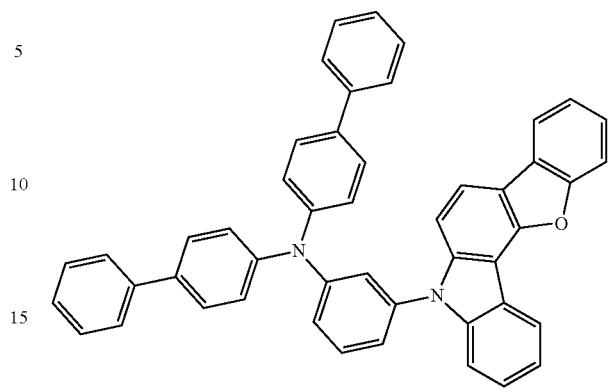
HT-2-87
HT-2-88
HT-2-89
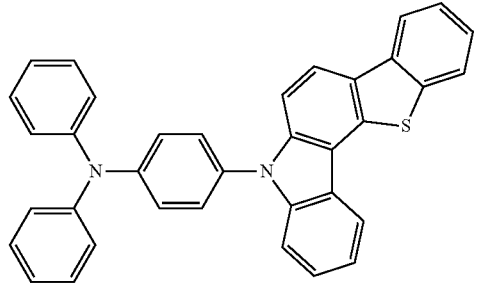

HT-2-90
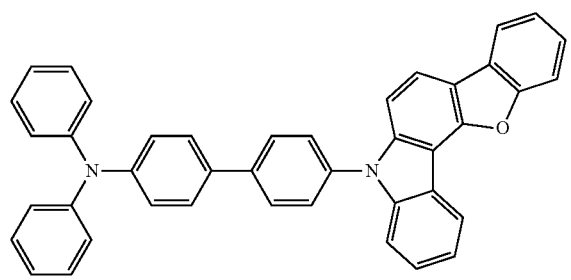
HT-2-91
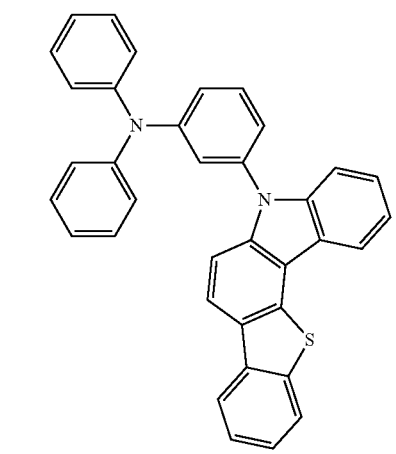
HT-2-92
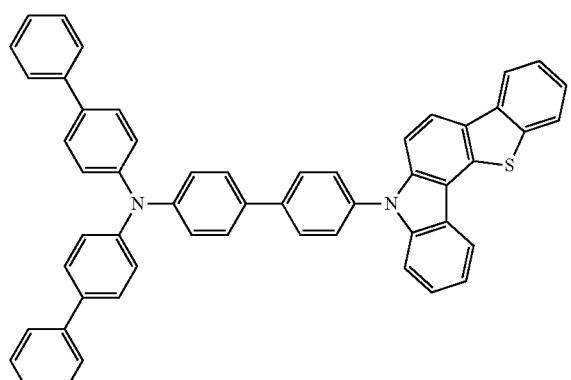
HT-2-93
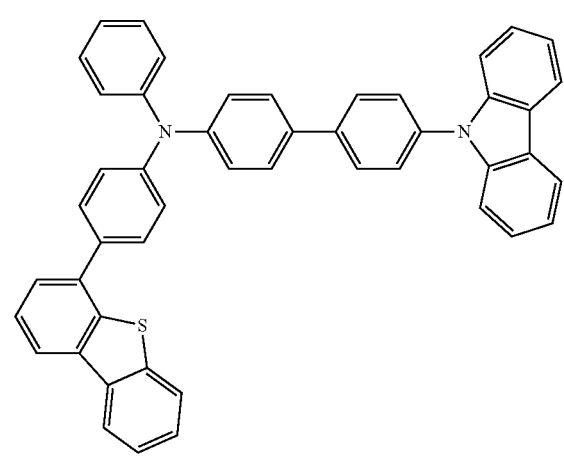
HT-2-94
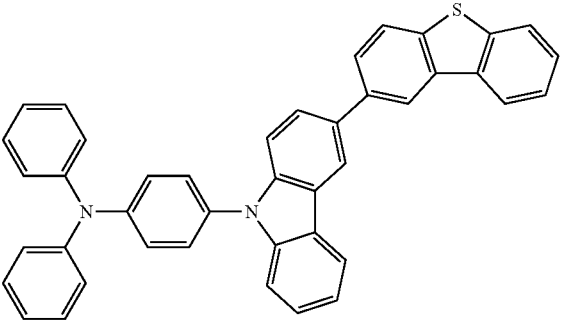
HT-2-95
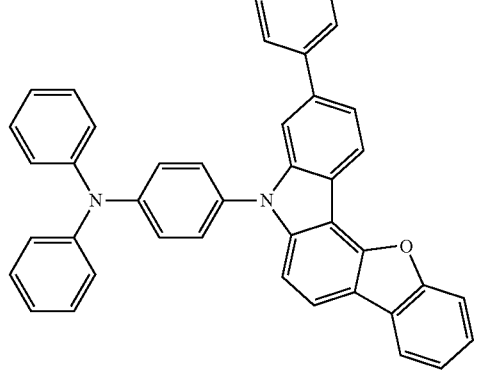
HT-2-96
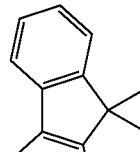
HT-2-97
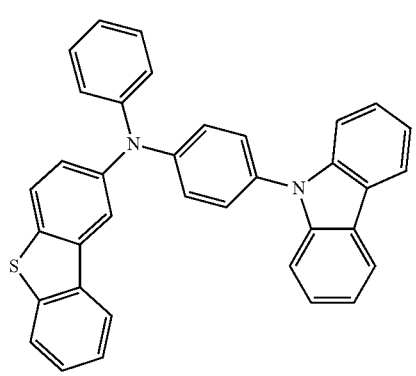

HT-2-98
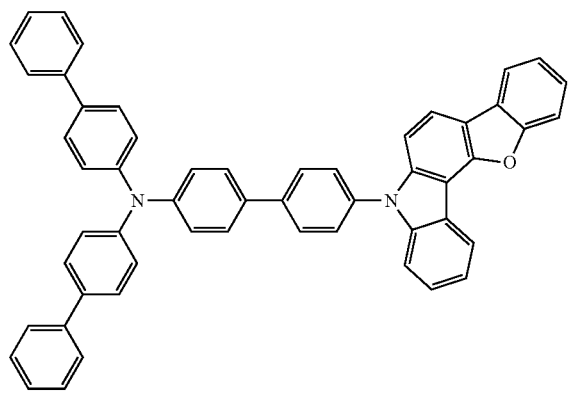
HT-2-102
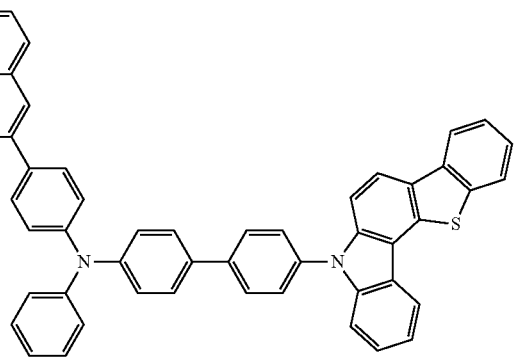
HT-2-99
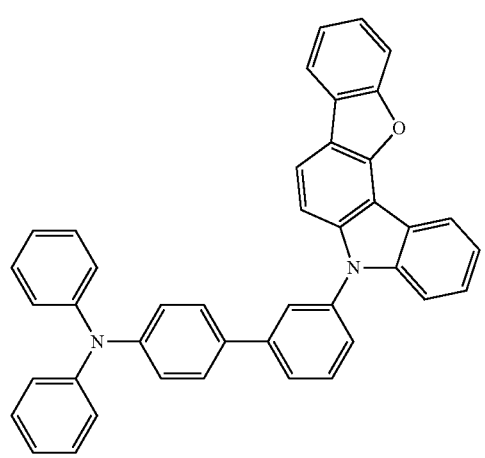
HT-2-103
HT-2-100
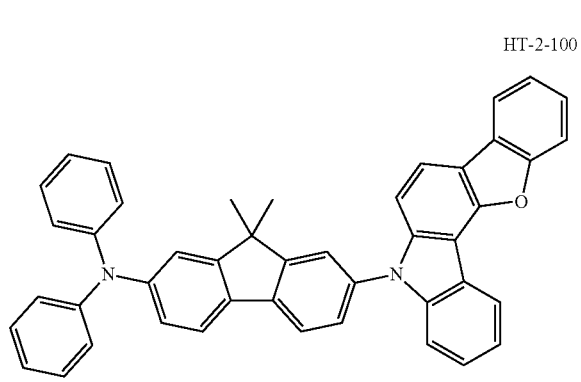
HT-2-104
HT-2-101
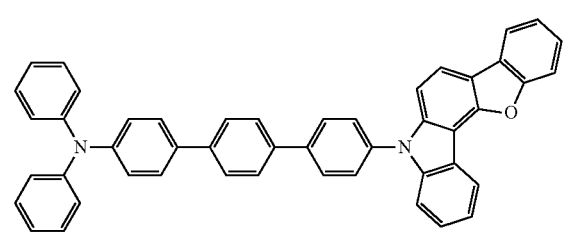
HT-2-105
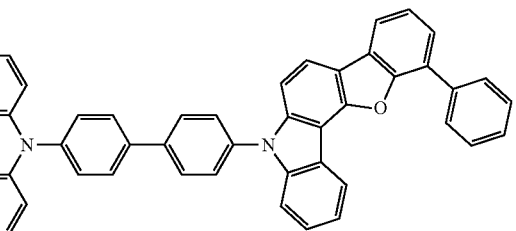

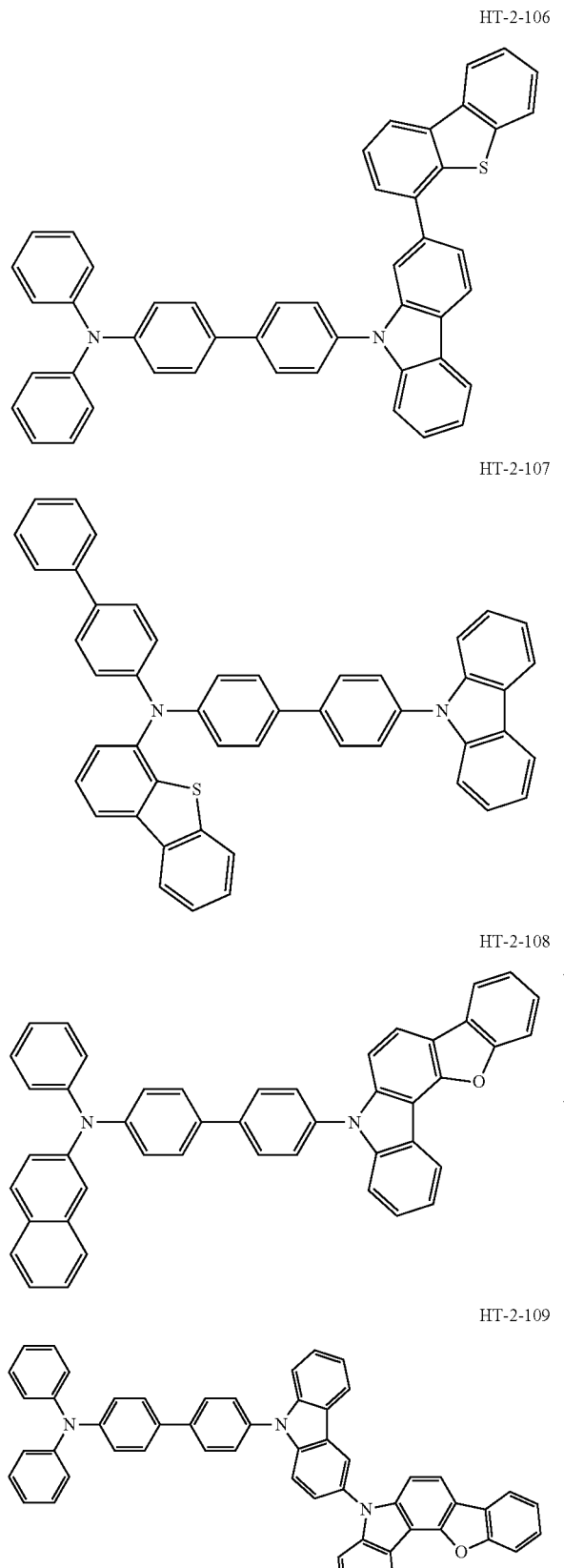
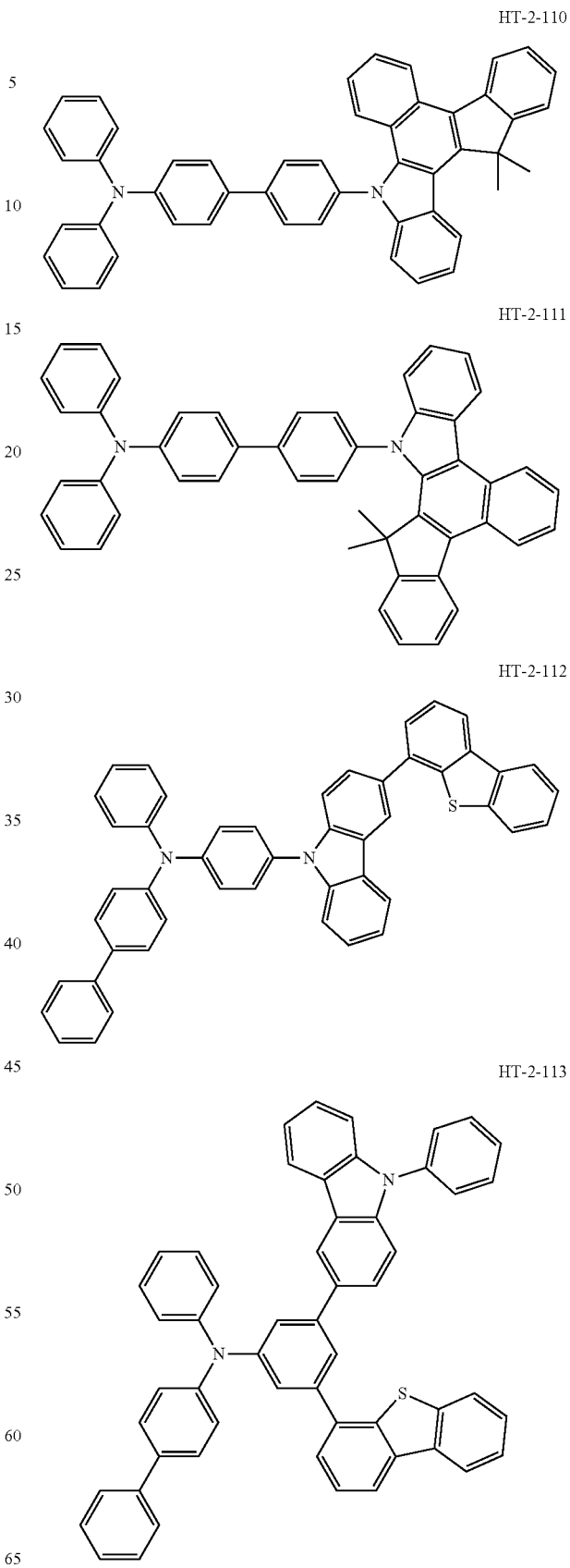

HT-2-114
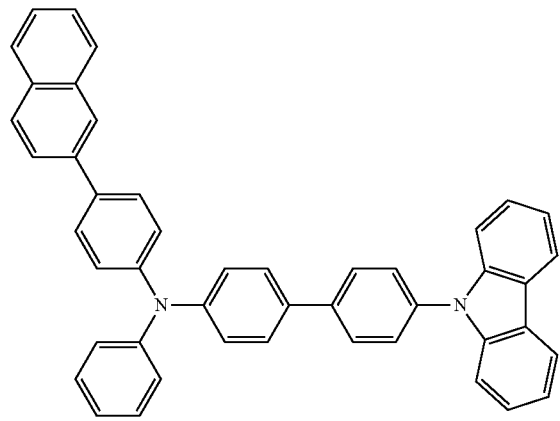
HT-2-117
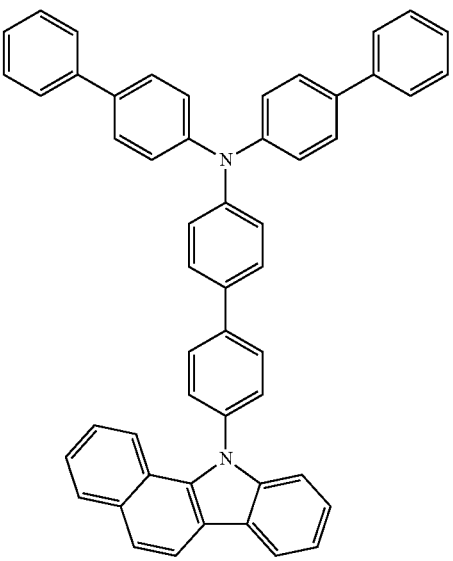
HT-2-115
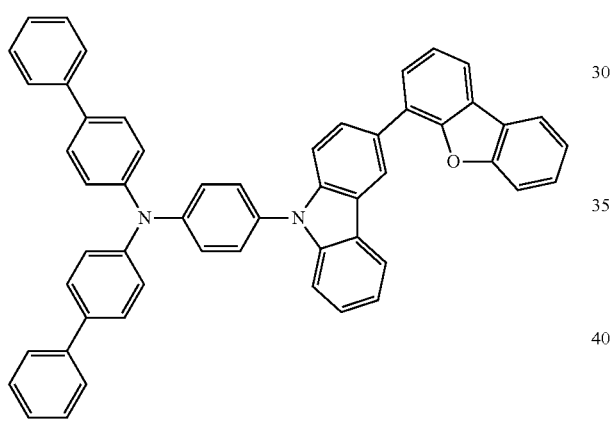
HT-2-116
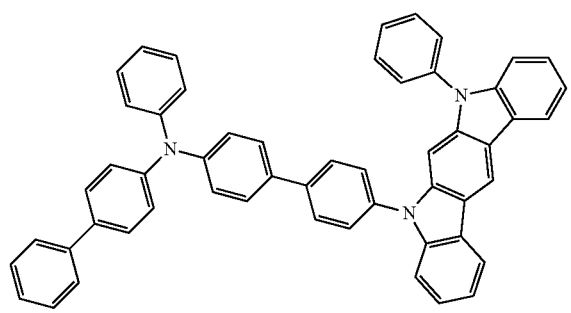
HT-2-118
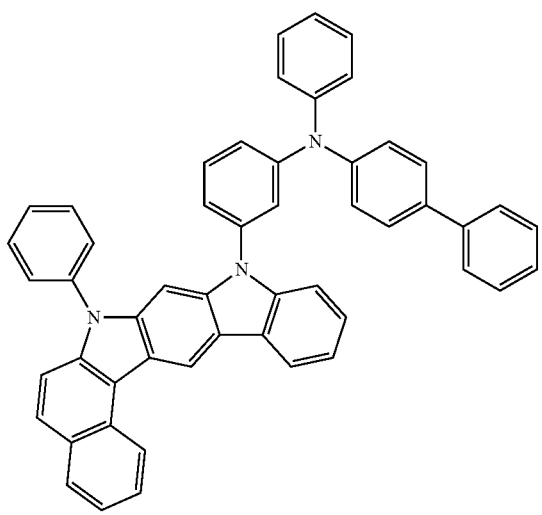

HT-2-119
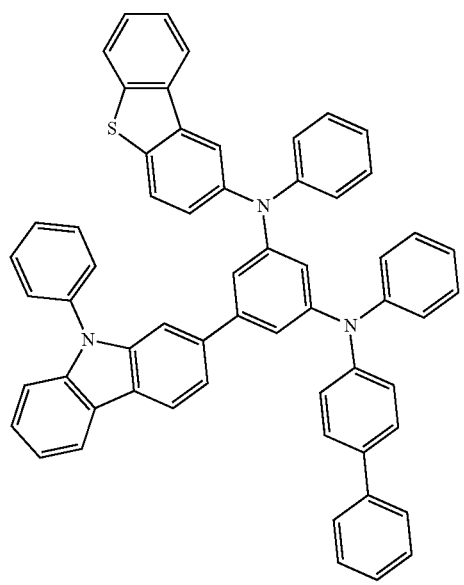
HT-2-122
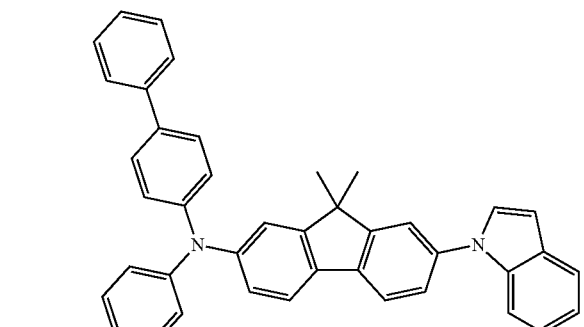
HT-2-123
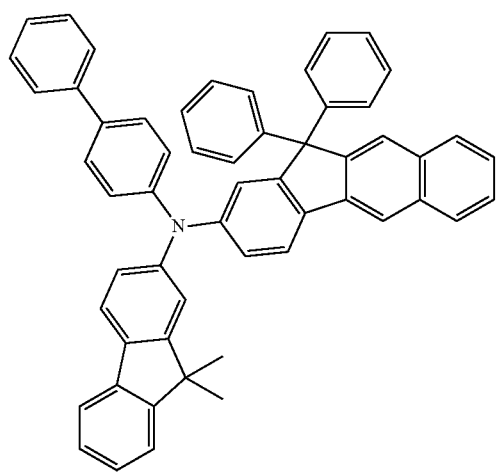
HT-2-120
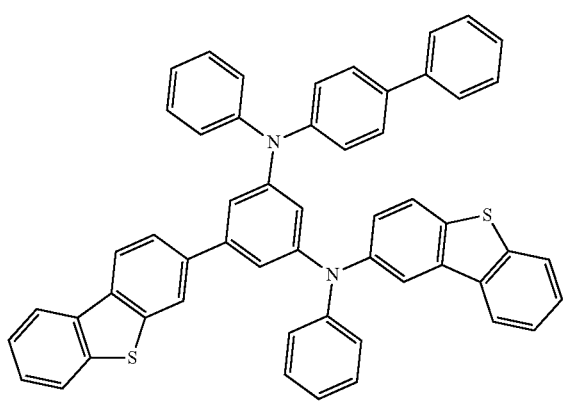
HT-2-121
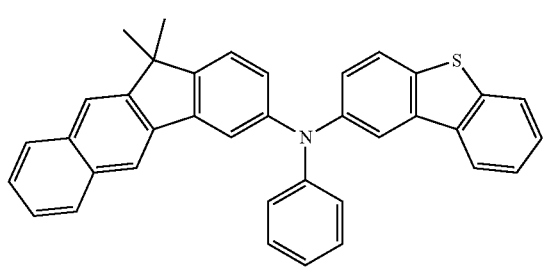
HT-2-124
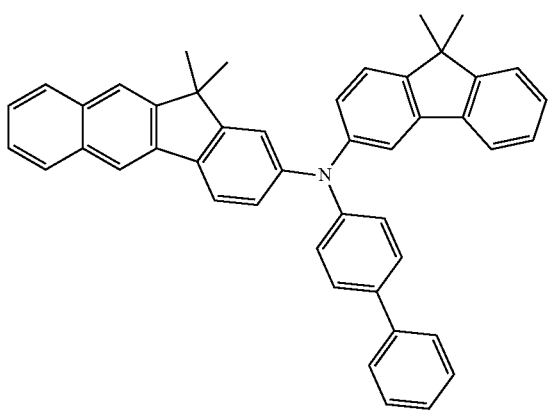

HT-2-125
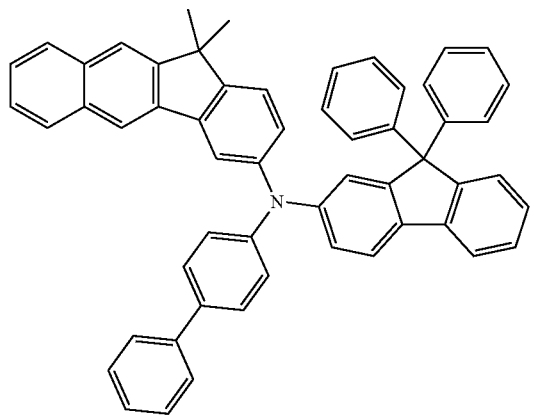
HT-2-126
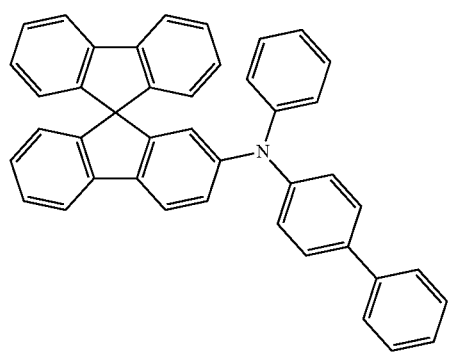
HT-2-127
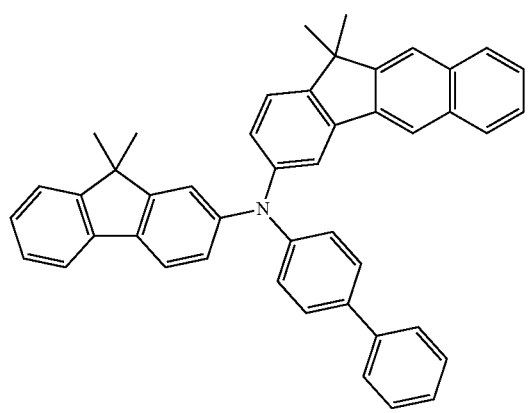
HT-2-128
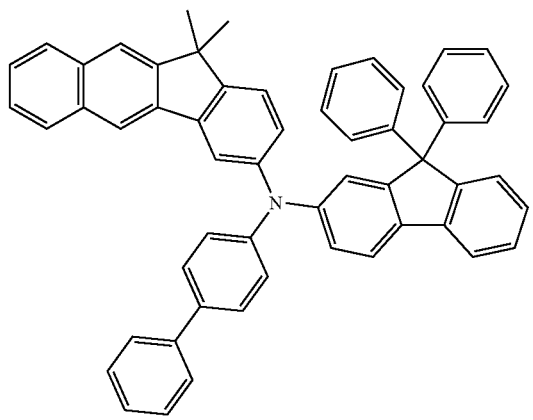
HT-2-129
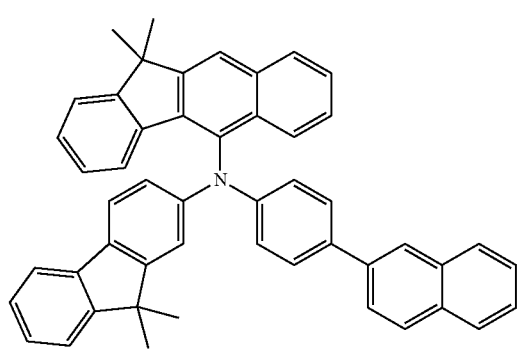
HT-2-130
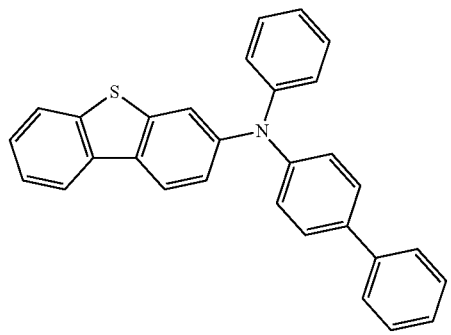
HT-2-131
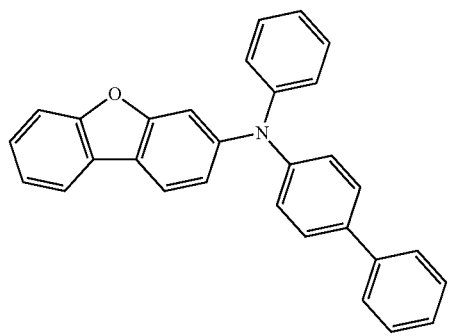

HT-2-132
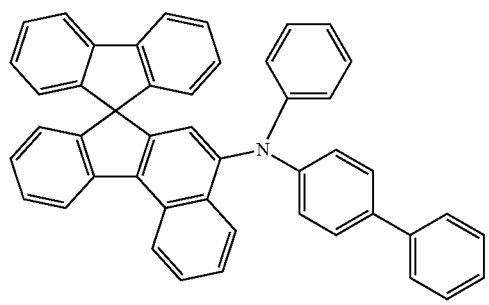
HT-2-133
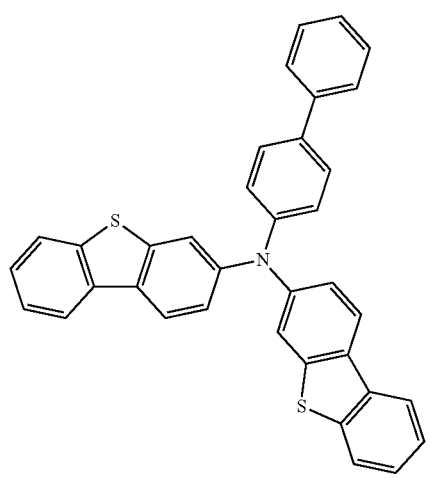
HT-2-134
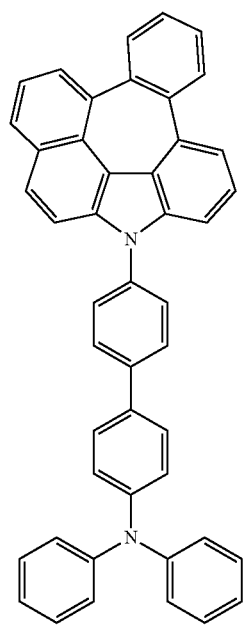
HT-2-135
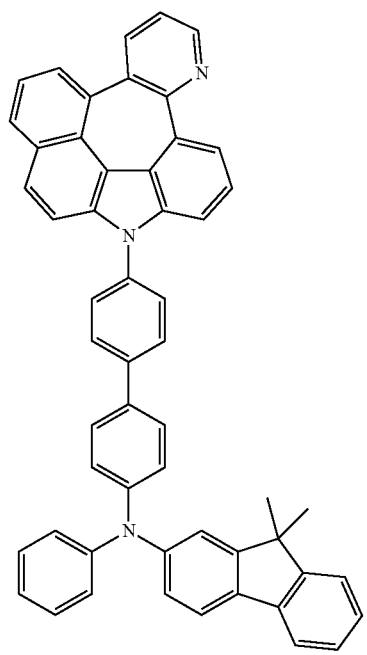
HT-2-136
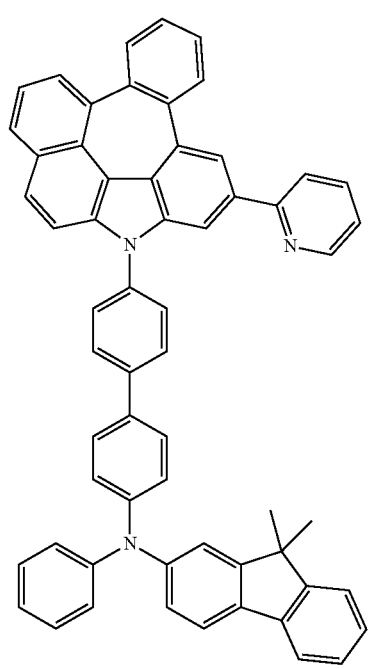

HT-2-137

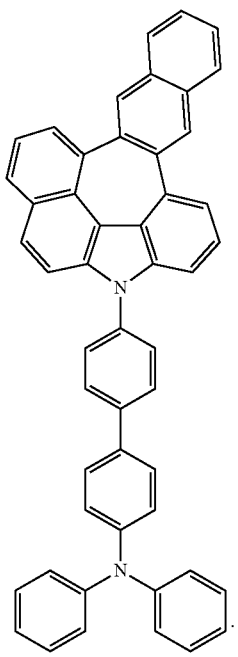

9. The organic electroluminescent device according to claim 1, wherein the hole transport zone comprises a p-doped hole injection layer, a hole transport layer, and a light-emitting auxiliary layer.

10. An organic electroluminescent device comprising a first electrode, a second electrode facing the first electrode, a light-emitting layer between the first electrode and the second electrode, and a hole transport zone between the first electrode and the light-emitting layer, wherein the light-emitting layer comprises at least one compound selected from the following compounds:

C-1

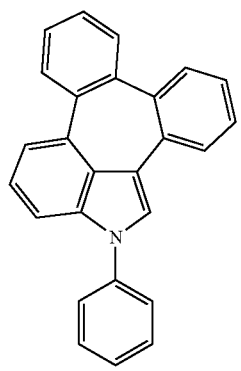

C-2

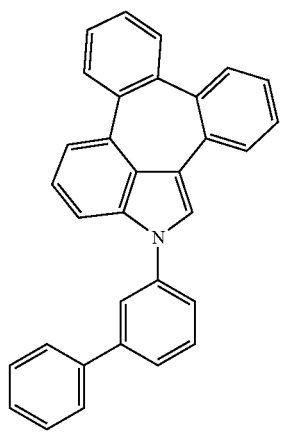

C-3

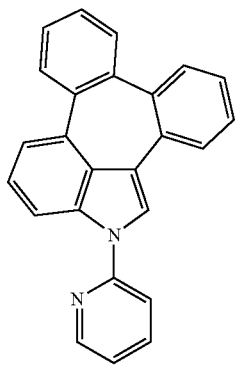

C-4

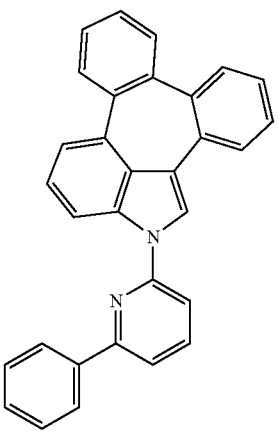

C-5

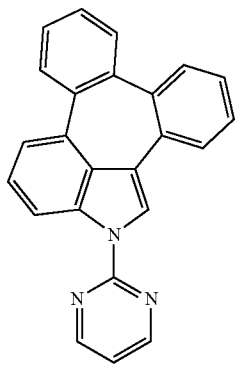

C-6
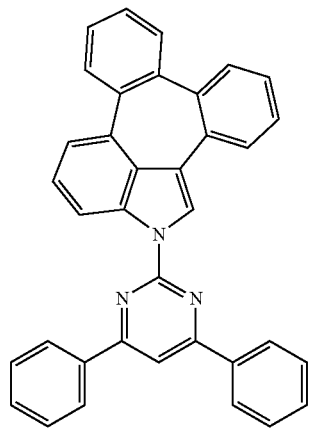
C-7
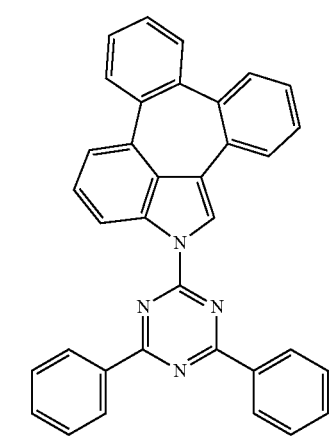
C-8
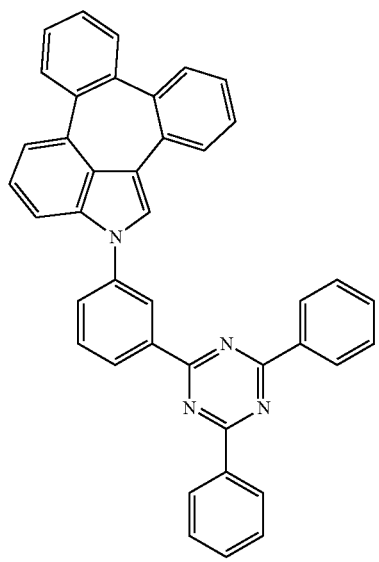
C-9
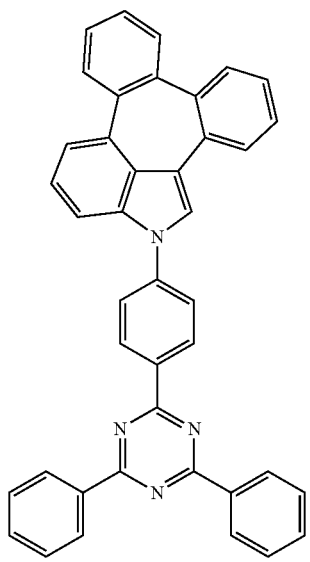
C-10
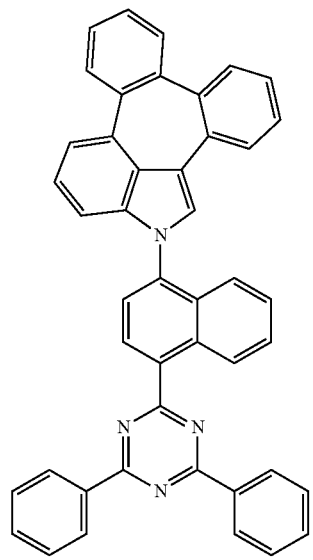

C-11
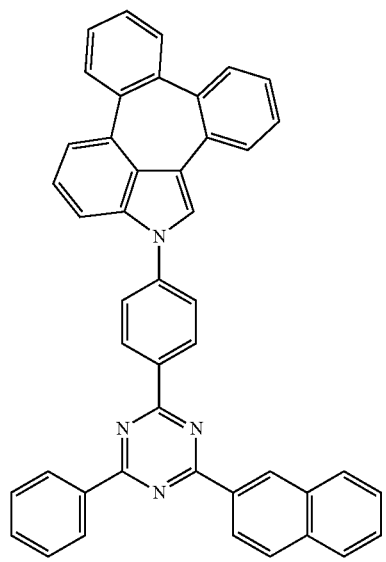
C-12
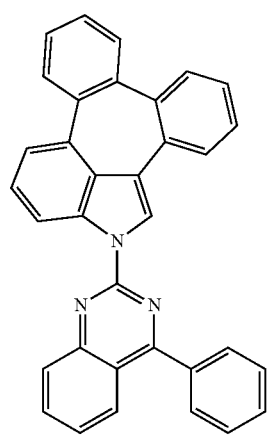
C-13
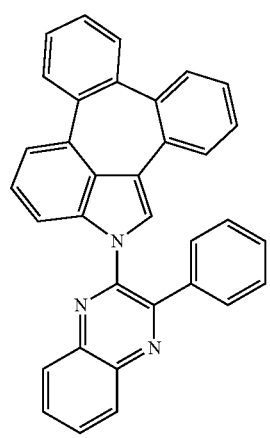
C-14
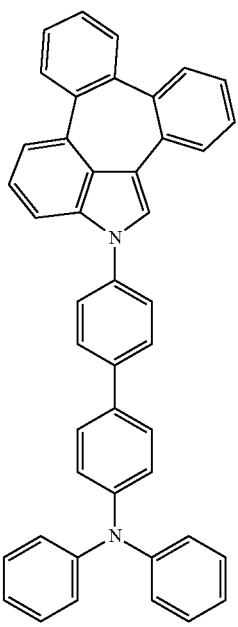
C-15
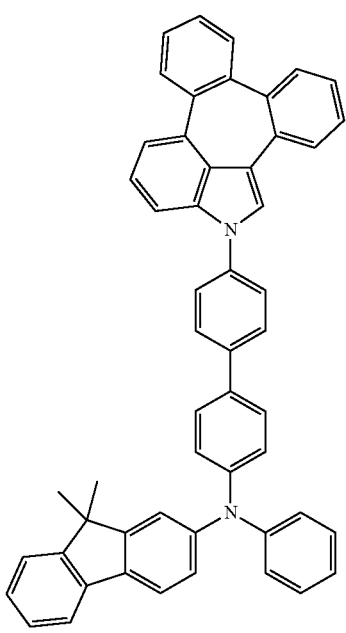

-continued
C-16
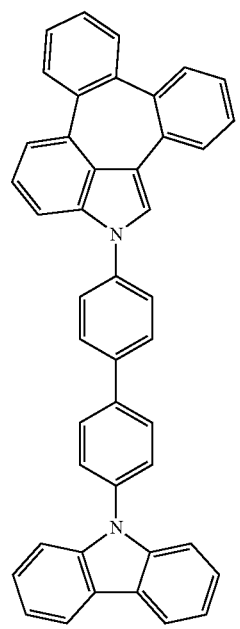
C-17
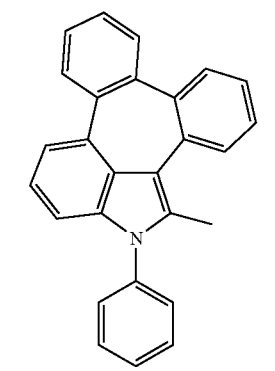
C-18
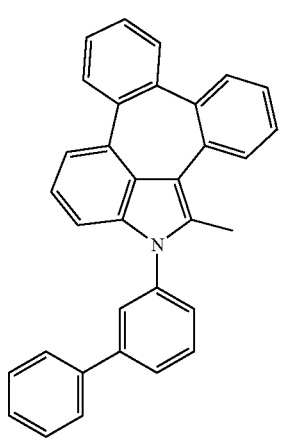
C-19
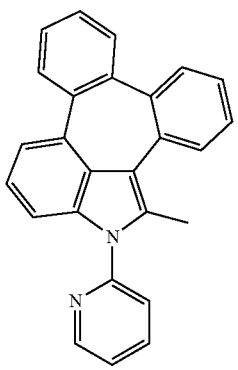
C-20
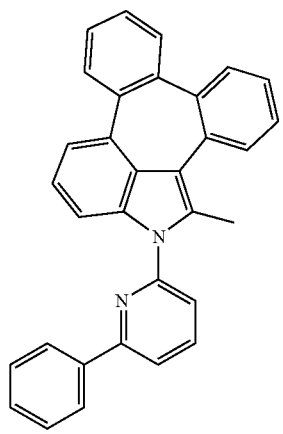
C-21
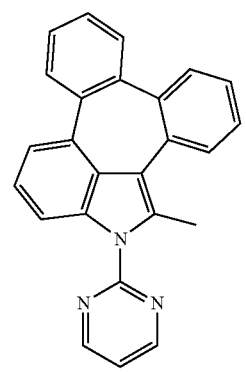
C-22
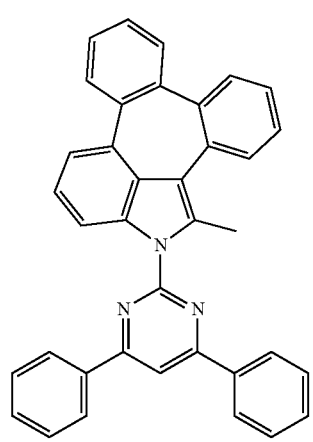

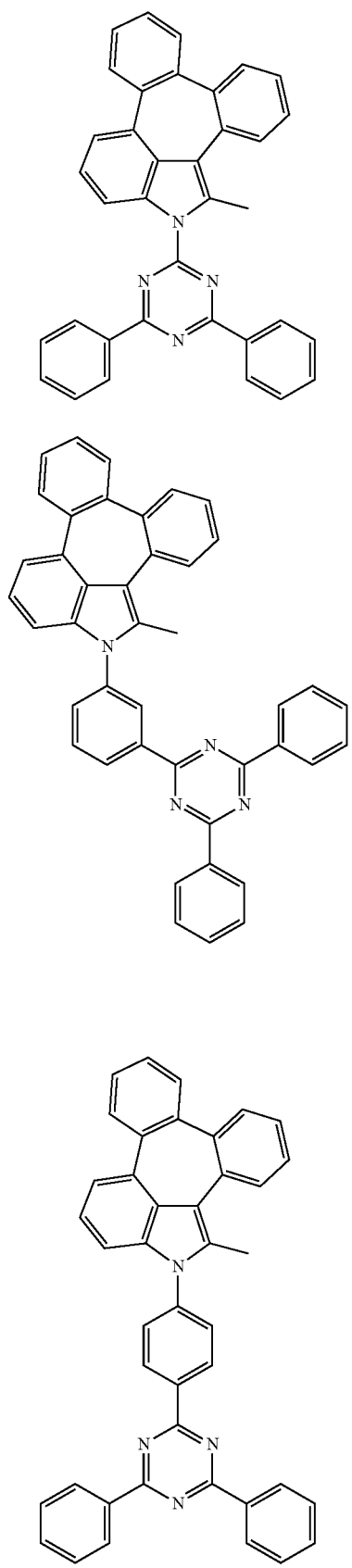
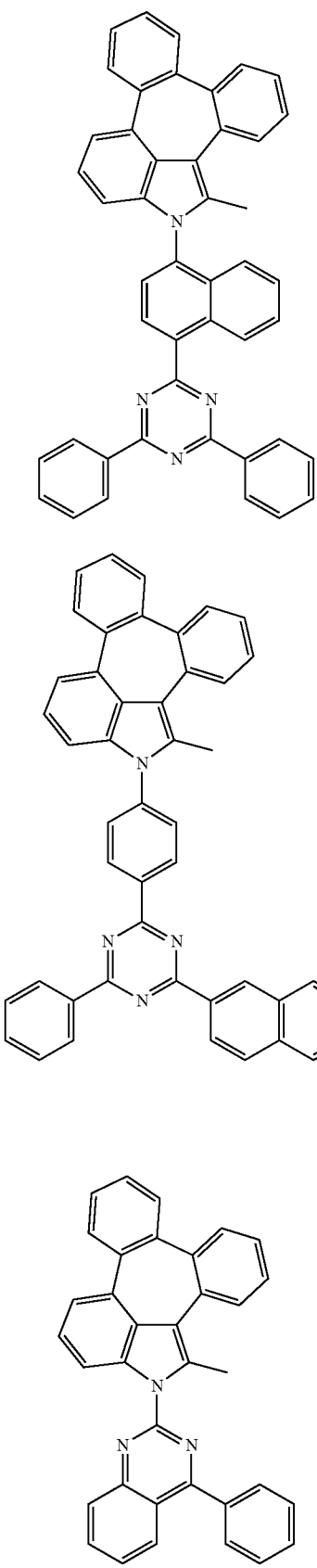

C-29
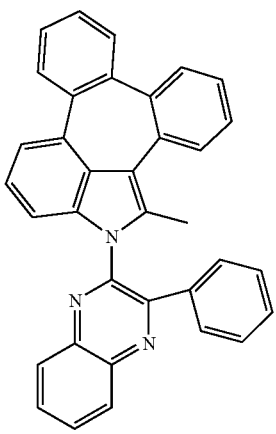
C-30
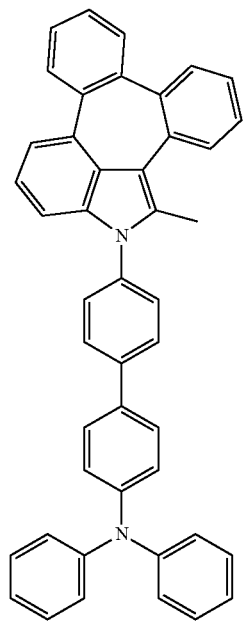
C-31
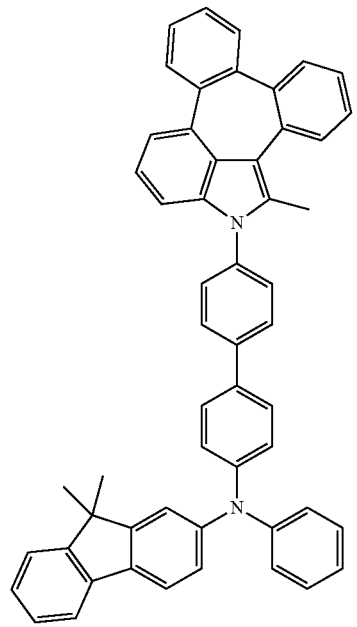
C-32
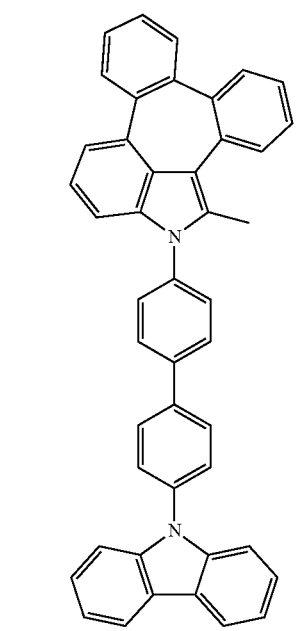
C-33
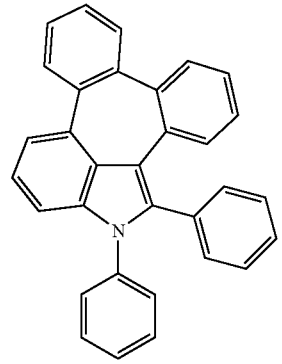

-continued
C-34
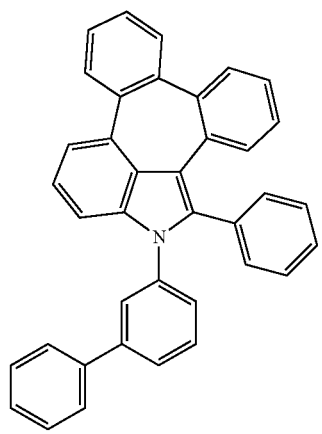
C-35
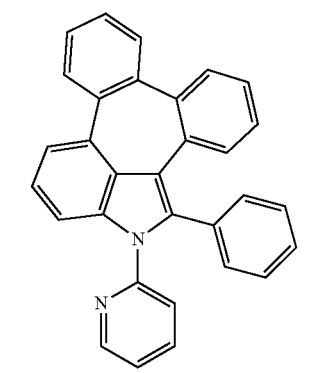
C-36
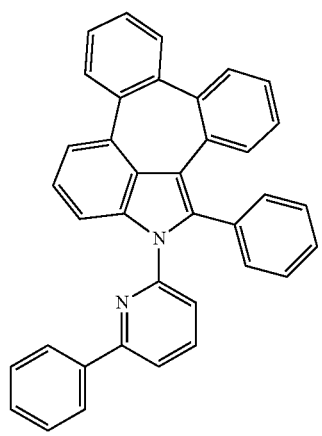
C-37
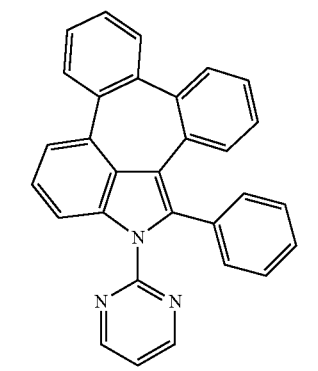
-continued
C-38
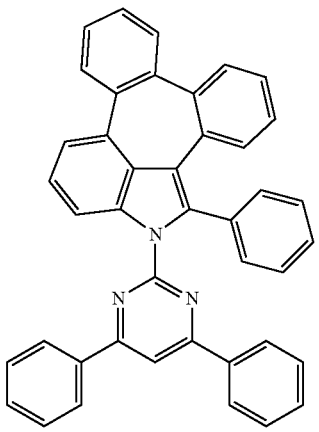
C-39
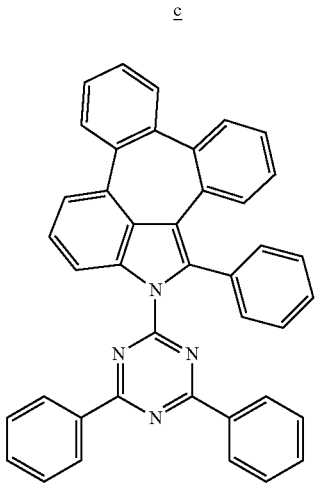
C-40
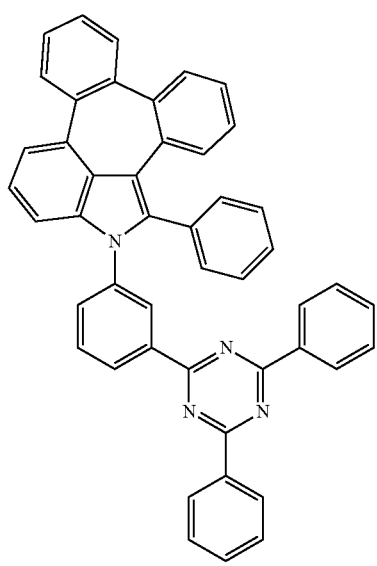

357
-continued
C-41
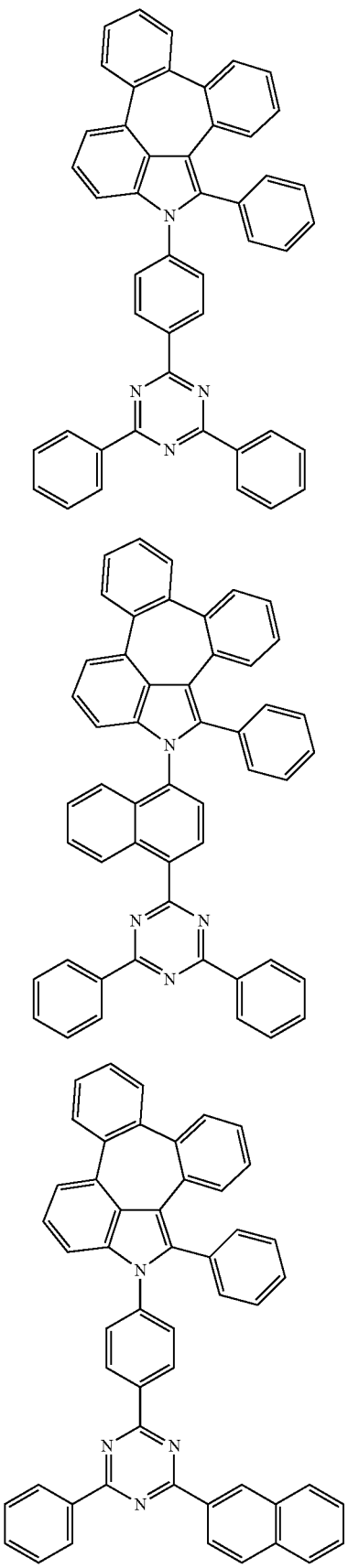
C-42
C-43
358
-continued
C-44
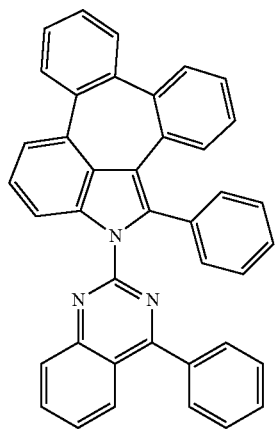
C-45
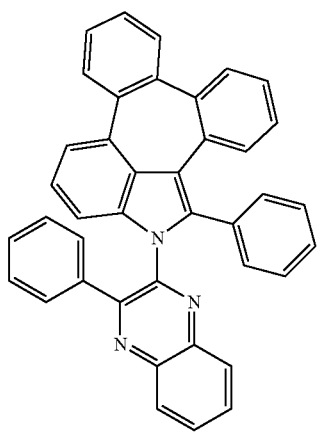
C-46
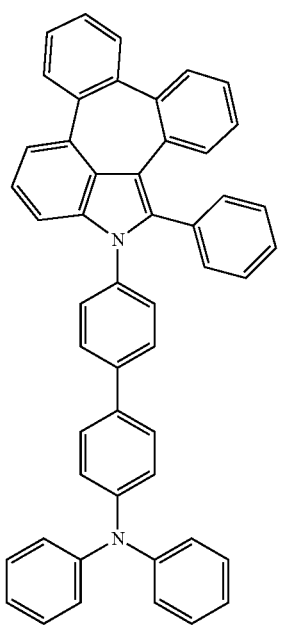

C-47
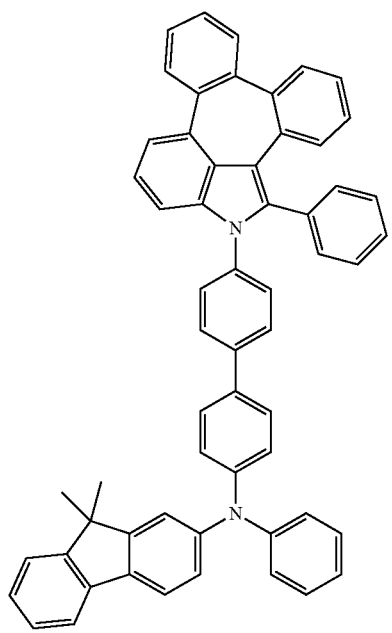
C-48
C-49
C-50
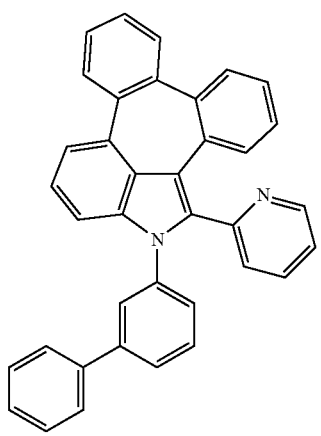
C-51
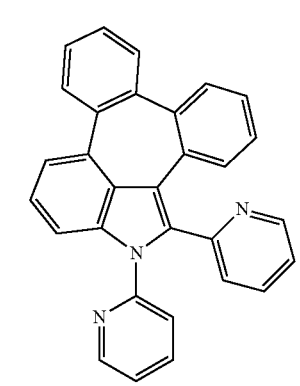
C-52
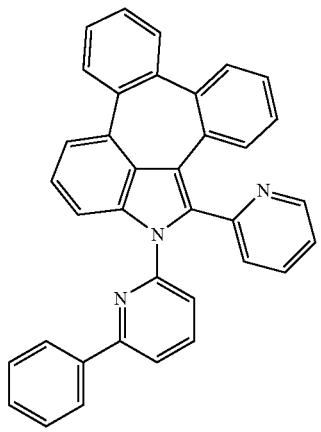
C-53
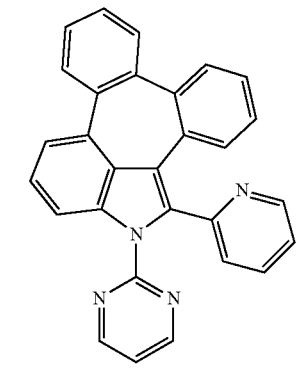

C-54
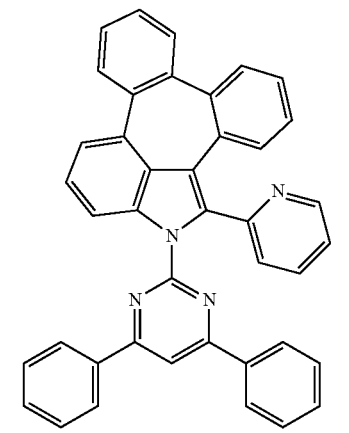
C-55
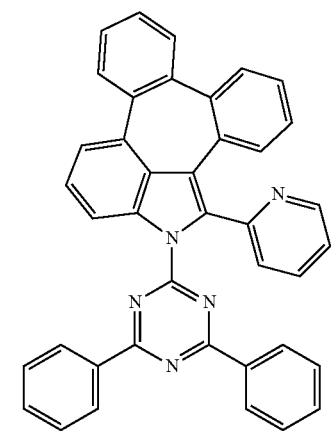
C-56
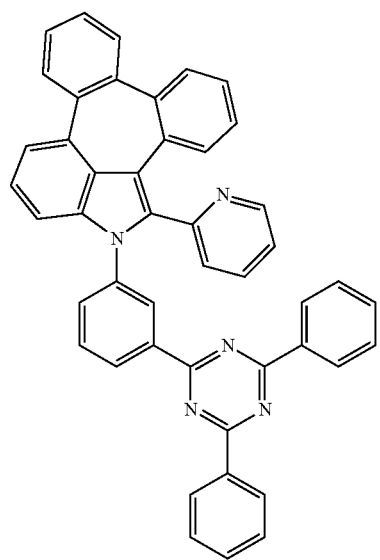
C-57
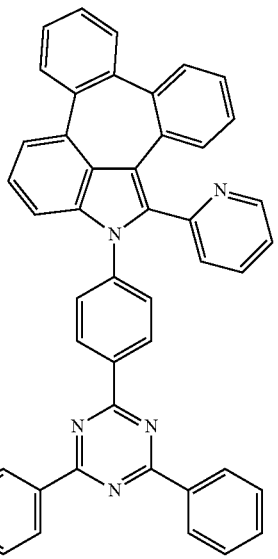
C-58
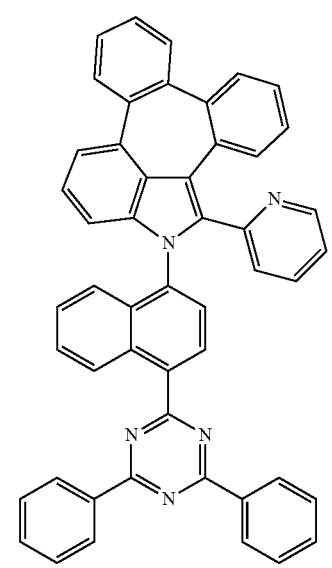
C-59
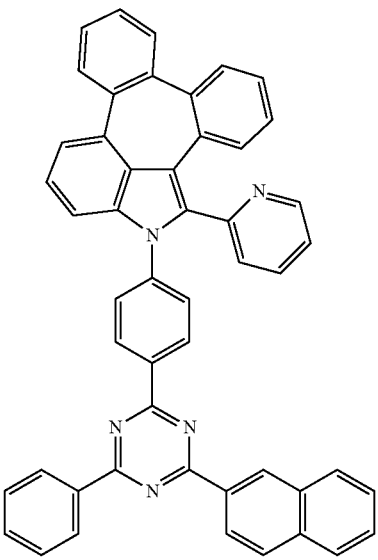

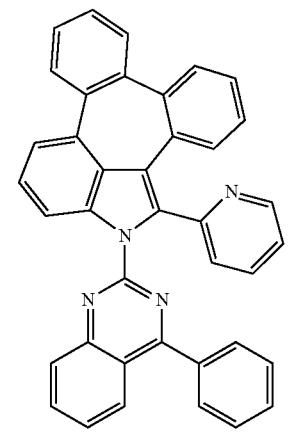
C-60
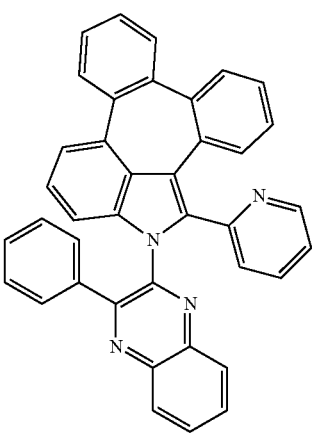
C-61
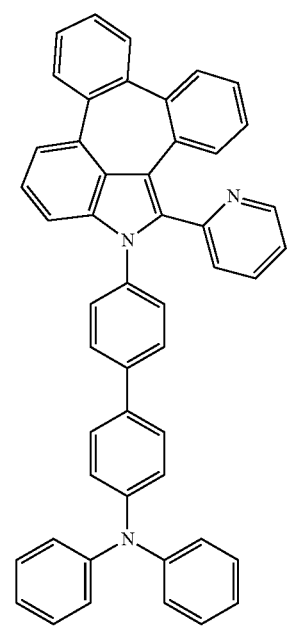
C-62
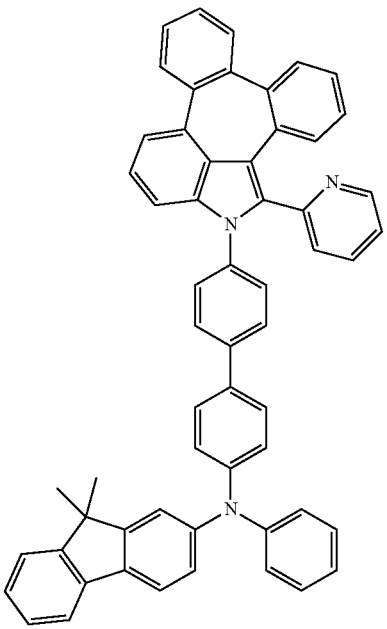
C-63
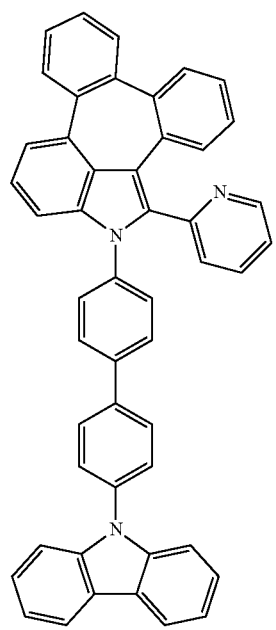
C-64
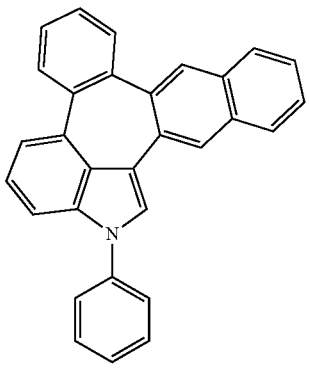
C-65

C-66 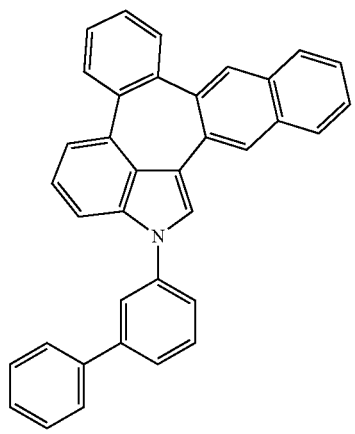
C-67 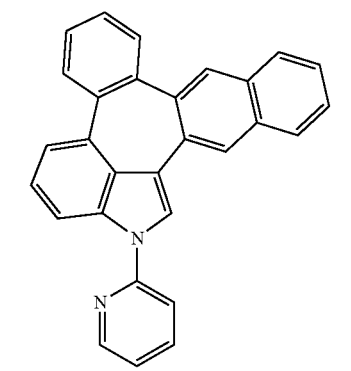
C-68 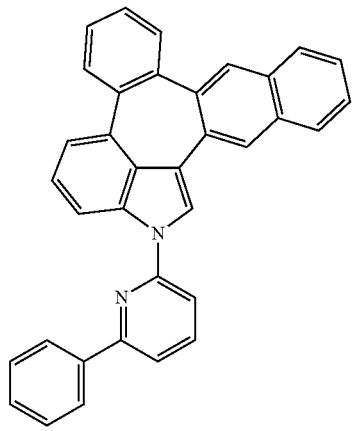
C-69 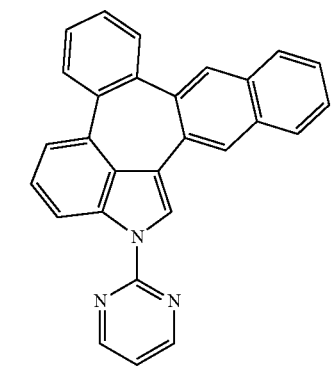
C-70 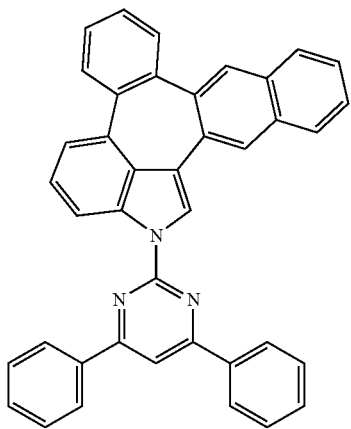
C-71 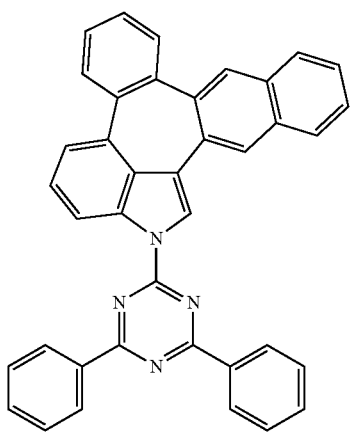
C-72 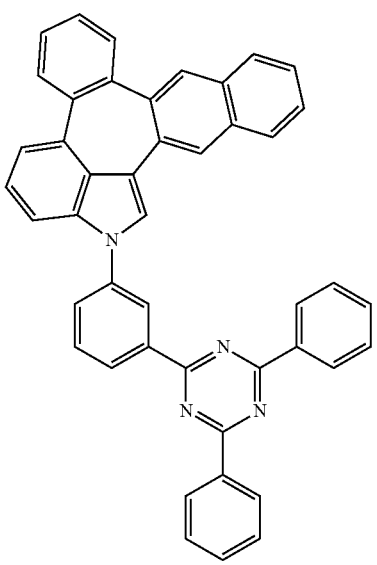

C-73
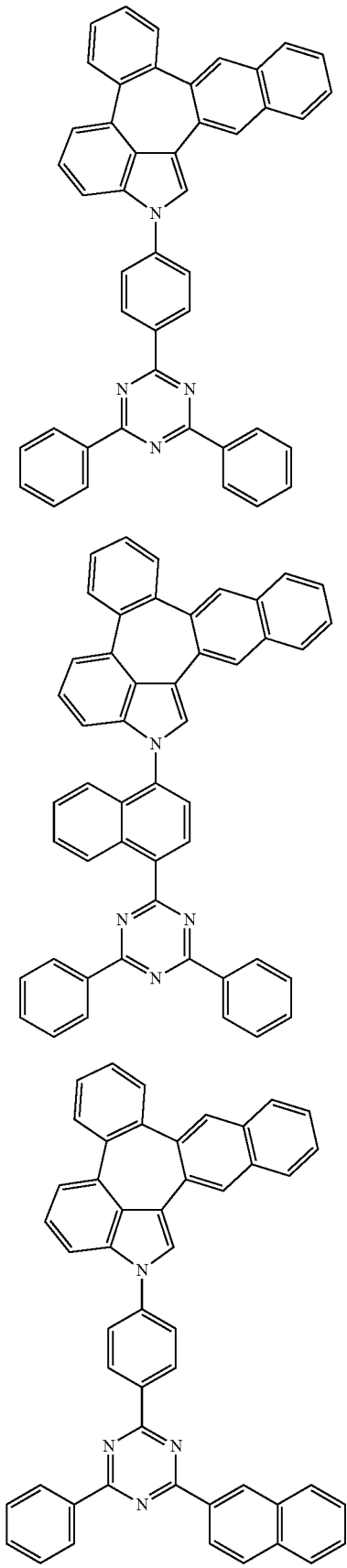
C-74
C-75
C-76
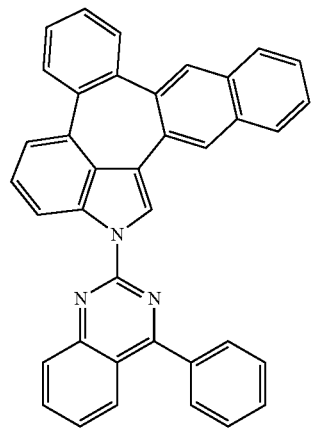
C-77
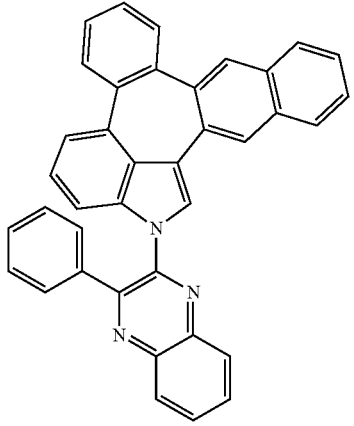
C-78
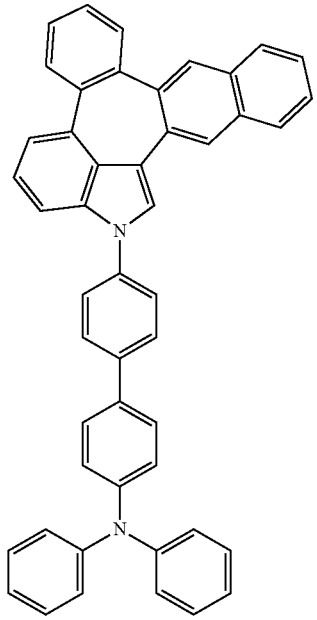

C-79
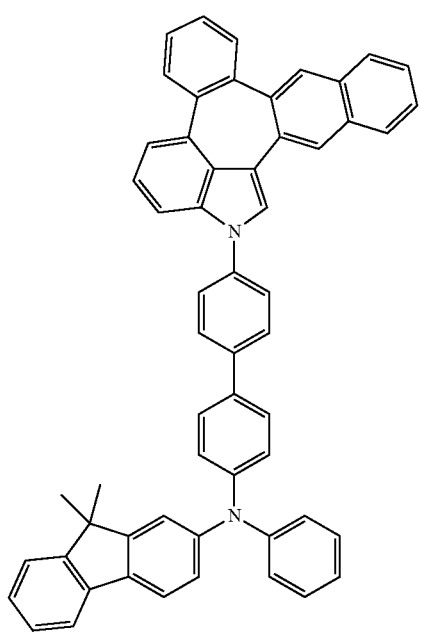
C-80
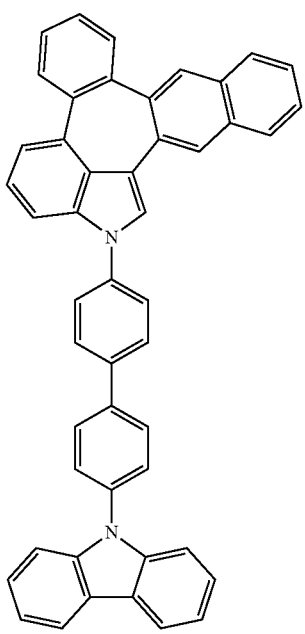
C-81
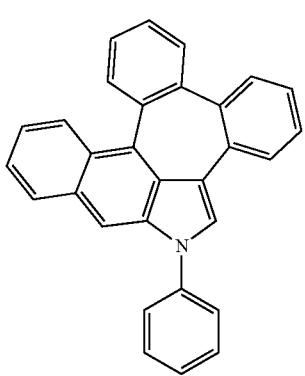
C-82
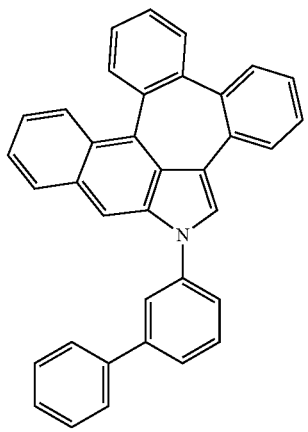
C-83
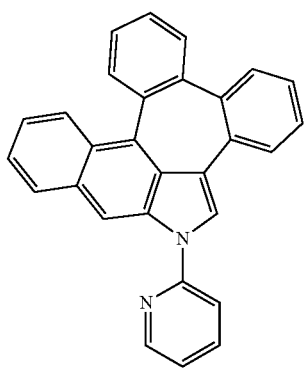
C-84
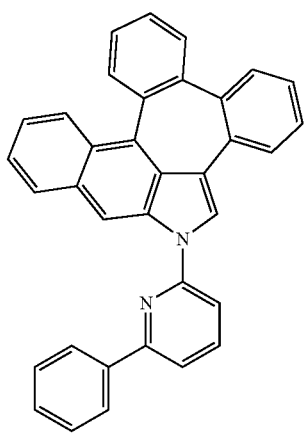
C-85
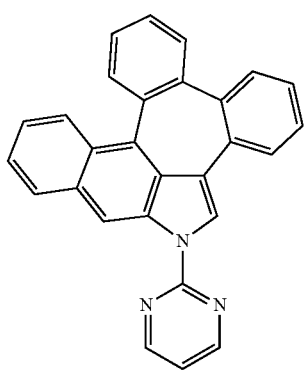

-continued
C-86
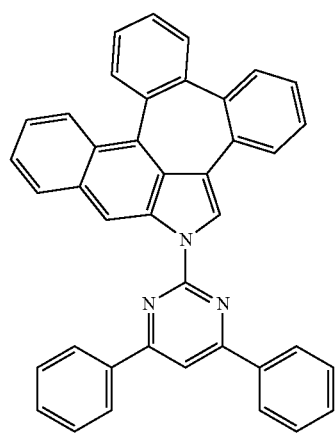
C-87
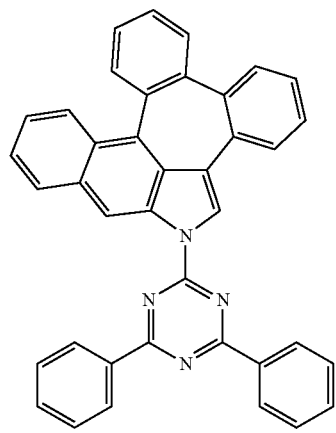
C-88
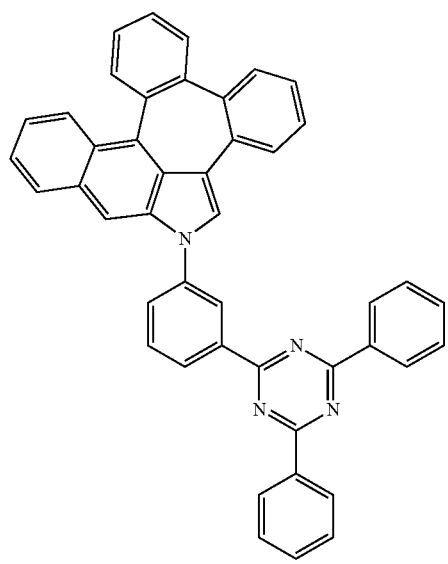
-continued
C-89
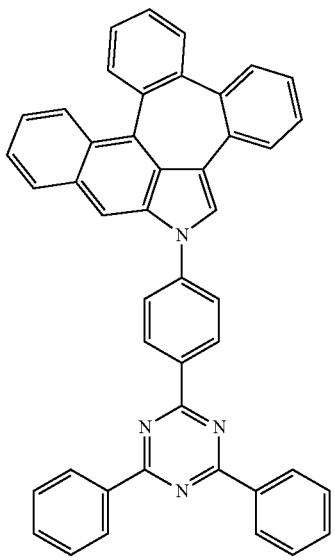
C-90
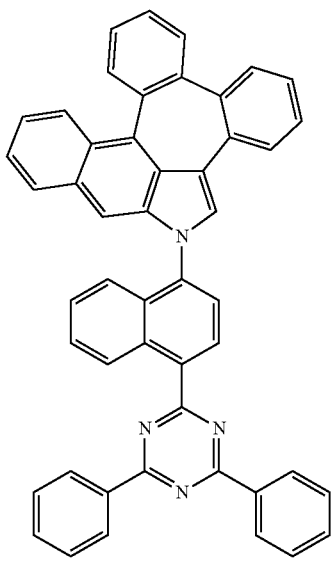

C-91
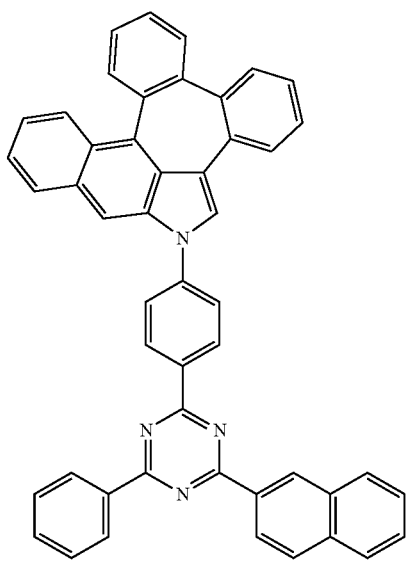
C-92
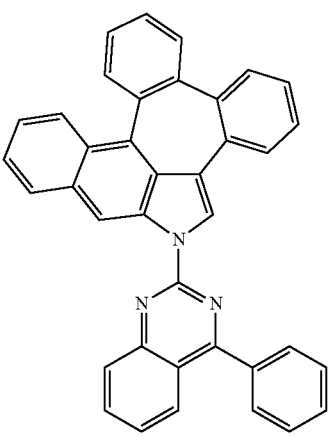
C-93
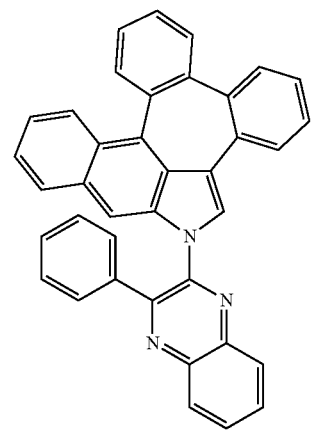
C-94
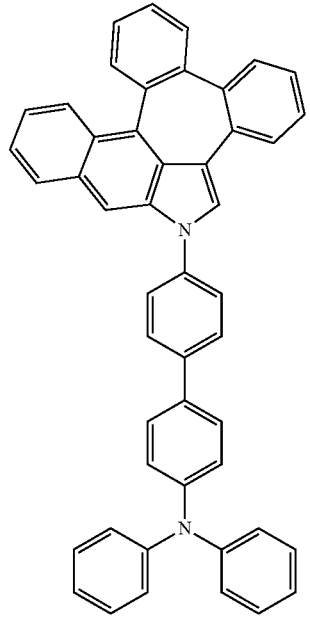
C-95
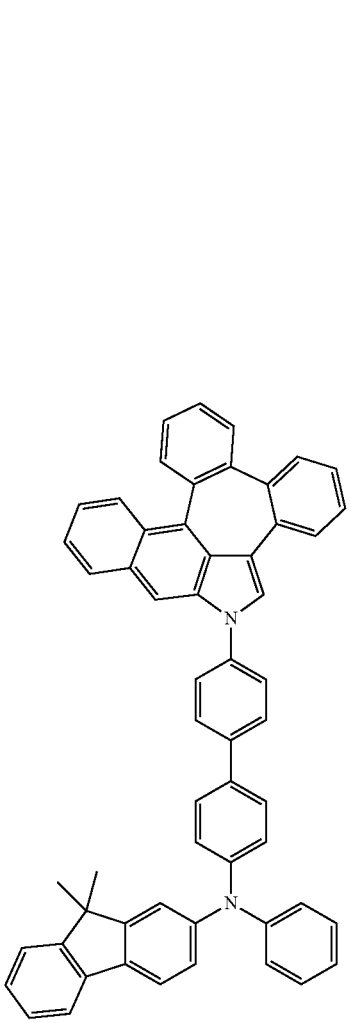

-continued
C-96
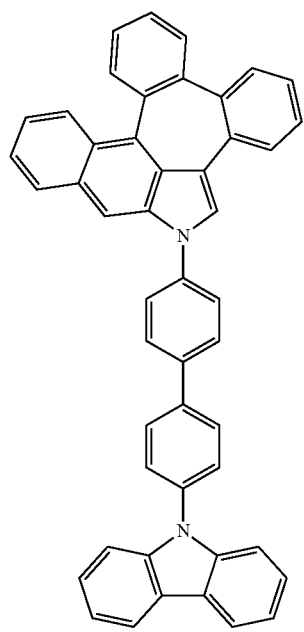
C-97
C-98
C-99
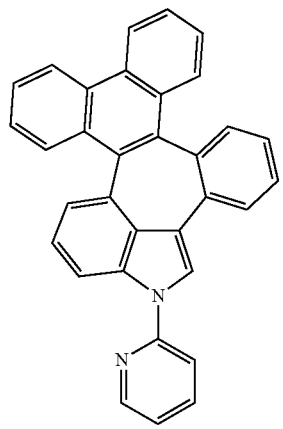
C-100
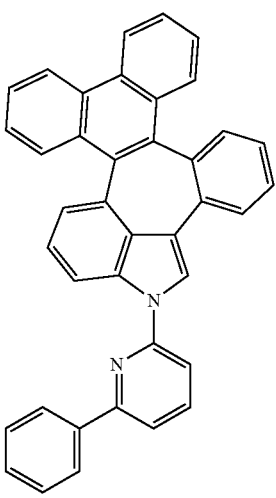
C-101
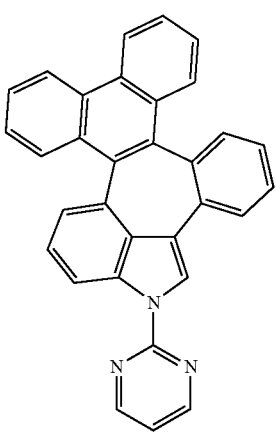

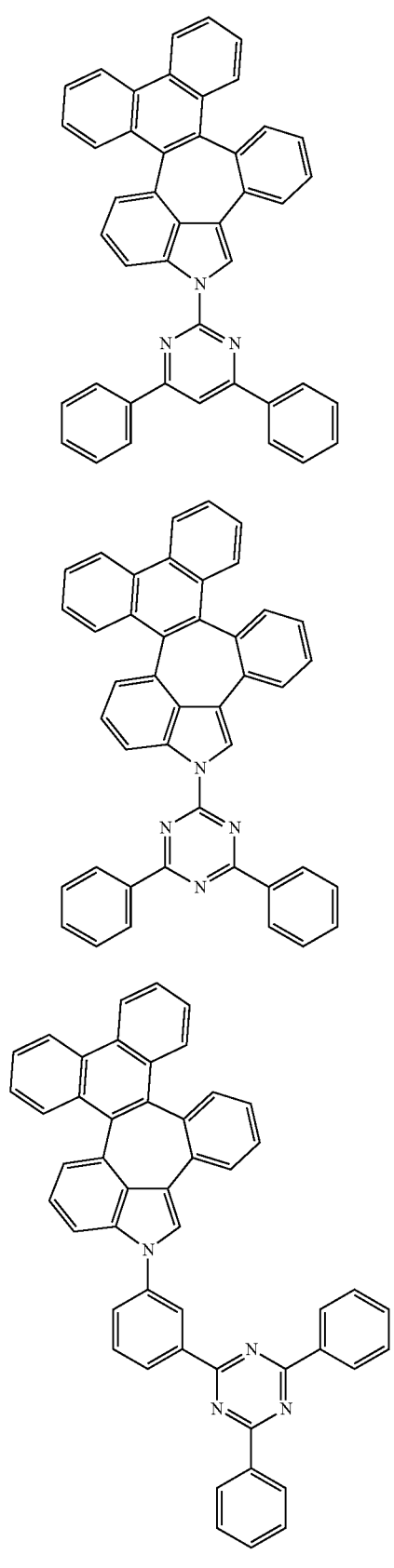

C-107
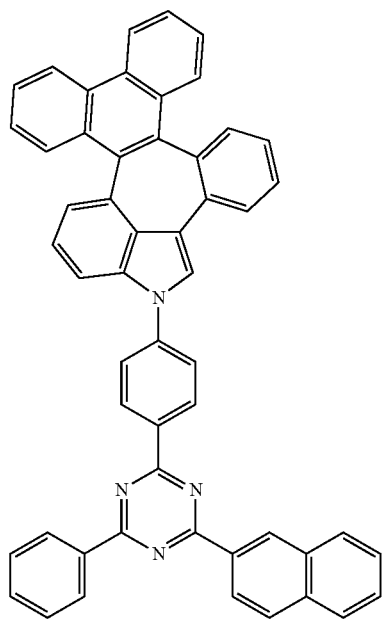
C-108
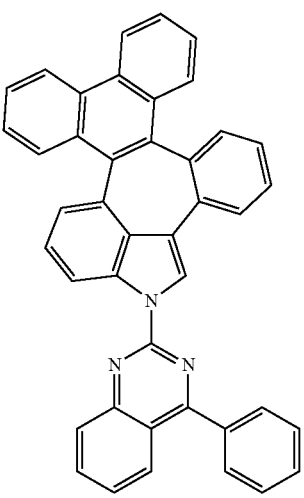
C-109
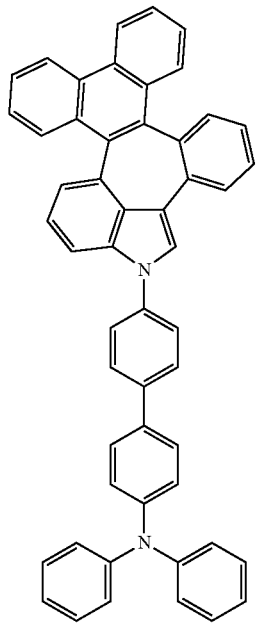
C-110
C-111

C-112 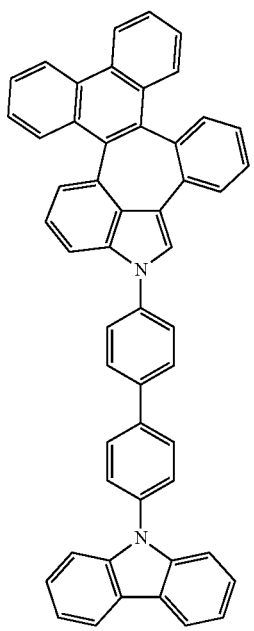
C-113
C-114
C-115 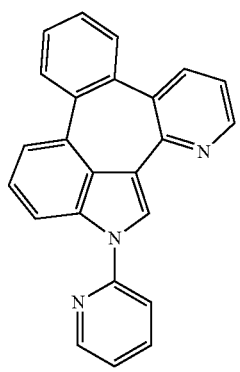
C-116 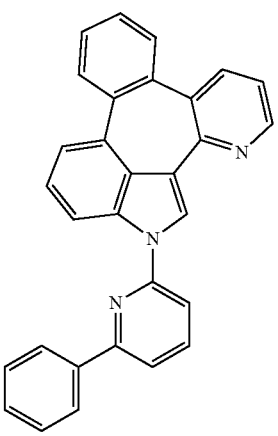
C-117 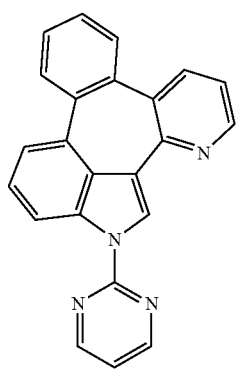
C-118 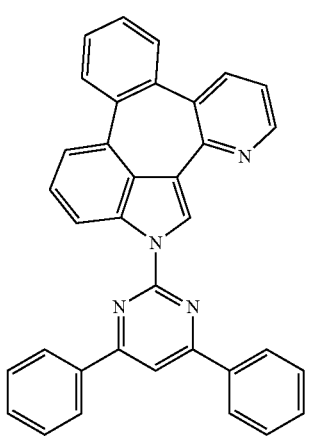

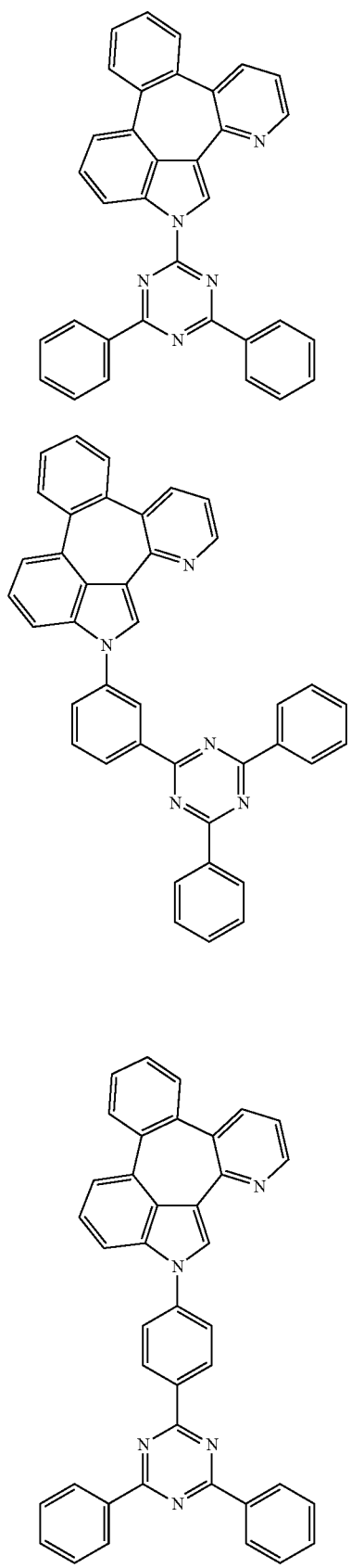
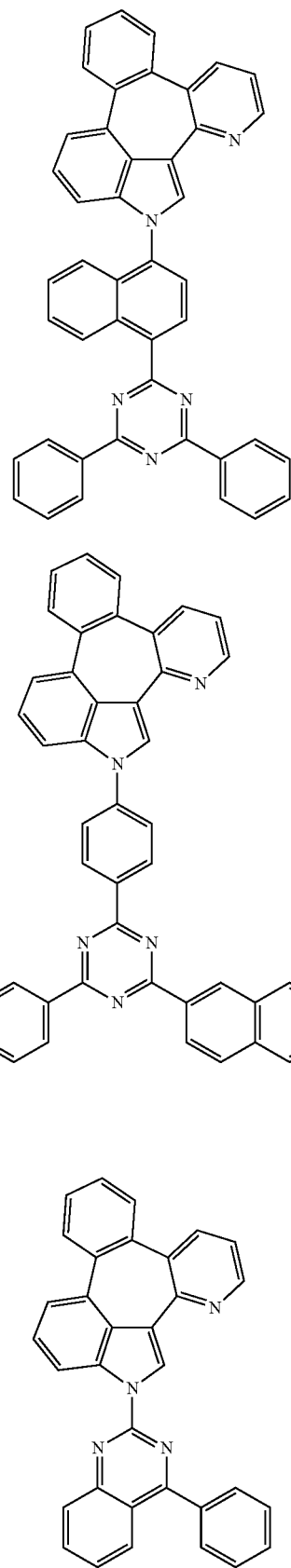

C-125
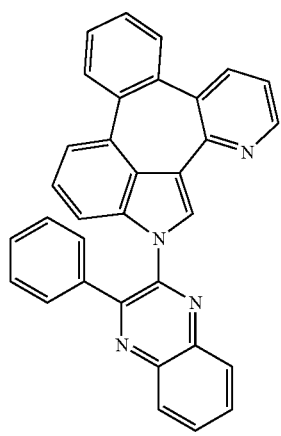
C-126
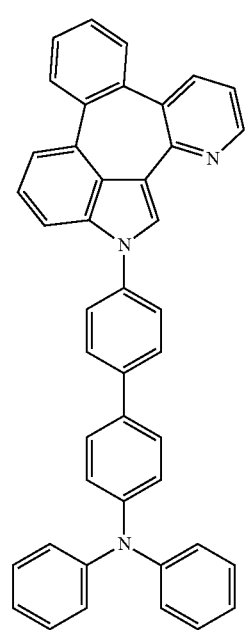
C-127
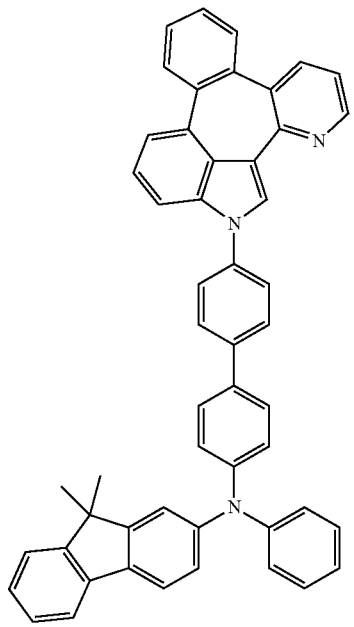
C-128
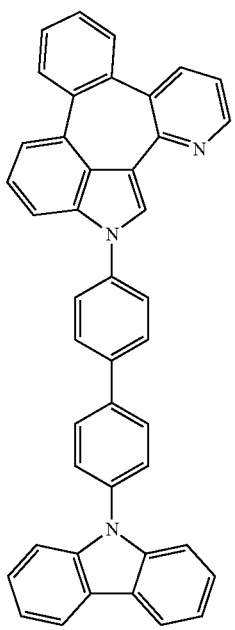

C-129
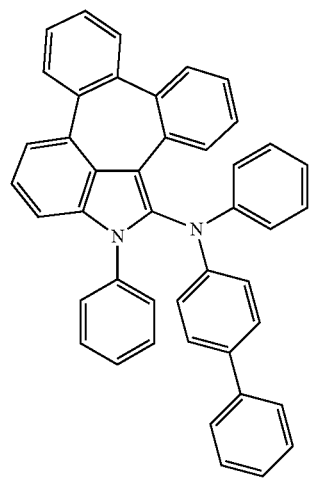
C-130
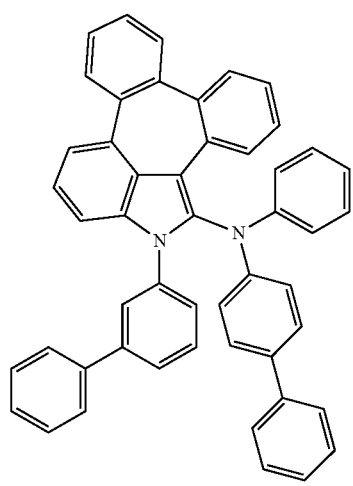
C-131
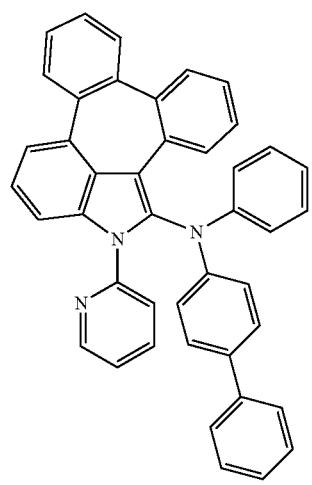
C-132
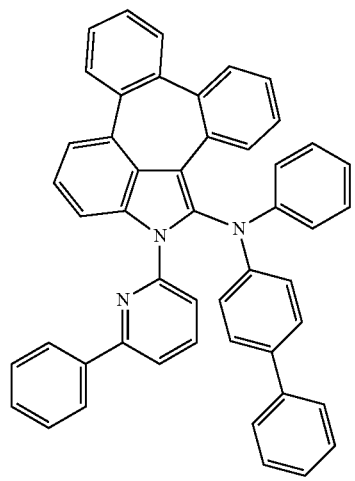
C-133
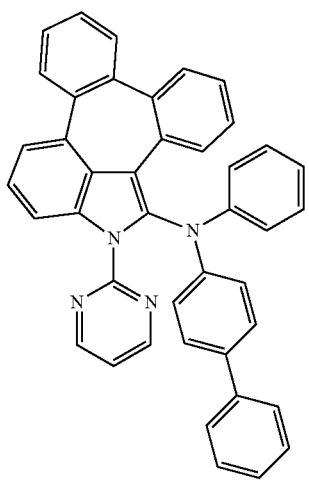
C-134
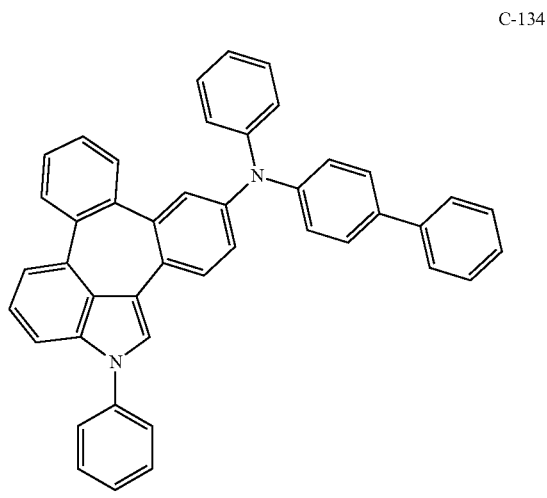

C-135
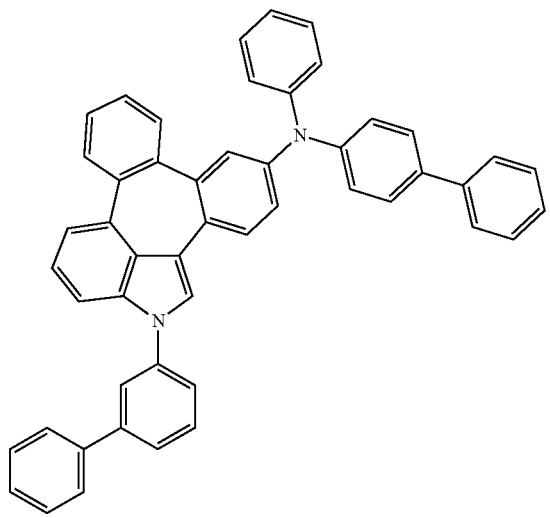
C-136
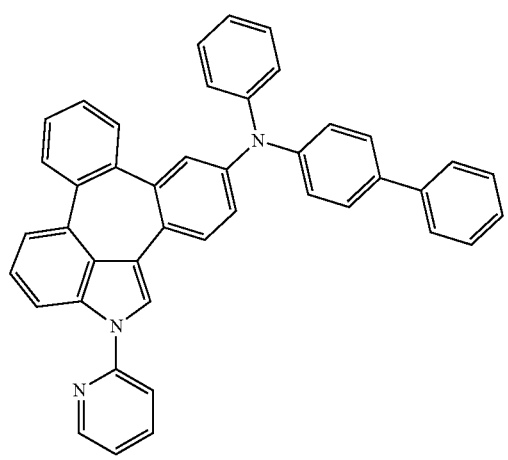
C-137
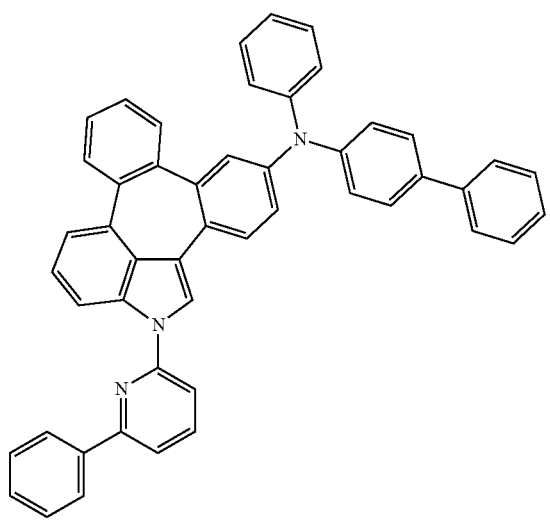
C-138
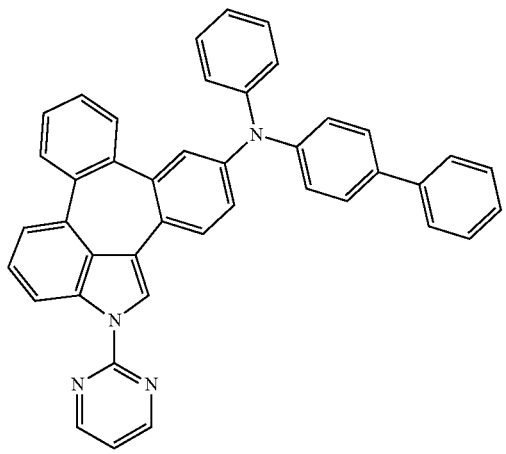
C-139
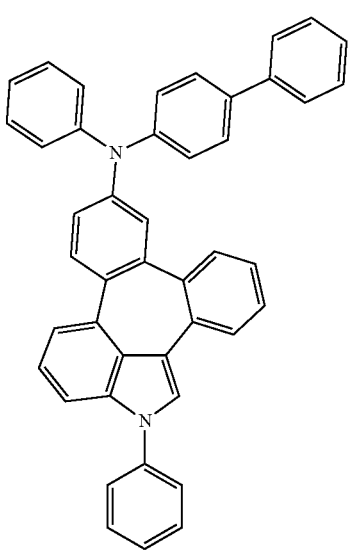
C-140
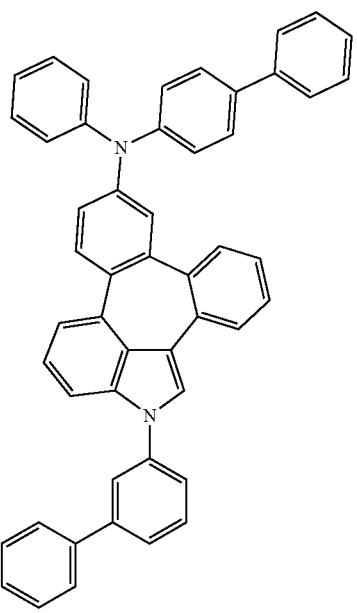

-continued
C-141
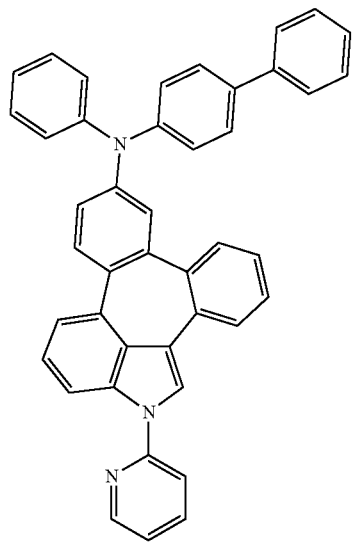
C-143
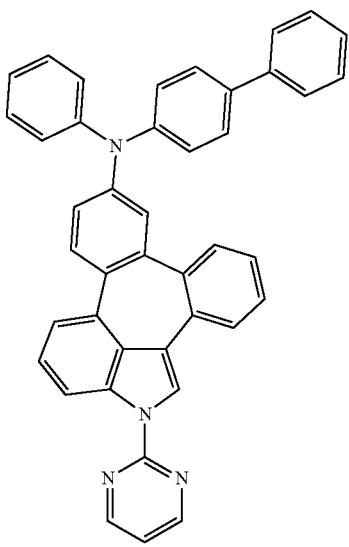
C-144
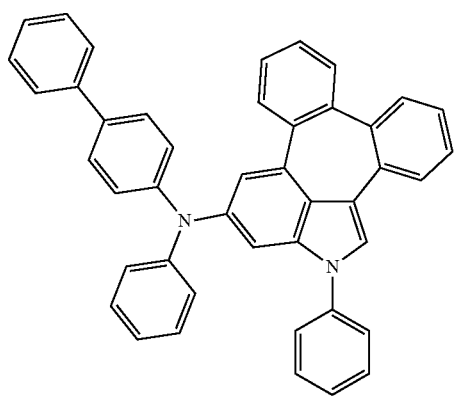
C-142
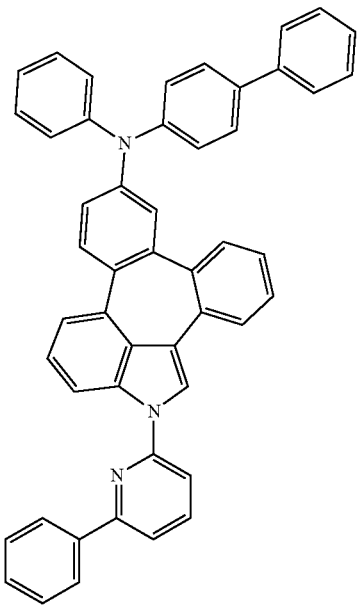
C-145
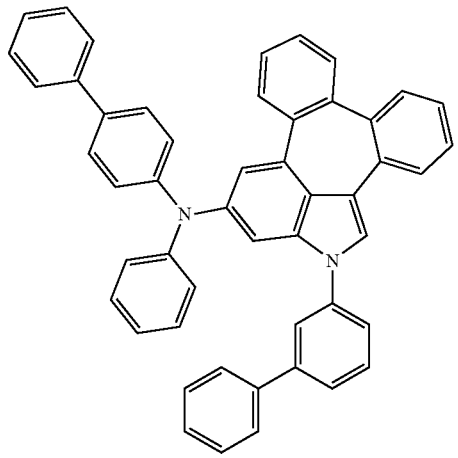

-continued
C-146
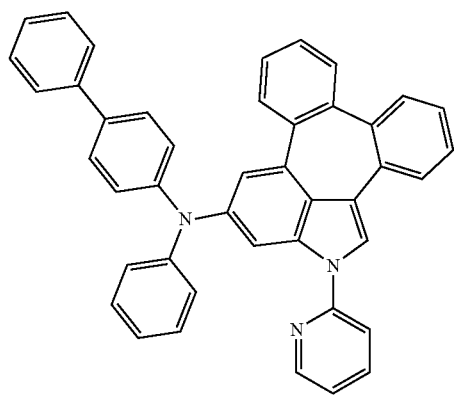
C-147
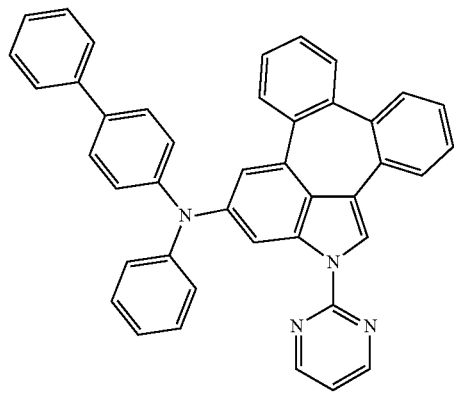
C-148
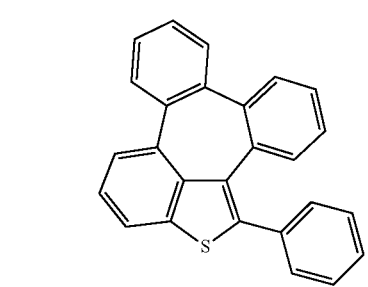
-continued
C-150
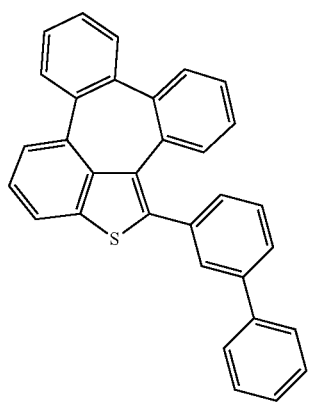
C-151
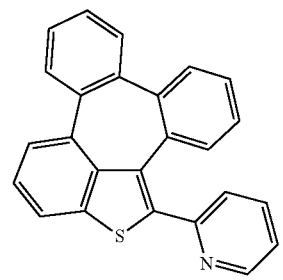
C-152
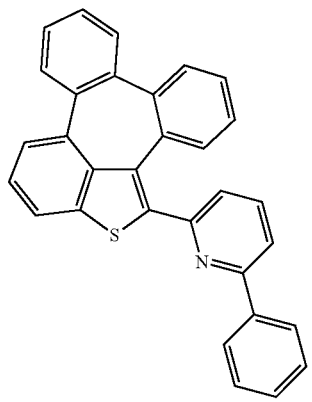
C-149
C-153
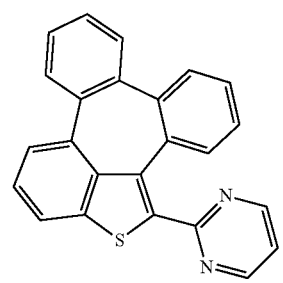

C-154
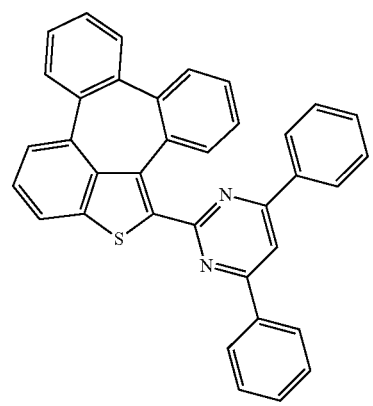
C-155
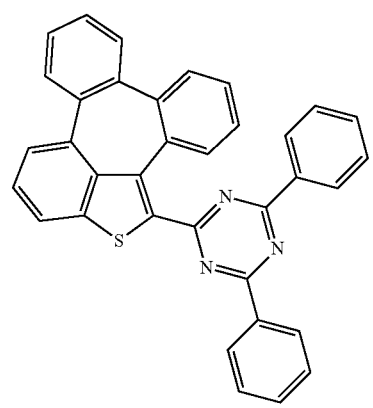
C-156
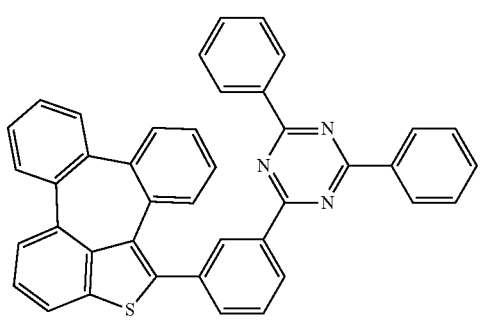
C-157
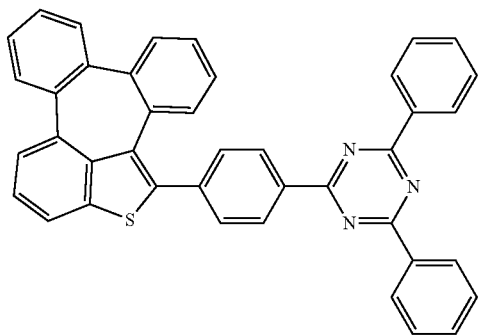
C-158
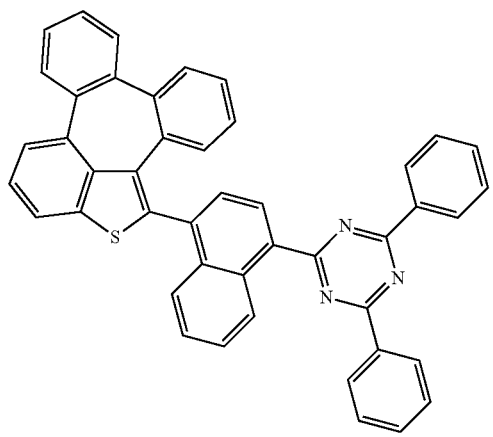
C-159
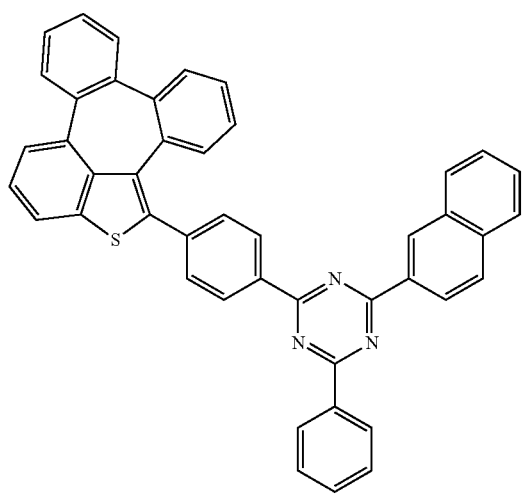
C-160
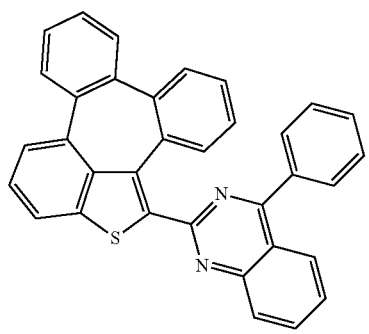

C-161
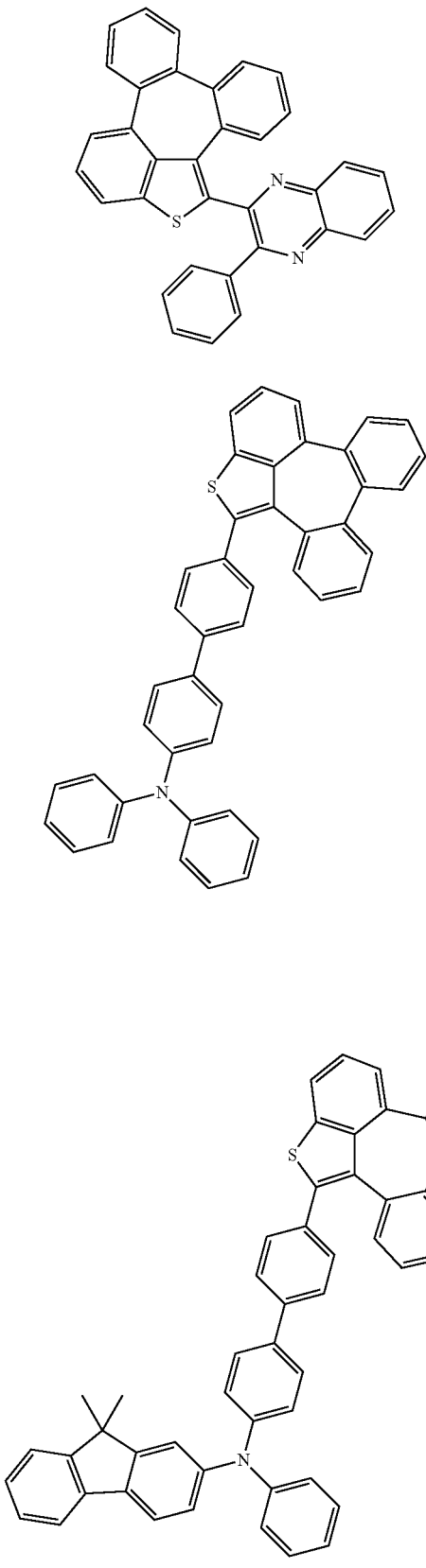
C-162
C-163
C-164
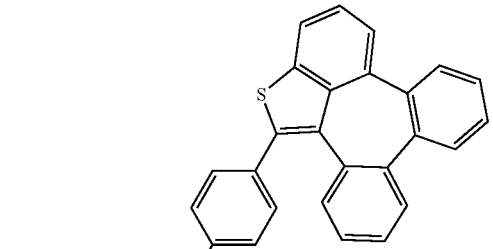
C-165
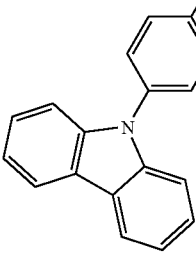
C-166
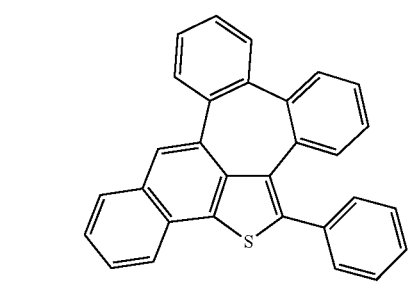
C-167
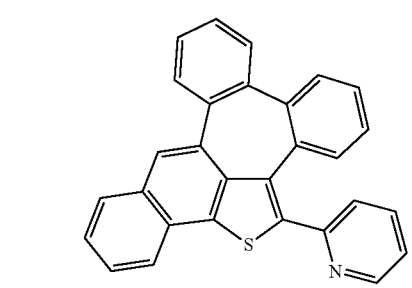

-continued
C-168
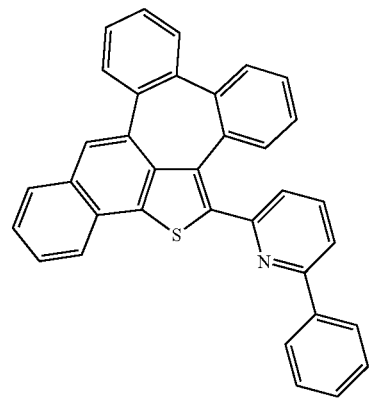
C-169
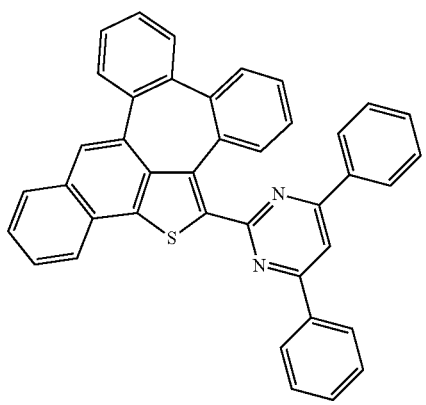
C-170
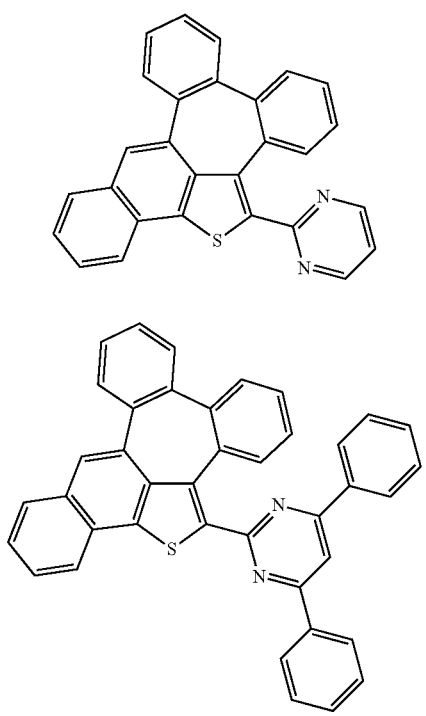
C-171
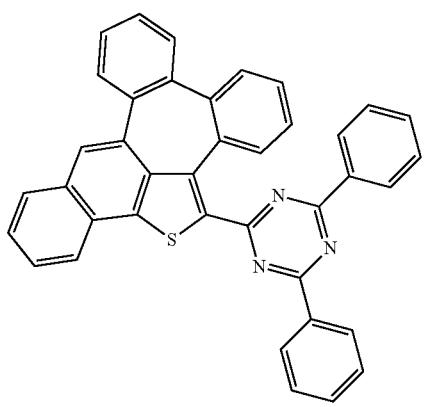
-continued
C-172
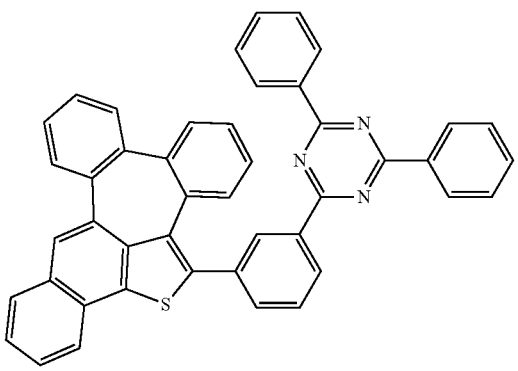
C-173
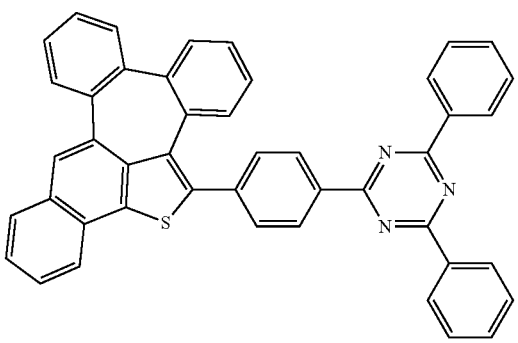
C-174
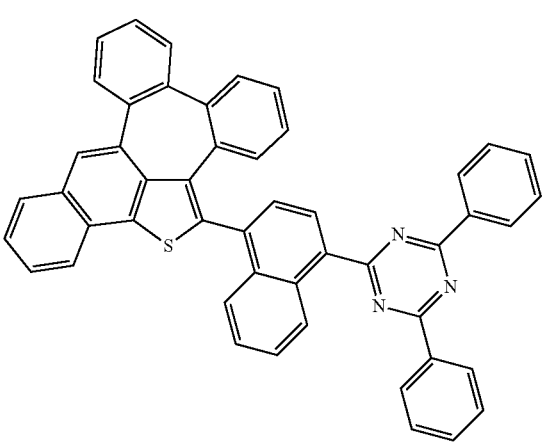

C-175
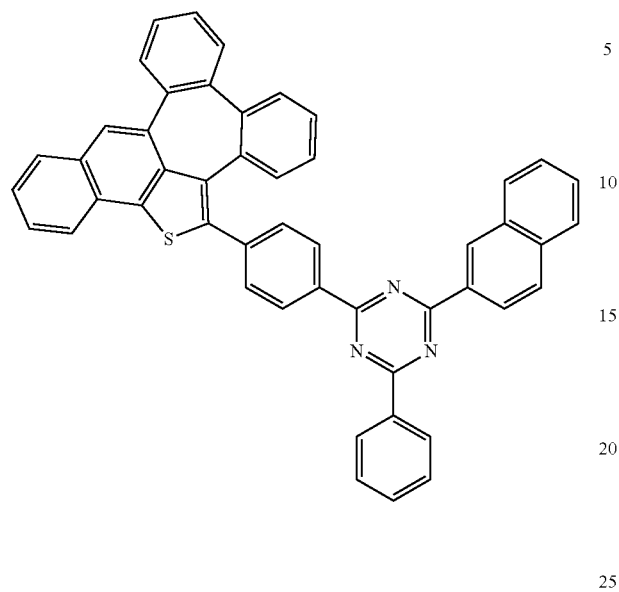
C-178
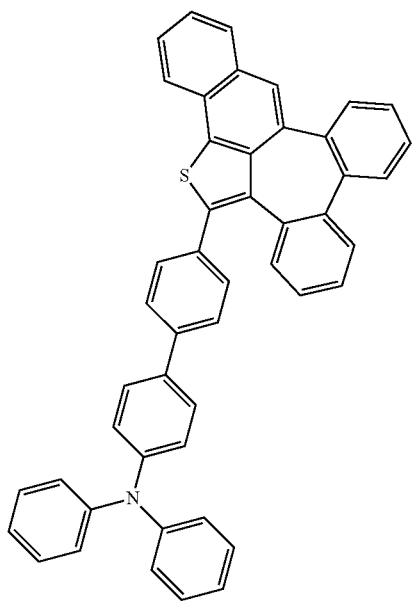
C-176
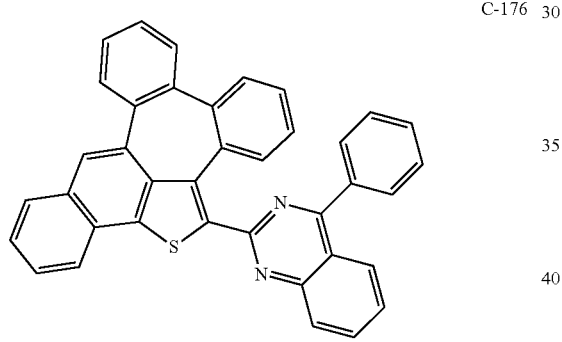
C-177
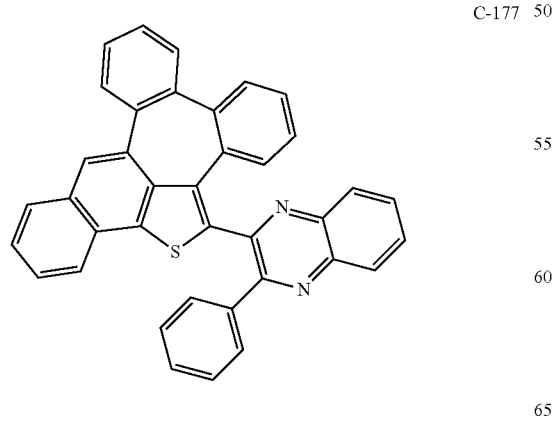
C-179
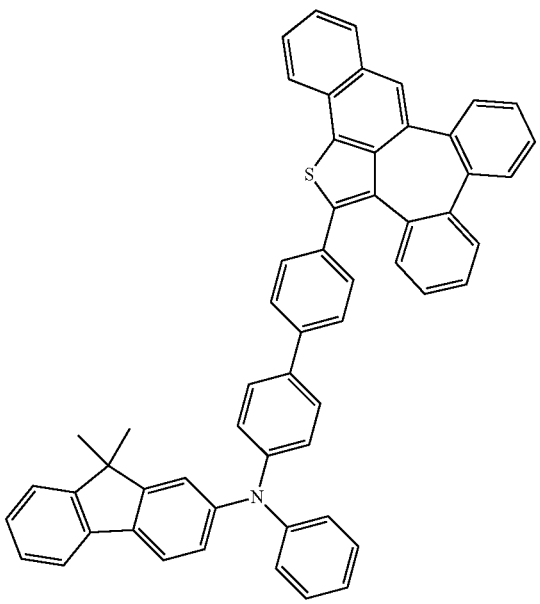

C-180 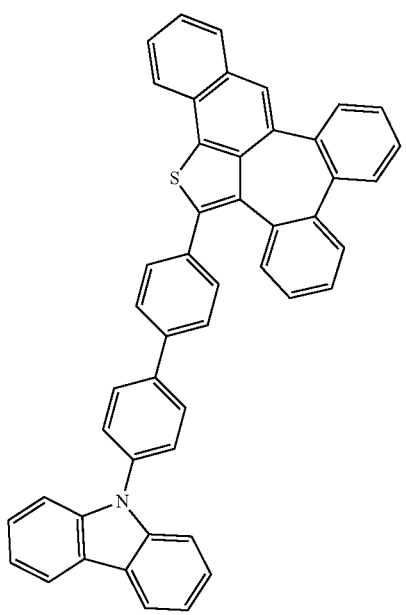
C-181 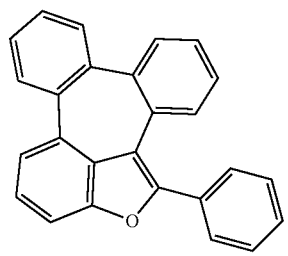
C-182 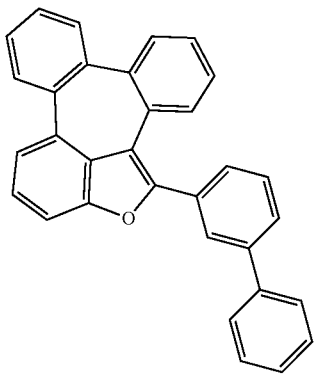
C-183 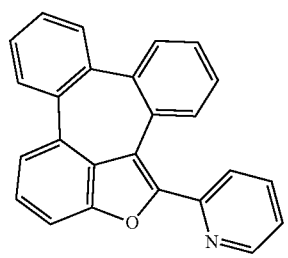
C-184 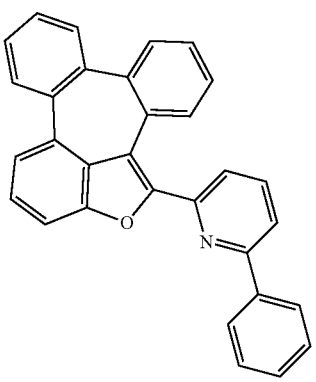
C-185 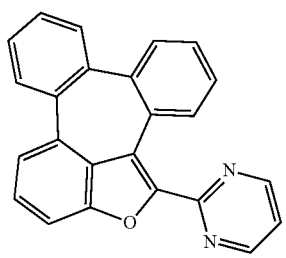
C-186 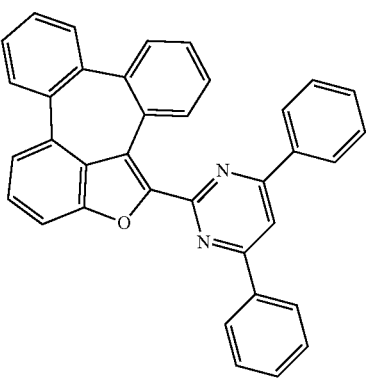
C-187 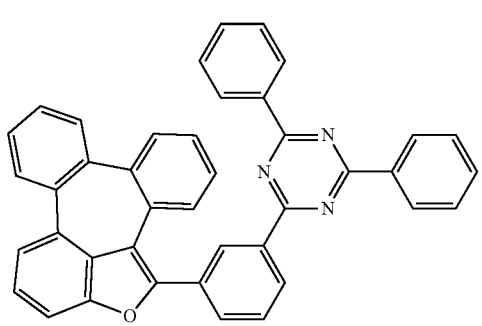

C-188
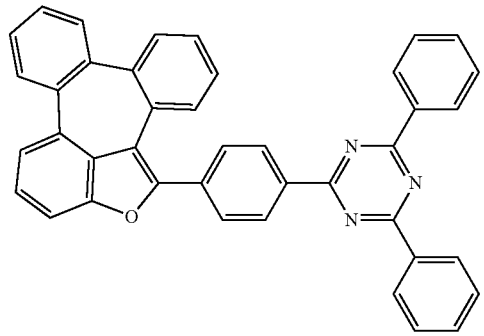
C-189
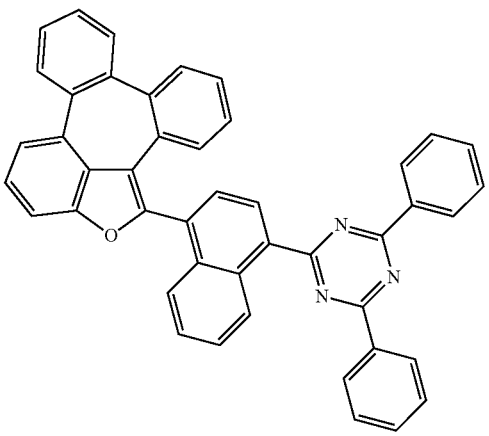
C-190
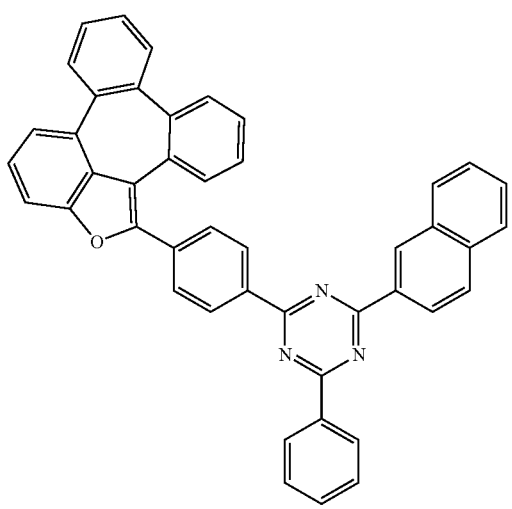
C-191
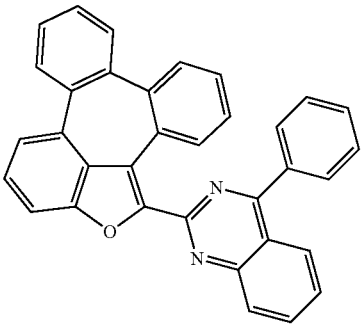
C-192
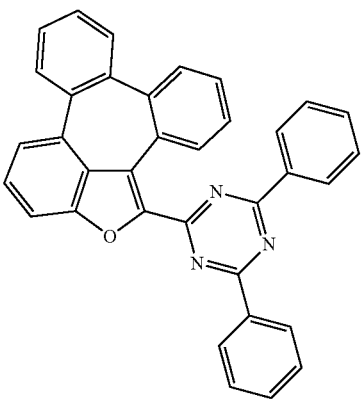
C-193
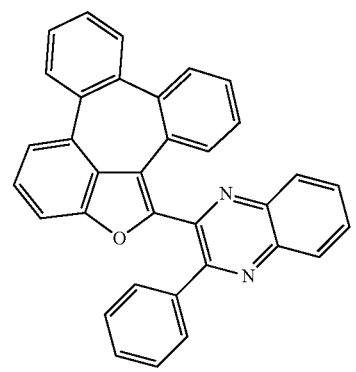
C-194
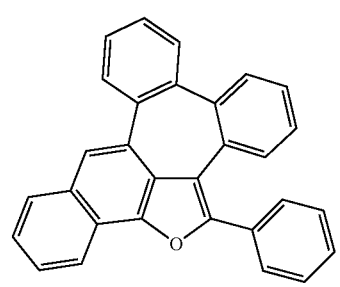

C-195 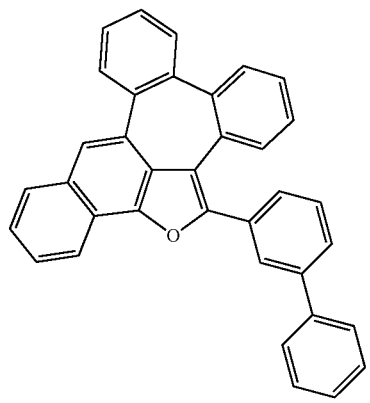
C-196 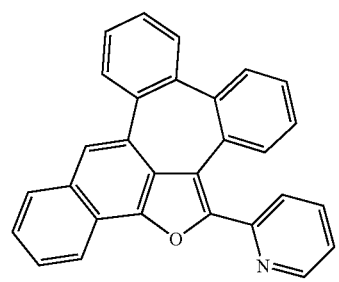
C-197 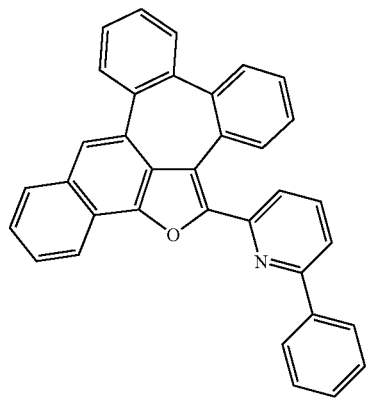
C-198 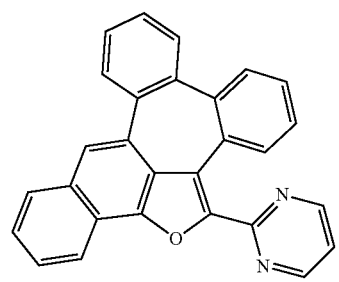
C-199 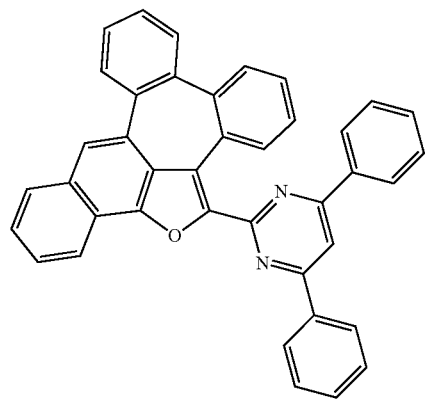
C-200 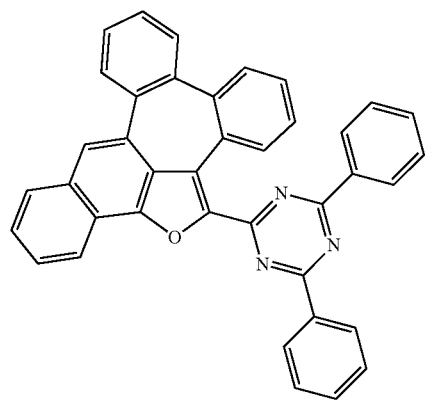
C-201 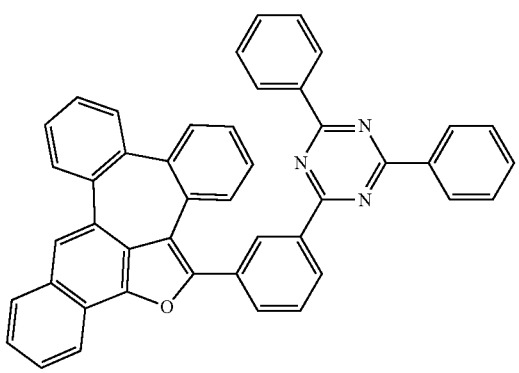
C-202 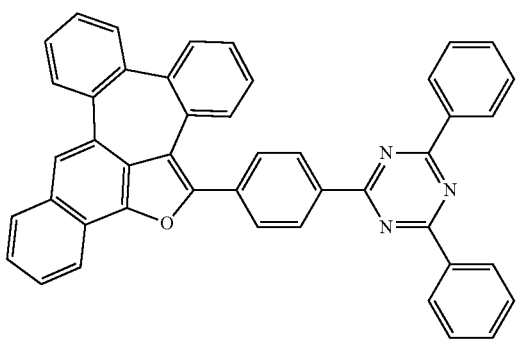

C-203
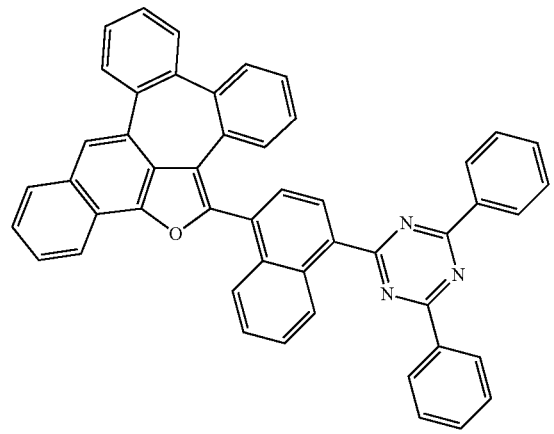
C-204
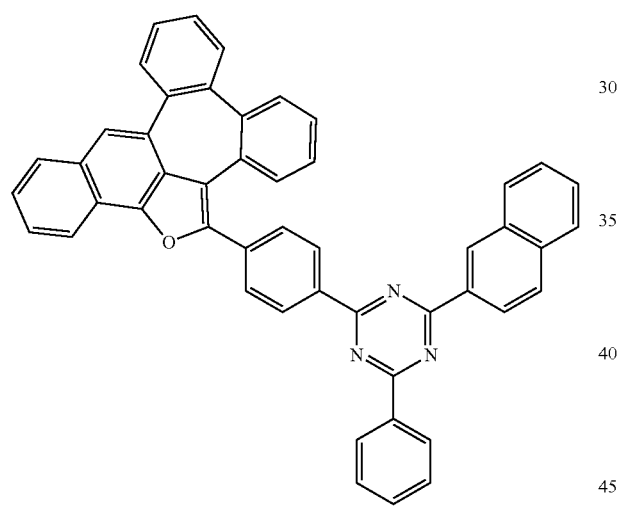
C-205
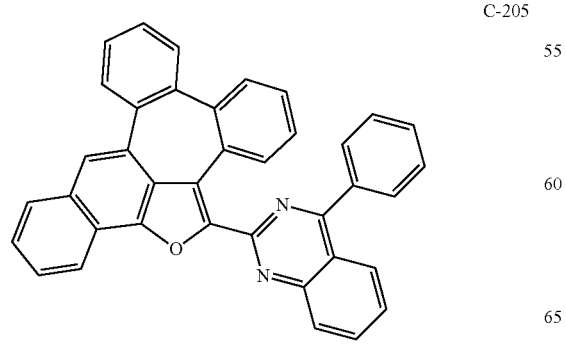
C-206
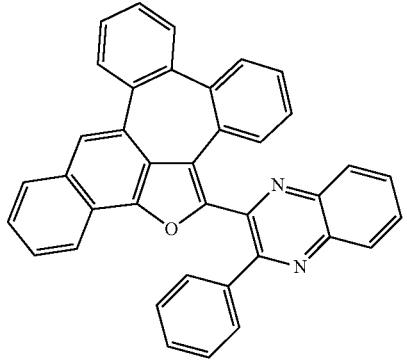
C-207
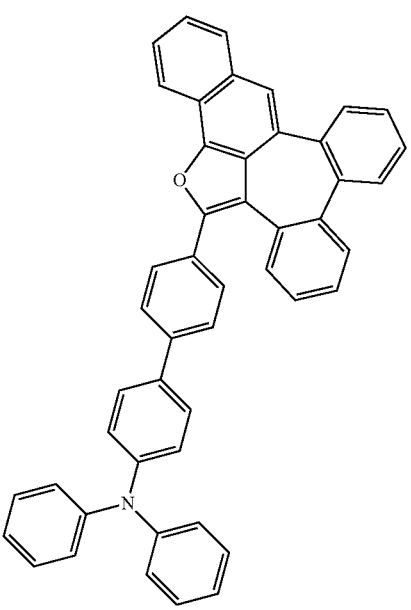
C-208
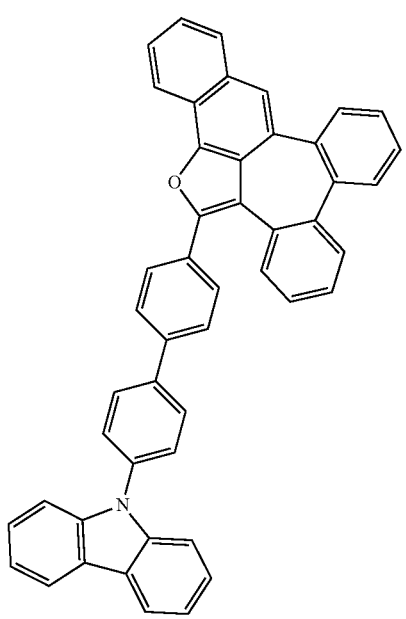

411
-continued
C-209
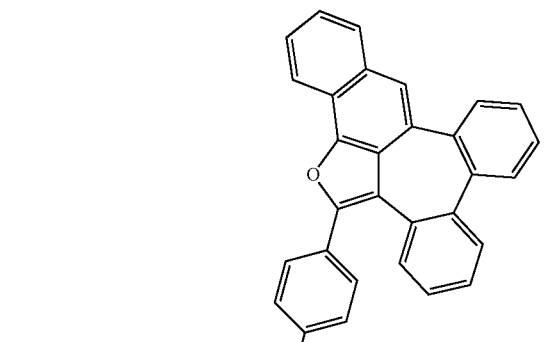
C-210
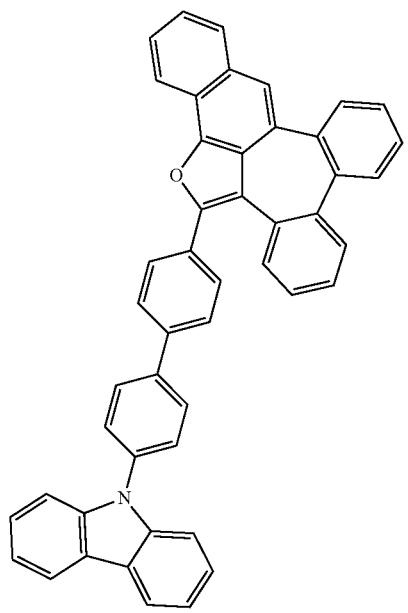
C-211
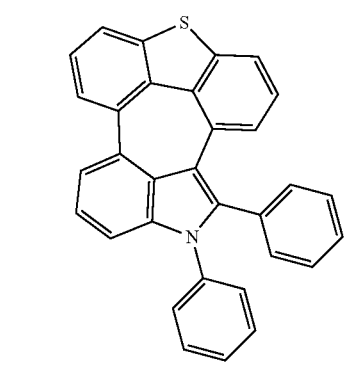
412
-continued
C-212
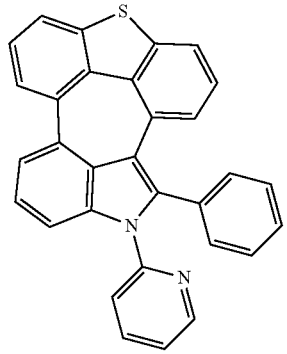
C-213
C-214
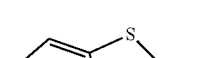

-continued
C-215
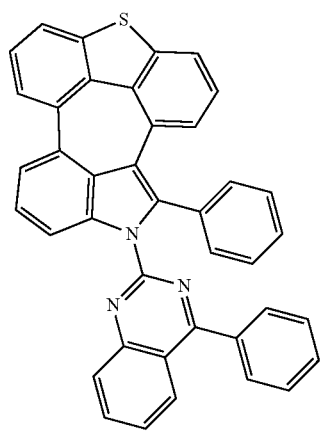
C-216
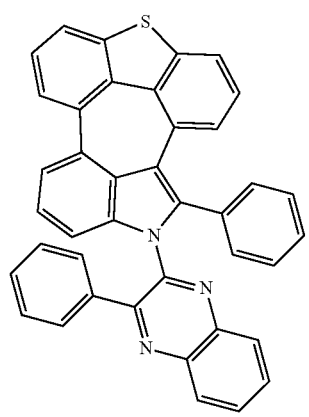
C-217
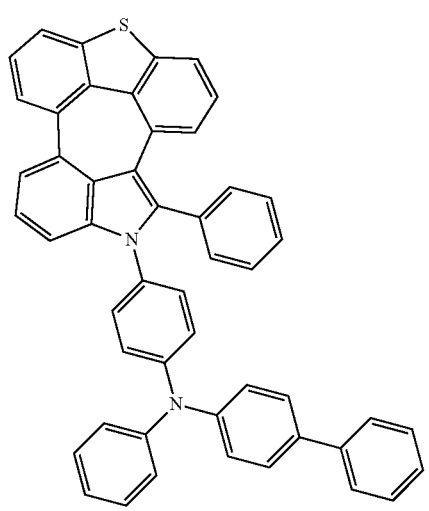
-continued
C-218
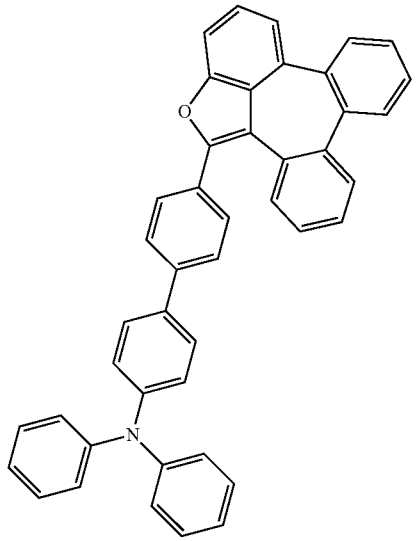
C-219
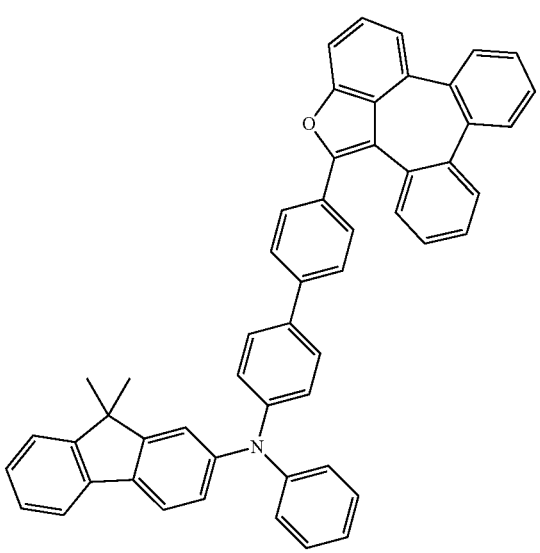
C-220
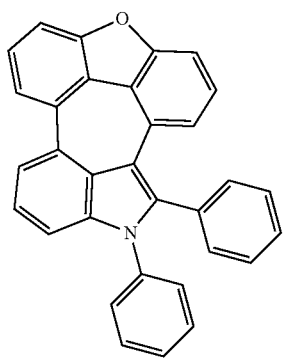

C-221 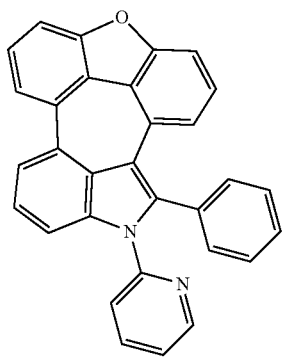
C-222 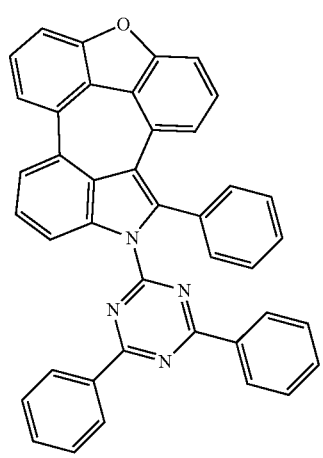
C-223 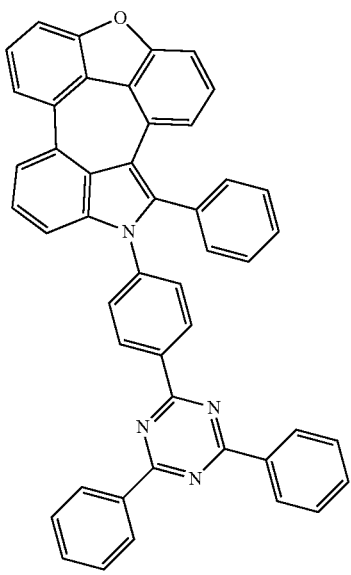
C-224 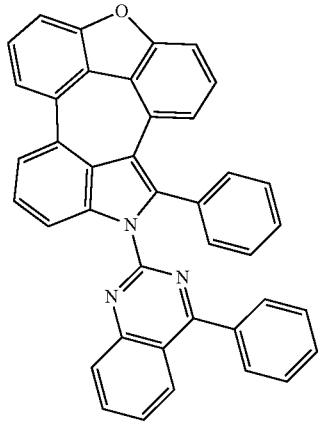
C-225 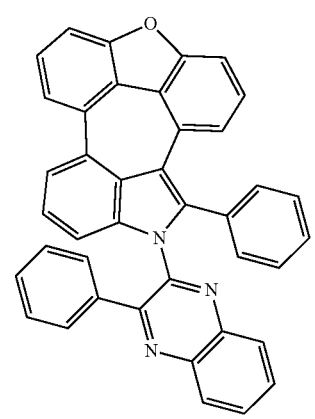
C-226 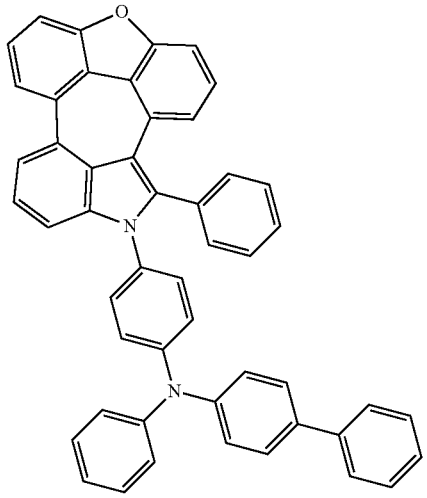

C-227
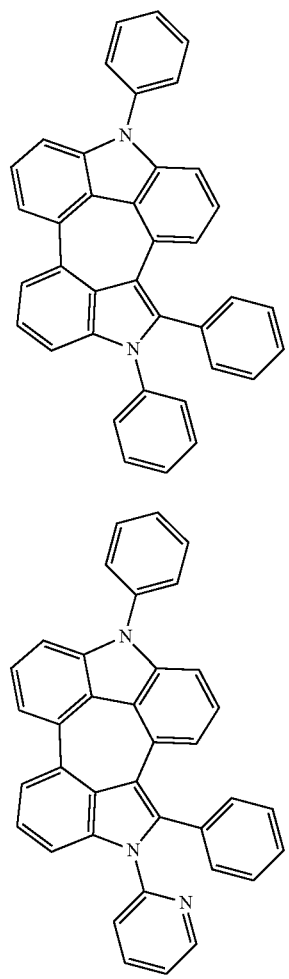
C-228
C-229
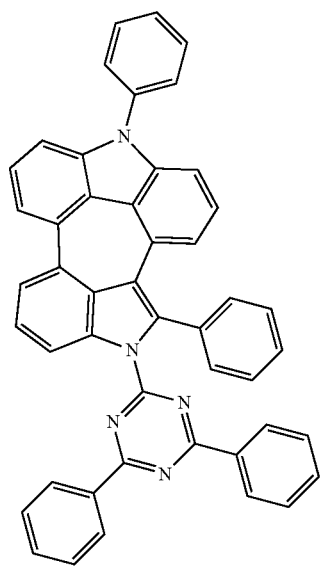
C-230
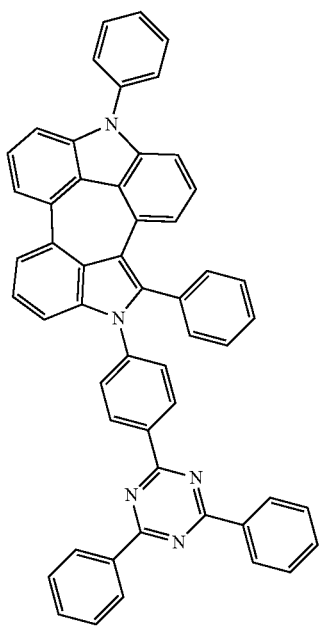
C-231

-continued
C-232
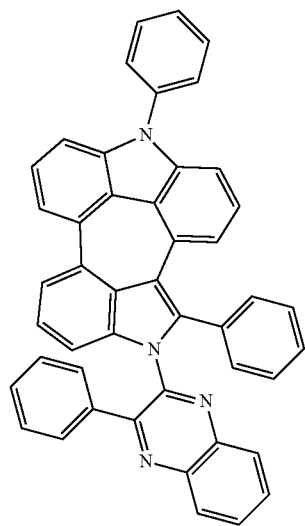
C-233
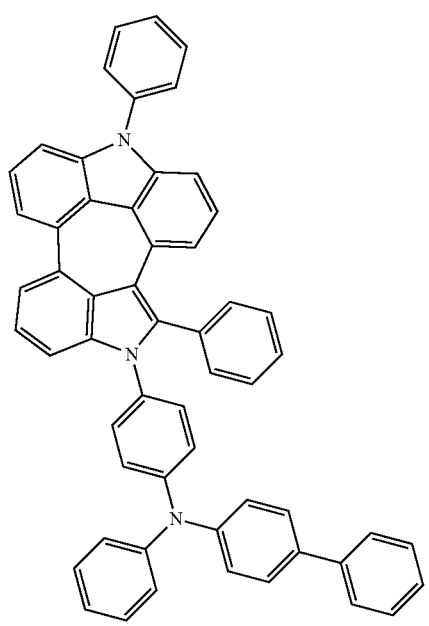
C-234
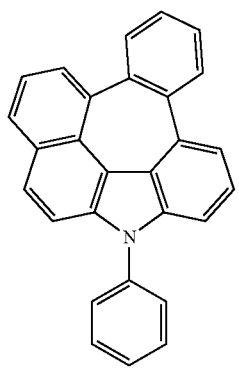
-continued
C-235
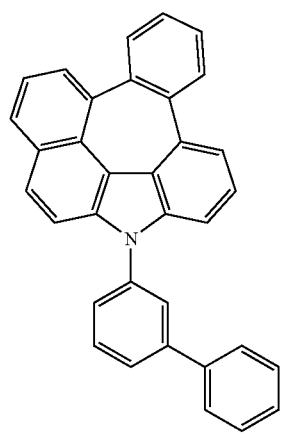
C-236
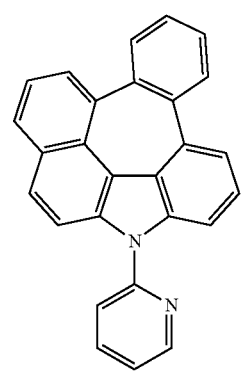
C-237
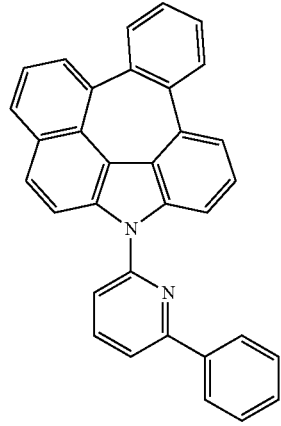
C-238
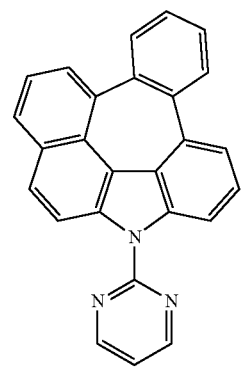

-continued
C-239
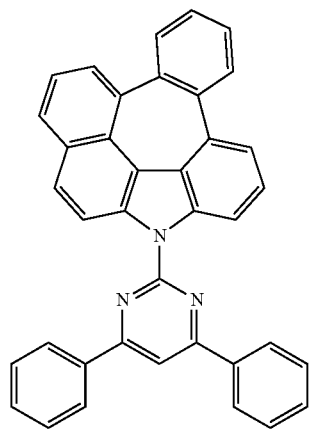
C-240
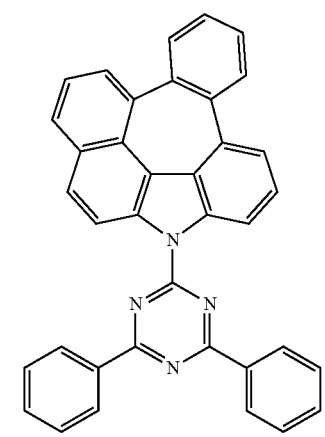
C-241
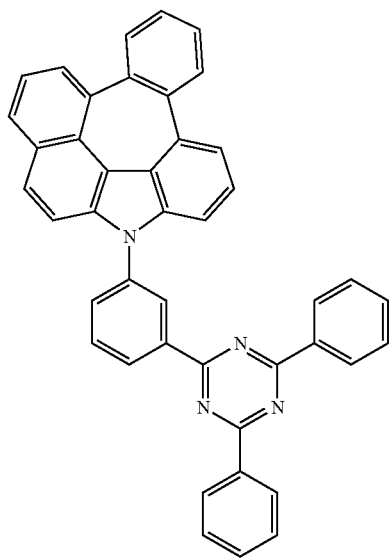
-continued
C-242
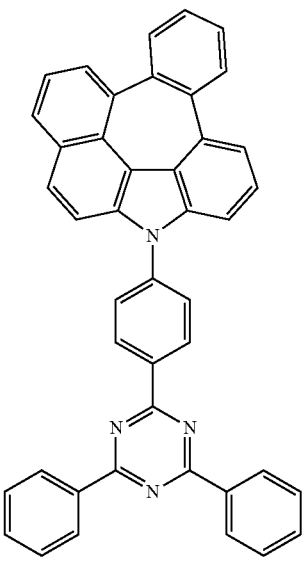
C-243
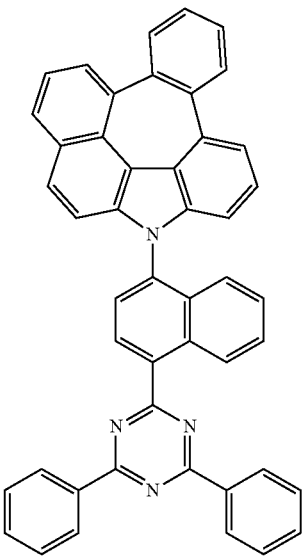

C-244
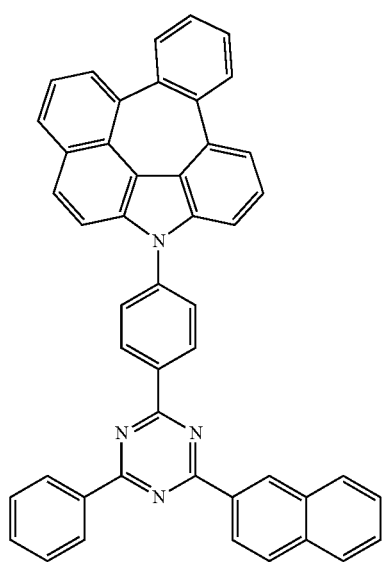
C-247
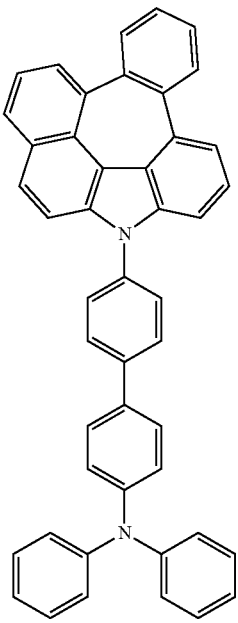
C-245
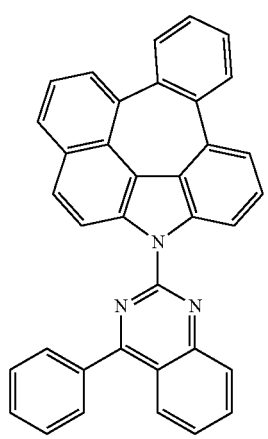
C-246
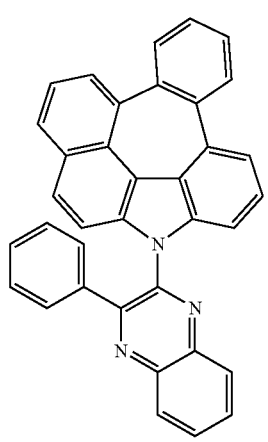
C-248
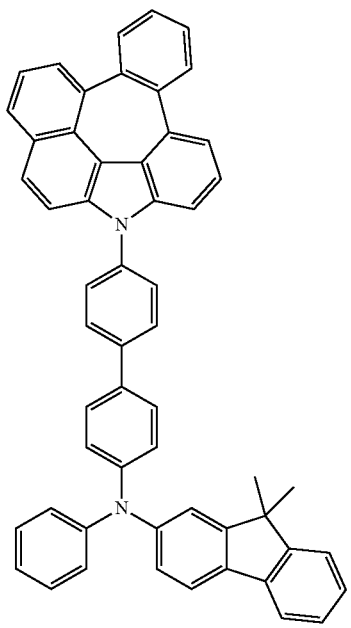

C-249
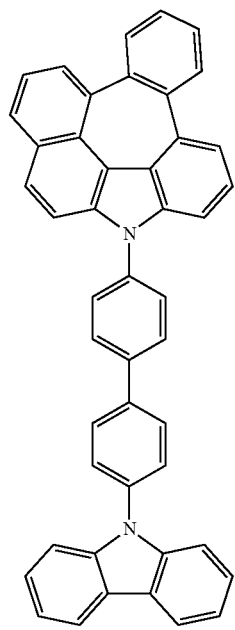
C-250
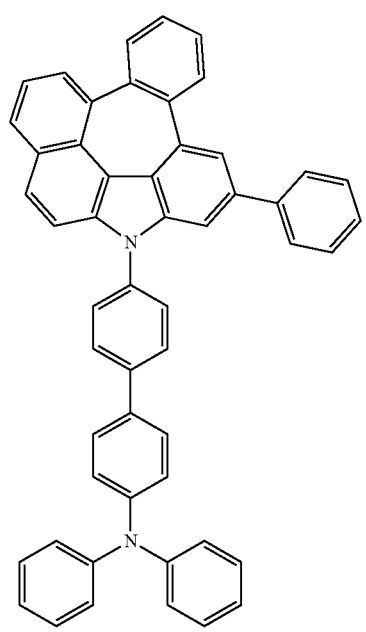
C-251
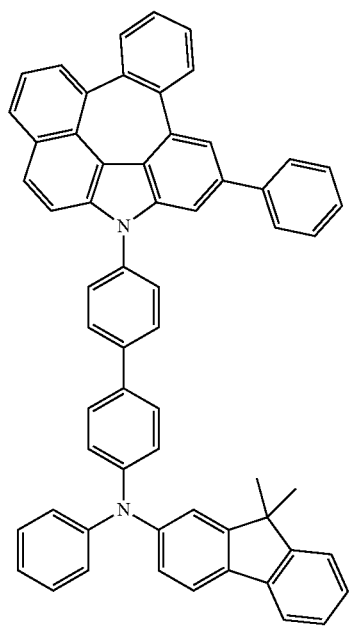
C-252
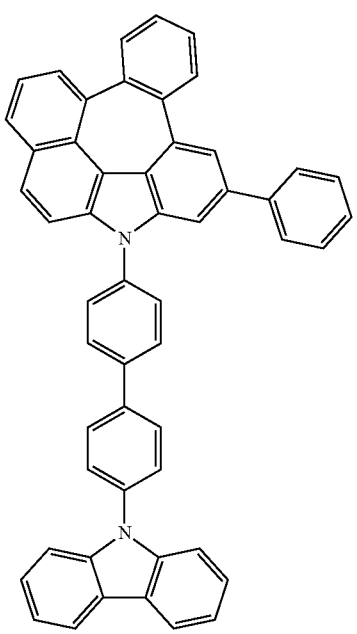

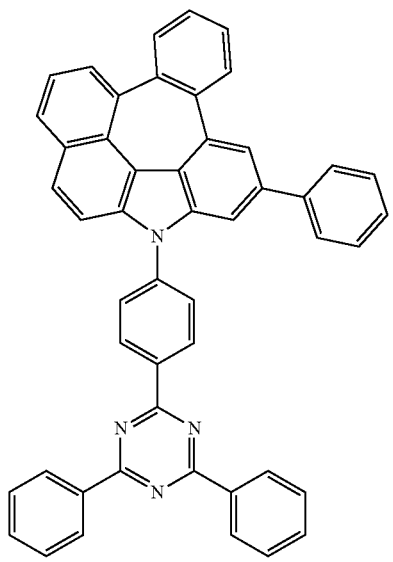
C-253
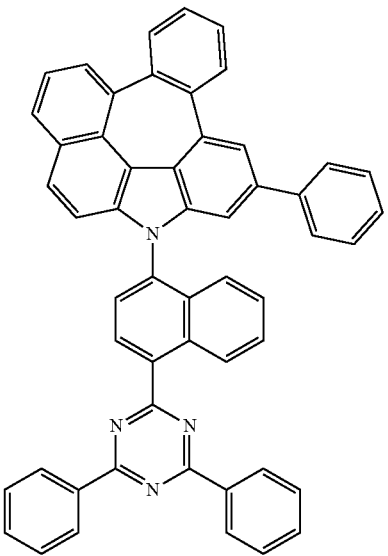
C-255
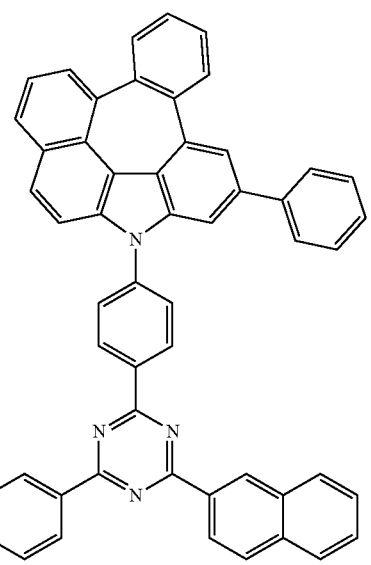
C-256
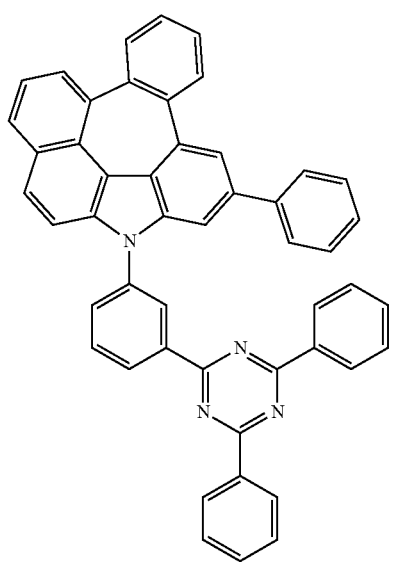
C-254
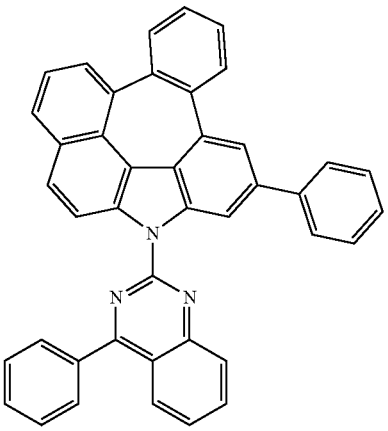
C-257

C-258
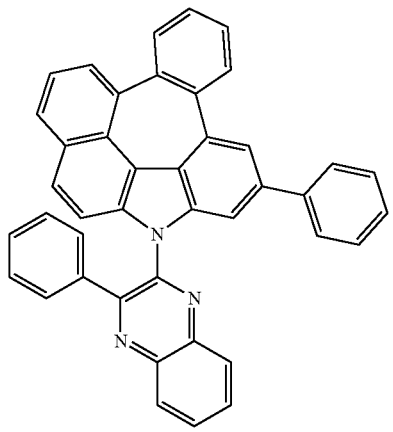
C-259
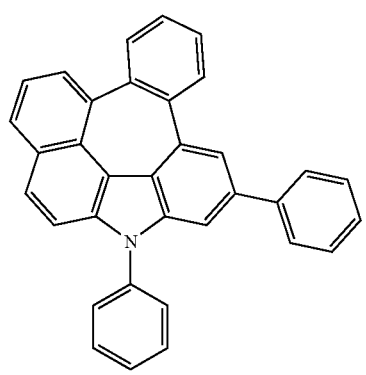
C-260
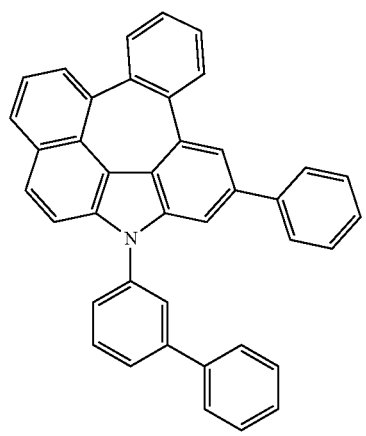
C-261
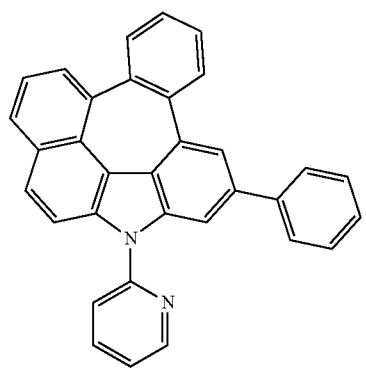
C-262
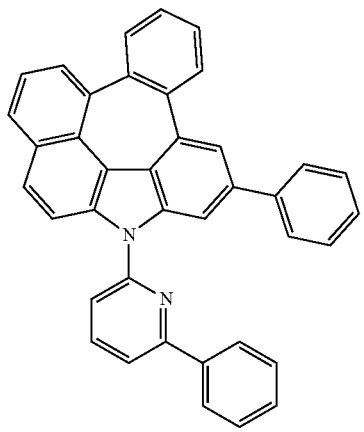
C-263
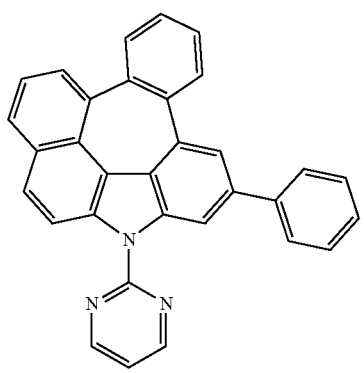
C-264
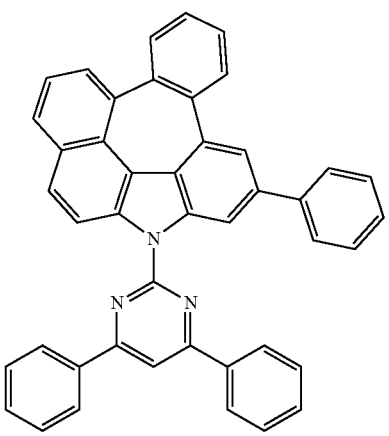
C-265
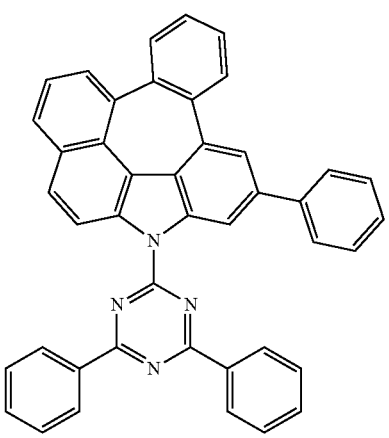

431
-continued
C-266
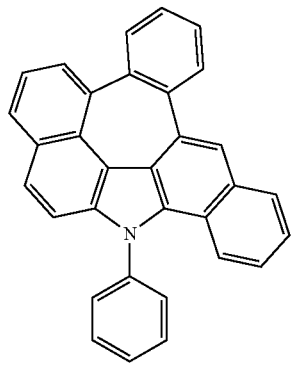
C-267
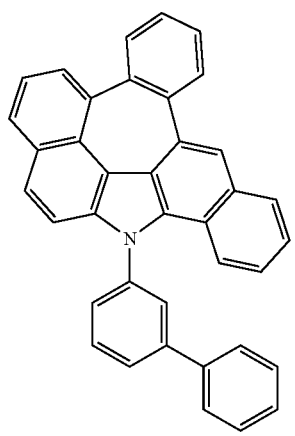
C-268
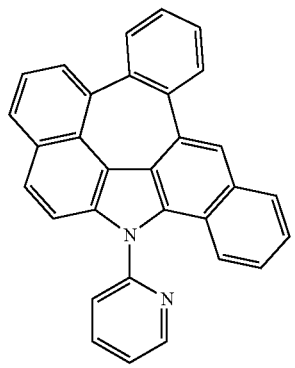
C-269
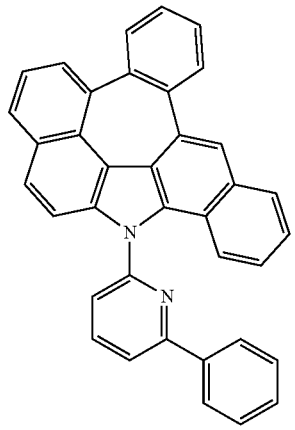
432
-continued
C-270
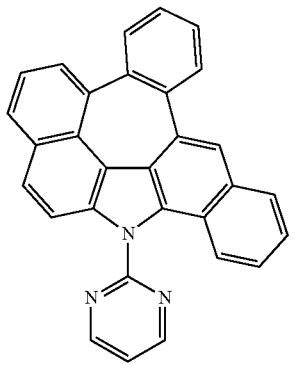
C-271
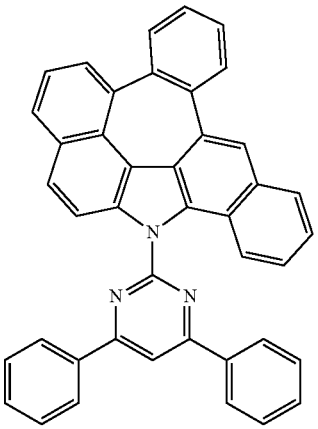
C-272
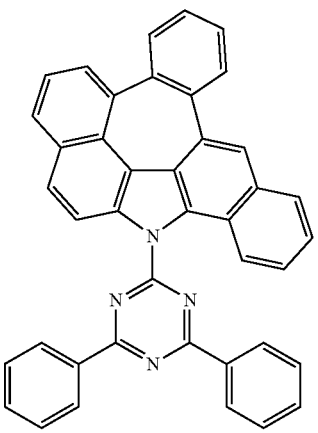
C-273
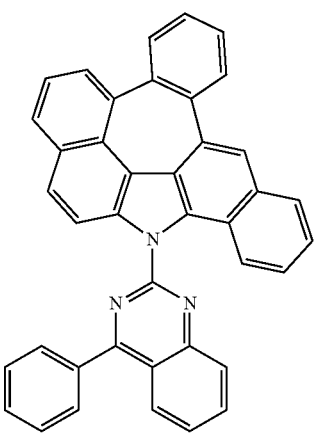

C-274
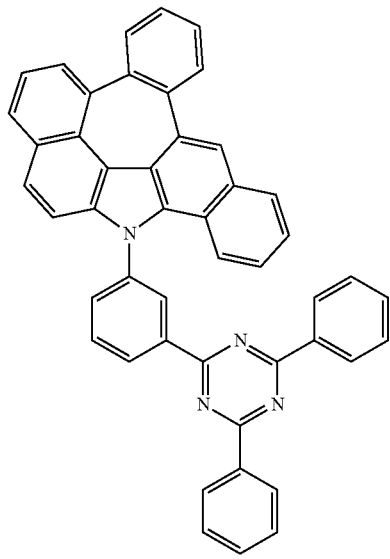
C-275
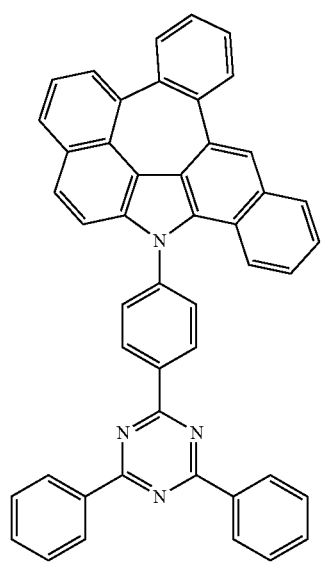
C-276
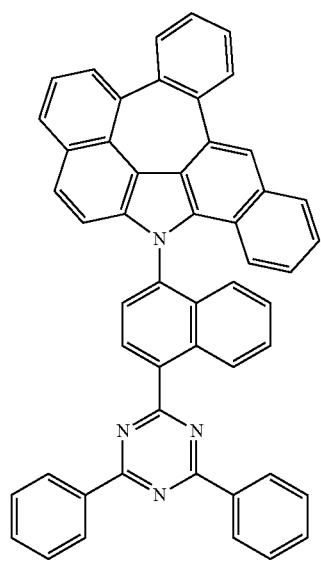
C-277
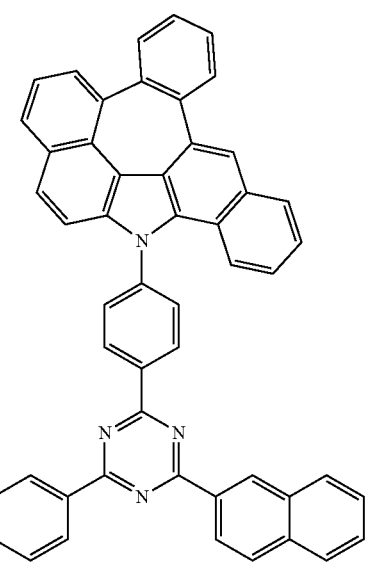
C-278
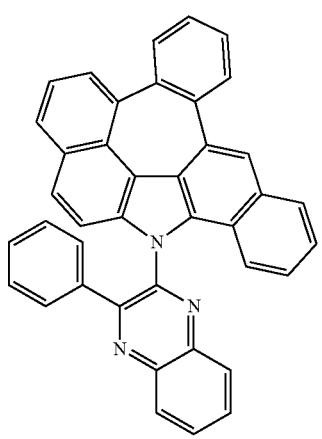
C-279
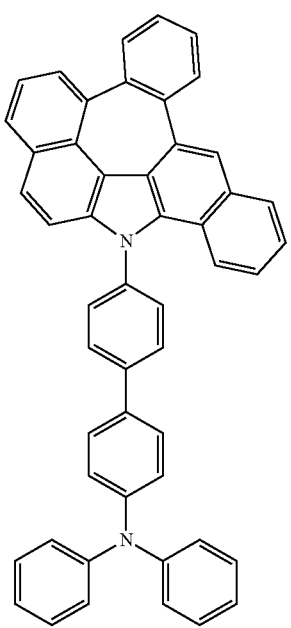

C-280
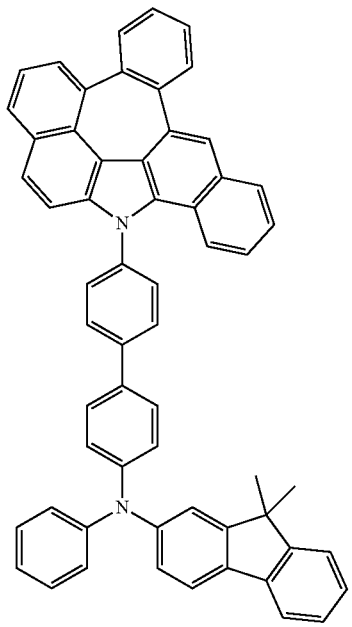
C-281
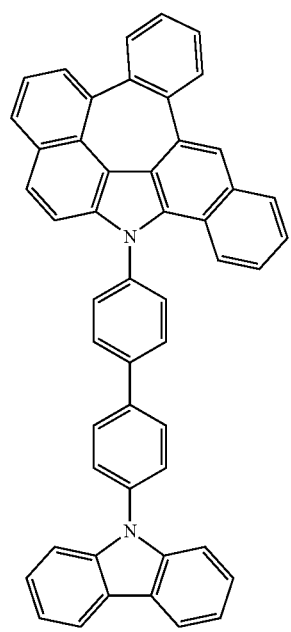
C-282
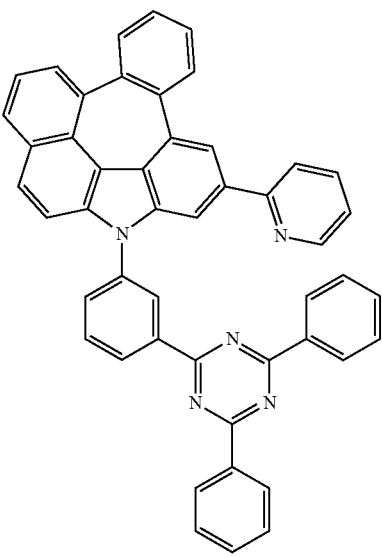
C-283
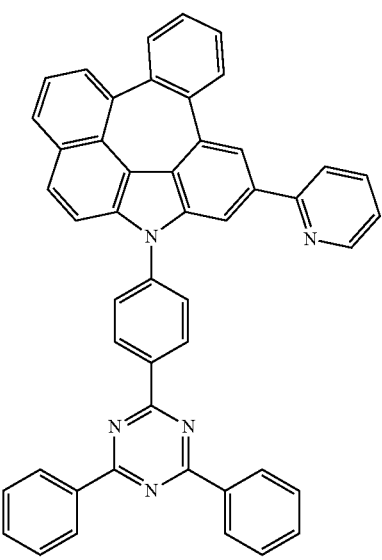
C-284
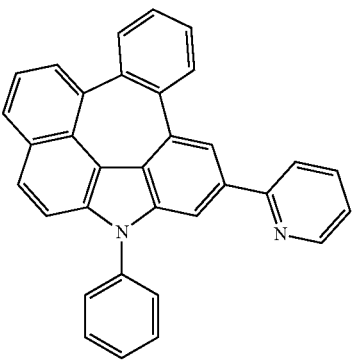

C-285
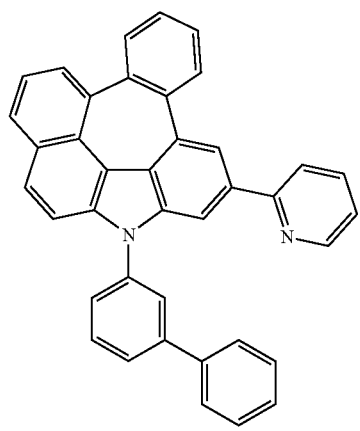
C-286
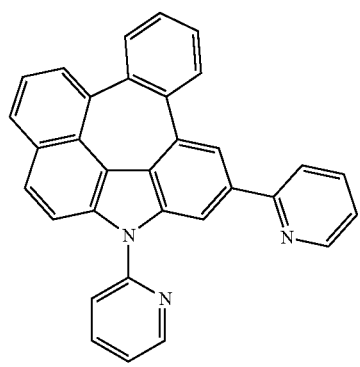
C-287
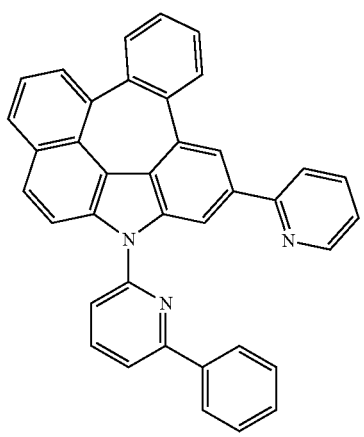
C-288
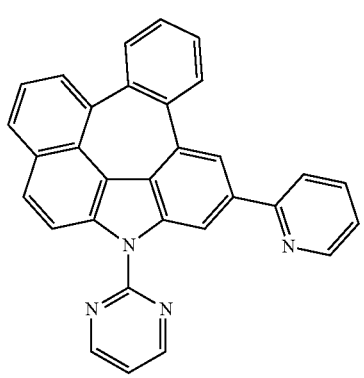
C-289
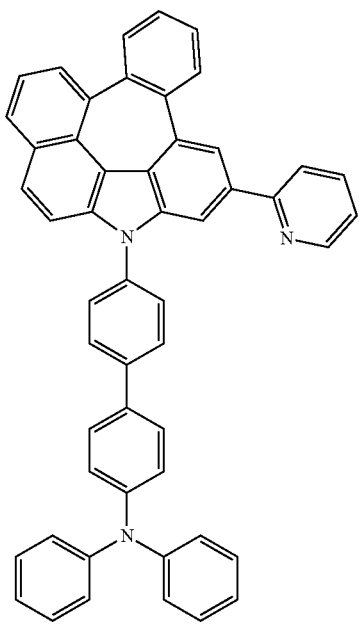
C-290
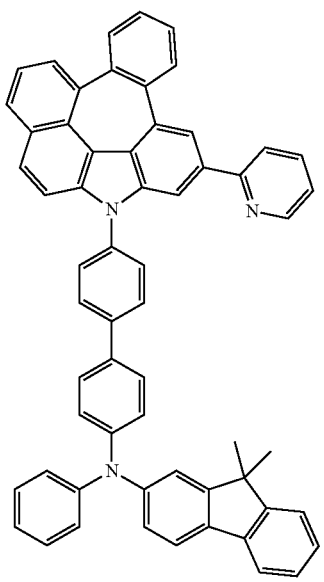

-continued
C-291
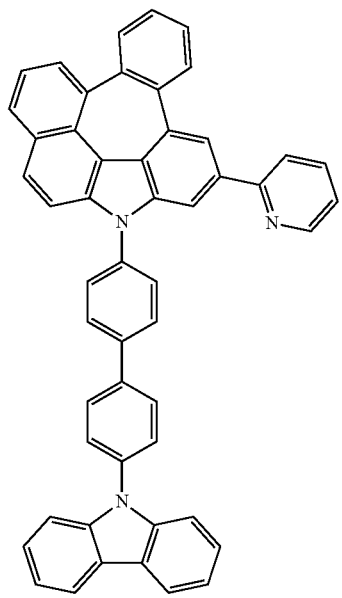
C-292
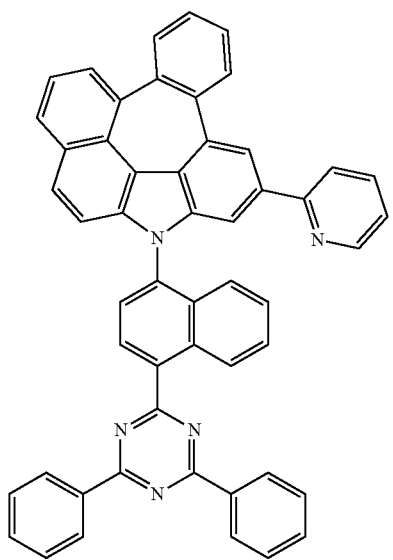
C-293
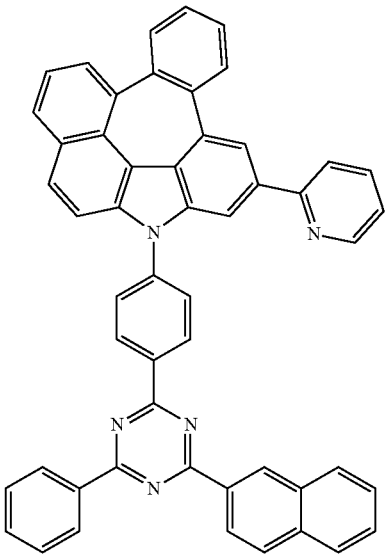
C-294
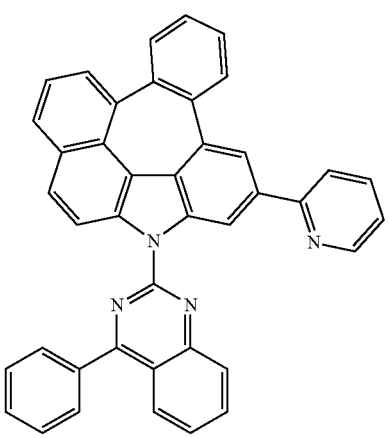
C-295
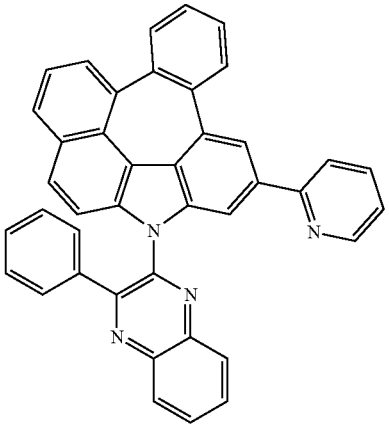

C-296
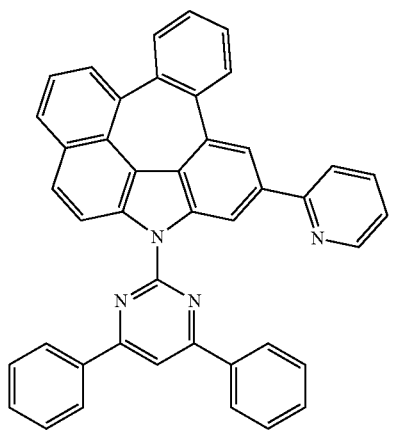
C-299
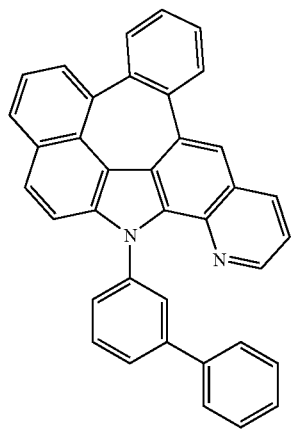
C-297
C-300
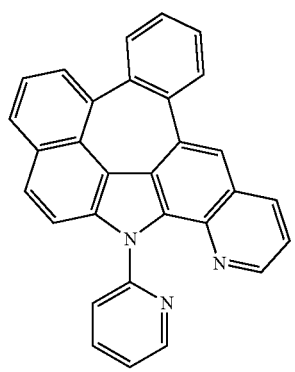
C-301
C-298
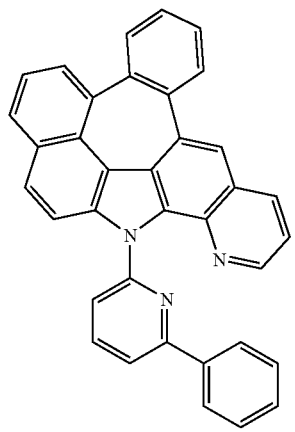
C-302
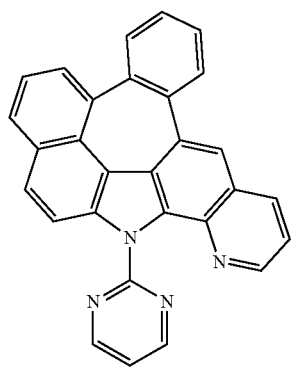

C-303
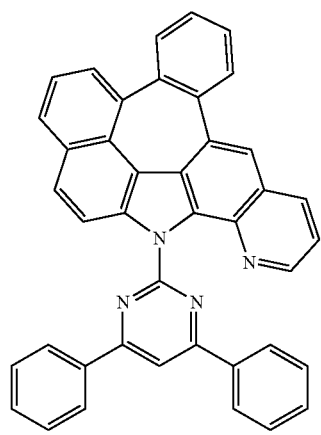
C-304
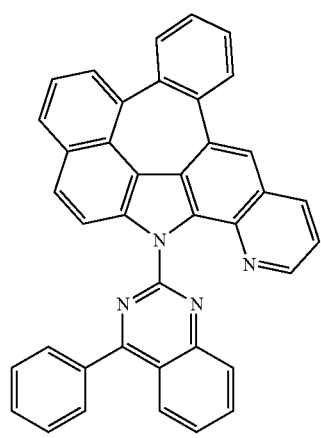
C-305
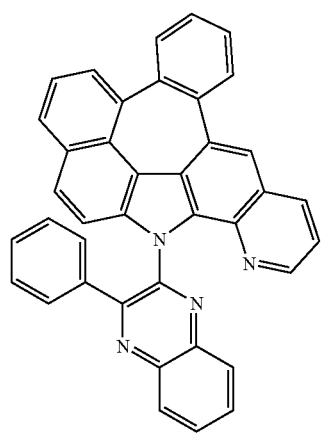
C-306
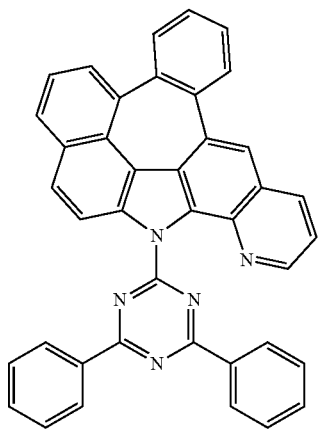
C-307
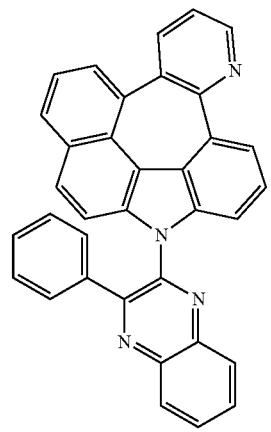
C-308
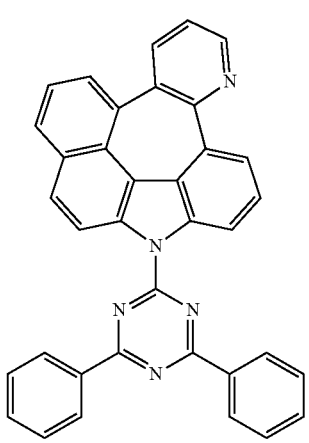

C-309
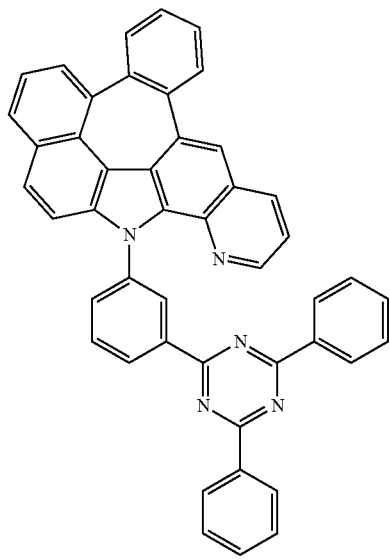
C-310
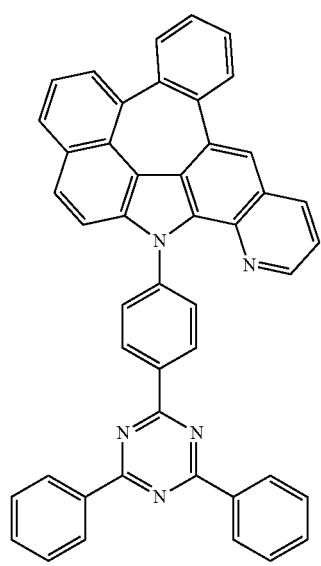
C-311
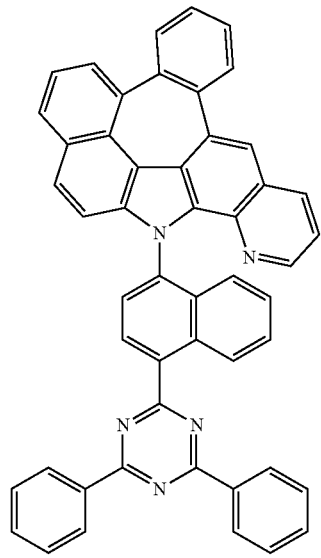
C-312
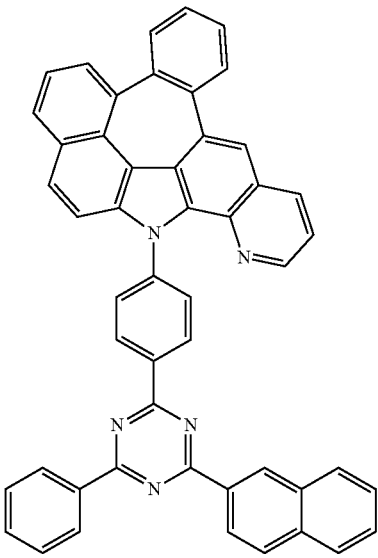
C-313
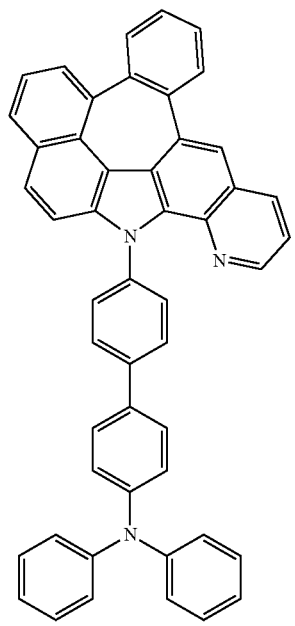

C-314
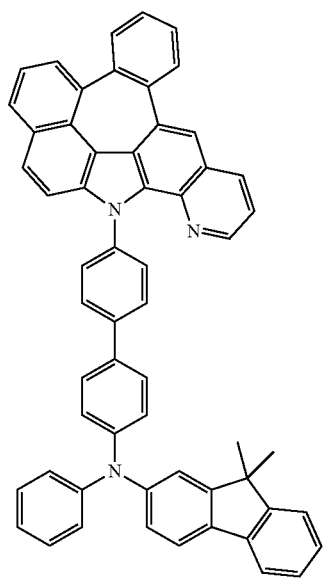
C-315
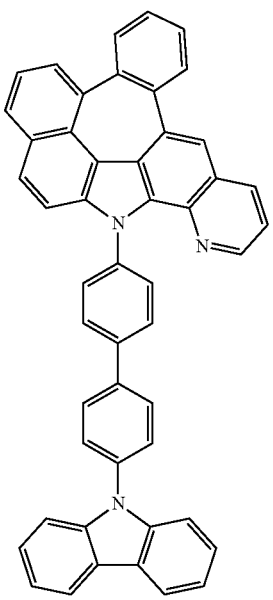
C-316
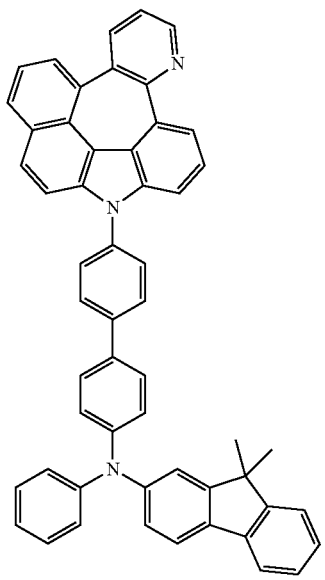
C-317
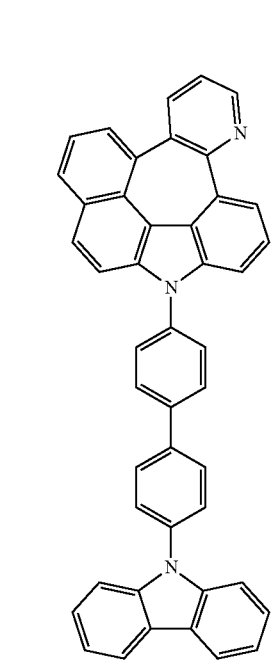

-continued
C-318
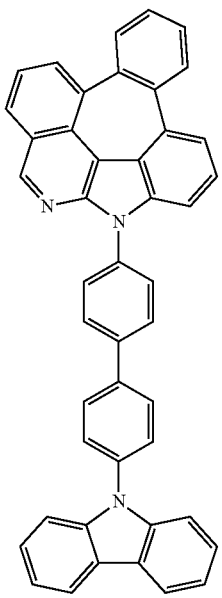
C-319
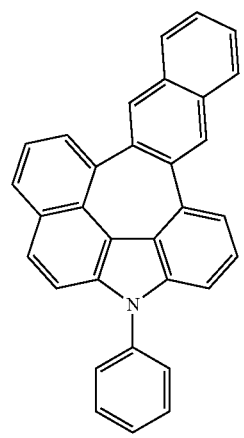
C-320
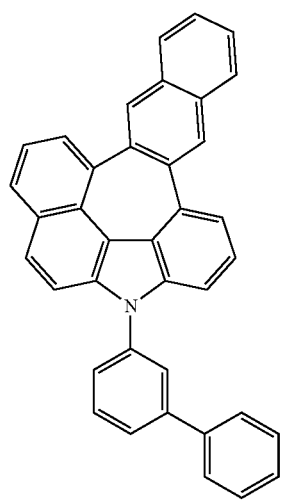
-continued
C-321
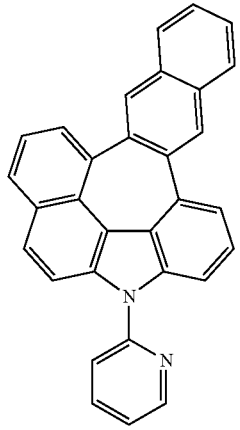
C-322
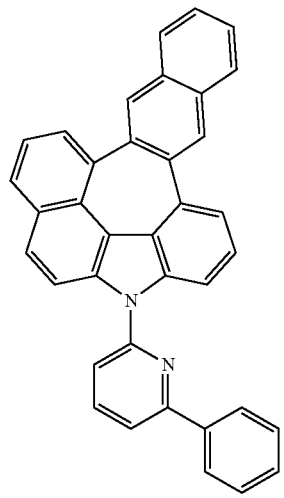
C-323
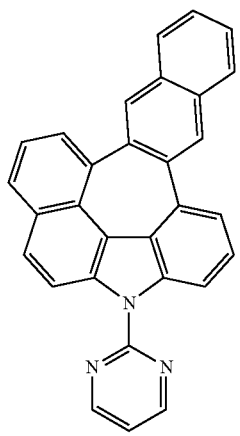

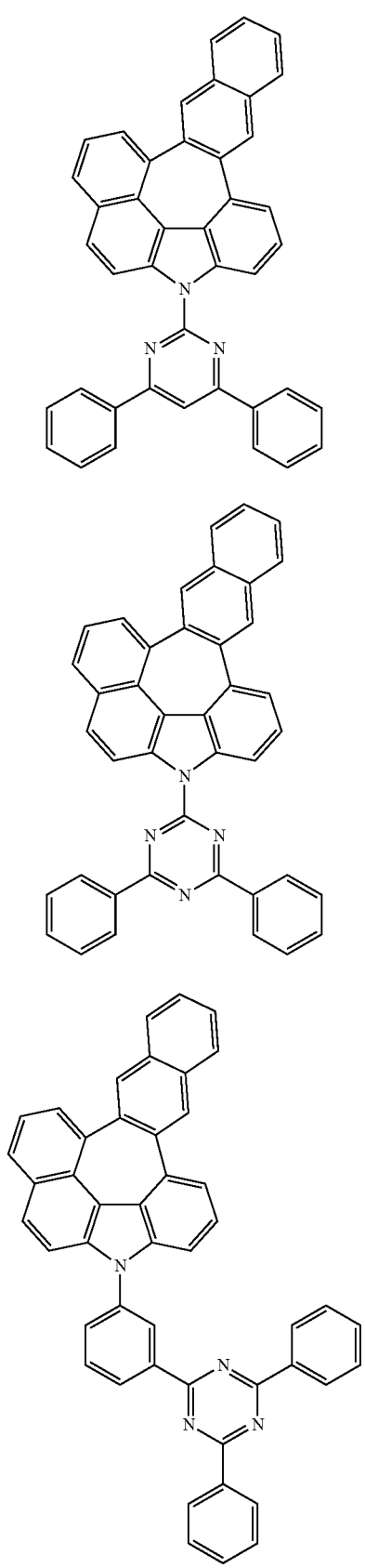

C-329
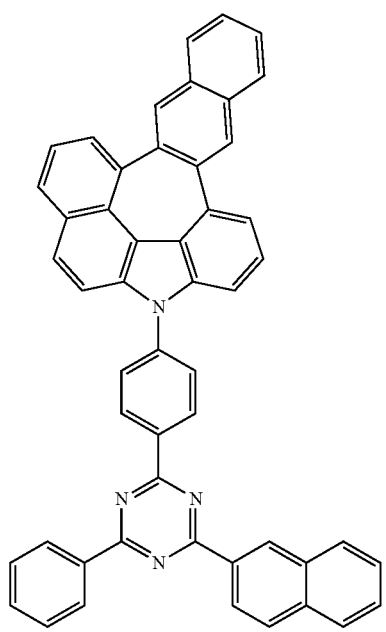
C-330
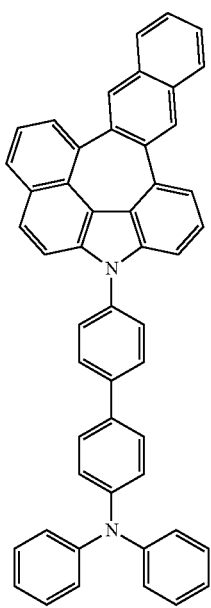
C-331
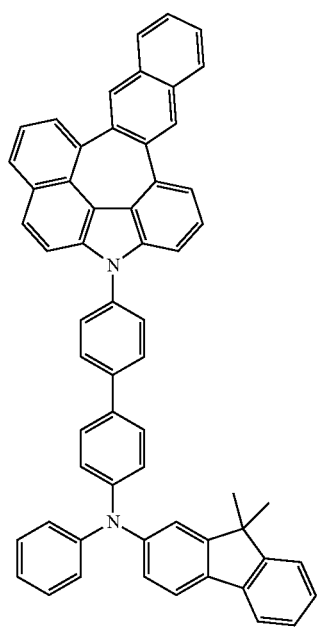
C-332
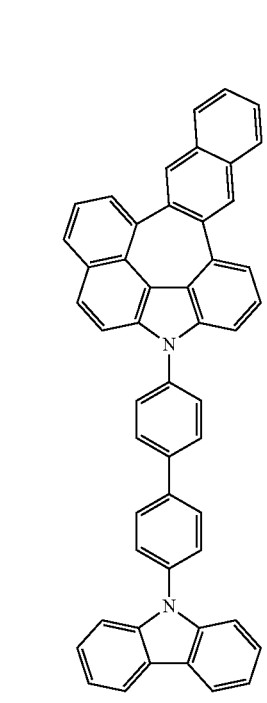

C-333
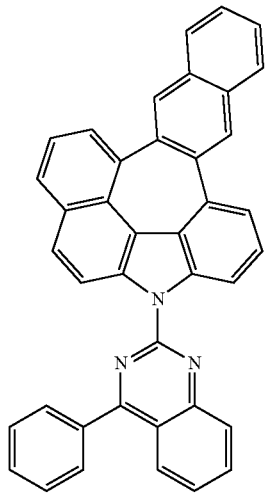
C-334
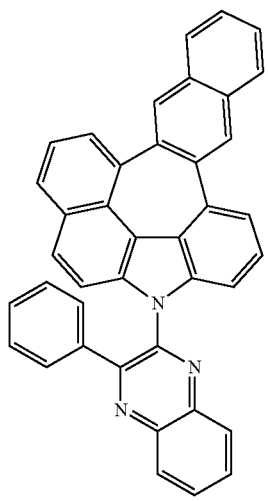
C-335
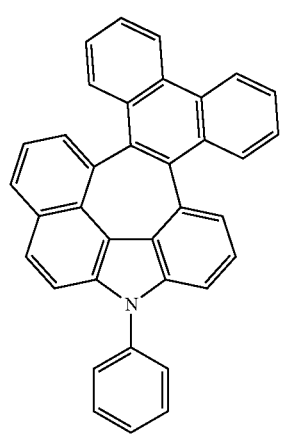
C-336
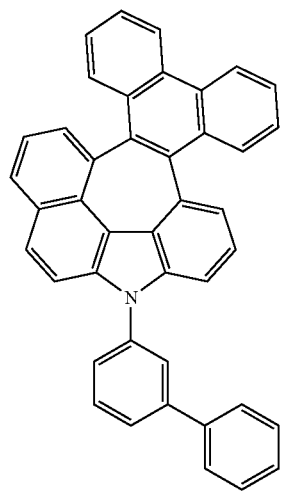
C-337
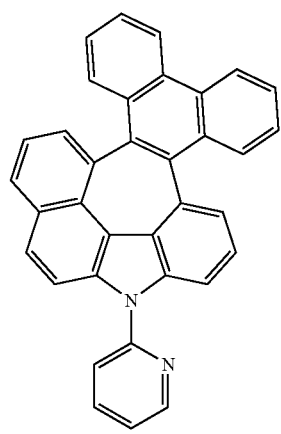
C-338
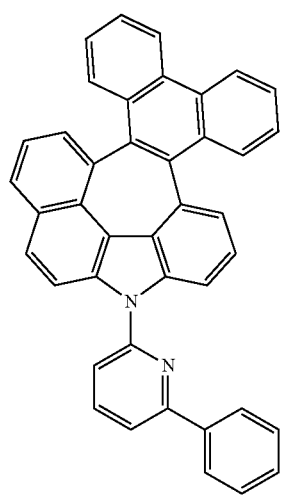

-continued
C-339
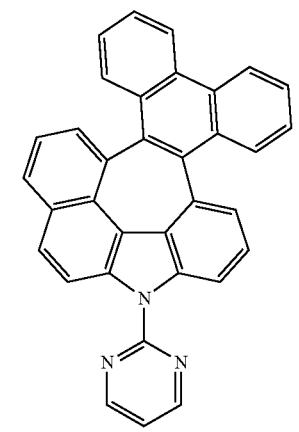
C-340
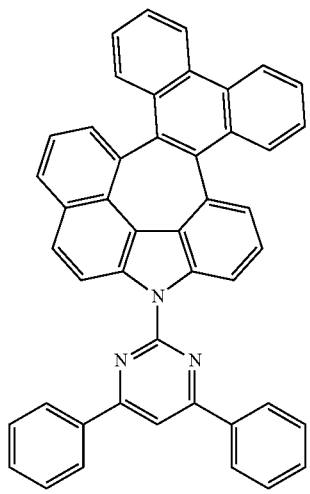
C-341
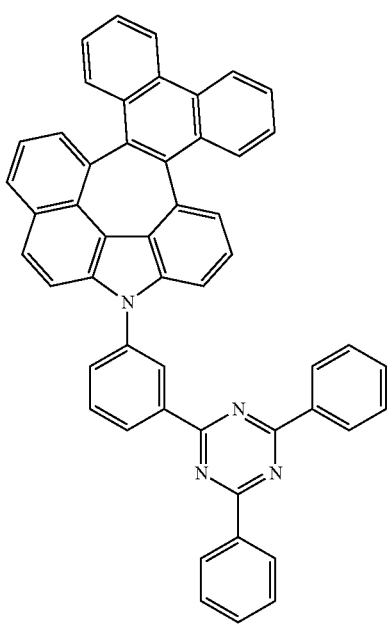
-continued
C-342
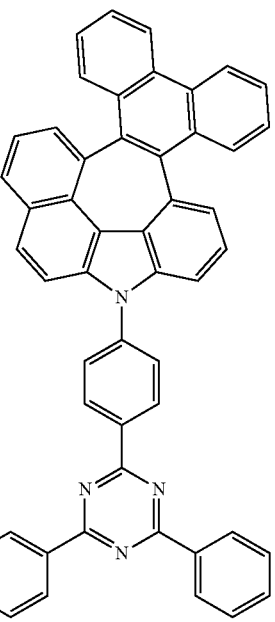
C-343
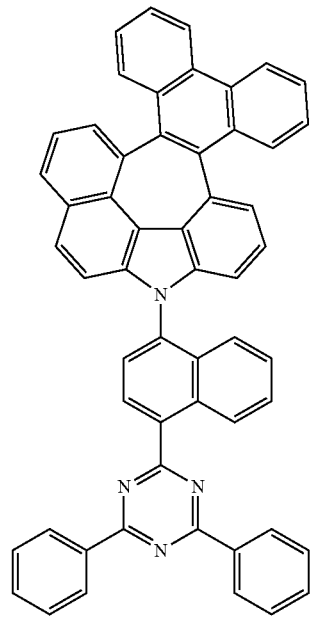

C-344
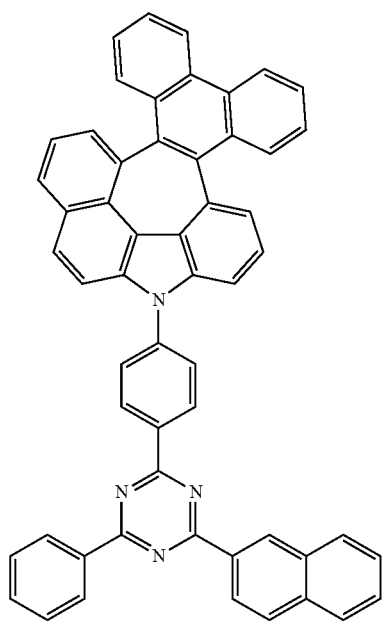
C-346
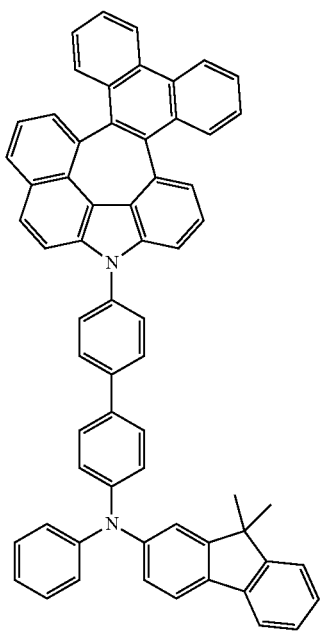
C-345
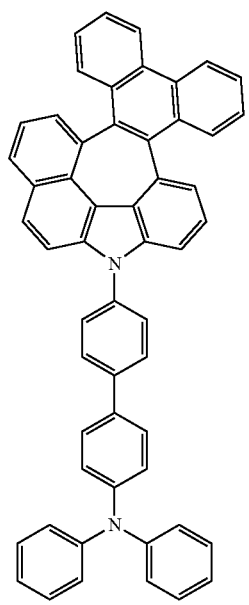
C-347
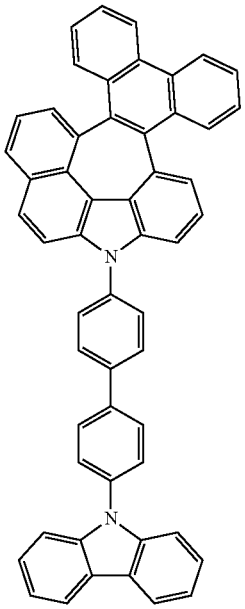

C-348
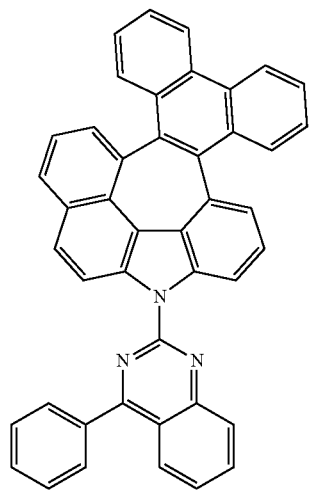
C-351
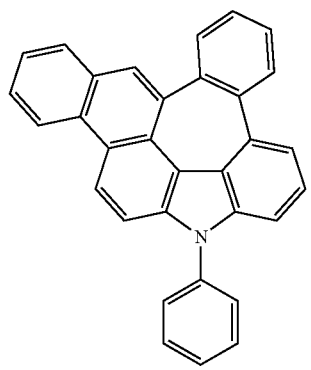
C-352
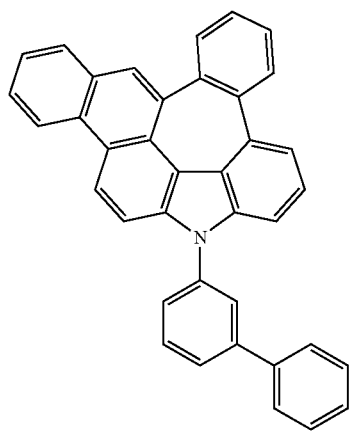
C-349
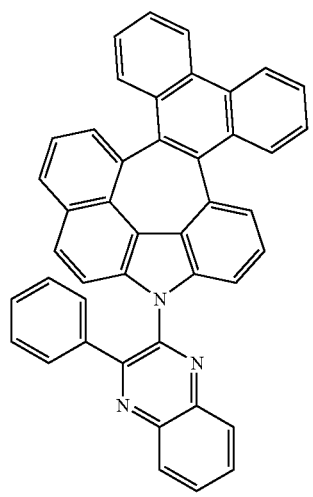
C-353
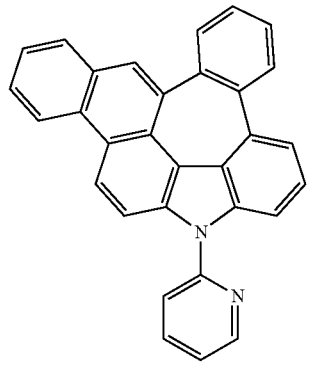
C-350
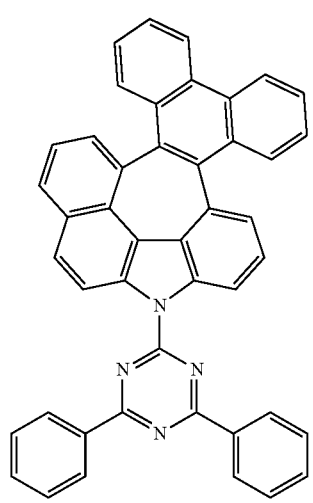
C-354
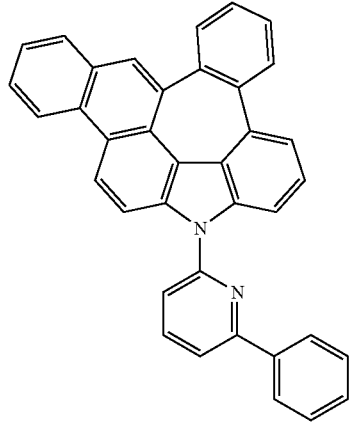

C-355
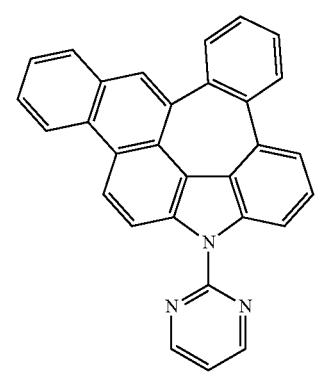
C-356
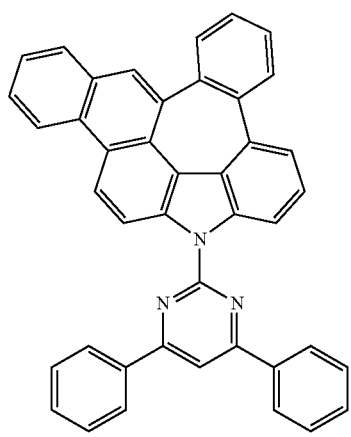
C-357
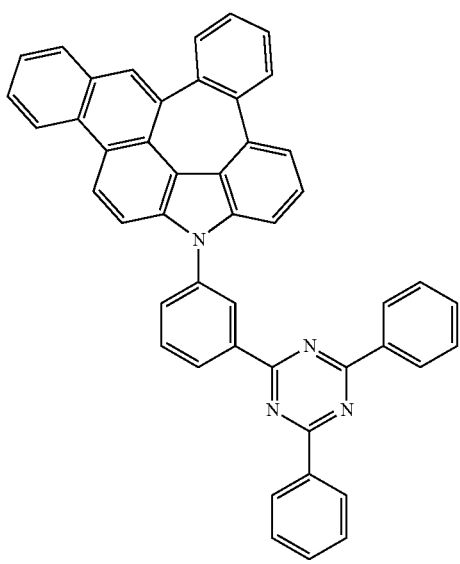
C-358
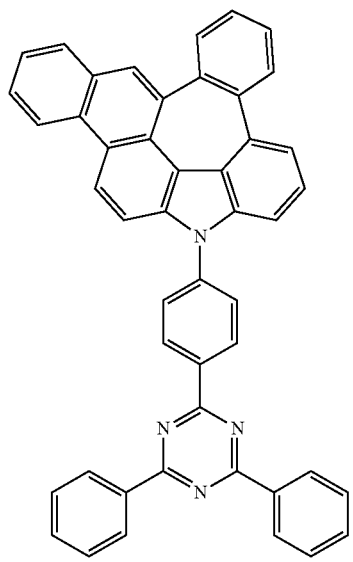
C-359
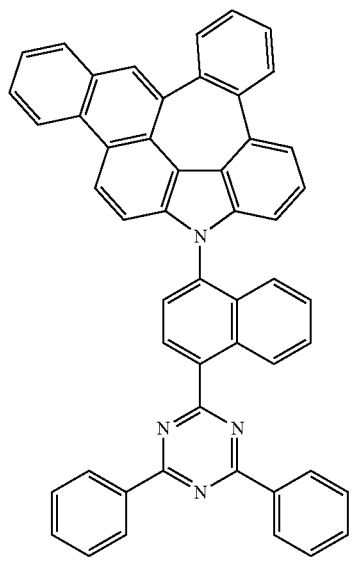

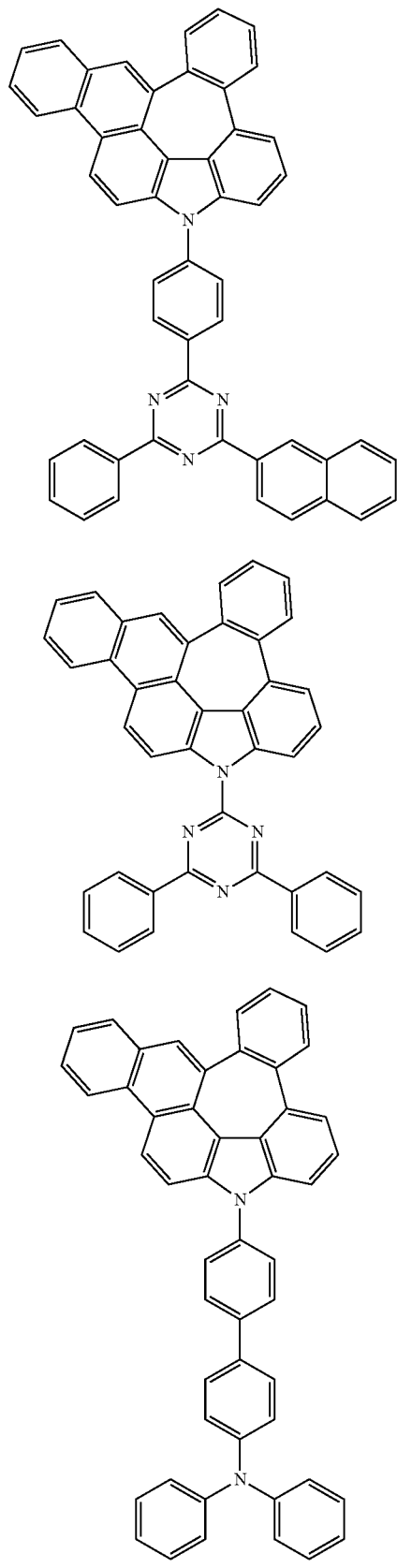
C-360
C-361
C-362
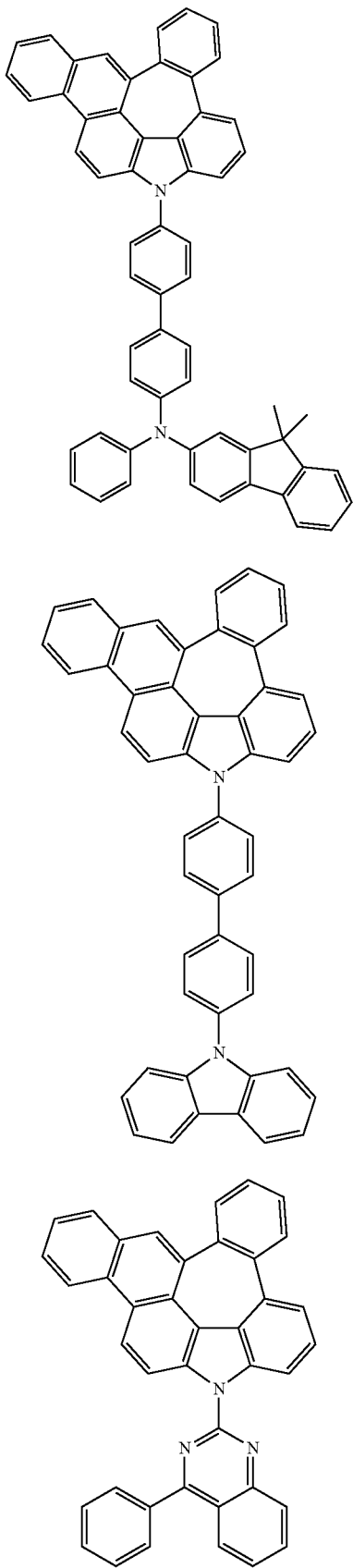
C-363
C-364
C-365

C-366
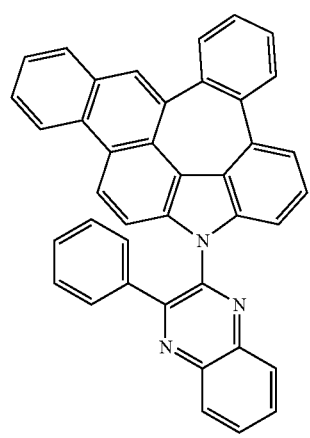
C-367
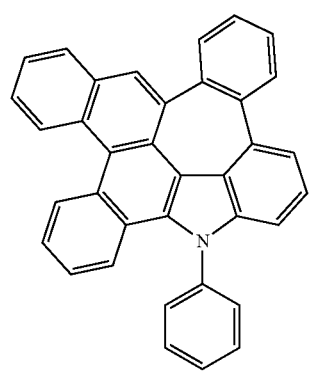
C-368
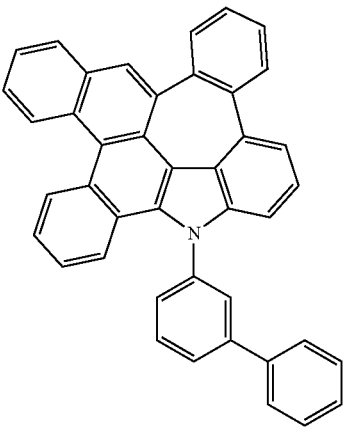
C-369
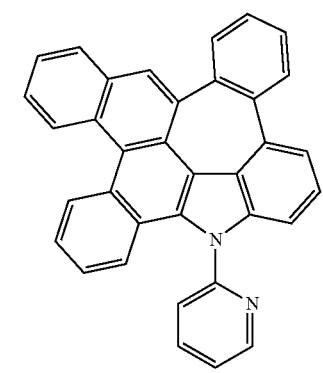
C-370
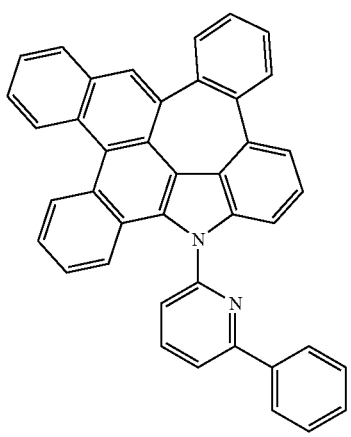
C-371
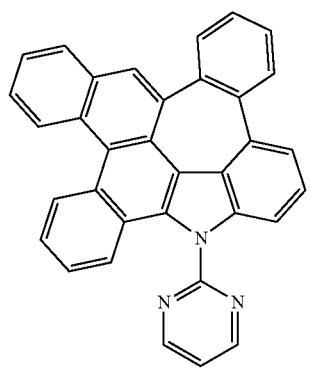
C-372
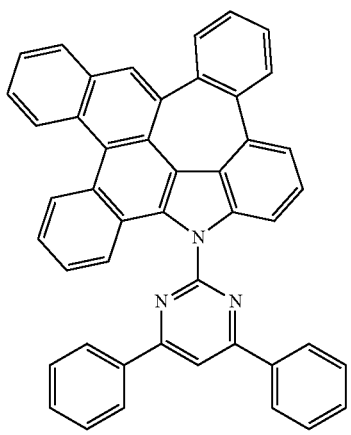

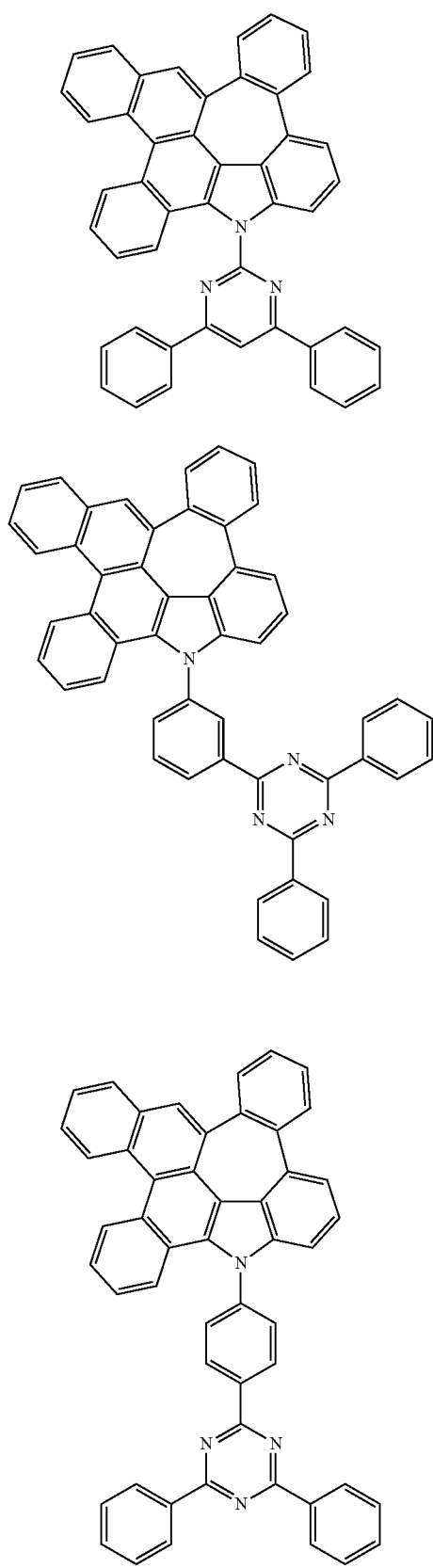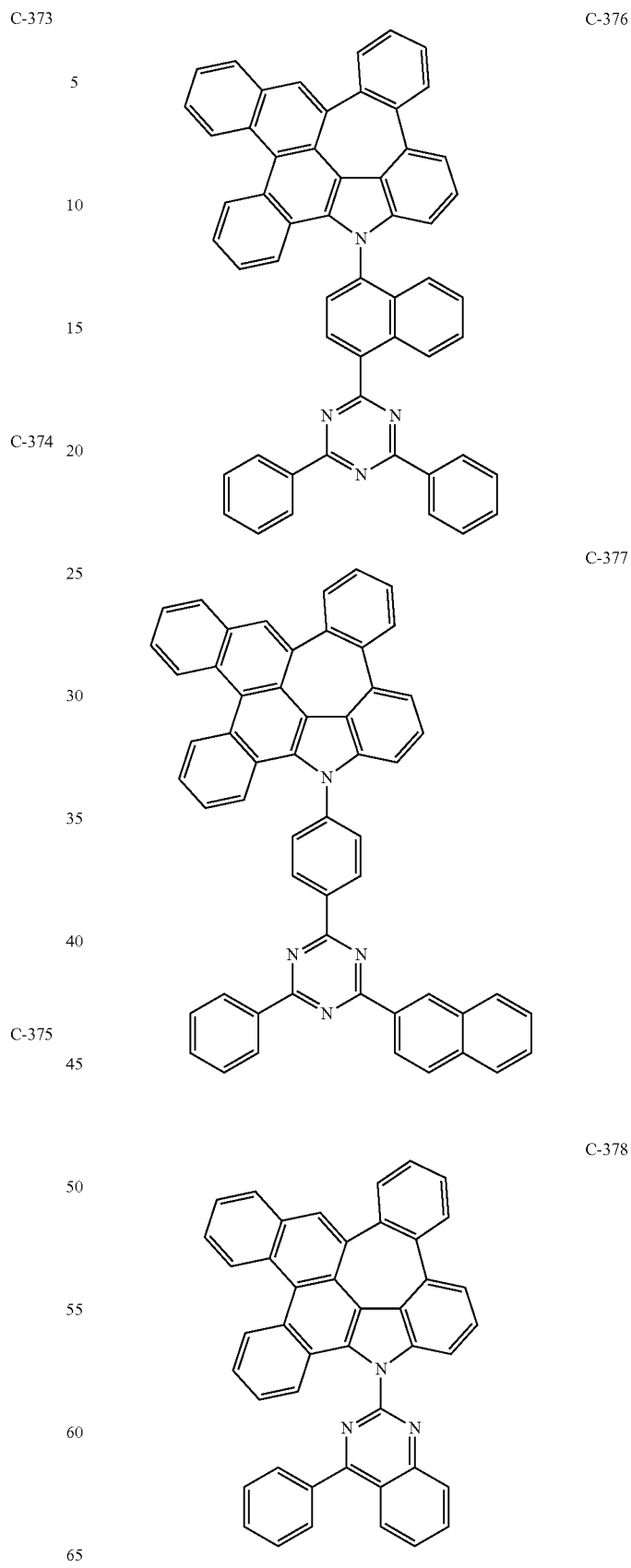

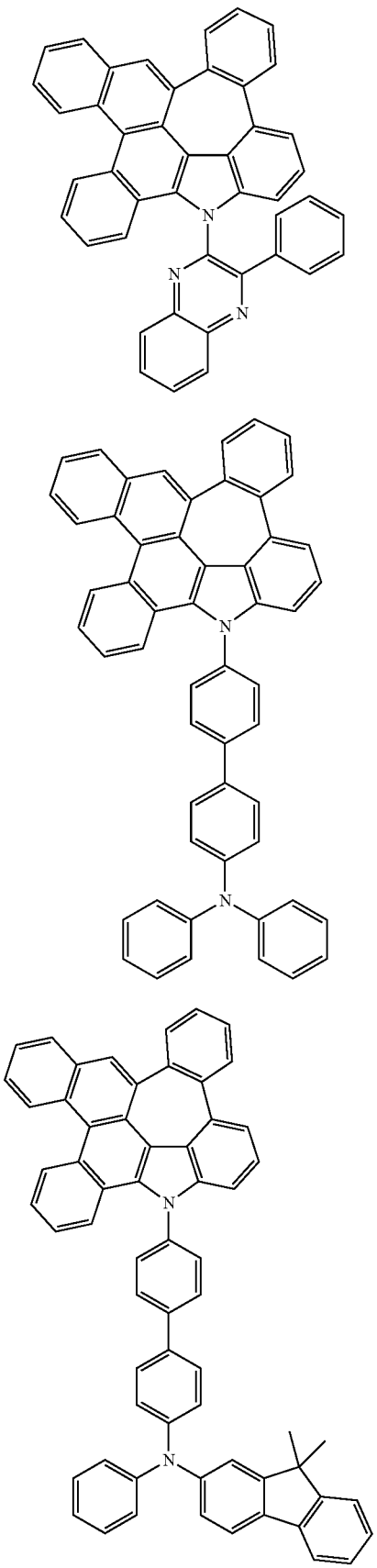
C-379
C-380
C-381
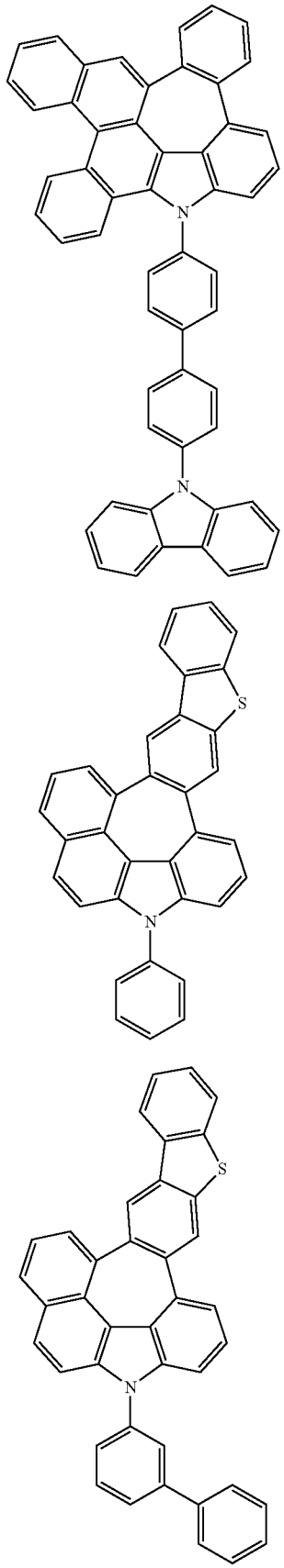
C-382
C-383
C-384

C-385
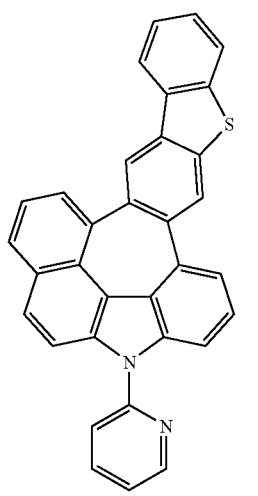
C-386
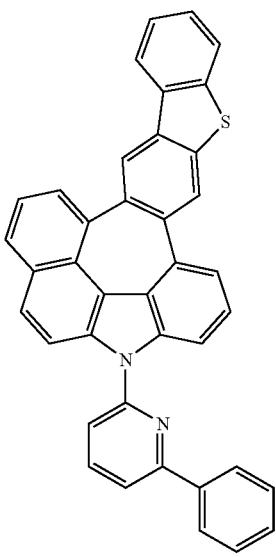
C-387
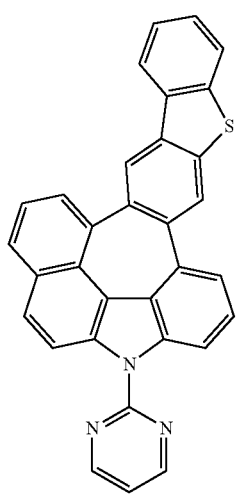
C-388
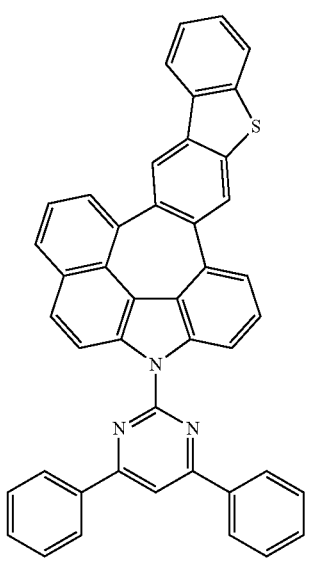
C-389
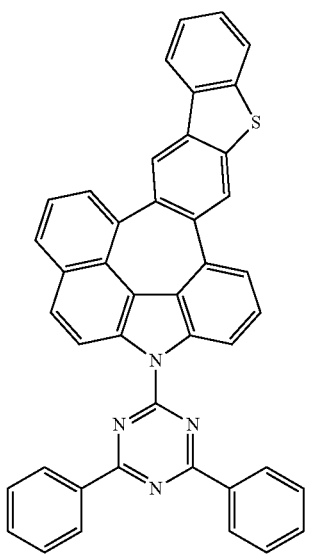

C-390
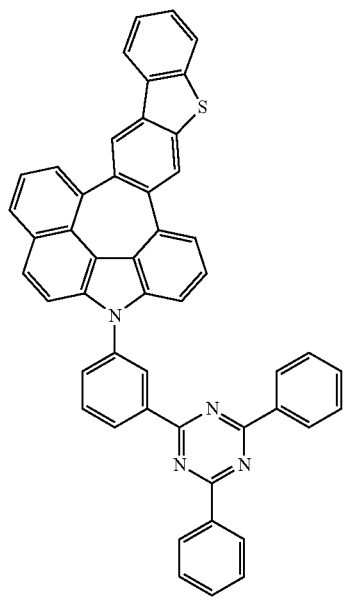
C-392
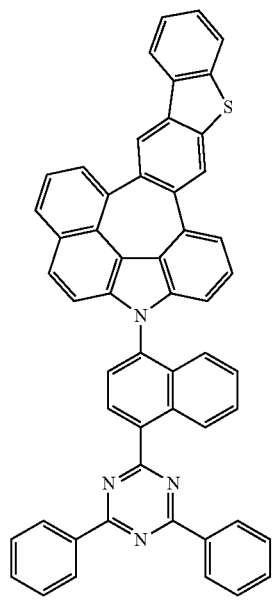
C-391
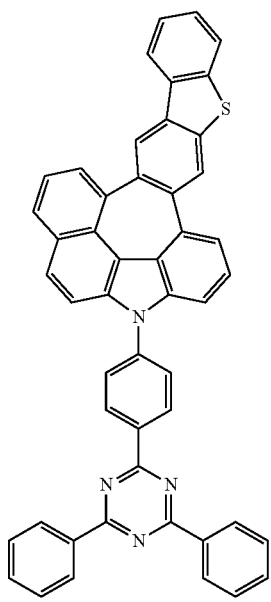
C-393
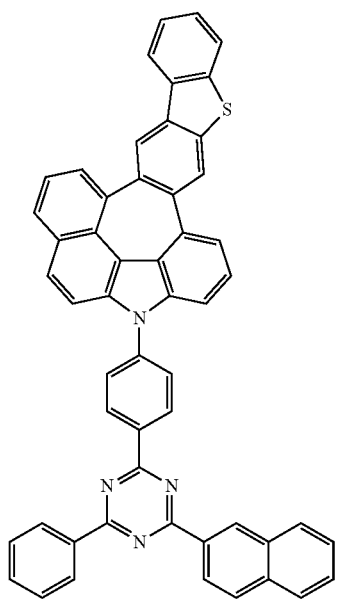

-continued
C-394
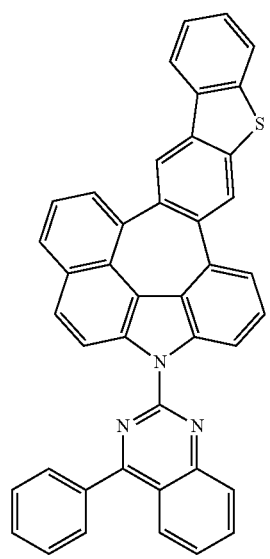
C-395
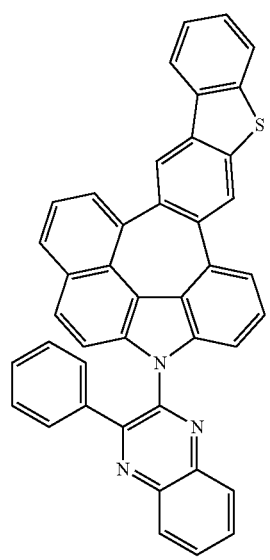
C-396
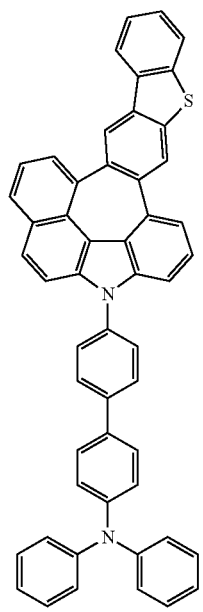
C-397
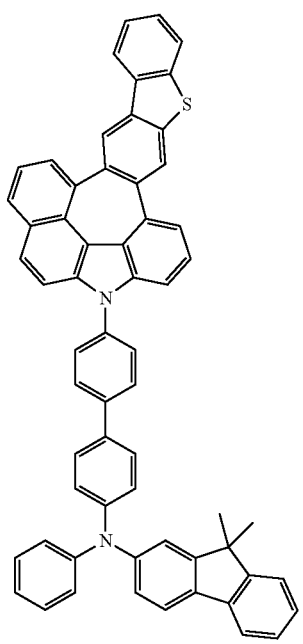

479
-continued
C-398
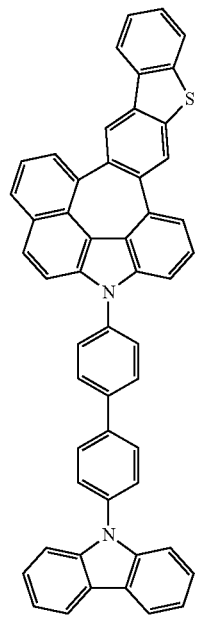
C-399
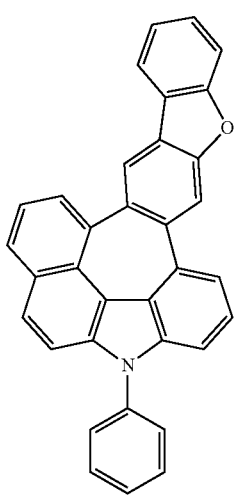
C-400
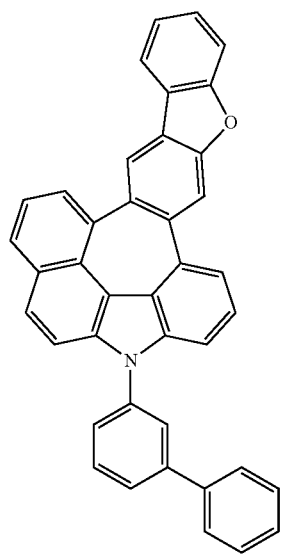
480
-continued
C-401
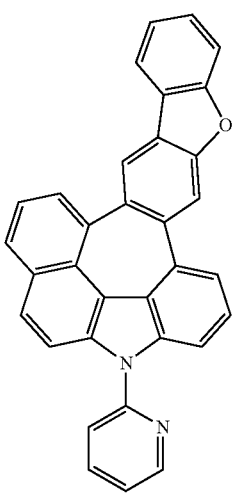
C-402
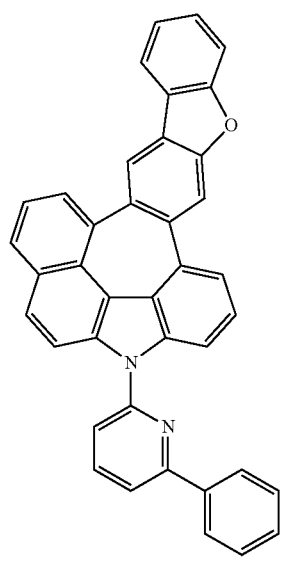
C-403
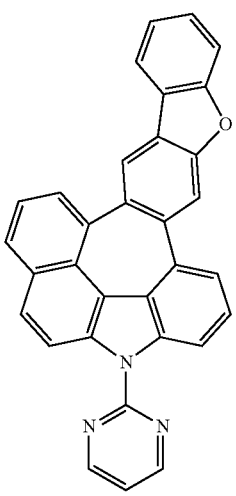

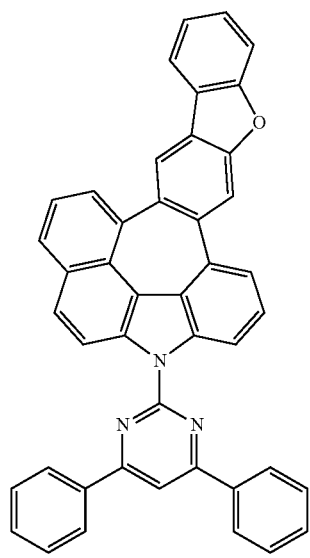
C-404
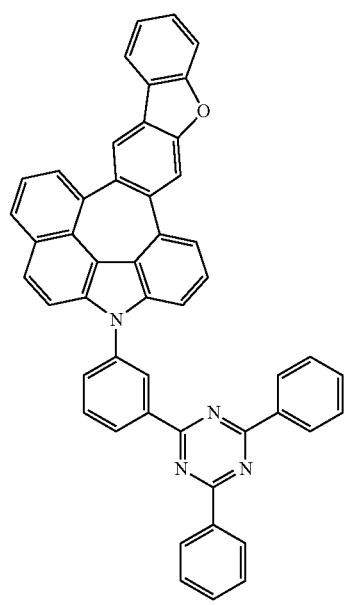
C-406
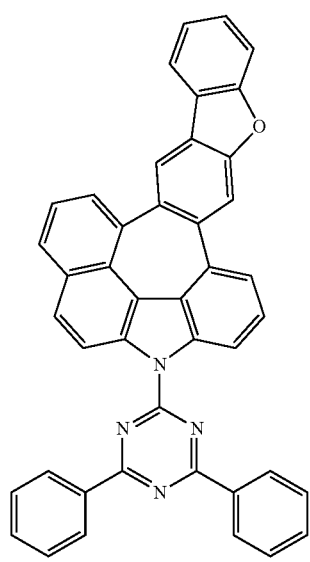
C-405
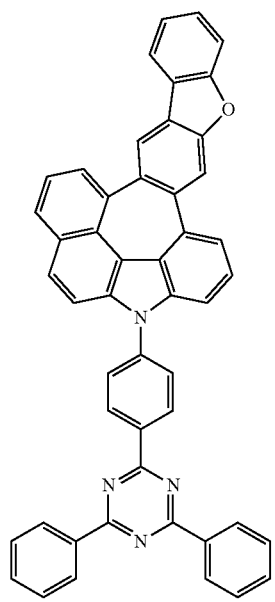
C-407

C-408
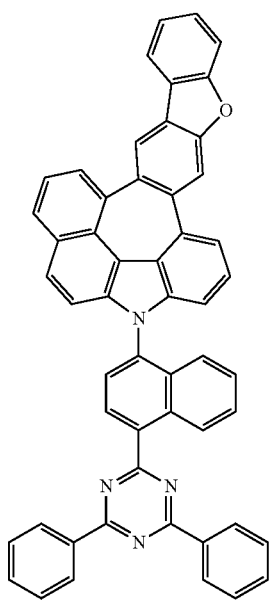
C-410
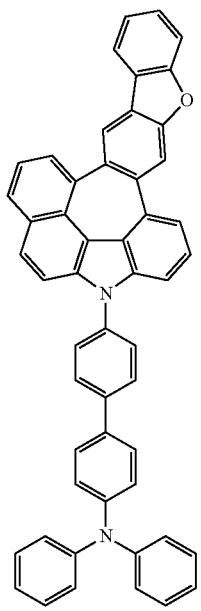
C-409
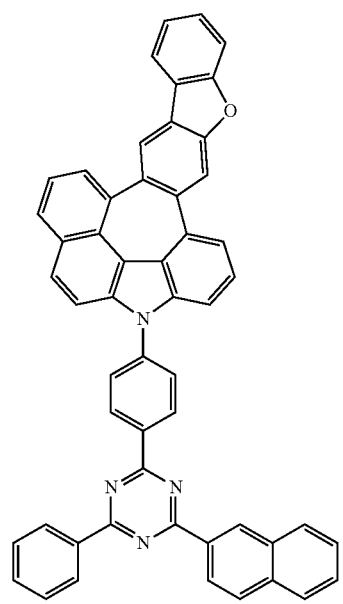
C-411
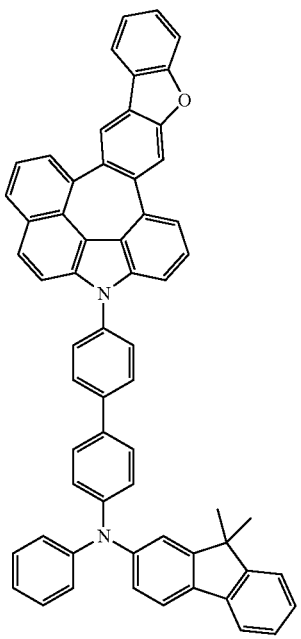

C-412
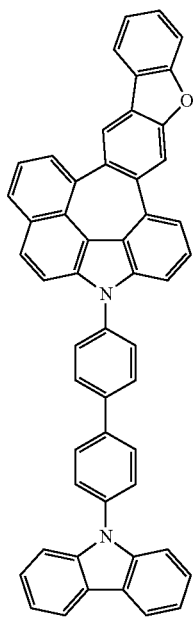
C-413
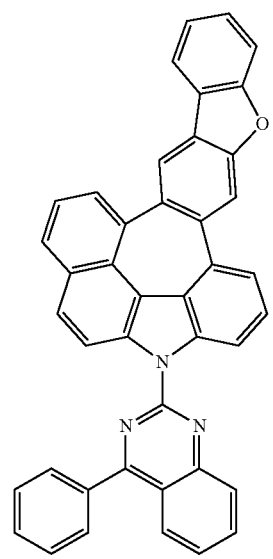
C-414
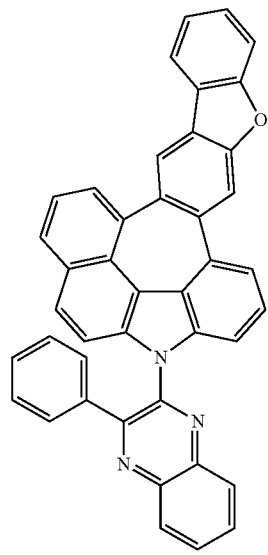
C-415
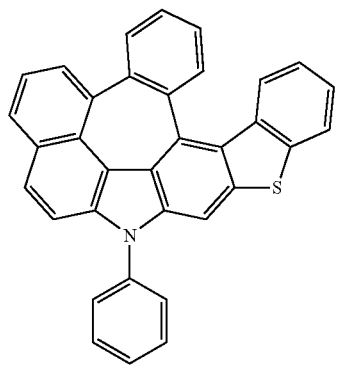
C-416
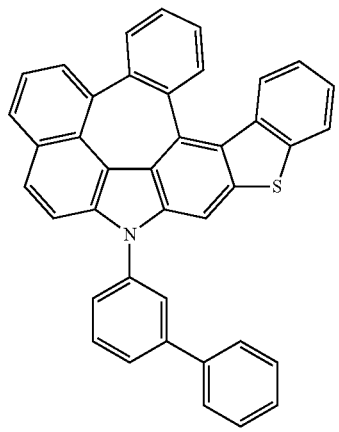

-continued
C-417
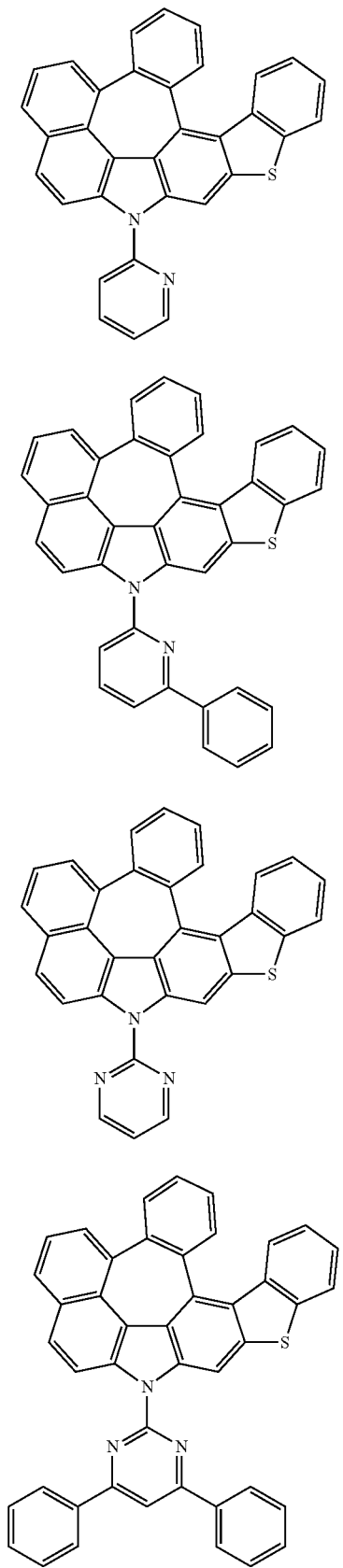
C-418
C-419
C-420
-continued
C-421
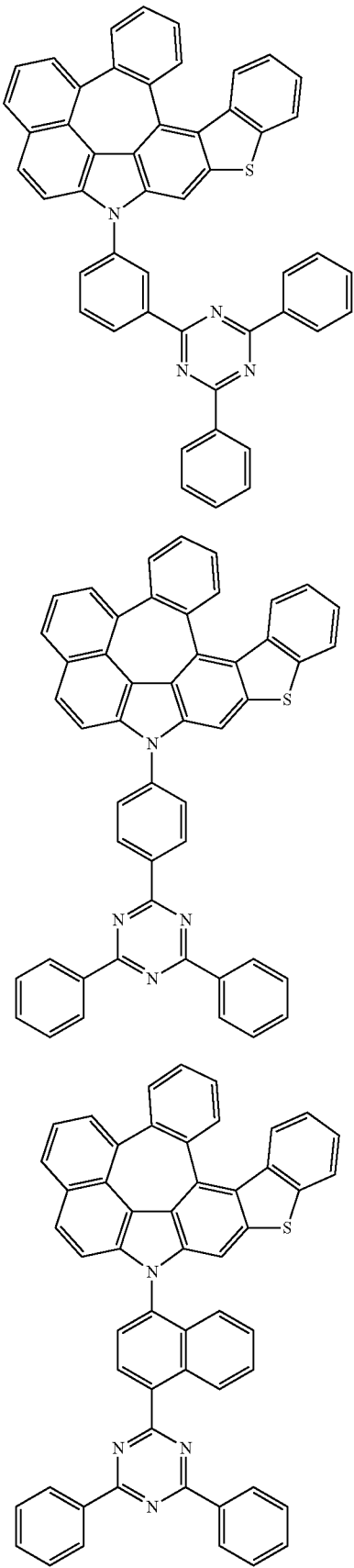
C-422
C-423

-continued
C-424
C-425
C-426
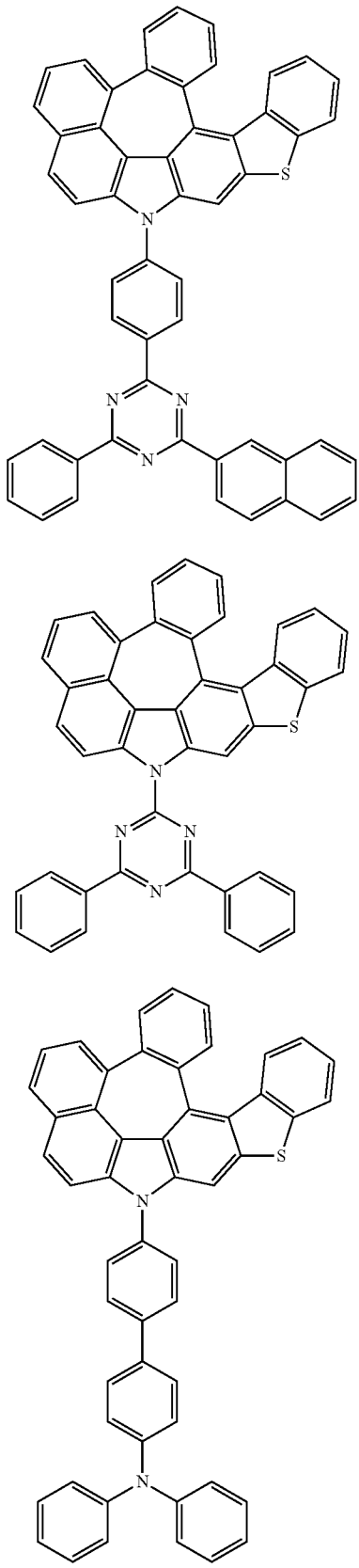
-continued
C-427
C-428
C-429
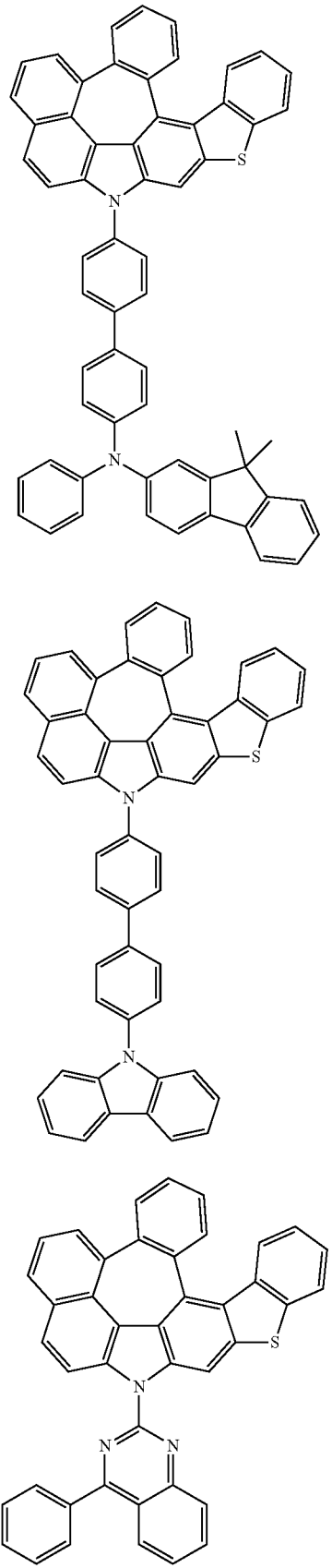

C-430
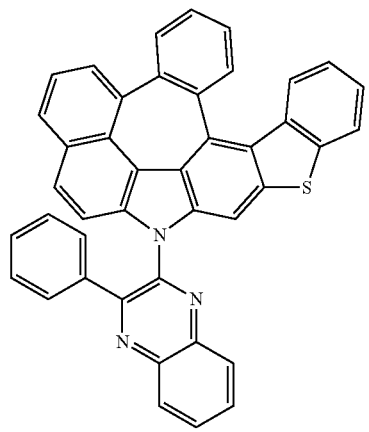
C-431
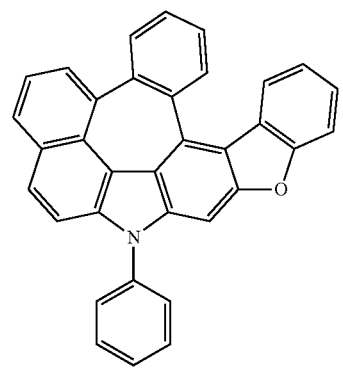
C-432
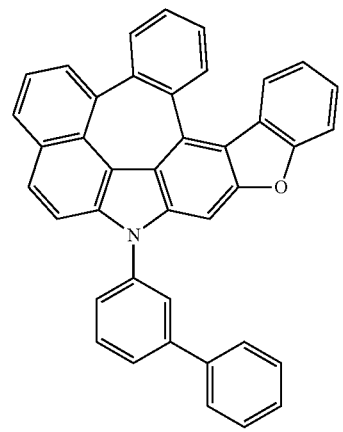
C-433
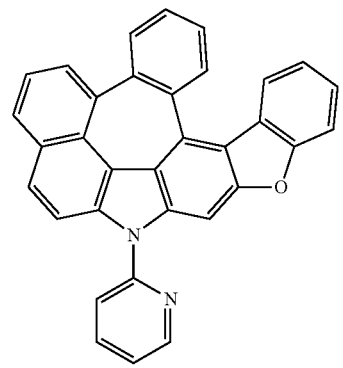
C-434
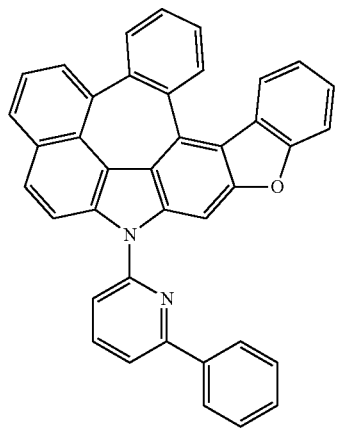
C-435
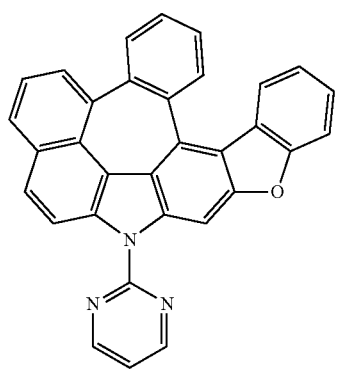
C-436
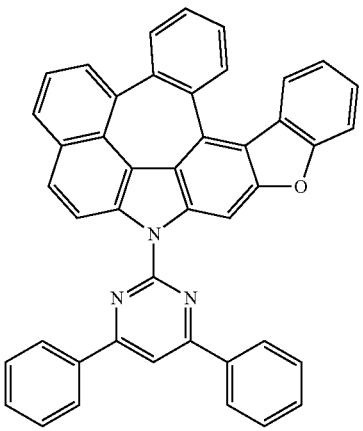
C-437
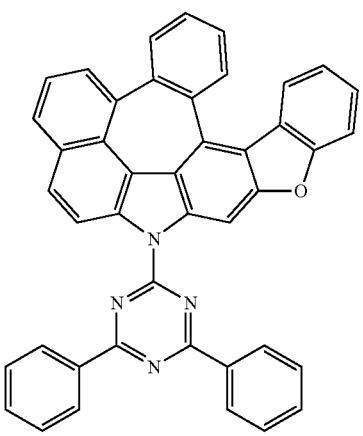

C-438
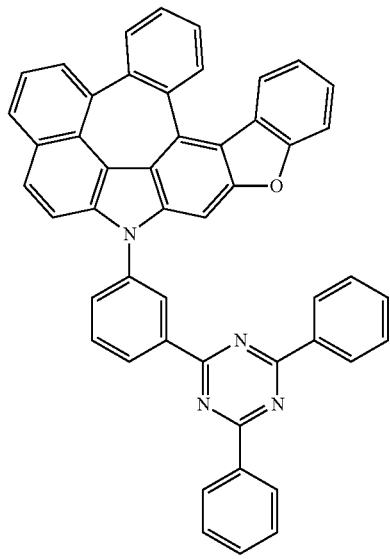
C-349
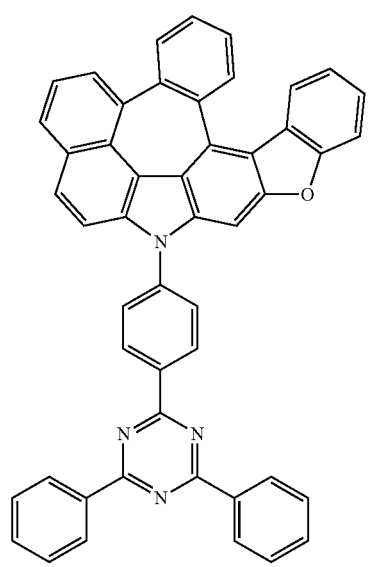
C-440
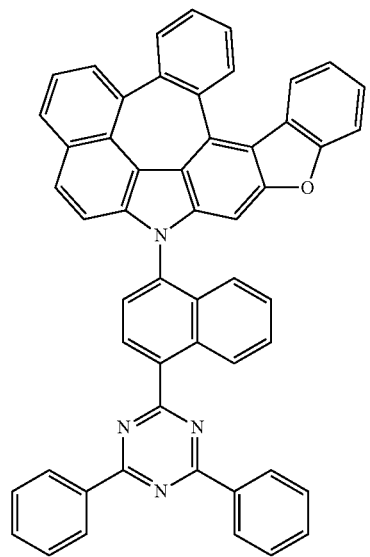
C-441
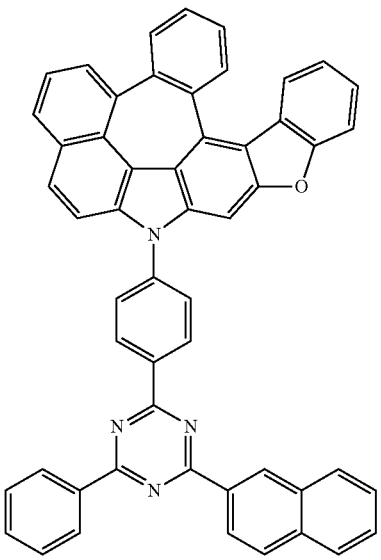
C-442
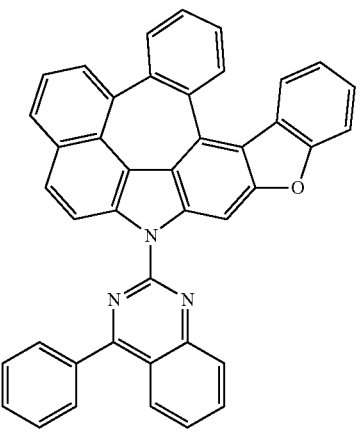
C-443
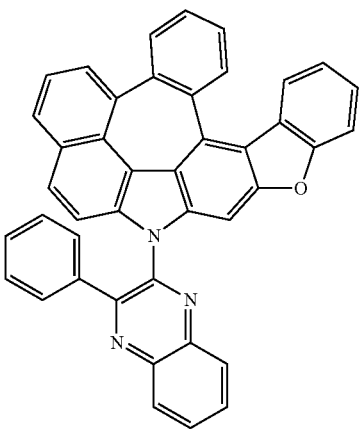

C-444
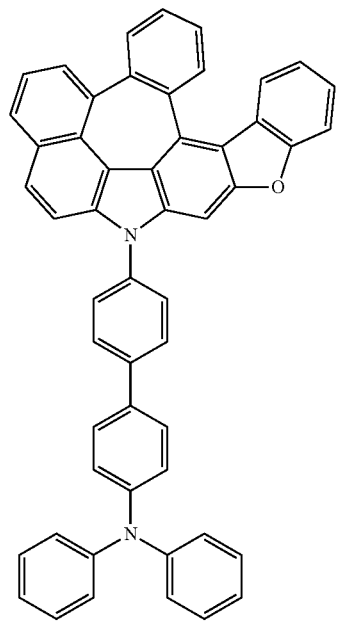
C-446
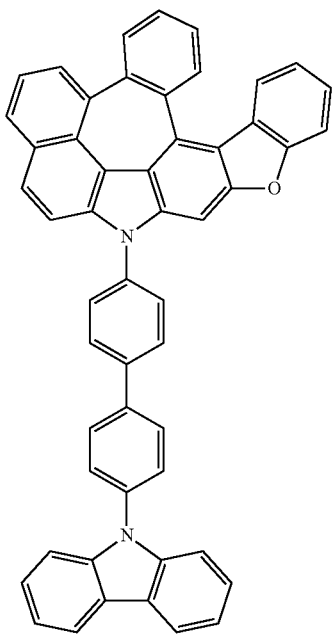
C-447
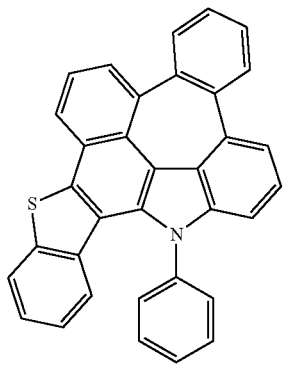
C-445
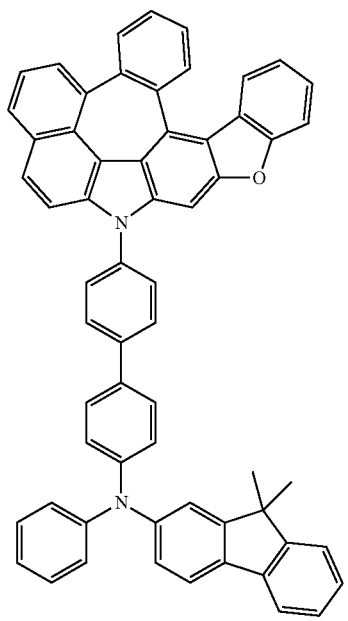
C-448
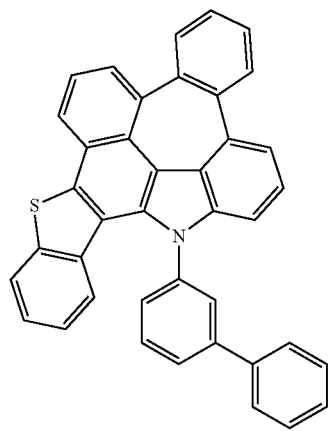

-continued
C-449
C-450
C-451
C-452
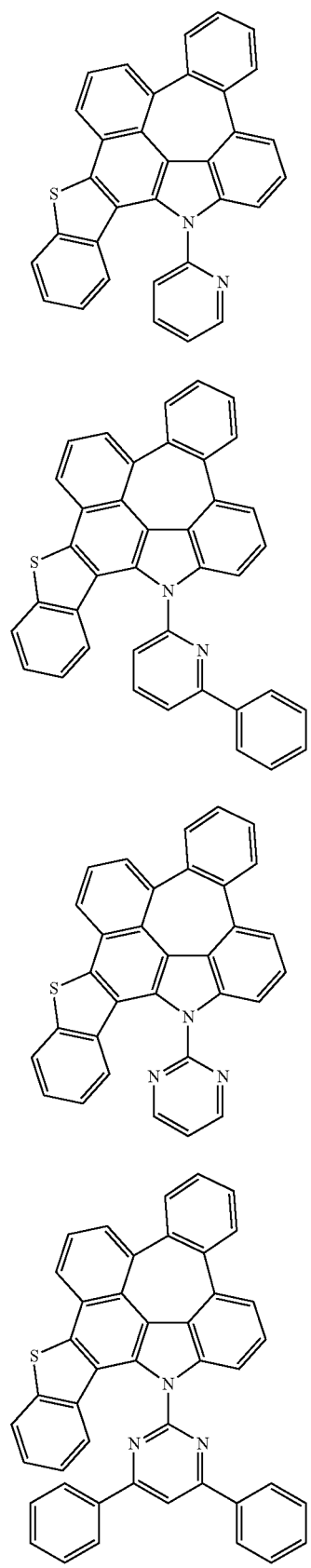
-continued
C-453
C-454
C-455
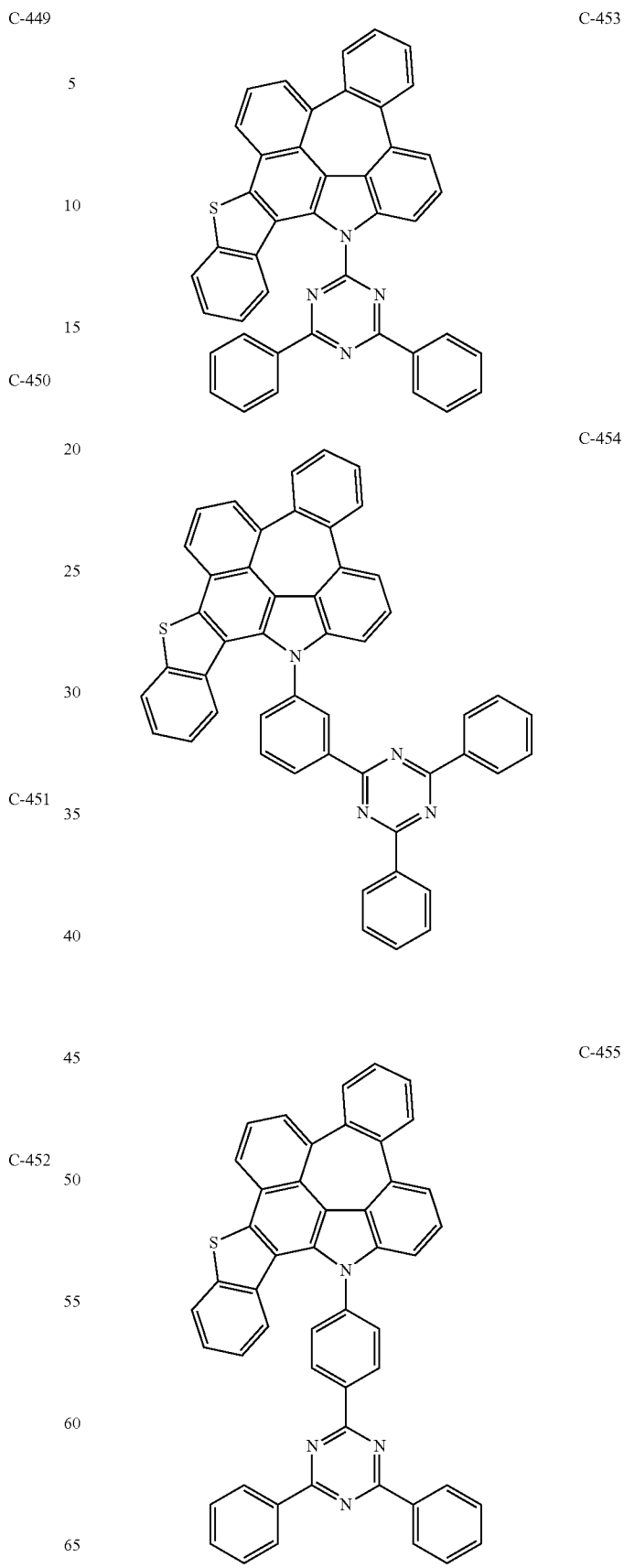

-continued
C-456
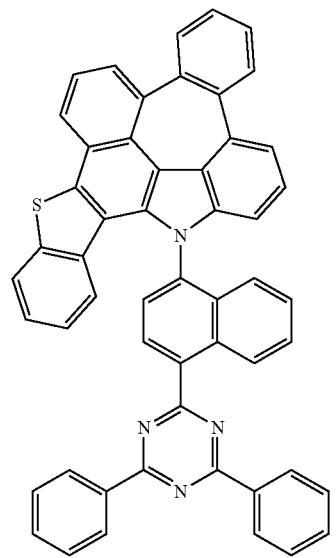
C-457
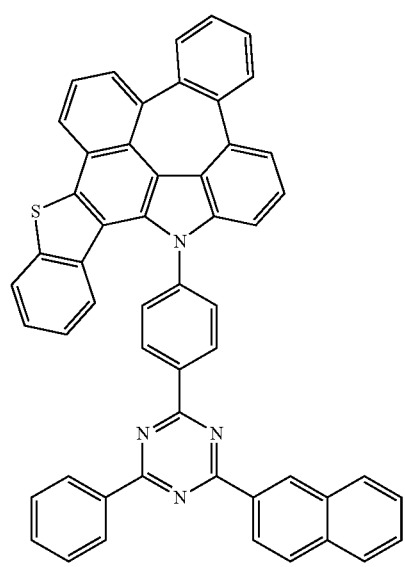
C-458
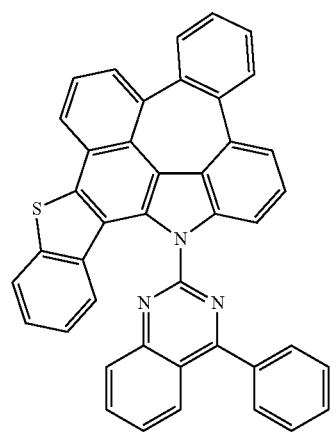
-continued
C-459
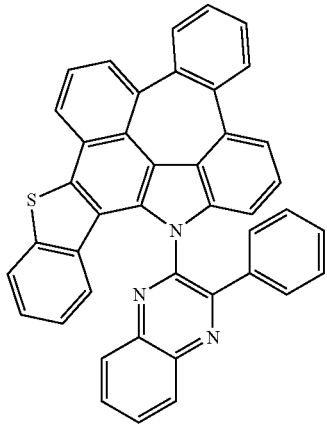
C-460
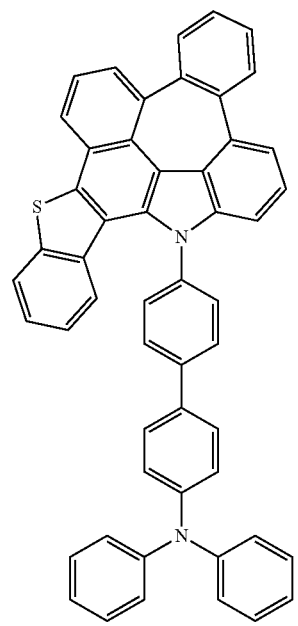
C-461
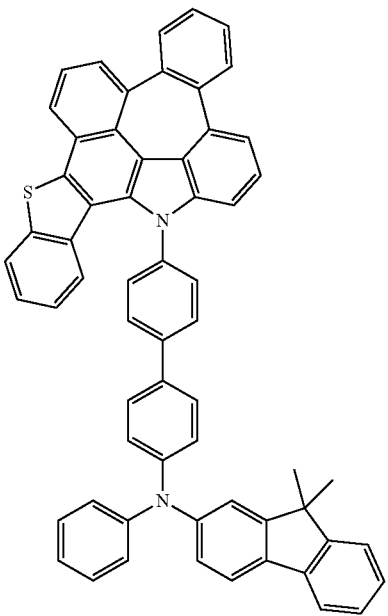

C-462
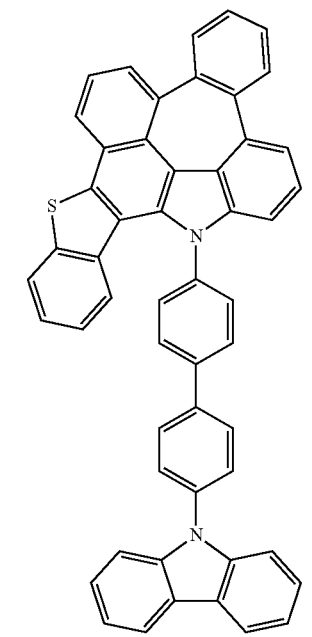
C-463
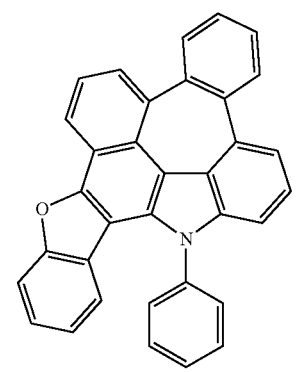
C-464
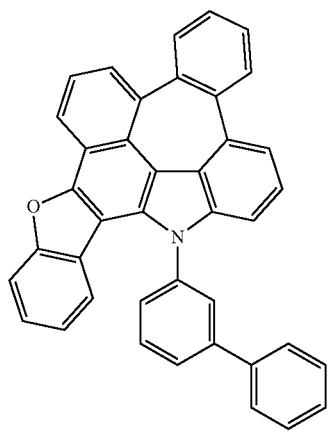
C-465
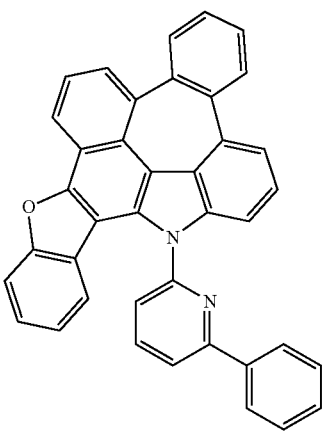
C-466
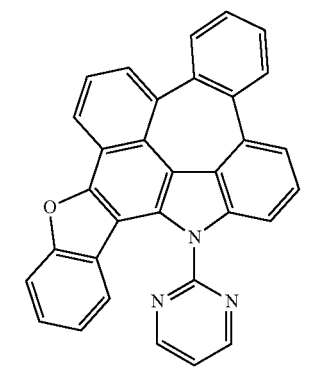
C-467
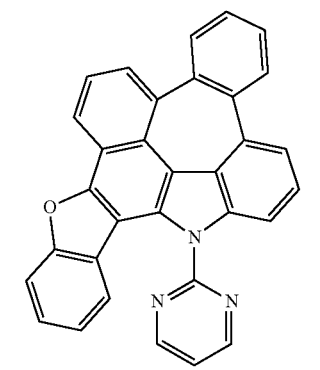
C-468
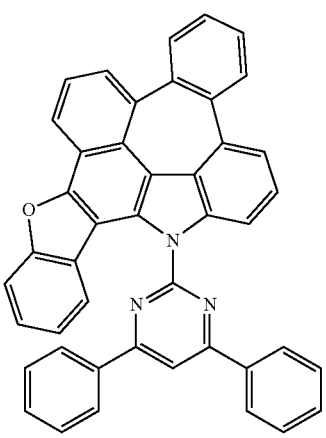

-continued
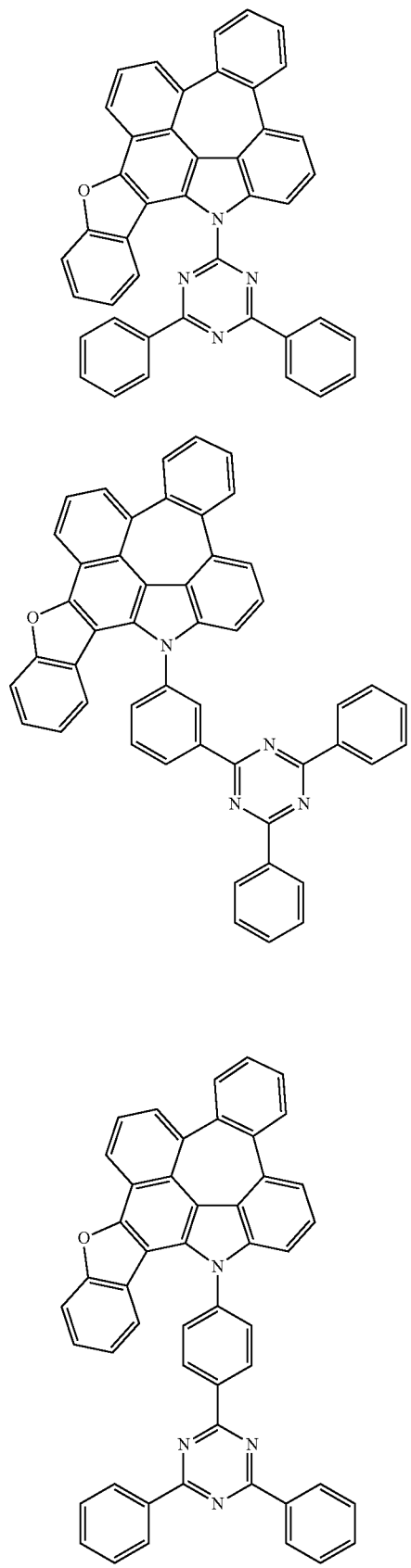
C-469
C-470
C-471
-continued
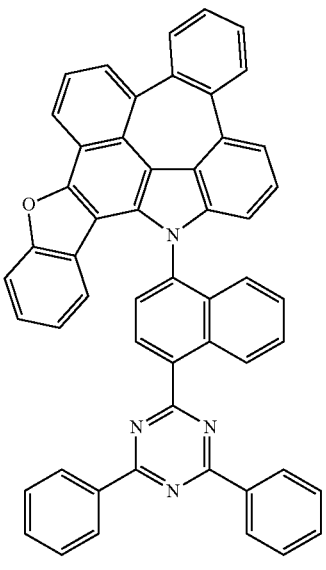
C-472
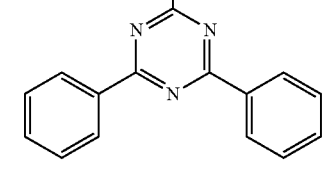
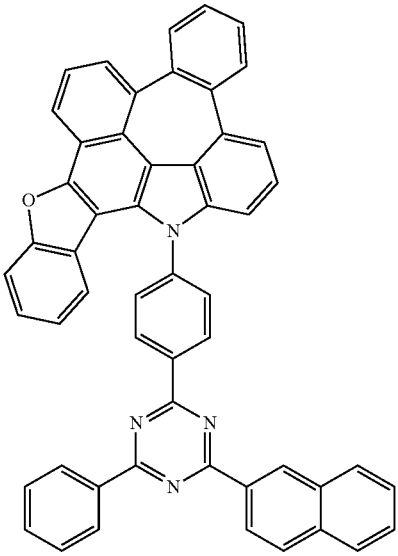
C-473
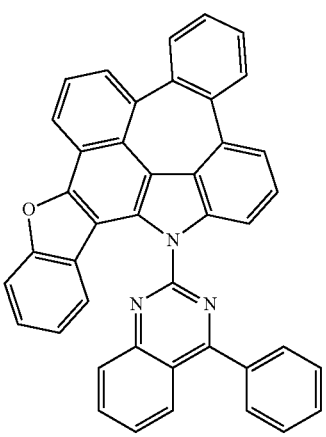
C-474

C-475
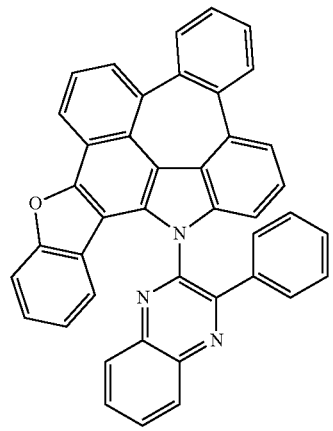
C-476
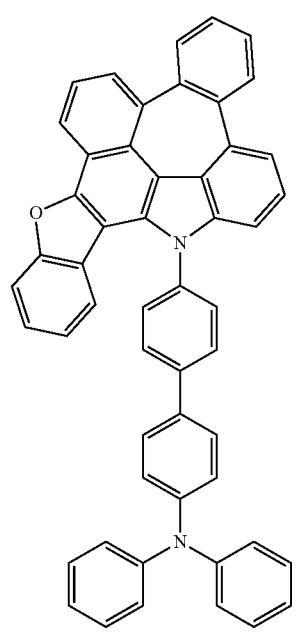
C-477
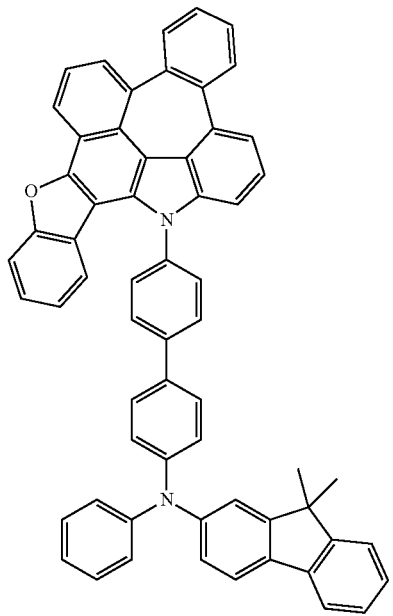
C-478
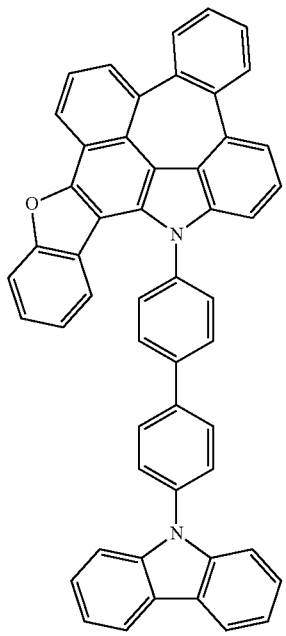
C-479
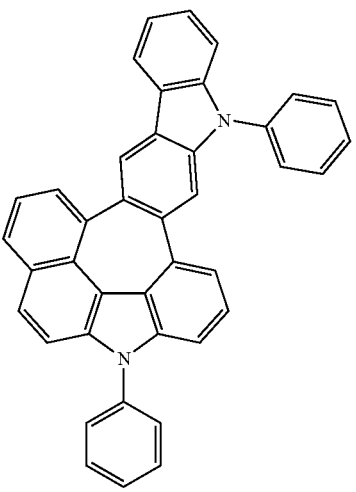

C-480
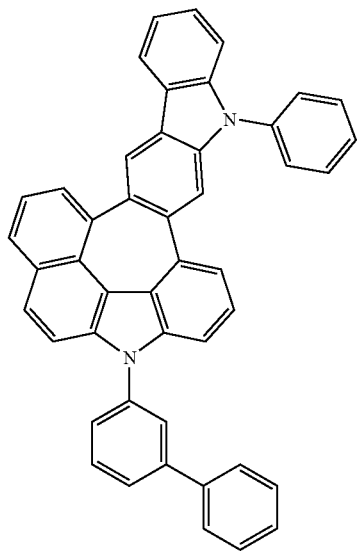
C-481
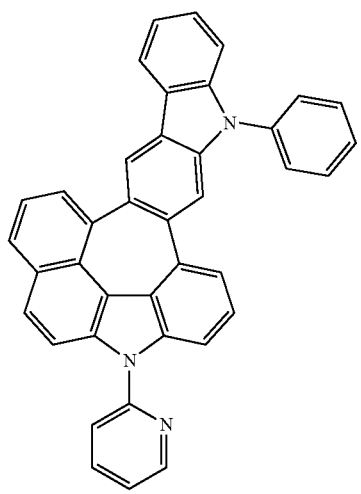
C-482
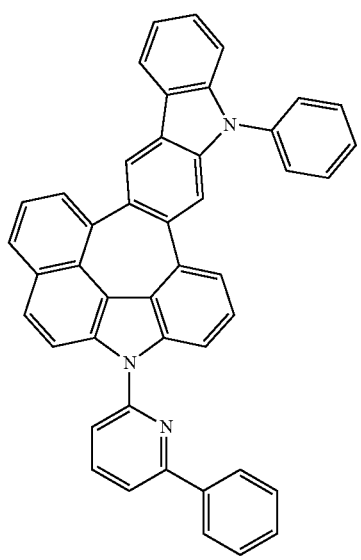
C-483
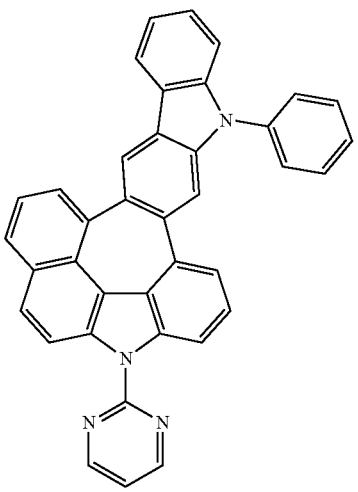
C-484
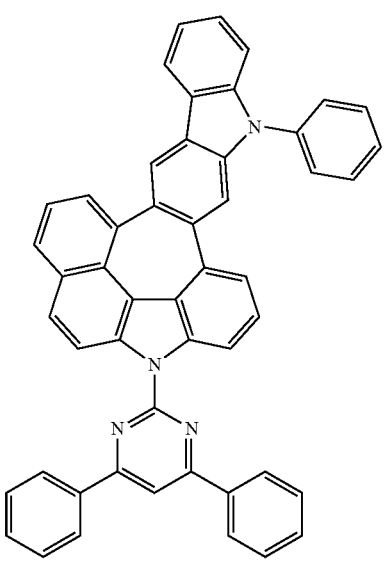
C-485
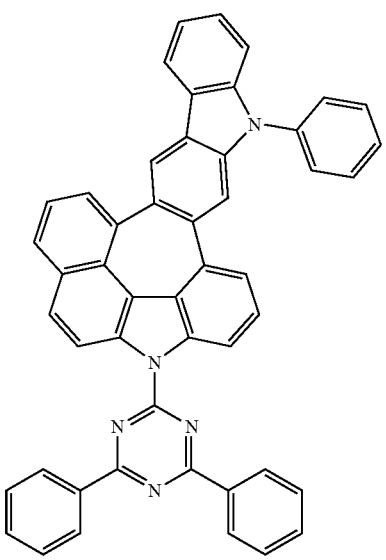

C-486
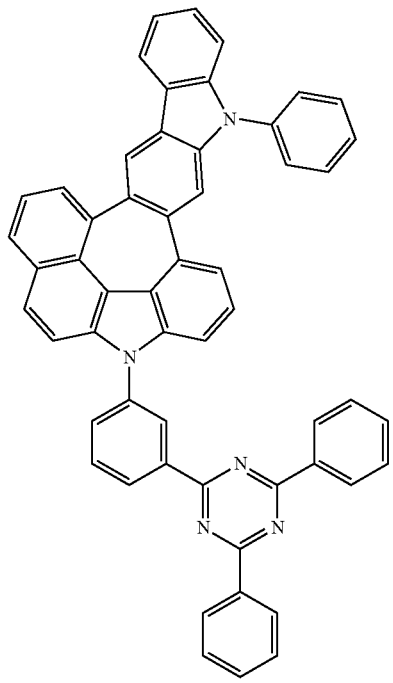
C-488
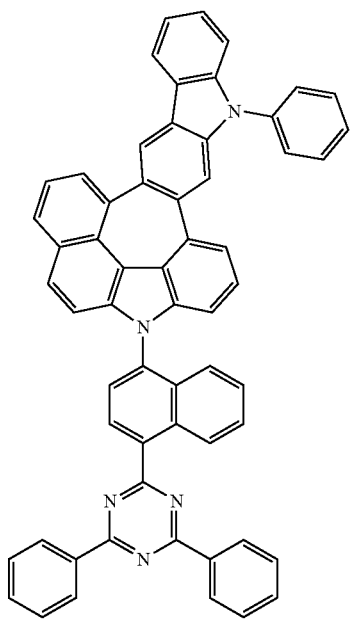
C-487
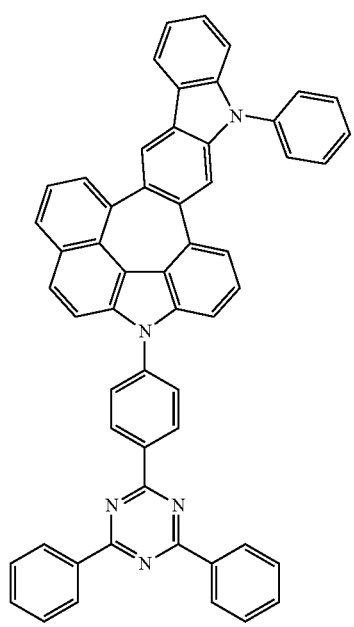
C-489
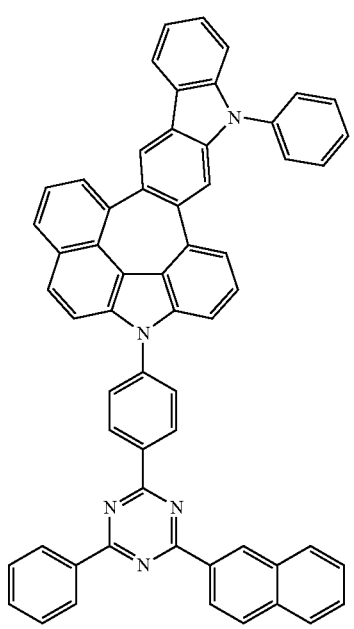

C-490
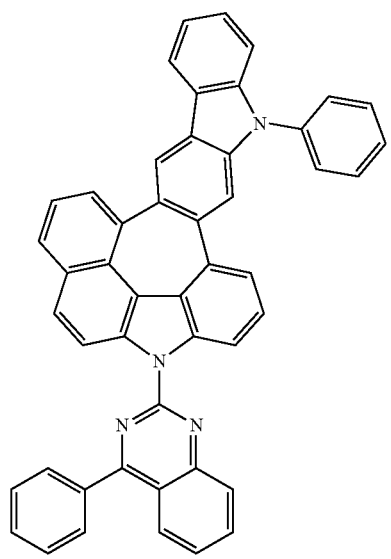
C-491
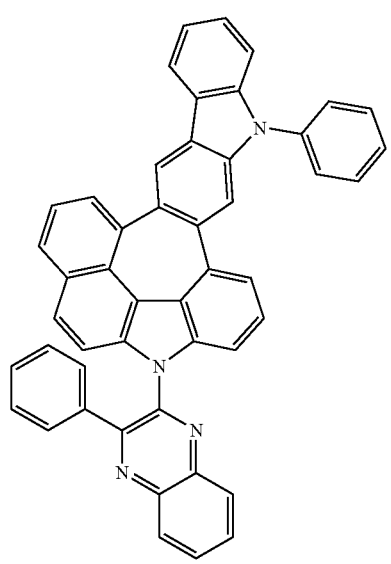
C-492
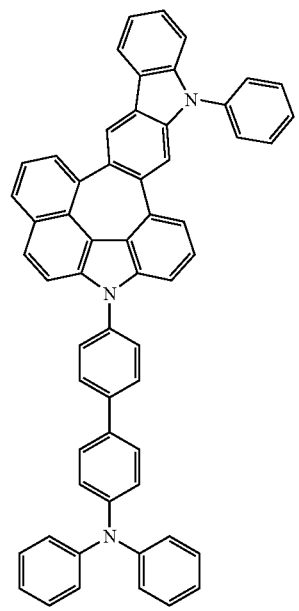
C-493
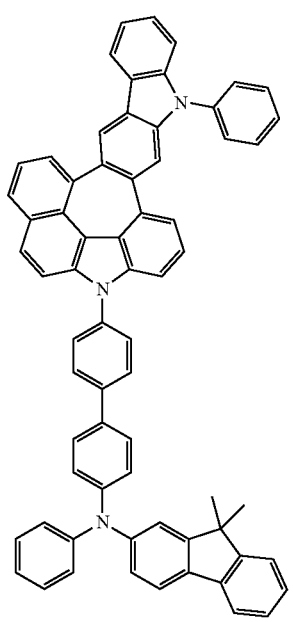

C-494
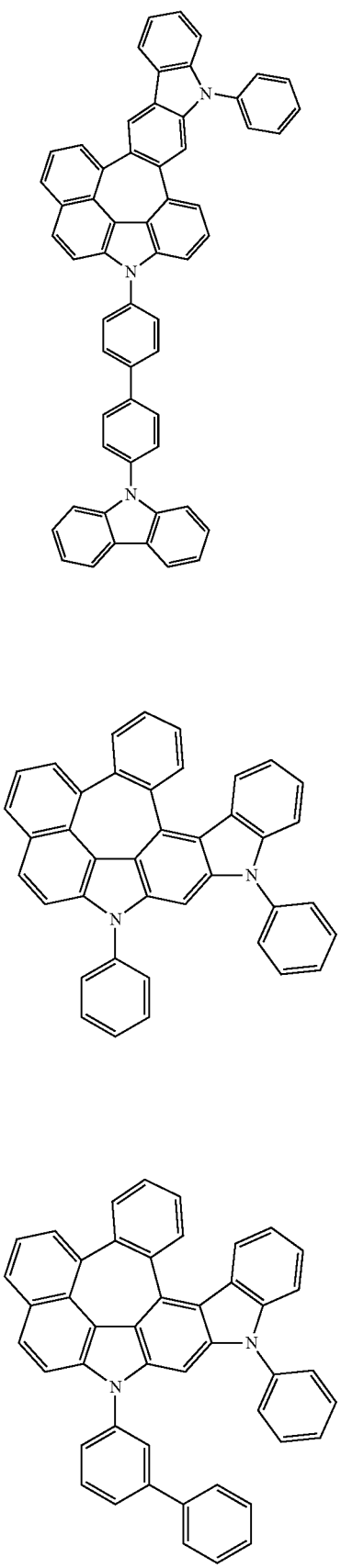
C-495
C-496
C-497
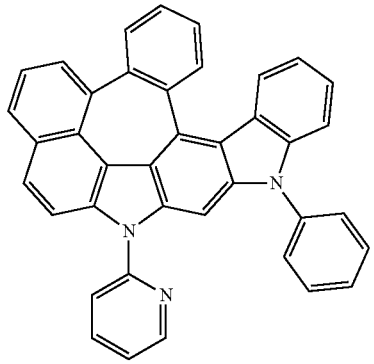
C-498
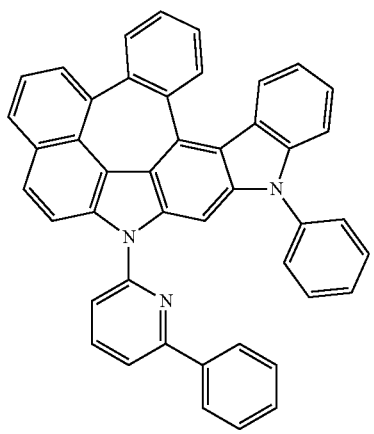
C-499
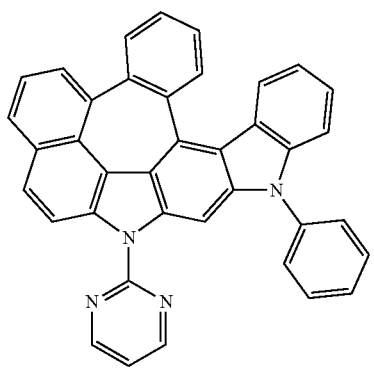
C-500
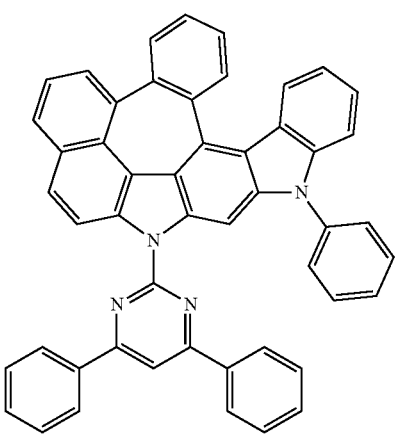

-continued
C-501
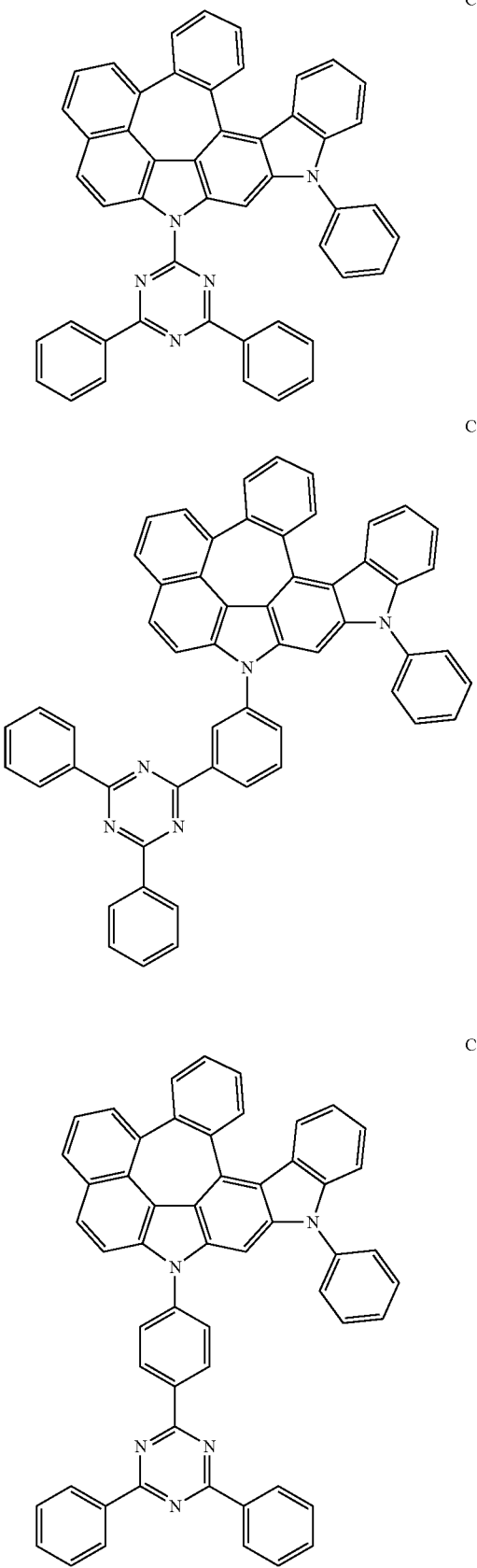
C-502
C-503
-continued
C-504
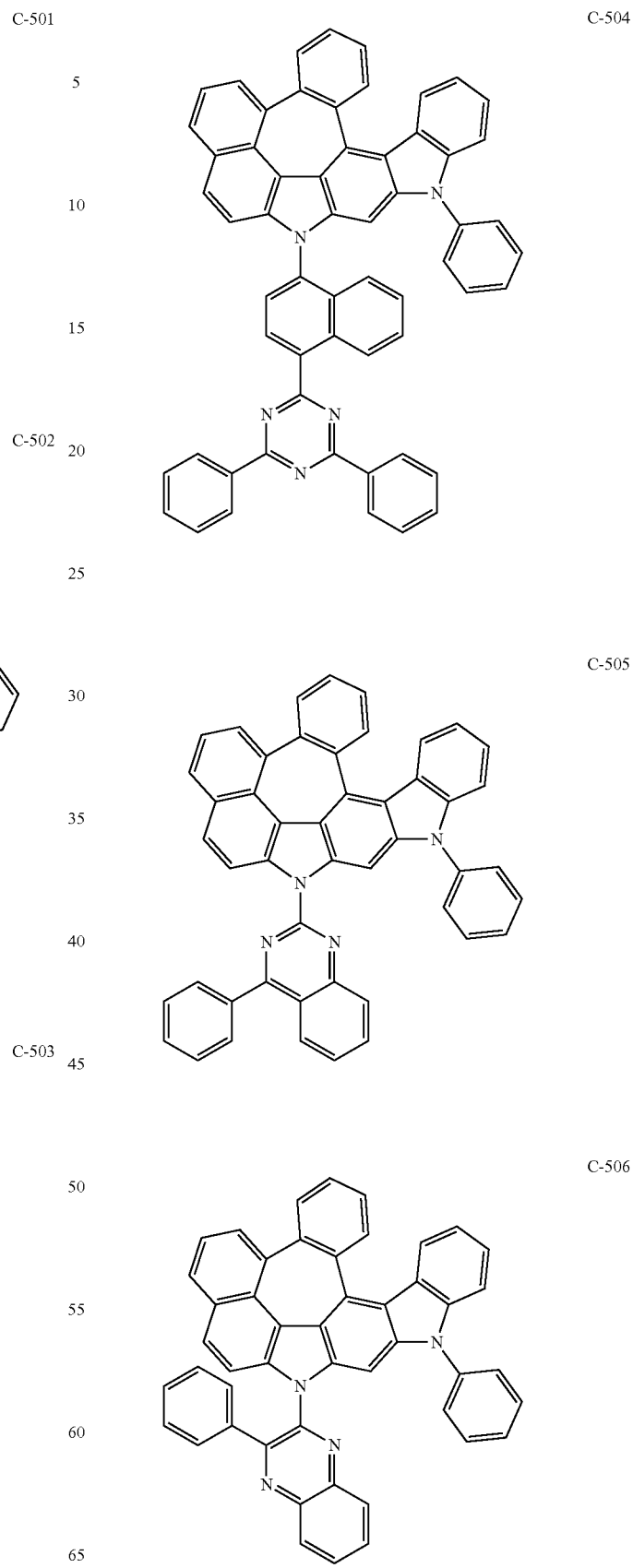
C-505
C-506

C-507
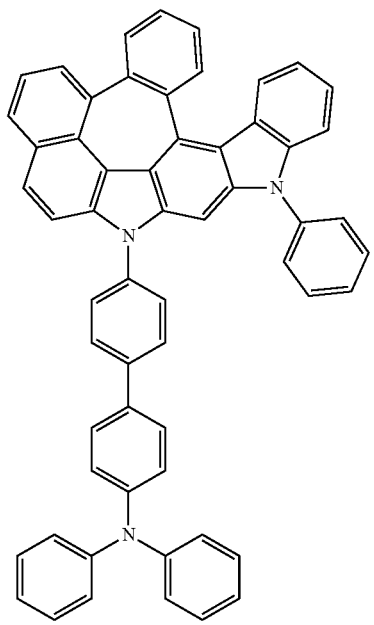
C-508
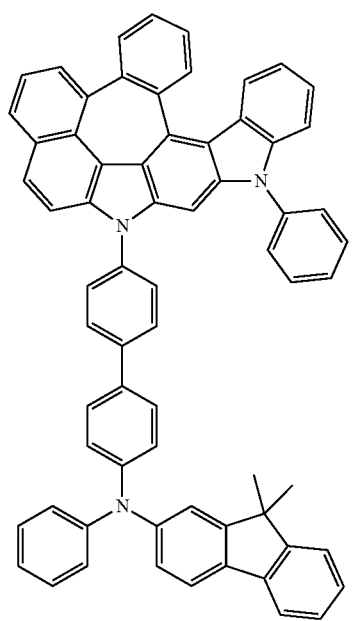
C-509
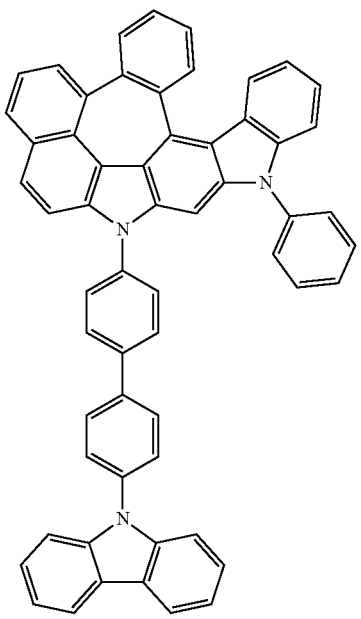
C-510
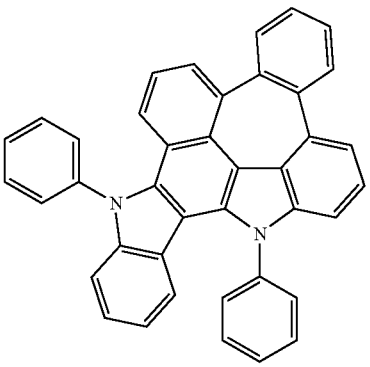
C-511
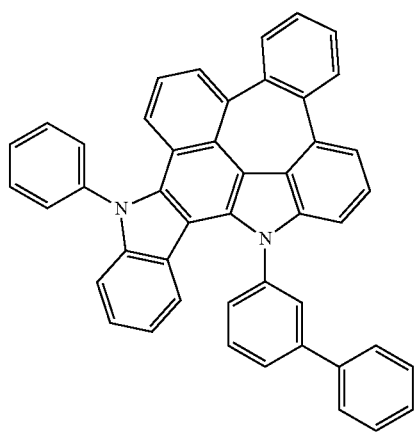

-continued
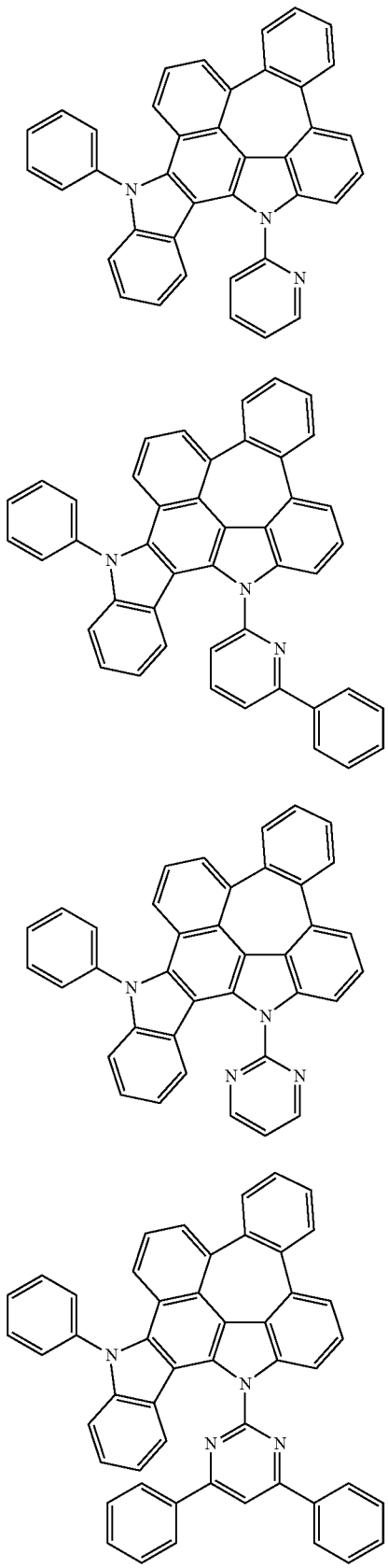
C-512
C-513
C-514
C-515
-continued
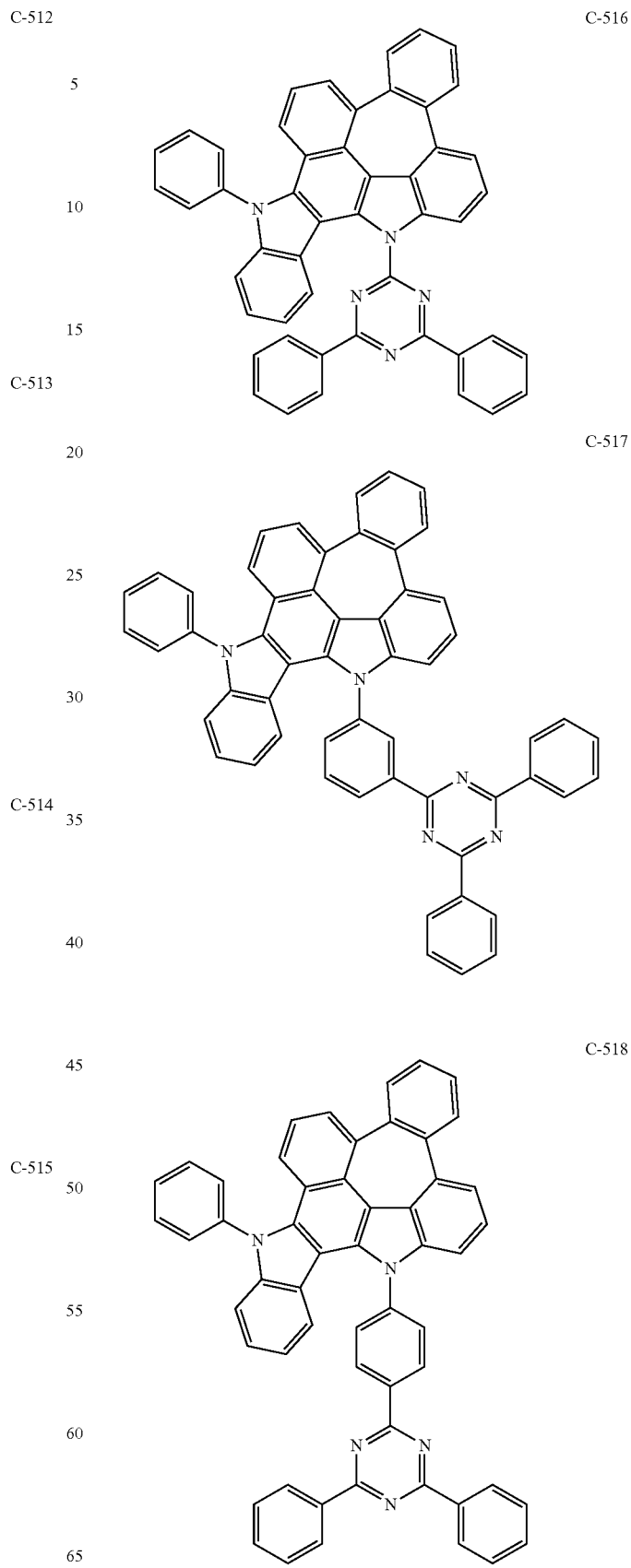
C-516
C-517
C-518

-continued
C-519
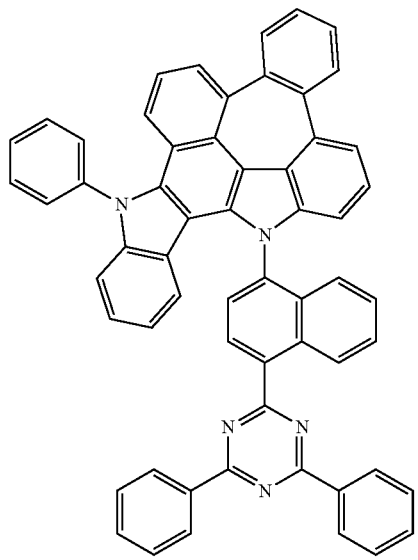
C-520
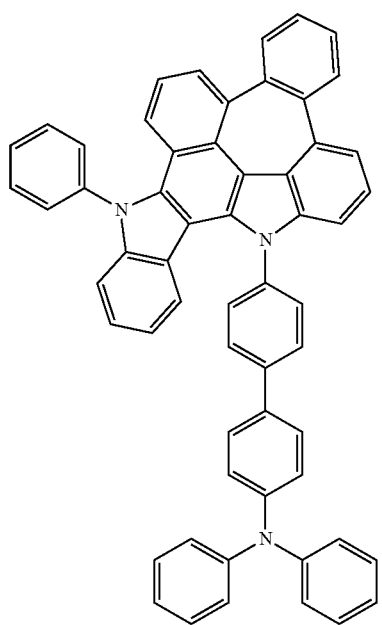
C-521
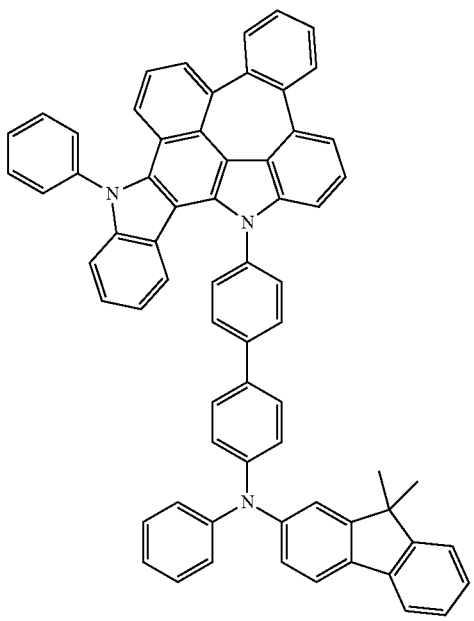
C-522
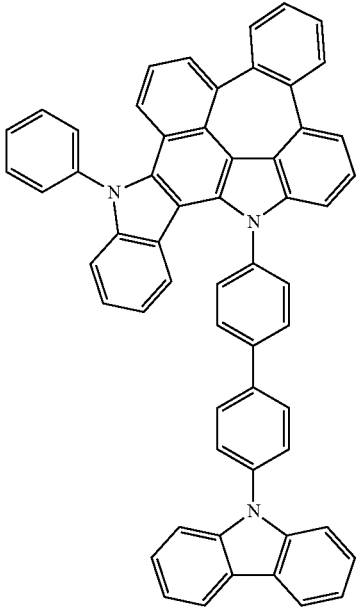

-continued
C-523
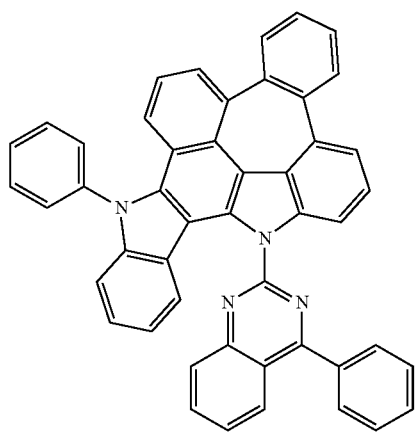
C-524
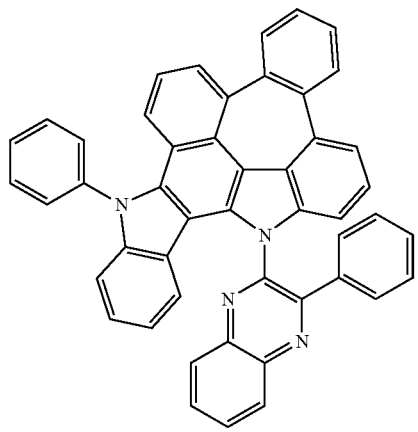
C-525
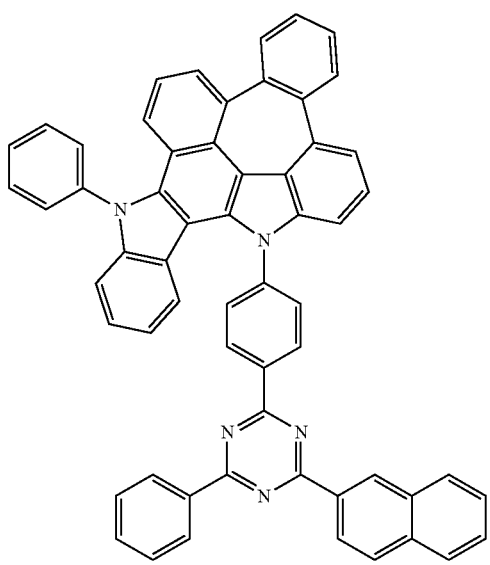
-continued
C-526
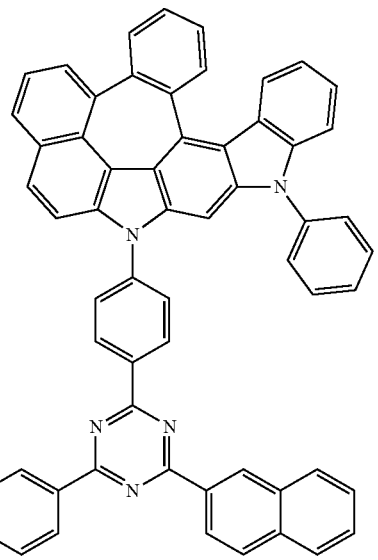
C-527
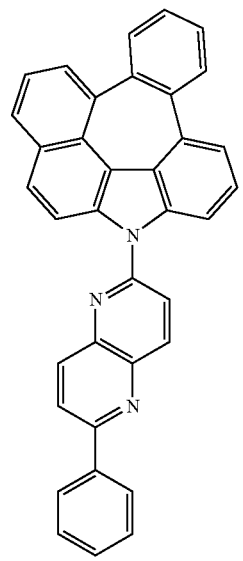
C-528
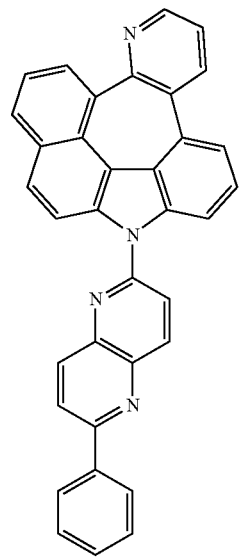

C-529
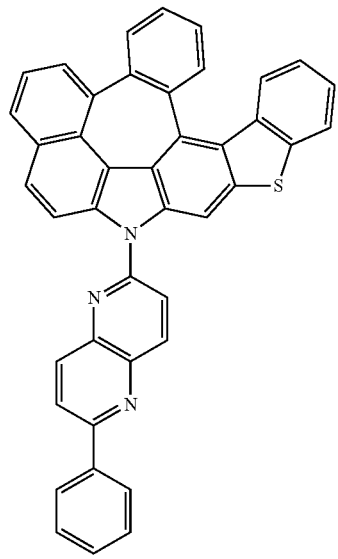
C-530
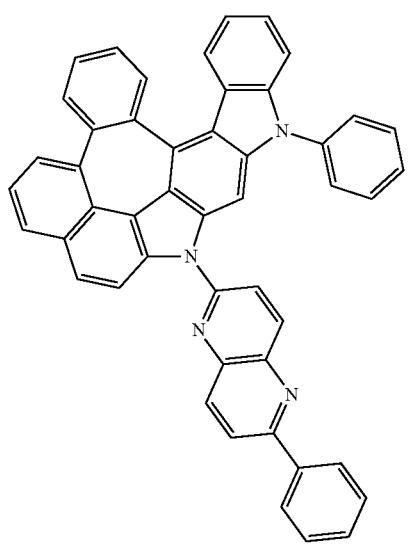
C-531
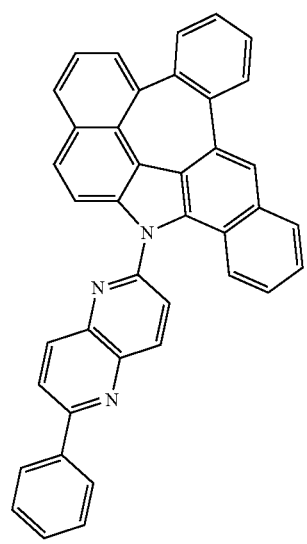
C-532
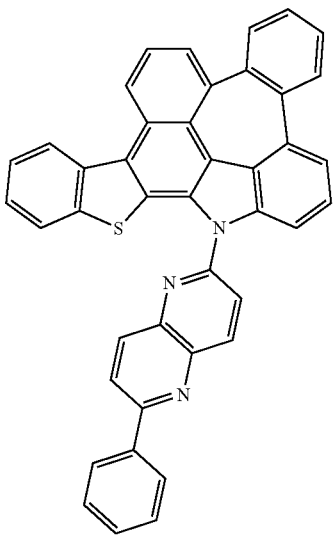
C-533
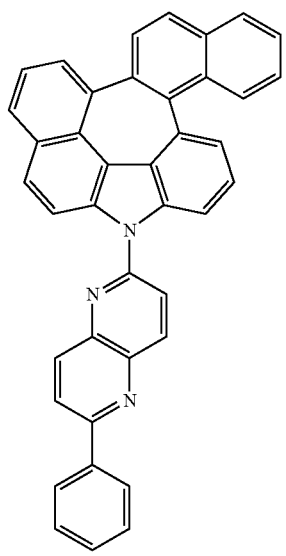
C-534
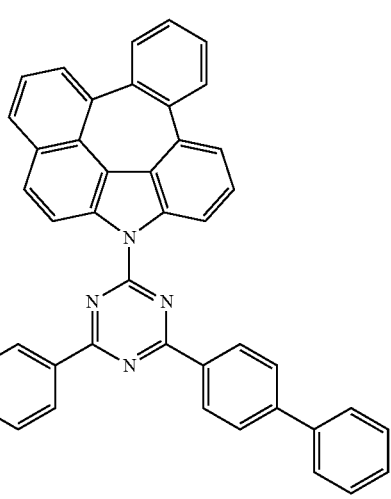

C-535
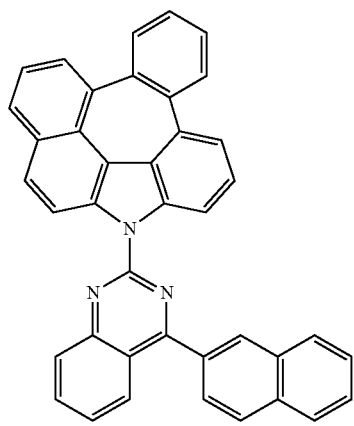
C-538
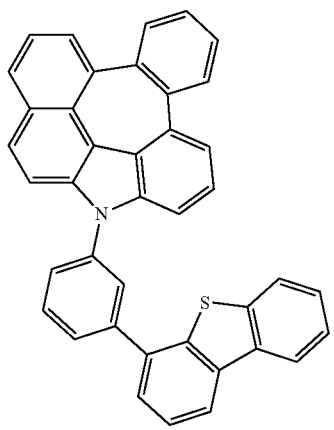
C-536
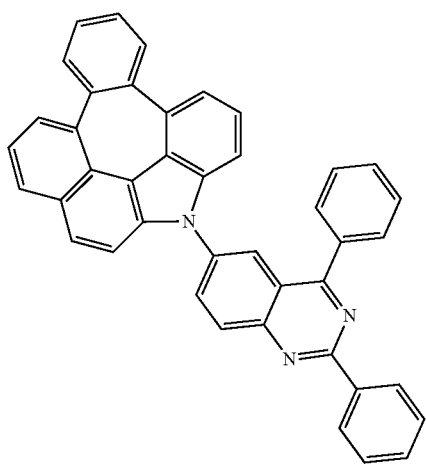
C-539
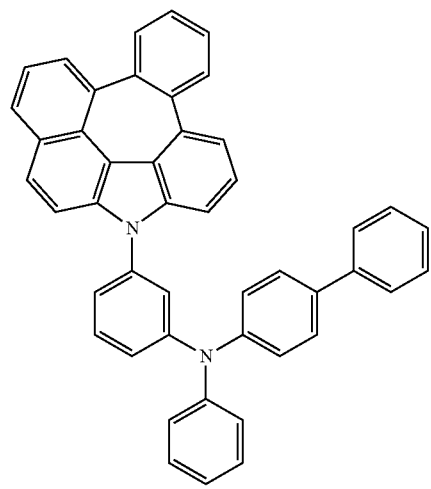
C-537
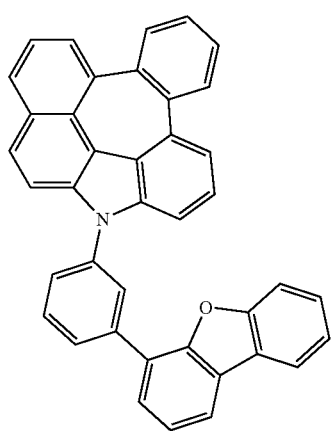
C-540
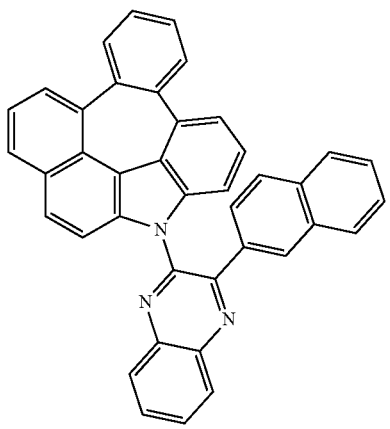

C-541
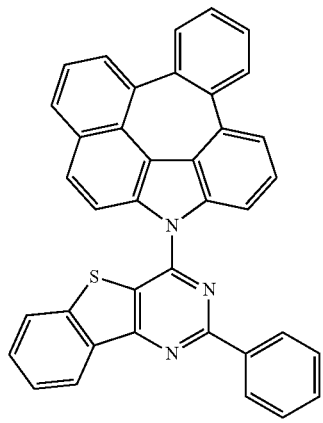
C-542
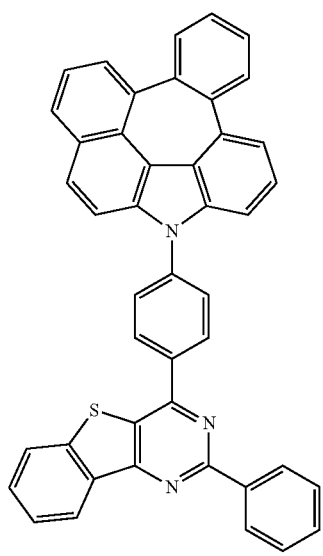
C-543
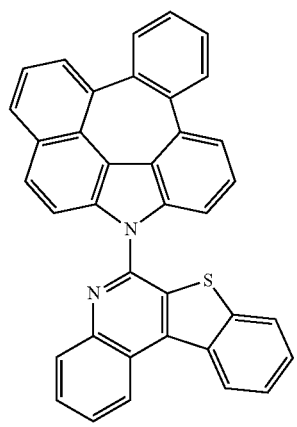
C-544
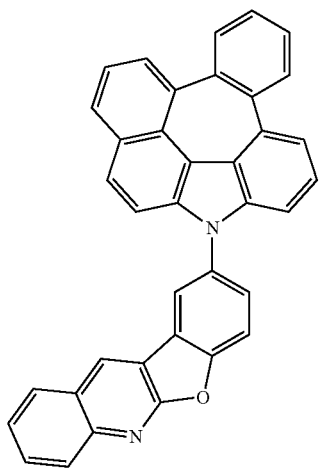
C-545
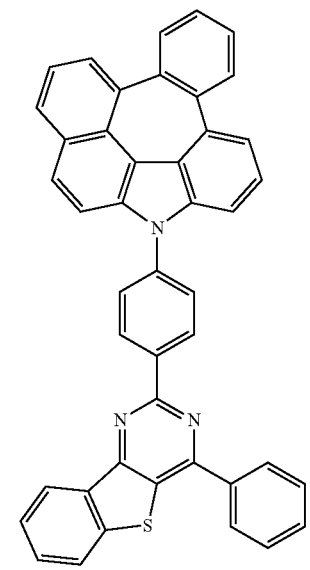
C-546
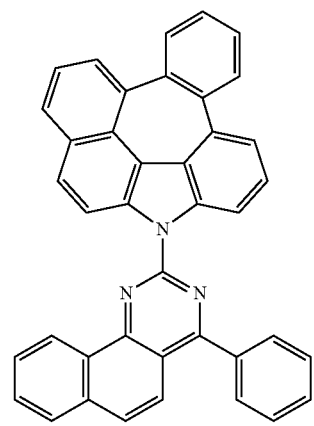

-continued
C-547
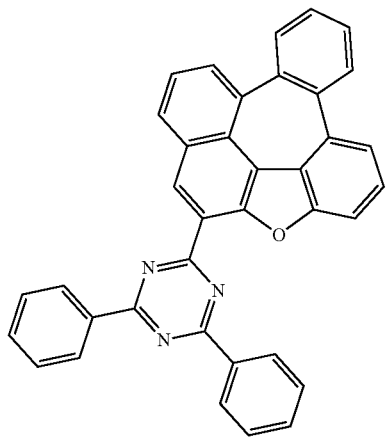
C-548
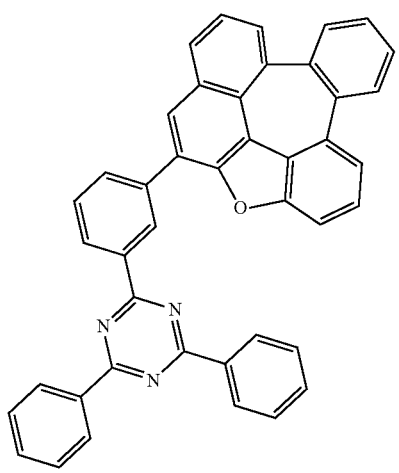
C-549
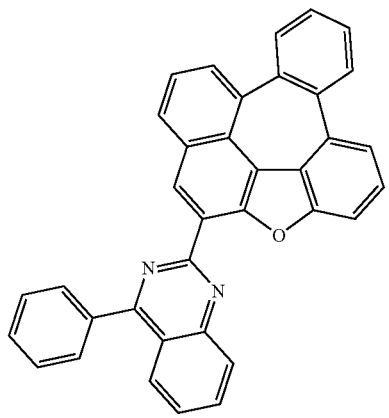
-continued
C-550
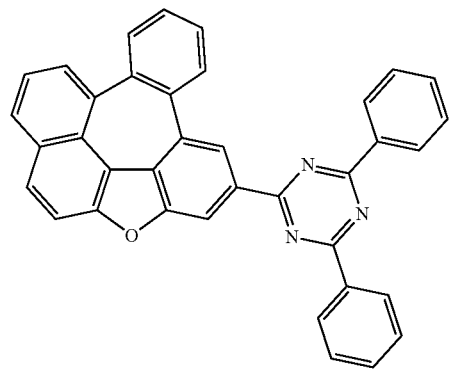
C-551
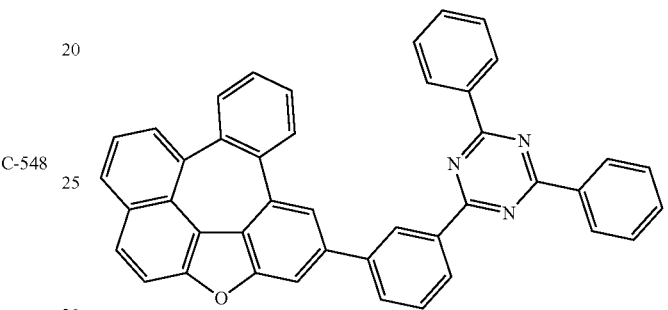
C-552
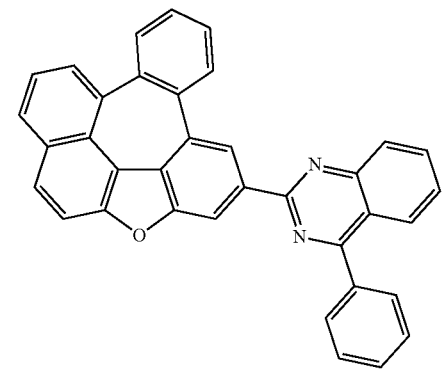
C-553
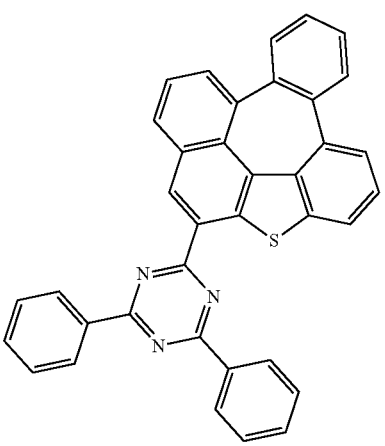

-continued
C-554
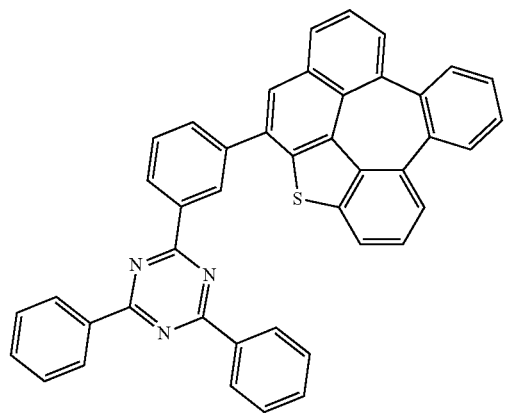
C-555
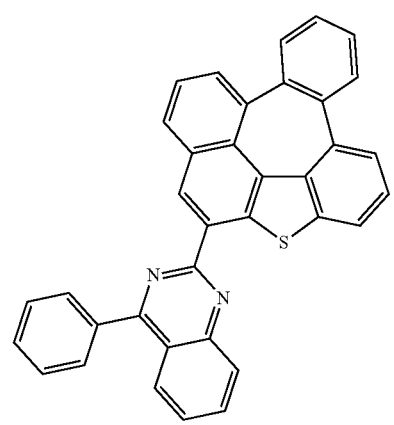
C-556
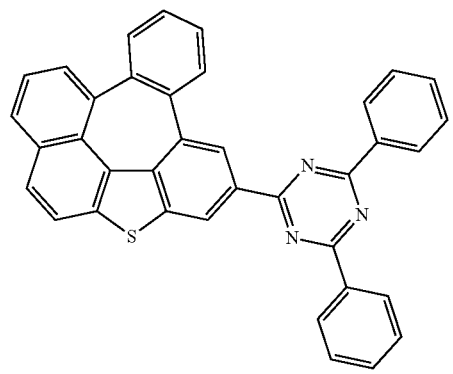
C-557
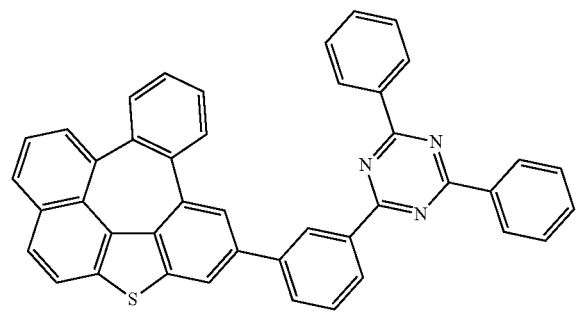
-continued
C-558
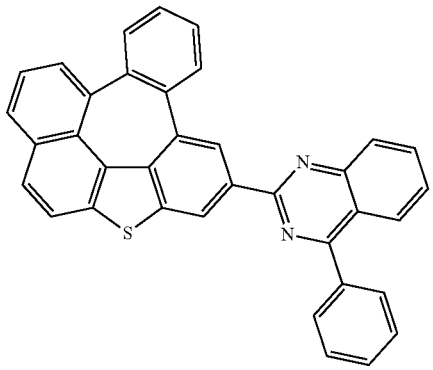
C-559
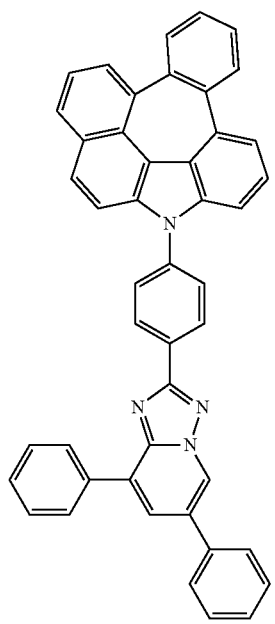
C-560
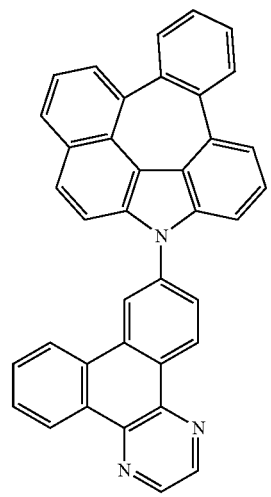

C-561
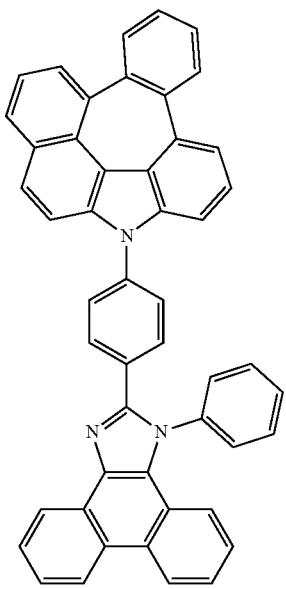
C-562
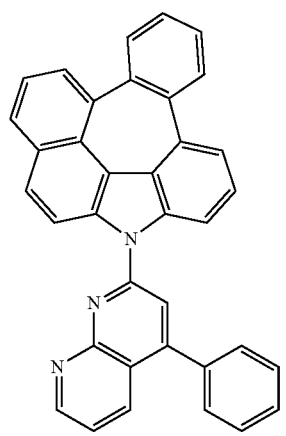
C-563
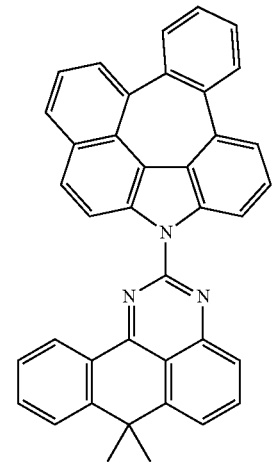
C-564
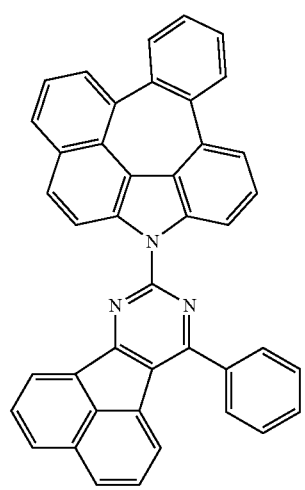
C-565
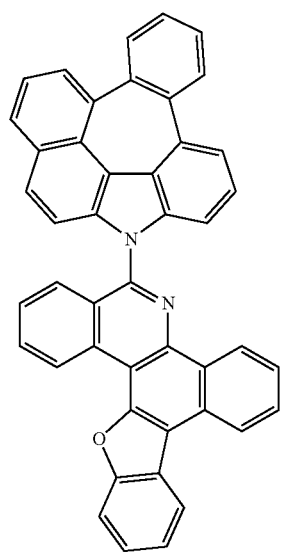
C-566
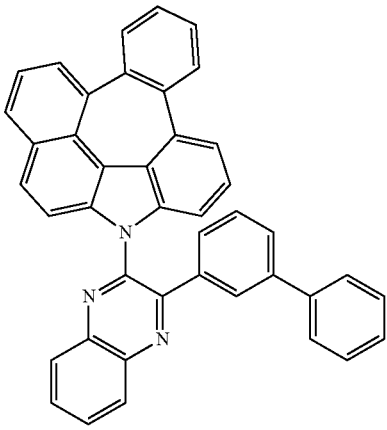

-continued
C-567
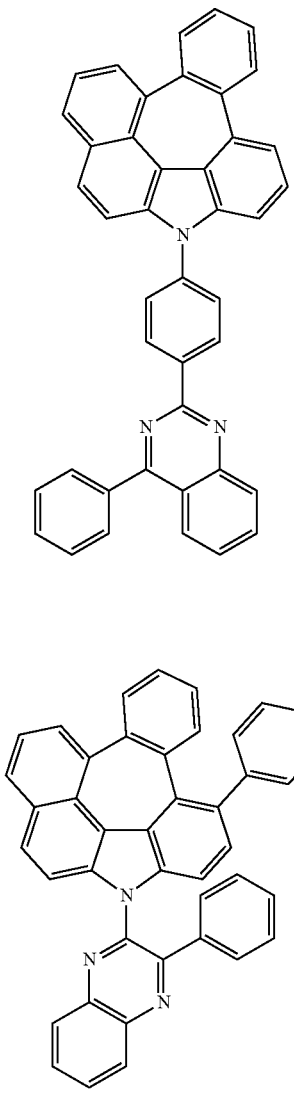
C-568
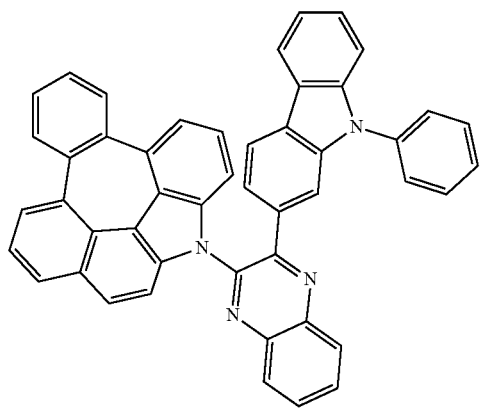
-continued
C-569
C-570
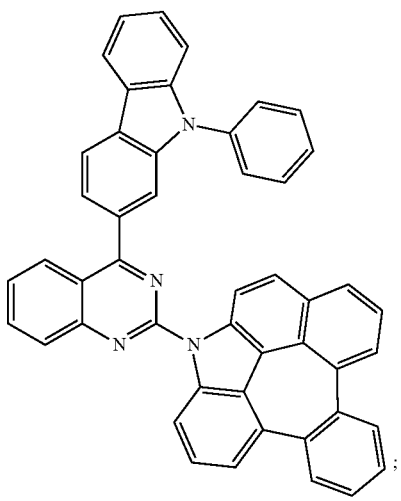
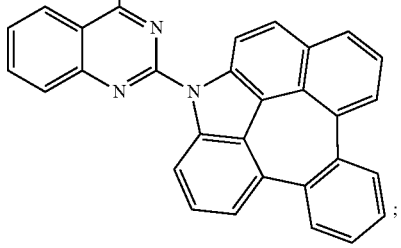
and
the hole transport zone comprises an arylamine derivative, and the HOMO energy level of the arylamine derivative satisfies the following equation 11:
$$-5.0\ eV \leq HOMO \leq -4.65\ eV \quad (11).$$
* * * * *